US010196373B2

(12) United States Patent
Turkson et al.

(10) Patent No.: US 10,196,373 B2
(45) Date of Patent: *Feb. 5, 2019

(54) SUBSTITUTED 2-HYDROXY-4-(2-(PHENYL-SULFONAMIDO)ACETAMIDO)BENZOIC ACID ANALOGS AS INHIBITORS OF STAT PROTEIN

(71) Applicants: University of Central Florida Research Foundation, Inc., Orlando, FL (US); THE GOVERNING COUNCIL OF THE UNIVERSITY OF TORONTO, Toronto (CA)

(72) Inventors: James Turkson, Orlando, FL (US); Patrick Gunning, Mississauga (CA)

(73) Assignees: THE GOVERNING COUNCIL OF THE UNIVERSITY OF TORONTO, Toronto (CA); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 437 days.

This patent is subject to a terminal disclaimer.

(21) Appl. No.: 14/452,183

(22) Filed: Aug. 5, 2014

(65) Prior Publication Data
US 2015/0038708 A1 Feb. 5, 2015

Related U.S. Application Data

(63) Continuation of application No. 13/813,916, filed as application No. PCT/US2011/046340 on Aug. 2, 2011, now Pat. No. 8,846,707.
(Continued)

(51) Int. Cl.
*C07D 239/02* (2006.01)
*C07D 401/04* (2006.01)
(Continued)

(52) U.S. Cl.
CPC ............ *C07D 401/04* (2013.01); *A61K 31/18* (2013.01); *C07C 311/19* (2013.01);
(Continued)

(58) Field of Classification Search
None
See application file for complete search history.

(56) References Cited

U.S. PATENT DOCUMENTS 6,383,790 B1 5/2002 Shokat
8,586,749 B2 * 11/2013 Turkson ................ C07C 311/19
546/230
(Continued)

FOREIGN PATENT DOCUMENTS

AU   2011285836   8/2011
CA   2757912      4/2010
(Continued)

OTHER PUBLICATIONS

Merriam-Webster, An Encyclopedia Britannica Company: http://www.merriam-webster.com/dictionary/derivative; analog, Oct. 28, 2015.*
(Continued)

*Primary Examiner* — Shengjun Wang
(74) *Attorney, Agent, or Firm* — Meunier Carlin & Curfman LLC

(57) ABSTRACT

In one aspect, the invention relates to substituted 2-hydroxy-4-(2-(phenylsulfonamido)acetamido)benzoic acid analogs, derivatives thereof, and related compounds, which are useful as inhibitors of STAT protein activity; synthetic methods for making the compounds; pharmaceutical compositions comprising the compounds; and methods of treating disorders of uncontrolled cellular proliferation associated with a STAT protein activity dysfunction using the compounds and compositions. This abstract is intended as a scanning tool for purposes of searching in the particular art and is not intended to be limiting of the present invention.

6 Claims, 26 Drawing Sheets
Specification includes a Sequence Listing.

Related U.S. Application Data

(60) Provisional application No. 61/369,796, filed on Aug. 2, 2010, provisional application No. 61/422,046, filed on Dec. 10, 2010.

(51) Int. Cl.
    *A61K 31/18*     (2006.01)
    *C07C 311/19*     (2006.01)
    *C07C 311/29*     (2006.01)
    *C07C 311/42*     (2006.01)
    *C07C 323/49*     (2006.01)
    *C07D 207/48*     (2006.01)
    *C07D 211/26*     (2006.01)
    *C07D 211/96*     (2006.01)
    *C07D 213/42*     (2006.01)
    *C07D 215/36*     (2006.01)
    *C07D 233/84*     (2006.01)
    *C07C 311/46*     (2006.01)
    *C07D 211/34*     (2006.01)
    *C07D 211/60*     (2006.01)

(52) U.S. Cl.
    CPC .......... *C07C 311/29* (2013.01); *C07C 311/42* (2013.01); *C07C 311/46* (2013.01); *C07C 323/49* (2013.01); *C07D 207/48* (2013.01); *C07D 211/26* (2013.01); *C07D 211/34* (2013.01); *C07D 211/60* (2013.01); *C07D 211/96* (2013.01); *C07D 213/42* (2013.01); *C07D 215/36* (2013.01); *C07D 233/84* (2013.01); *C07C 2601/14* (2017.05)

(56) References Cited

U.S. PATENT DOCUMENTS

| | | | |
|---|---|---|---|
| 8,846,707 B2 * | 9/2014 | Turkson ................ | A61K 31/18 514/275 |
| 2009/0069420 A1 | 3/2009 | Turkson | |
| 2012/0130079 A1 * | 5/2012 | Turkson ................ | C07C 311/19 546/230 |

FOREIGN PATENT DOCUMENTS

| | | |
|---|---|---|
| CA | 2807292 | 8/2011 |
| CN | 201180047549.0 | 8/2011 |
| EP | 10761975.1 | 4/2010 |
| EP | 11815234.7 | 8/2011 |
| IN | 1158/DELNP/2013 | 8/2011 |
| JP | 2013523292 | 8/2011 |
| KR | 10-2013-7005401 | 8/2011 |
| WO | 2010/117438 | 10/2010 |
| WO | 2012/018868 | 2/2012 |

OTHER PUBLICATIONS

Fletcher, S. et al., ChemBioChem 2009, 10, 1959-1964.*
Office Action issued by the Canadian Patent Office for Application 2,807,292 dated Aug. 25, 2015.
Office Action issued by the Canadian Patent Office for Application 2,807,292 dated May 29, 2016.
Abdulghani J, et al. (2008) Stat3 promotes metastatic progression of prostate cancer. Am J Path. 172: 1717-1728.
Akca H, et al. (2006) Activation of the AKT and STAT3 pathways and prolonged survival by a mutant EGFR in human lung cancer cells. Lung Cancer. 54: 25-33.
Alimirah F, et al. (2006) DU-145 and PC-3 human prostate cancer cell lines express androgen receptor: implications for the androgen receptor functions and regulation. FEBS Lett. 580: 2294-2300.
Almaras son O, et al. (2004) Crystal engmeenng of the composition of pharmaceutical phases. Do pharmaceutical co-crystals represent a new path to improved medicines? Chem Commun (Camb). 7: 1889-1896.
Becker S, et al. (1998) Three-dimensional structure of the Stat3beta homodimer bound to DNA. Nature. 394: 145-151.
Berishaj M, et al. (2007) Stat3 is tyrosine-phosphorylated through the interleukin-6/glycoprotein 130/Janus kinase pathway in breast cancer. Breast Cancer Res. 3: 1-8.
Bhasin D, et al. (2008) Design, synthesis, and studies of small molecule STAT3 inhibitors. Bioorg Med Chem Lett. 18: 391-395.
Blaskovich MA, et al. (2003) Discovery of JSI-124 (cucurbitacin I), a selective Janus kinase/signal transducer and activator of transcription 3 signaling pathway inhibitor with potent antitumor activity against human and murine cancer cells in mice. Cancer Res. 63: 1270-1279.
Boulares AH, et al. (1999) Role of poly(ADP-ribose) polymerase (PARP) cleavage in apoptosis. Caspase 3-resistant PARP mutant increases rates of apoptosis in transfected cells. J Biot Chem. 274: 22932-22940.
Bowman T, et al. (2000) STATs in oncogenesis. Oncogene. 19: 2474-2488.
Bromberg J, et al. (2000) The role of STATs in transcriptional control and their impact on cellular function. Oncogene. 19: 2468-2473.
Bromberg J. (2000) Signal transducers and activators of transcription as regulators of growth, apoptosis and breast development. Breast Cancer Res. 2: 86-90.
Bromberg JF, et al. (1999) Stat3 as an oncogene. Cell. 98: 295-303.
Buettner R, et al. (2002) Activated STAT signaling in human tumors provides novel molecular targets for therapeutic intervention. Clin Cancer Res. 8: 945-954.
Burke WM, et al. (2001) Inhibition of constitutively active Stat3 suppresses growth of human ovarian and breast cancer cells. Oncogene. 20: 7925-7934.
Byrn et al, Solid State Chemistry of Drugs, Second Edition, 1999.
Carlesso N, et al. (1996) Tyrosyl phosphorylation and DNA binding activity of signal transducers and activators of transcription (STAT) proteins in hematopoietic cell lines transformed by Bcr/Abl. J Exp Med. 183: 811-820.
Carro M, et al. (2010) The transcriptional network for mesenchymal transformation of brain tumours. Nature. 463: 318-325.
Catlett-Falcone R, et al. (1999) Constitutive activation of Stat3 signaling confers resistance to apoptosis in human U266 myeloma cells. Immunity. 10: 105-115.
Chen J, et al. (2007) Design and synthesis of a new, conformationally constrained, macrocyclic small-molecule inhibitor of STAT3 via 'click chemistry'. Bioorg Med Chem Lett. Bioorg Med Chem Lett. 17: 3939-3942.
Chen J, et al. (2010) Structure-Based Design of Conformationally Constrained, Cell-Permeable STAT3 Inhibitors. ACS Med Chem Lett. 13: 85-89.
Coleman DR IV, et al. (2005) Investigation of the binding determinants of phosphopeptides targeted to the SRC homology 2 domain of the signal transducer and activator of transcription 3. Development of a high-affinity peptide inhibitor. J Med Chem. 48: 6661-6670.
Coleman DR IV, et al. (2008) Solid Phase Synthesis of Phosphopeptides Incorporating 2,2-Dimethyloxazolidine Pseudoproline Analogs: Evidence for trans Leu-Pro Peptide Bonds in Stat3 Inhibitors. Int J Pept Res Ther. 14: 1-9.
Darnell JE, Jr. (1996) The JAK-STAT pathway: summary of initial studies and recent advances. Recent Prog Horm Res. 51: 391-403.
Darnell JE, Jr. (2002) Transcription factors as targets for cancer therapy. Nat Rev Cancer. 2: 740-749.
Darnell JE. (2005) Validating Stat3 in cancer therapy. Nat Med. 11: 595-596.
Dourlat J, et al. (2007) New syntheses of tetrazolylmethylphenylalanine and 0-malonyltyrosine as pTyr mimetics for the design of STAT3 dimerization inhibitors. Bioorg Med Chem Lett. 17: 3939-3942.
Farr AG, et al. (1989) Medullary epithelial cell lines from murine thymus constitutively secrete IL-1 and hematopoietic growth factors and express class II antigens in response to recombinant interferon-gamma. Cell Immunol. 119: 427-.

(56) References Cited

OTHER PUBLICATIONS

Faruqi T, et al. (2001) Rael mediates STAT3 activation by autocrine IL-6. Proc Natl Acad Sci USA. 98: 9014-9019.
Ferbeyre G, et al. (2011) The role of StatS transcription factors as tumor suppressors or oncogenes. Biochim Biophys Acta. 1815: 104-114.
Filmus J, et al. (1987) Epidermal growth factor receptor gene-amplified MDA-468 breast cancer cell line and its nonamplified variants. 7: 251-257.
Fletcher S, et al. (2008) Mild, efficient amd rapid 0-debenzylation of orithosubstituted with trifluoroacetic acid. Tetrehedron Letters. 49: 4817-4819.
Fletcher S, et al. (2008) Molecular approaches towards the inhibition of the signal transducer and activator of transcription 3 (Stat3) protein. ChemMedChem. 3: 1159-1168.
Fletcher S, et al. (2009) Disruption of transcriptionally active Stat3 dimers with non-phosphorylated, salicylic acid-based small molecules: potent in vitro and tumor cell activities. ChemBioChem. 10: 1959-1964.
Fletcher S, et al. (2009) Molecular disruption of oncogenic signal transducer and activator of transcription 3 (STAT3) protein. Biochem Cell Biol. 87: 825-833.
Fletcher, S. et al, Disruption of Transcriptionally Active Stat3 Dimers with Nonphosphorylated, Salicylic Acid-Based Small Molecules: Potent in vitro and Tumor Cell Activities, ChemBioChem 2009, 10, 1959-1964.
Fuh B, et al. (2009) LLL-3 inhibits STAT3 activity, suppresses glioblastoma cell growth and prolongs survival in a mouse glioblastoma model. Br J Cancer. 100: 106-112.
Garcia R, et al. (2001) Constitutive activation of Stat3 by the Src and JAK tyrosine kinases participates in growth regulation of human breast carcinoma cells. Oncogene. 20: 2499-2513.
Gough DJ, et al. (2009) Mitochondrial STAT3 supports Ras-dependent oncogenic transformation. Science. 324: 1713-1716.
Gouilleux-Gruart V, et al. (1996) ST AT-related transcription factors are constitutively activated in peripheral blood cells from acute leukemia patients. Blood. 87: 1692-1697.
Gouilleux-Gruart V, et al. (1997) Activated Stat related transcription factors in acute leukemia. Leuk Lymphoma. 28: 83-88.
Gouillex F, et al. (1995) Prolactin and interleukin-2 receptors in T lymphocytes signal through MGF-STAT5-like transcription factor. Endocrinology. 136: 5700-5708.
Gritsko T, et al. (2006) Persistent activation of stat3 signaling induces survivin gene expression and confers resistance to apoptosis in human breast cancer cells. Clin Cancer Res. 12: 11-19.
Grivennikov SI, et al. (2010) Dangerous liaisons: STAT3 and NF-kappaB collaboration and crosstalk in cancer. Cytokine Growth Factor Rev. 21: 11-19.
Gunning PT, et al. (2007) Isoform selective inhibition of STA TI or STAT3 homodimerization via peptidomimetic probes: structural recognition of Stat SH2 domains. Bioorg Med Chem Lett. 17: 1875-1878.
Gunning PT, et al. (2008) Targeting protein-protein interactions: suppression of Stat3 dimerization with rationally designed small-molecule, nonpeptidic SH2 domain binders. Chembiochem. 9: 2800-2803.
Haftchenary S, et al. (2011) Inhibiting aberrant Stat3 function with molecular therapeutics: a progress report. Anticancer Drugs. 22: 115-127.
Haura EB, et al. (2005) Mechanisms of disease: Insights into the emerging role of signal transducers and activators of transcription in cancer. Nat Clin Pract Oncol. 2: 315-324.
Huang C, et al. (2006) Inhibition of STAT3 activity with AG490 decreases the invasion of human pancreatic cancer cells in vitro. Cancer Sci. 97(12): 1417-1423.
Inghirami G, et al. (2005) New and old functions of STAT3: a pivotal target for individualized treatment of cancer. Cell Cycle. 4: 1131-1133.

Johnson PJ, et al. (1985) Overexpressed pp60c-src can induce focus formation without complete transformation ofNIH 3T3 cells. Mol Cell Biol. 5: 1073-1083.
Jones G, et al. (1997) Development and validation of a genetic algorithm for flexible docking. J Mol Biol. 267: 727-748.
Kaptein A, et al. (1996) Dominant negative stat3 mutant inhibits interleukin-6-induced Jak-STAT signal transduction. J Biol Chem. 271: 5961-5964.
Kopantzev Y, et al. (2002) IL-6 mediated activation of STAT3 bypasses Janus kinases in terminally differentiated B lineage cells. Oncogene. 21: 6791-6900.
Kortylewski M, et al. (2007) Stat3 as a potential target for cancer immunotherapy. J Immunother. 30: 131-139.
Kortylewski M, et al.. (2008) Role of Stat3 in suppressing anti-tumor immunity. Curr Opin Immunol. 20: 228-233.
Lai SY, et al. (2010) Defining the role of the JAK-STAT pathway in head and neck and thoracic malignancies: implications for future therapeutic approaches. Drug Resist Updat. 13: 67-78.
Liby K, et al. (2006) the synthetic triterpenoid CDDO-Imidazolide suppresses STAT phosphorylation and induces apoptosis in myeloma and lung cancer cells. 12: 4288-4293.
Lin L, et al. (2010) A novel small molecule, LLL12, inhibits STAT3 phosphorylation and activities and exhibits potent growth-suppressive activity in human cancer cells. Neoplasia. 12: 39-50.
Maegawa T, et al. (2007) Pd/C(en) catalyzed chemoselective hydrogenation in the presence of aryl nitriles. 55: 837-839.
Mandal PK, et al. (2007) Solid-phase synthesis of Stat3 inhibitors incorporating 0-carbamoylserine and 0-carbamoylthreonine as glutamine mimics. Bioorg Med Chem Lett. 17: 654-656.
Maritano D, et al. (2004) The STAT3 isoforms alpha and beta have unique and specific functions. Nat Immunol. 5: 401-409.
Mora SB, et al. (2002) Constitutive activation of Stat3 in human prostate tumors and cell lines: direct inhibition of Stat3 signaling induces apoptosis of prostate cancer cells. Cancer Res. 62: 6659-6666.
Muller J, et al. (2008) Discovery of chromone-based inhibitors of the transcription factor STATS. Chembiochem. 9: 723-727.
Neculai D, et al. (2005) Structure of the unphosphorylated STAT5a dimer. J Biol Chem. 280: 40782-40787.
Niu G, et al. (2002) Constitutive Stat3 activity up-regulates VEGF expression and tumor angiogenesis. Oncogene. 21: 2000-2008.
Ouyang H, et al. (2000) Immortal human pancreatic duct epithelial cell lines with near normal genotype and phenotype. Am J Pathol. 157: 1623-1631.
Page BD, et al. (2011) Signal transducer and activator of transcription 3 inhibitors: a patent review. Expert Opin Ther Pat. 21: 65-83.
Pandey PN, et al. (1982) Palladium-Catalyzed Hydrodehalogenation of Haloaromatic Compounds. 10: 876-878.
Pardanani A, et al. (2011) JAK inhibitor therapy for myelofibrosis: critical assessment of value and limitations. Leukemia. 25: 218-225.
Quintas-Cardama A, et al. (2011) Janus kinase inhibitors for the treatment of myeloproliferative neoplasias and beyond. Nat Rev Drug Discov. 10: 127-140.
Razgulin AV, et al. (2006) Binding properties of aromatic carbon-bound fluorine. J Med Chem. 49: 7902-7906.
Real PJ, et al. (2002) Resistance to chemotherapy via Stat3-dependent overexpression of Bcl-2 in metastatic breast cancer cells. Oncogene. 21: 7611-7618.
Ren Z, et al. (2003) Identification of a high-affinity phosphopeptide inhibitor of Stat3. Bioorg Med Chem Lett. 13: 633-636.
S.R. Vippagunta et al., Advanced Drug Delivery Reviews 48 (2001) 3-26.
Schlessinger K, et al. (2005) Malignant transformation but not normal cell growth depends on signal transducer and activator of transcription 3. Cancer Res. 65: 5282-5834.
Schroder M, et al. (2004) Preassociation of nonactivated STAT3 molecules demonstrated in living cells using bioluminescence resonance energy transfer: a new model of STAT activation? J Leukoc Biol. 75: 792-797.
Schust J, et al. (2004) A high-throughput fluorescence polarization assay for signal transducer and activator of transcription 3. Anal Biochem. 330: 114-118.

(56) References Cited

OTHER PUBLICATIONS

Schust J, et al. (2006) Stattic: a small-molecule inhibitor of STAT3 activation and dimerization. Chem Biol. 13: 1235-1242.
Sehgal PB. (2008) Paradigm shifts in the cell biology of STAT signaling. Semin Cell Dev Biol. 19: 329-340.
Seidel HM, et al. (1995) Spacing of palindromic half sites as a determinant of selective STAT (signal transducers and activators of transcription) DNA binding and transcriptional activity. Proc Natl Acad Sci USA. 92: 3041-3045.
Shahani VM, et al. (2011) Design, synthesis, and in vitro characterization of novel hybrid peptidomimetic inhibitors of STAT3 protein. Bioorg Med Chem. 19(5): 1823-1838.
Shahani VM, et al. (2011) Identification of Purine-Scaffold Small-Molecule Inhibitors of Stat3 Activation by QSAR Studies. ACS Med Chem Lett. 2(1): 79-84.
Shuai K, et al. (1994) Interferon activation of the transcription factor Stat91 involves dimerization through SH2-phosphotyrosyl peptide interactions. Cell. 76: 821-828.
Siddiquee K, et al. (2007a) Selective chemical probe inhibitor of Stat3, identified through structure-based virtual screening, induces antitumor activity. Proc Natl Acad Sci USA. 104: 7391-7396.
Siddiquee K, et al. (2007b) An oxazole-based small-molecule Stat3 inhibitor modulates Stat3 stability and processing and induces antitumor cell effects. ACS Chem Biol. 2: 787-798.
Siddiquee K, et al. (2008) STAT3 as a target for inducing apoptosis in solid and hematological tumors. Cell Res. 18: 254-267.
Song H, et al. (2005) A low-molecular-weight compound discovered through virtual database screening inhibits Stat3 function in breast cancer cells. Proc Natl Acad Sci USA. 102: 4700-4705.
Sun J, et al. (2005) Cucurbitacin Q: a selective STAT3 activation inhibitor with potent antitumor activity. Oncogene. 24: 3236-3245.
Tan SH, et al. (2008) Signal transducer and activator of transcription 5A/B in prostate and breast cancers. Endocr Relat Cancer. 15: 367-390.
Turkson J, et al. (1998) Stat3 activation by Src induces specific gene regulation and is required for cell transformation. Mol Cell Biol. 18: 2545-2552.
Turkson J, et al. (1999) Requirement for Ras/Rael-mediated p38 and c-Jun N-terminal kinase signaling in Stat3 transcriptional activity induced by the Src oncoprotein. Mol Cell Biol. 19: 7519-7528.
Turkson J, et al. (2001) Phosphotyrosyl peptides block Stat3-mediated DNA binding activity, gene regulation, and cell transformation. J Biol Chem. 276: 45443-45455.
Turkson J, et al. (2004) Inhibition of constitutive signal transducer and activator of transcription 3 activation by novel platinum complexes with potent antitumor activity. Mol Cancer Ther. 3: 1533-1542.
Turkson J, et al. (2004) Novel peptidomimetic inhibitors of signal transducer and activator of transcription 3 dimerization and biological activity. Mol Cancer Ther. 3: 261-269.
Turkson J, et al. (2005) A novel platinum compound inhibits constitutive Stat3 signaling and induces cell cycle arrest and apoptosis of malignant cells. J Biol Chem. 280: 32979-32988.
Turkson J. (2004) STAT proteins as novel targets for cancer drug discovery. Expert Opin Ther Targets. 8: 409-422.
Turkson, J. and Jove, R. (2000) STAT proteins: novel molecular targets for cancer drug discovery. Oncogene. 19: 6613-6626.
Valerio C, et al. (2000) Regioselective chlorocarbonylation of polybenzyl cores and functionalization using dendritic and organometallic nucleophiles. J Org Chem. 65: 1996-2002.
Van De Waterbeemd, H. Property based design: Optimization of Drug Absorption and Pharmokinetics, vol. 44, No. 9, Apr. 26, 2001. p. 1313-1333.

Wagner M, et al. (1999) Enhanced expression of the type II transforming growth factor-beta receptor is associated with decreased survival in human pancreatic cancer. Pancreas. 19: 370-376.
Wang C, et al. (1989) Expression of a retinoic acid receptor gene in myeloid leukemia cells. Leukemia. 3: 264-269.
Wang T, et al. (2004) Regulation of the innate and adaptive immune responses by Stat-3 signaling in tumor cells. Nat Med. 10: 48-54.
Wang X, et al. (2011) KLF8 promotes human breast cancer cell invasion and metastasis by transcriptional activation ofMMP9. Oncogene. 30: 1901-1911.
Weber-Nordt RM, et al. (1996) Constitutive activation of STAT proteins in primary lymphoid and myeloid leukemia cells and in Epstein-Barr virus (EBV)- related lymphoma cell lines. Blood. 88: 809-816.
Wei D, et al. (2003) Stat3 activation regulates the expression of vascular endothelial growth factor and human pancreatic cancer anglogenesls and metastasis. Oncogene. 22: 319-329.
Wu P, et al. (1997) A high-throughput STAT binding assay using fluorescence polarization. Anal Biochem. 249: 29-36.
Xie TX, et al. (2004) Stat3 activation regulates the expression of matrix metalloproteinase-2 and tumor invasion and metastasis. Oncogene. 23: 3550-3560.
Yang J, et al. (2005) Novel roles of unphosphorylated STAT3 in oncogenesis and transcriptional regulation. Cancer Res. 65: 939-947.
Yu C, et al. (1995) Enhanced DNA-binding activity of a Stat3-related protein in cells transformed by the Src oncoprotein. Science. 269: 81-83.
Yu H, et al. (2004) The STATs of cancer—new molecular targets come of age. Nat Rev Cancer. 4: 97-105.
Yu H, et al. (2009) STATs in cancer inflammation and immunity: a leading role for STAT3. Nat Rev Cancer. 9: 798-809.
Yue P, et al. (2009) Targeting STAT3 in cancer: how successful are we? Expert Opin Investig Drugs. 18: 45-56.
Zhang G, et al. (1997) Early detection of apoptosis using a fluorescent conjugate of annexin V. Biotechniques. 23: 525-531.
Zhang S, et al. (2007) PTPIB as a drug target: recent developments in PTPIB inhibitor discovery. Drug Discov Today. 12: 373-381.
Zhang X, et al. (2010) A novel small-molecule disrupts Stat3 SH2 domain-phosphotyrosine interactions and Stat3-dependant tumor processes. Biochem Pharmacology. 79: 1398-1409.
Zhang Y, et al. (2000) Activation of Stat3 in v-Src-transformed fibroblasts requires cooperation of Jakl kinase activity. J Biol Chem. 275: 24935-24944.
Zhao S., et al. (2008). Inhibition of STAT3 Tyr705 phosphorylation by Smad4 suppresses transforming growth factor beta-mediated invasion and metastasis in pancreatic cancer cells. Cancer Res. 68: 4221-4228.
Zhao W, et al. (2010) A cell-permeable Stat3 SH2 domain mimetic inhibits Stat3 activation and induces antitumor cell effects in vitro. J Biol Chem. 285: 35855-35865.
International Search Report dated Dec. 1912011 for PCT Application No. PCT/US2011/46340 filed on Aug. 12212011, which published as WO 20121018868 on Feb. 9, 2012 (Applicants—University of Central Florida Research Foundation, et al. // Inventors—James Turkson, et al.) (3 Pages).
Written Opinion dated Dec. 1912011 for PCT Application No. PCT/US2011/46340 filed on Aug. 12212011, which published as WO 20121018868 on Feb. 9, 2012 (Applicants—University of Central Florida Research Foundation, et al. // Inventors—James Turkson, et al. (8 Pages).
International Preliminary Report on Patentability dated Feb. 5, 2013 for PCT Application No. PCT/US2011/46340 filed on Aug. 12212011, which published as WO 2012/018868 on Feb. 9, 2012 (Applicants—University of Central Florida Research Foundation, et al. // Inventors—James Turkson, et al.) (9 Pages).

* cited by examiner (a)

(b)

(a)

(b)

(c)

(d)

(a)

(b)

SUBSTITUTED 2-HYDROXY-4-(2-(PHENYL-SULFONAMIDO)ACETAMIDO)BENZOIC ACID ANALOGS AS INHIBITORS OF STAT PROTEIN

CROSS-REFERENCE TO RELATED APPLICATIONS

This application is a continuation application of U.S. application Ser. No. 13/813,916 filed May 10, 2013, while is a national phase application of PCT/US2011/046340 filed Aug. 2, 2011, which claims priority to U.S. Application No. 61/369,796 filed Aug. 2, 2010 and to U.S. Application No. 61/422,046 filed Dec. 10, 2010, each of which is hereby incorporated by reference in its entirety.

The Sequence Listing submitted on Oct. 17, 2014 as a text file named "26150_0007U4 Sequence_Listing.txt," created on Oct. 15, 2014, and having a size of 4,096 bytes is hereby incorporated by reference pursuant to 37 C.F.R. § 1.52(e)(5).

STATEMENT REGARDING FEDERALLY SPONSORED RESEARCH

This invention was made with government support under grant numbers CA106439 and CA128865 awarded by the National Cancer Institute of the National Institutes of Health. The United States government has certain rights in the invention.

BACKGROUND

STAT proteins were originally discovered as latent cytoplasmic transcription factors that mediate cytokine and growth factor responses (Darnell, J. E., Jr. (1996) Recent Prog. Norm. Res. 51, 391-403; Darnell. J. E. (2005) Nat. Med. 11, 595-596). Seven members of the family, STAT1, STAT2, STAT3, STAT4, STAT5a and STAT5b, and STAT6, mediate several physiological effects including growth and differentiation, survival, development and inflammation. STATs are SH2 domain-containing proteins. Upon ligand binding to cytokine or growth factor receptors. STATs become phosphorylated on critical Tyr residue (Tyr705 for STAT3) by growth factor receptors, cytoplasmic Janus kinases (Jaks) or Src family kinases. Two phosphorylated and activated STAT monomers dimerize through reciprocal pTyr-SH2 domain interactions, translocate to the nucleus, and bind to specific DNA-response elements of target genes, thereby inducing gene transcription (Darnell, J. E., Jr. (1996) Recent Prog. Norm. Res. 51, 391-403; Darnell. J. E. (2005) Nat. Med. 11, 595-596). In contrast to normal STAT signaling, many human solid and hematological tumors harbor aberrant STAT3 activity (Turkson, J. Expert Opin. Ther. Targets 2004, 8, 409-422; Darnell, J. E., Jr. (1996) Recent Prog. Norm. Res. 51, 391-403; Darnell. J. E. (2005) Nat. Med. 11, 595-596). In contrast to normal STAT signaling, many human solid and hematological tumors harbor aberrant STAT3 activity (3 and Darnell. J. E. (2005) Nat. Med. 11, 595-596; Bowman, T., et al. (2000) Oncogene 19, 2474-2488; Buettner, et al. (2002) Clin. Cancer Res. 8, 945-954; Yu, H. and Jove. R. (2004) Nat. Rev. Cancer 4, 97-105; Haura, E. B., et al. (2005) Nat. Clin. Pract. Oncol. 2, 315-324).).

Constitutive STAT3 activity mediates dysregulated growth and survival, angiogenesis, as well as suppresses the host's immune surveillance of the tumor, making constitutively-active STAT3 a critical molecular mediator of carcinogenesis and tumor progression.

Genetic and other molecular evidence reveals persistent Tyr phosphorylation of STAT3 is mediated by aberrant upstream Tyr kinases and shows cancer cell requirement for constitutively-active and dimerized STAT3 for tumor maintenance and progression. Thus, in numerous proof-of-concept studies (Turkson, J.; et al. Mol. Cancer Ther. 2004, 3, 261-269; Turkson, J.; et al. J. Biol. Chem. 2001, 276, 45443-45455; Siddiquee, K.; et al. Proc. Natl. Acad. Sci. U.S.A. 2007, 104, 7391-7396; Turkson, J.; et al. Mol. Cancer Ther. 2004, 3, 1533-1542; and Turkson, J.; et al. J. Biol. Chem. 2005, 280, 32979-32988), inhibition of STAT3 activation or disruption of dimerization induces cancer cell death and tumor regression. How aberrant STAT3 is regulated for meeting the tumor-specific requirements in malignant cells remains undefined. There have been no studies into defining the molecular details of how malignant cells regulate aberrant STAT3 and how this regulation changes upon STAT3 inhibition prior to the onset of phenotypic changes, although knowing these events will facilitate efforts in modulating aberrant STAT3 for managing human cancers. Small-molecule STAT3 inhibitors thus provide tools for probing the molecular dynamics of the cellular processing of STAT3 to understand STAT3's role as a signaling intermediate and a molecular mediator of the events leading to carcinogenesis and malignant progression.

Stat5 signaling, like Stat3 signaling, is transiently activated in normal cells and is deactivated by a number of different cytosolic and nuclear regulators, including phosphatases, SOCS, PIAS, and proteasomal degradation. Like Stat3, Stat5 has gained notoriety for its aberrant role in human cancers and tumorigenesis, having been found to be constitutively activated in many cancers, including those of the breast, liver, prostate, blood, skin, head and neck. (Müller, J., et al. ChemBioChem 2008, 9, 723-727). In cancer cells, Stat5 is routinely constitutively phosphorylated which leads to the aberrant expression of Stat5 target genes resulting in malignant transformation. Cancer cells harbouring persistently activated Stat5 over express anti-apoptotic proteins, such as Bcl-xL, Myc and MCL-1, conferring significant resistance to natural apoptotic cues and administered chemotherapeutic agents. Of particular interest, Stat5 has been identified as a key regulator in the development and progression of acute myelogenic (AML) and acute lymphoblastic leukemias (ALL; Gouilleux-Gruart, V., et al. Leukemia and Lymphoma 1997, 28, 83-88; Gouilleux-Gruart, V., et al. Blood 1996, 87, 1692-1697; Weber-Nordt, R. M., et al. Blood 1996, 88, 809-816). Moreover, inhibitors of upstream Stat5 activators (such as JAK and FLT3) have been shown to exhibit promising anti-cancer properties (Pardanani, A., et al. Leukemia 2011, 25, 218-225; Quintás-Cardama, A., et al. Nature Reviews Drug Discovery 2011, 10, 127-140).

Despite advances in drug discovery directed to identifying inhibitors of STAT protein activity, there is still a scarcity of compounds that are both potent, efficacious, and selective activators of STAT3 and STAT5 and also effective in the treatment of cancer and other diseases associated with dysfunction in STAT3, STAT5 or both proteins, and diseases in which one or both of STAT3 and STAT5 is involved. These needs and other needs are satisfied by the present invention.

SUMMARY

In accordance with the purpose(s) of the invention, as embodied and broadly described herein, the invention, in one aspect, relates to compounds useful as inhibitors of STAT. In a further aspect, the disclosed compounds and products of disclosed methods of making, or a pharmaceutically acceptable salt, hydrate, solvate, or polymorph thereof, are modulators of STAT activity, methods of making same, pharmaceutical compositions comprising same, and methods of treating disorders associated with a STAT activity dysfunction using same. In a still further aspect, the present invention relates to compounds that bind to a STAT protein and negatively modulate STAT activity. The disclosed compounds can, in one aspect, exhibit subtype selectivity. In a further aspect, the disclosed compounds exhibit selectivity for the STAT3 member of the STAT protein family. In a still further aspect, the disclosed compounds exhibit selectivity for the STAT5 member of the STAT protein family.

Also disclosed are pharmaceutical compositions comprising a therapeutically effective amount of a disclosed compound and a pharmaceutically acceptable carrier.

Disclosed are methods for the treatment of a disorder associated with STAT activity dysfunction in a mammal comprising the step of administering to the mammal a therapeutically effective amount of a disclosed compound, or a pharmaceutically acceptable salt, hydrate, solvate, or polymorph thereof.

Also disclosed are method for inhibition of STAT activity in a mammal comprising the step of administering to the mammal a therapeutically effective amount of least one disclosed compound, or a pharmaceutically acceptable salt, hydrate, solvate, or polymorph thereof.

Also disclosed are methods for inhibiting STAT activity in at least one cell, comprising the step of contacting the at least one cell with an effective amount of least one disclosed compound, or a pharmaceutically acceptable salt, hydrate, solvate, or polymorph thereof.

Also disclosed are uses of a disclosed compound, or a pharmaceutically acceptable salt, hydrate, solvate, or polymorph thereof. In a further aspect, the invention relates to pharmaceutical compositions comprising a pharmaceutically acceptable carrier and an effective amount of a disclosed compound, or a pharmaceutically acceptable salt, hydrate, solvate, or polymorph thereof.

Also disclosed are kits comprising at least one disclosed compound, or a pharmaceutically acceptable salt, hydrate, solvate, or polymorph thereof, and one or more of: (a) at least one agent known to decrease STAT3 activity; (b) at least one agent known to increase STAT3 activity; (c) at least one agent know to treat a disease of uncontrolled cellular proliferation; (d) at least one agent known to treat psoriasis; (e) at least one agent known to treat pulmonary arterial hypertension; or (f) instructions for treating a disorder associated with STAT3 dysfunction.

Also disclosed are kits comprising at least one disclosed compound, or a pharmaceutically acceptable salt, hydrate, solvate, or polymorph thereof, and one or more of: (a) at least one agent known to decrease STAT5 activity; (b) at least one agent known to increase STAT5 activity; (c) at least one agent know to treat a disease of uncontrolled cellular proliferation; or (d) instructions for treating a disorder associated with a STAT5 dysfunction.

Also disclosed are methods for manufacturing a medicament comprising combining at least one disclosed compound or at least one disclosed product with a pharmaceutically acceptable carrier or diluent. In a further aspect, the invention relates to the use of a disclosed compound in the manufacture of a medicament for the treatment of a disorder associated with STAT activity dysfunction. In a yet further aspect, the STAT activity dysfunction is a STAT3 activity dysfunction. In an even further aspect, the STAT activity dysfunction is a STAT5 activity dysfunction. In a still further aspect, the invention relates to the used of disclosed compound in the manufacture of a medicament for the treatment of a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
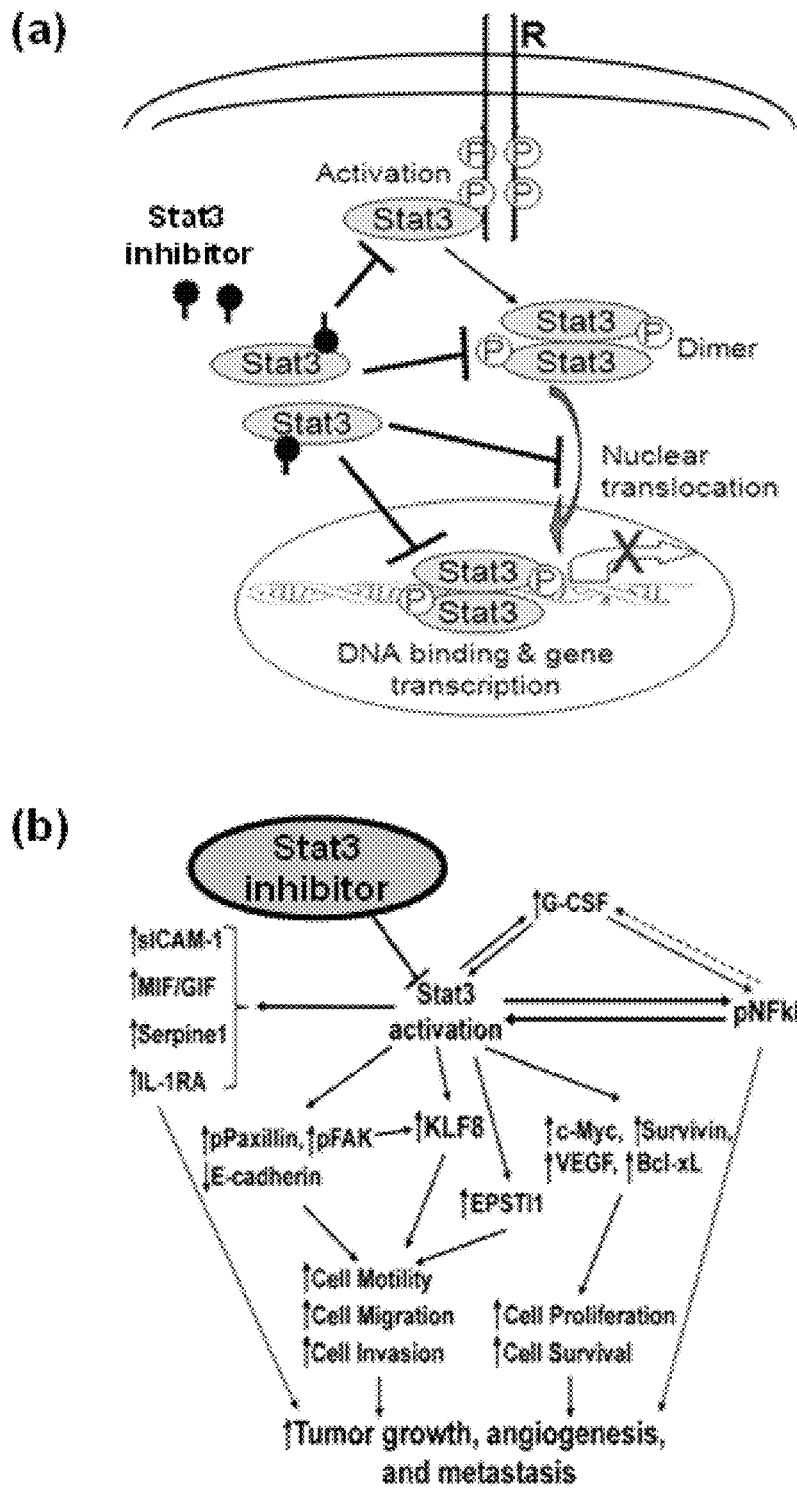
FIG. 1 shows in Panels A and B, various representative models for inhibition of Stat3 activation and transcriptional activity and the consequent effects on Stat3-dependent events, tumor processes, and tumor growth.
Figure 2:
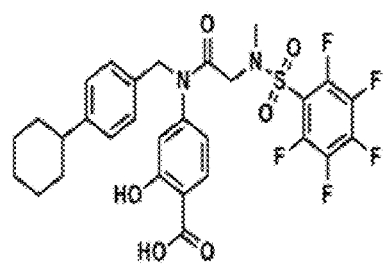
FIG. 2 shows the structure of a representative compound (Panel A) and representative computational modeling of the indicated compound binding to the SH2 domain of STAT3 (Panel B). The left side of Panel B shows a monomer Stat3 with the solvent-accessible surface of the SH2 domain with hydrophilic residues and hydrophobic residues highlighted, and overlaid with the indicated compound. The right side of Panel B shows three solvent-accessible sub-pockets of the SH2 domain surface accessed by the indicated compound, with the pentafluorobenzene sulfonamide component projecting into the third sub-pocket composed of Lys591, Gly594, Ile634, and Arg595.
Figure 2:
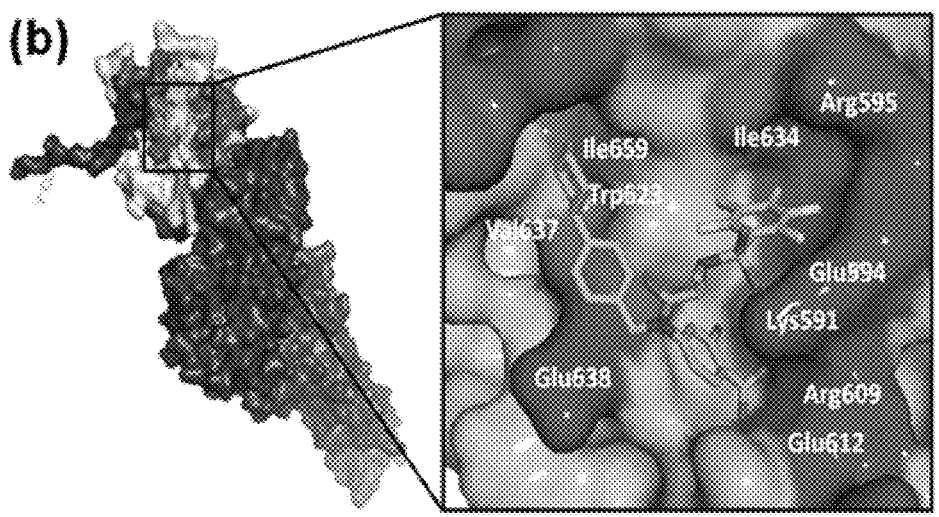
Figure 3:
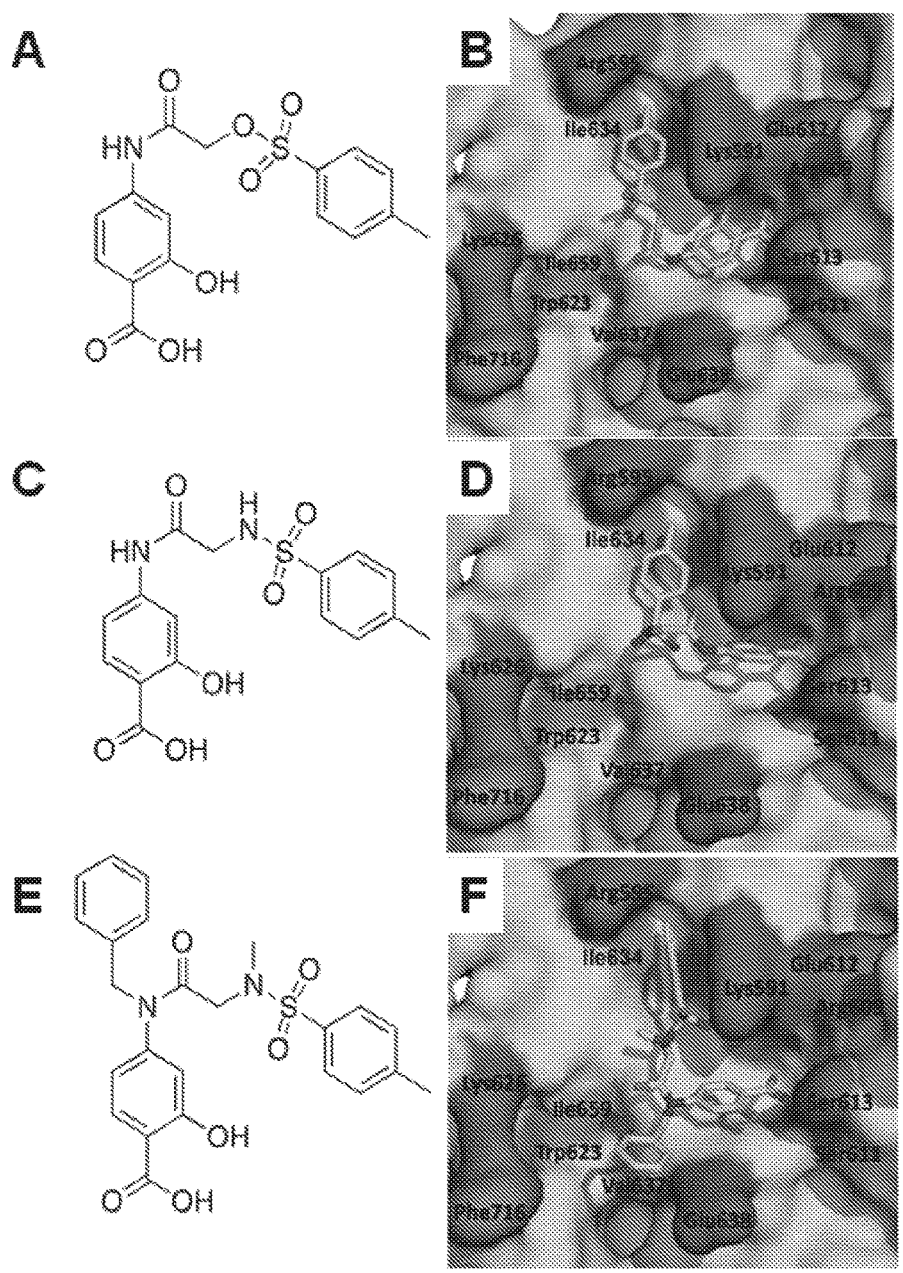
FIG. 3 shows representative computational modeling of representative compounds. The figure shows the compound on the left side and the low energy GOLD20 docking conformation of compound in the SH2 domain on the right side. The hydrophobic and hydrophilic are highlighted.
Figure 4:
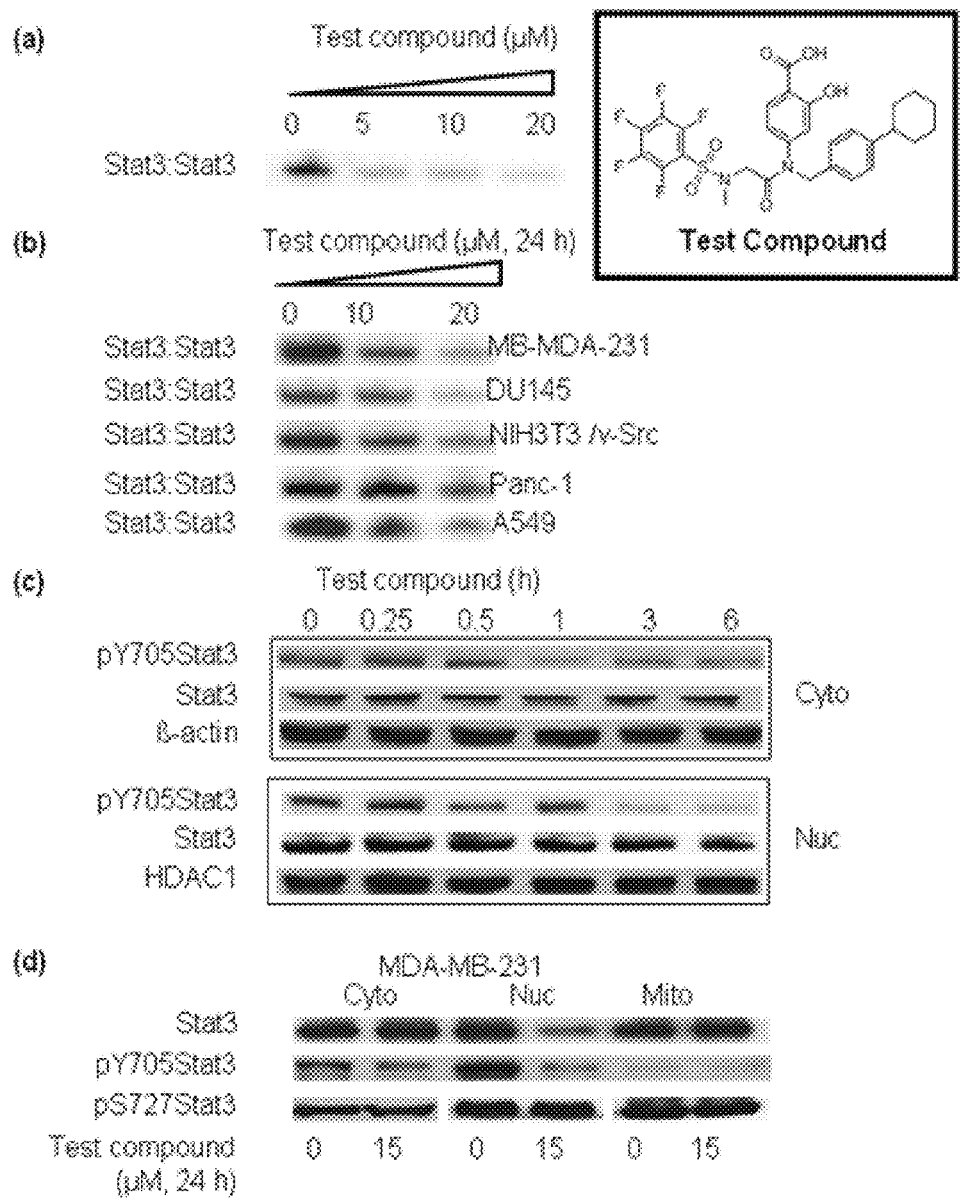
FIG. 4 shows representative data for the indicated test compound. The data show modulation of Stat3 activation and intracellular distribution. (a and b) EMSA analysis of Stat3 DNA-binding activity in nuclear extracts of equal total protein (a) pre-treated with 0-20 µM test compound, or (b) prepared from the designated tumor cells treated with 0-20 µM test compound; and (c and d) immunoblotting analysis of cytosolic (Cyto), nuclear (Nuc) or mitochondrial (Mito) fractions of equal total protein prepared from MDA-MB-231 cells untreated (0) or treated with test compound at (c) 10 µM for the indicated times, or (d) 15 µM for 24 h and probing for pY705Stat3, Stat3, pS727Stat3, histone deacetylase 1 (HDAC1) or β-actin. Positions of Stat3:DNA complexes or proteins in gel are labeled; control lanes (0) represent nuclear extracts treated with 0.05% DMSO, or nuclear extracts, whole-cell lysates, or nuclear, cytosolic or membrane fractions prepared from 0.05% DMSO-treated cells. Data are representative of 3-4 independent determinations.
Figure 5:
FIG. 5 shows representative data for the effect of representative disclosed compounds, wherein the compound ID corresponds to the compound ID given in Table 1, on STAT3:STAT3 binding as determined in an EMSA assay.
Figure 5:
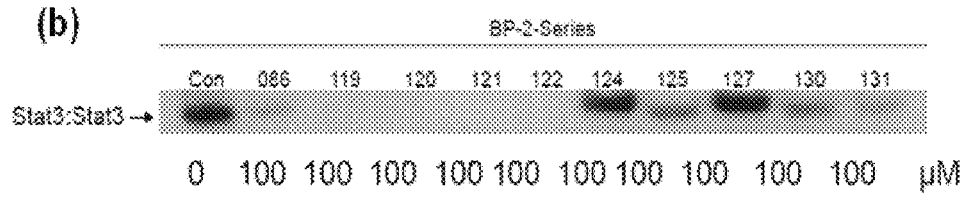
Figure 5:
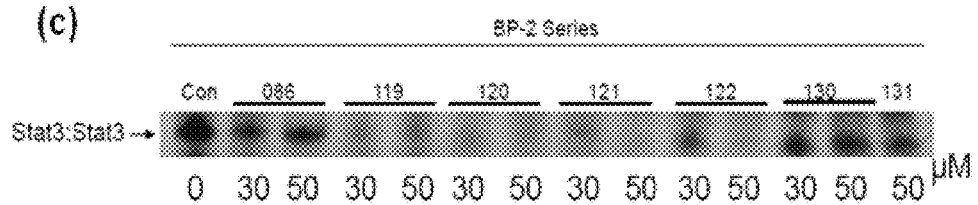
Figure 5:
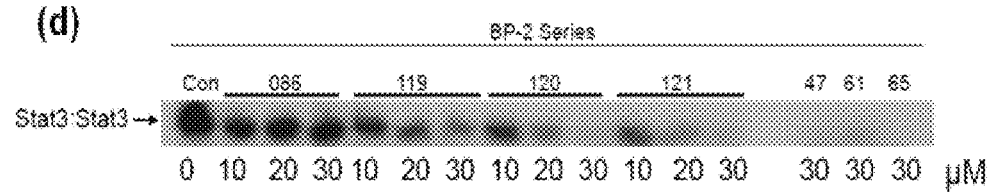
Figure 6:
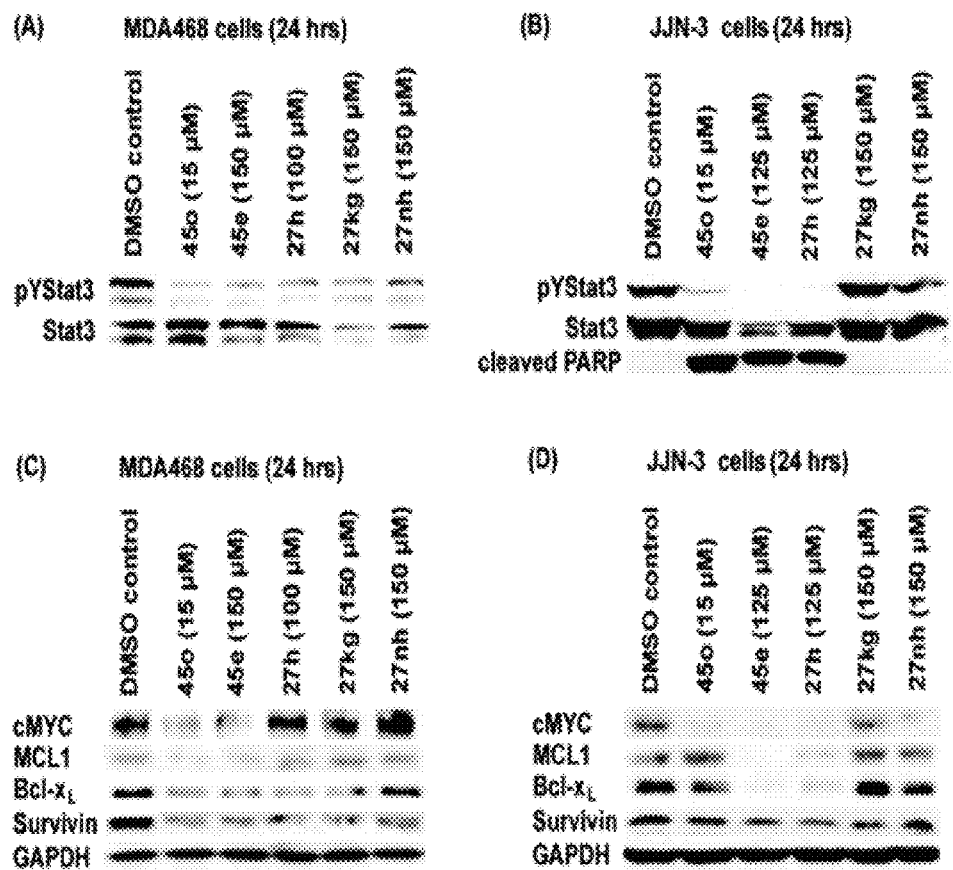
FIG. 6 shows representative data for the effect of representative disclosed compounds, wherein the compound ID corresponds to the compound ID given in Table 1, on STAT3-regulated genes. The figure shows SDS-Page and Western blotting analysis of whole cell lysates prepared from MDA-468 human breast cancer and multiple myeloma JJN3 cells untreated (DMSO, control) or treated with 45o (15 µM), 45e (125 or 150 µM), 27h (100 or 125 µM), 27kg (150 µM) and 27nh (150 µM) for 24 hrs and subjected to immunoblotting analysis for (A, B) pY705Stat3, Stat3; (C, D) c-Myc, Bcl-$x_L$, Mcl-1 and Survivin. Positions of protein in gel are shown.
Figure 7:
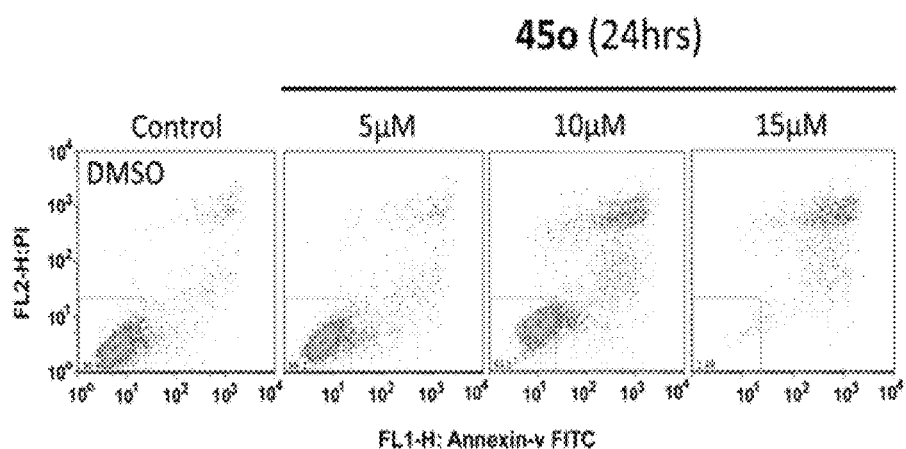
FIG. 7 shows representative data for a disclosed compound wherein the compound ID corresponds to the compound ID given in Table 1, on apoptosis. The figure shows results for induction of apoptosis in JJN3 cell lines treated with vehicle control or indicated concentration of 45o for 24 hr. % viable cells determined by exclusion of Annexin V and PI staining.
Figure 8:
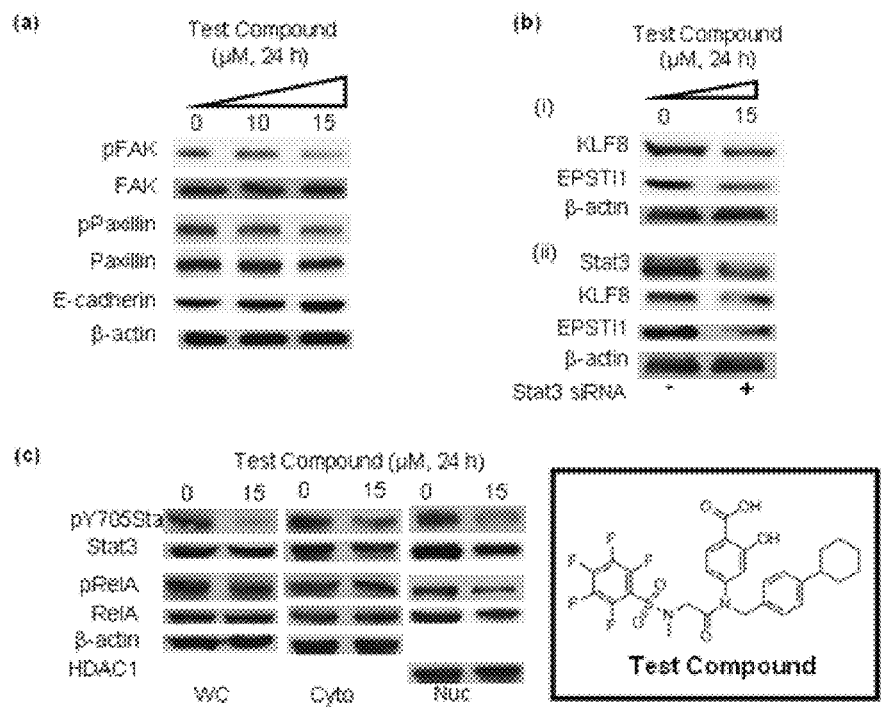
FIG. 8 shows representative data for the effect of the indicated test compound on STAT3 mediated cellular function in the presence and absence of STAT3 siRNA. The effect of the test compound was assessed for on FAK, paxillin, E-Cadherin, KLF8, EPSTI1, and NF|B induction and sICAM, G-CSF and MIF/GIF production. (Panels A and B) Immunoblotting analysis of whole-cell lysates prepared from MDA-MB-231 cells treated with (a and b(i)) 0-15 µM test compound for 24 h or (b(ii)) transfected with control (–) or Stat3 siRNA (+) and probing for FAK, phospho-FAK, paxillin, phospho-paxillin, E-cadherin, KLF8, EPSTI1, or β-actin, (c), immunoblotting analysis of (c) whole-cell (WC), nuclear (Nuc), or cytosolic (Cyto) lysates of MDA-MB-231 cells treated with or without 15 µM test compound. Data are representative of 3-4 independent determinations. Values, mean±S.D., n=9. *p<0.05 and **p–<0.01.
Figure 9:
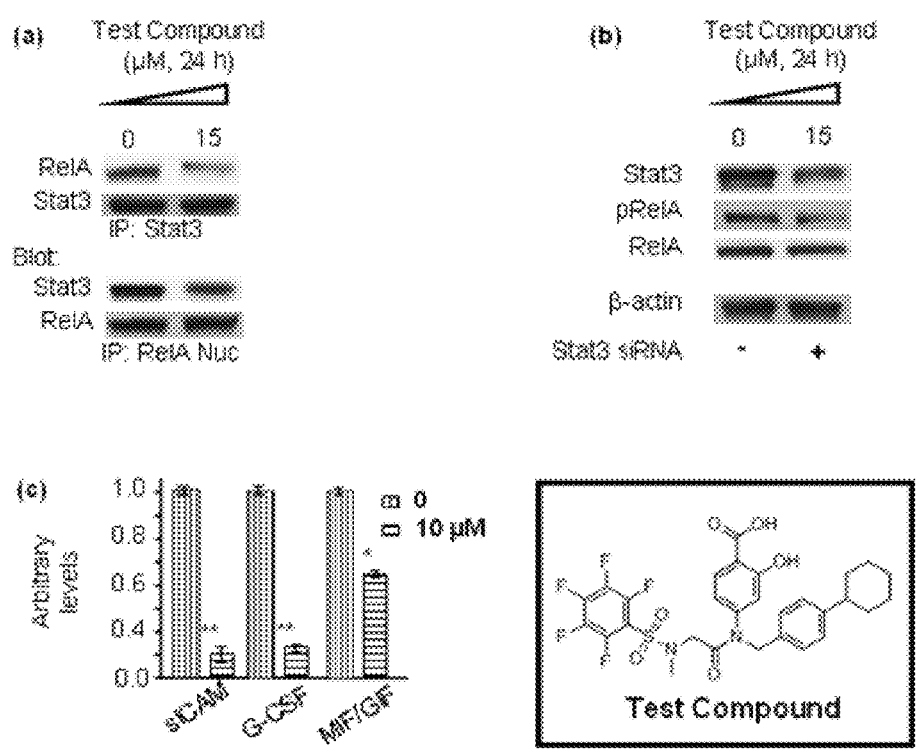
FIG. 9 shows data for the effect of the indicated test compound on STAT3 mediated cellular function in the presence and absence of STAT3 siRNA. The effect of the test compound was assessed for on FAK, paxillin, E-Cadherin, KLF8, EPSTI1, and NF|B induction and sICAM, G-CSF and MIF/GIF production. (Panel A) immunocomplexes of Stat3 (upper panel) or RelA (lower panel) prepared from MDA-MB-231 cells, or (Panel B) whole-cell lysates of MDA-MB-231 cells transfected with control (–) or Stat3 siRNA (+) and probing for pY705Stat3, Stat3, pRelA, RelA, β-actin or HDAC1; and (Panel C) a plot of GCSF, sICAM, and MIF/GIF levels assayed in conditioned medium from cultures of MDA-MB-231 cells treated with or without 10 µM test compound for 48 h. Positions of proteins in gel are shown. Data are representative of 3-4 independent determinations. Values, mean±S.D., n=9. *p<0.05 and **p–<0.01.
Figure 10:
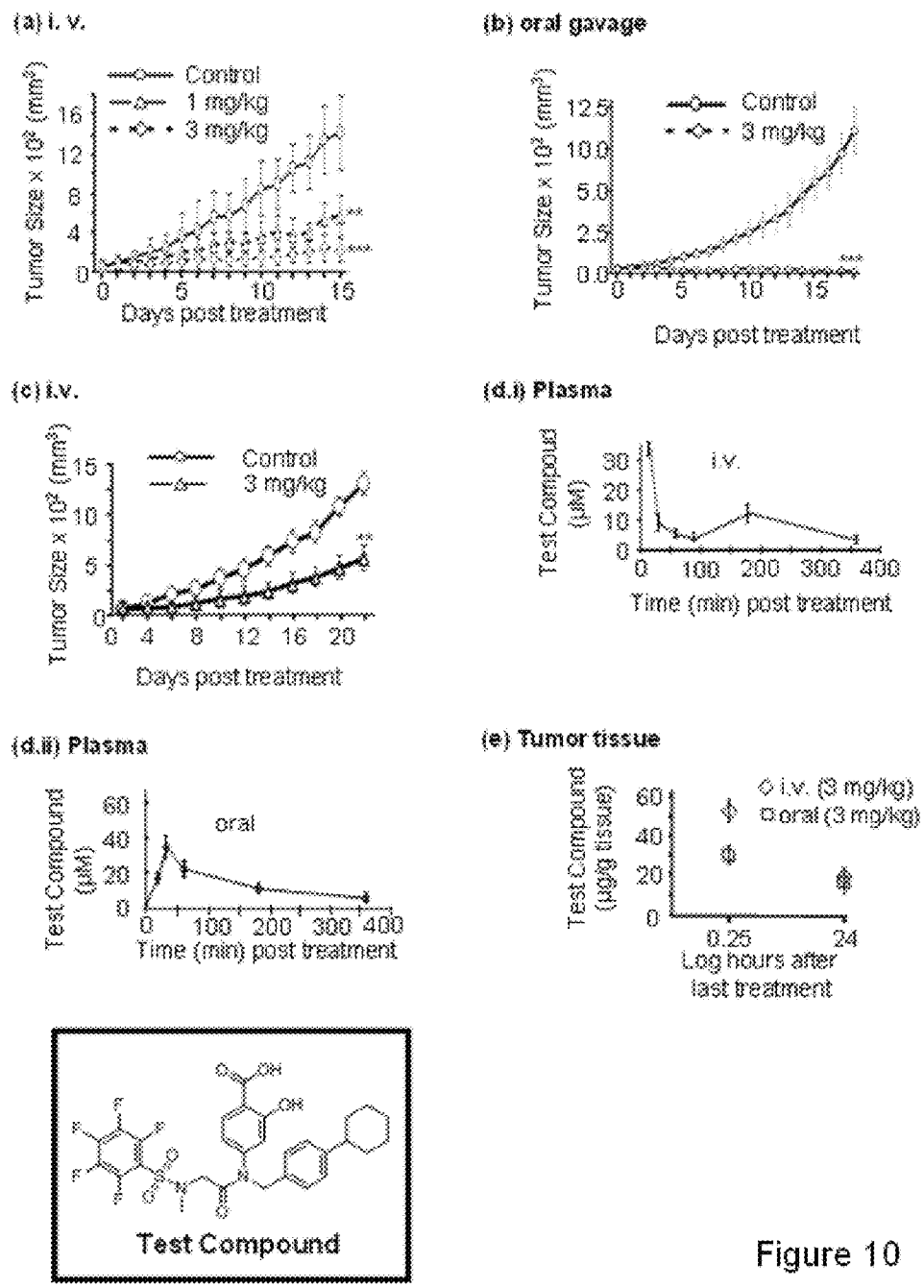
FIG. 10 shows representative data for the effect of a representative disclosed compound in an in vivo model of cancer. The figure shows data for growth of human breast and non-small cell lung tumor xenografts and the effects and the in vivo pharmacokinetic properties of the indicated test compound. (a, b, and c) Mice bearing human breast (MDA-MB-231) (a, b) or non-small cell lung (A549) (c) tumors were administered test compound via i.v., 1 or 3 mg/kg or vehicle (0.05% DMSO in PBS) (a and c) or oral gavage, 3 mg/kg or vehicle (0.05% DMSO) (b) every 2 or 3 days. Tumor sizes, measured every 2 or 3 days were converted to tumor volumes and plotted against days of treatment; and (d and e) graphical representations of the analyses of test compound in (d) plasma samples collected from mice 15-360 min post single dosing of 3 mg/kg via i.v. (i) or oral gavage (ii), and (e) tumor tissues extracted 15 min or 24 hours after the last dosing with 3 mg/kg, i.v. or oral gavage. Values, mean±S.D., n=7-10. *p–<0.05, p–<0.01, and *p–<0.005.
Figure 11:
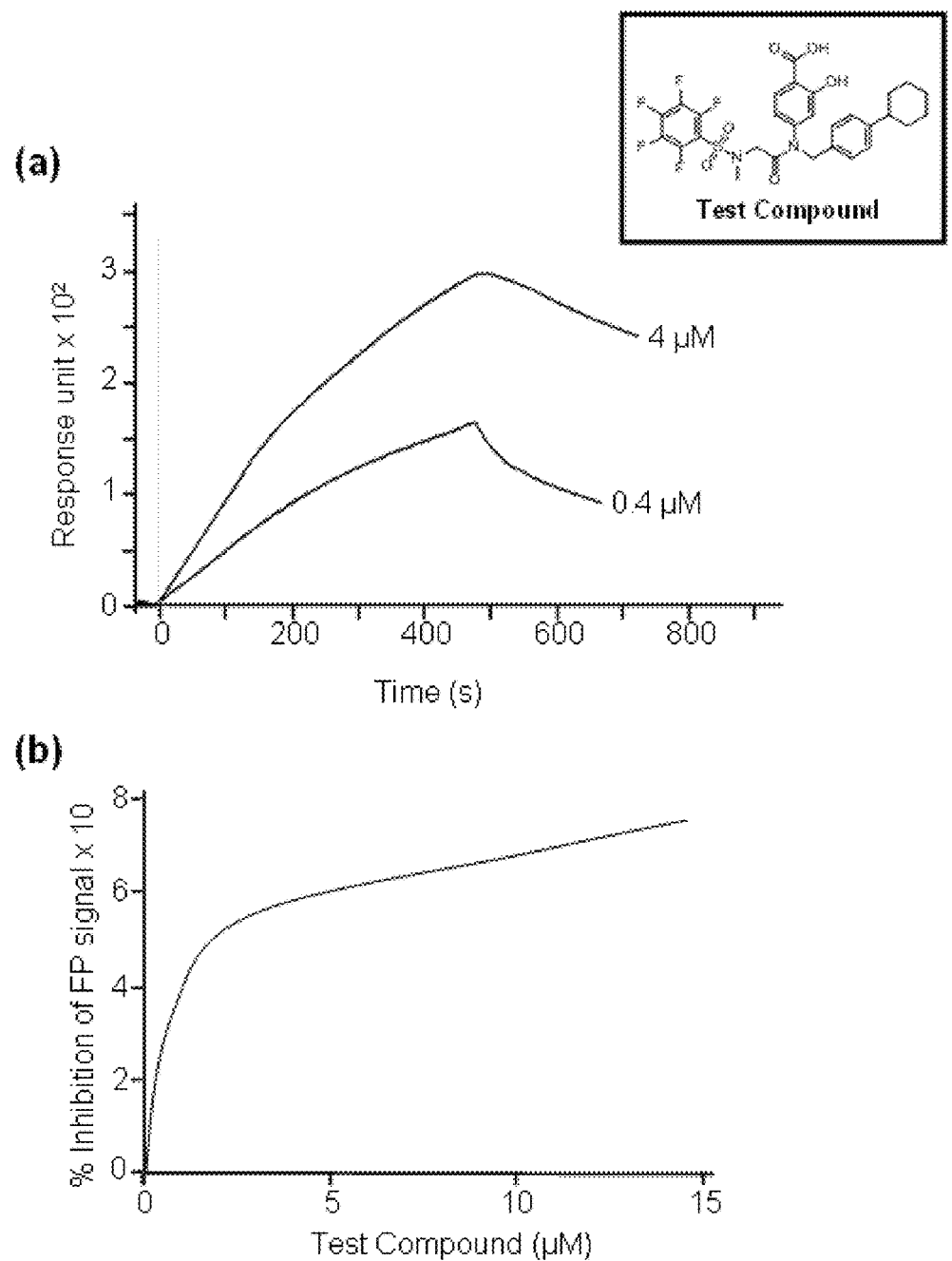
FIG. 11 shows representative data for a representative disclosed compound analyzed in surface plasmon resonance (SPR) and fluorescence polarization (FP) assays. (a) SPR analysis of the binding of increasing concentration of test compound to the full-length Stat3; and (b) FP assay of the binding to the 5-carboxyfluorescein-GpYLPQTV-$NH_2$ probe of a fixed amount of purified His-Stat3 (200 nM) in the presence of increasing concentrations of test compound. Data are representative of 3 independent determinations.
Figure 12:
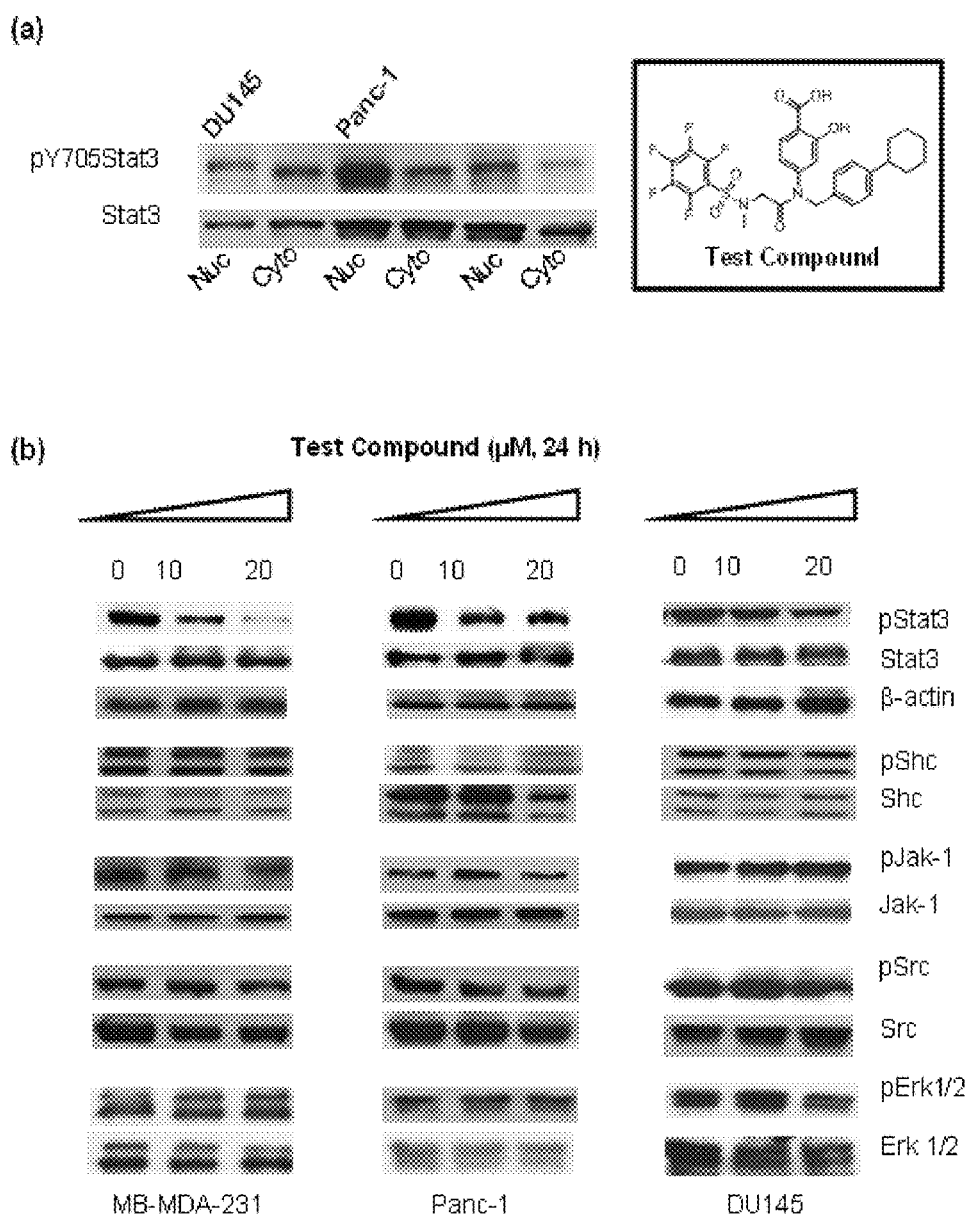
FIG. 12 shows representative data for the effect of a representative disclosed compound on induction of STAT3 activation and transcriptional activity, other signaling proteins, and known STAT3-regulated genes. (Panels A and B) Immunoblotting analysis of (Panel A) nuclear (Nuc) or cytosolic (Cyto) lysates or (Panel B) whole-cell lysates of equal total protein prepared from the designated tumor cells treated with 0-20 µM BP-1-102 for 24 h and probing for pY705Stat3, Stat3, pS727Stat3, pShc, Shc, pJaks, Jak, pSrc, Src, pErk1/2, Erk1/2, or β-actin. Values are the mean and S.D. of 3 independent determinations each performed in triplicate. *p–<0.05 and **p–<0.01.
Figure 13:
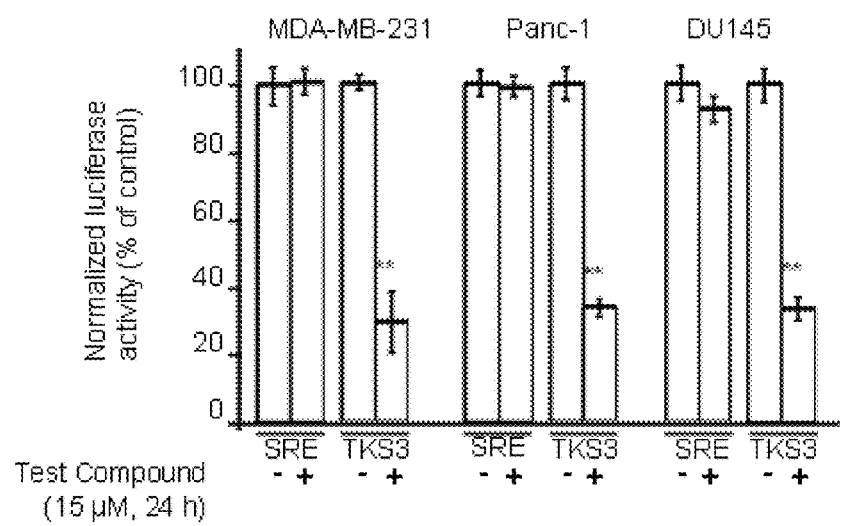
FIG. 13 shows representative data for the effect of a representative disclosed compound on induction of STAT3 activation and transcriptional activity, other signaling proteins, and known STAT3-regulated genes. Panel (a) shows Cytosolic extracts of equal total protein were prepared from 24-h BP-1-102-treated or untreated MDA-MB-231, Panc-1, or DU145 cells transiently-transfected with the Stat3-dependent (pLucTKS3, TKS3) or the Stat3-independent (pLuc-SRE, SRE) luciferase reporter and analyzed for luciferase activity using a luminometer; and Panel (b) shows immunoblotting analysis of whole-cell lysates prepared from tumor cell lines treated with or without 15 µM BP-1-102 for 24 hand probing for c-Myc, Cyclin D1, Bcl-xL, Survivin, VEGF, and β-actin. Positions of proteins in gel are labelled; control (0) or (–) represents cytosolic or whole-cell lysates prepared from 0.05% DMSO-treated cells. Data are representative of 3-4 independent determinations. Values are the mean and S.D. of 3 independent determinations each performed in triplicate. *p–<0.05 and **p–<0.01.
Figure 13:
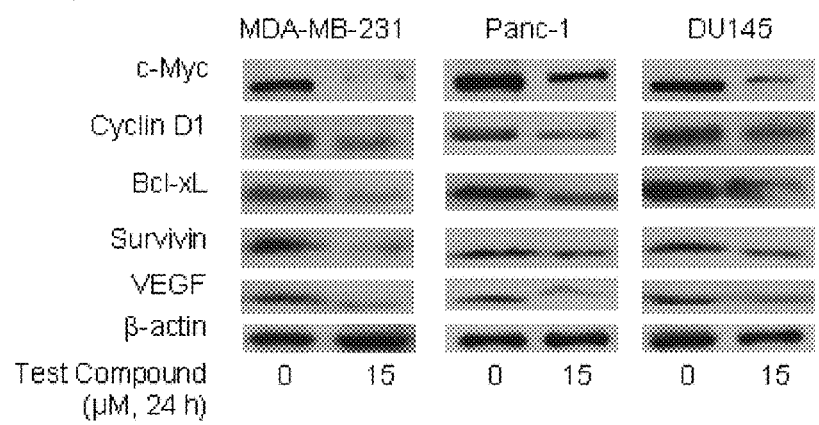
Figure 13:
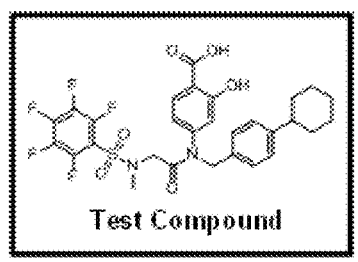
Figure 14:
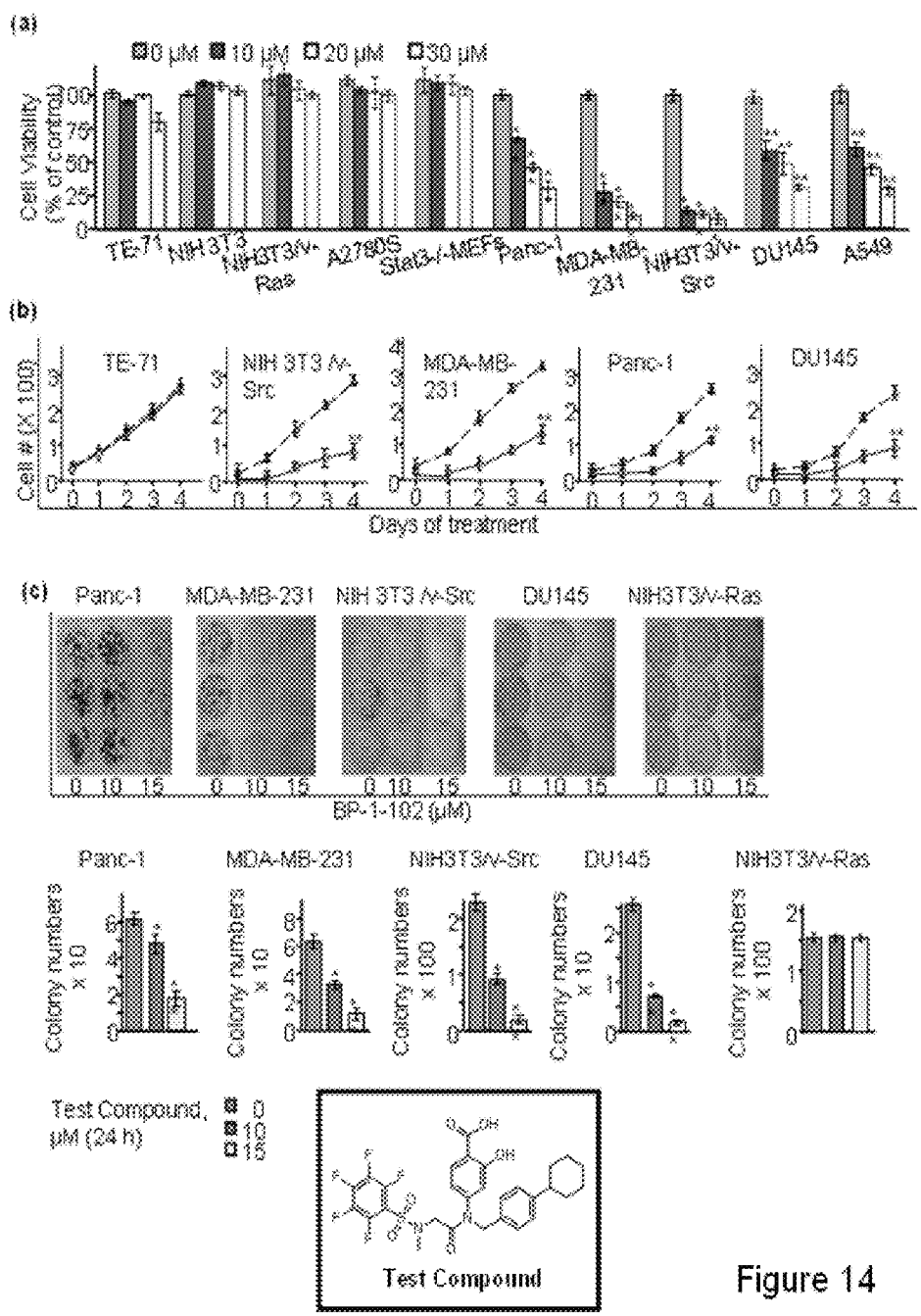
FIG. 14 shows representative data for the effect of a representative disclosed compound on suppression of viability, survival, migration and invasion in vitro of malignant cells. The figure shows results for the assessment of the indicated test compound in the indicated assays. (Panels A-C) Tumor cells harboring aberrantly-active Stat3 (MDA-MB-231, DU145, Panc-1, and NIH3T3/v-Src) or cells that do not (NIH3T3, NIH3T3/v-Ras, mouse *thymus* stromal epithelial cells, TE-71, Cisplatin-sensitive ovarian cancer cells, A2780s, or the Stat3-null mouse embryonic fibroblasts, Stat3–/–MEFs) and growing in culture were treated once (Panel A) with 0-30 µM BP-1-102 for 24 h and subjected to CyQuant cell viability assay or (Panel B) with or without 15 µM BP-1-102 for 24-96 h cell and cell viability was assessed each day by trypan blue exclusion/phase contrast microscopy and plotted, or (Panel C) seeded as a single-cell culture were treated once with 0-15 µM BP-1-102 for 24 h and allowed to culture until large colonies were visible, which were stained with crystal violet and photographed (upper panel) or enumerated and plotted (lower panel)
Figure 15:
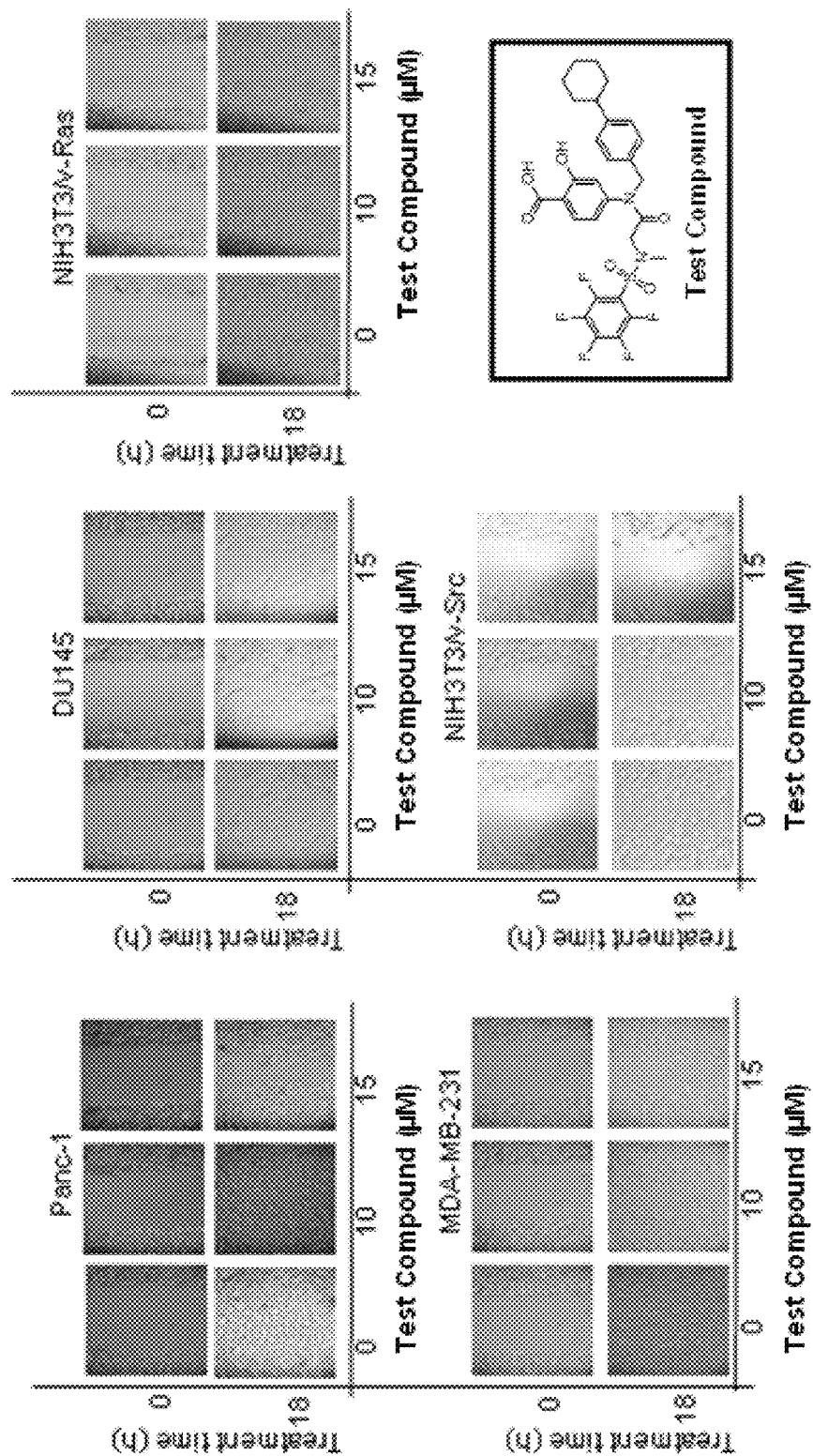
FIG. 15 shows representative data for the effect of a representative disclosed compound on suppression of viability, survival, migration and invasion in vitro of malignant cells. The figure shows results for the effect of the indicated test compound in a wound-healing assay of cultures of malignant cells harboring aberrant Stat3 activity (MDA-MB-221, DU145, Panc-1, NIH3T3/v-Src) or not (NIHT3T/v-Ras) were wounded and treated once with 0-15 µM BP-1-102 for 16 h and allowed to migrate into the denuded area, represented as photomicrographs.
Figure 16:
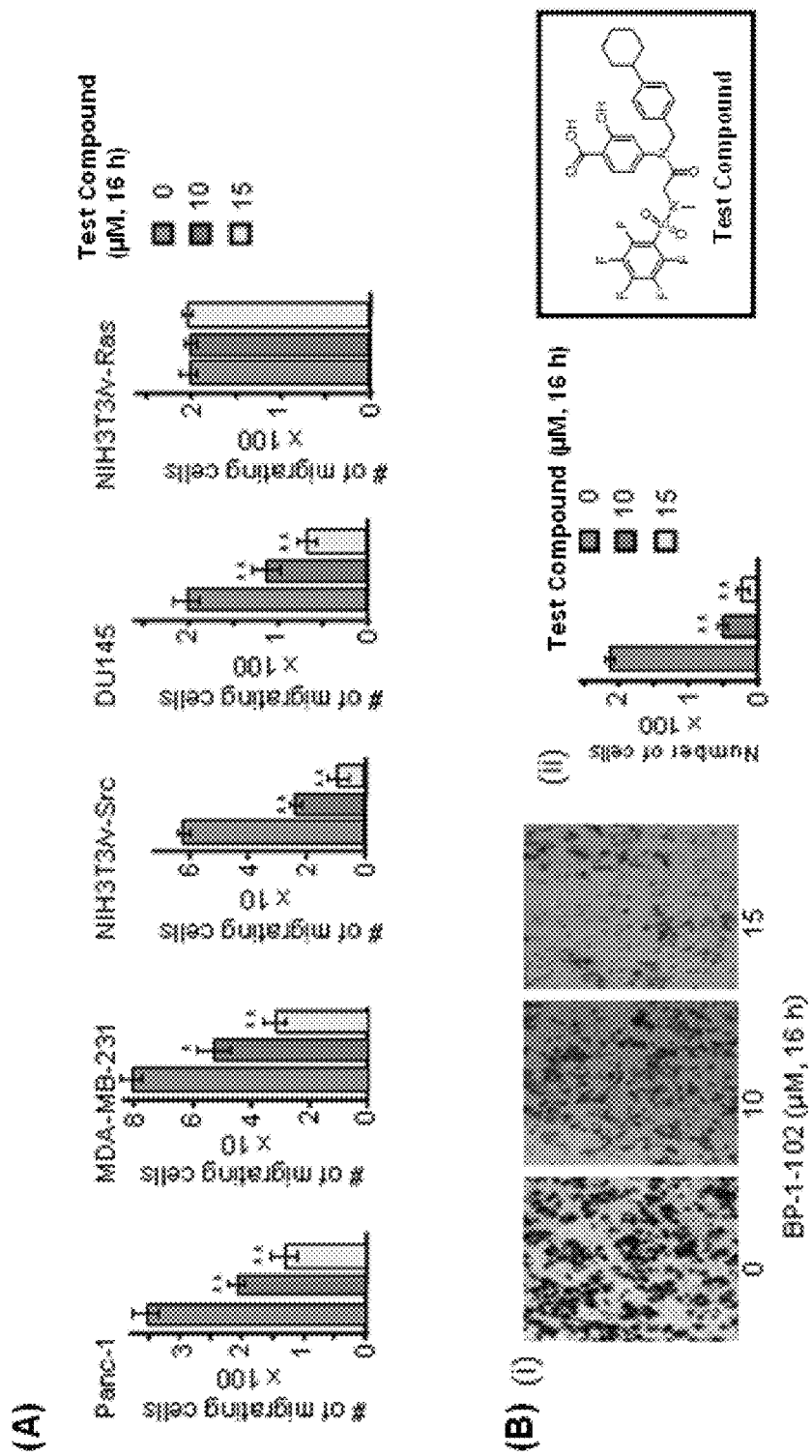
FIG. 16 shows representative data for the effect of a representative disclosed compound on suppression of viability, survival, migration and invasion in vitro of malignant cells. Panel A shows results for the effect of the indicated test compound in a wound-healing assay of cultures of malignant cells harboring aberrant Stat3 activity (MDA-MB-221, DU145, Panc-I, NIH3T3/v-Src) or not (NIHT3T/v-Ras) were wounded and treated once with 0-15 µM BP-1-102 for 16 h and allowed to migrate into the denuded area, represented as plots of migrated cells; and Bio-Coat migration/invasion chamber assay and the effects of 16-h-treatment with 0-15 µM BP-1-102 on the invasion of MDA-MB-231 cells, represented as (Panel B(i)) photomicrographs or (Panel B(ii)) plots of number of invaded cells.
Figure 17:
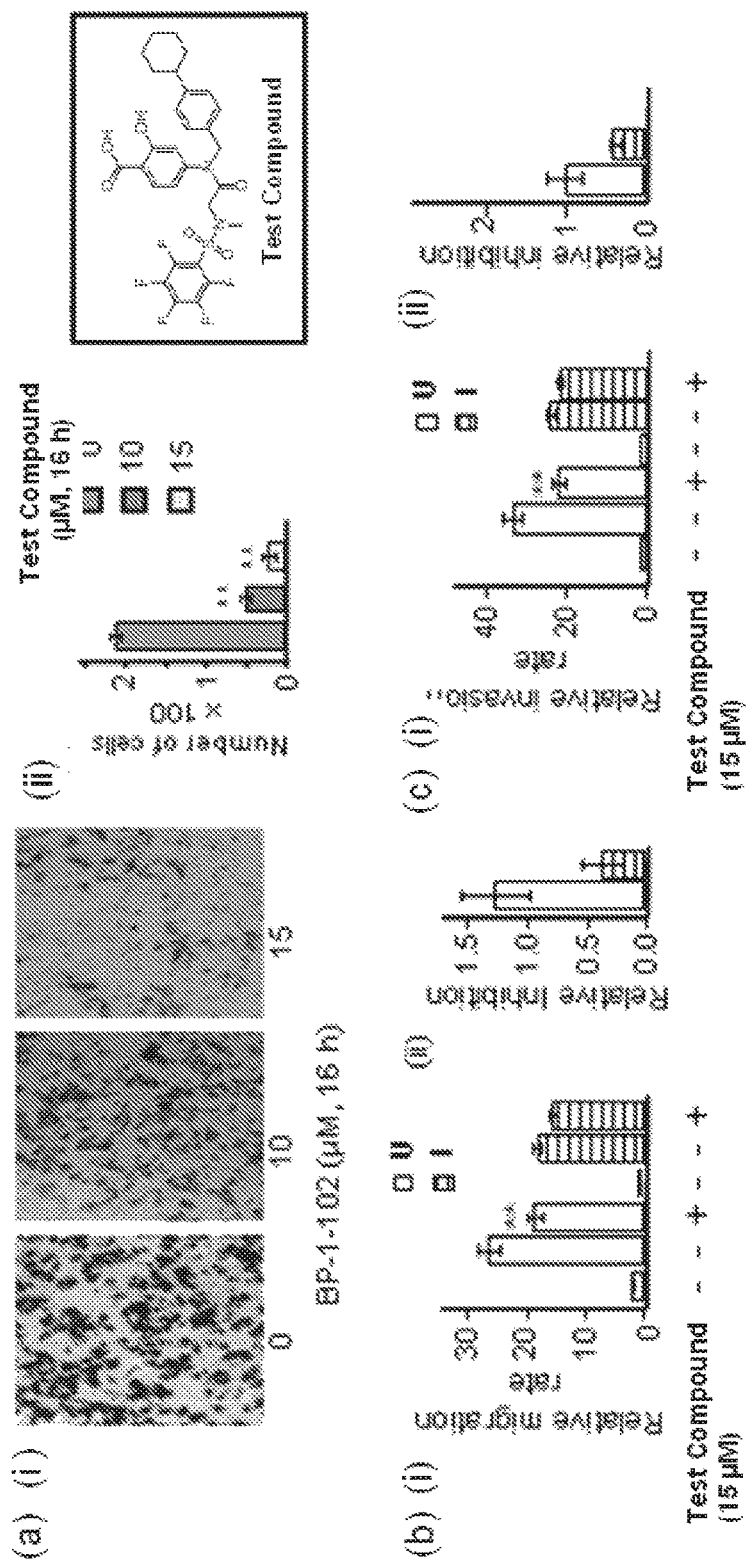
FIG. 17 shows representative data for the effect of a representative disclosed compound on suppression of viability, survival, migration and invasion in vitro of malignant cells. Panels a(i), b(i) and b(ii)) migration and (Panels c(i) and c(ii)) invasion of doxycycline (Dox)-induced (I) or un-induced (U) MDA-MB-231-K8ikd cells, represented as (Panel b(i) and c(i)) rates or (Panel b(ii) and c(ii)) relative inhibition derived from bars 2 versus 3 or 5 versus 6 in (Panel a(i)) and normalized to the U condition. Visualization was done at 10× magnification by light microscopy. Data are representative of 3-4 independent determinations. Values are the mean and S.D. of 4 independent determinations each performed in triplicates. *p–<0.05, p–<0.01, and *p–<0.005.
Figure 18:
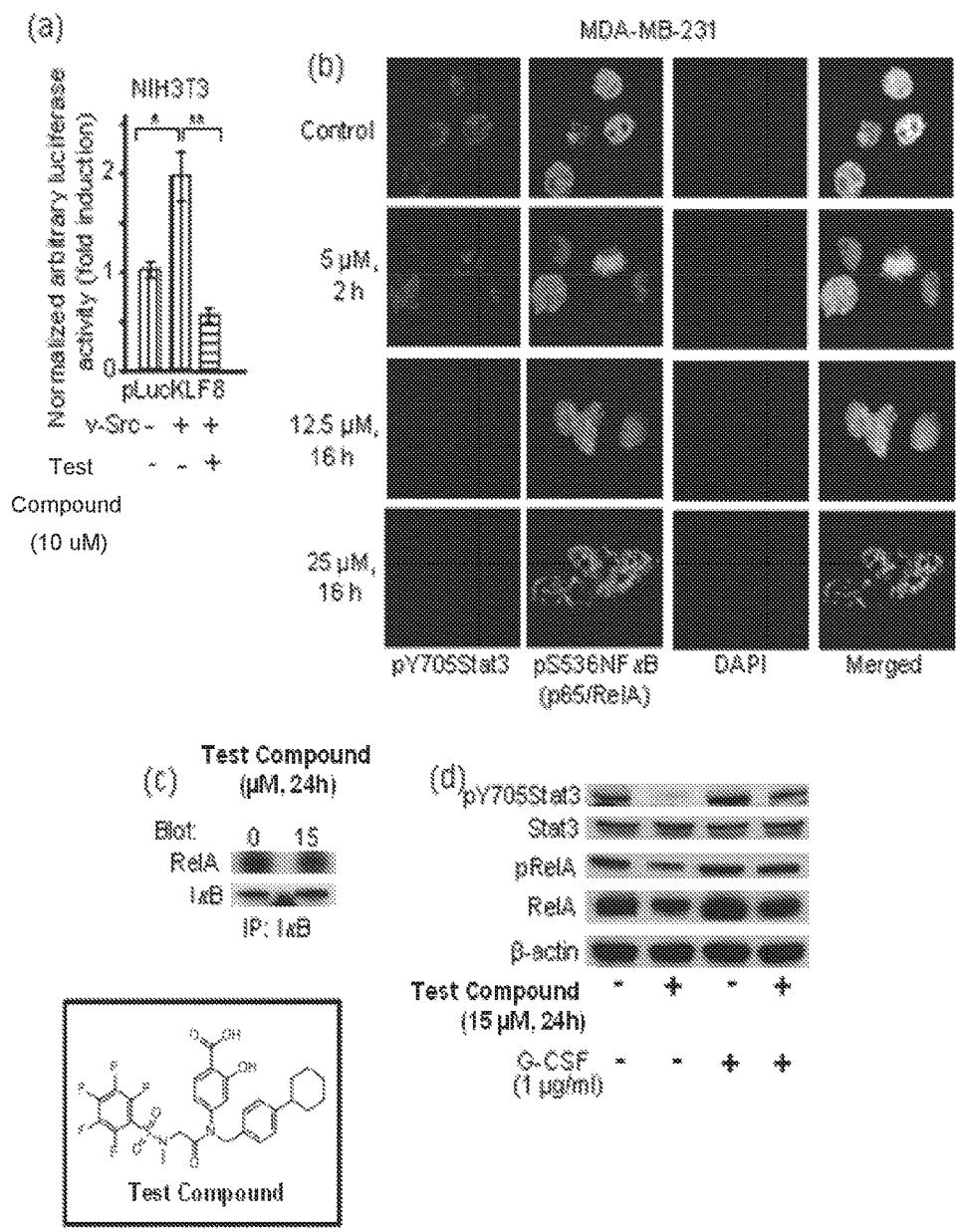
FIG. 18 shows representative data for the effect of a representative disclosed compound on the transcriptional induction of KLF8 and the activation and localization of NFκB/p65RelA. (Panel A) normalized luciferase reporter activity in cytosolic extracts of equal total protein prepared from normal NIH3T3 fibroblasts transiently co-transfected with the KLF8 promoter-driven luciferase reporter, pLucKLF8, v-Src and β-galactosidase expression vectors and the effect of 16-h treatment with BP-1-102; (Panel B) immunofluorescence imaging/confocal microscopy of Stat3 colocalization with p65RelA in MDA-MB-231 cells growing in culture and treated with or without 5-25 µM BP-1-102 for 2 or 16 h, fixed and stained with (i) anti-Stat3 antibody and secondary AlexaFluor546 antibody or (ii) anti-p65RelA and secondary AlexaFluor488 antibody, or DAPI nuclear staining (blue). Images were captured using Leica TCS SP5 laser-scanning confocal microscope; (Panel C) IκB immunecomplex prepared from MDA-MB-231 cells treated with or without 15 µM BP-1-102 and probing for RelA or IκB; and (Panel D) immunoblotting analysis of whole-cell lysates of MDA-MB-231 cells stimulated with G-CSF in the presence or absence of BP-1-102 and probing for pY705Stat3, Stat3, pRelA, RelA, and β-actin. Data are representative of 3 independent studies. Values are the mean and S.D. of 2 independent determinations each performed in triplicates. *p–<0.05, and **p–<0.01.
Figure 19:
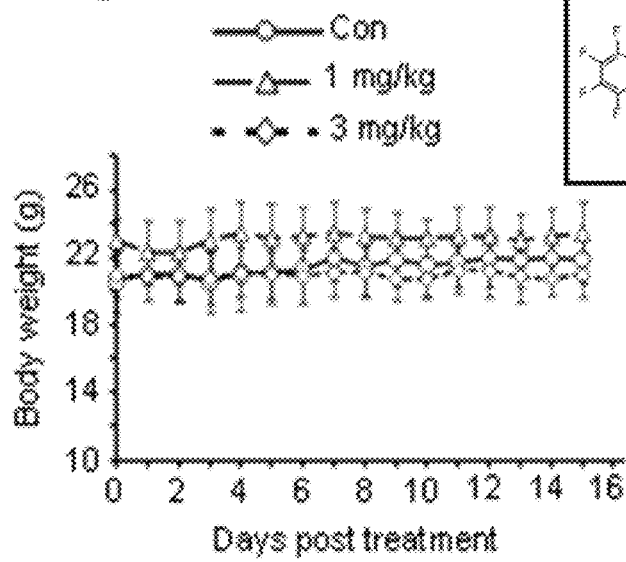
FIG. 19 shows representative data for the effect of a representative disclosed compound on STAT3 activity, Stat3-regulated genes, cytokine production, and factors that promote tumor motility, migration and invasiveness, and weights of mice. (Panels A and B) Mice bearing human breast (MDA-MB-231) and treated with BP-1-102 via (a) i.v., 1 or 3 mg/kg or vehicle (0.1% DMSO in PBS) or (Panel B) oral gavage 1 or 3 mg/kg or vehicle (0.1% DMSO) every 1-3 days. Mice were weighed every day or every 2 days and weights plotted against days of treatment. Values are the mean and S.D. from replicates of 7-10 tumor-bearing mice in each group.
Figure 19:
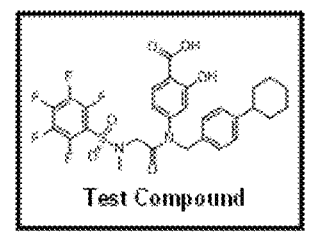
Figure 19:
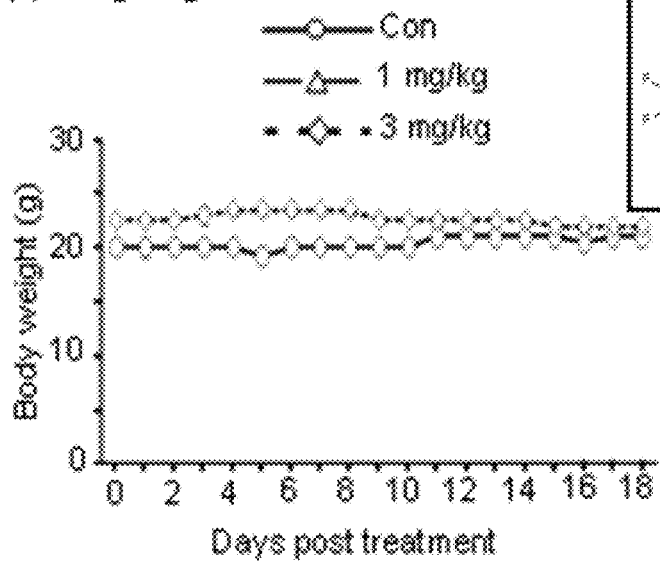
Figure 19:
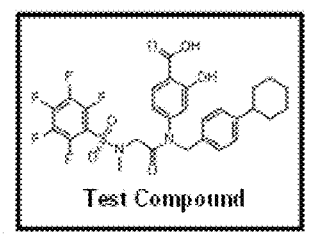
Figure 20:
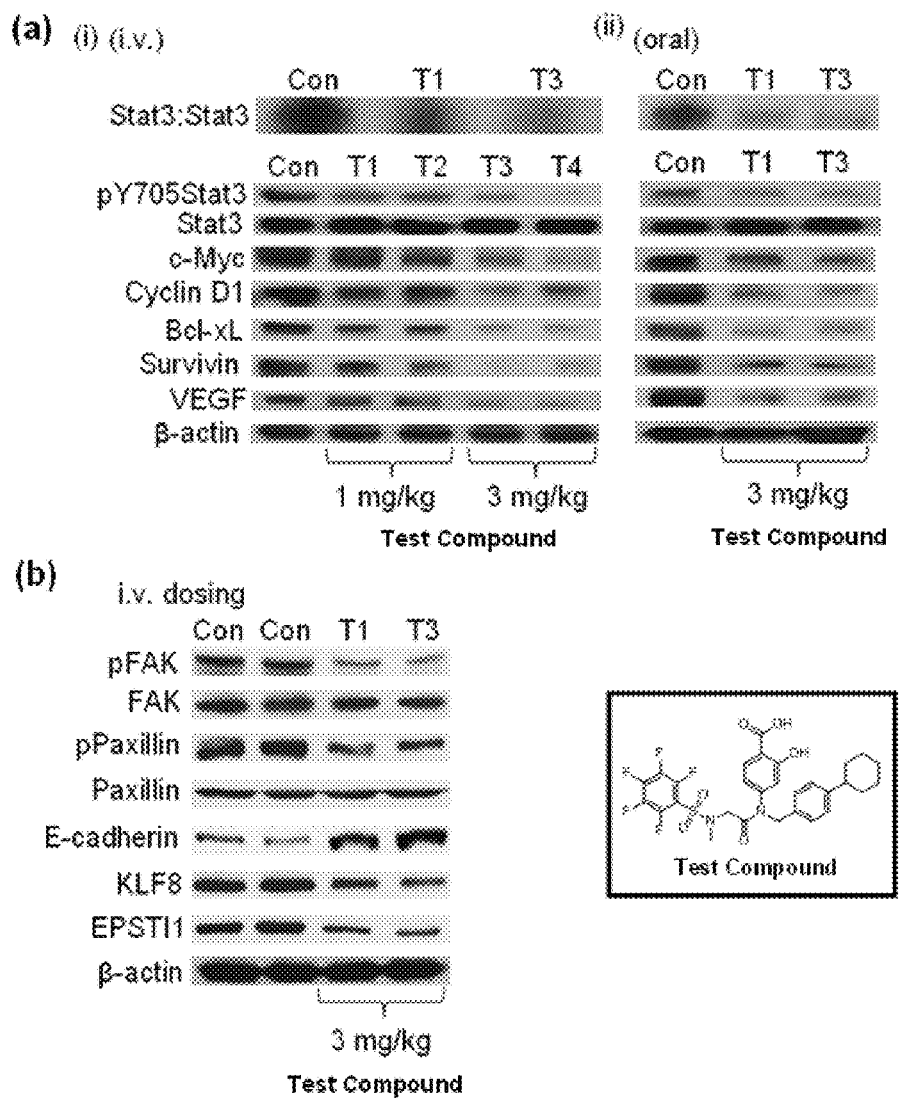
FIG. 20 shows representative data for the effect of a representative disclosed compound on STAT3 activity, Stat3-regulated genes, cytokine production, and factors that promote tumor motility, migration and invasiveness, and weights of mice. Tumor lysates prepared from control (Con) human breast tumor xenografts or residual tumor (T1-T4) tissues from mice treated with test compound (1 or 3 mg/kg) via i.v. or oral gavage were subjected to (a, upper panel) Stat3 DNA-binding activity/EMSA analysis or (a, lower panel and b) immunoblotting analysis probing for pY705Stat3, Stat3, c-Myc, Cyclin D1, Bcl-xL, Survivin, VEGF, pFAK, FAK, pPaxillin, Paxillin, E-cadherin, KLF8, EPSTI1, pRelA, RelA, or β-actin as indicated.
Figure 21:
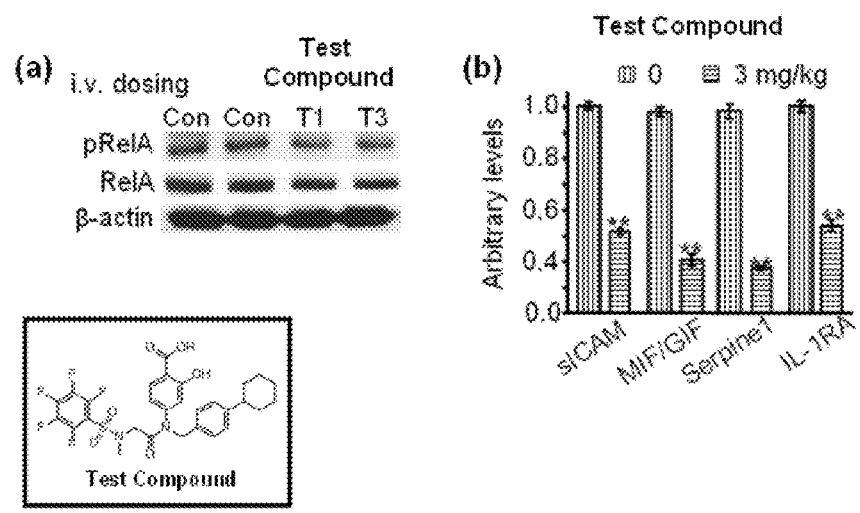
FIG. 21 shows representative data for the effect of a representative disclosed compound on STAT3 activity, Stat3-regulated genes, cytokine production, and factors that promote tumor motility, migration and invasiveness, and weights of mice. Tumor lysates prepared from control (Con) human breast tumor xenografts or residual tumor (T1-T4) tissues from mice treated with test compound (1 or 3 mg/kg) via i.v. or oral gavage were subjected to) immunoblotting analysis probing for pY705Stat3, Stat3, c-Myc, Cyclin D1, Bcl-xL, Survivin, VEGF, pFAK, FAK, pPaxillin, Paxillin, E-cadherin, KLF8, EPSTI1, pRelA, RelA, or β-actin, as indicated (Panel A), or analysis for sICAM, MIG/GIF Serpine1, and IL-1RA levels (Panel B). Positions of Stat3:DNA complexes or proteins in gel are labeled; control (Con or 0) represents tumor tissue lysates prepared from 0.05% DMSO-treated mice. Data are representative of 3-4 independent determinations. Values are the mean and S.D. from replicates of 7-10 tumor-bearing mice in each group.
Figure 22:
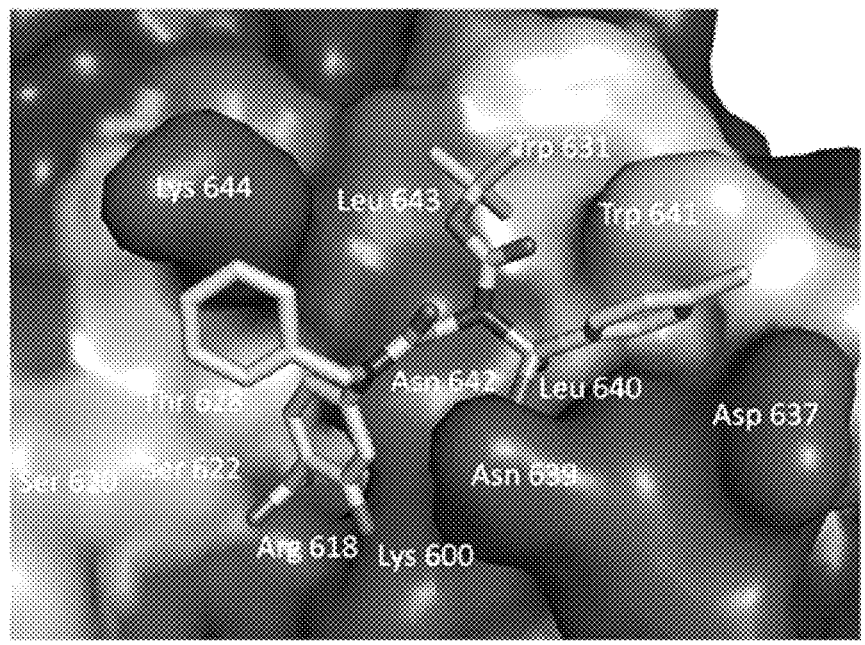
FIG. 22 shows representative computational modeling of a representative compound. The figure shows the compound docked in the STAT5 SH2 domain (low energy GOLD[45]-docked) with hydrophobic and hydrophilic residues highlighted.
Figure 23:
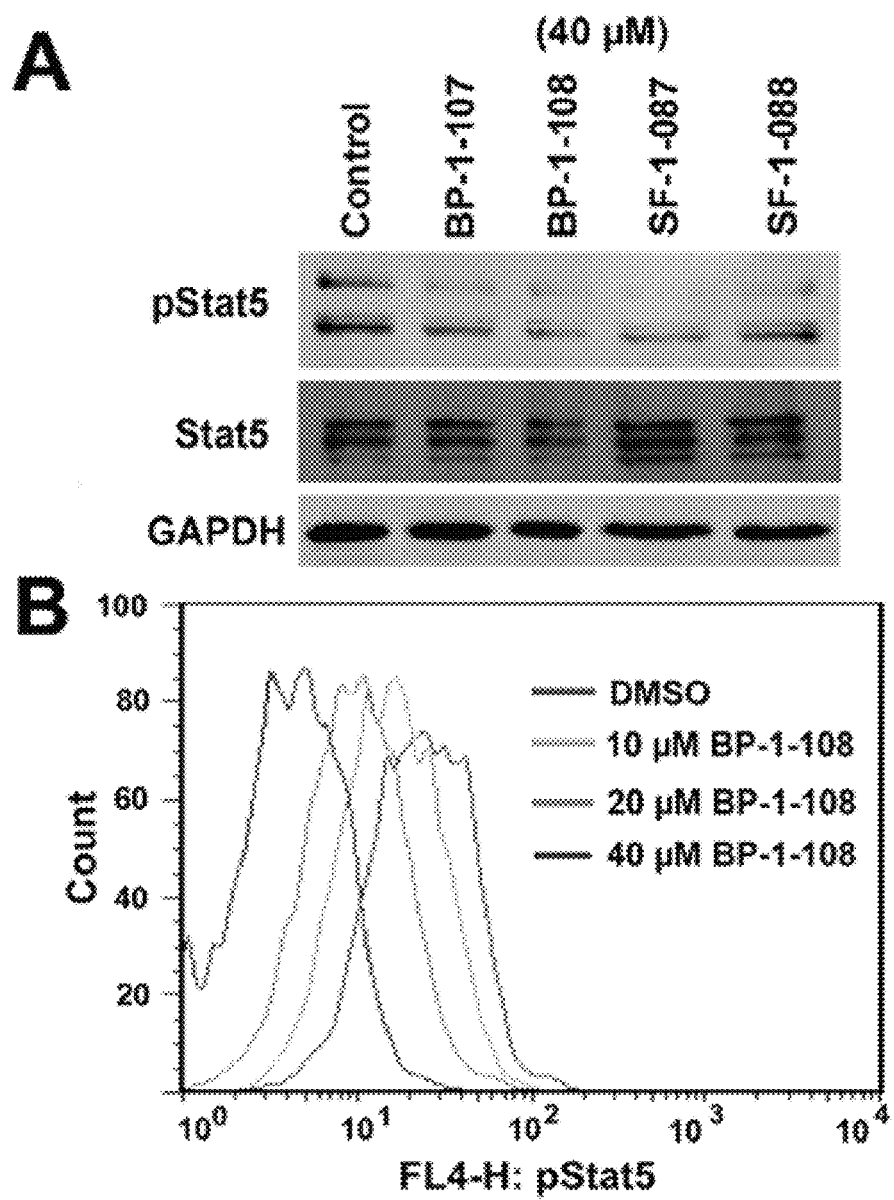
FIG. 23 shows representative data for inhibition of phosphorylation of STAT5 by representative disclosed compounds. (Panel A) shows Western blot analysis of Stat5 inhibition in K562 cells treated with BP-1-107 (corresponding to compound ID 45b in Table I), BP-1-108 (corresponding to compound ID 45c in Table I), SF-1-087 and SF-1-088; B (the latter two compounds have corresponding compound IDs used in the experimental methods). (Panel B) shows dose-dependant inhibition of pStat5 by BP-1-108 (compound ID 45c) as measured by phospho-flow cytometry.
Figure 24:
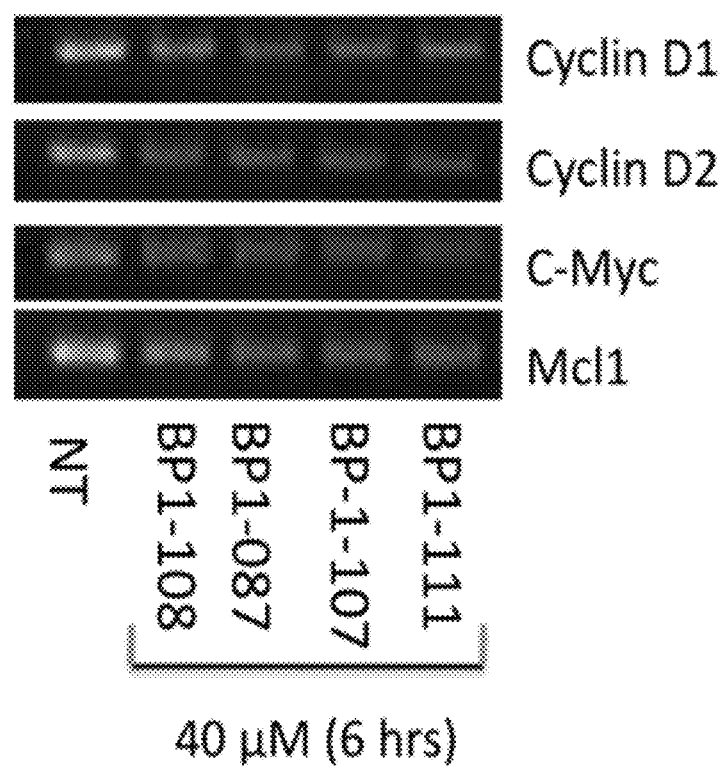
FIG. 24 shows representative data for inhibition of expression of STAT5-regulated proteins by representative disclosed compounds. The figure shows SDS-PAGE and Western blotting analysis of K562 whole cell lysates treated with BP-1-108, BP-1-75 (corresponding to compound ID 27na in Table I), BP-1-111 (corresponding to compound ID 45k in Table I) and SF-1-087 and probed with anti-cMyc, cyclin D1, cyclin D2 and MCL-1 antibodies.
Figure 25:
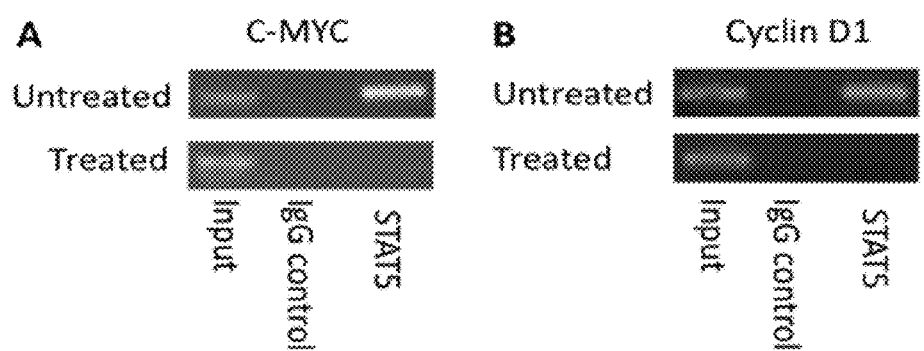
FIG. 25 shows representative data for the effect of a representative disclosed compound on binding of STAT5 for c-myc and cyclin D1 promoter regions. The figure shows results for chromatin immunoprecipitation of C-MYC and Cyclin D1 promoters using STAT5 antibody in K562 cells treated with 40 µM BP-1-108 (corresponding to compound ID 45c in Table I).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "STAT" and "signal transducer and activator of transcription" can be used interchangeably, and refer to a protein family comprising at least the following members: STAT1, 2, 3, 4, 5a, 5b, and 6. The STAT family of proteins are latent cytoplasmic transcription factors that mediate cellular responses to cytokines, growth factors, and other polypeptide ligands.

As used herein, the terms "STAT3," "signal transducer and activator of transcription 3 (acute-phase response)," and "signal transducer and activator of transcription 3" can be used interchangeably and refer to a a transcription factor encoded by a gene designated in human as the STAT3 gene, which has a human gene map locus of 17q21 and described by Entrez Gene cytogenetic band: 17q21.31; Ensembl cytogenetic band: 17q21.2; and, HGNC cytogenetic band: 17q21. The term STAT3 refers to a human protein that has 770 amino acids and has a molecular weight of about 88,068 Da. The term is inclusive of splice isoforms or variants, and also inclusive of that protein referred to by such alternative designations as: APRF, MGC16063, Acute-phase response factor, DNA-binding protein APRF, HIES as used by those skilled in the art to that protein encoded by human gene STAT3. The term is also inclusive of the non-human ortholog or homolog thereof.

As used herein, "STAT5," refers to STAT5A and/or STAT5B. If specific reference to either STAT5A or STAT5B is required, the specific term will be used herein.

As used herein, "STAT5A" and "signal transducer and activator of transcription 5A" can be used interchangeably and refer to a a transcription factor encoded by a gene designated in human as the STAT5A gene, which has a human gene map locus described by Entrez Gene cytogenetic band: 17q11.2; Ensembl cytogenetic band: 17q21.2; and, HGNC cytogenetic band: 17q11.2. The term STAT5A refers to a human protein that has 794 amino acids and has a molecular weight of about 90,647 Da. The term is inclusive of splice isoforms or variants, and also inclusive of that protein referred to by such alternative designations as MGF and STAT5 as used by those skilled in the art to that protein encoded by human gene STAT5A. The term is also inclusive of the non-human ortholog or homolog thereof.

As used herein, "STAT5B" and "signal transducer and activator of transcription 5B" can be used interchangeably and refer to a a transcription factor encoded by a gene designated in human as the STAT5B gene, which has a human gene map locus described by Entrez Gene cytogenetic band: 17q11.2; Ensembl cytogenetic band: 17q21.2; and, HGNC cytogenetic band: 17q11.2. The term STAT5A refers to a human protein that has 787 amino acids and has a molecular weight of about 89,866 Da. The term is inclusive of splice isoforms or variants, and also inclusive of that protein referred to by such alternative designations as transcription factor STAT5B as used by those skilled in the art to that protein encoded by human gene STAT5A. The term is also inclusive of the non-human ortholog or homolog thereof.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more oncological disorders or cancers prior to the administering step. In some aspects of the disclosed method, the subject has been diagnosed with a need for inhibition or negative modulation of STAT3 prior to the administering step. In some aspects of the disclosed method, the subject has been diagnosed with a need for treatment of one or more oncological disorders or cancers associated with STAT3 dysfunction prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by STAT3 inhibition" means having been subjected to a physical examination by a person of skill, for example, a physician, and found to have a condition that can be diagnosed or treated by a compound or composition that can inhibit or negatively modulate STAT3. As a further example, "diagnosed with a need for inhibition of STAT3" refers to having been subjected to a physical examination by a person of skill, for example, a physician, and found to have a condition characterized by a dysfunction in STAT3 activity. Such a diagnosis can be in reference to a disorder, such as an oncological disorder or disease, cancer and/or disorder of uncontrolled cellular proliferation and the like, as discussed herein. For example, the term "diagnosed with a need for inhibition of STAT3 activity" refers to having been subjected to a physical examination by a person of skill, for example, a physician, and found to have a condition that can be diagnosed or treated by inhibition of STAT3 activity. For example, "diagnosed with a need for modulation of STAT3 activity" means having been subjected to a physical examination by a person of skill, for example, a physician, and found to have a condition that can be diagnosed or treated by modulation of STAT3 activity, e.g. negative modulation. For example, "diagnosed with a need for treatment of one or more disorder of uncontrolled cellular proliferation associated with STAT3 dysfunction" means having been subjected to a physical examination by a person of skill, for example, a physician, and found to have one or disorders of uncontrolled cellular proliferation, e.g. a cancer, associated with STAT3 dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to STAT3 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target STAT3 protein, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In some contexts, an $IC_{50}$ can refer to the plasma concentration of a substance that is required for 50% inhibition in vivo, as further defined elsewhere herein. More commonly, $IC_{50}$ refers to the half maximal (50%) inhibitory concentration (IC) of a substance required to inhibit a process or activity in vitro.

As used herein, "STAT3 $IC_{50}$" refers to the concentration of a substance (e.g., a compound or a drug) that is required for 50% inhibition of a STAT3 activity. In some contexts, an $IC_{50}$ can refer to the plasma concentration of a substance that is required for 50% inhibition of an in vivo activity or process as further defined elsewhere herein, e.g. tumor growth in an animal or human. In other contexts, STAT3 $IC_{50}$ refers the half maximal (50%) inhibitory concentration (IC) of a substance or compound required to inhibit a process or activity an in vitro context, e.g. a cell-free or cell-based assay. For example, the STAT3 $IC_{50}$ can be in the context of the half-maximal concentration required to inhibit cell growth. As discussed below, the response is measured in a cell-line with aberrant STAT3 activity. Alternatively, the response is measured in a cell-line with persistently active STAT3. The response can be determined using a cell-line derived from a human breast cancer, human pancreatic cancer, and human prostate cancer. For example, the response can be measured in a cell-line selected from MDA-MB-231, Panc-1, and DU-145. Cell-lines transfected with specific genes can also be used. For example, the response can be measured in a cell-line transfected with v-Src. Alternatively, the cell-line transfected with v-Src is a permanent cell-line. In some cases, the STAT3 $IC_{50}$ is the half-maximal concentration required to inhibit STAT3 activity in a cell-free assay, e.g. an electrophoretic mobility shift assay ("EMSA"). Alternatively, the STAT3 $IC_{50}$ is the half-maximal concentration required to inhibit cell-growth, cell viability or cell migration activity.

As used herein, the term "STAT3 $K_D$" refers to the binding affinity of a compound or substance for the STAT3 determined in an in vitro assay. The $K_D$ of a substance for a protein can be determined by a variety of methods known to one skilled in the art, e.g. equilibrium dialysis, analytical ultracentrifugation and surface plasmon resonance ("SPR") analysis. As typically used herein, STAT3 $K_D$ is defined as the ratio of association and dissociation rate constants determined using SPR analysis using purified STAT3 protein.

As used herein, the term "STAT3 $K_i$" refers to the inhibition constant for the displacement of a STAT3 SH2 probe from STAT3 protein. For example, the STAT3 SH2 can be fluorescence-labelled GpYLPQTV. As described herein, the fluorescence label is 5-carboxyfluorescein, although other suitable fluorescence probes can be used as determined to be useful and convenient by one skilled in the art.

As used herein, "STAT5 $IC_{50}$" refers to the concentration of a substance (e.g., a compound or a drug) that is required for 50% inhibition of a STAT3 activity. In some contexts, an $IC_{50}$ can refer to the plasma concentration of a substance that is required for 50% inhibition of an in vivo activity or process as further defined elsewhere herein, e.g. tumor growth in an animal or human. In other contexts, STAT5 $IC_{50}$ refers the half maximal (50%) inhibitory concentration (IC) of a substance or compound required to inhibit a process or activity an in vitro context, e.g. a cell-free or cell-based assay. For example, the STAT5 $IC_{50}$ can be in the context of the half-maximal concentration required to inhibit cell growth. As discussed below, the response is measured in a cell-line with aberrant STAT5 activity. Alternatively, the response is measured in a cell-line with persistently active STAT5. The response can be determined using a cell-line derived from a human breast cancer, human pancreatic cancer, and human prostate cancer. For example, the response can be measured in a cell-line selected from K562 and MV-4-11 cells. Cell-lines transfected with specific genes can also be used. In some cases, the STAT5 $IC_{50}$ is the half-maximal concentration required to inhibit STAT5 activity in a cell-free assay, e.g. an electrophoretic mobility shift assay ("EMSA"). Alternatively, the STAT5 $IC_{50}$ is the half-maximal concentration required to inhibit cell-growth, cell viability or cell migration activity.

As used herein, the term "STAT5 $K_D$" refers to the binding affinity of a compound or substance for the STAT5 determined in an in vitro assay. The $K_D$ of a substance for a protein can be determined by a variety of methods known to one skilled in the art, e.g. equilibrium dialysis, analytical ultracentrifugation and surface plasmon resonance ("SPR") analysis. As typically used herein, STAT5 $K_D$ is defined as the ratio of association and dissociation rate constants determined using SPR analysis using purified STAT5 protein.

As used herein, the term "STAT5 $K_i$" refers to the inhibition constant for the displacement of a STAT3 SH2 probe from STAT5 protein. For example, the STAT5 SH2 can be fluorescence-labelled GpYLPQTV. As described herein, the fluorescence label is 5-carboxyfluorescein, although other suitable fluorescence probes can be used as determined to be useful and convenient by one skilled in the art.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus.

Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1$C(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1$S(O)$_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group.

The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}R°$; —$O(CH_2)_{0-4}R°$, —$O$—$(CH_2)_{0-4}C(O)OR°$); —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —$CH=CHPh$, which may be substituted with $R°$; —$(CH_2)_{0-4}O(CH_2)_{0-1}$-pyridyl which may be substituted with $R°$; —$NO_2$; —$CN$; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)$O$—$N(R°)_2$; or —$(C_{1-4}$ straight or branched)alkylene)$C(O)O$—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(halo$R^•$), —$(CH_2)_{0-2}OH$, —$(CH_2)_{0-2}OR^•$, —$(CH_2)_{0-2}CH(OR^•)_2$; —$O$(halo$R^•$), —$CN$, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)$C(O)OR^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^•$, -(halo$R^•$), —$OH$, —$OR^•$, —$O$(halo$R^•$), —$CN$, —$C(O)OH$, —$C(O)OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —$OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, -(halo$R^•$), —$OH$, —$OR^•$, —$O$(halo$R^•$), —$CN$, —$C(O)OH$, —$C(O)OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides—including chloro, bromo, and iodo—and pseudohalides (sulfonate esters)—including triflate, mesylate, tosylate, and brosylate. It is also contemplated that a hydroxyl moiety can be converted into a leaving group via Mitsunobu reaction.

The terms "hydrolysable group" and "hydrolysable moiety" refer to a functional group capable of undergoing hydrolysis, e.g., under basic or acidic conditions. Examples of hydrolysable residues include, without limitatation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

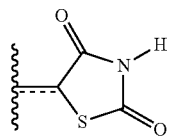

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively.

Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an a-hydrogen can exist in an equilibrium of the keto form and the enol form.

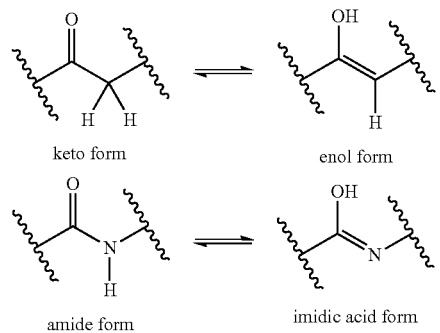

keto form    enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

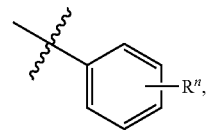

which is understood to be equivalent to a formula:

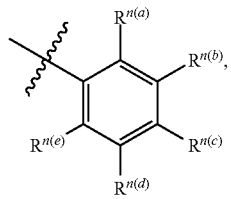

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1- and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of STAT. In a further aspect, the disclosed compounds and products of disclosed methods of making are modulators of STAT activity. In various aspects, the present invention relates to compounds that bind to a STAT protein and negatively modulate STAT activity. In a further aspect, the disclosed compounds exhibit inhibition of STAT activity. The compounds can, in one aspect, exhibit subtype selectivity. In a further aspect, the compounds exhibit selectivity for the STAT3 member of the STAT protein family. In a yet further aspect, the compounds exhibit selectivity for the STAT5 members of the STAT protein family.

In one aspect, the compounds of the invention are useful in the treatment of a disorder of uncontrolled cellular proliferation associated with STAT dysfunction and other diseases in which a STAT protein is involved, as further described herein. In a further aspect, the STAT is STAT3. In a still further aspect, the compounds are useful in the treatment of a disorder of uncontrolled cellular proliferation or other disorder associated with a STAT3 dysfunction. In a yet further aspect, the compounds are useful in the treatment of a disorder of uncontrolled cellular proliferation or other disorder associated with a STAT5 dysfunction.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by Formula (I):

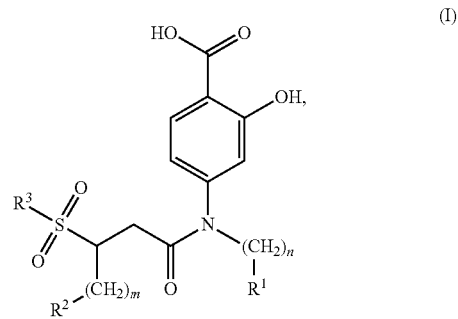

wherein each of m and n is independently an integer from 0-3; wherein $R^1$ is selected from $A^1$, $A^2$, $-(A^1)-(A^2)$, $-(A^2)-(A^3)$, $-(A^3)-(A^2)$, $-(A^3)-(A^4)$, $-(A^5)-(A^1)-(A^7)$, $-(A^5)-(A^2)-(A^8)$, $-(A^5)-(A^3)-(A^7)$, and $-(A^5)-(A^6)-L-(A^7)$; wherein $A^1$ is C3-C6 cycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkylthio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkylthio, (C1-C6)-alk-(C1-C6)-polyhaloalkylthio, $CO_2H$, $(C=O)R^4$, $(C=O)OR^4$, and $(C=O)NHR^4$; wherein $A^2$ is C3-C6 heterocycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^5$, (C=O)OR$^5$, and (C=O)NHR$^5$; wherein A$^3$ is aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^6$, (C=O)OR$^6$, and (C=O)NHR$^6$; wherein A$^4$ is aryl, and substituted with 1-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^7$, (C=O)OR$^7$, and (C=O)NHR$^7$; wherein A$^5$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^8$, (C=O)OR$^8$, and (C=O)NHR$^8$; wherein A$^6$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^9$, (C=O)OR$^9$, and (C=O)NHR$^9$; wherein A$^7$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^{10}$, (C=O)OR$^{10}$, and (C=O)NHR$^{10}$; wherein A$^8$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)R$^{11}$, (C=O)OR$^{11}$, and (C=O)NHR$^{11}$; wherein L is selected from —(C=O)— and —SO$_2$—; wherein R$^2$ is selected from C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl; or wherein R$^2$ is aryl, and substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)OR$^{11}$, and (C=O)NHR$^{11}$; wherein R$^3$ is aryl substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy; wherein each of R$^4$, R$^5$, R$^6$, R$^7$, R$^8$, R$^9$, R$^{10}$, and R$^{11}$ is independently selected from hydrogen, C1-C6 alkyl, C1-C6 haloalkyl, and C1-C6 polyhaloalkyl; or a pharmaceutically acceptable salt, hydrate, solvate, or polymorph thereof.

In a further aspect, the compound of Formula I has a structure represented by a formula:

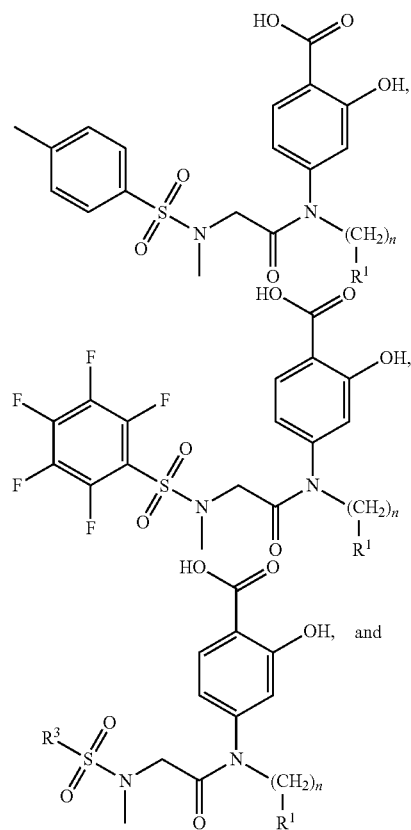

-continued
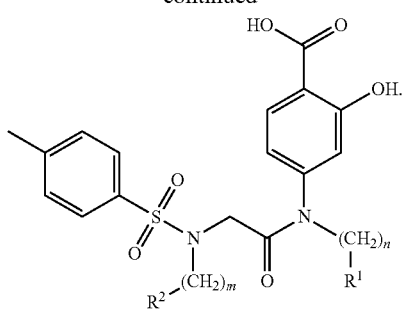
In a further aspect, the compound of Formula I has a structure represented by a formula:
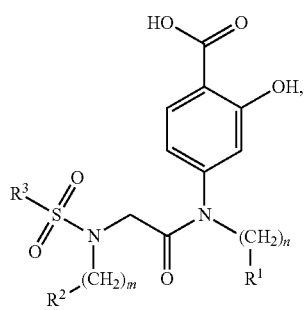
wherein each of m is 0 and n is 0; wherein R¹ is selected from a structure represented by a formula:
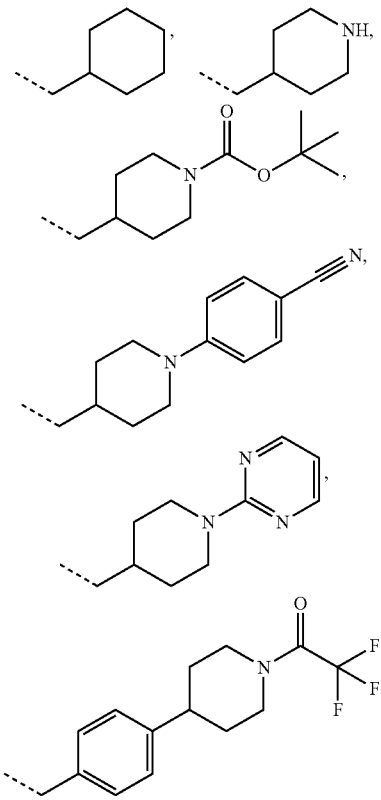
-continued
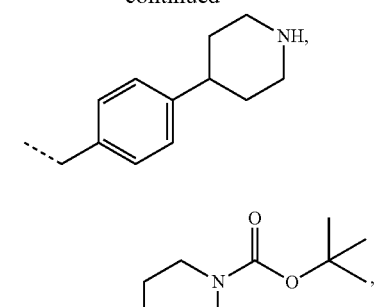
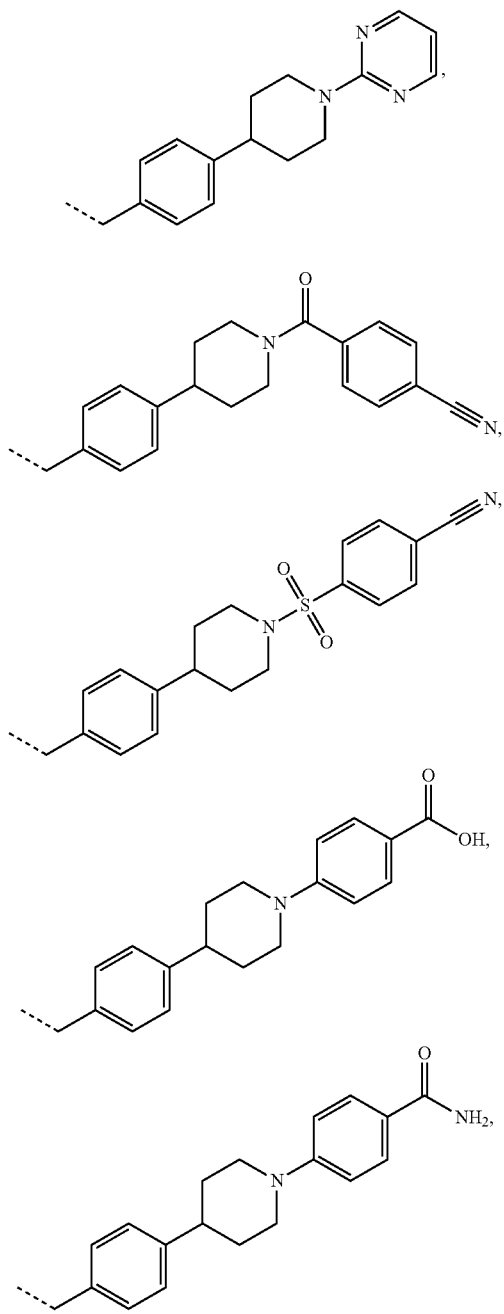

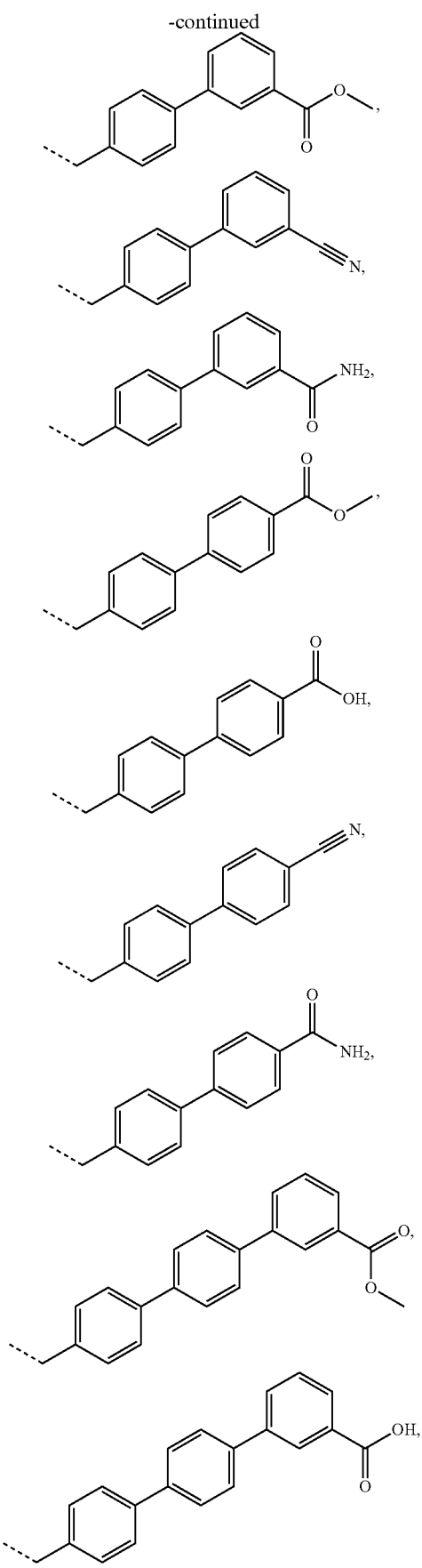
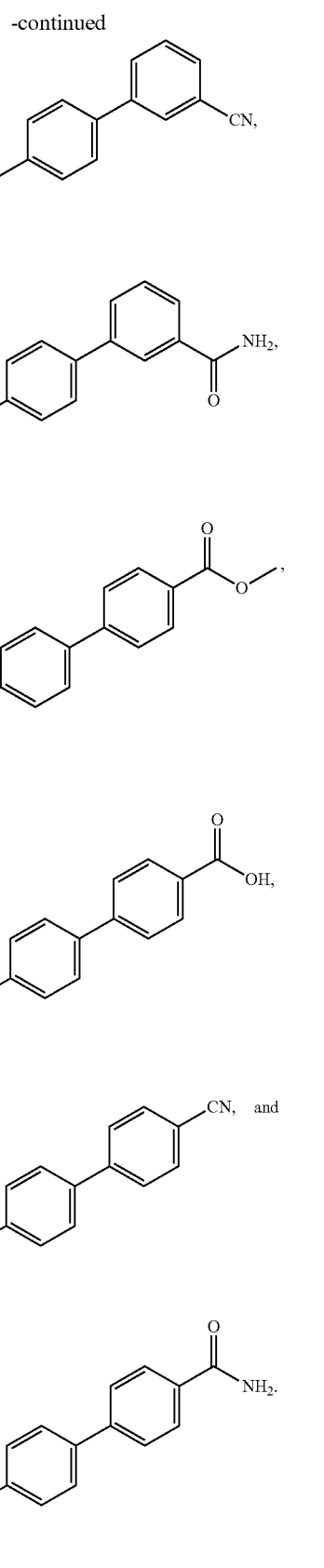
wherein R² is selected from a structure represented by a formula: —CH₃,

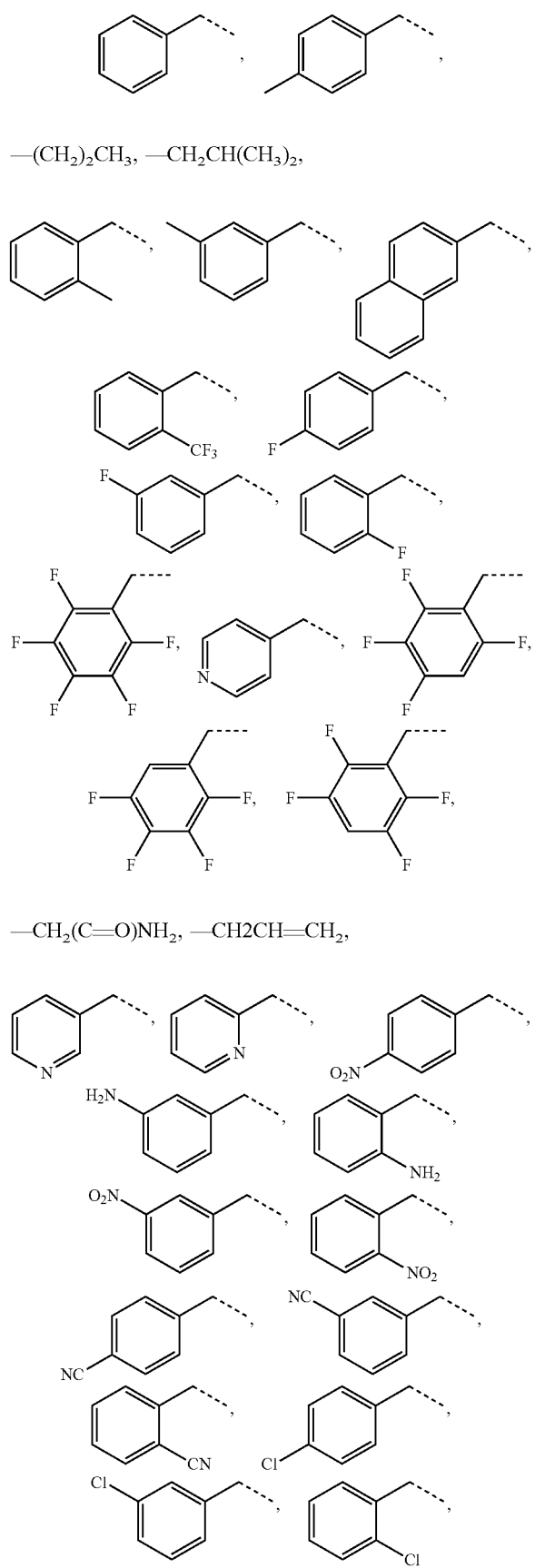
—$CH_2(C=O)NH_2$, —$CH_2CH=CH_2$,
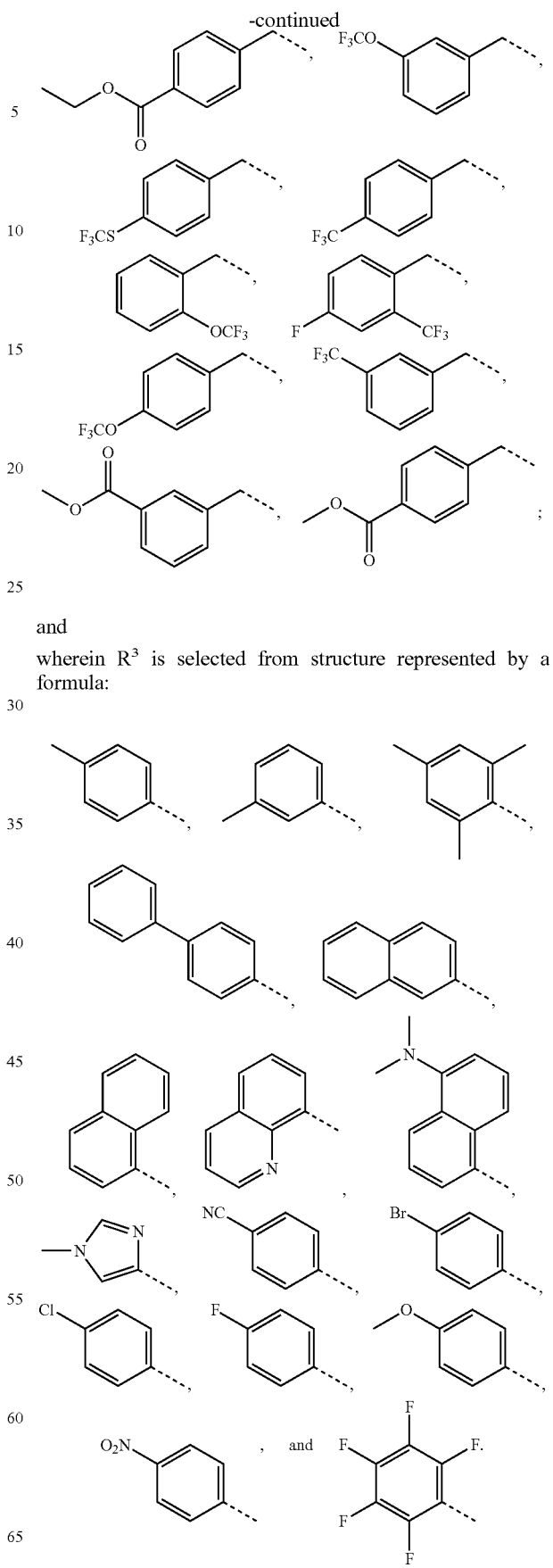
and
wherein $R^3$ is selected from structure represented by a formula:

In a further aspect, the compound of Formula I has a structure represented by a formula:
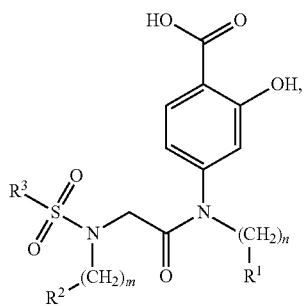
wherein each of m and n is 0; wherein $R^1$ is selected from a structure represented by a formula:
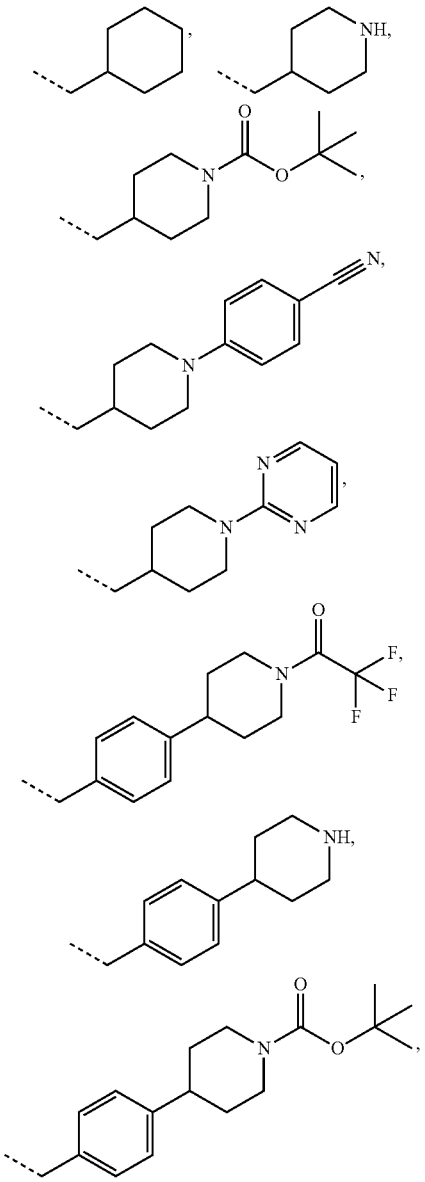
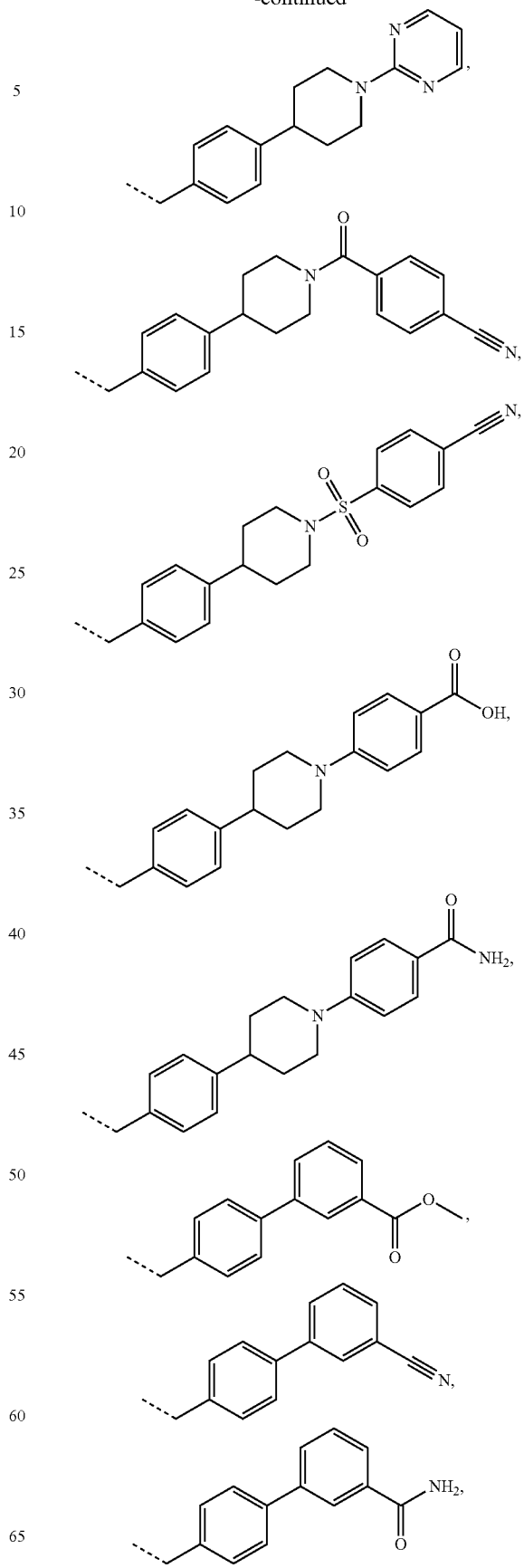

-continued
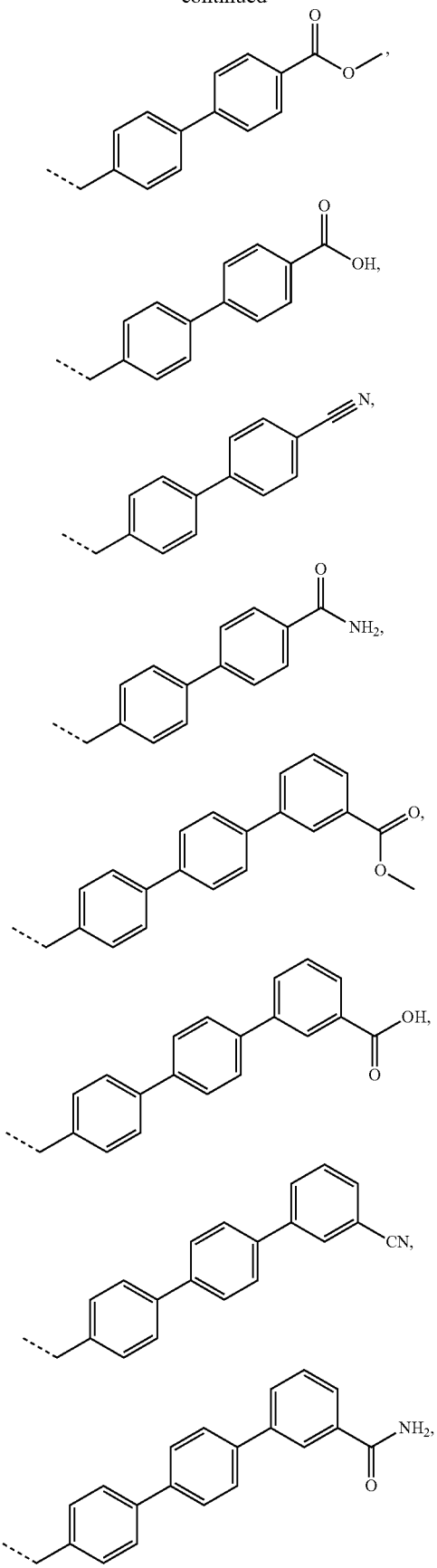
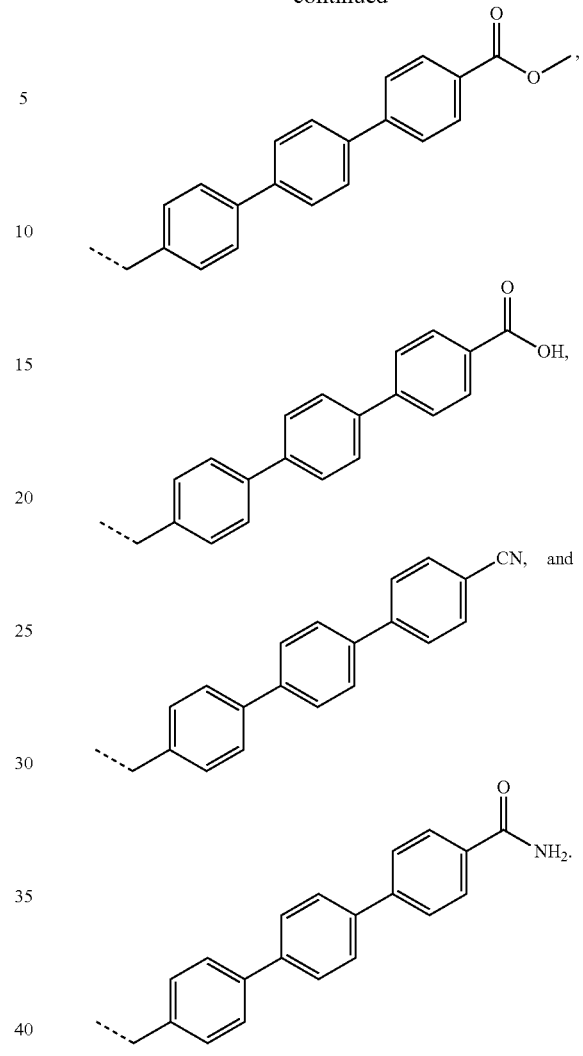
wherein R² is —CH₃; and wherein R³ is a structure represented by a formula:
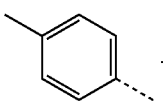
In one aspect, the invention relates to a compound having a structure represented by Formula (II):
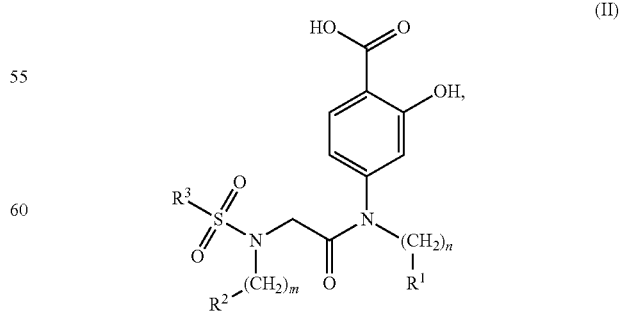
wherein m is an integer from 0-3 when R² is aryl; wherein m=0 when R² is non-aryl; wherein n is an integer from 0-3;

wherein R[1] is -(A[5])-(A[6])-L-(A[7]); wherein A[5] is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^8$, and $(C=O)NHR^8$; wherein A[6] is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^9$, and $(C=O)NHR^9$; wherein A[7] is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{10}$, and $(C=O)NHR^{10}$; wherein L is optionally present, and when present is selected from —(C=O)— and —$SO_2$—; wherein $R^2$ is selected from C3-C8 alkyl, C3-C8 alkenyl, C3-C8 alkynyl, C3-C8 haloalkyl, C3-C8 haloalkenyl, C3-C8 haloalkynyl, C3-C8 polyhaloalkyl, C3-C8 polyhaloalkenyl, C3-C8 polyhaloalkynyl; or wherein $R^2$ is aryl, and substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{11}$, and $(C=O)NHR^{11}$; wherein $R^3$ is aryl substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy; wherein each of $R^8$, $R^9$, $R^{10}$, and $R^{11}$ is independently selected from hydrogen, C1-C6 alkyl, C1-C6 haloalkyl, and C1-C6 polyhaloalkyl; or a pharmaceutically acceptable salt, hydrate, solvate, or polymorph thereof.

In a further aspect, the compound of Formula II has a structure represented by a formula:

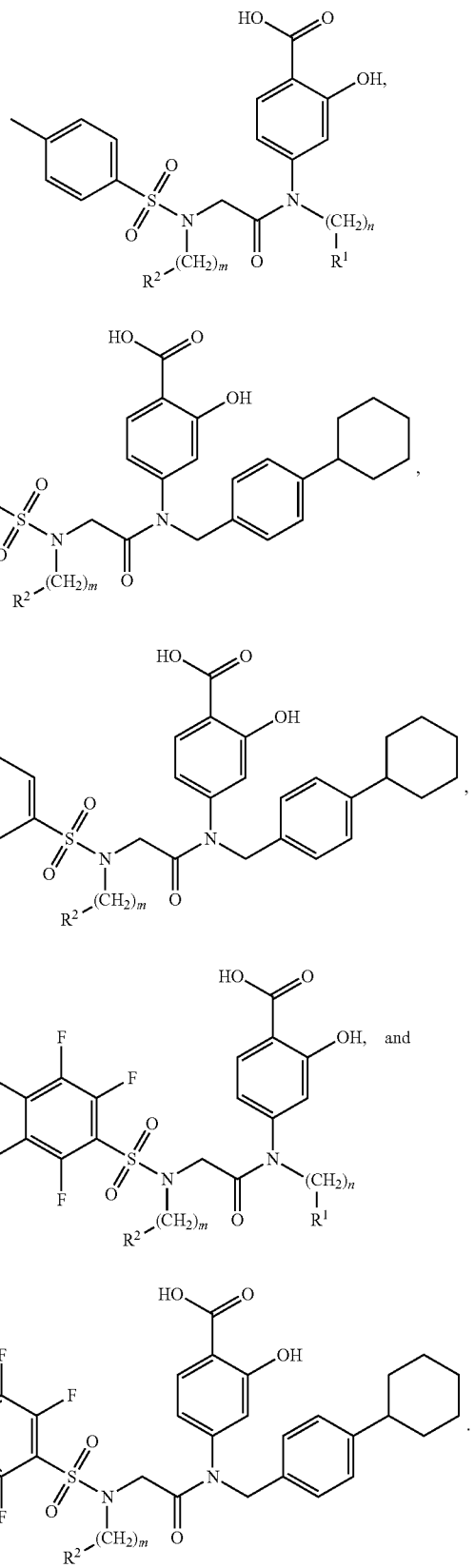

In a further aspect, the compound of Formula II has a structure represented by a formula:
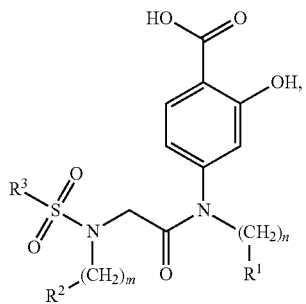
wherein each of m and n is 0; wherein $R^1$ is selected from a structure represented by a formula:
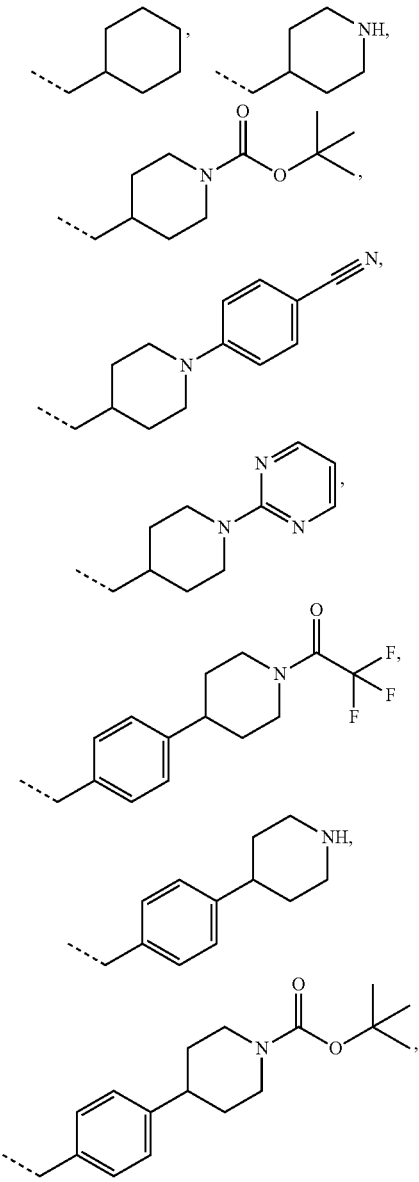
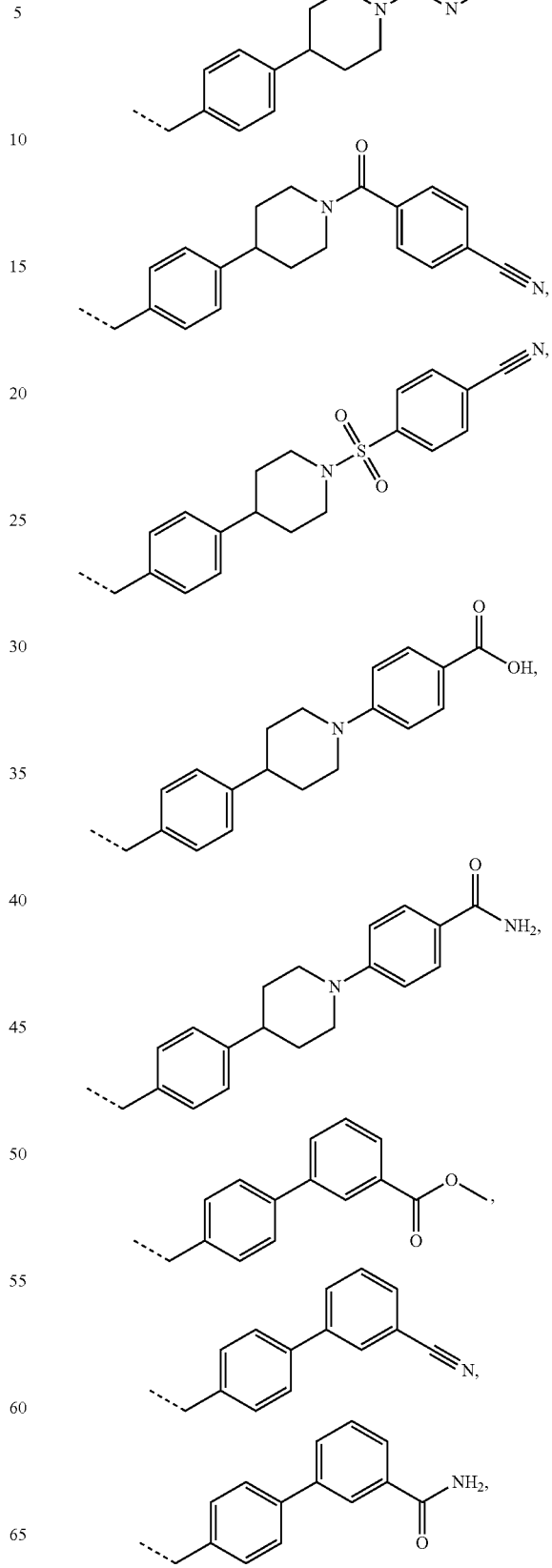

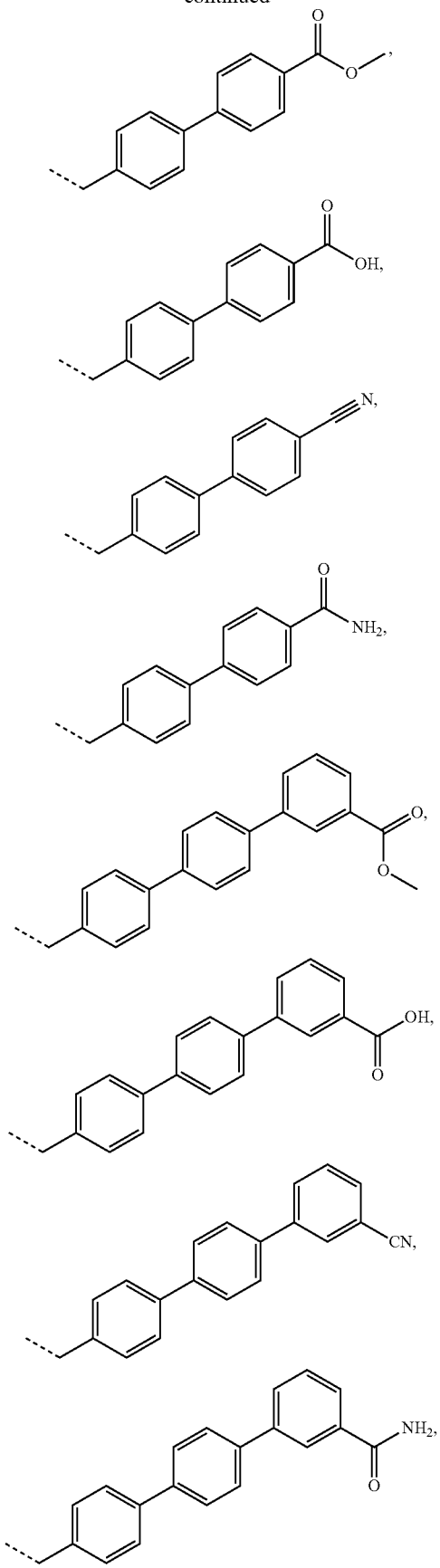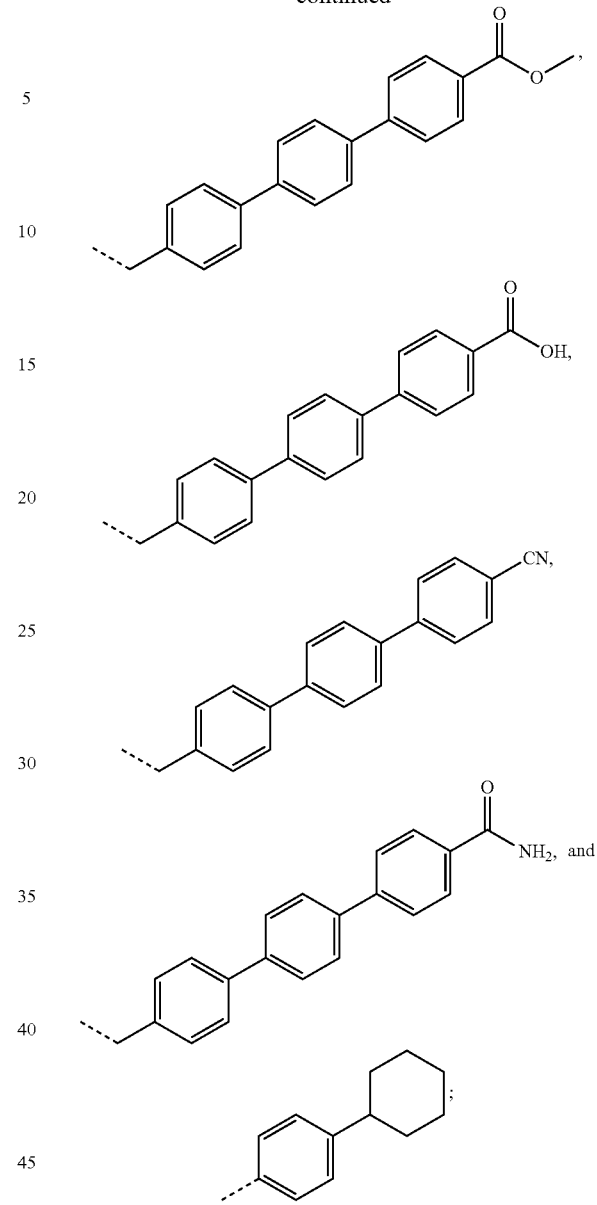
wherein $R^2$ is selected from a structure represented by a formula:
$-(CH_2)_2CH_3$, $-CH_2CH(CH_3)_2$, $-CH2CH\!=\!CH_2$,
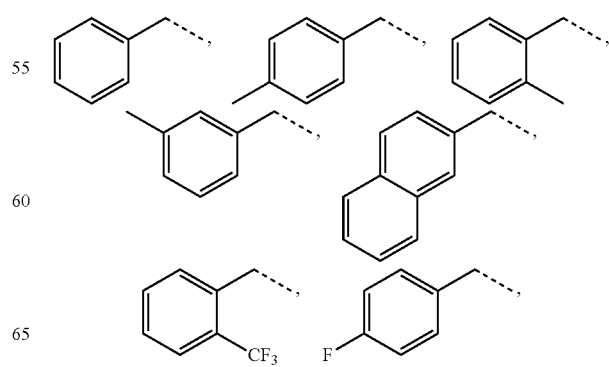

47
-continued
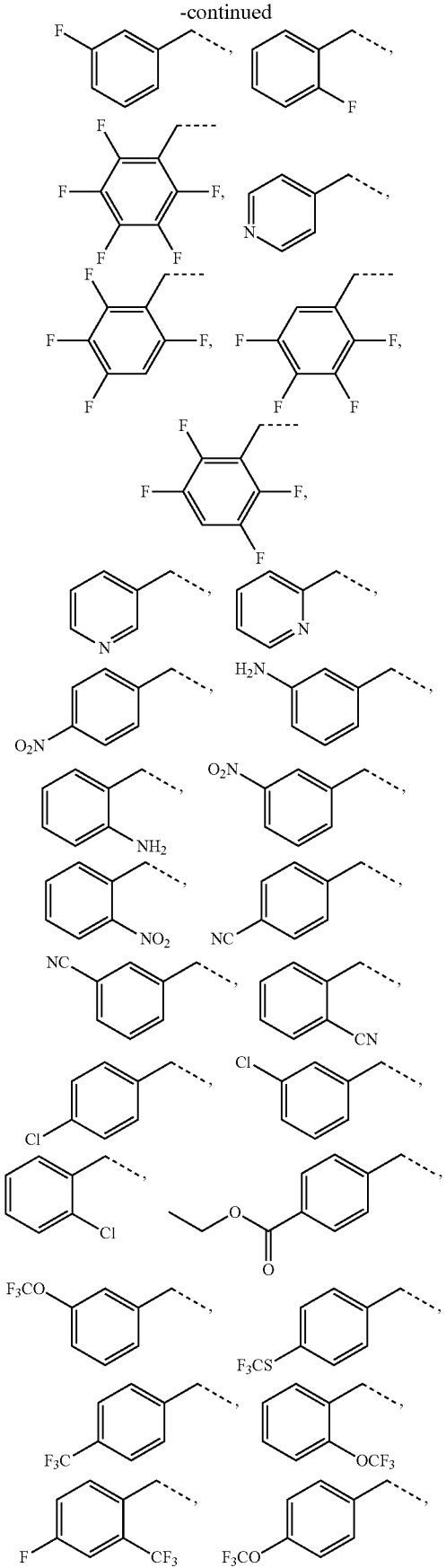
48
-continued
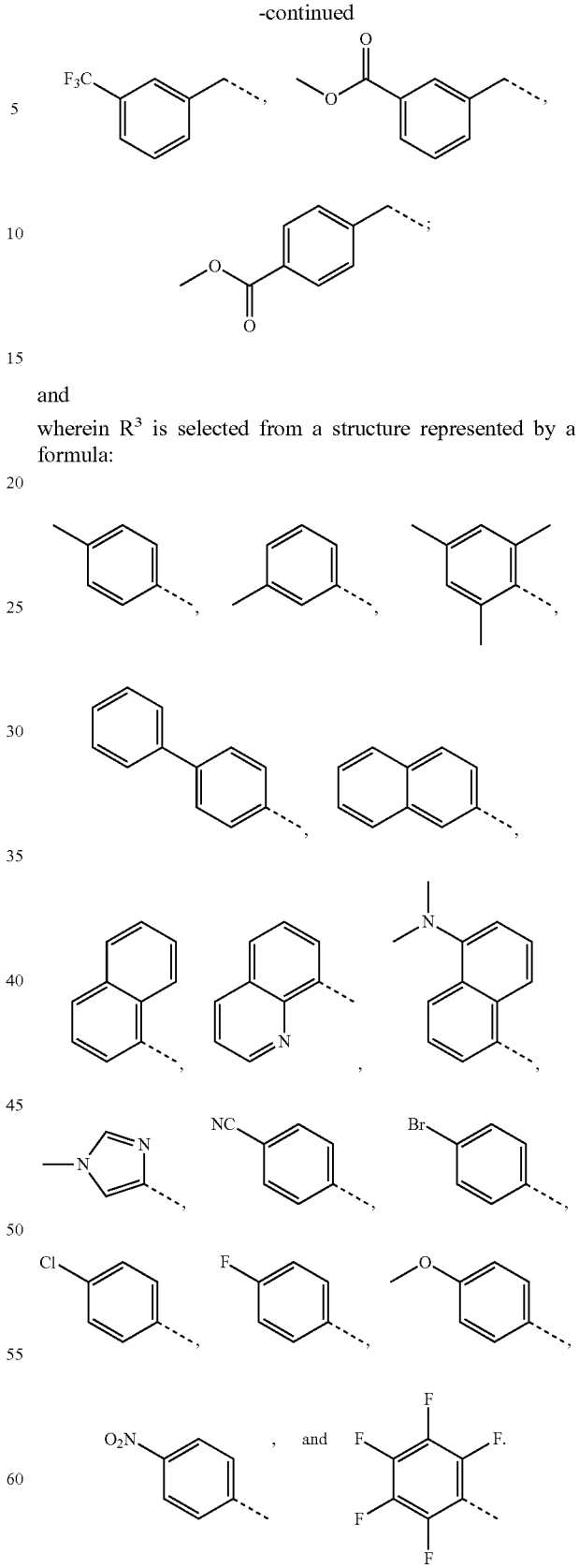
and
wherein R³ is selected from a structure represented by a formula:
In a further aspect, the compound of Formula II has a structure represented by a formula:

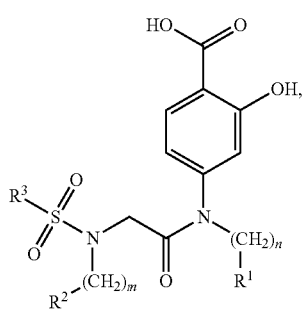
wherein each of m and n is 0; wherein R¹ is a structure represented by a formula:
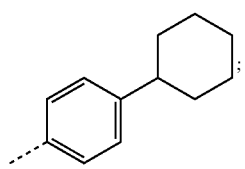
wherein R² is selected from a structure represented by a formula:
—(CH$_2$)$_2$CH$_3$, —CH$_2$CH(CH$_3$)$_2$, —CH2CH=CH$_2$,
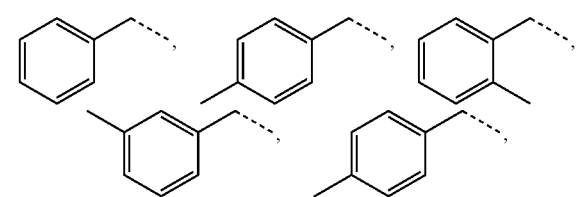
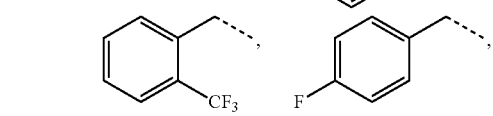
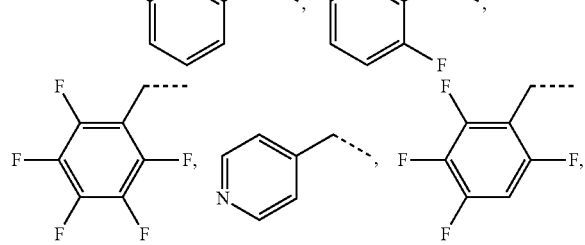
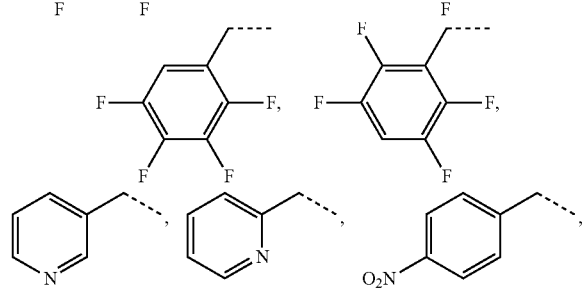
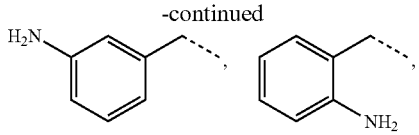
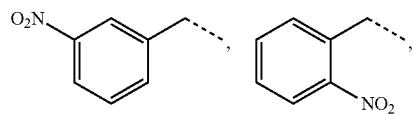
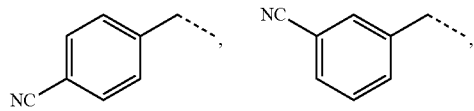
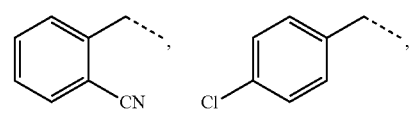
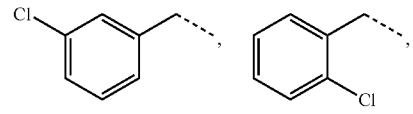
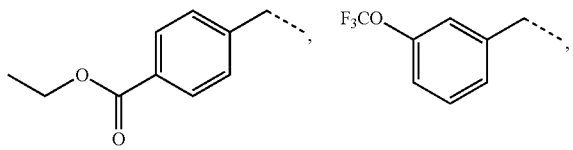
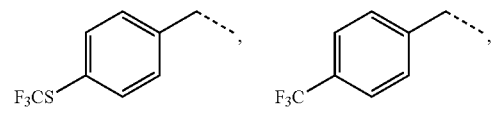
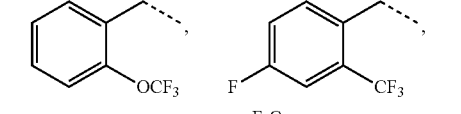
and
wherein R³ is a structure represented by a formula:
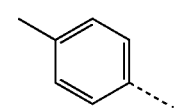
In one aspect, the invention relates to a compound having a structure represented by Formula (III):

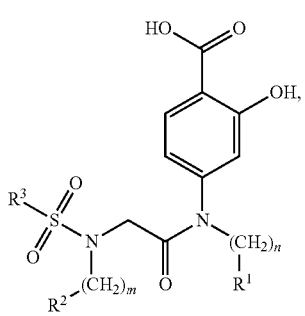

(III)

wherein each of m and n is independently an integer from 0-3; wherein $R^1$ is $-(A^5)-(A^6)-L-(A^7)$; wherein $A^5$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^8$, and $(C=O)NHR^8$; wherein $A^6$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^9$, and $(C=O)NHR^9$; wherein $A^7$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{10}$, and $(C=O)NHR^{10}$; wherein L is optionally present, and when present is selected from —(C=O)— and —$SO_2$—; wherein $R^2$ is selected from C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl; or wherein $R^2$ is aryl, and substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^7$, and $(C=O)NHR^7$; wherein $R^3$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy; wherein each of $R^8$, $R^9$, $R^{10}$, and $R^{11}$ is independently selected from hydrogen, C1-C6 alkyl, C1-C6 haloalkyl, and C1-C6 polyhaloalkyl; or a pharmaceutically acceptable salt, hydrate, solvate, or polymorph thereof.

In a further aspect, the compound of Formula III has a structure represented by a formula:

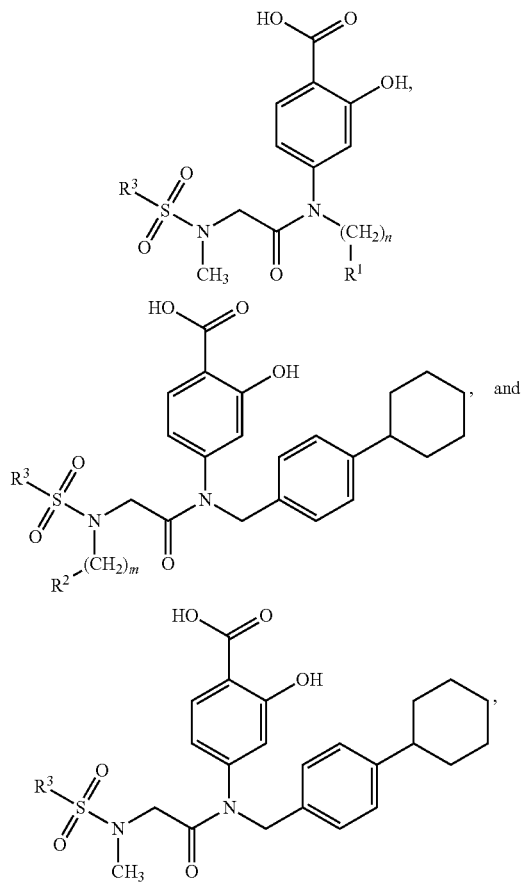

In a further aspect, the compound of Formula III has a structure represented by a formula:

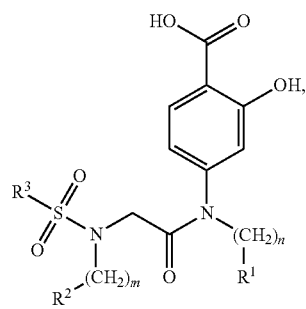

wherein each of m is 0 and n is 0; wherein $R^1$ is selected from a structure represented by a formula:

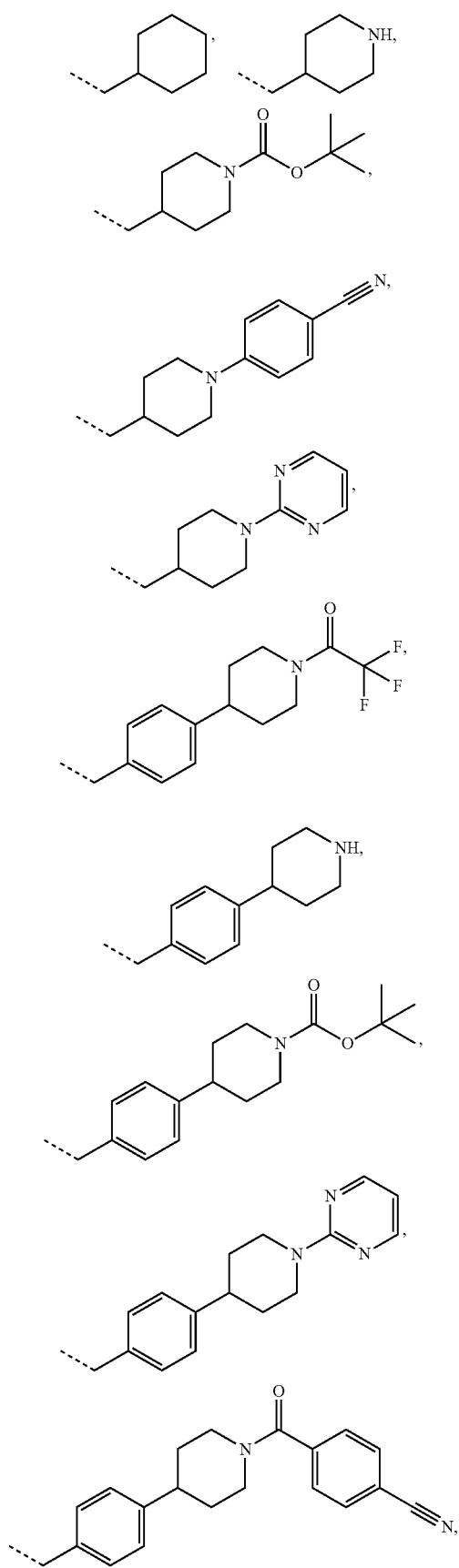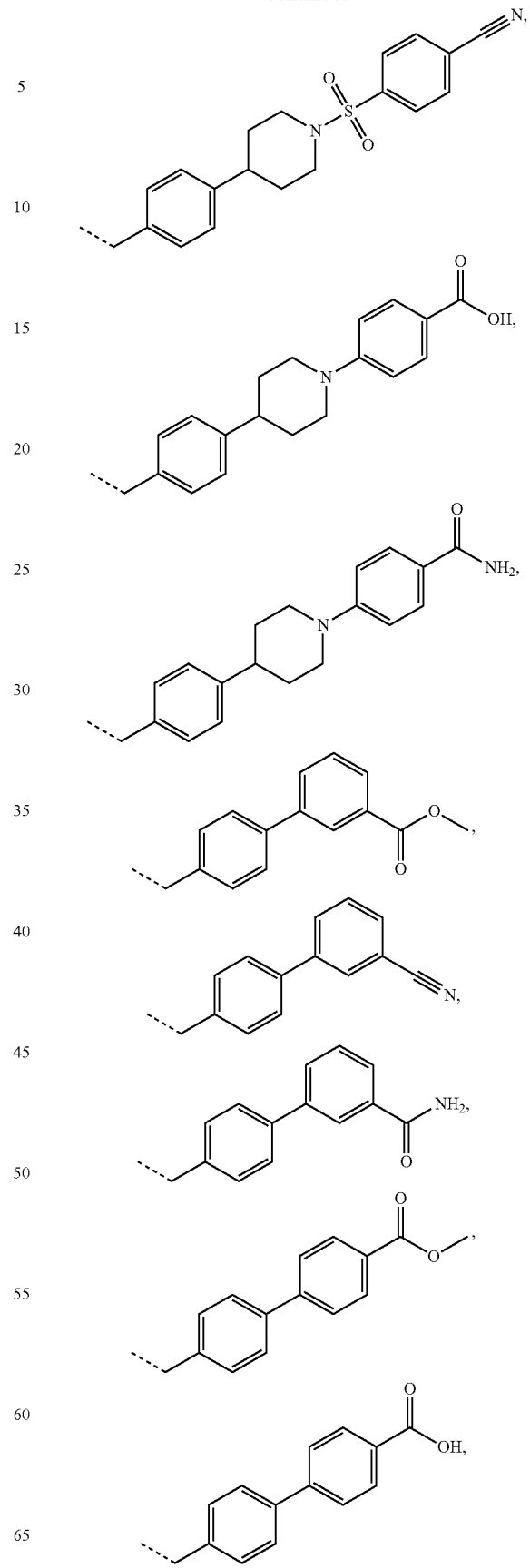

-continued
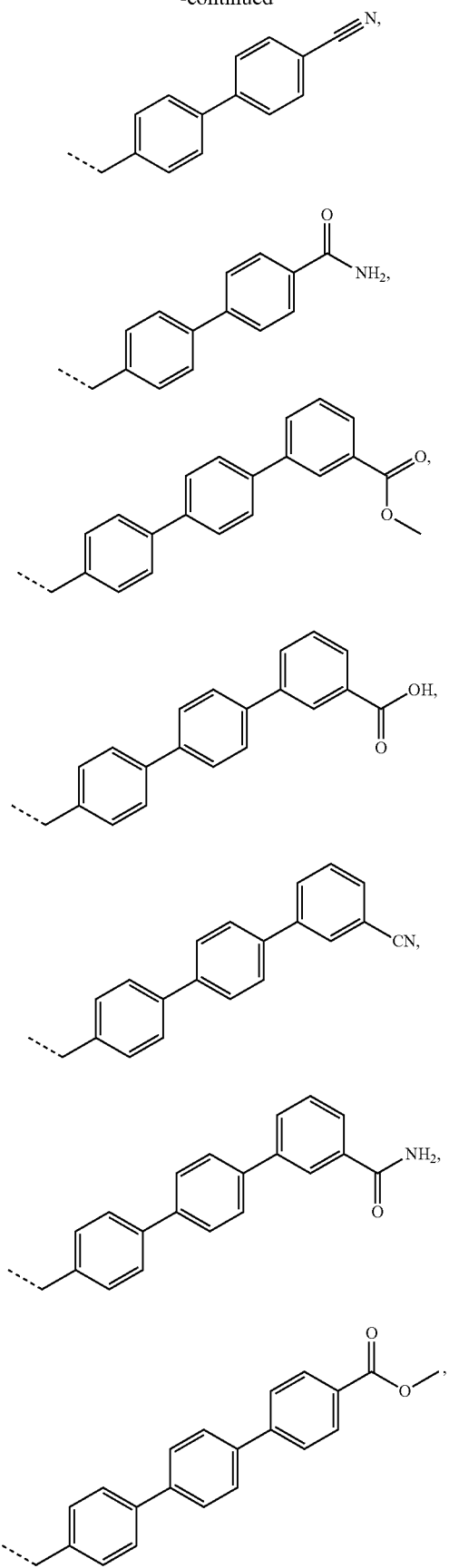
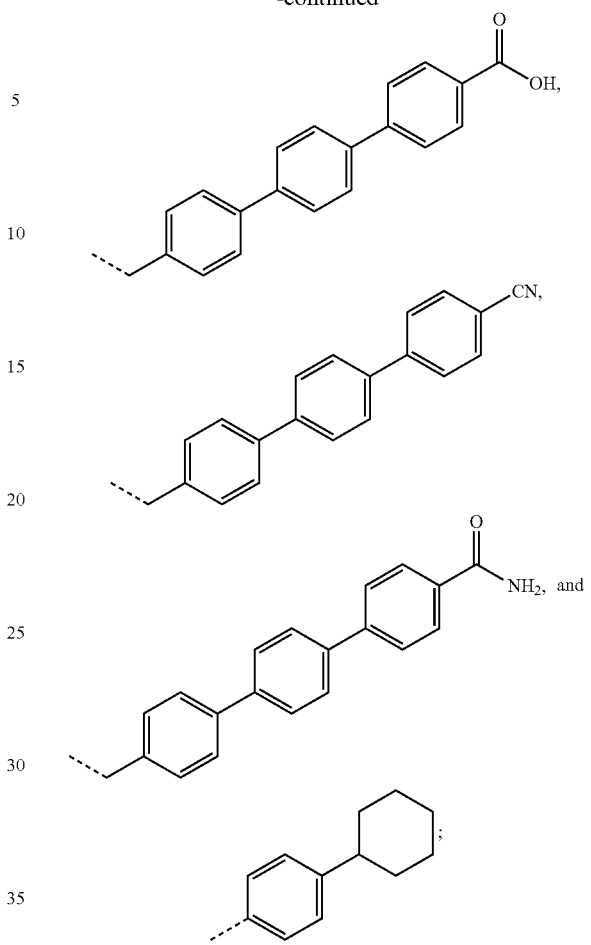
wherein R² is selected from a structure represented by a formula:
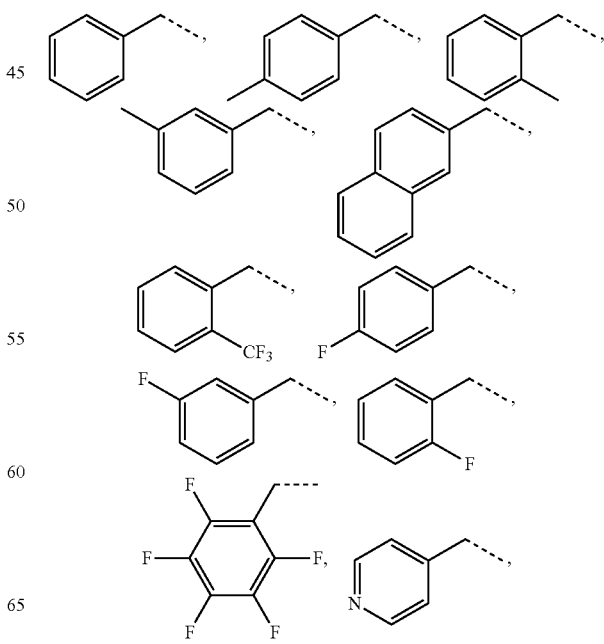

57
-continued
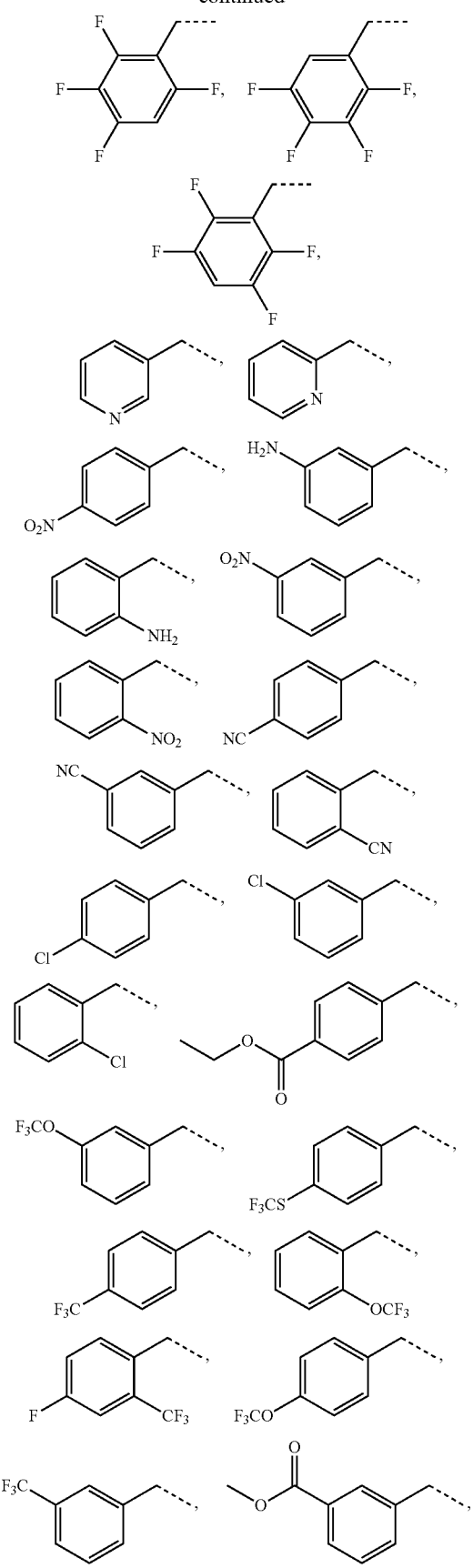
58
-continued
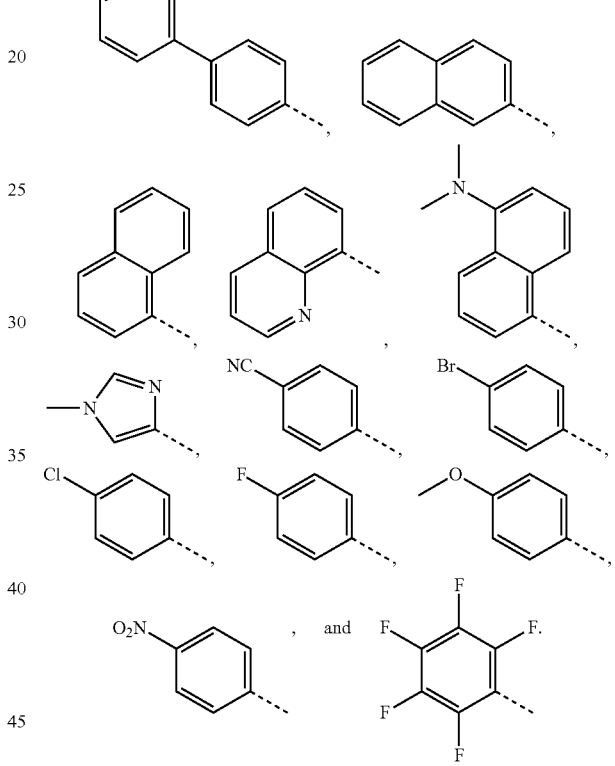
—CH$_3$, —CH$_2$(C═O)NH$_2$, —CH2CH═CH$_2$, —(CH$_2$)$_2$CH$_3$, —CH$_2$CH(CH$_3$)$_2$,
and
wherein R$^3$ is selected from a structure represented by a formula:
In a further aspect, the compound of Formula III has a structure represented by a formula:
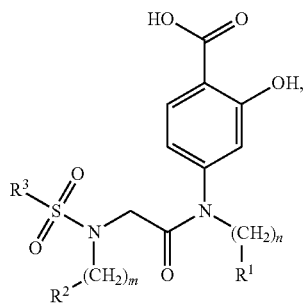
wherein each of m is 0 and n is 0; wherein R$^1$ is a structure represented by a formula:

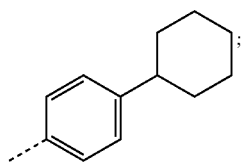

wherein R² is —CH₃; and wherein R³ is selected from a structure represented by a formula:

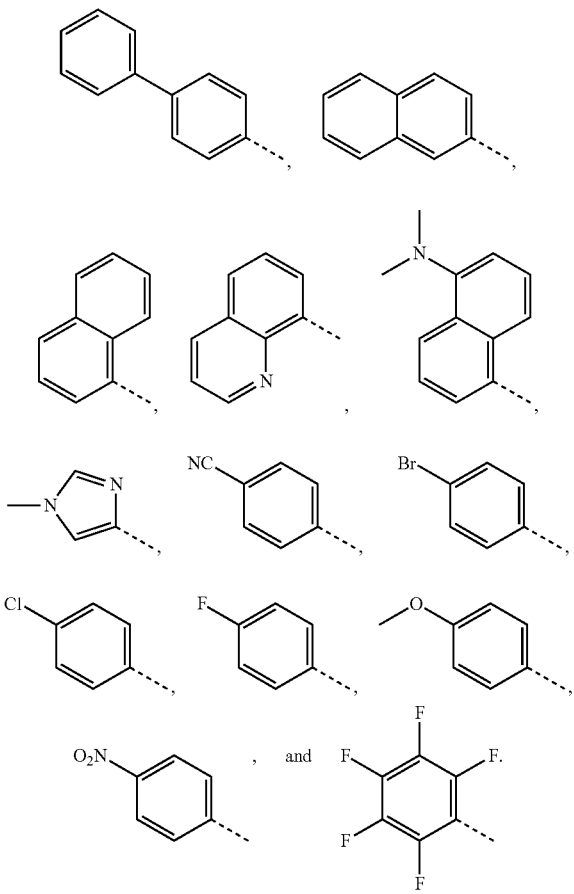

In one aspect, the invention relates to a compound having a structure represented by Formula (IV):

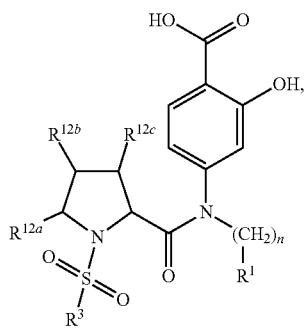

wherein n is an integer from 0-3; wherein R¹ is -(A⁵)-(A⁶)-L-(A⁷); wherein A⁵ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁸, and (C=O)NHR⁸; wherein A⁶ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁹, and (C=O)NHR⁹; wherein A⁷ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR¹⁰, and (C=O)NHR¹⁰; wherein L is optionally present, and when present is selected from —(C=O)— and —SO₂—; wherein R³ is aryl substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy; wherein each of R⁸, R⁹, R¹⁰, R¹²ᵃ, R¹²ᵇ, and R¹²ᶜ is independently selected from hydrogen, C1-C6 alkyl, C1-C6 haloalkyl, and C1-C6 polyhaloalkyl; or a pharmaceutically acceptable salt, hydrate, solvate, or polymorph thereof.

In a further aspect, the compound of Formula IV has a structure represented by a formula:

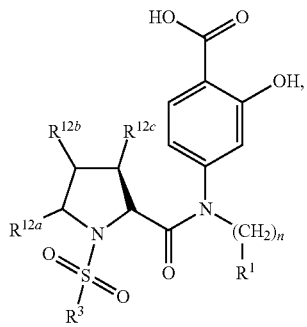

-continued

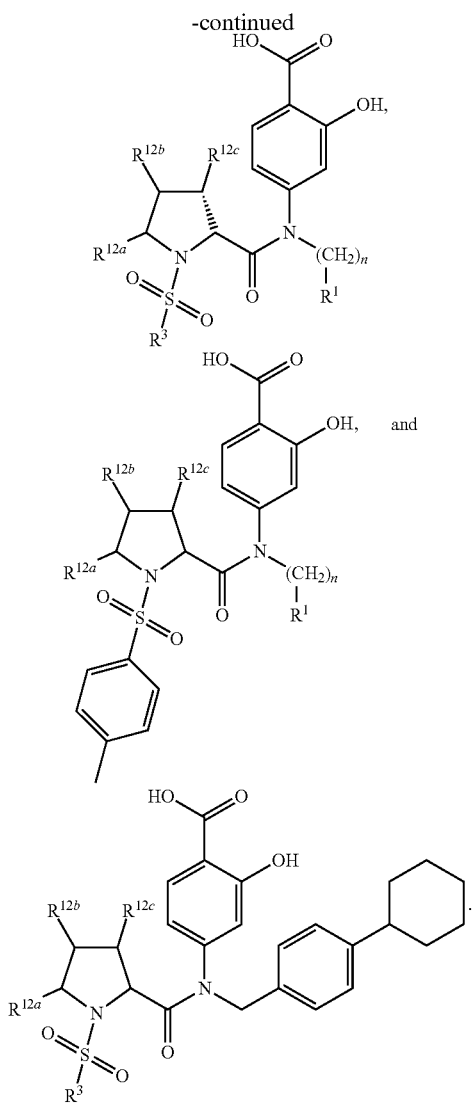

a. $A^1$ Groups

In one aspect, $A^1$ is C3-C6 cycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^4$, $(C=O)OR^4$, and $(C=O)NHR^4$.

In a further aspect, $A^1$ is C3-C6 cycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^4$, and $(C=O)NHR^4$.

In a further aspect, $A^1$ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^4$, and $(C=O)NHR^4$. In a further aspect, the groups are selected from $CO_2H$, $(C=O)OR^4$, and $(C=O)NHR^4$.

b. $A^2$ Groups

In one aspect, $A^2$ is C3-C6 heterocycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^5$, $(C=O)OR^5$, and $(C=O)NHR^5$.

In a further aspect, $A^2$ is C3-C6 heterocycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^5$, and $(C=O)NHR^5$.

In a further aspect, $A^2$ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^5$, and $(C=O)NHR^5$. In a further aspect, the groups are selected from $CO_2H$, $(C=O)OR^5$, and $(C=O)NHR^5$.

c. $A^3$ Groups

In one aspect, $A^3$ is aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^6$, $(C=O)OR^6$, and $(C=O)NHR^6$.

In a further aspect, $A^3$ is aryl substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁶, and (C=O)NHR⁶.

In a further aspect, A³ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁶, and (C=O)NHR⁶. In a further aspect, the groups are selected from CO₂H, (C=O)OR⁶, and (C=O)NHR⁶.

d. A⁴ Groups

In one aspect, A⁴ is aryl, and substituted with 1-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)R⁷, (C=O)OR⁷, and (C=O)NHR⁷.

In a further aspect, A⁴ is aryl substituted with 1-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁷, and (C=O)NHR⁷.

In a further aspect, A⁴ is substituted with 1-2 groups, 2-3 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁷, and (C=O)NHR⁷. In a further aspect, the groups are selected from CO₂H, (C=O)OR⁷, and (C=O)NHR⁷.

e. A⁵ Groups

In one aspect, A⁵ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)R⁸, (C=O)OR⁸, and (C=O)NHR⁸.

In a further aspect, A⁵ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁸, and (C=O)NHR⁸.

In a further aspect, A⁵ is C3-C6 cycloalkyl. In a further aspect, A⁵ is C3-C6 heterocycloalkyl. In a further aspect, A⁵ is aryl.

In a further aspect, A⁵ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)R⁸, (C=O)OR⁸, and (C=O)NHR⁸. In a further aspect, the groups are selected from CO₂H, (C=O)R⁸, (C=O)OR⁸, and (C=O)NHR⁸.

f. A⁶ Groups

In one aspect, A⁶ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)R⁹, (C=O)OR⁹, and (C=O)NHR⁹.

In a further aspect, A⁶ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR⁹, and (C=O)NHR⁹.

In a further aspect, A⁶ is C3-C6 cycloalkyl. In a further aspect, A⁶ is C3-C6 heterocycloalkyl. In a further aspect, A⁶ is aryl.

In a further aspect, A⁶ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)R⁹, $(C=O)OR^9$, and $(C=O)NHR^9$. In a further aspect, the groups are selected from $CO_2H$, $(C=O)R^9$, $(C=O)OR^9$, and $(C=O)NHR^9$.

g. $A^7$ Groups

In one aspect, $A^7$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^{10}$, $(C=O)OR^{10}$, and $(C=O)NHR^{10}$.

In a further aspect, $A^7$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{10}$, and $(C=O)NHR^{10}$.

In a further aspect, $A^7$ is C3-C6 cycloalkyl. In a further aspect, $A^7$ is C3-C6 heterocycloalkyl. In a further aspect, $A^7$ is aryl.

In a further aspect, $A^7$ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^{10}$, $(C=O)OR^{10}$, and $(C=O)NHR^{10}$. In a further aspect, the groups are selected from $CO_2H$, $(C=O)R^{10}$, $(C=O)OR^{10}$, and $(C=O)NHR^{10}$.

h. $A^8$ Groups

In one aspect, $A^8$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^{11}$, $(C=O)OR^{11}$, and $(C=O)NHR^{11}$.

In a further aspect, $A^8$ is selected from C3-C6 cycloalkyl, C3-C6 heterocycloalkyl, and aryl, and substituted with 0-3 groups selected from halo, hydroxyl, amino, nitro, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^{11}$, $(C=O)OR^{11}$, and $(C=O)NHR^{11}$.

In a further aspect, $A^8$ is C3-C6 cycloalkyl. In a further aspect, $A^8$ is C3-C6 heterocycloalkyl. In a further aspect, $A^8$ is aryl.

In a further aspect, $A^8$ is substituted with 1-3 groups, 1-2 groups, 2-3 groups, 0 groups, 1 group, 2 groups, or 3 groups.

In a further aspect, the groups are selected from halo, hydroxyl, amino, nitro, and cyano. In a further aspect, the groups are selected from C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^{11}$, $(C=O)OR^{11}$, and $(C=O)NHR^{11}$. In a further aspect, the groups are selected from $CO_2H$, $(C=O)R^{11}$, $(C=O)OR^{11}$, and $(C=O)NHR^{11}$.

i. L Groups

In one aspect, L is selected from $-(C=O)-$ and $-SO_2-$. In a further aspect, L is optionally present, and when present is selected from $-(C=O)-$ and $-SO_2-$. In a further aspect, L is $-(C=O)-$. In a further aspect, L is $-SO_2-$. In a further aspect, L is present. In a further aspect, L is absent.

j. $R^1$ Groups

In one aspect, $R^1$ is selected from $A^1$, $A^2$, $-(A^1)-(A^2)$, $-(A^2)-(A^3)$, $-(A^3)-(A^2)$, $-(A^3)-(A^4)$, $-(A^5)-(A^1)-(A^7)$, $-(A^5)-(A^2)-(A^8)$, $-(A^5)-(A^3)-(A^7)$, and $-(A^5)-(A^6)-L-(A^7)$.

In a further aspect, $R^1$ is $A^1$. In a further aspect, $R^1$ is $A^2$. In a further aspect, $R^1$ is $-(A^1)-(A^2)$. In a further aspect, $R^1$ is $-(A^2)-(A^3)$. In a further aspect, $R^1$ is $-(A^3)-(A^2)$. In a further aspect, $R^1$ is $-(A^3)-(A^4)$. In a further aspect, $R^1$ is $-(A^5)-(A^1)-(A^7)$. In a further aspect, $R^1$ is $-(A^5)-(A^2)-(A^8)$. In a further aspect, $R^1$ is $-(A^5)-(A^3)-(A^7)$. In a further aspect, $R^1$ is $-(A^5)-(A^6)-L-(A^7)$. In a further aspect, $R^1$ is $-(A^5)-(A^6)-L-(A^7)$.

In a further aspect, $R^1$ is selected from

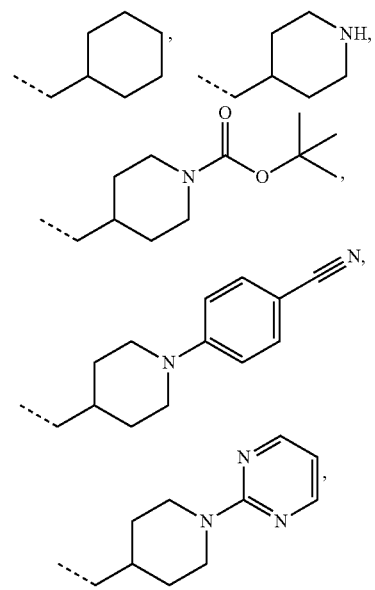

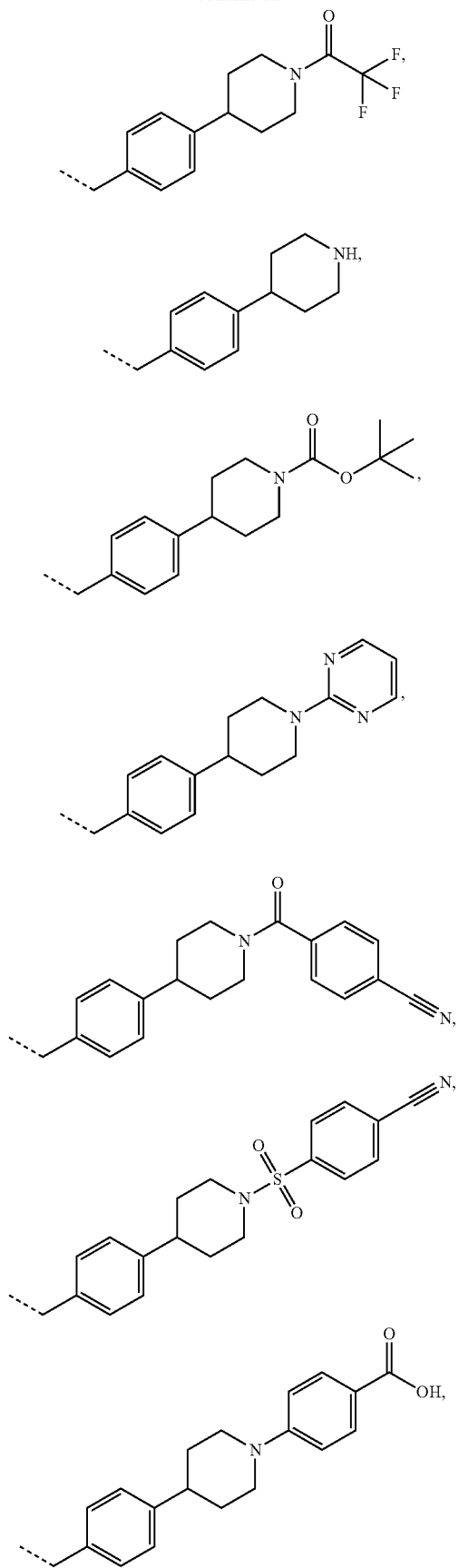
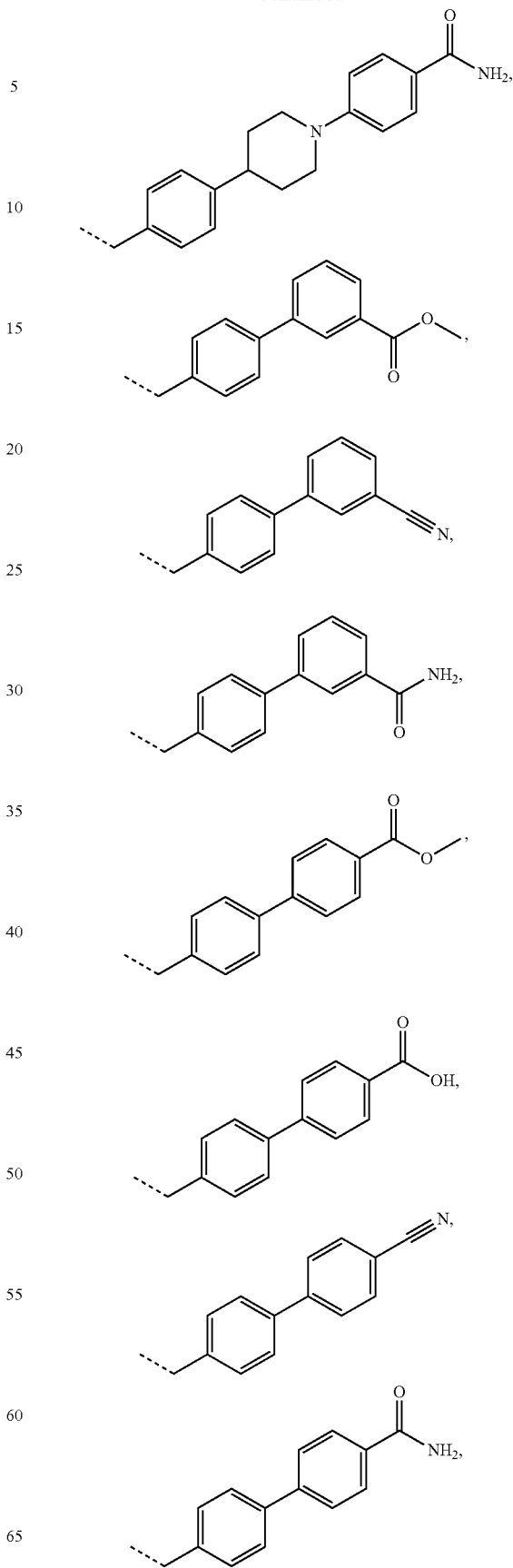

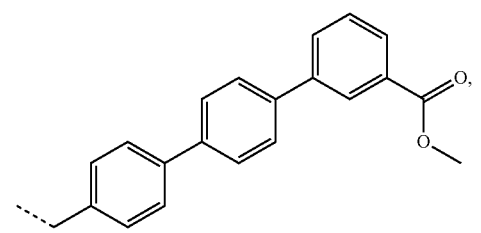
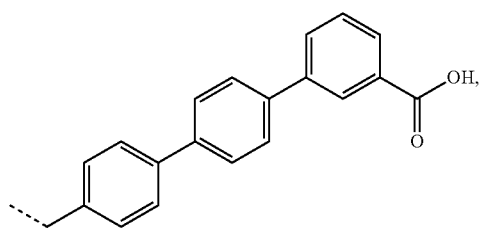
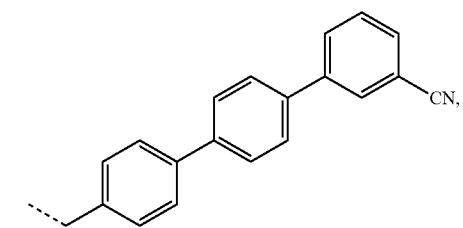
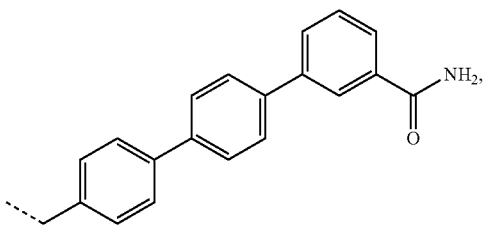
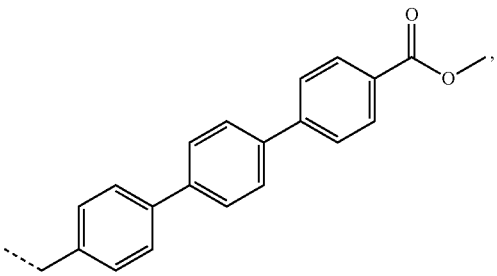
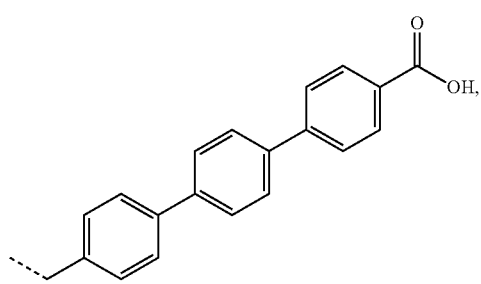
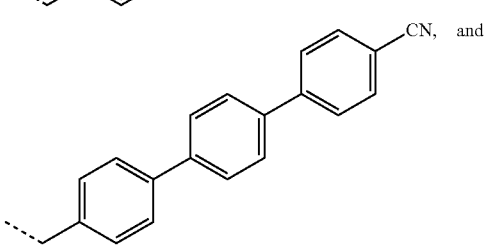
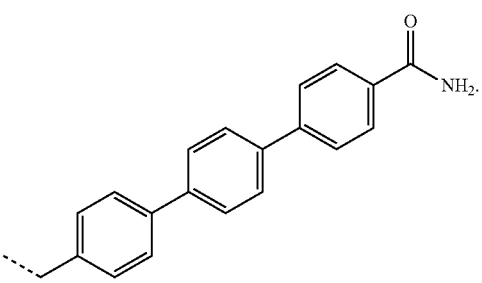
In a further aspect, R¹ is
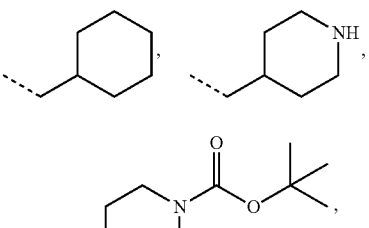
In a further aspect, R¹ is selected from
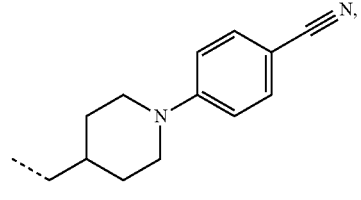
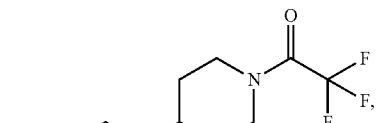
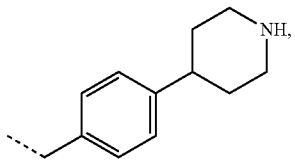

71
-continued
72
-continued
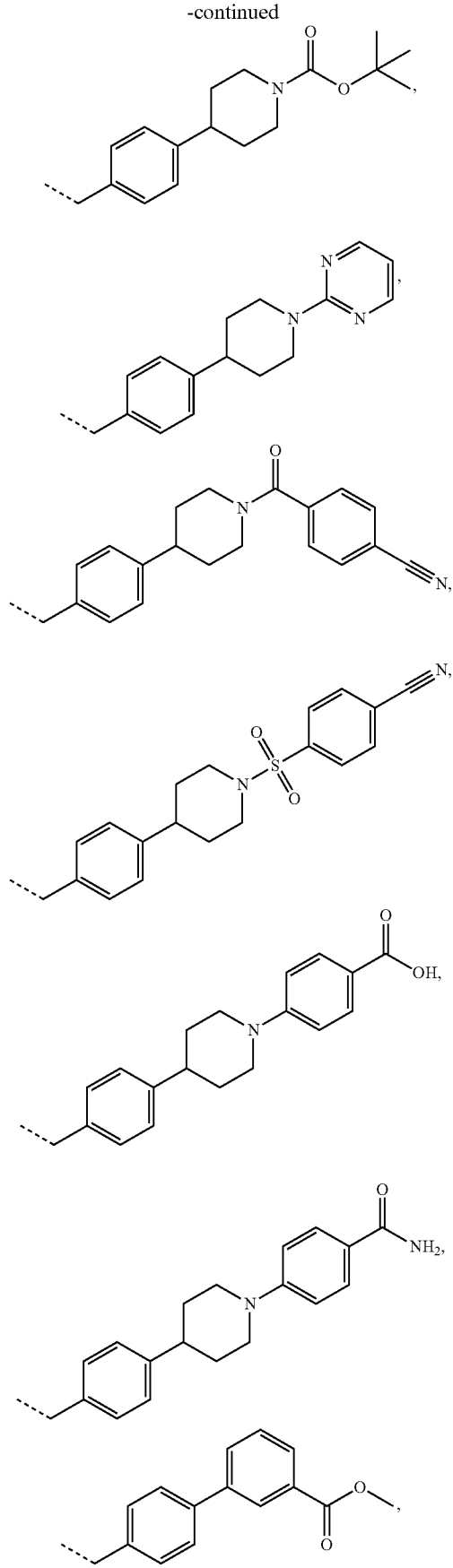
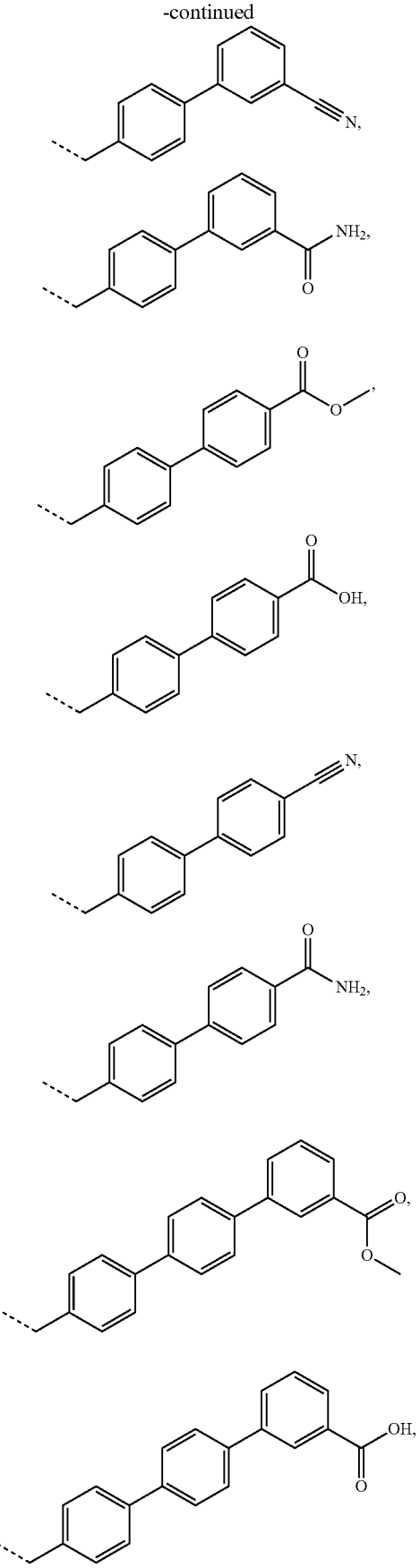

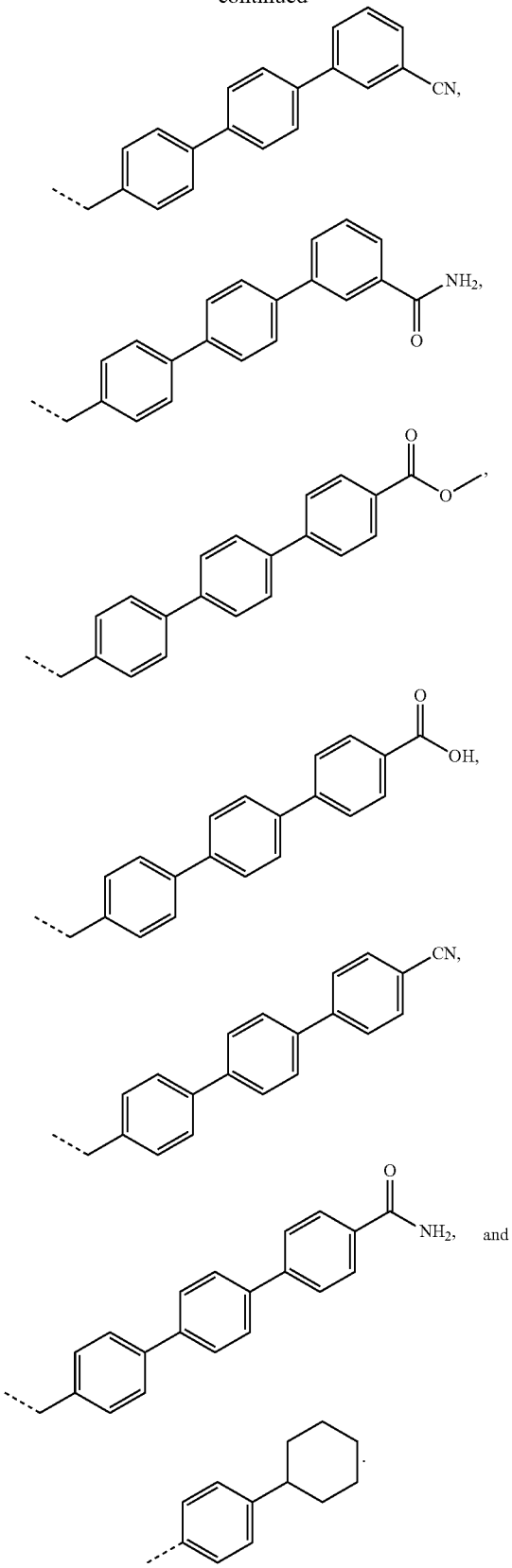

In a further aspect, $R^1$ is selected from biphenyl and terphenyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)R^4$, $(C=O)OR^4$, and $(C=O)NHR^4$.

In a further aspect, $R^1$ is biphenyl. In a further aspect, $R^1$ is terphenyl. In further aspects, $R^1$ is substituted with 1-3 groups, 1-2 groups, 2-3 groups, 0 groups, 1 group, 2 groups, or 3 groups.

k. $R^2$ Groups

In one aspect, $R^2$ is selected from C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, and C2-C6 polyhaloalkynyl.

In a further aspect, $R^2$ is selected from C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, and C2-C6 polyhaloalkynyl; or wherein $R^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{11}$, and $(C=O)NHR^{11}$.

In a further aspect, $R^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{11}$, and $(C=O)NHR^{11}$.

In a further aspect, $R^2$ is selected from C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, and C2-C6 polyhaloalkynyl; or wherein $R^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^7$, and $(C=O)NHR^7$.

In a further aspect, $R^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^7$, and $(C=O)NHR^7$.

In a further aspect, $R^2$ is selected from hydrogen, C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl, (C=O)OR$^{13}$, and (C=O)NR$^{13}$R$^{14}$; or wherein $R^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkylthio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)OR$^{13}$, and (C=O)NR$^{13}$R$^{14}$.

In a further aspect, $R^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)OR$^{13}$, and (C=O)NR$^{13}$R$^{14}$.

In various aspects, $R^2$ is aryl substituted with 0-4 groups, 0-3 groups, 0-2 groups, 0-1 groups, 1-5 groups, 1-4 groups, 1-3 groups, 1-2 groups, 2-3 groups, 0 groups, 1 group, 2 groups, 3 groups, 4 groups, or 5 groups.

In a further aspect, wherein $R^2$ is —CH$_3$.

In a further aspect, $R^2$ is selected from —CH$_3$,

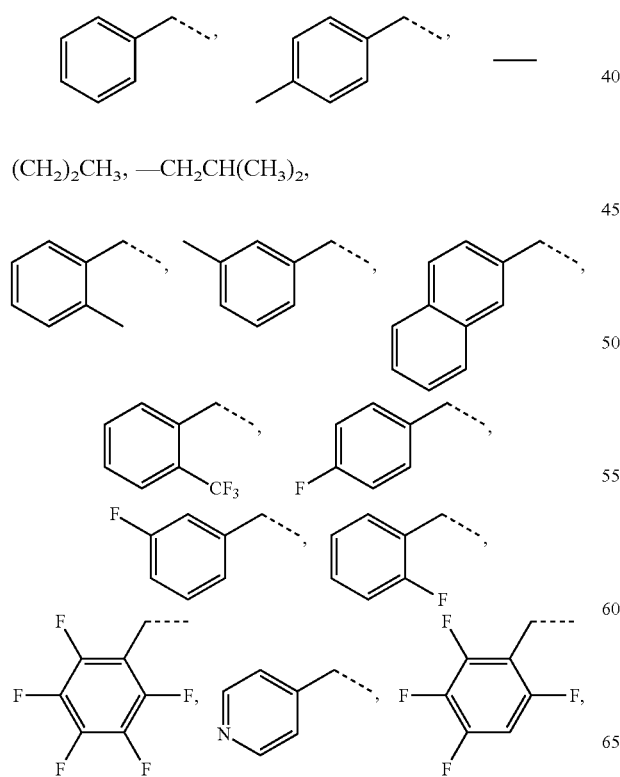

(CH$_2$)$_2$CH$_3$, —CH$_2$CH(CH$_3$)$_2$,

-continued

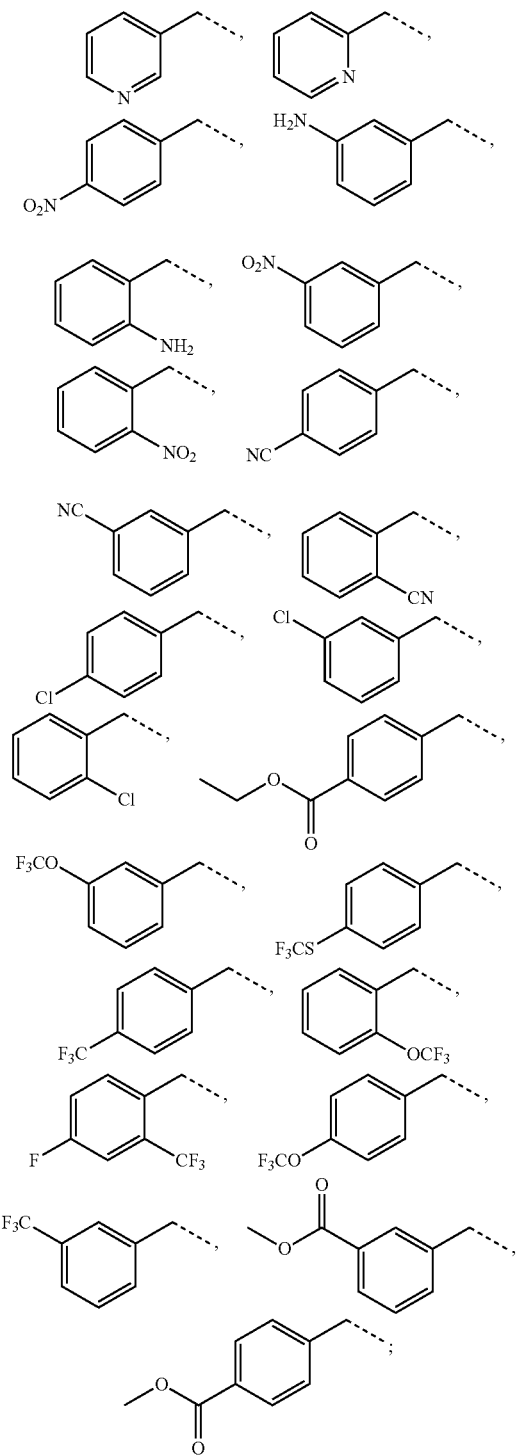

—CH$_2$(C=O)NH$_2$, —CH2CH=CH$_2$,

In a further aspect, R² is selected from —(CH₂)₂CH₃, —CH₂CH(CH₃)₂, —CH2CH=CH₂,
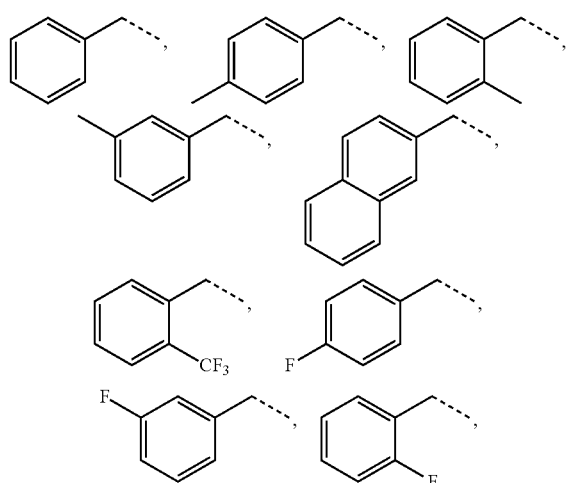
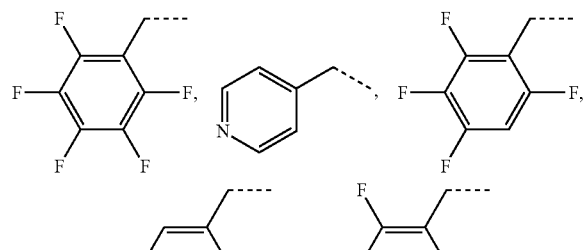
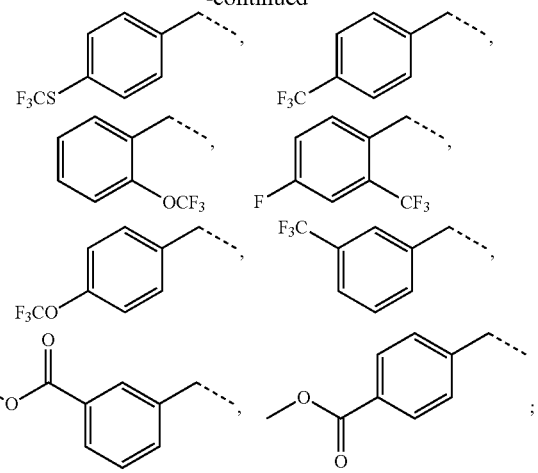
In a further aspect, R² is selected from —CH₃,
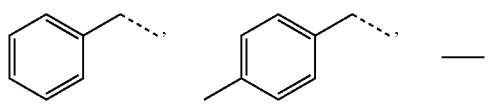
(CH₂)₂CH₃, —CH₂CH(CH₃)₂,
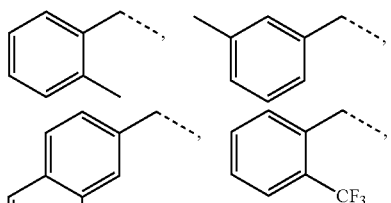
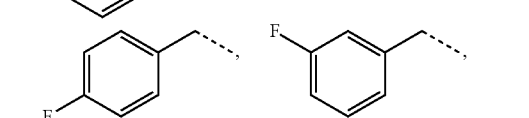
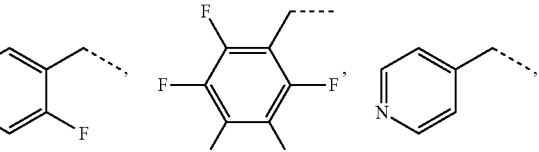
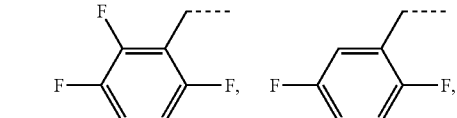
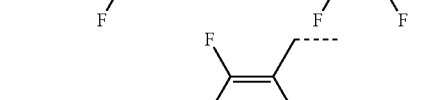
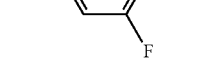
—CH₂(C=O)NH₂, —CH2CH=CH₂,

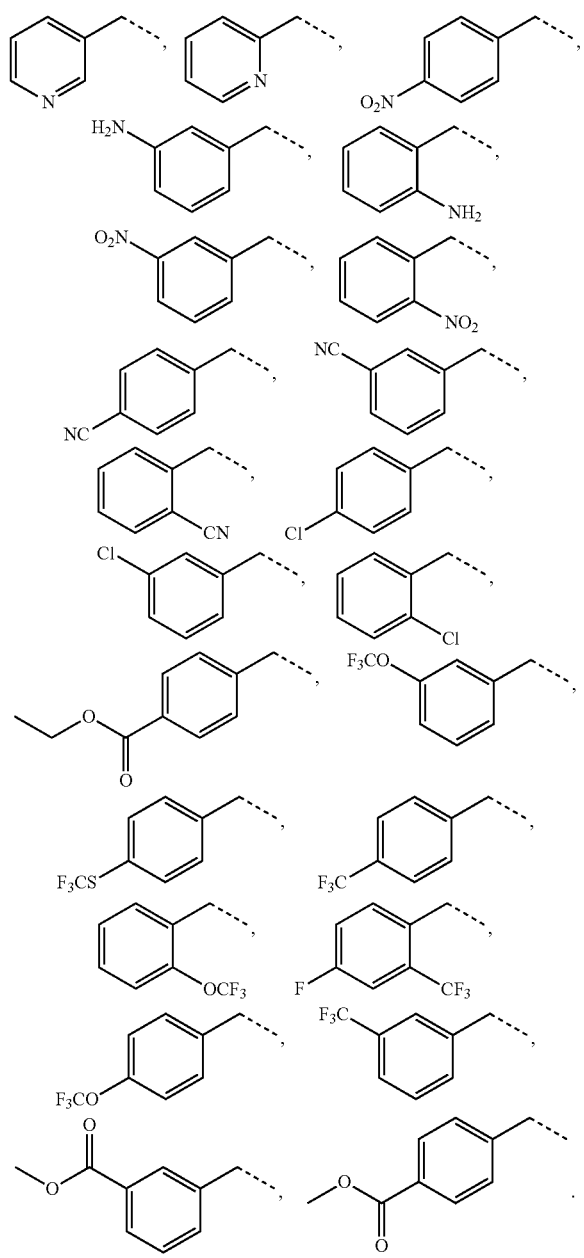

In a further aspect, R² is selected from phenyl, napthyl, and monocyclic C3-C6 heteroaryl, and substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR¹¹, and (C=O)NHR¹¹.

In a further aspect, R² is phenyl. In a further aspect, R² is napthyl. In a further aspect, R² is monocyclic C3-C6 heteroaryl. In further aspects, R² is substituted with 0-4 groups, 0-3 groups, 0-2 groups, 0-1 groups, 1-5 groups, 1-4 groups, 1-3 groups, 1-2 groups, 2-3 groups, 0 groups, 1 group, 2 groups, 3 groups, 4 groups, or 5 groups.

1. R³ Groups

In one aspect, R³ is aryl substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy.

In a further aspect, R³ is

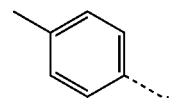

In a further aspect, R³ is selected from

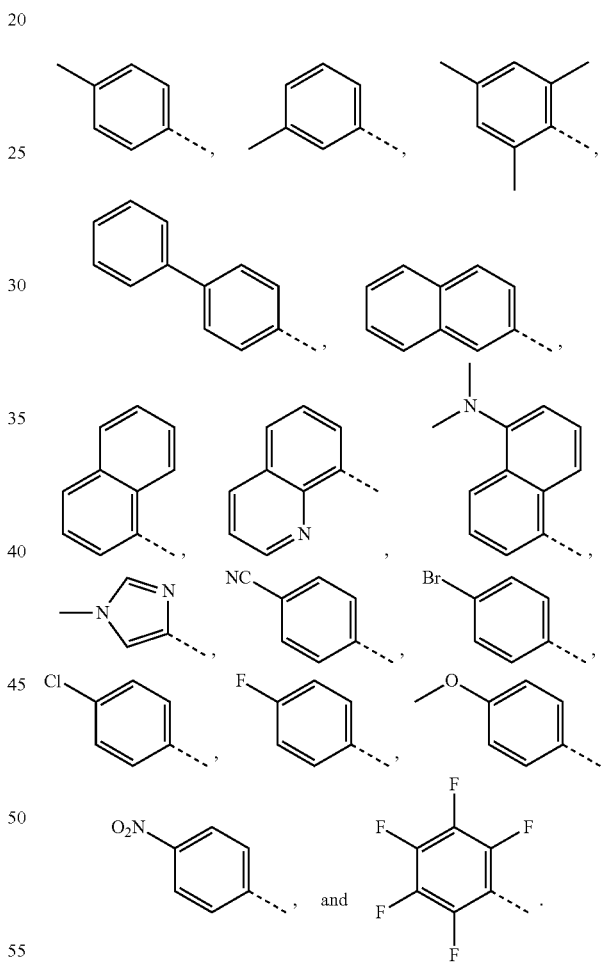

In a further aspect, R³ is selected from

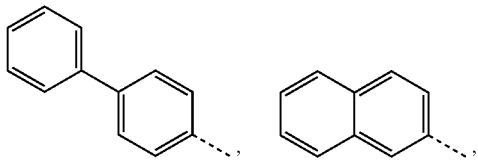

-continued

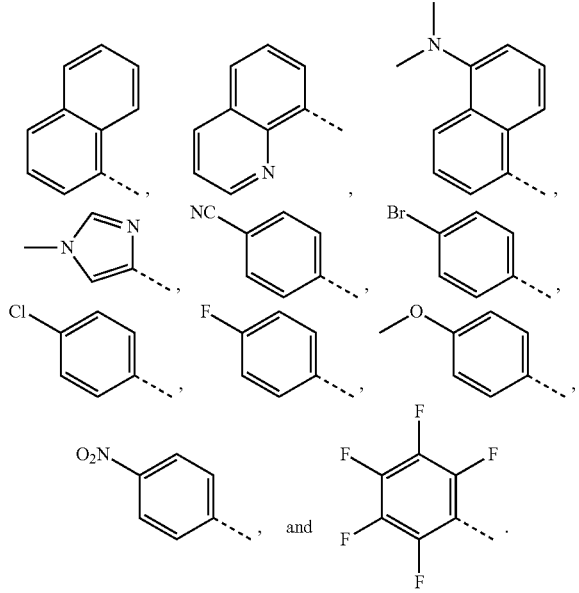

In a further aspect, R³ is selected from phenyl, biphenyl, napthyl, and imidazole, and substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy.

In a further aspect, R³ is phenyl. In a further aspect, R³ is biphenyl. In a further aspect, R³ is napthyl. In a further aspect, R³ is imidazole. In a further aspect, R³ is pentafluorophenyl.

In further aspects, R³ is substituted with 0-4 groups, 0-3 groups, 0-2 groups, 0-1 groups, 1-5 groups, 1-4 groups, 1-3 groups, 1-2 groups, 2-3 groups, 0 groups, 1 group, 2 groups, 3 groups, 4 groups, or 5 groups.

m. R⁴ Groups

In one aspect, R⁴ is selected from hydrogen, C1-C6 alkyl, C1-C6 haloalkyl, and C1-C6 polyhaloalkyl. In a further aspect, R⁴ is selected from C1-C6 alkyl, C1-C6 haloalkyl, and C1-C6 polyhaloalkyl. In a further aspect, R⁴ is hydrogen. In a further aspect, R⁴ is C1-C6 alkyl. In a further aspect, R⁴ is C1-C6 haloalkyl. In a further aspect, R⁴ is C1-C6 polyhaloalkyl.

n. R⁵ Groups

In one aspect, R⁵ is selected from hydrogen, C1-C6 alkyl, C1-C6 haloalkyl, and C1-C6 polyhaloalkyl. In a further aspect, R⁵ is selected from C1-C6 alkyl, C1-C6 haloalkyl, and C1-C6 polyhaloalkyl. In a further aspect, R⁵ is hydrogen. In a further aspect, R⁵ is C1-C6 alkyl. In a further aspect, R⁵ is C1-C6 haloalkyl. In a further aspect, R⁵ is C1-C6 polyhaloalkyl.

O. R⁶ Groups

In one aspect, R⁶ is selected from hydrogen, C1-C6 alkyl, C1-C6 haloalkyl, and C1-C6 polyhaloalkyl. In a further aspect, R⁶ is selected from C1-C6 alkyl, C1-C6 haloalkyl, and C1-C6 polyhaloalkyl. In a further aspect, R⁶ is hydrogen. In a further aspect, R⁶ is C1-C6 alkyl. In a further aspect, R⁶ is C1-C6 haloalkyl. In a further aspect, R⁶ is C1-C6 polyhaloalkyl.

p. R⁷ Groups

In one aspect, R⁷ is selected from hydrogen, C1-C6 alkyl, C1-C6 haloalkyl, and C1-C6 polyhaloalkyl. In a further aspect, R⁷ is selected from C1-C6 alkyl, C1-C6 haloalkyl, and C1-C6 polyhaloalkyl. In a further aspect, R⁷ is hydrogen. In a further aspect, R⁷ is C1-C6 alkyl. In a further aspect, R⁷ is C1-C6 haloalkyl. In a further aspect, R⁷ is C1-C6 polyhaloalkyl.

q. R⁸ Groups

In one aspect, R⁸ is selected from hydrogen, C1-C6 alkyl, C1-C6 haloalkyl, and C1-C6 polyhaloalkyl. In a further aspect, R⁸ is selected from C1-C6 alkyl, C1-C6 haloalkyl, and C1-C6 polyhaloalkyl. In a further aspect, R⁸ is hydrogen. In a further aspect, R⁸ is C1-C6 alkyl. In a further aspect, R⁸ is C1-C6 haloalkyl. In a further aspect, R⁸ is C1-C6 polyhaloalkyl.

r. R⁹ Groups

In one aspect, R⁹ is selected from hydrogen, C1-C6 alkyl, C1-C6 haloalkyl, and C1-C6 polyhaloalkyl. In a further aspect, R⁹ is selected from C1-C6 alkyl, C1-C6 haloalkyl, and C1-C6 polyhaloalkyl. In a further aspect, R⁹ is hydrogen. In a further aspect, R⁹ is C1-C6 alkyl. In a further aspect, R⁹ is C1-C6 haloalkyl. In a further aspect, R⁹ is C1-C6 polyhaloalkyl.

s. R^N Groups

In one aspect, R¹⁰ is selected from hydrogen, C1-C6 alkyl, C1-C6 haloalkyl, and C1-C6 polyhaloalkyl. In a further aspect, R¹⁰ is selected from C1-C6 alkyl, C1-C6 haloalkyl, and C1-C6 polyhaloalkyl. In a further aspect, R¹⁰ is hydrogen. In a further aspect, R¹⁰ is C1-C6 alkyl. In a further aspect, R¹⁰ is C1-C6 haloalkyl. In a further aspect, R¹⁰ is C1-C6 polyhaloalkyl.

t. R¹¹ Groups

In one aspect, R¹¹ is an optionally substituted group selected from hydrogen, C1-C6 alkyl, C1-C6 haloalkyl, and C1-C6 polyhaloalkyl. In a further aspect, R¹¹ is selected from C1-C6 alkyl, C1-C6 haloalkyl, and C1-C6 polyhaloalkyl. In a further aspect, R¹¹ is hydrogen. In a further aspect, R¹¹ is C1-C6 alkyl. In a further aspect, R¹¹ is C1-C6 haloalkyl. In a further aspect, R¹¹ is C1-C6 polyhaloalkyl.

u. R¹² Groups

In one aspect, R¹²ª is selected from hydrogen, C1-C6 alkyl, C1-C6 haloalkyl, and C1-C6 polyhaloalkyl. In a further aspect, R¹²ª is selected from C1-C6 alkyl, C1-C6 haloalkyl, and C1-C6 polyhaloalkyl. In a further aspect, R¹²ª is hydrogen. In a further aspect, R¹²ª is C1-C6 alkyl. In a further aspect, R¹²ª is C1-C6 haloalkyl. In a further aspect, R¹²ª is C1-C6 polyhaloalkyl.

In a further aspect, R¹² is selected from hydrogen, C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl, (C=O)OR¹³, (C=O)NR¹³R¹⁴; and aryl, wherein aryl is substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkylthio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO₂H, (C=O)OR¹³, and (C=O)NR¹³R¹⁴.

In one aspect, R¹²ᵇ is selected from hydrogen, C1-C6 alkyl, C1-C6 haloalkyl, and C1-C6 polyhaloalkyl. In a further aspect, R¹²ᵇ is selected from C1-C6 alkyl, C1-C6 haloalkyl, and C1-C6 polyhaloalkyl. In a further aspect, $R^{12b}$ is hydrogen. In a further aspect, $R^{12b}$ is C1-C6 alkyl. In a further aspect, $R^{12b}$ is C1-C6 haloalkyl. In a further aspect, $R^{12b}$ is C1-C6 polyhaloalkyl.

In a further aspect, $R^{12b}$ is selected from hydrogen, C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl, (C=O)OR$^{13}$, (C=O)NR$^{13}$R$^{14}$; and aryl, wherein aryl is substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkylthio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)OR$^{13}$, and (C=O)NR$^{13}$R$^{14}$.

In one aspect, $R^{12c}$ is selected from hydrogen, C1-C6 alkyl, C1-C6 haloalkyl, and C1-C6 polyhaloalkyl. In a further aspect, $R^{12c}$ is selected from C1-C6 alkyl, C1-C6 haloalkyl, and C1-C6 polyhaloalkyl. In a further aspect, $R^{12c}$ is hydrogen. In a further aspect, $R^{12c}$ is C1-C6 alkyl. In a further aspect, $R^{12c}$ is C1-C6 haloalkyl. In a further aspect, $R^{12c}$ is C1-C6 polyhaloalkyl.

In a further aspect, $R^{12c}$ is selected from hydrogen, C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl, (C=O)OR$^{13}$, (C=O)NR$^{13}$R$^{14}$; and aryl, wherein aryl is substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkylthio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)OR$^{13}$, and (C=O)NR$^{13}$R$^{14}$.

v. $R^{13}$ Groups

In one aspect, $R^{13}$ is selected from hydrogen, C1-C6 alkyl, C1-C6 haloalkyl, and C1-C6 polyhaloalkyl. In a further aspect, $R^{13}$ is selected from C1-C6 alkyl, C1-C6 haloalkyl, and C1-C6 polyhaloalkyl. In a further aspect, $R^{13}$ is hydrogen. In a further aspect, $R^{13}$ is C1-C6 alkyl. In a further aspect, $R^{13}$ is C1-C6 haloalkyl. In a further aspect, $R^{13}$ is C1-C6 polyhaloalkyl.

w. $R^{14}$ GROUPS

In one aspect, $R^{14}$ is selected from hydrogen, C1-C6 alkyl, C1-C6 haloalkyl, and C1-C6 polyhaloalkyl. In a further aspect, $R^{14}$ is selected from C1-C6 alkyl, C1-C6 haloalkyl, and C1-C6 polyhaloalkyl. In a further aspect, $R^{14}$ is hydrogen. In a further aspect, $R^{14}$ is C1-C6 alkyl. In a further aspect, $R^{14}$ is C1-C6 haloalkyl. In a further aspect, $R^{14}$ is C1-C6 polyhaloalkyl.

x. Integer Values (M and N)

In one aspect, m is an integer from 0-3. In a further aspect, m is an integer from 0-2. In a yet further aspect, m is an integer that is 0 or 1. In a still further aspect, m is 0. In an even further aspect, m is 1. In a yet further aspect, m is 2. In a still further aspect, m is 3. In an even further aspect, m is an integer from 1-3. In a yet further aspect, m is an integer from 2-3.

In one aspect, n is an integer from 0-3. In a further aspect, n is an integer from 0-2. In a yet further aspect, n is an integer that is 0 or 1. In a still further aspect, n is 0. In an even further aspect, n is 1. In a yet further aspect, n is 2. In a still further aspect, n is 3. In an even further aspect, n is an integer from 1-3. In a yet further aspect, n is an integer from 2-3.

y. Leaving Groups

In one aspect, X is halide or pseudohalide. In a further aspect, X is halogen, for example, fluoro, chloro, bromo, or iodo. In a further aspect, X is chloro, bromo, or iodo. In a further aspect, X is bromo or iodo. In a further aspect, X is chloro. In one aspect, X is pseudohalide, for example, triflate, mesylate, tosylate, or brosylate. In a further aspect, X is a group capable of undergoing a transition-metal mediated coupling reaction.

2. Example Compounds

In one aspect, a compound of Formula I can be present as one or more of the following structures:

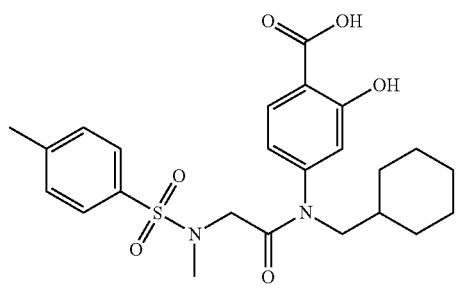

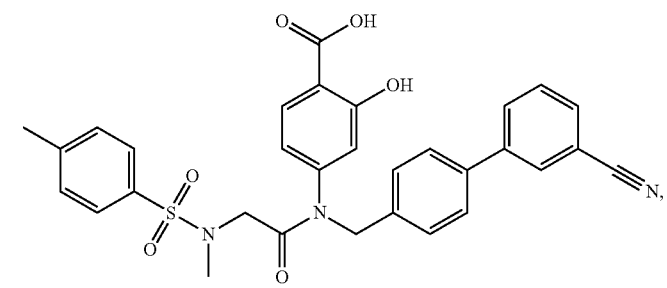

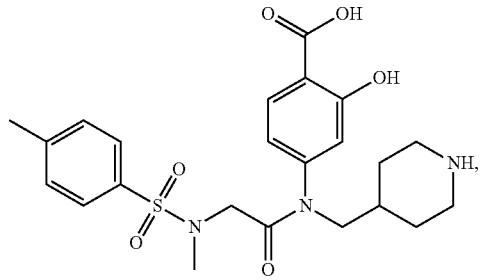

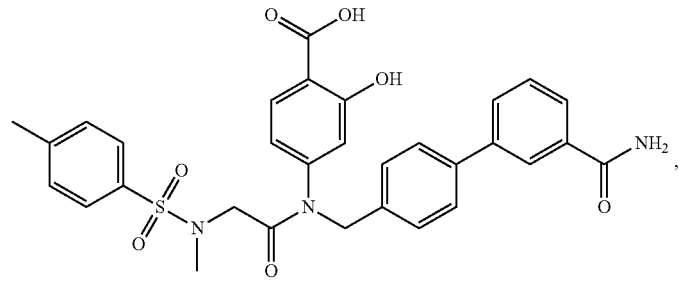

-continued
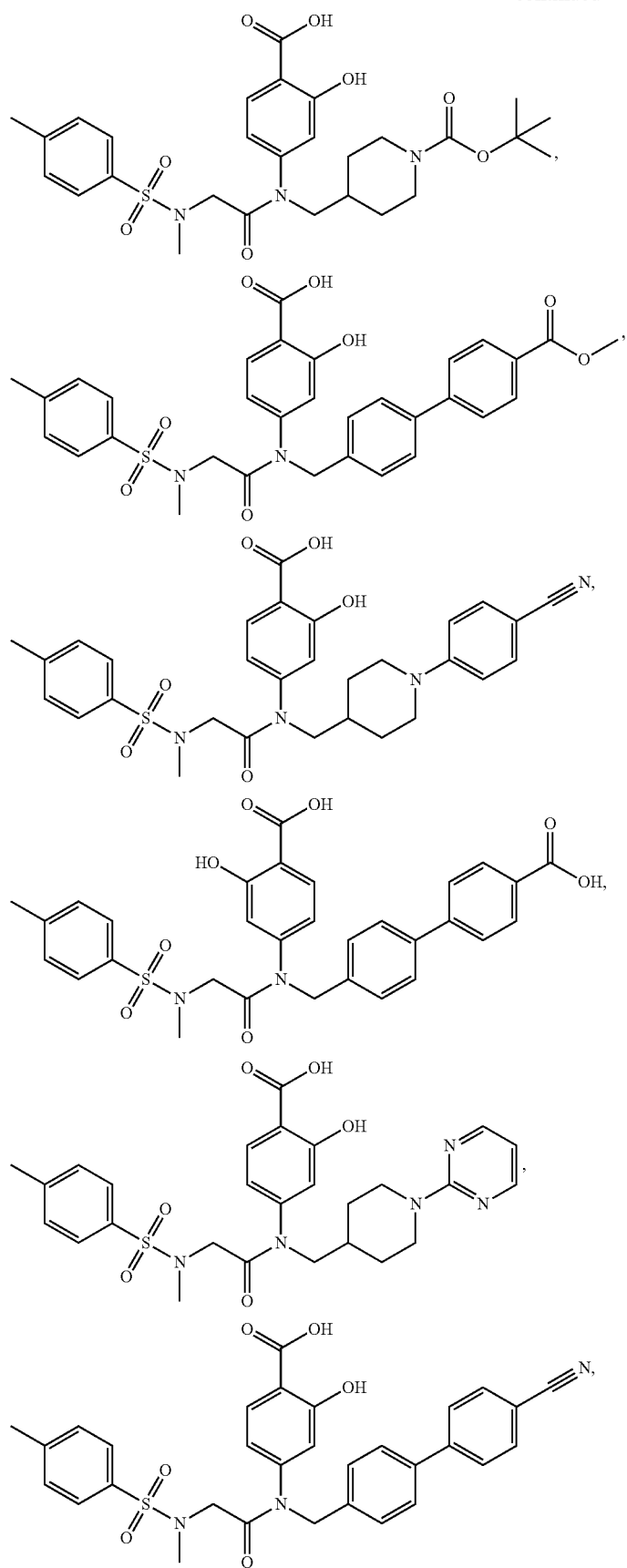

-continued
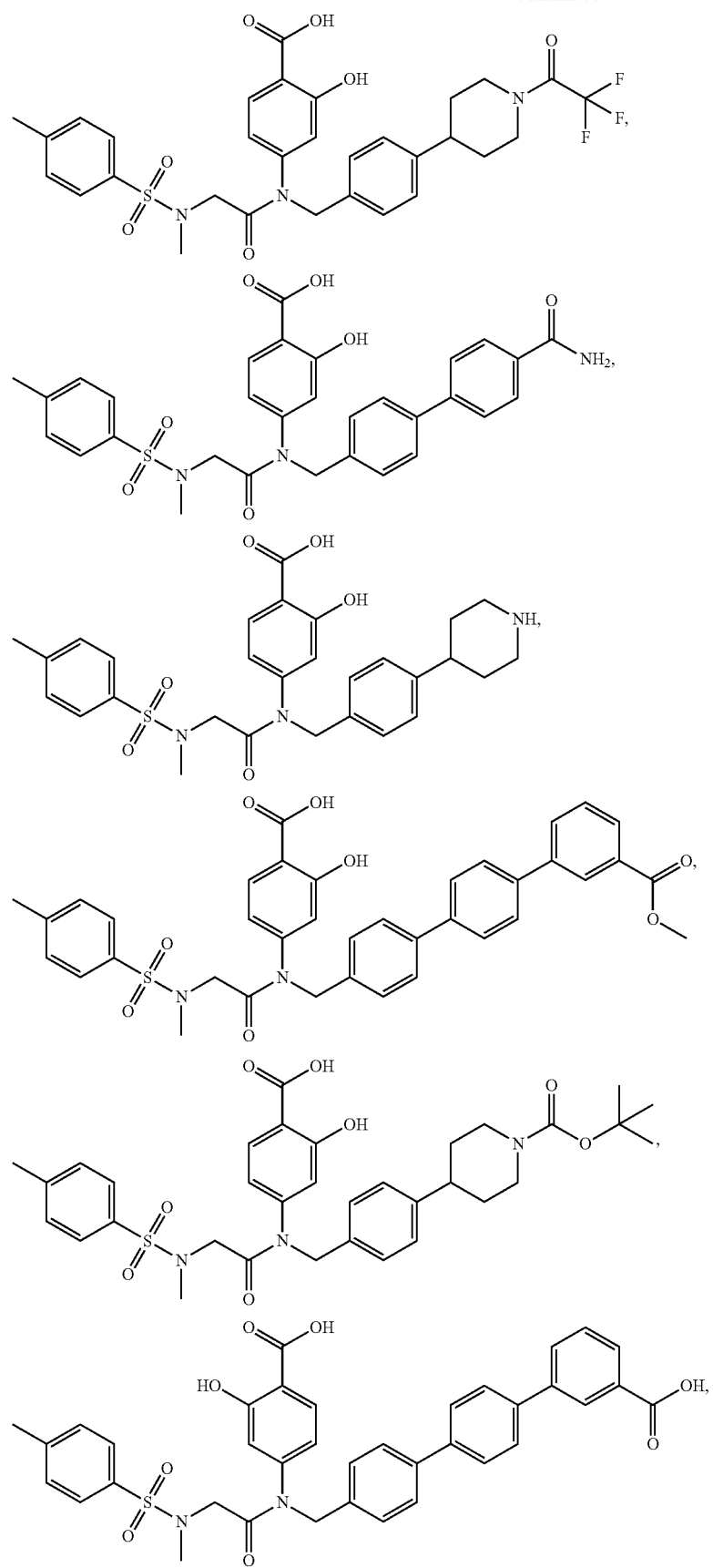

-continued
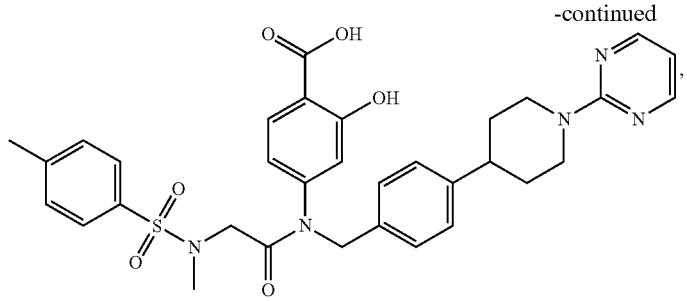
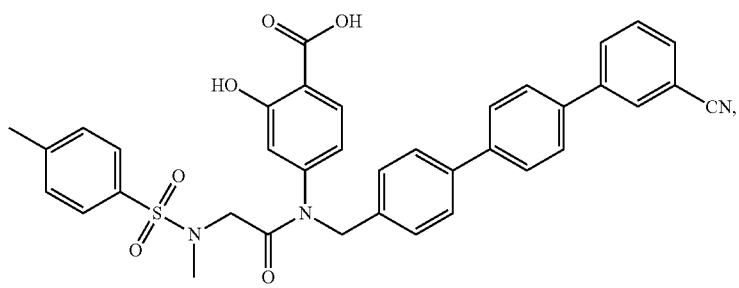
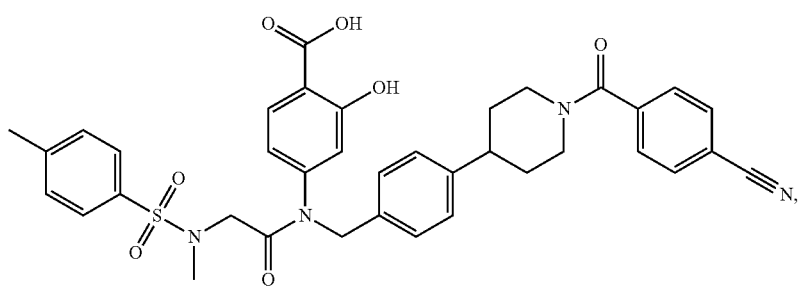
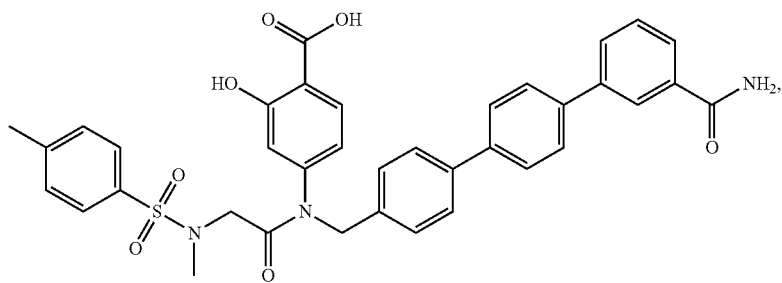
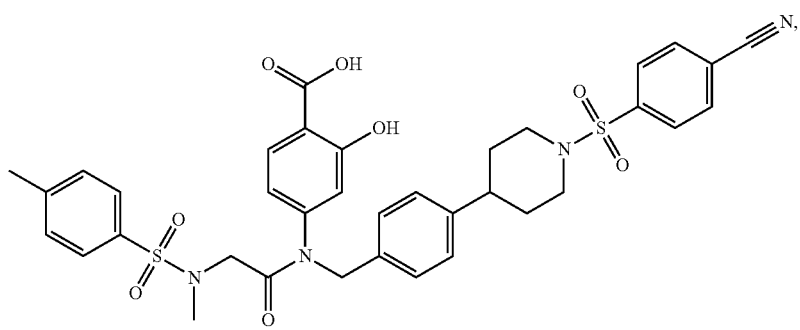

-continued
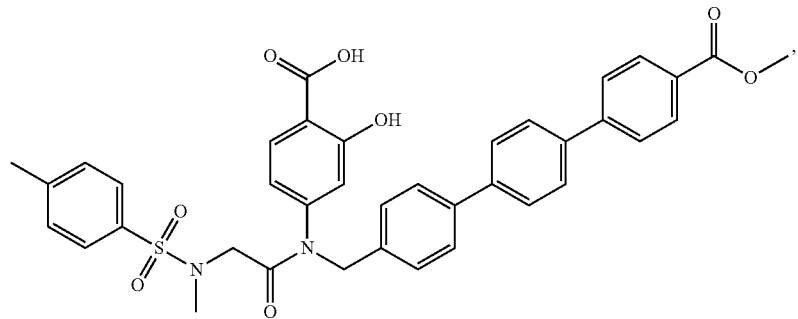
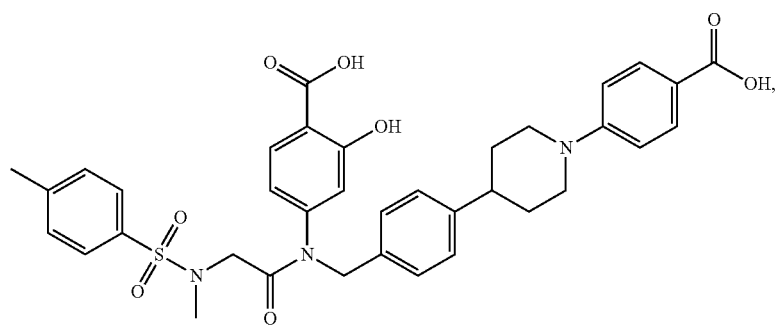
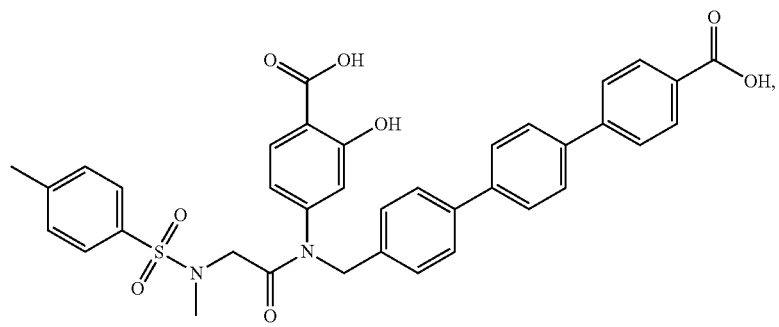
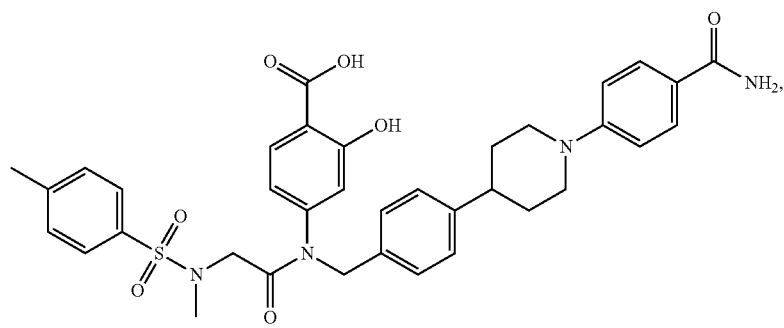
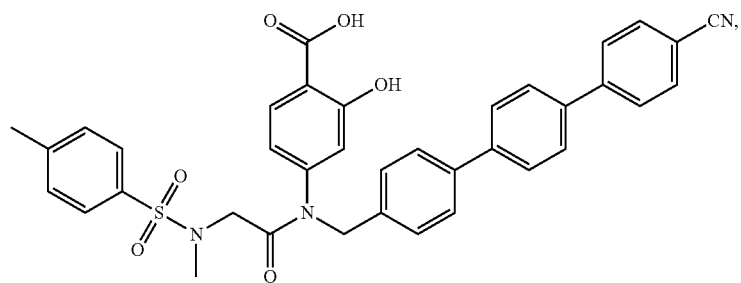

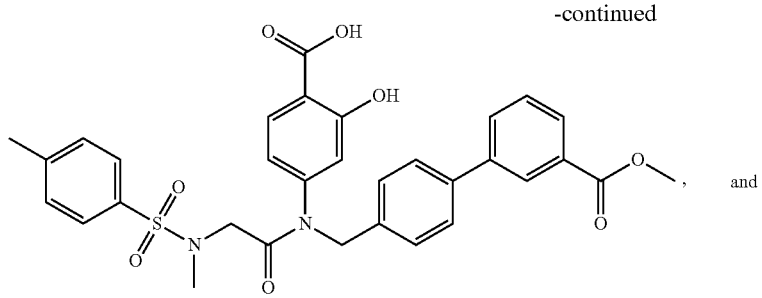
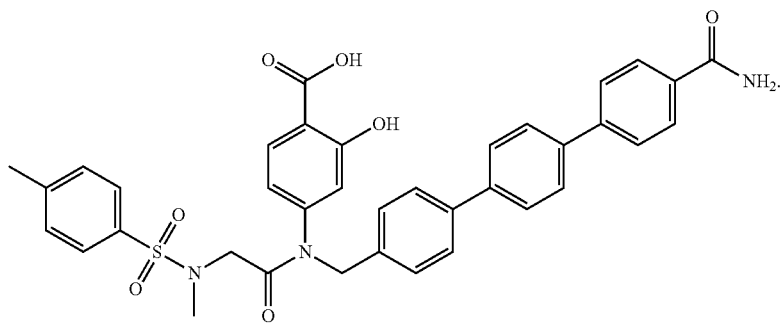
In one aspect, a compound of Formula I can be present as one or more of the following structures:
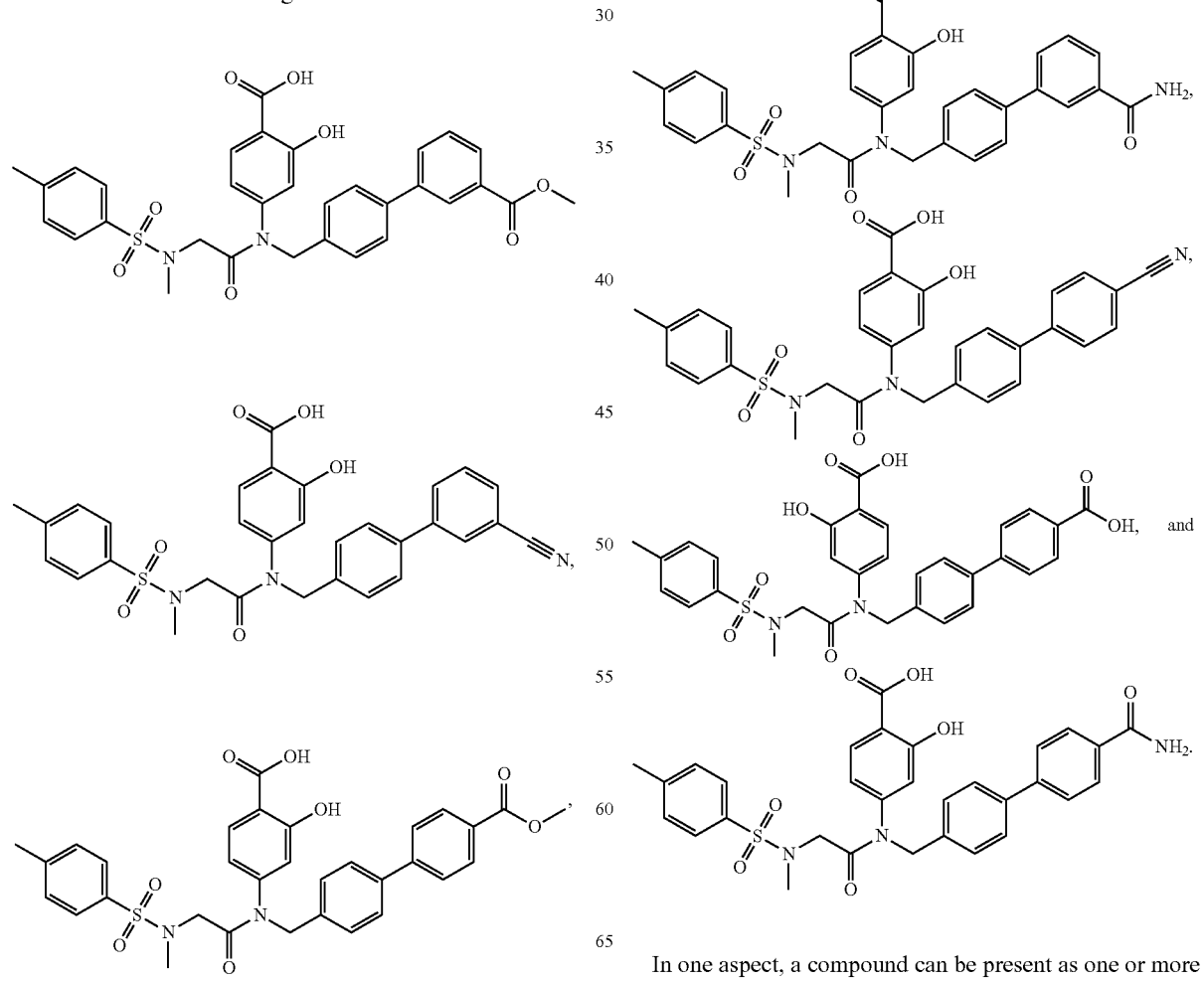
In one aspect, a compound can be present as one or more of the following structures:

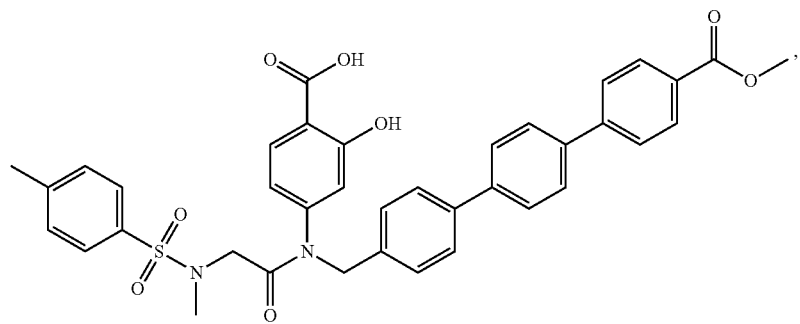
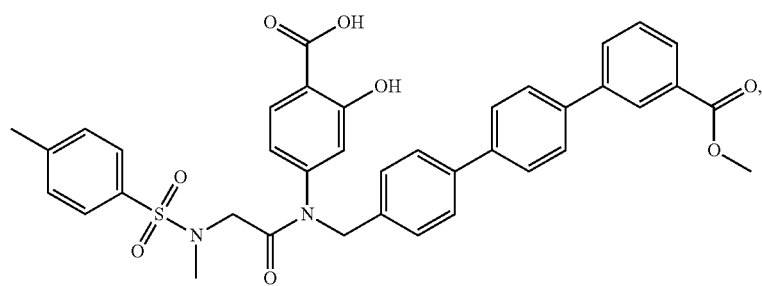
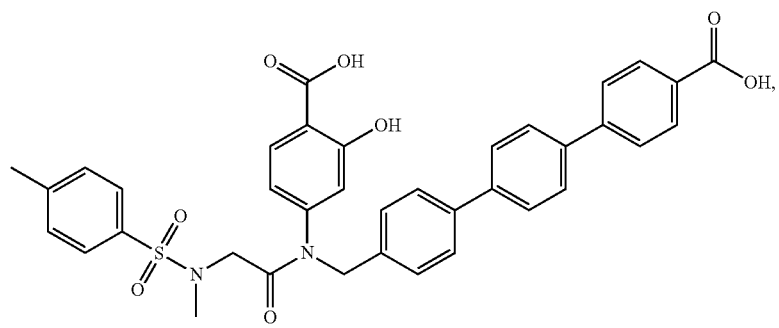
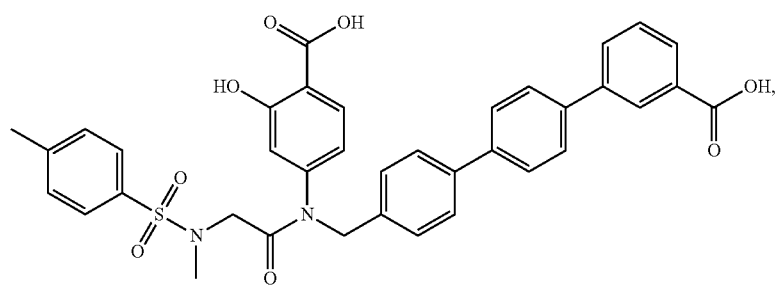
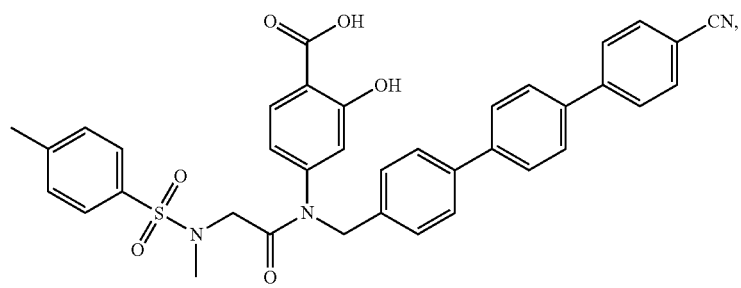

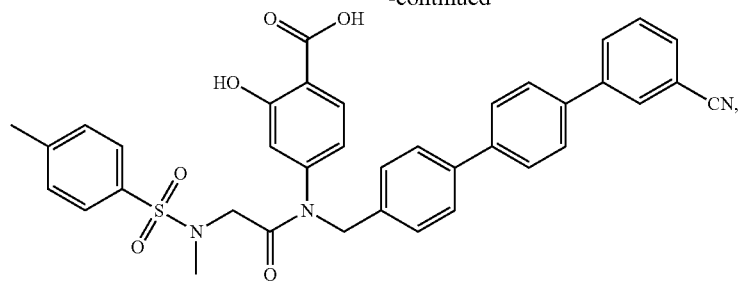
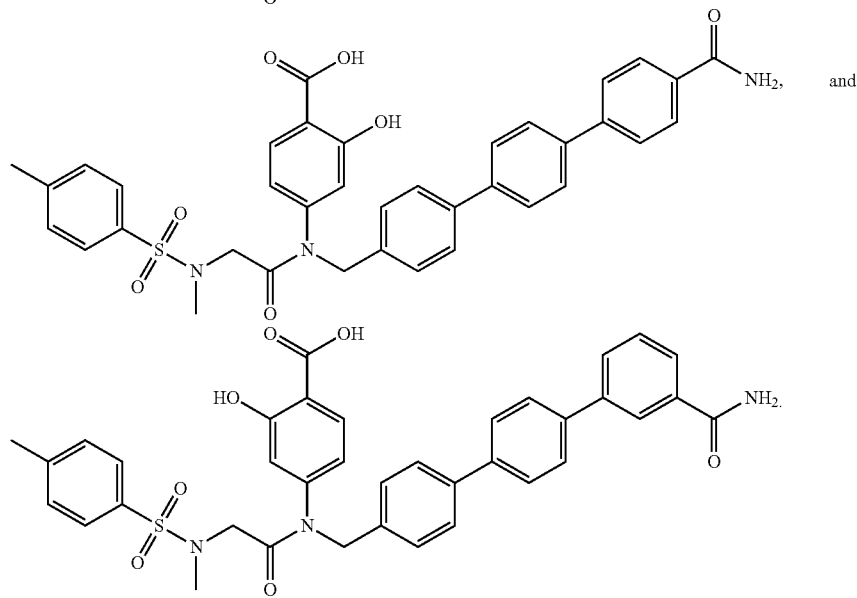
In one aspect, a compound of Formula II can be present as one or more of the following structures:
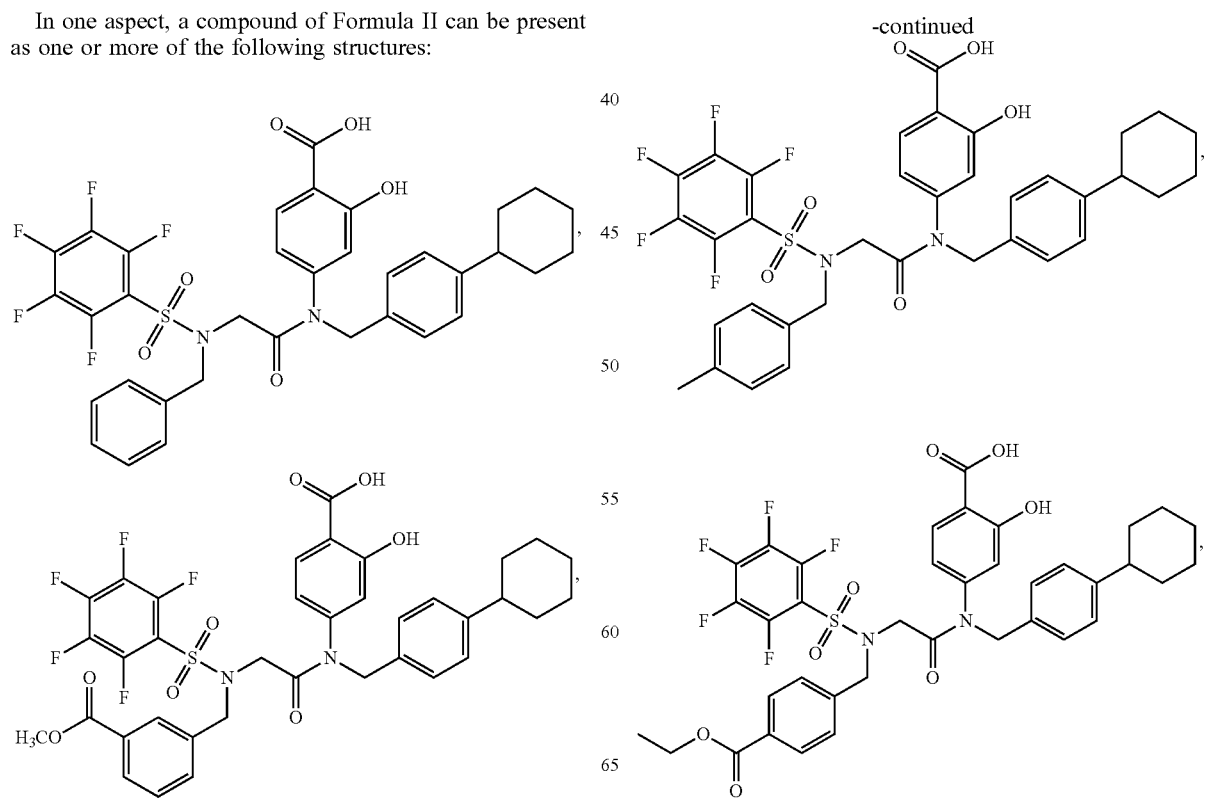

99
-continued
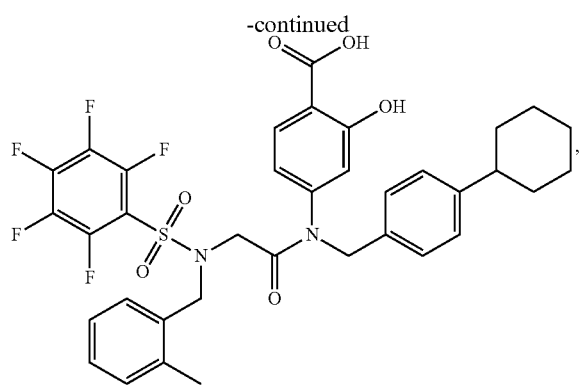
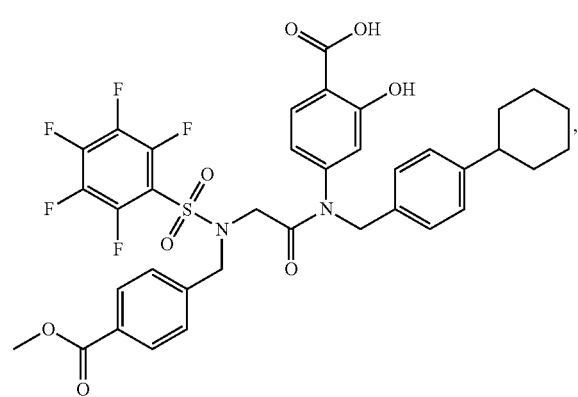
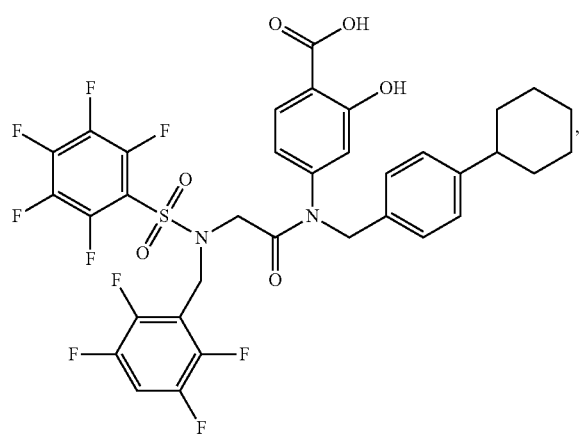
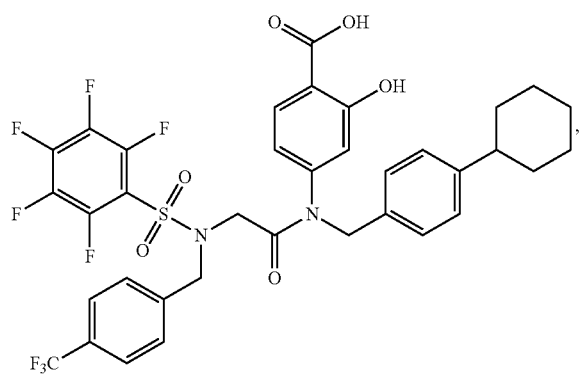
100
-continued
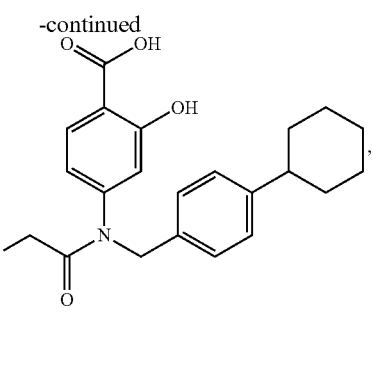
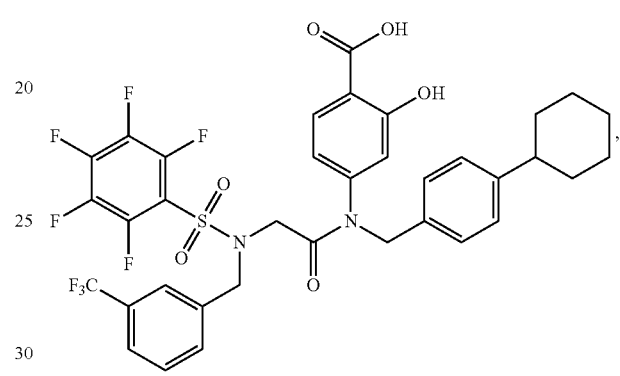
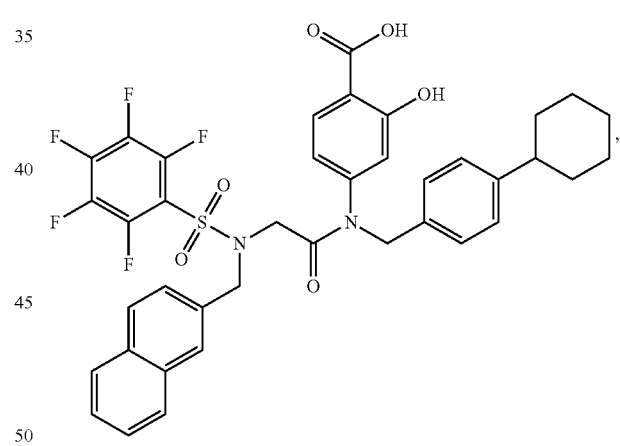
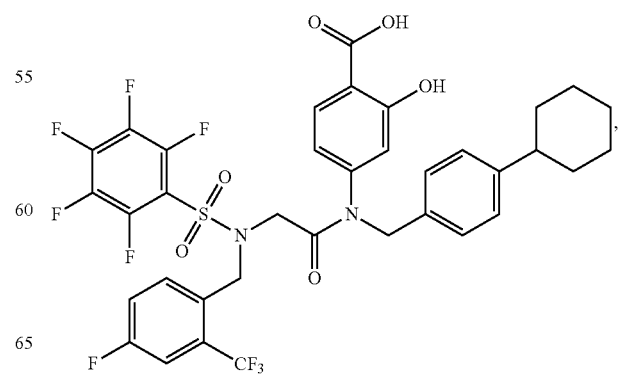

-continued
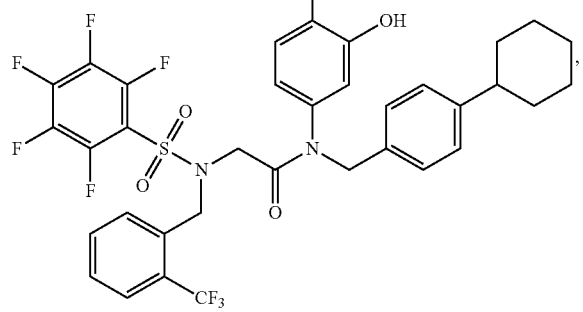
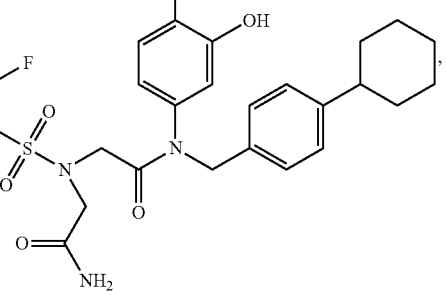
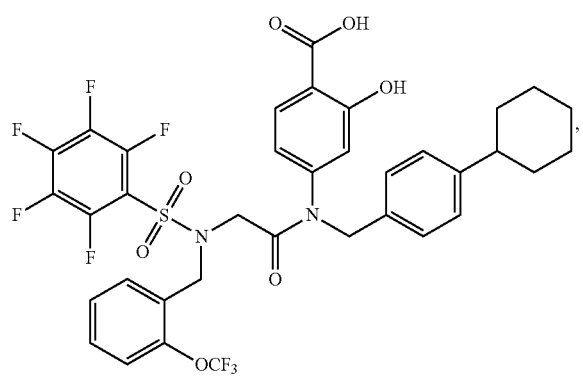
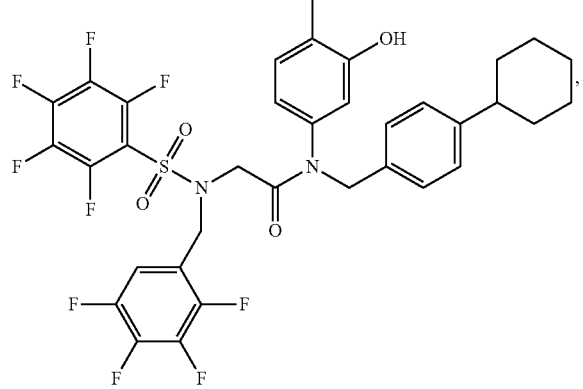
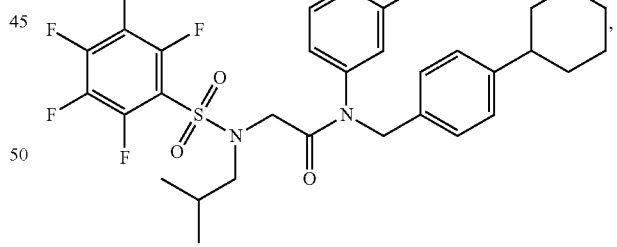
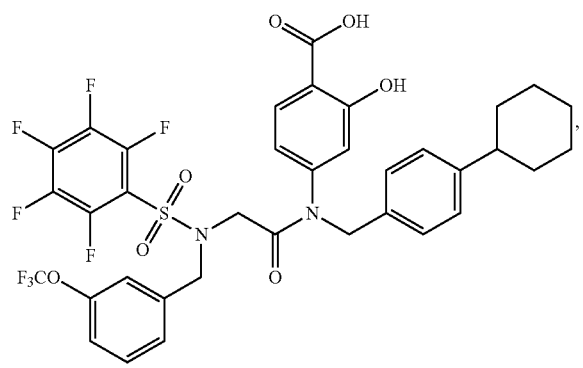 [SMILES: O=C(O)c1ccc(N(Cc2ccc(C3CCCCC3)cc2)C(=O)CN(Cc2cccc([N+](=O)[O-])c2)S(=O)(=O)c2c(F)c(F)c(F)c(F)c2F)cc1O]

103
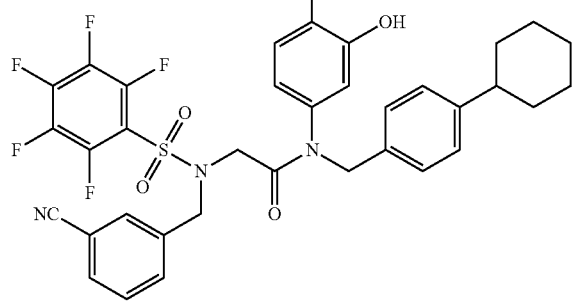
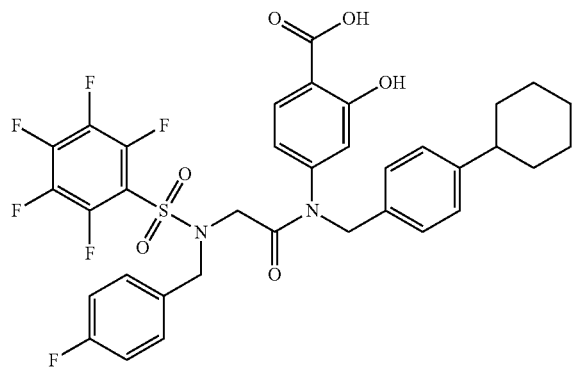
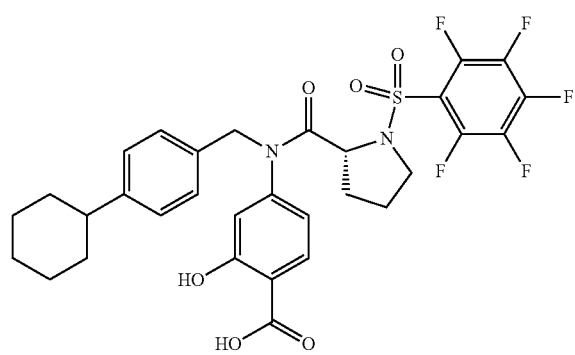
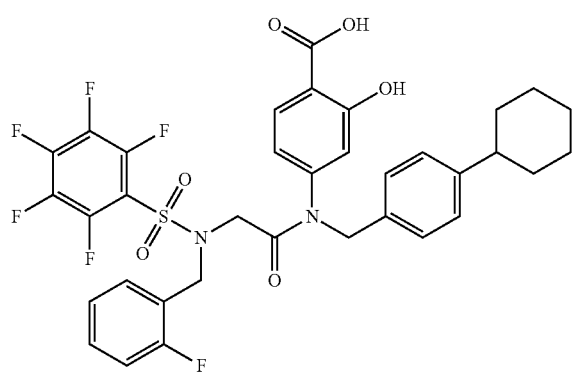
104
-continued
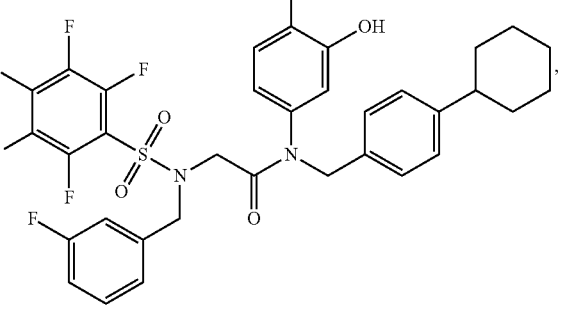
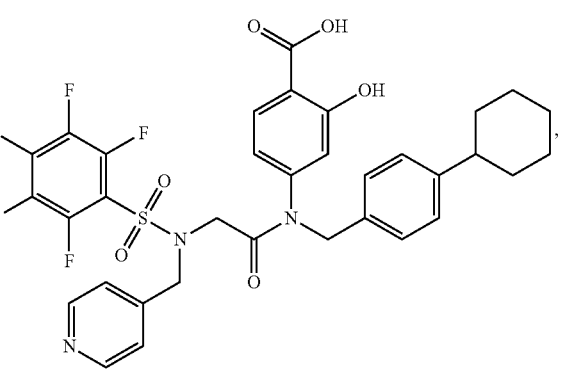
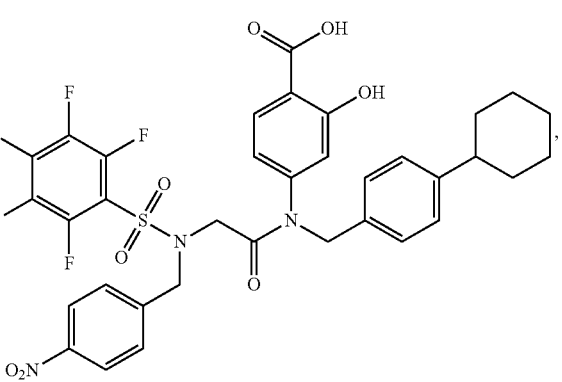
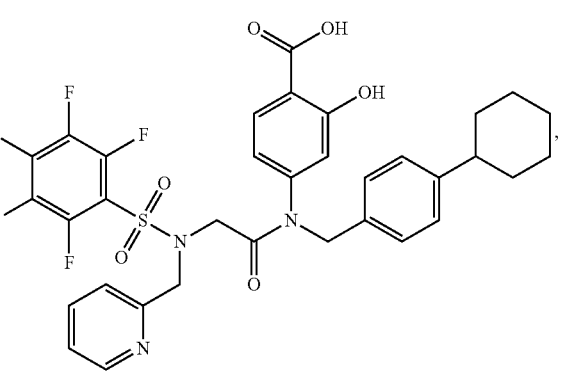

105
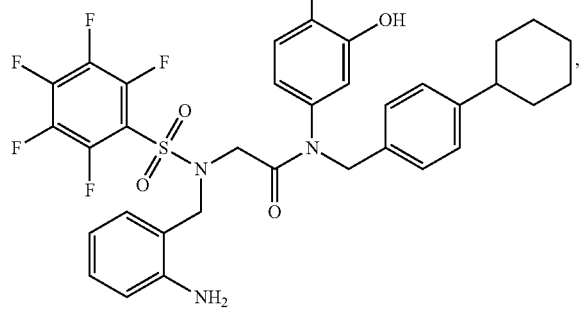
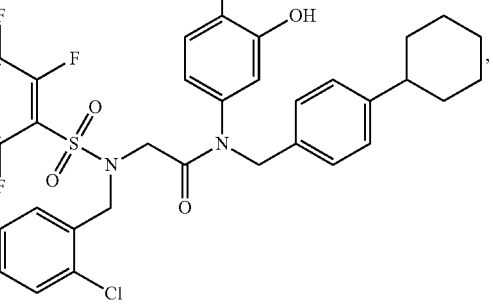
106
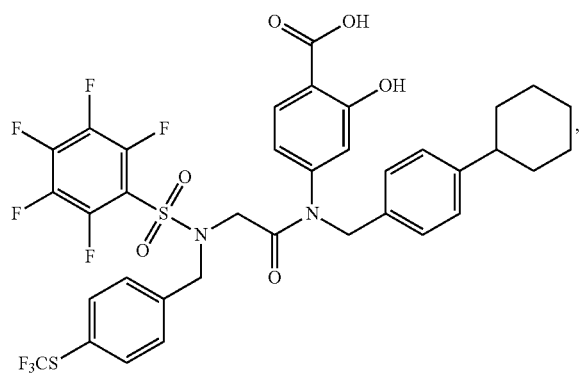
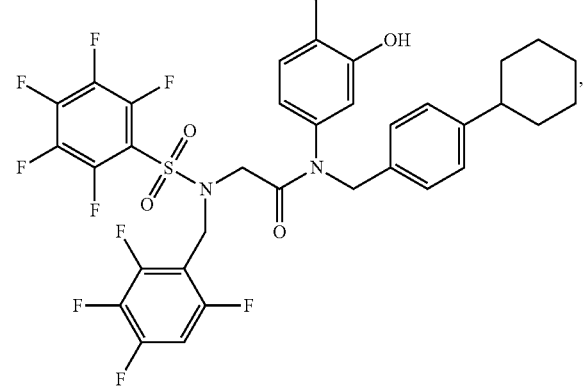
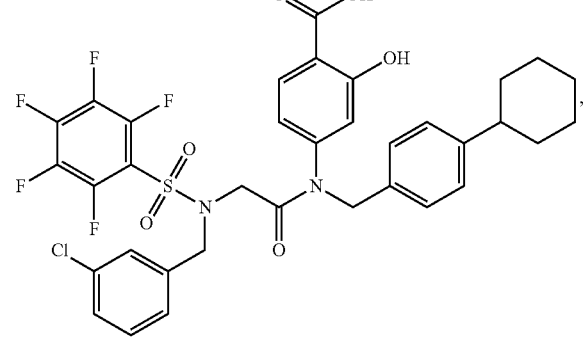
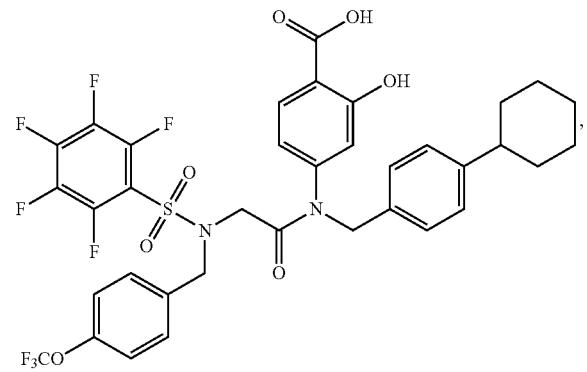

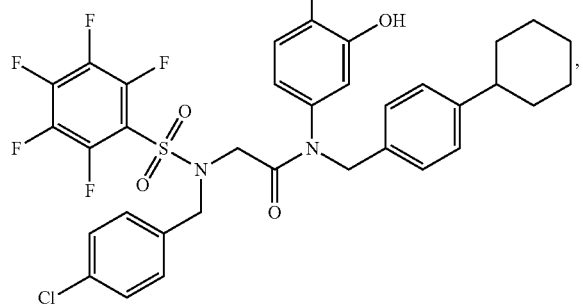
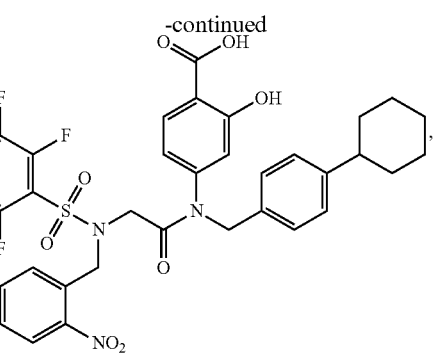
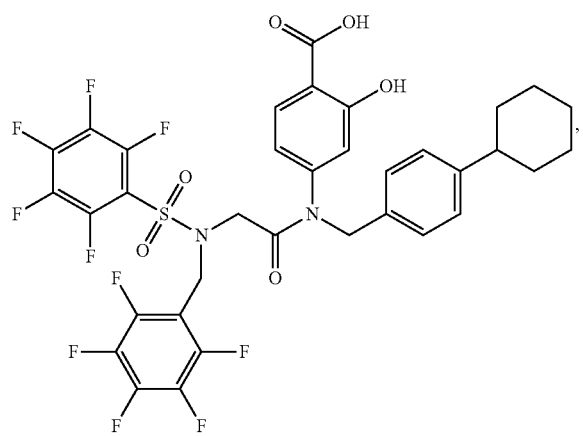
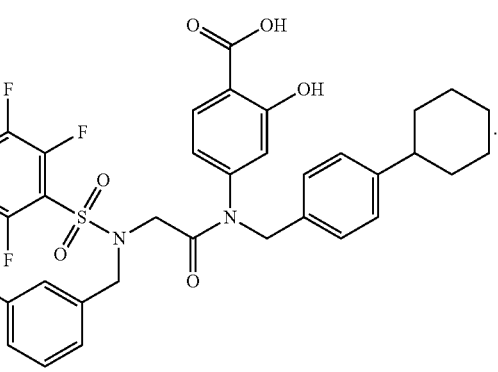
In one aspect, a compound of Formula II can be present as one or more of the following structures:
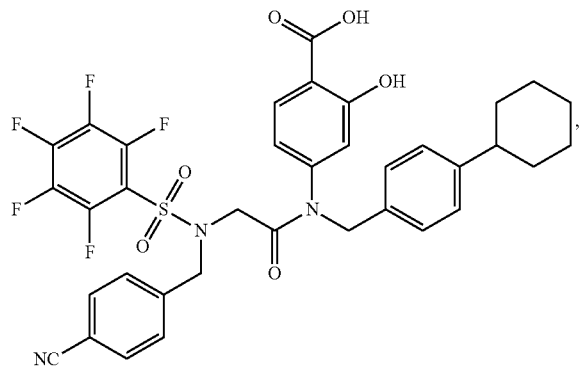
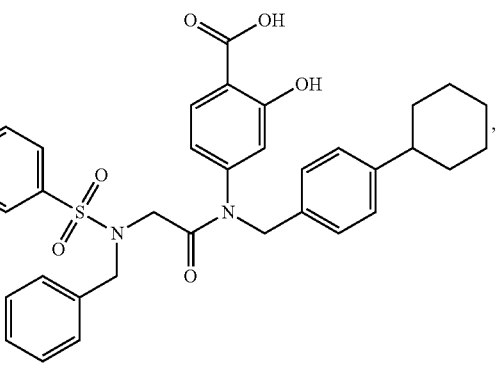
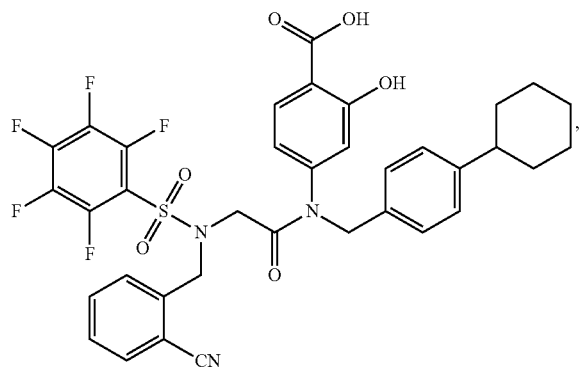
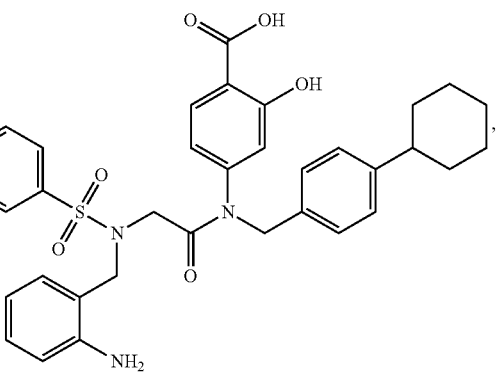

109
-continued
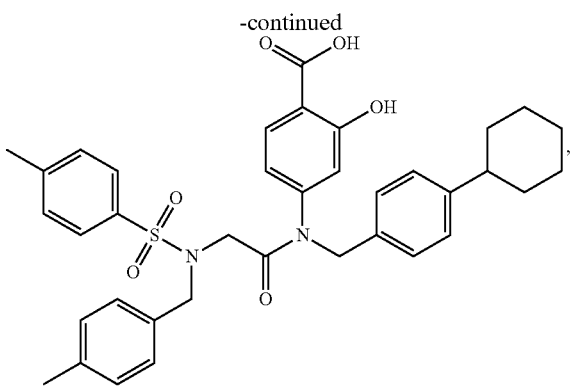
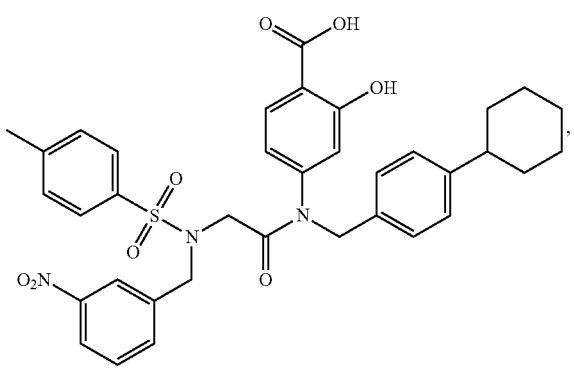
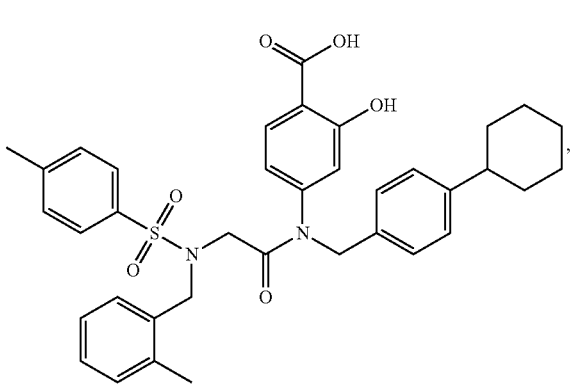
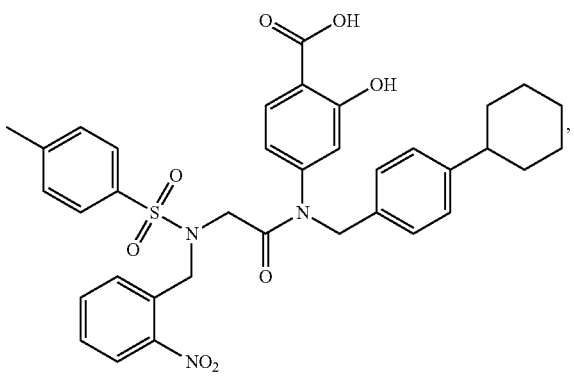
110
-continued
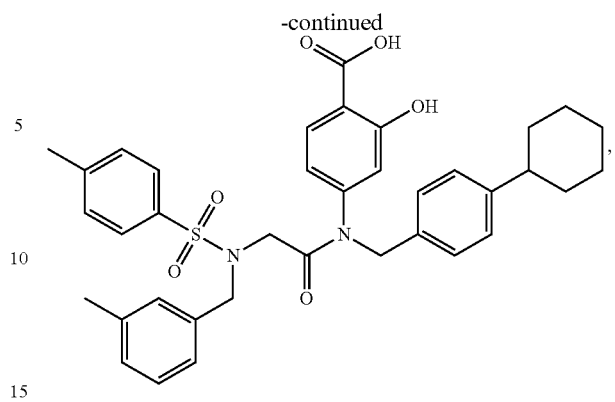
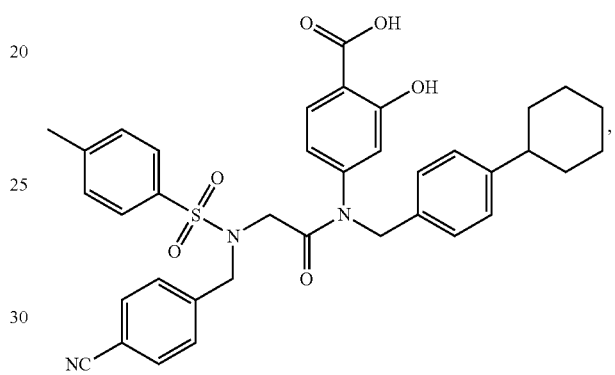
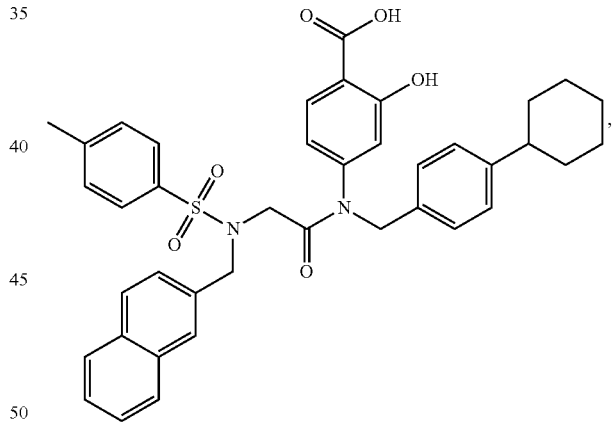
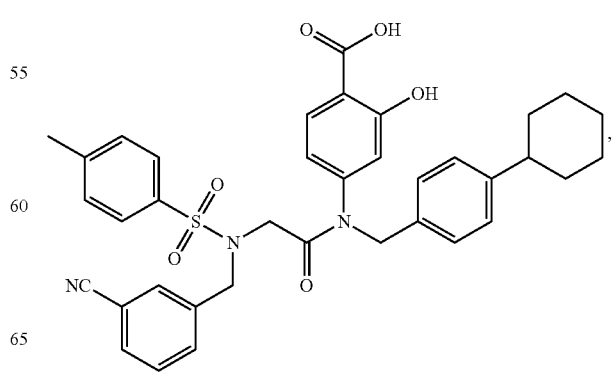

111
-continued
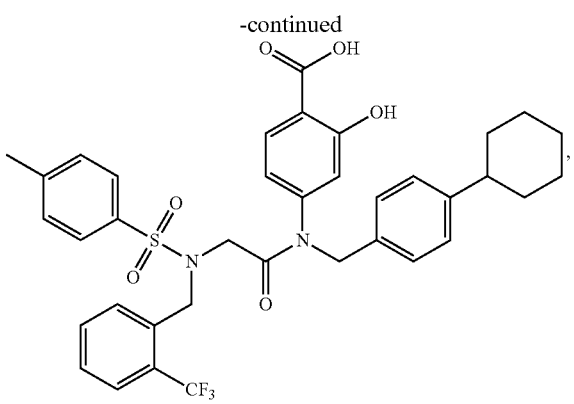
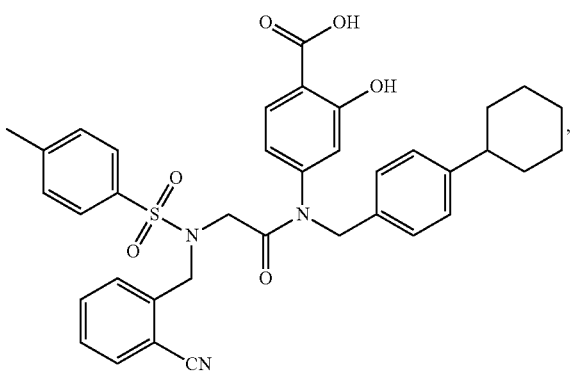
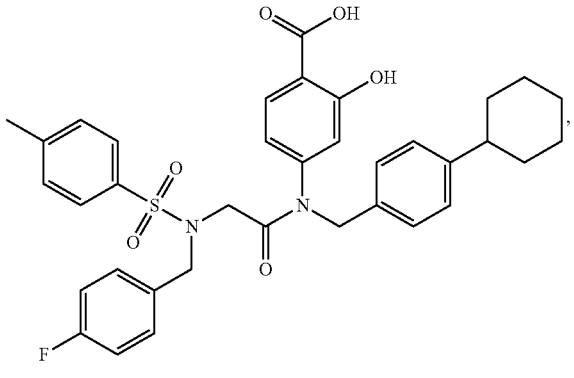
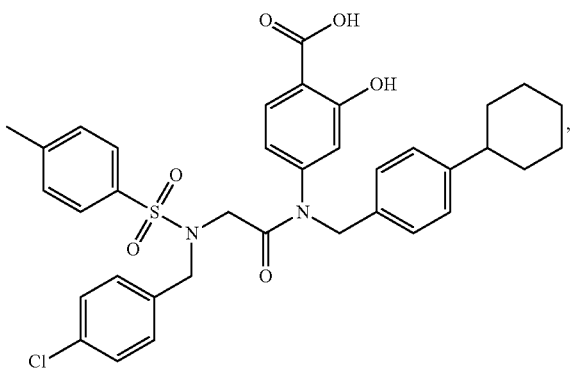
112
-continued
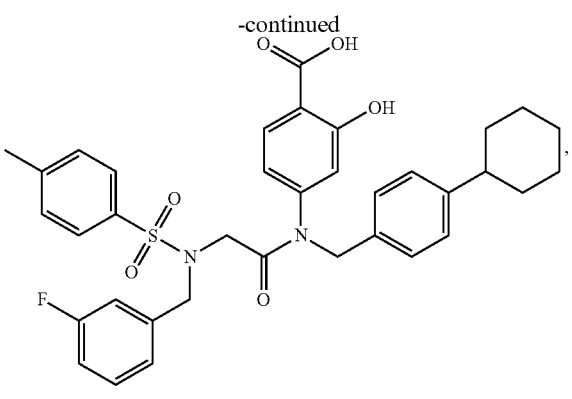
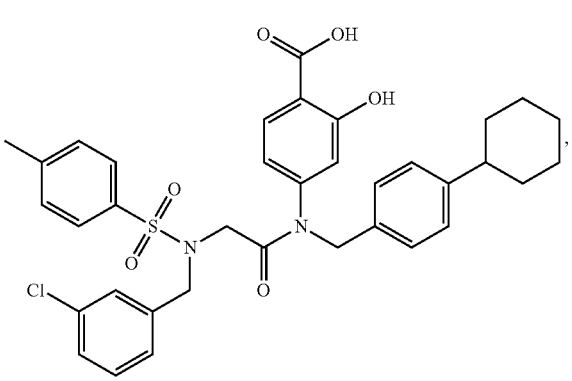
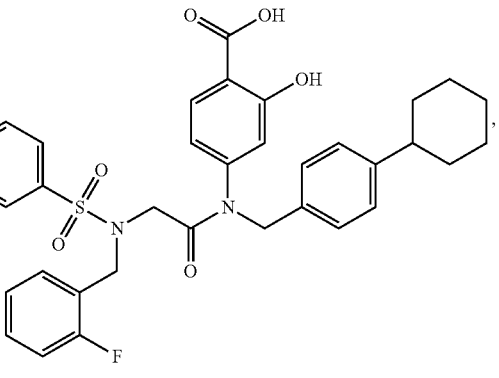
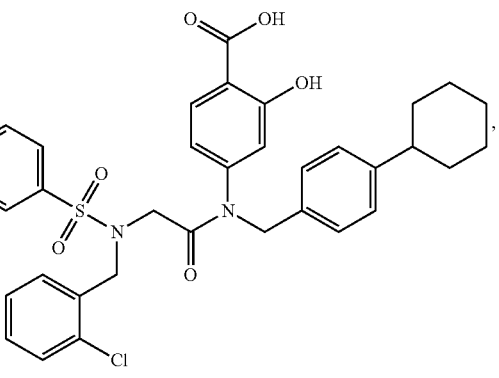

113
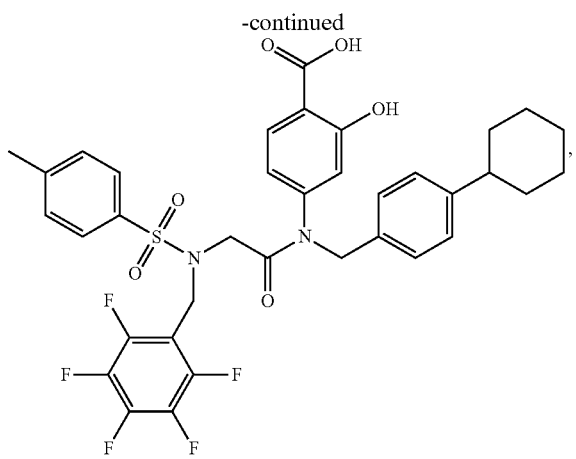
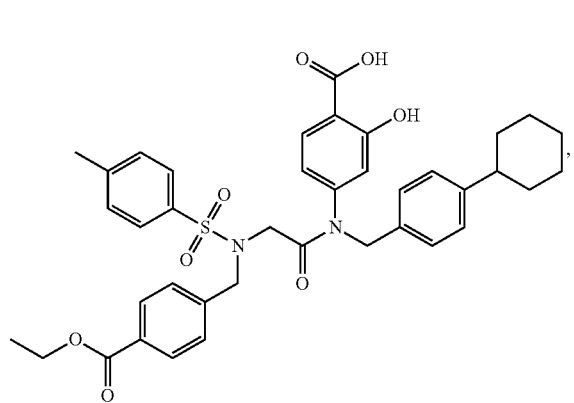
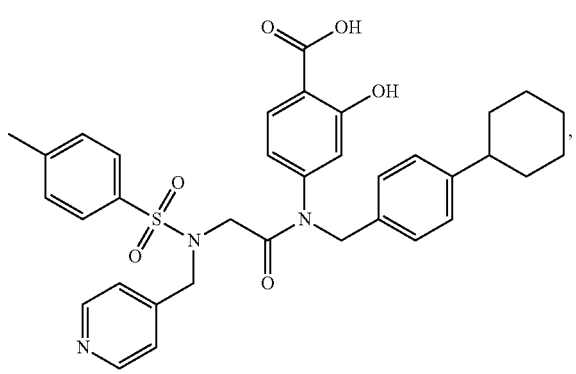
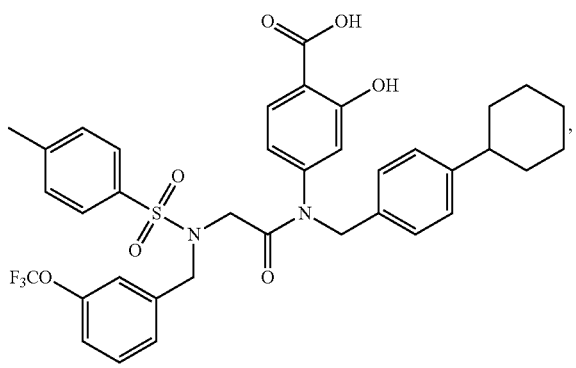
114
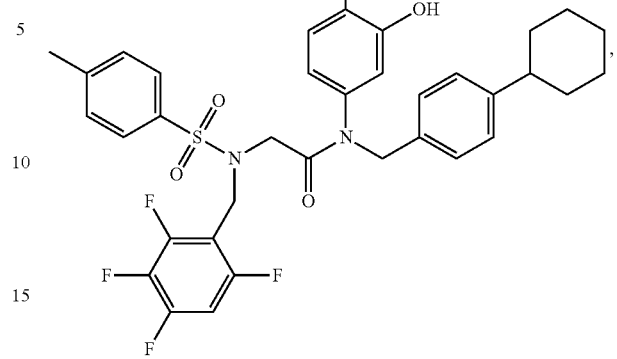
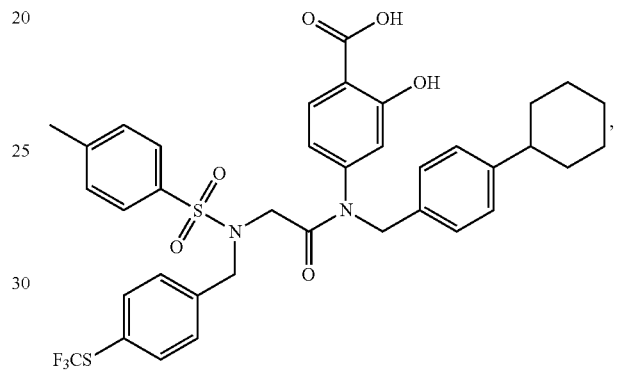
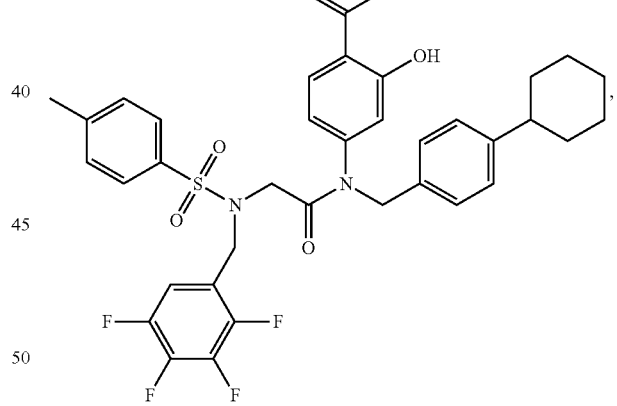
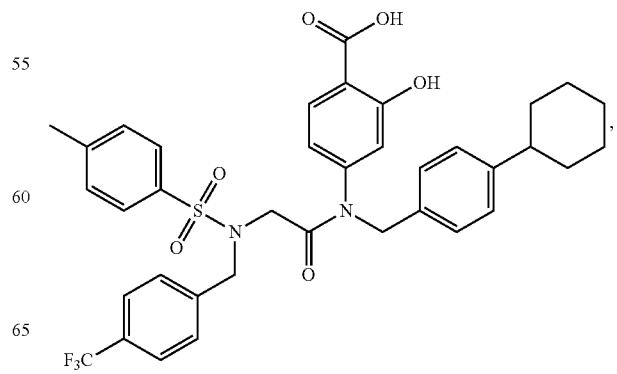

115
-continued
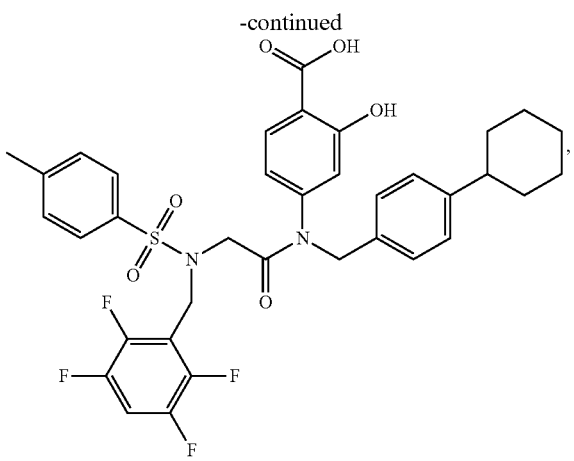
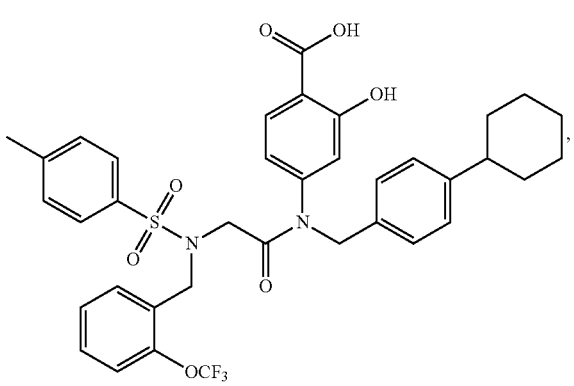
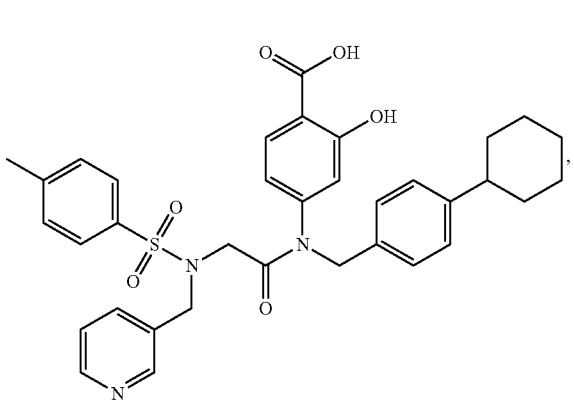
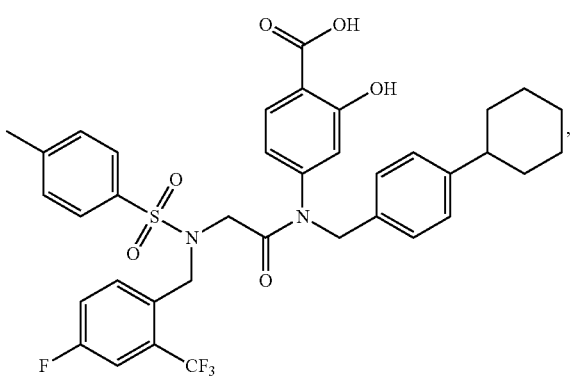 [SMILES: Cc1ccc(S(=O)(=O)N(CC(=O)N(Cc2ccc(C3CCCCC3)cc2)c2ccc(C(=O)O)c(O)c2)Cc2ccc(OC(F)(F)F)cc2)cc1]
116
-continued
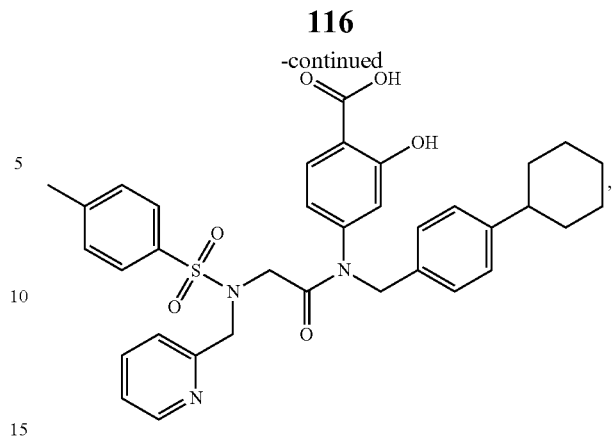
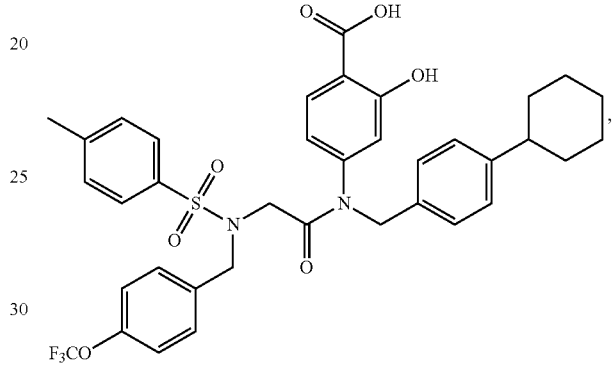
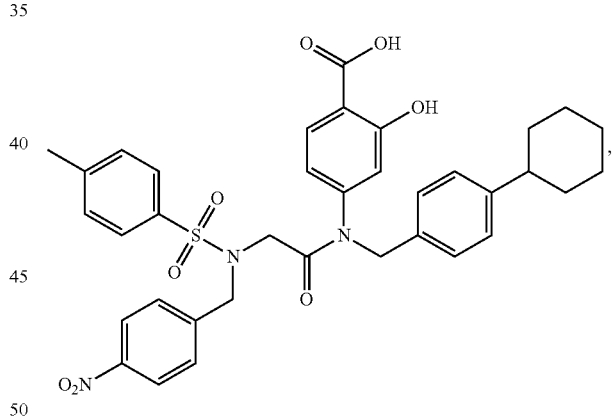
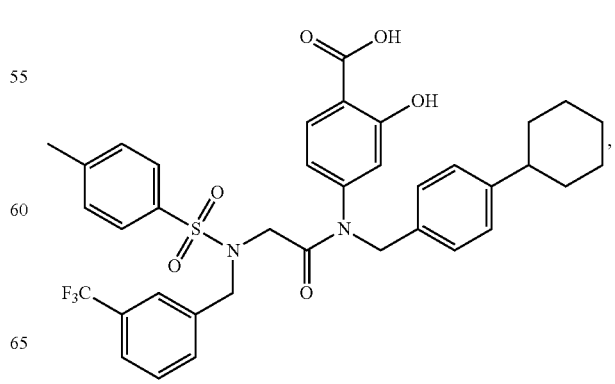

117
-continued
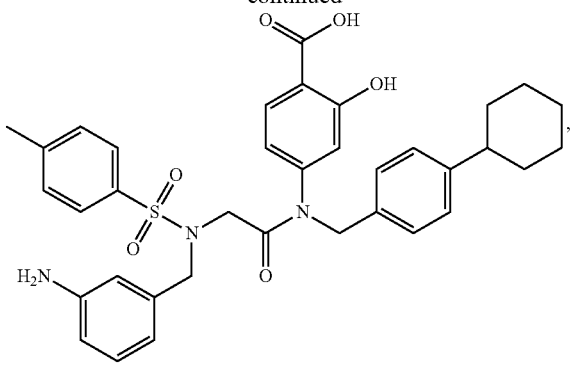
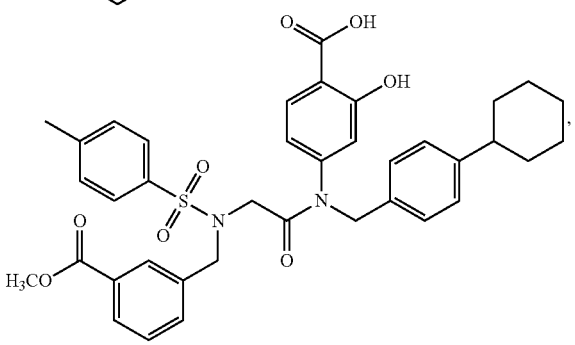
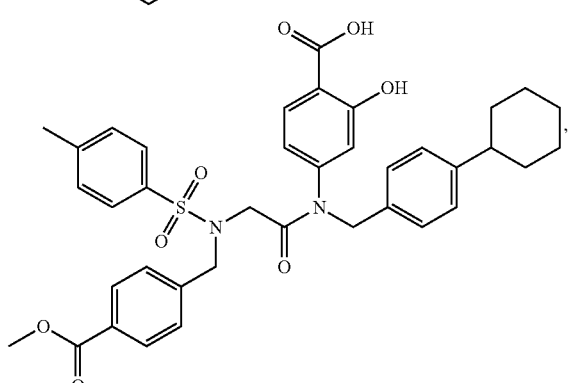
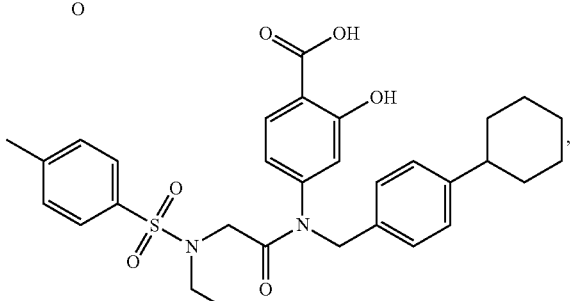
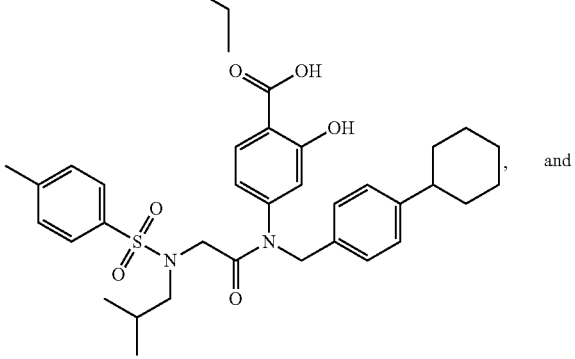
and
118
-continued
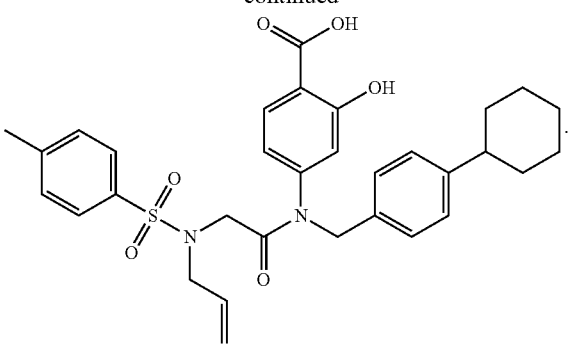
In one aspect, a compound of Formula II can be present as one or more of the following structures:
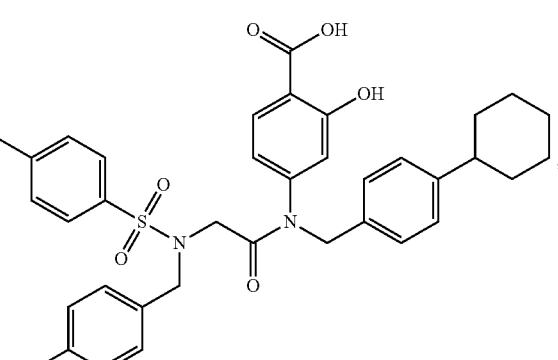
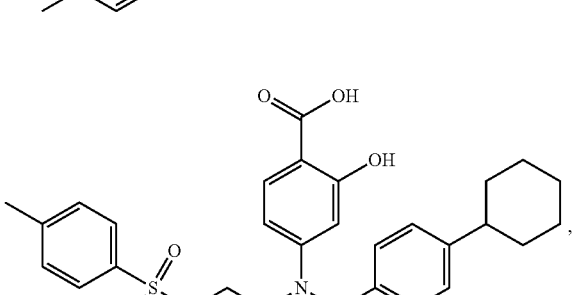
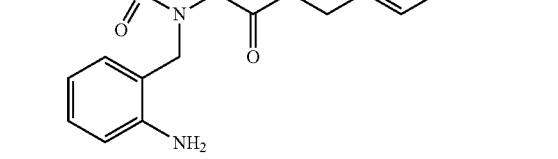
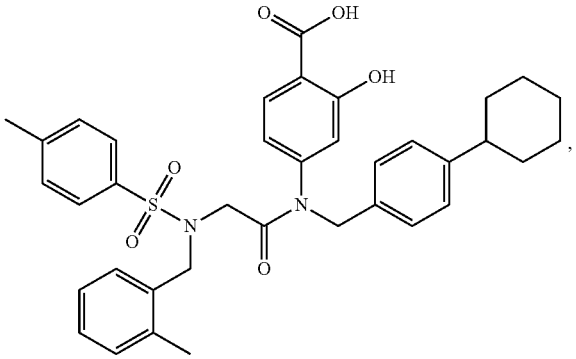

119
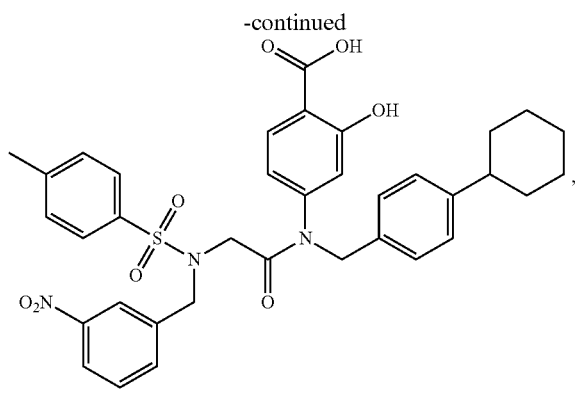
120
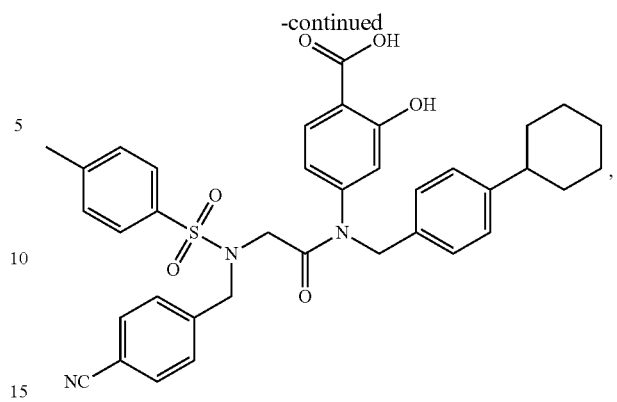
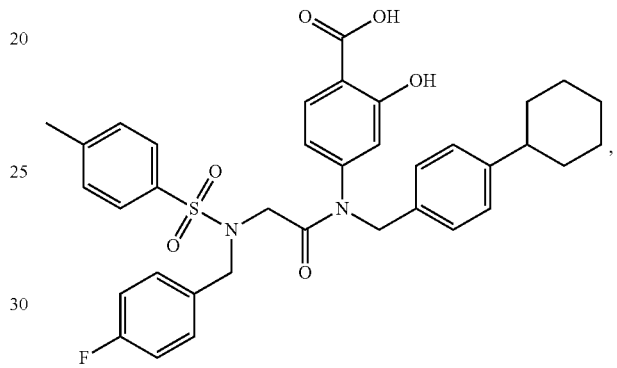
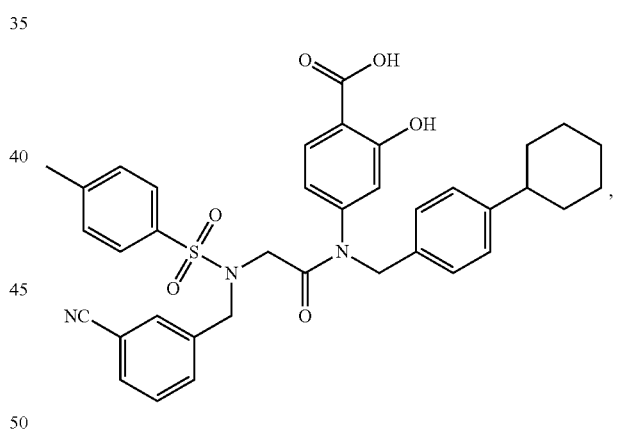
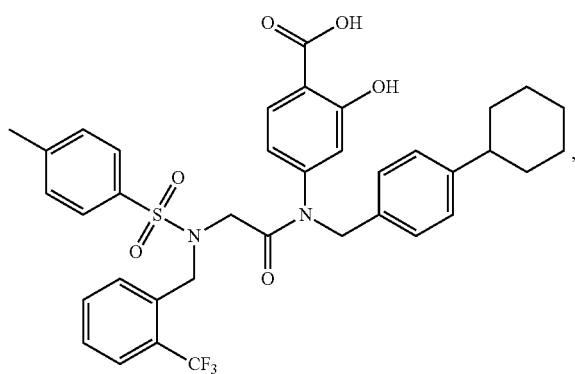
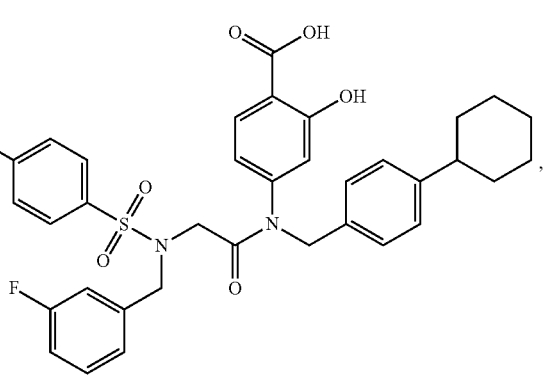

121
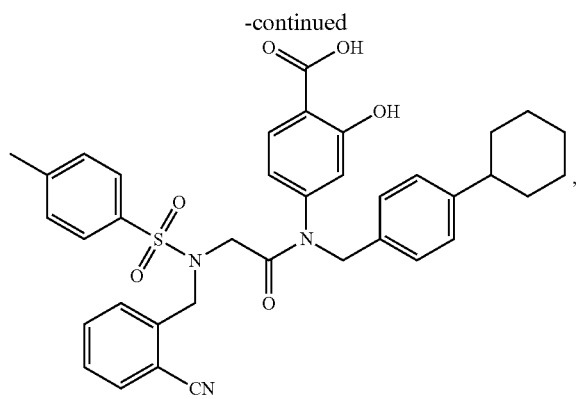
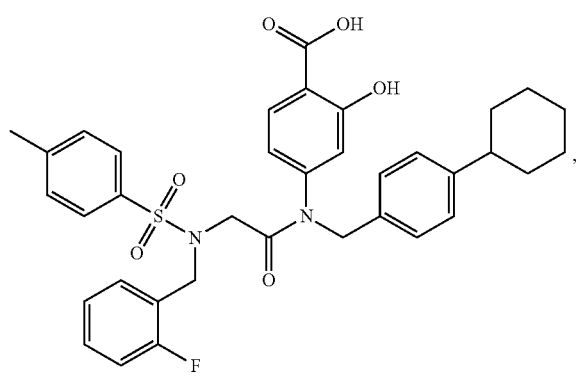
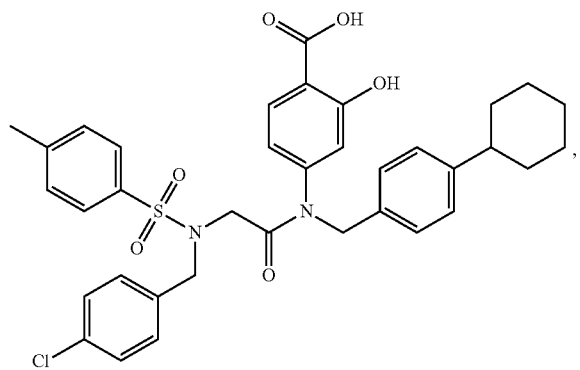
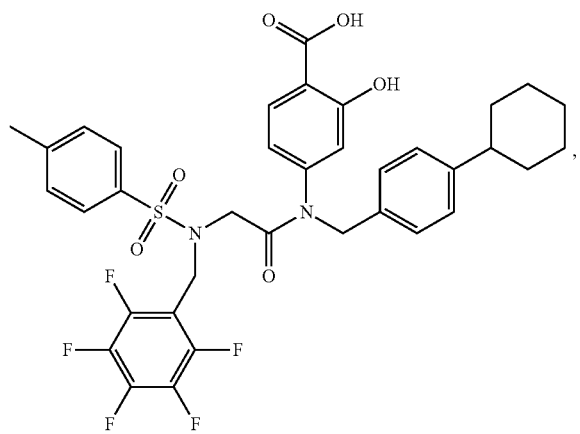
122
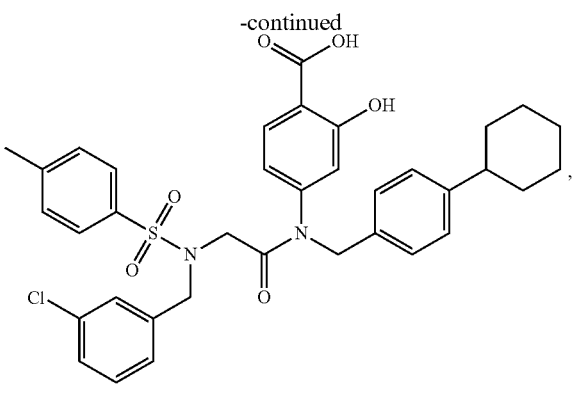
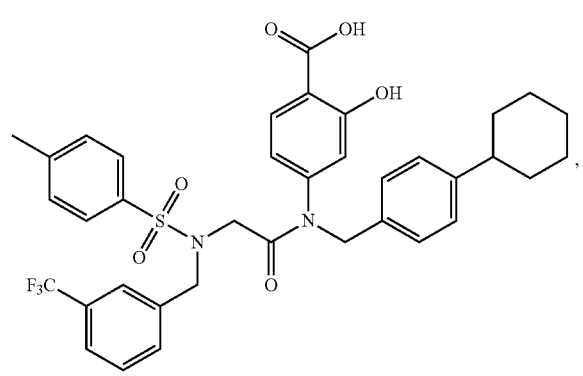
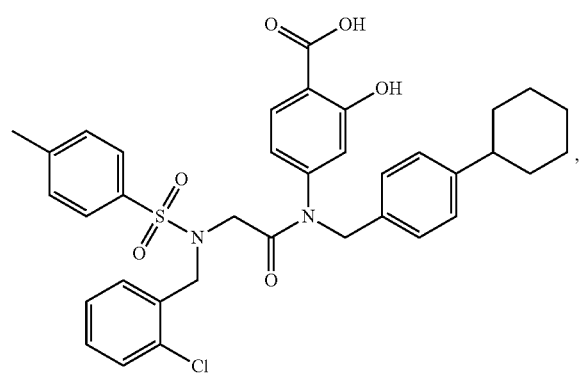
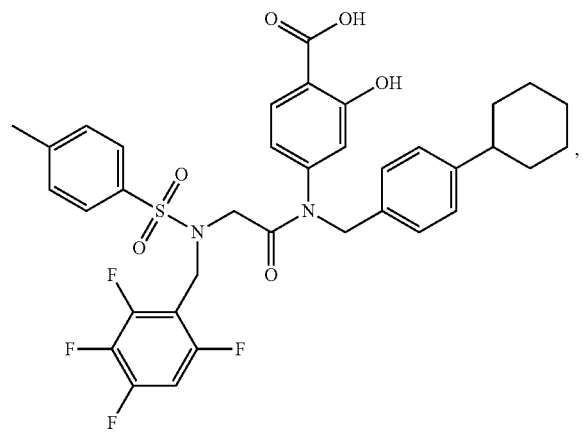

123
-continued
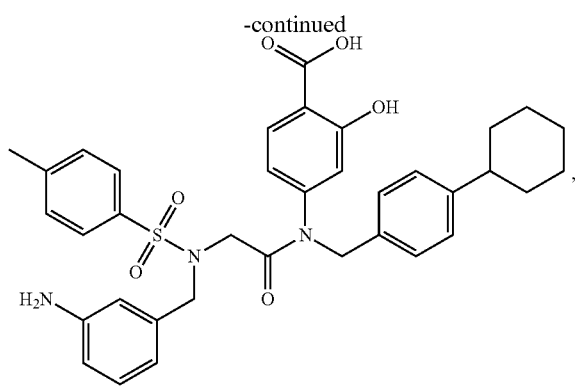
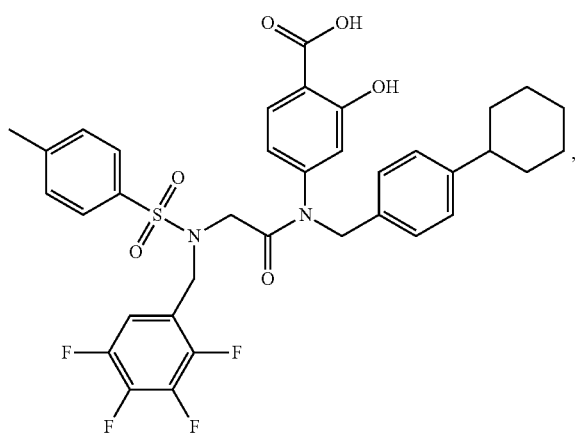
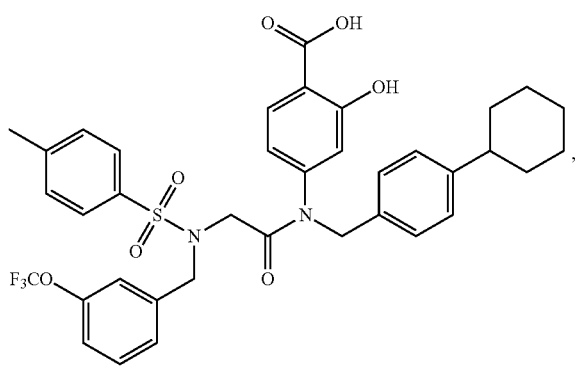
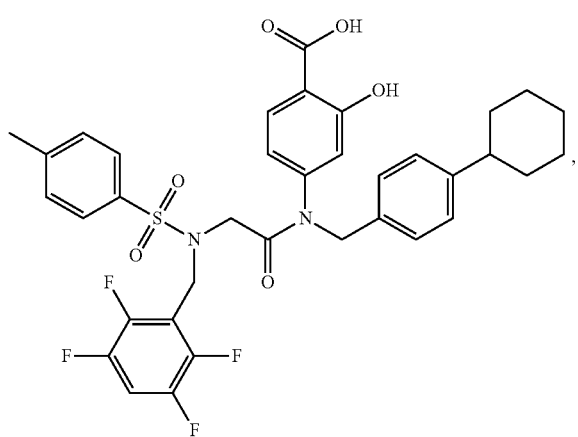
124
-continued
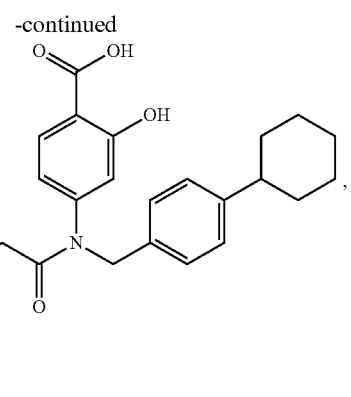
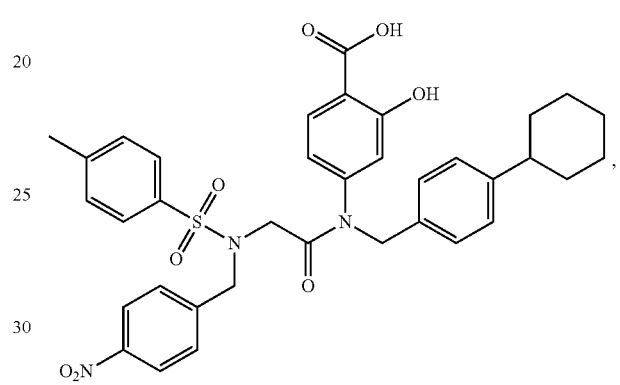
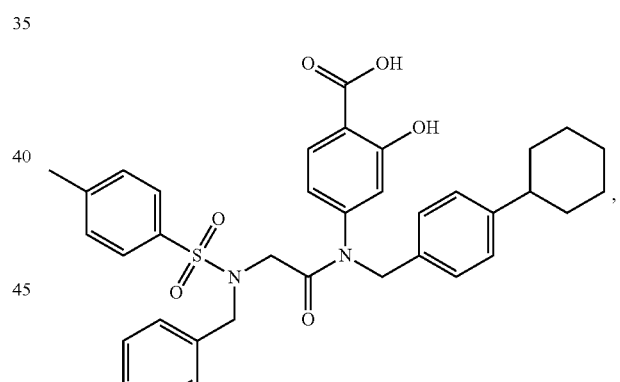
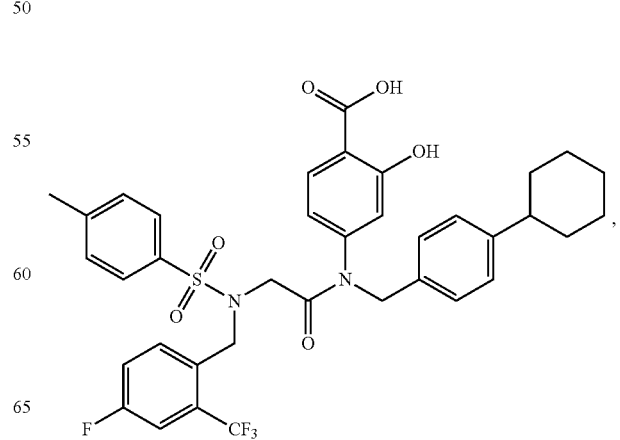

125
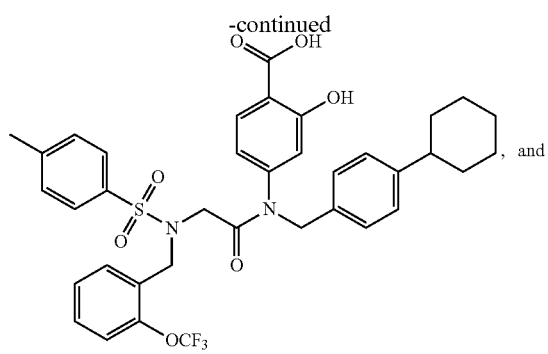, and
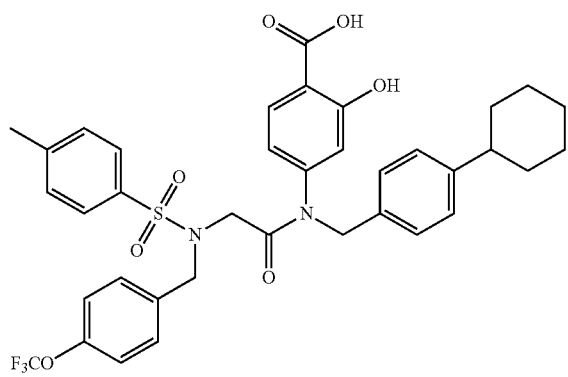
In one aspect, a compound of Formula II can be present as one or more of the following structures:
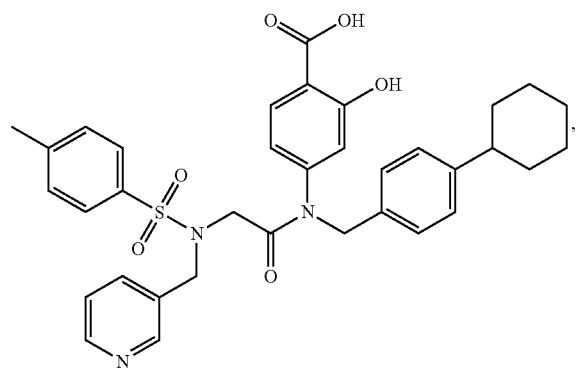,
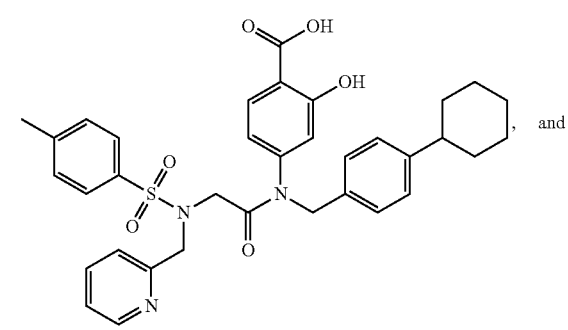, and
126
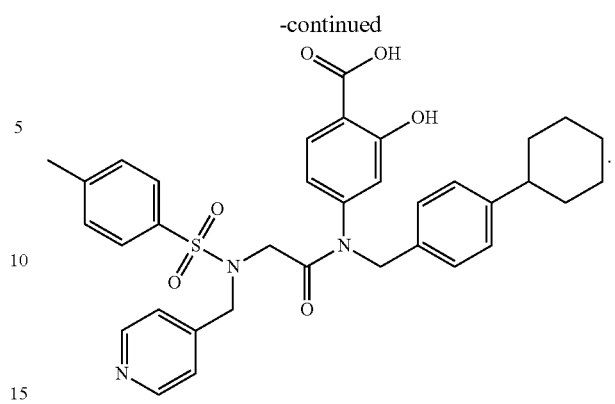
In one aspect, a compound of Formula II can be present as one or more of the following structures:
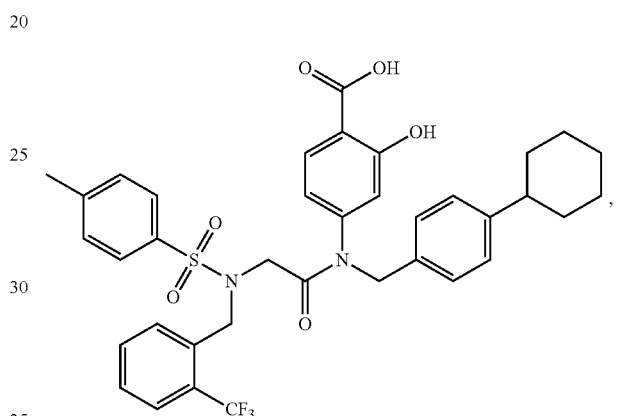,
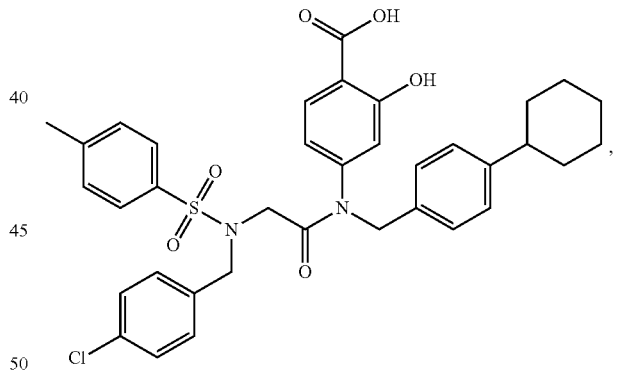,
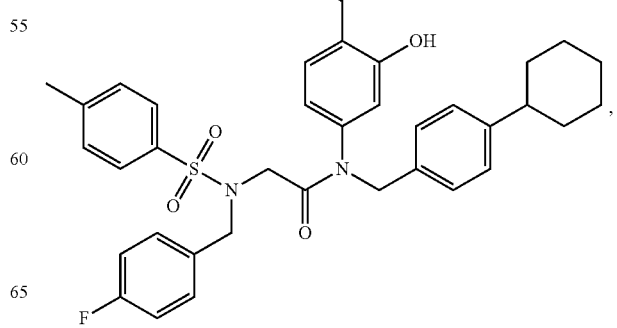, 127
-continued
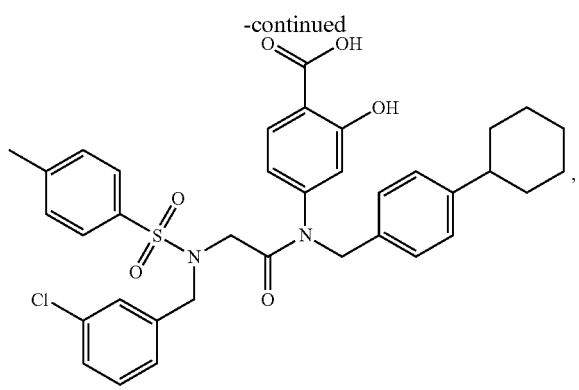
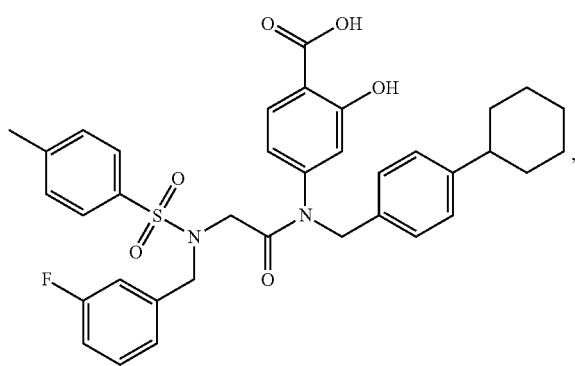
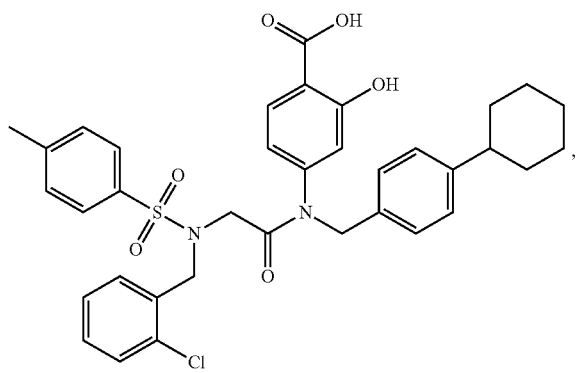
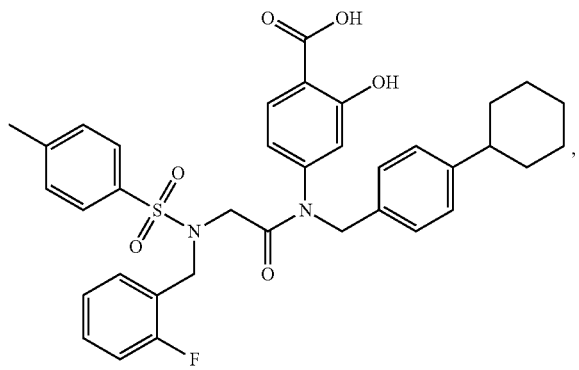
128
-continued
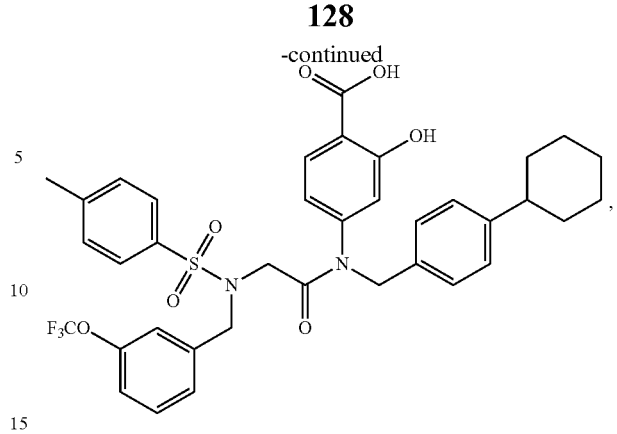
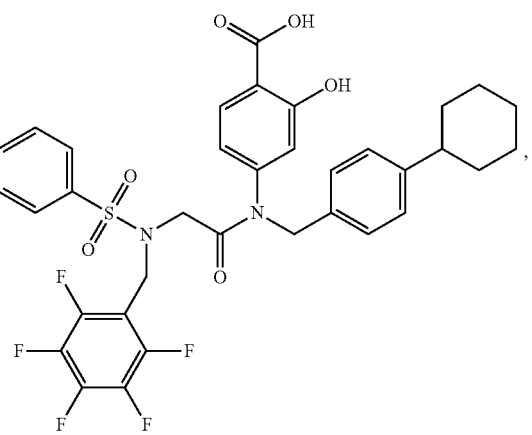
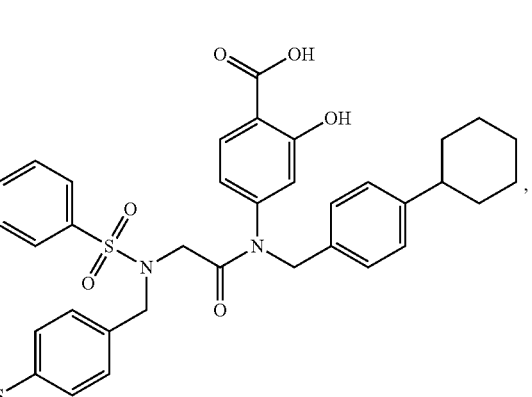
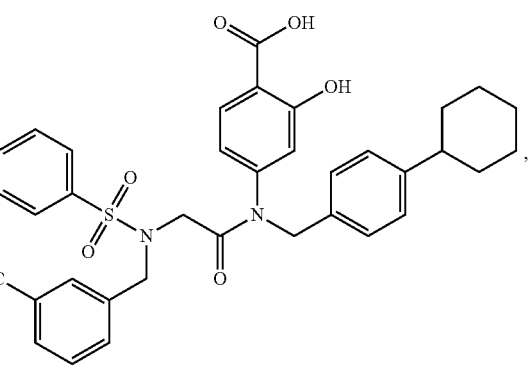

129
-continued
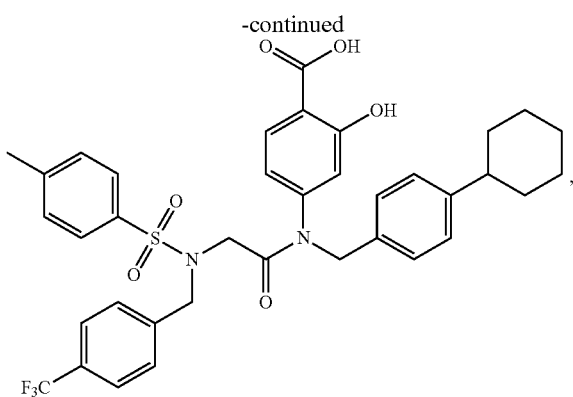
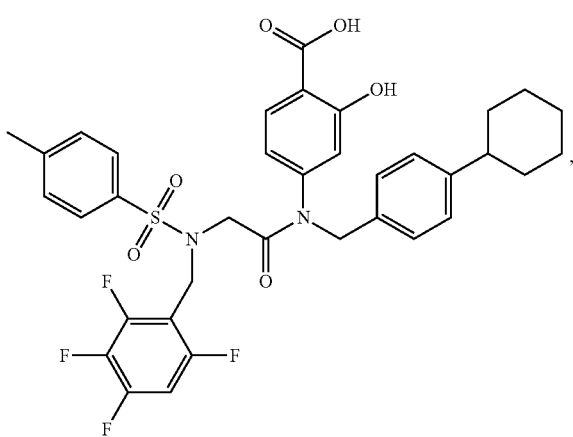
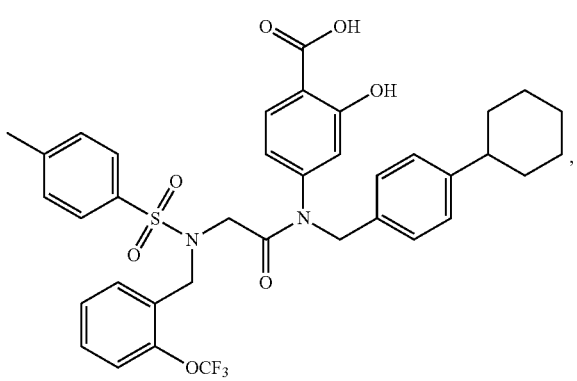
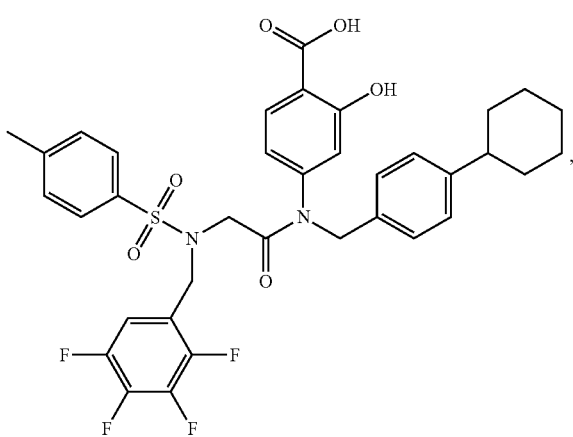
130
-continued
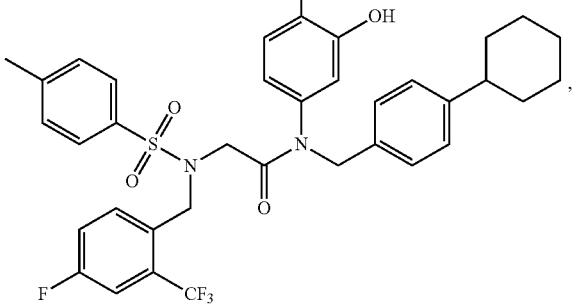
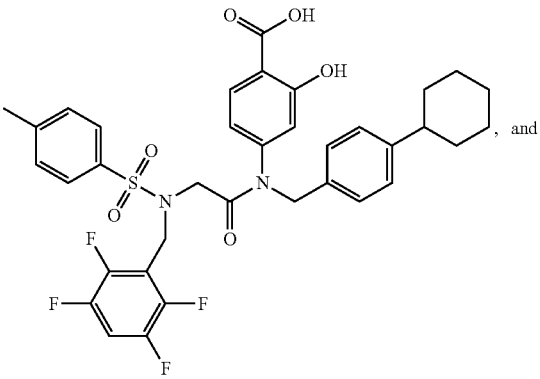, and
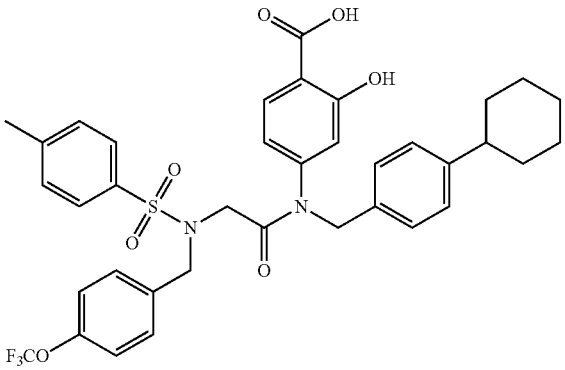.
In one aspect, a compound of Formula II can be present as one or more of the following structures:
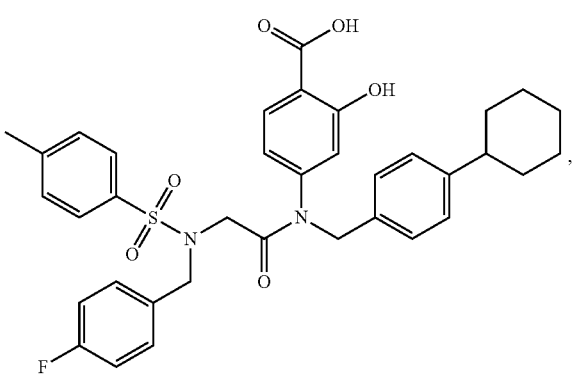

131
-continued
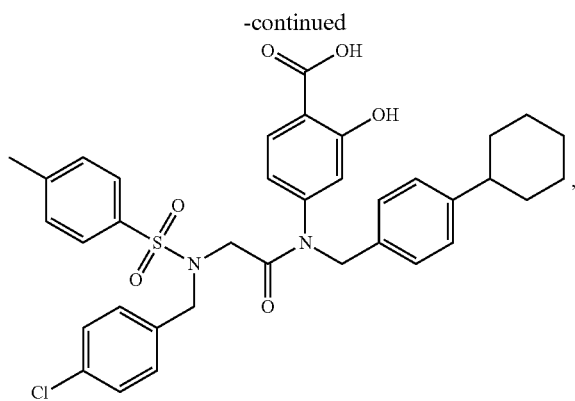
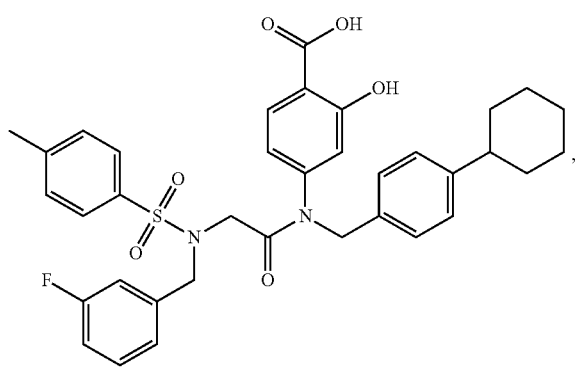
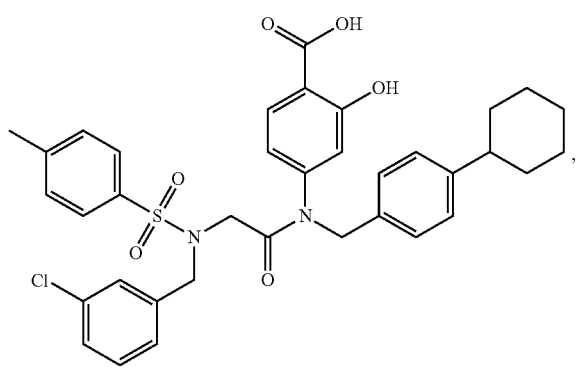
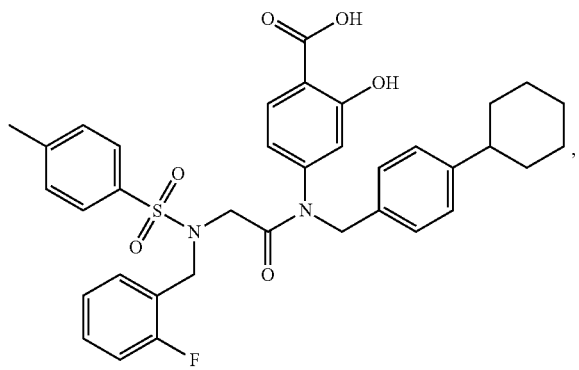
132
-continued
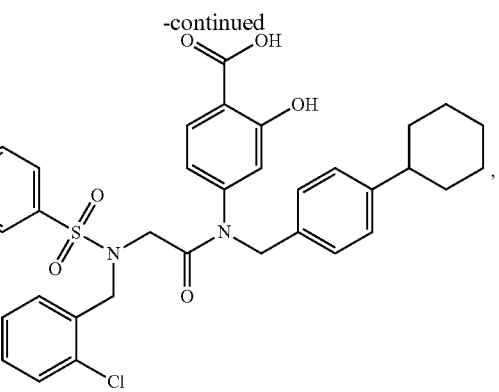
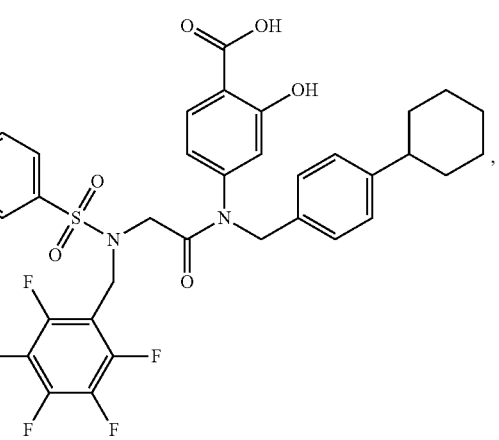
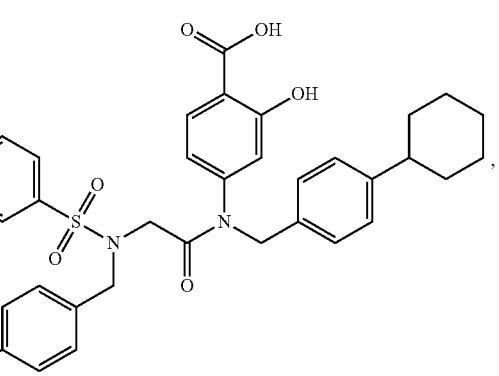
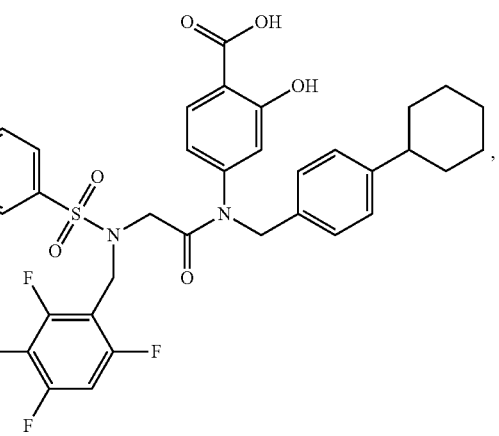

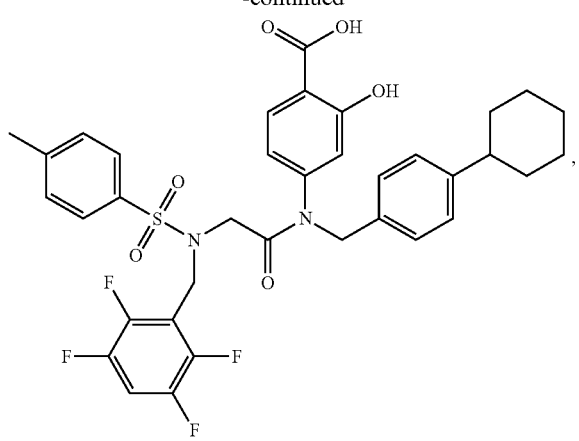
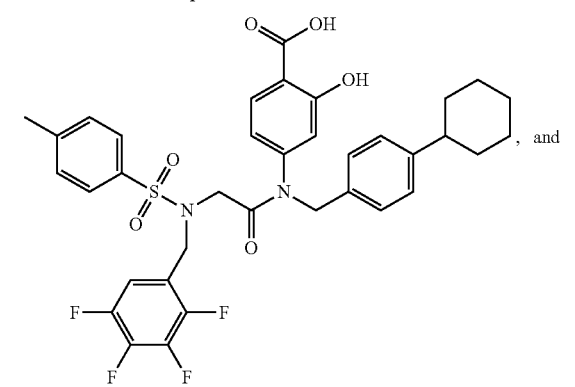, and
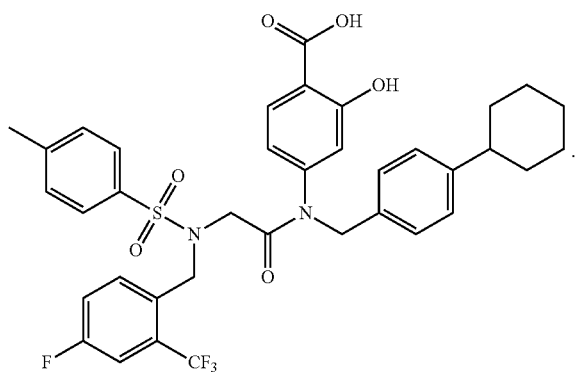
In one aspect, a compound of Formula II can be present as one or more of the following structures:
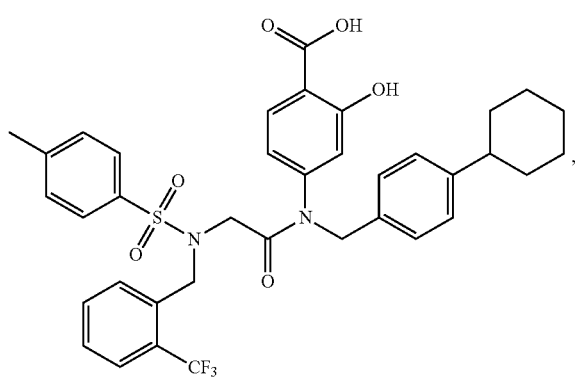

135
-continued
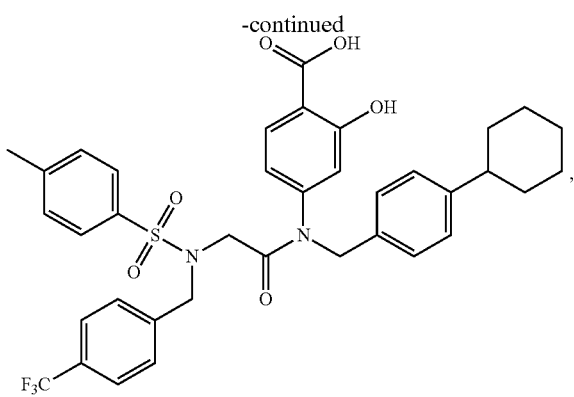
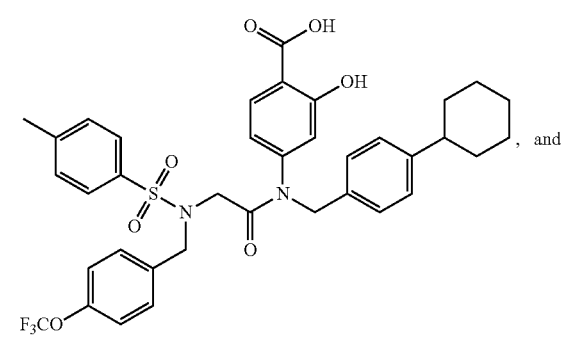
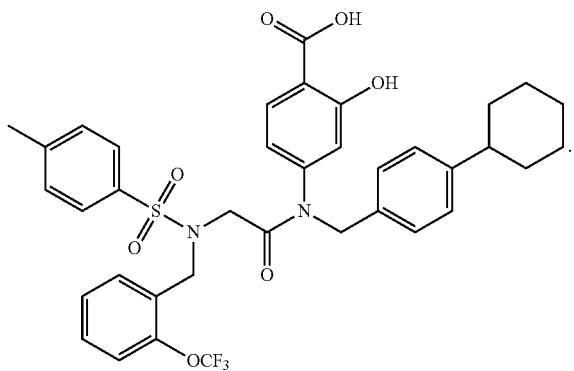
In one aspect, a compound of Formula II can be present as one or more of the following structures:
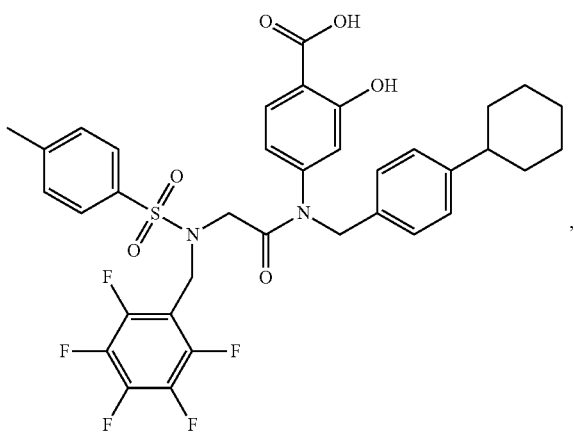
136
-continued
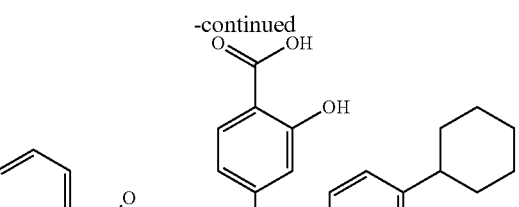
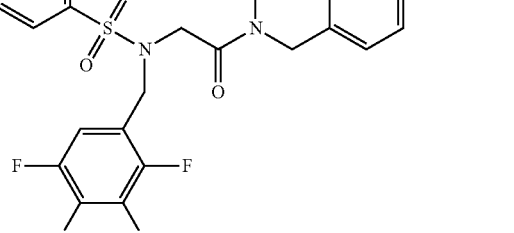, and
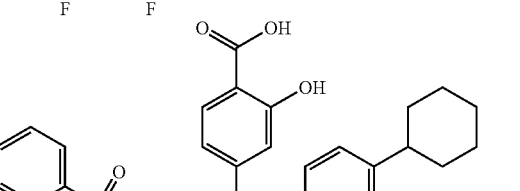
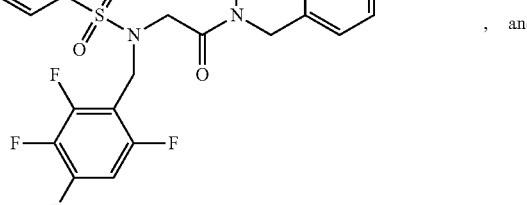
In one aspect, a compound of Formula II can be present as one or more of the following structures:
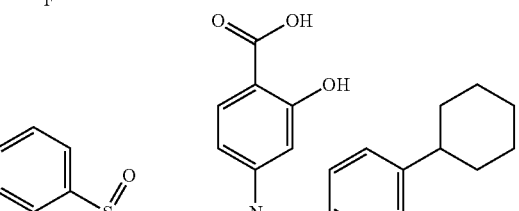
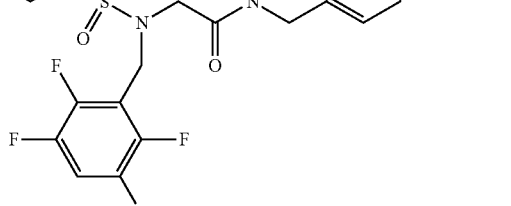, 137 138
-continued -continued
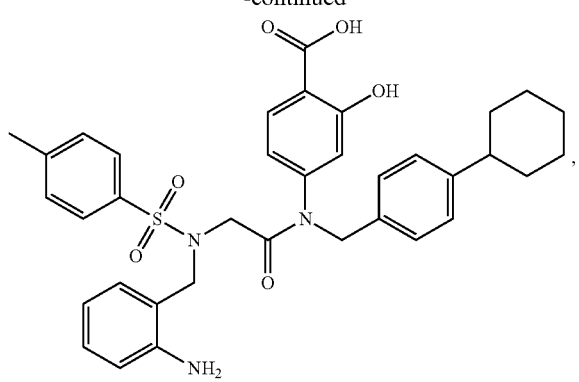
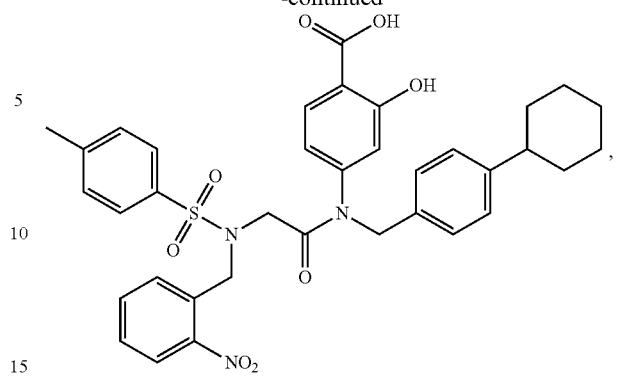

139
-continued
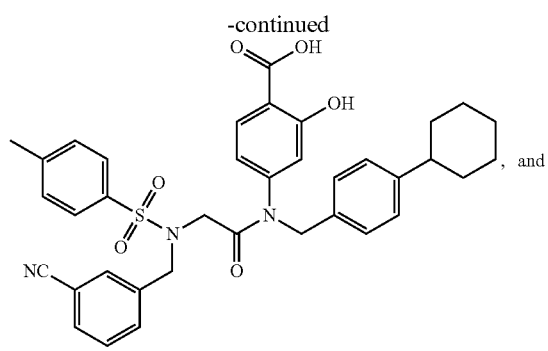
, and
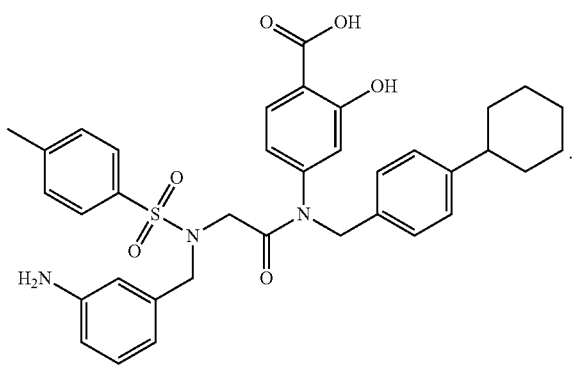
In one aspect, a compound of Formula II can be present as one or more of the following structures:
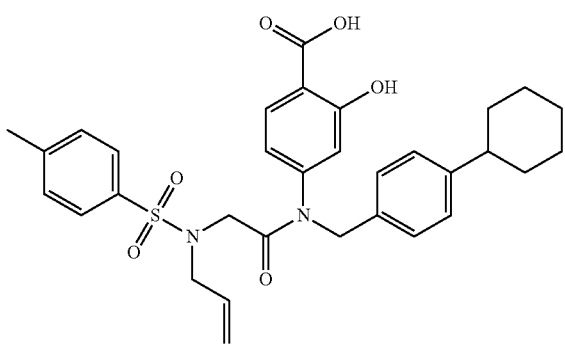
,
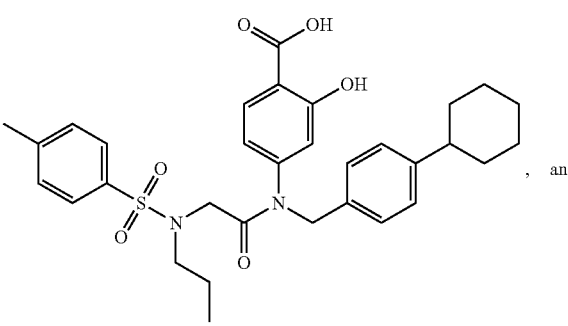
, and
140
-continued
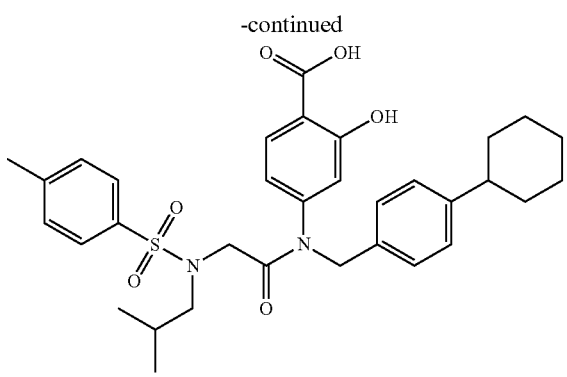
.
In one aspect, a compound of Formula II can be present as one or more of the following structures:
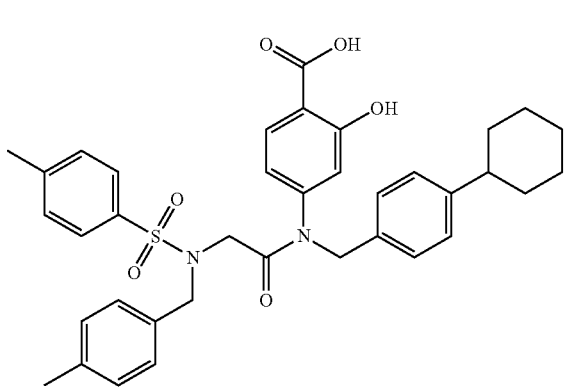
,
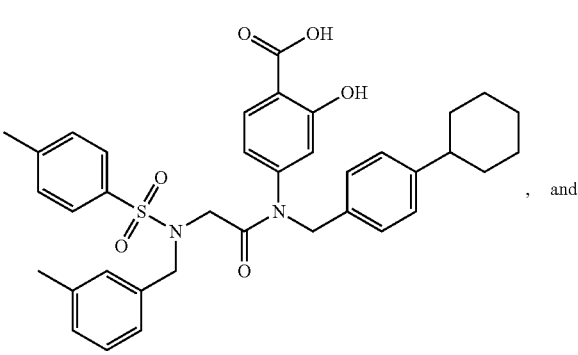
, and
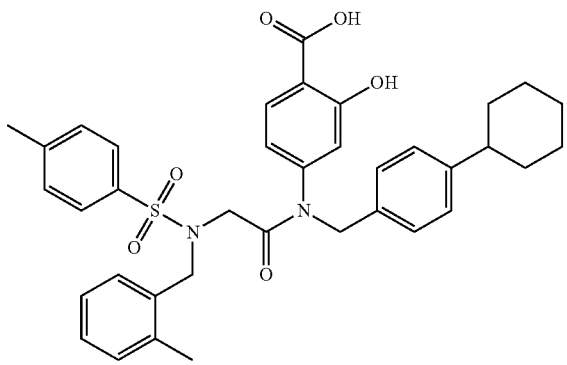
.
In one aspect, a compound of Formula III can be present as one or more of the following structures:

141
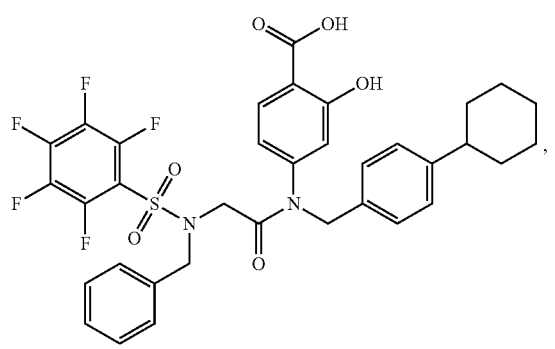
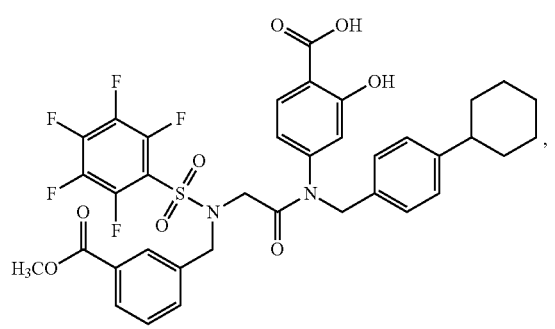
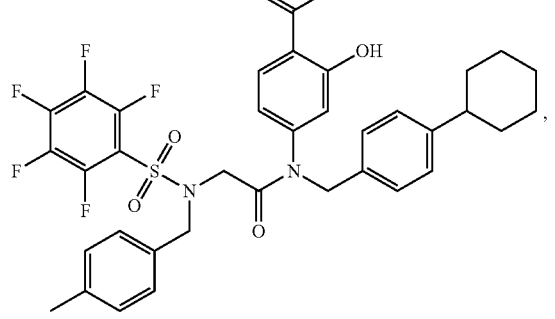
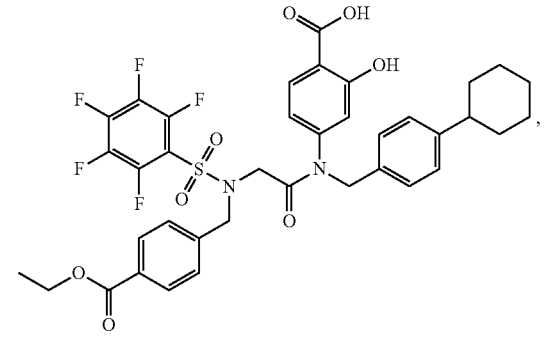
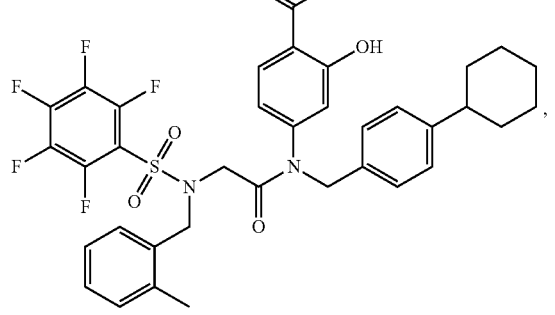
142
-continued
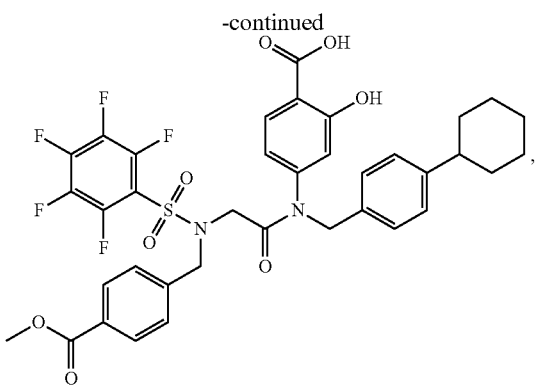
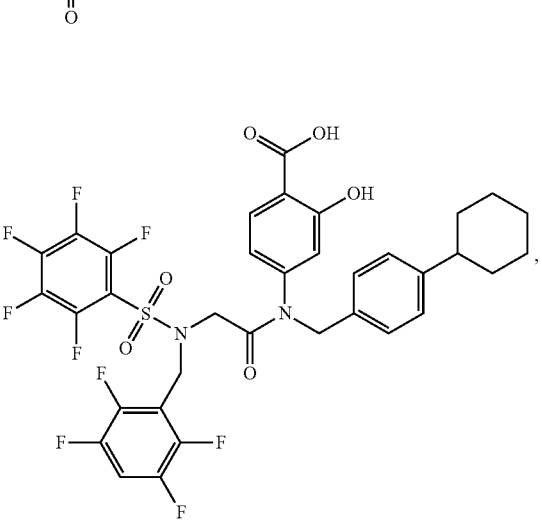
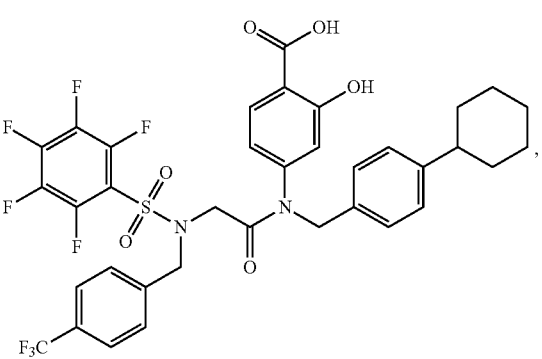
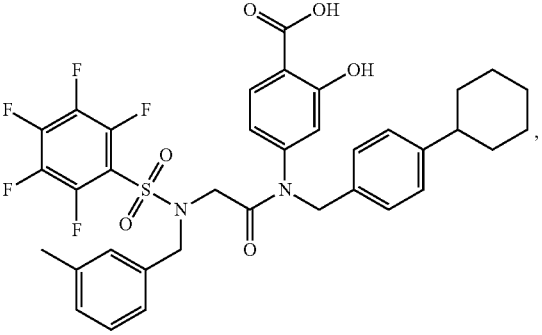

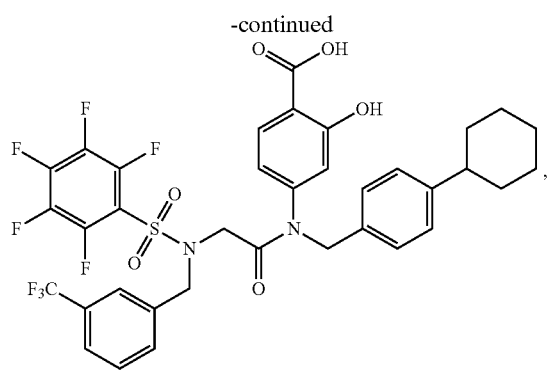
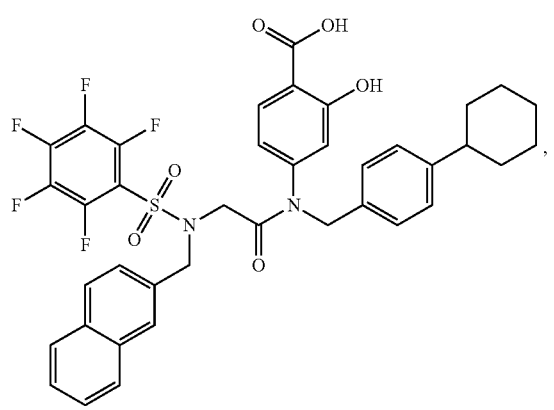
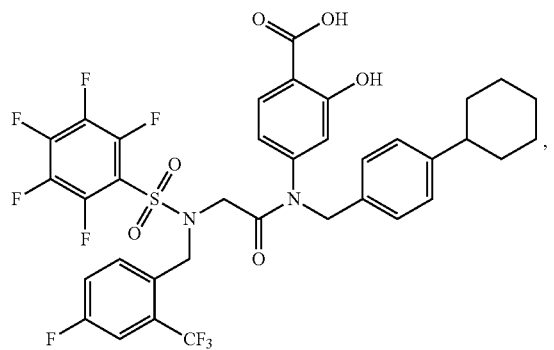
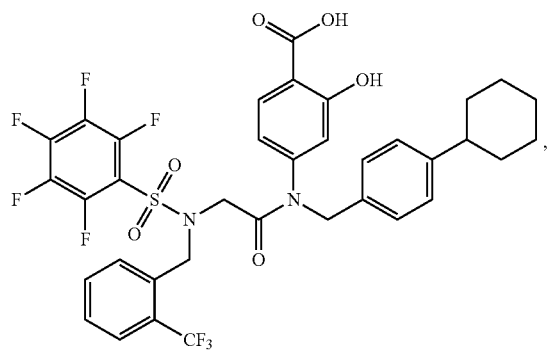
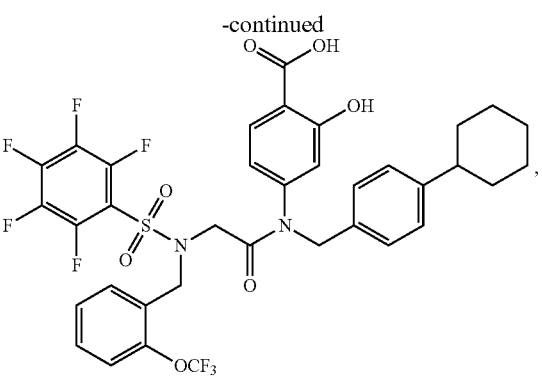
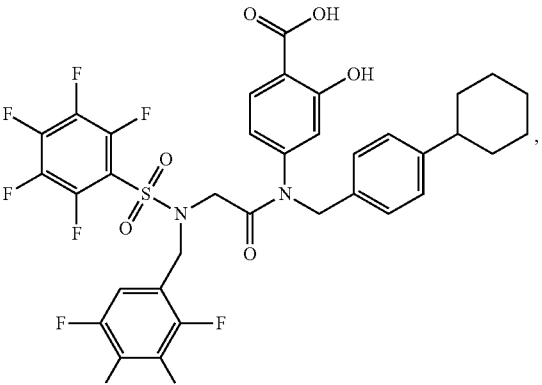
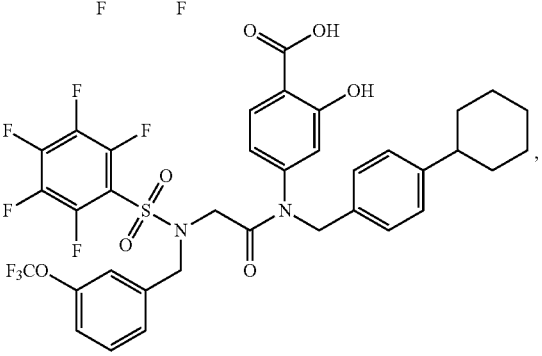
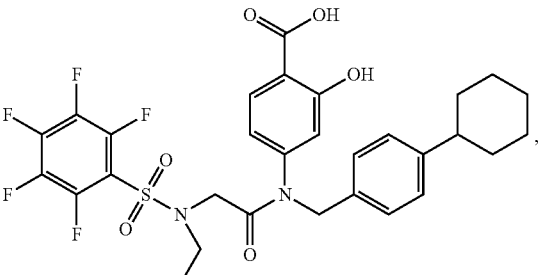
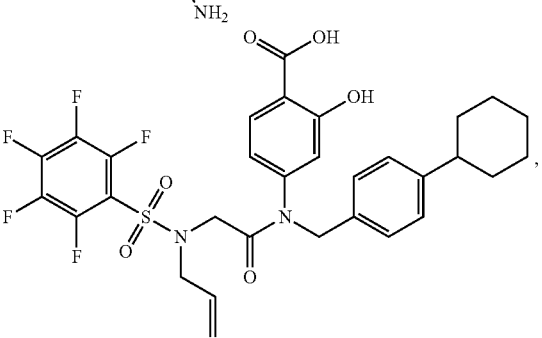

145
-continued
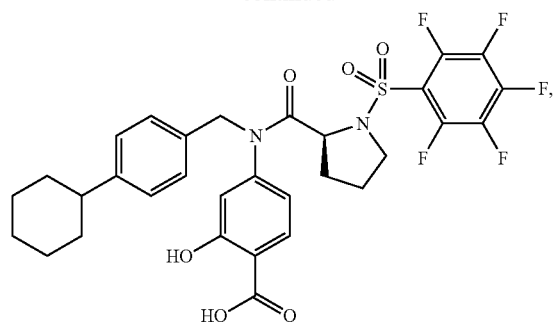
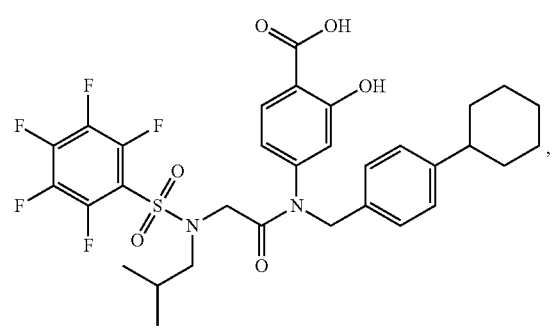
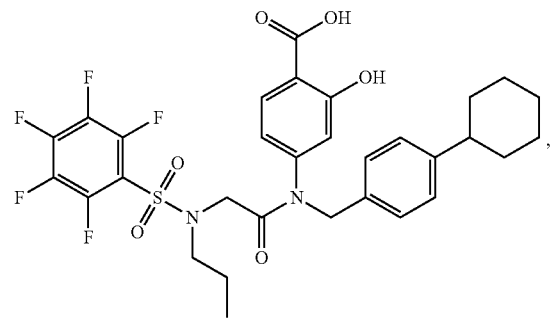
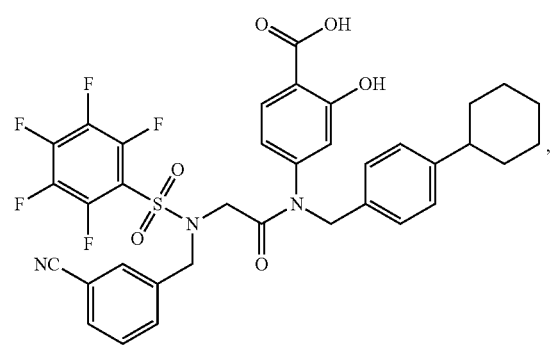
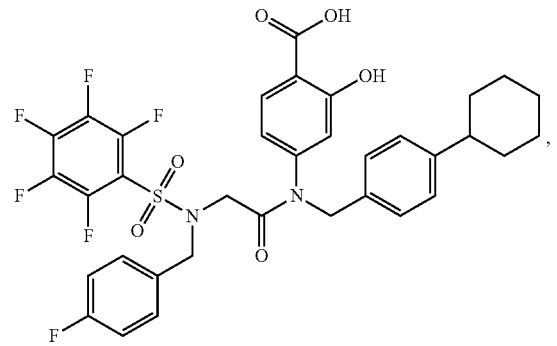
146
-continued
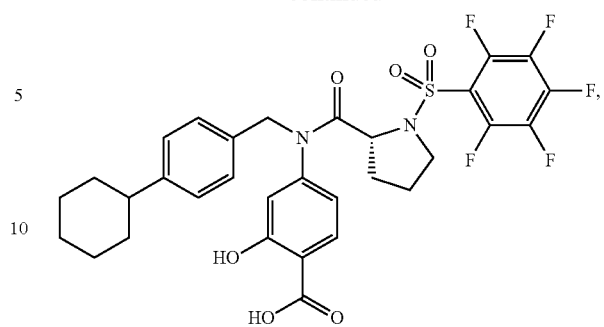
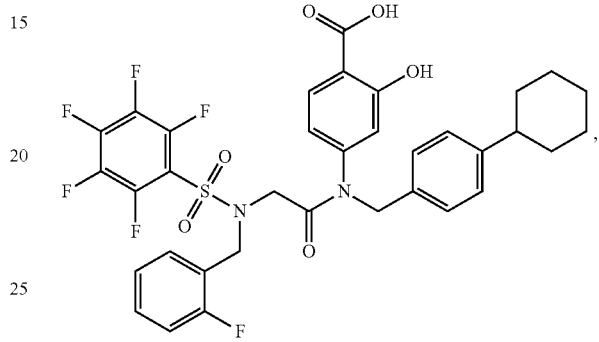
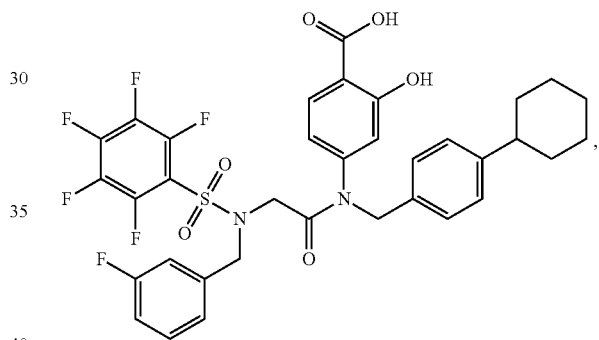
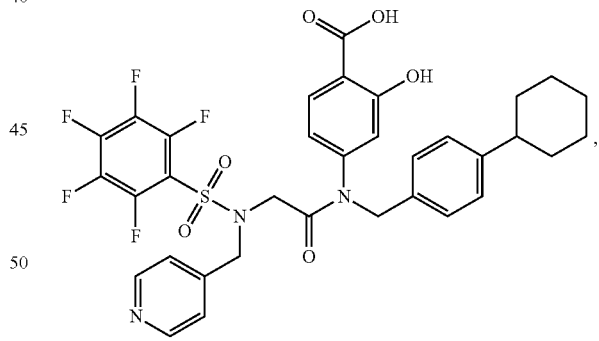
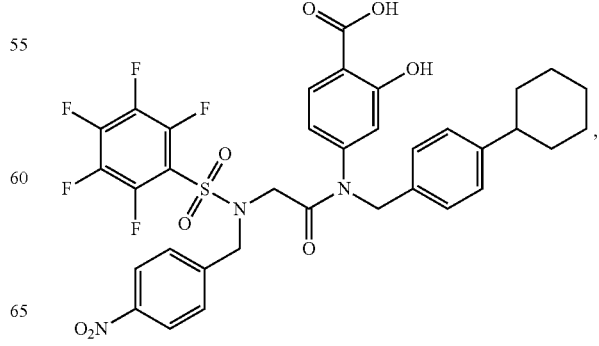

147
-continued
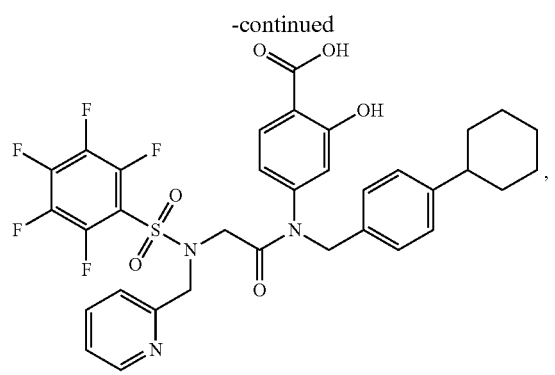
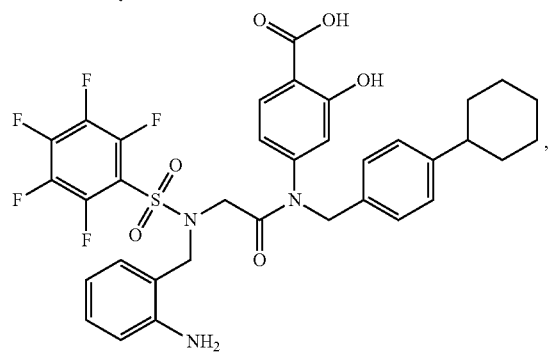
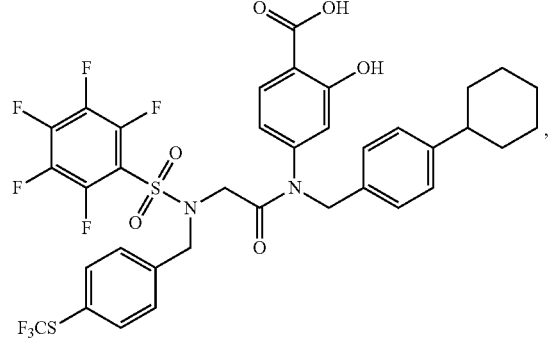
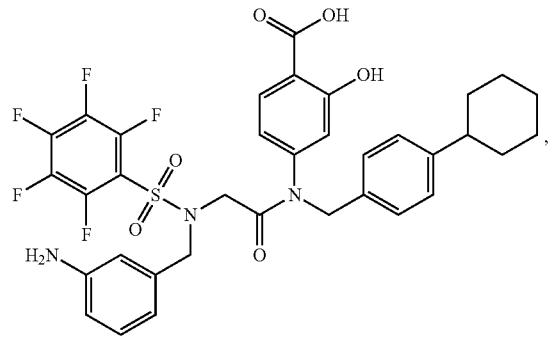
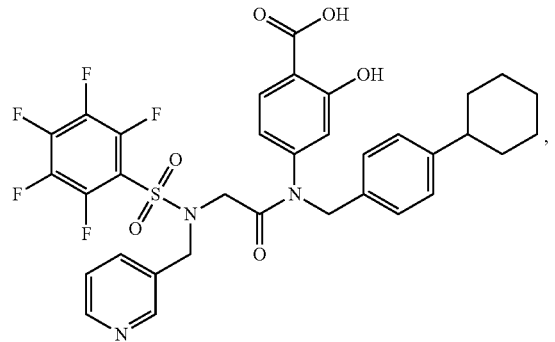
148
-continued
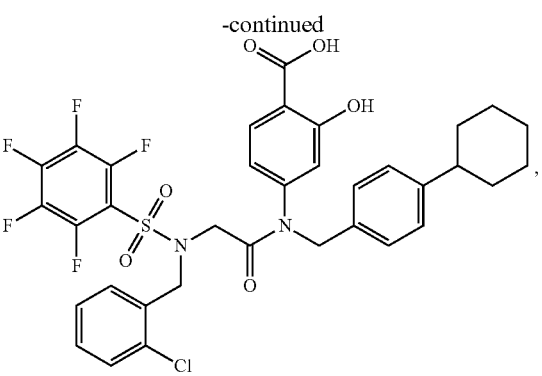
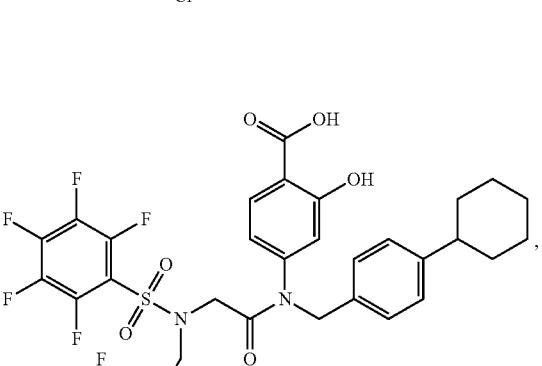
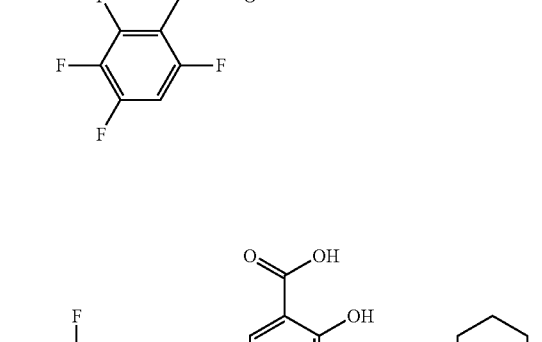
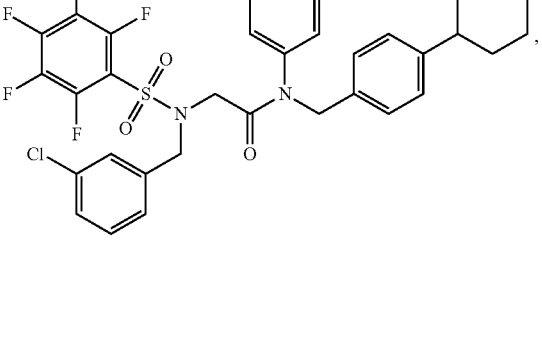
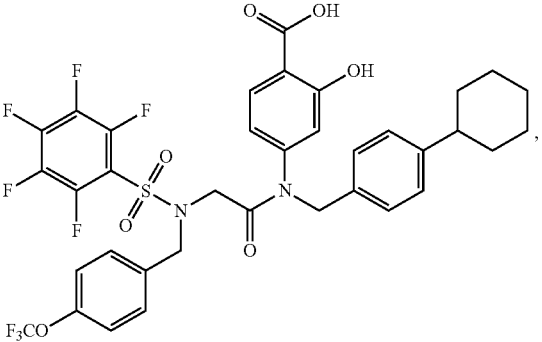

149
-continued
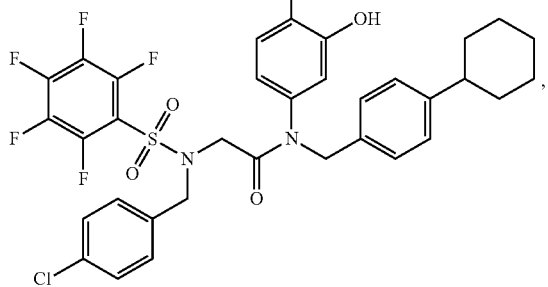
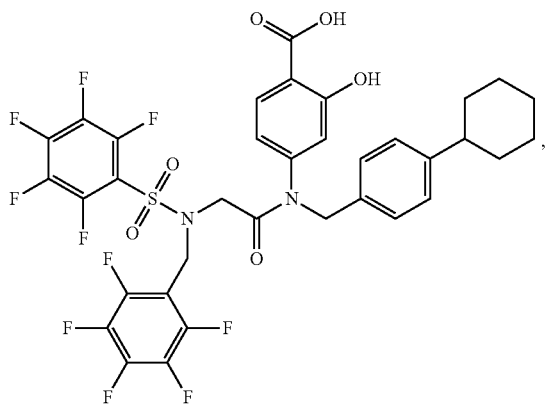
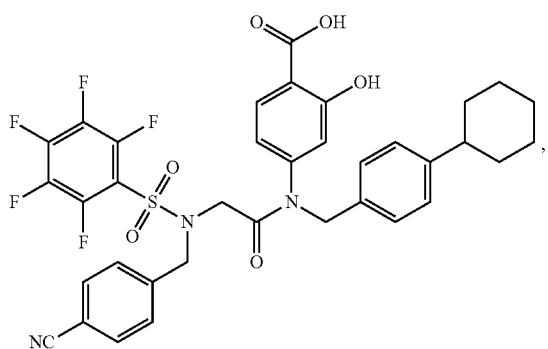
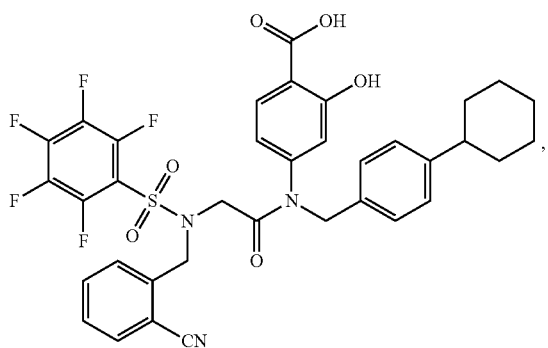
150
-continued
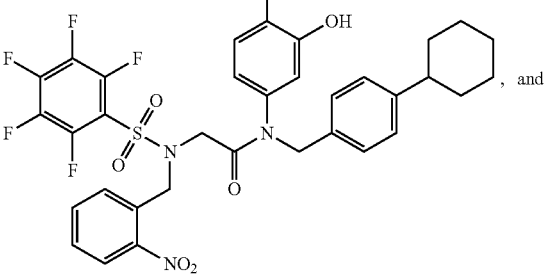, and
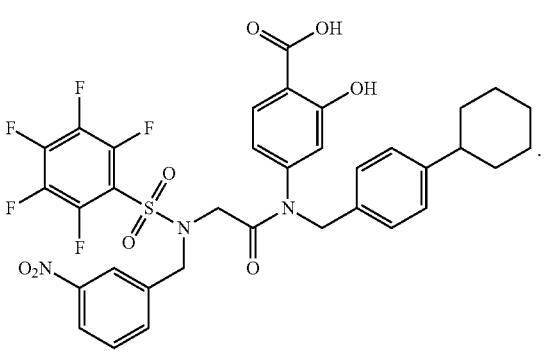.
In one aspect, a compound of Formula III can be present as one or more of the following structures:
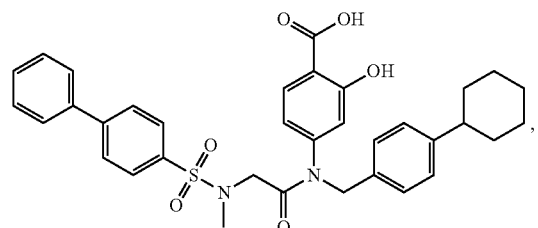,
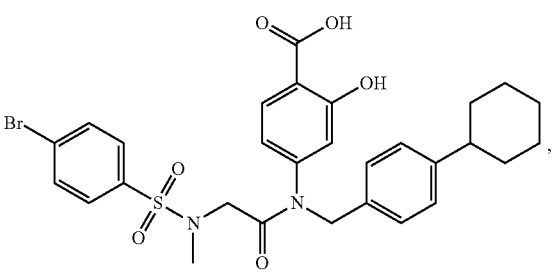,
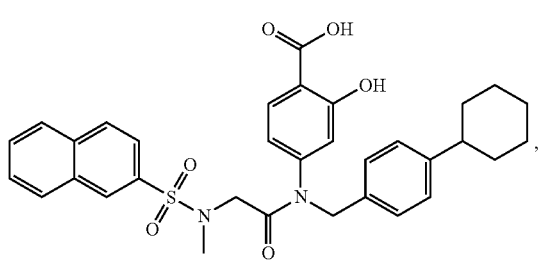, 151
-continued
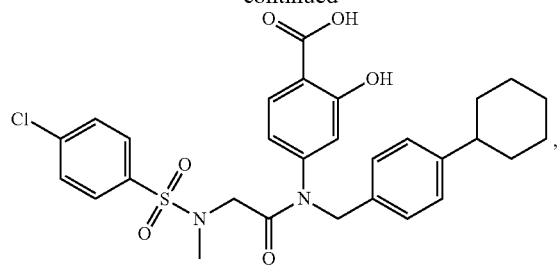
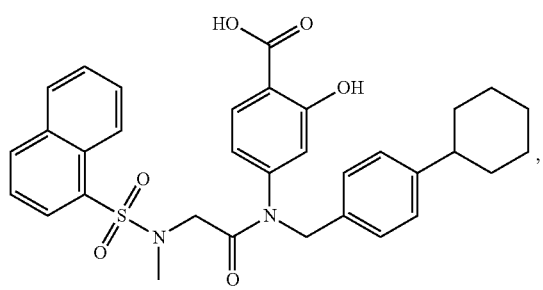
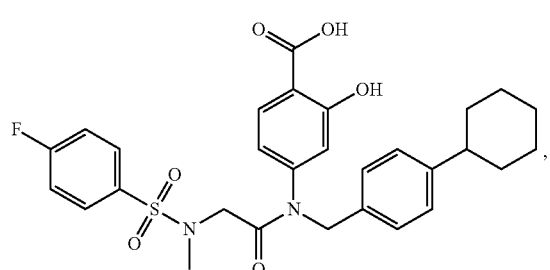
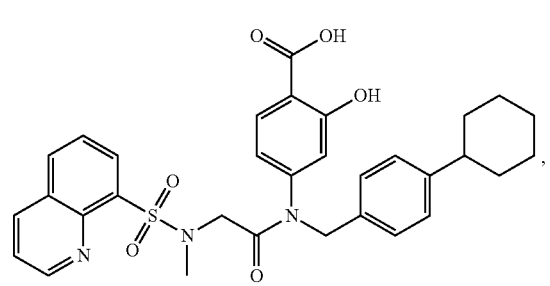
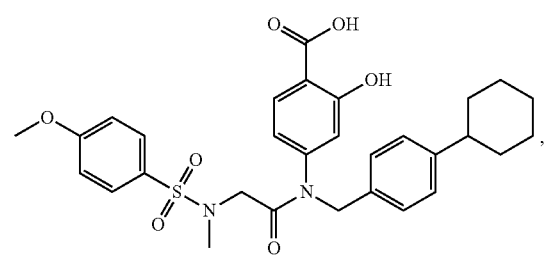
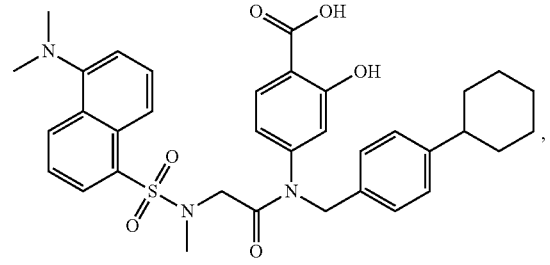
152
-continued
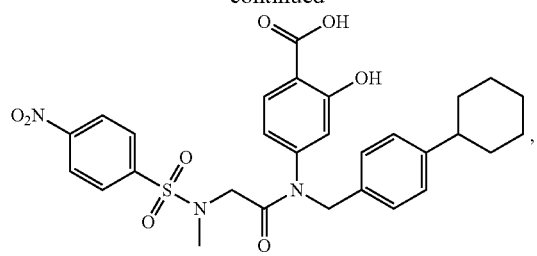
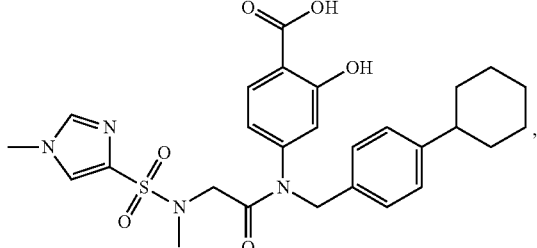
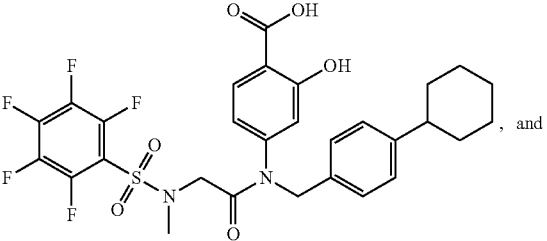
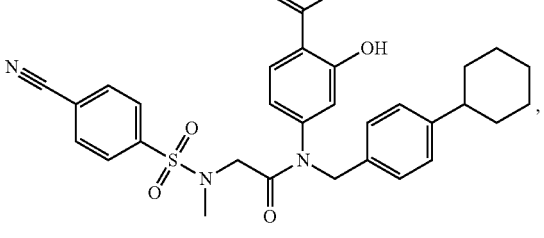, and
In one aspect, a compound of Formula III can be present as one or more of the following structures:
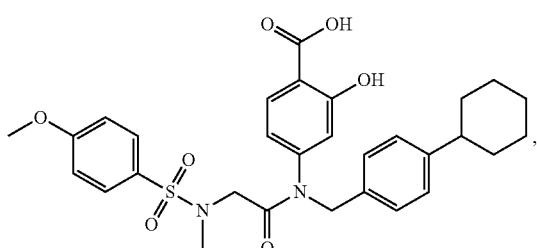
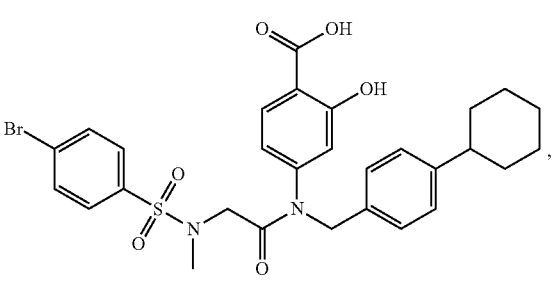

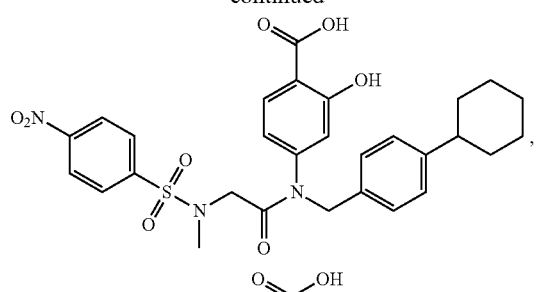
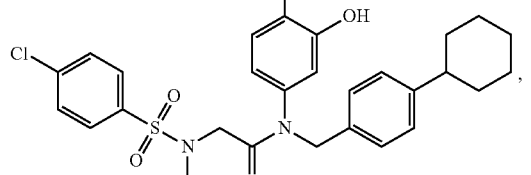
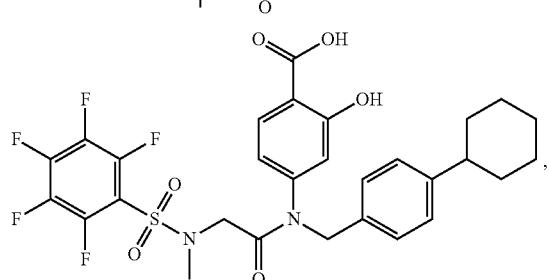
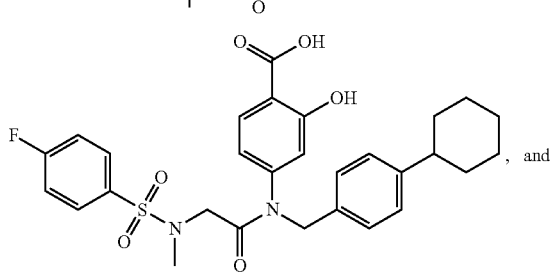
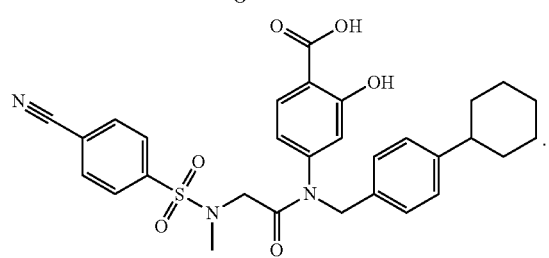
In one aspect, a compound of Formula III can be present as one or more of the following structures:
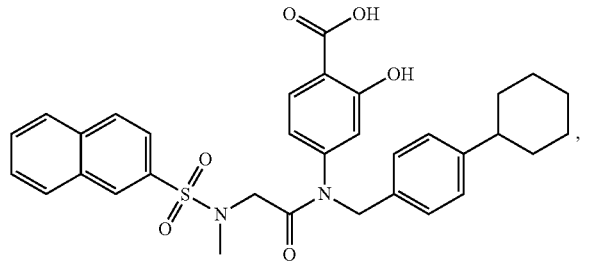
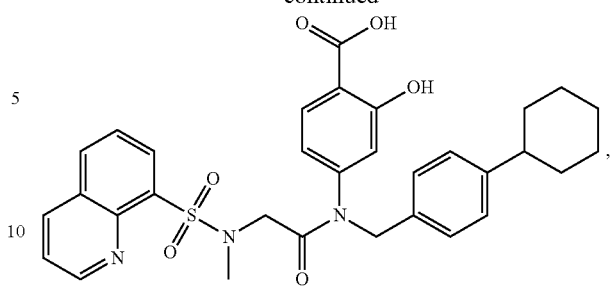
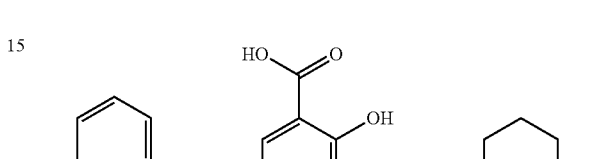
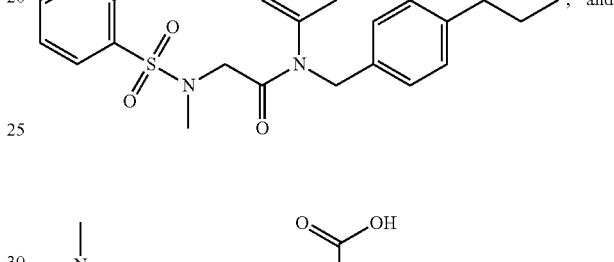, and
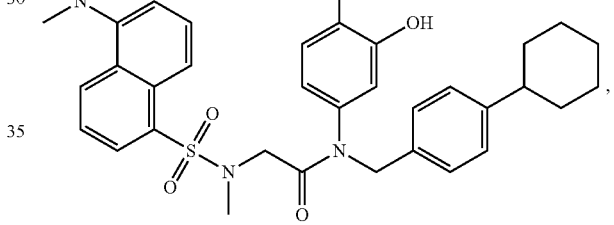
In one aspect, a compound of Formula III can be present as one or more of the following structures:
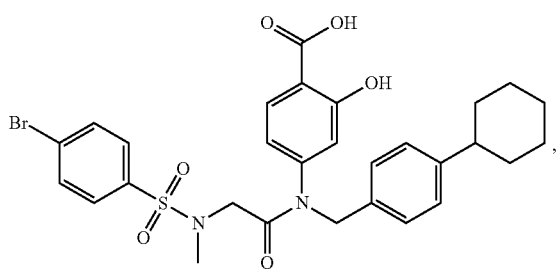
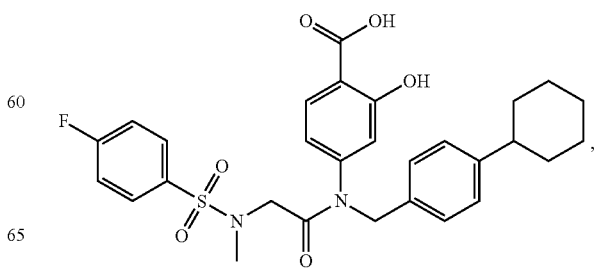

-continued

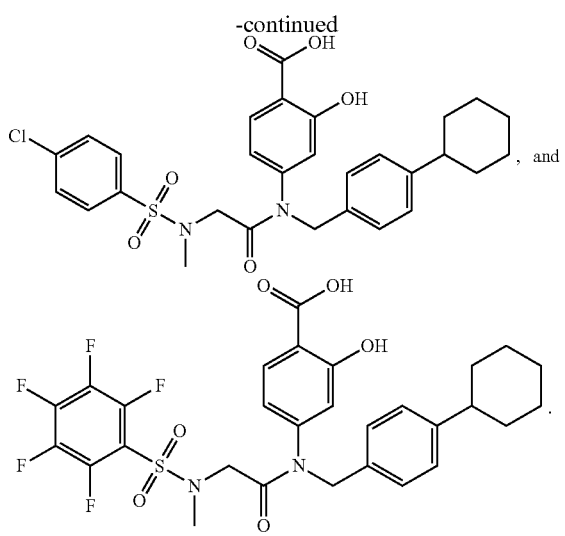

In one aspect, a compound of Formula III can be present as one or more of the following structures:

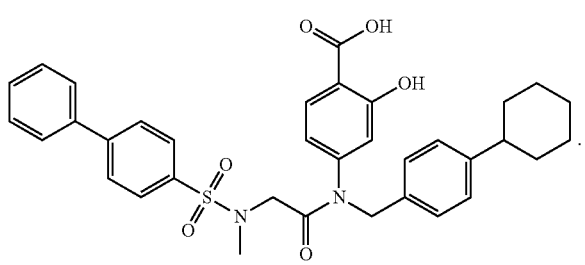 [SMILES: CN(CC(=O)N(Cc1ccc(C2CCCCC2)cc1)c1ccc(C(=O)O)c(O)c1)S(=O)(=O)c1ccc(-c2ccccc2)cc1]

In one aspect, a compound of Formula III can be present as one or more of the following structures:

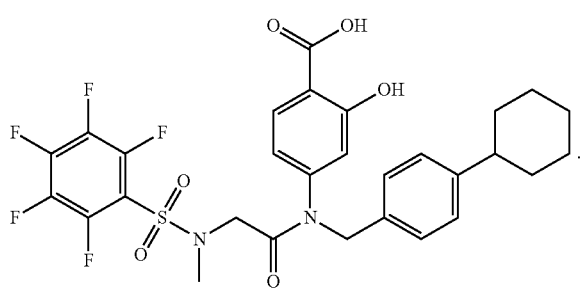 [SMILES: CN(CC(=O)N(Cc1ccc(C2CCCCC2)cc1)c1ccc(C(=O)O)c(O)c1)S(=O)(=O)c1c(F)c(F)c(F)c(F)c1F]

In one aspect, a compound of Formula III can be present as one or more of the following structures:

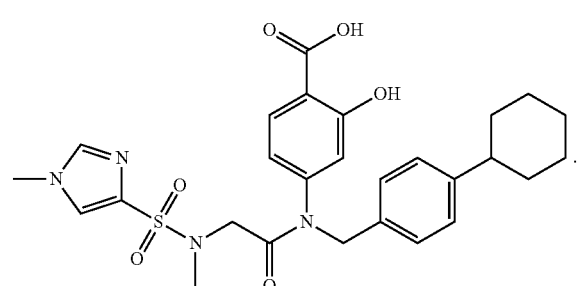

In one aspect, a compound of Formula IV can be present as one or more of the following structures:

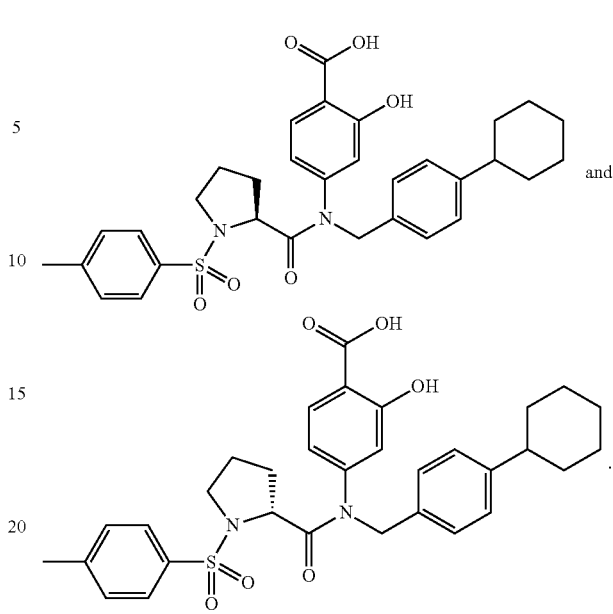

It is understood that the disclosed compounds can be used in connection with the disclosed methods, compositions, kits, and uses. In a further aspect, it is understood that the disclosed compounds further comprise pharmaceutically acceptable salts, hydrates, solvates, or polymorphs thereof.

The pharmaceutically acceptable derivatives of the compounds can include any suitable derivative, such as pharmaceutically acceptable salts as discussed below, isomers, radiolabeled analogs, tautomers, and the like.

It is contemplated that one or more compounds can optionally be omitted from the disclosed invention.

3. Modulation of STAT3 Activity

In one aspect, the disclosed compounds exhibit inhibition of STAT3 protein activity. In a yet further aspect, the disclosed compounds exhibit selective inhibition of STAT3 protein activity. In a still further aspect, the disclosed compounds prevent STAT3 protein dimerization. In a yet further aspect, the disclosed compounds exhibit disruption of pre-formed or existing STAT3 dimers. In a still further aspect, the disclosed compounds exhibit binding to the SH2 domain of STAT3.

Inhibition of STAT3 activity can be determined by a variety of both in vitro and in vivo methods known to one skilled in the art. For example, inhibition of STAT3 protein activity can be determined using a electrophoretic mobility shift assay ("EMSA"). In one aspect, the disclosed compounds exhibit inhibition of STAT3 protein activity with an $IC_{50}$ in an EMSA assay of less than about 300 µM, less than about 100 µM, less than about 50 µM, less than about 10 µM, less than about 1 µM, less than about 500 nM, or of less than about 100 nM.

In one aspect, the disclosed compounds are selective for STAT3. In a further aspect, selective inhibition of STAT3 activity is determined using an EMSA assay. In various further aspects, the compound inhibits STAT3 activity in a EMSA assay with an $IC_{50}$ less than the $IC_{50}$ for one or more of STAT1, STAT2, STAT4, STAT5a, STAT5b, or STATE. That is, a disclosed compound can have selectivity for the STAT3 protein vis-à-vis one or more of STAT1, STAT2, STAT4, STAT5a, STAT5b, or STAT6 proteins. For example, in one aspect, a disclosed compound can inhibit STAT3 with an $IC_{50}$ of about 5-fold less than that for STAT1, of about 10-fold less than that for STAT1, of about 20-fold less than that for STAT1, of about 30-fold less than that for STAT1, or of about 50-fold less than that for STAT1. In a further aspect, a disclosed compound can inhibit STAT3 with an $IC_{50}$ of about 5-fold less than that for STAT2, of about 10-fold less than that for STAT2, of about 20-fold less than that for STAT2, of about 30-fold less than that for STAT2, or of about 50-fold less than that for STAT2. In a still further aspect, a disclosed compound can inhibit STAT3 with an $IC_{50}$ of about 5-fold less than that for STAT4, of about 10-fold less than that for STAT4, of about 20-fold less than that for STAT4, of about 30-fold less than that for STAT4, or of about 50-fold less than that for STAT4. In a yet further aspect, a disclosed compound can inhibit STAT3 with an $IC_{50}$ of about 5-fold less than that for STAT5a, of about 10-fold less than that for STAT5a, of about 20-fold less than that for STAT5a, of about 30-fold less than that for STAT5a, or of about 50-fold less than that for STAT5a. In an even further aspect, a disclosed compound can inhibit STAT3 with an $IC_{50}$ of about 5-fold less than that for STAT5b, of about 10-fold less than that for STAT5b, of about 20-fold less than that for STAT5b, of about 30-fold less than that for STAT5b, or of about 50-fold less than that for STAT5b. In a still further aspect, a disclosed compound can inhibit STAT3 with an $IC_{50}$ of about 5-fold less than that for STAT6, of about 10-fold less than that for STAT6, of about 20-fold less than that for STAT6, of about 30-fold less than that for STAT6, or of about 50-fold less than that for STAT6.

In various aspects, the disclosed compounds exhibit binding to a STAT protein. In a further aspect, the disclosed compounds exhibit binding to the SH2 domain of a STAT protein. In a still further aspect, the disclosed compounds exhibit binding to STAT3 protein. In a yet further aspect, the disclosed compounds exhibit binding to the SH2 domain of STAT3. The binding affinity of a disclosed compound for a STAT protein, e.g. STAT3 protein, can be determined by various methods known to one skilled in the art. For example, inhibition of STAT protein activity can be determined using a surface plasmon resonance ("SPR") assay. In one aspect, the disclosed compounds exhibit binding to STAT protein with a $K_D$ of less than about 50 μM, less than about 10 μM, less than about 1 μM, less than about 500 nM, or of less than about 100 nM. In a further aspect, the $K_D$ is determined using an SPR method. In a still further aspect, the binding is determined using STAT3 protein.

In various further aspects, the binding to STAT3 is selective. In a further aspect, the disclosed compounds exhibit a $K_D$ for STAT3 binding less than the $K_D$ for one or more of STAT1, STAT2, STAT4, STAT5a, STAT5b, or STAT6. That is, a disclosed compound can have selectivity for the STAT3 protein vis-à-vis one or more of STAT1, STAT2, STAT4, STAT5a, STAT5b, or STAT6 proteins. For example, in one aspect, a disclosed compound can bind STAT3 with a $K_D$ of about 5-fold less than that for STAT1, of about 10-fold less than that for STAT1, of about 20-fold less than that for STAT1, of about 30-fold less than that for STAT1, or of about 50-fold less than that for STAT1. In a further aspect, a disclosed compound can bind STAT3 with a $K_D$ of about 5-fold less than that for STAT2, of about 10-fold less than that for STAT2, of about 20-fold less than that for STAT2, of about 30-fold less than that for STAT2, or of about 50-fold less than that for STAT2. In a still further aspect, a disclosed compound can bind STAT3 with a $K_D$ of about 5-fold less than that for STAT4, of about 10-fold less than that for STAT4, of about 20-fold less than that for STAT4, of about 30-fold less than that for STAT4, or of about 50-fold less than that for STAT4. In a yet further aspect, a disclosed compound can bind STAT3 with a $K_D$ of about 5-fold less than that for STAT5a, of about 10-fold less than that for STAT5a, of about 20-fold less than that for STAT5a, of about 30-fold less than that for STAT5a, or of about 50-fold less than that for STAT5a. In an even further aspect, a disclosed compound can bind STAT3 with a $K_D$ of about 5-fold less than that for STAT5b, of about 10-fold less than that for STAT5b, of about 20-fold less than that for STAT5b, of about 30-fold less than that for STAT5b, or of about 50-fold less than that for STAT5b. In a still further aspect, a disclosed compound can bind STAT3 with a $K_D$ of about 5-fold less than that for STAT6, of about 10-fold less than that for STAT6, of about 20-fold less than that for STAT6, of about 30-fold less than that for STAT6, or of about 50-fold less than that for STAT6.

In a further aspect, the disclosed compounds exhibit inhibition of binding a reporter molecule to a STAT protein. In a further aspect, the disclosed compounds exhibit inhibition of binding of a reporter molecule to the SH2 domain of a STAT protein. In a still further aspect, the disclosed compounds exhibit inhibition of binding of a reporter molecule to the STAT3 protein. In a yet further aspect, the disclosed compounds exhibit inhibition of binding of a reporter molecule to the SH2 domain of STAT3. The inhibition of binding of a reporter molecule to a STAT protein, e.g. STAT3 protein, can by a disclosed compound can be determined by various methods known to one skilled in the art. For example, inhibition of a reporter molecule to STAT3 can be determined using a fluorescence polarization assay. In a further aspect, the compound exhibits inhibition with an $K_i$ of less than about 300 μM. In a still further aspect, the compound exhibits inhibition with an $K_i$ of less than about 100 μM. In a yet further aspect, the compound exhibits inhibition with an $K_i$ of less than about 50 μM. In an even further aspect, the compound exhibits inhibition with an $K_i$ of less than about 10 μM. In a still further aspect, the compound exhibits inhibition with an $K_i$ of less than about 1 μM. In an even further aspect, the compound exhibits inhibition with an $K_i$ of less than about 0.1 μM. In a still further aspect, the report molecule is a fluorescently labeled peptide. In a yet further aspect, the fluorescently-labeled reporter peptide is 5-carboxyfluorescein-GpYLPQTV-NH2.

Alternatively, the inhibition of STAT protein activity can be determined in a cell-based assay. There are a variety of cell-based assays that are suitable for determination of inhibition of STAT protein activity known to one skilled in the art. For example, cell growth inhibition or cell arrest can be determined using a cell, either a permanent cell-line or a primary cell culture that has a STAT protein with dysfunction activity. In a further aspect, the STAT protein is STAT3. In a yet further aspect, the STAT3 protein dysfunction is one wherein the STAT3 protein is has acquired a gain of function mutation. Alternatively, the STAT3 protein has a phenotype of persistent or constitutive activity. For example, the STAT3 protein can have a persistent or constitutive activity due to a dysfunction in an upstream regulatory protein. In a further aspect, the STAT3 protein is overexpressed.

In one aspect, the disclosed compounds and products of disclosed methods of making inhibit cell growth. In a still further aspect, the disclosed compounds and products of disclosed methods inhibit cell growth in an in vitro assay system. In an even further aspect, the in vitro assay system makes use of a cell-line derived from a from cancer or tumor selected from breast cancer, prostate cancer, and pancreatic cancer. In a yet further aspect, the cell-line is derived from a human source. In a yet further aspect, the disclosed compounds inhibit cell growth in a cell with a persistently active STAT3 protein. In an even further aspect, the cell-line has an activated STAT3 protein. In a still further aspect, the cell-line is selected from MDA-MB-231, MDA-468, Panc-1, DU145, OPM2, OCL-AML2, and A549. In an even further aspect, the cell-line is selected from DU-145, Panc-1, and MDA-MB-231. In a still further aspect, the inhibition of cell growth by the disclosed compounds is determined in a cell-line expressing v-Src. In an even further aspect, the cell-line is transformed with v-Src. In a yet further aspect, cell-line which is transformed in the NIH3T3 cell-line. In one aspect, the disclosed compounds exhibit inhibition of cell growth activity in an in vitro cell-based assay with an $IC_{50}$ of less than about 300 less than about 100 µM, less than about 50 µM, less than about 10 µM, less than about 1 µM, less than about 500 nM, or of less than about 100 nM.

In one aspect, the disclosed compounds and products of disclosed methods of making inhibit cell migration. In a still further aspect, the disclosed compounds and products of disclosed methods inhibit cell migration in an in vitro assay system. In an even further aspect, the in vitro assay system makes use of a cell-line derived from a from cancer or tumor selected from breast cancer, prostate cancer, and pancreatic cancer. In a yet further aspect, the cell-line is derived from a human source. In a yet further aspect, the disclosed compounds inhibit cell growth in a cell with a persistently active STAT3 protein. In an even further aspect, the cell-line has an activated STAT3 protein. In a still further aspect, the cell-line is selected from MDA-MB-231, MDA-468, Panc-1, DU145, OPM2, OCL-AML2, and A549. In an even further aspect, the cell-line is selected from DU-145, Panc-1, and MDA-MB-231. In a still further aspect, the inhibition of cell migration by of the disclosed compound is determined in a cell-line expressing v-Src. In an even further aspect, the cell-line is transformed with v-Src. In a yet further aspect, cell-line which is transformed in the NIH3T3 cell-line. In one aspect, the disclosed compounds exhibit inhibition of cell migration in an in vitro cell-based assay with an $IC_{50}$ of less than about 300 µM, less than about 100 µM, less than about 50 µM, less than about 10 µM, less than about 1 µM, less than about 500 nM, or of less than about 100 nM.

Alternatively, the modulatory effects, e g inhibition, of the disclosed compounds can be determined using other types of cell-based assays, e.g. determination of the level of pY705STAT3 levels in cells following treatment with a disclosed compound and compared to the pY705STAT3 levels in control cells versus the unphosphorylated form of STAT3 in the same cell lysate. Determination of pY705STAT3 can be carried by immunoblots of cell lysates, e.g. whole-cell lysates, nuclear extracts, and cytosolic lysates. Other markers of STAT3 inhibition can be assessed in similar fashion, and include markers selected from the phosphorylated and unphosphorylated forms Shc, Jaks, Src, and Erk1/2. In a further aspect, the cellular marker determined by immunoblotting is selected from c-myc, cyclin D1, Bcl-xL, suvivin, and VEGF. In various further aspects, the effect of the disclosed compounds on the STAT3 transcriptional activity can be determined using a luciferase-based transcriptional reporter assay. Briefly, the appropriate cell-type, e.g. DU145, Panc-1, or MDA-MB-231, is transiently transfected with a plasmid, e.g. pLucTKS3 wherein expression of luciferase is STAT3-dependent, and compared to the expression of luciferase in a cell-line transiently transfected with a plasmid wherein the expression of luciferase is not dependent upon STAT3, e.g. pLucSRE.

4. Modulation of Stat5 Activity

In one aspect, the disclosed compounds exhibit inhibition of STAT5 protein activity. In a yet further aspect, the disclosed compounds exhibit selective inhibition of STAT5 protein activity. In a still further aspect, the disclosed compounds prevent STAT5 protein dimerization. In a yet further aspect, the disclosed compounds exhibit disruption of pre-formed or existing STAT5 dimers. In a still further aspect, the disclosed compounds exhibit binding to the SH2 domain of STAT5.

Inhibition of STAT5 activity can be determined by a variety of both in vitro and in vivo methods known to one skilled in the art. For example, inhibition of STAT5 protein activity can be determined using a electrophoretic mobility shift assay ("EMSA"). In one aspect, the disclosed compounds exhibit inhibition of STAT5 protein activity with an $IC_{50}$ in an EMSA assay of less than about 300 µM, less than about 100 µM, less than about 50 µM, less than about 10 µM, less than about 1 µM, less than about 500 nM, or of less than about 100 nM.

In one aspect, the disclosed compounds are selective for STAT5. In a further aspect, selective inhibition of STAT5 activity is determined using an EMSA assay. In various further aspects, the compound inhibits STAT5 activity in a EMSA assay with an $IC_{50}$ less than the $IC_{50}$ for one or more of STAT1, STAT2, STAT3, STAT4, or STAT6. That is, a disclosed compound can have selectivity for the STAT3 protein vis-à-vis one or more of STAT1, STAT2, STAT3, STAT4, or STAT6 proteins. For example, in one aspect, a disclosed compound can inhibit STAT5 with an $IC_{50}$ of about 5-fold less than that for STAT1, of about 10-fold less than that for STAT1, of about 20-fold less than that for STAT1, of about 30-fold less than that for STAT1, or of about 50-fold less than that for STAT1. In a further aspect, a disclosed compound can inhibit STAT5 with an $IC_{50}$ of about 5-fold less than that for STAT2, of about 10-fold less than that for STAT2, of about 20-fold less than that for STAT2, of about 30-fold less than that for STAT2, or of about 50-fold less than that for STAT2. In a still further aspect, a disclosed compound can inhibit STAT5 with an $IC_{50}$ of about 5-fold less than that for STAT3, of about 10-fold less than that for STAT3, of about 20-fold less than that for STAT3, of about 30-fold less than that for STAT3, or of about 50-fold less than that for STAT3. In a yet further aspect, a disclosed compound can inhibit STAT5 with an $IC_{50}$ of about 5-fold less than that for STAT4, of about 10-fold less than that for STAT4, of about 20-fold less than that for STAT4, of about 30-fold less than that for STAT4, or of about 50-fold less than that for STAT4. In a still further aspect, a disclosed compound can inhibit STAT5 with an $IC_{50}$ of about 5-fold less than that for STAT6, of about 10-fold less than that for STAT6, of about 20-fold less than that for STAT6, of about 30-fold less than that for STAT6, or of about 50-fold less than that for STAT6.

In various aspects, the disclosed compounds exhibit binding to a STAT protein. In a further aspect, the disclosed compounds exhibit binding to the SH2 domain of a STAT protein. In a still further aspect, the disclosed compounds exhibit binding to STAT5 protein. In a yet further aspect, the disclosed compounds exhibit binding to the SH2 domain of STAT5. The binding affinity of a disclosed compound for a STAT protein, e.g. STAT5 protein, can be determined by various methods known to one skilled in the art. For example, inhibition of STAT protein activity can be determined using a surface plasmon resonance ("SPR") assay. In one aspect, the disclosed compounds exhibit binding to STAT5 protein with a $K_D$ of less than about 50 µM, less than about 10 µM, less than about 1 µM, less than about 500 nM, or of less than about 100 nM. In a further aspect, the $K_D$ is determined using an SPR method. In a still further aspect, the binding is determined using STAT3 protein.

In various further aspects, the binding to STAT5 is selective. In a further aspect, the disclosed compounds exhibit a $K_D$ for STAT3 binding less than the $K_D$ for one or more of STAT1, STAT2, STAT3, STAT4, or STAT6. That is, a disclosed compound can have selectivity for the STAT3 protein vis-à-vis one or more of STAT1, STAT2, STAT3, STAT4, or STAT6 proteins. For example, in one aspect, a disclosed compound can bind STAT5 with a $K_D$ of about 5-fold less than that for STAT1, of about 10-fold less than that for STAT1, of about 20-fold less than that for STAT1, of about 30-fold less than that for STAT1, or of about 50-fold less than that for STAT1. In a further aspect, a disclosed compound can bind STAT5 with a $K_D$ of about 5-fold less than that for STAT2, of about 10-fold less than that for STAT2, of about 20-fold less than that for STAT2, of about 30-fold less than that for STAT2, or of about 50-fold less than that for STAT2. In a still further aspect, a disclosed compound can bind STAT5 with a $K_D$ of about 5-fold less than that for STAT3, of about 10-fold less than that for STAT3, of about 20-fold less than that for STAT3, of about 30-fold less than that for STAT3, or of about 50-fold less than that for STAT3. In a yet further aspect, a disclosed compound can bind STAT5 with a $K_D$ of about 5-fold less than that for STAT4, of about 10-fold less than that for STAT4, of about 20-fold less than that for STAT4, of about 30-fold less than that for STAT4, or of about 50-fold less than that for STAT4. In a still further aspect, a disclosed compound can bind STAT5 with a $K_D$ of about 5-fold less than that for STAT6, of about 10-fold less than that for STAT6, of about 20-fold less than that for STAT6, of about 30-fold less than that for STAT6, or of about 50-fold less than that for STAT6.

In a further aspect, the disclosed compounds exhibit inhibition of binding a reporter molecule to a STAT protein. In a further aspect, the disclosed compounds exhibit inhibition of binding of a reporter molecule to the SH2 domain of a STAT protein. In a still further aspect, the disclosed compounds exhibit inhibition of binding of a reporter molecule to the STAT5 protein. In a yet further aspect, the disclosed compounds exhibit inhibition of binding of a reporter molecule to the SH2 domain of STAT5. The inhibition of binding of a reporter molecule to a STAT protein, e.g. STAT5 protein, can by a disclosed compound can be determined by various methods known to one skilled in the art. For example, inhibition of a reporter molecule to STAT3 can be determined using a fluorescence polarization assay. In a further aspect, the compound exhibits inhibition with an $K_i$ of less than about 300 µM. In a still further aspect, the compound exhibits inhibition with an $K_i$ of less than about 100 µM. In a yet further aspect, the compound exhibits inhibition with an $K_i$ of less than about 50 µM. In an even further aspect, the compound exhibits inhibition with an $K_i$ of less than about 10 µM. In a still further aspect, the compound exhibits inhibition with an $K_i$ of less than about 1 µM. In an even further aspect, the compound exhibits inhibition with an $K_i$ of less than about 0.1 µM. In a still further aspect, the report molecule is a fluorescently labeled peptide. In a yet further aspect, the fluorescently-labeled reporter peptide is 5-carboxyfluorescein-GpYLPQTV-NH2.

Alternatively, the inhibition of STAT protein activity can be determined in a cell-based assay. There are a variety of cell-based assays that are suitable for determination of inhibition of STAT protein activity known to one skilled in the art. For example, cell growth inhibition or cell arrest can be determined using a cell, either a permanent cell-line or a primary cell culture that has a STAT protein with dysfunction activity. In a further aspect, the STAT protein is STAT5.

In a yet further aspect, the STAT5 protein dysfunction is one wherein the STAT5 protein is has acquired a gain of function mutation. Alternatively, the STAT5 protein has a phenotype of persistent or constitutive activity. For example, the STAT5 protein can have a persistent or constitutive activity due to a dysfunction in an upstream regulatory protein. In a further aspect, the STAT5 protein is overexpressed. In a further aspect, the cell harbors an active oncogene is associated with STAT5 dysfunction. For example, cell-lines with the BCR-Abl oncogene are associated with a STAT5 dysfunction. In a further aspect, the cell-line has a FLT-3 dysfunction, e.g. a constitutively active FLT-3 protein. FLT-3 dysfunction is associated with STAT5 dysfunction in cell-lines.

In one aspect, the disclosed compounds and products of disclosed methods of making inhibit cell growth. In a still further aspect, the disclosed compounds and products of disclosed methods inhibit cell growth in an in vitro assay system. In an even further aspect, the in vitro assay system makes use of a cell-line derived from a from cancer or tumor selected from breast cancer, prostate cancer, and pancreatic cancer. In a yet further aspect, the cell-line is derived from a human source. In a yet further aspect, the disclosed compounds inhibit cell growth in a cell with a persistently active STAT5 protein. In an even further aspect, the cell-line has an activated STAT3 protein. In a still further aspect, the cell-line is selected from K562 and MV-4-11. In one aspect, the disclosed compounds exhibit inhibition of cell growth activity in an in vitro cell-based assay with an $IC_{50}$ of less than about 300 µM, less than about 100 µM, less than about 50 µM, less than about 10 µM, less than about 1 µM, less than about 500 nM, or of less than about 100 nM.

In one aspect, the disclosed compounds and products of disclosed methods of making inhibit cell migration. In a still further aspect, the disclosed compounds and products of disclosed methods inhibit cell migration in an in vitro assay system. In an even further aspect, the in vitro assay system makes use of a cell-line derived from a from cancer or tumor selected from breast cancer, prostate cancer, and pancreatic cancer. In a yet further aspect, the cell-line is derived from a human source. In a yet further aspect, the disclosed compounds inhibit cell growth in a cell with a persistently active STAT5 protein. In an even further aspect, the cell-line has an activated STAT5 protein. In a still further aspect, the cell-line is selected from MV-4-11 and K562. In one aspect, the disclosed compounds exhibit inhibition of cell migration in an in vitro cell-based assay with an $IC_{50}$ of less than about 300 µM, less than about 100 µM, less than about 50 µM, less than about 10 µM, less than about 1 µM, less than about 500 nM, or of less than about 100 nM.

Alternatively, the modulatory effects, e g inhibition, of the disclosed compounds can be determined using other types of cell-based assays, e.g. determination of the level of pSTAT5 levels in cells following treatment with a disclosed compound and compared to the pSTAT5 levels in control cells versus the unphosphorylated form of STAT5 in the same cell lysate by Western blot analysis. Other markers of STAT5 inhibition can be assessed in similar fashion other methods known to one skilled in the art (e.g. ELISA, real-time PCR, Northern blots and the like), and include markers selected from Bcl-xL, cyclin D1, cyclin D2, c-myc, and MCL-1. In various further aspects, the effect of the disclosed compounds on the STAT5 activity can be assessed by assays of apoptosis. In is contemplated that the pro-apoptotic activity of the compounds can be determined in an apoptosis assay as known to one skilled in the art. For example, the effect of the disclosed compounds on apoptosis can be determined using K562 or MV-4-11 cells and assessed from an annexin V/P1 assay. In a still further aspect, the effect of the disclosed compounds on STAT5 activity can be determined by a chromatin immunoprecipitation assay wherein the presence of STAT5 bound to the c-myc and/or cyclin D1 promoter is determined.

C. Methods of Making the Compounds

In one aspect, the invention relates to methods of making compounds useful as inhibitors of STAT. In a further aspect, the products of disclosed methods of making are modulators of STAT activity. In a yet further aspect, the products of disclosed methods of making bind to a STAT protein and negatively modulate STAT activity. The compounds can, in one aspect, exhibit subtype selectivity. In a still further aspect, the products of disclosed methods of making exhibit selectivity for the STAT3 member of the STAT protein family.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In a further aspect, the compound produced is useful in the treatment of a disorder of uncontrolled cellular proliferation associated with STAT dysfunction and other diseases in which a STAT protein is involved, as further described herein. In a further aspect, the STAT protein is STAT3.

1. Route I

In one aspect, substituted 2-hydroxy-4-(2-(phenylsulfonamido)acetamido)benzoic acid analogs of the present invention can be prepared generically by the synthetic scheme as shown below.

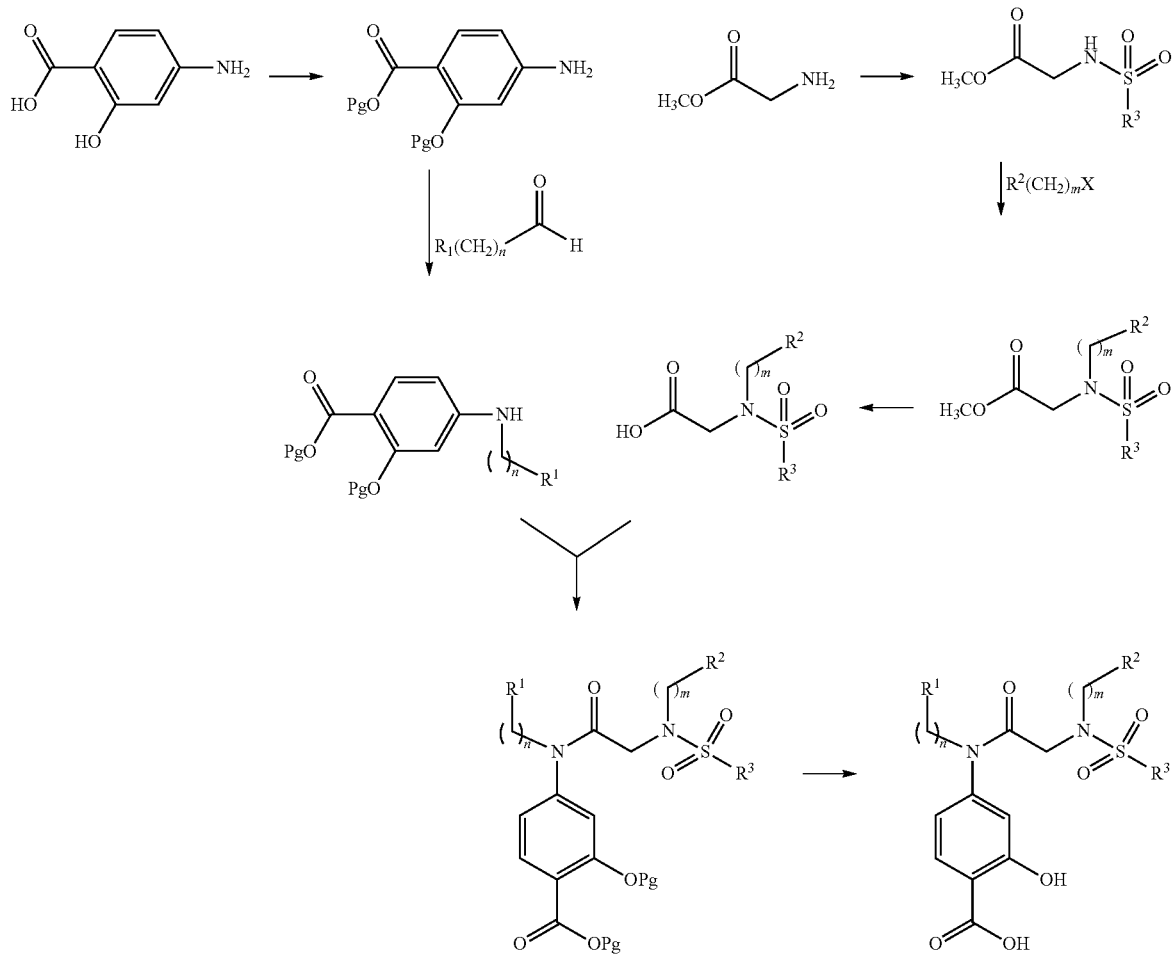

Pg = protecting group
X = halogen or leaving group

Compounds are represented in generic form, with substituents as noted in compound descriptions elsewhere herein. A more specific example is set forth below.

In one aspect, Route I begins with a suitable substituted 4-aminosalicylic acid (1.1) and benzyl bromide. The reaction of the 4-aminosalicylic acid derivative and benzyl bromide is typically carried out in a suitable solvent such as DMF. A suitable base, e.g., potassium tert-butoxide is added and the reaction stirred for about 15 minutes. Then the initial prescribed portion of benzyl bromide is added, and the reaction is maintained at room temperature (about 15-30° C.) for a suitable amount of time sufficient to complete the first phase of the reaction, e.g., about 4 hours. Then the reaction is cooled to about 0° C. and another prescribed amount of potassium tert-butoxide is added followed by the second prescribed amount of benzyl bromide is added. The reaction is stirred for a suitable amount of time sufficient to complete reaction, e.g., overnight (about 8 to 18 hours) and then water is added to afford compounds of type 1.2. The product, a compound of type 1.2, is isolated by methods known to one skilled in the art e.g., extraction with a solvent (e.g., ethyl acetate), washing (e.g., water), drying, filtering, and concentration under vacuum; followed by purification if necessary.

In one aspect, compounds of type 1.3, can be prepared by reaction of an amine (1.2) with a suitable aldehyde under reductive amination conditions. To a stirred solution of the amine, compounds of type 1.2, acetic acid and an anhydrous solvent, e.g., methanol with molecular sieves is added an aldehyde, e.g., $R^1(CH_2)_n$—CHO. The reaction is heated at a appropriate temperature, about 45° C., for a sufficient reaction time of about 3 hours and then allowed to cool to about room temperature. Then the reducing agent, e.g., sodium cyanoborohydride, is added to the reaction mixture and is allowed to stir for sufficient time to complete the reaction, overnight (about 8 to 18 hours) at an appropriate temperature (about 15-30° C.) Upon completion of the reaction, the reaction is diluted with a solvent, e.g., dichloromethane, filtered, and concentrated under vacuum to afford the product 1.3 upon purification if necessary.

In one aspect compounds of type 1.5 can be prepared by the reaction of a sulfonyl chloride, $R^3SO_2Cl$, with an amine, e.g., 1.4. To the amine, e.g., 1.4, dissolved in an appropriate solvent, e.g., dichloromethane, is added a suitable base, e.g., DIPEA. Then, the appropriate sulfonyl chloride, e.g., $R^3SO_2Cl$, is added and the reaction is stirred at room

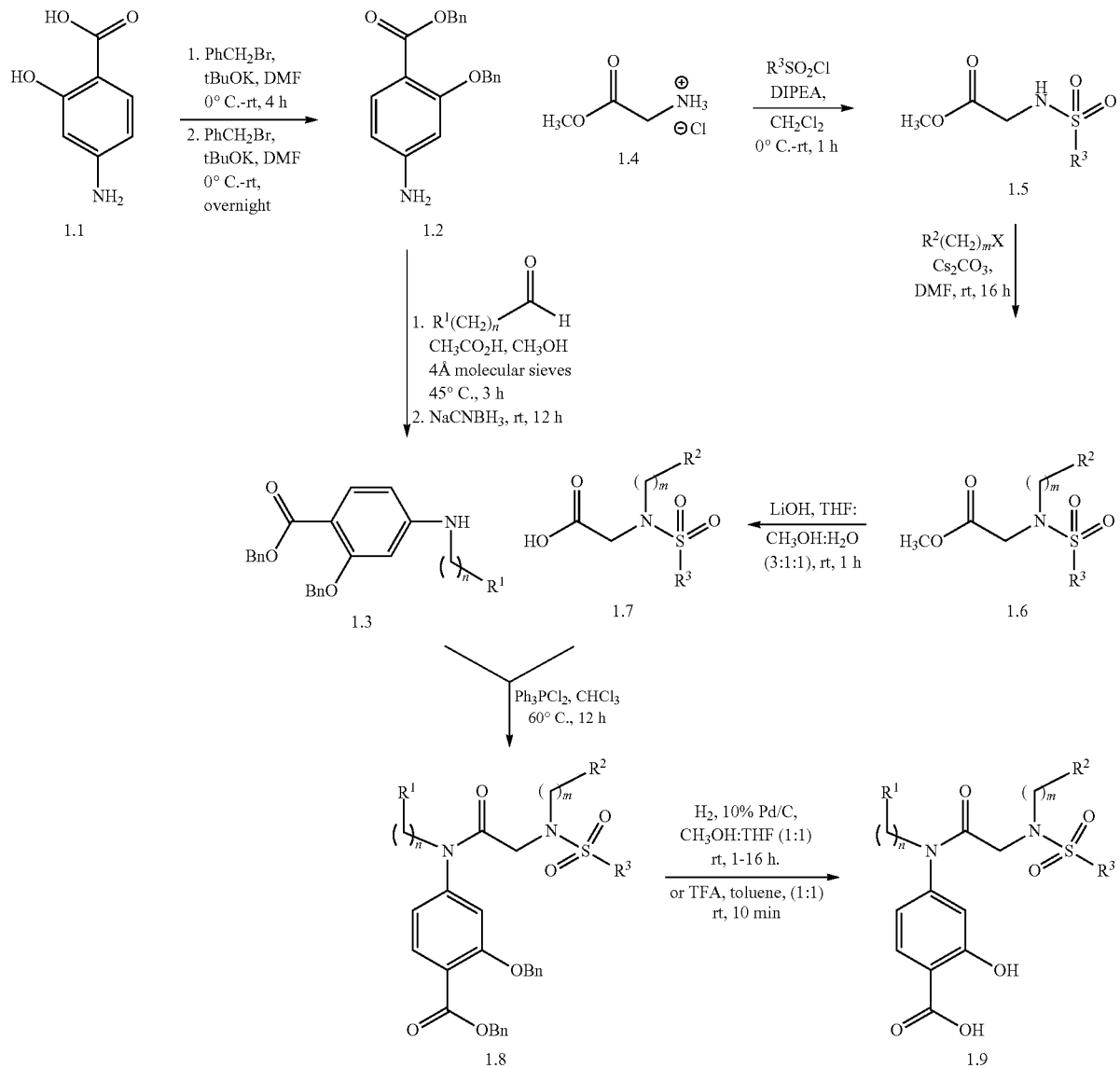

temperature (about 15-30° C.) until the reaction is complete (about 1 hour). The product, a compound of type 1.5, is isolated by methods known to one skilled in the art e.g., extraction with a solvent (e.g., dichloromethane), washing (e.g., water, brine), drying, filtering and concentration under vacuum; followed by purification if necessary.

In one aspect, compounds of type 1.4, can be prepared by the reaction of an alkyl halide, $R^2(CH_2)_mX$, to afford compounds of type 1.6. To a stirred solution of 1.4 and a base, e.g., cesium carbonate, in a suitable solvent, e.g., DMF is added a alkyl halide, e.g., $R^2(CH_2)_mX$. The reaction is allowed to stir for a sufficient amount of time to complete the reaction, e.g., overnight (about 8 to 18 hours, at room temperature (about 15-30° C.). The product, a compound of type 1.6, is isolated by methods known to one skilled in the art e.g., extraction with a solvent (e.g., dichloromethane), washing (e.g., brine), drying, filtering and concentration under vacuum; followed by purification if necessary.

In one aspect, compounds of type 1.6 can be converted to compounds of type 1.7 under the appropriate hydrolysis conditions. Compound 1.7 is dissolved in an appropriate solvent combination in the appropriate ratio, e.g., $CH_3OH$:$THF$:$H_2O$ (3:1:1) and then a base, e.g., $LiOH.H_2O$ is added at an appropriate room temperature, (about 15-30° C.). The mixture is stirred for an suitable amount of time, e.g., about 3 hours, to allow for completion reaction to occur. The solvents are evaporated, except for water. The remaining aqueous mixture is washed with an appropriate solvent, e.g., ethyl acetate. The alkaline, aqueous solution is treated with an aqueous acid, e.g., HCl (aq) to acidify (about pH 2). The product, a compound of type 1.7, is isolated by methods known to one skilled in the art e.g., extraction with a solvent (e.g., ethyl acetate), drying, filtering and concentration under vacuum; followed by purification if necessary.

In one aspect compounds of type 1.8 can be synthesized by reacting compounds of types 1.3 and 1.7 with each other. To a stirred solution of the secondary aniline of type 1.3 and the carboxylic acid of type 1.7 in a suitable solvent, e.g., chloroform, is added $PPh_3Cl_2$. The reaction is heated overnight (about 8-18 hours) at an appropriate temperature, e.g., about 60° C. Upon cooling, the solvent(s) are removed under reduced pressure. The concentrated residue is absorbed directly onto a suitable stationary phase, e.g., silica gel, and subjected to chromatography to give the product 1.8.

In one aspect compounds of type 1.9 can be prepared by the deprotection of compounds of type 1.8 using hydrogenolysis conditions. For example, the benzyl protected compounds of type 1.8 are dissolved in a suitable solvent such as $CH_3OH$:$THF$ (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 1.9, upon purification if necessary.

In one aspect compounds of type 1.9 can be prepared by the deprotection of compounds of type 1.8 under acidic conditions. For example, the benzyl protected compounds of type 1.8 are dissolved in a suitable solvent with trifluoroacetic acid, e.g., toluene:TFA (1:1, about 0.1 M). The mixture is stirred for a suitable amount of time to for completion of the reaction, e.g., 5 minutes, at the appropriate temperature, e.g., room temperature (about 15-30° C.). Upon completion of the reaction, the solvents are removed under reduced pressure to afford the product of type 1.9 upon purification if necessary.

2. Route II

In one aspect, substituted 2-hydroxy-4-(2-(phenylsulfonamido)acetamido)benzoic acid analogs of the present invention can be prepared generically by the synthetic scheme as shown below.

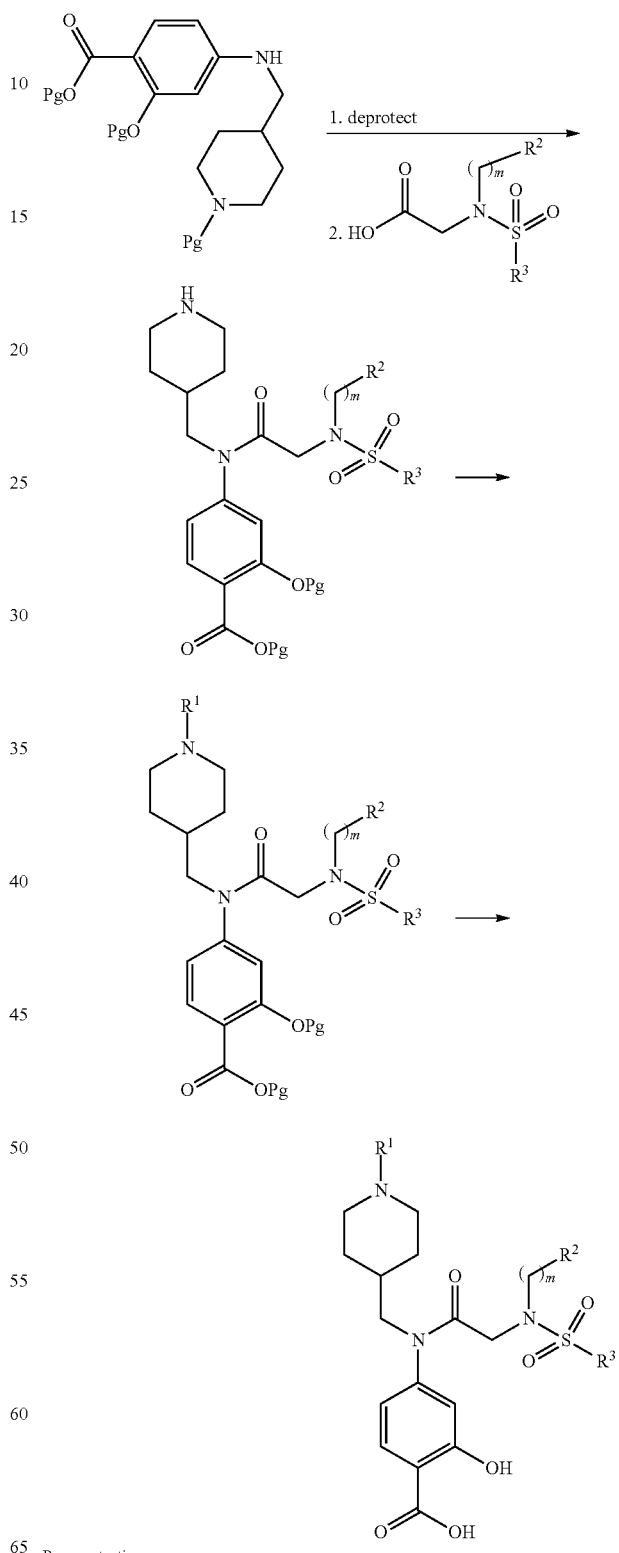

Pg = protecting group

Compounds are represented in generic form, with substituents as noted in compound descriptions elsewhere herein. A more specific example is set forth below.

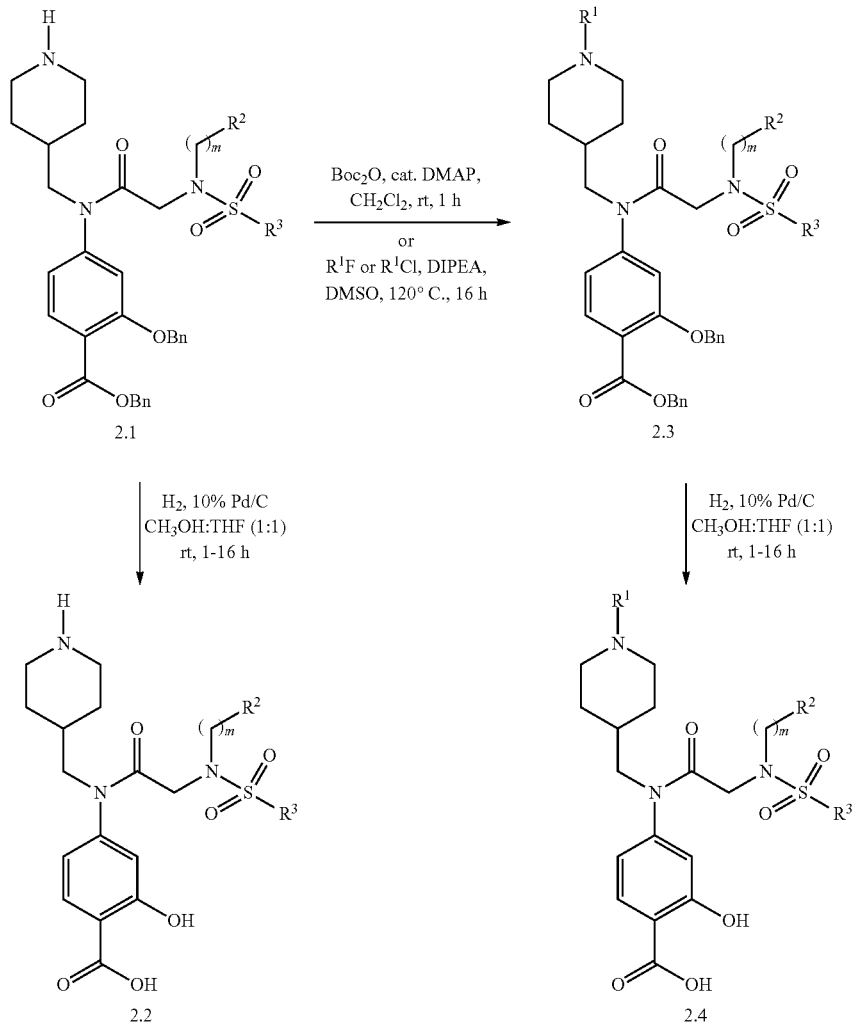

In one aspect, Route II begins with a suitable substituted 2-hydroxy-4-(2-(phenylsulfonamido)acetamido)benzoic acid analogs (2.1) to afford N-Boc derivatives 2.3. Amines of type 2.1 are mixed with a base, e.g., DIPEA in a suitable solvent, e.g., chloroform (about 0.1 M concentration). To this mixture is added $Boc_2O$, and mixture is allowed to stir overnight (8-18 hours) at room temperature (15-30° C.) until the reaction is completed. The product, the Boc protected compound of type 2.3, is isolated by methods known to one skilled in the art e.g., extraction with a solvent (e.g., dichloromethane), washing (e.g., water and brine), drying, filtering and concentration under vacuum; followed by purification if necessary.

In one aspect, a suitable substituted 2-hydroxy-4-(2-(phenylsulfonamido)-acetamido)benzoic acid analogs (2.1) to afford amine derivatives 2.3. The desired secondary amine of the type 2.1 and the appropriate aryl halide, e.g., an aryl fluoride (R'F) or aryl chloride ($R^1Cl$), are dissolved in a appropriate, anhydrous solvent such as DMSO. An appropriate base, e.g., DIPEA, is added and then the reaction is heated a suitable temperature (about 120° C.) and time (overnight, about 8-18 hours) to allow for enough time for the reaction to occur. The reaction is quenched with water. The product, compounds of type 2.3, is isolated by methods known to one skilled in the art e.g., extraction with a solvent (e.g., ethyl acetate), washing (e.g., brine), drying, filtering and concentration under vacuum; followed by purification if necessary.

In one aspect compounds of type 2.2 can be prepared by the deprotection of compounds of type 2.1 using hydrogenolysis conditions. For example, the benzyl protected compounds of type 2.1 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 2.2, upon purification if necessary.

In one aspect compounds of type 2.4 can be prepared by the deprotection of compounds of type 2.3 using hydrogenolysis conditions. For example, the benzyl protected compounds of type 2.3 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 2.4, upon purification if necessary.

3. Route III
In one aspect, substituted 2 substituted 2-hydroxy-4-(2-(phenylsulfonamido)acetamido)benzoic acid analogs of the present invention can be prepared generically by the synthetic scheme as shown below.
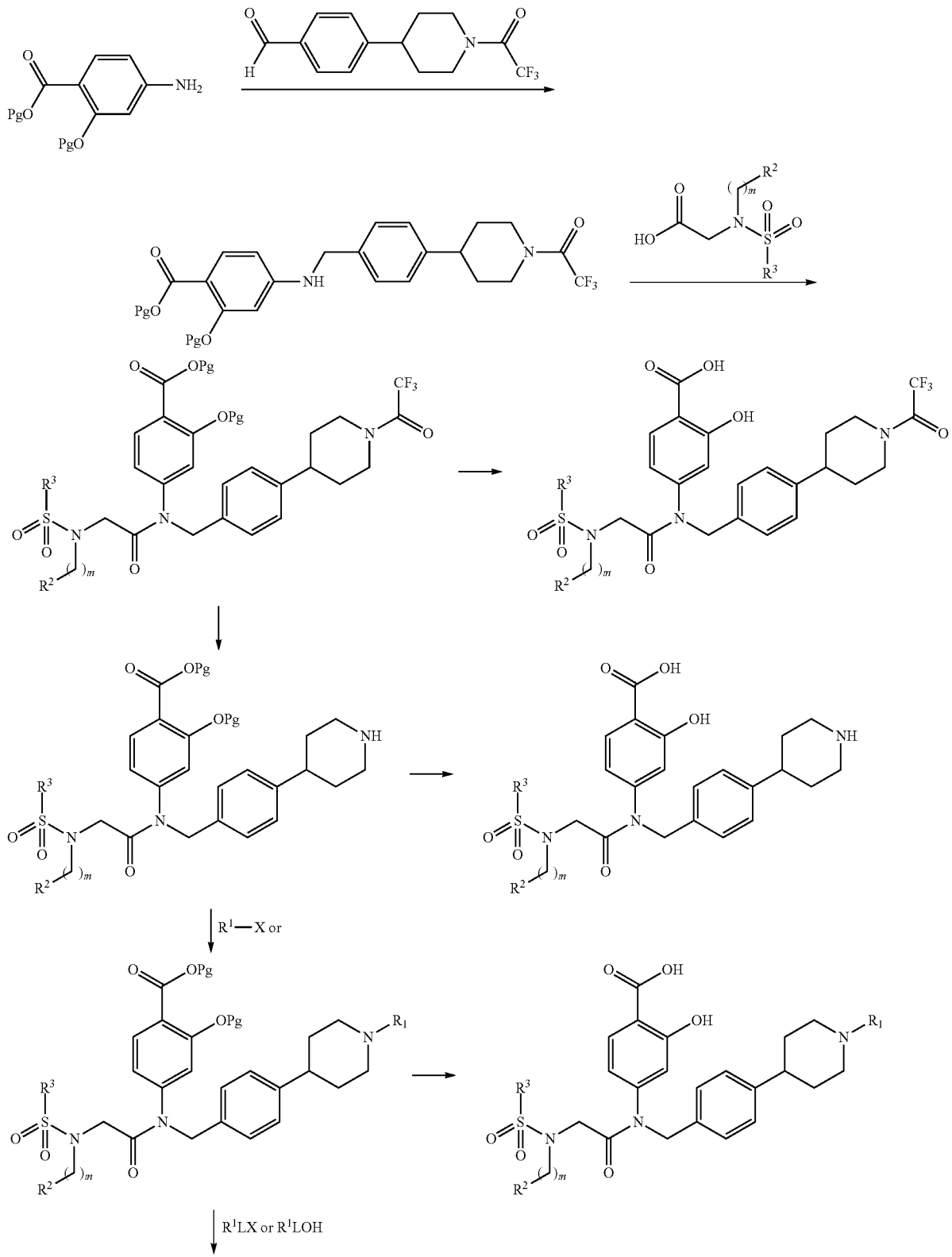

173
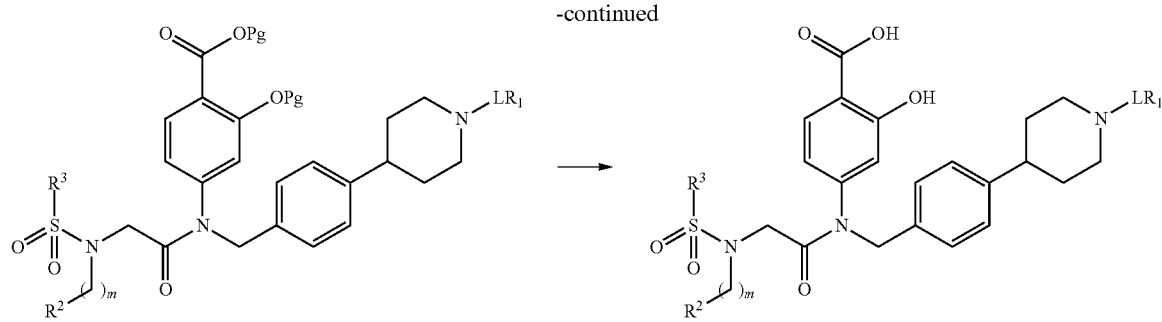
-continued
174
Pg = protecting group
Compounds are represented in generic form, with substituents as noted in compound descriptions elsewhere herein. A more specific example is set forth below.
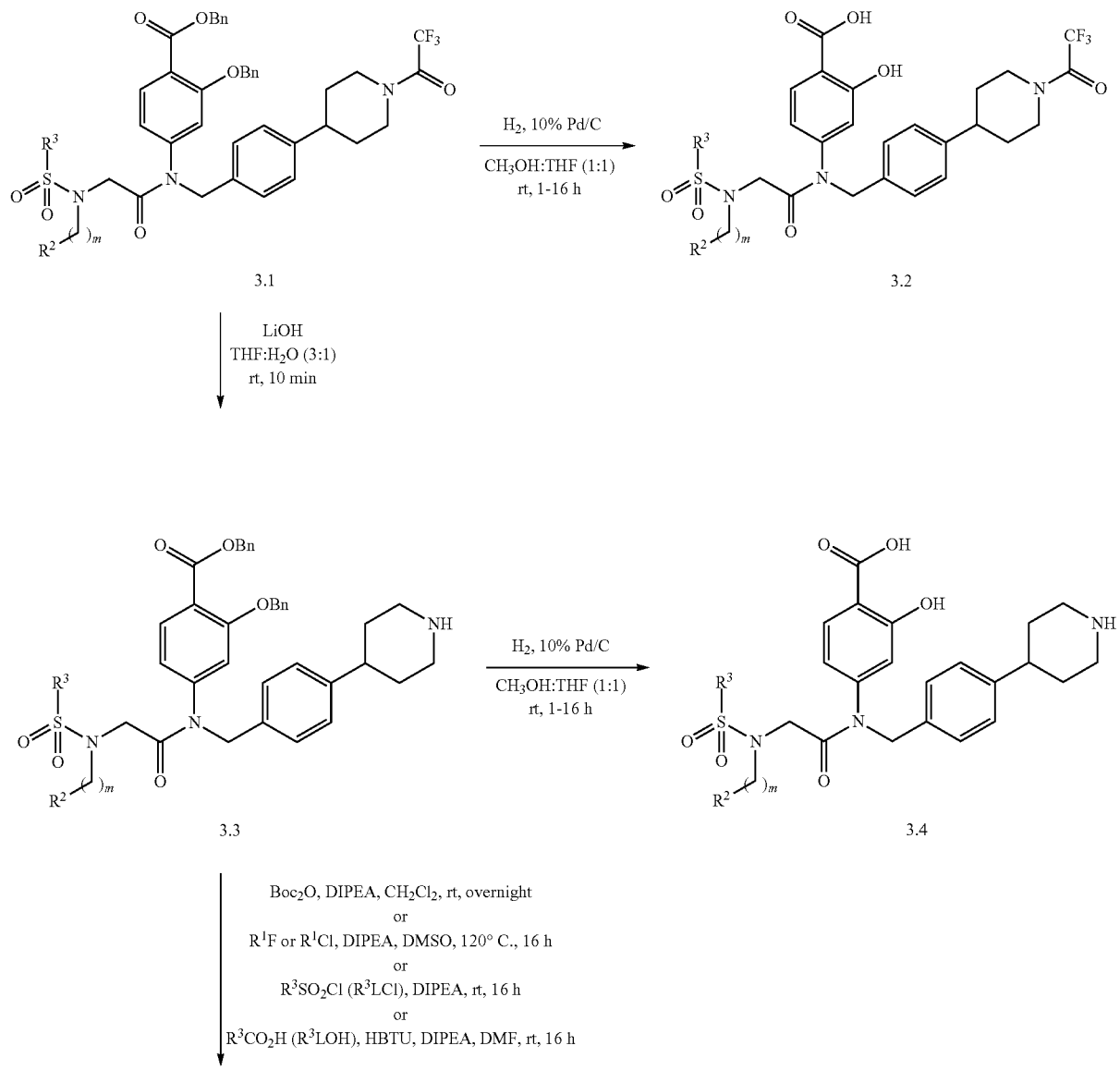

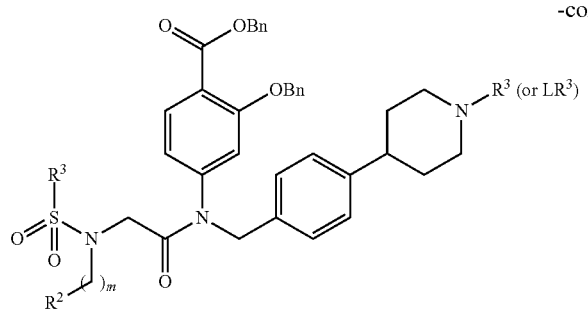

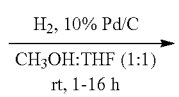

3.5

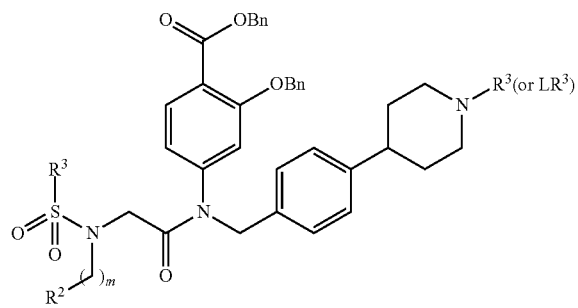

3.6

In one aspect, Route III begins with a suitable substituted 2-hydroxy-4-(2-(phenylsulfonamido)acetamido)benzoic acid analogs (3.1) to afford N-trifluoroacetyl derivatives 3.3. For example, compounds of type 3.1 can be converted to compounds of type 3.3 under the appropriate hydrolysis conditions. Compound 3.1 is dissolved in an appropriate solvent combination in the appropriate ratio, e.g., $CH_3OH$:$THF$:$H_2O$ (3:1:1) and then a base, e.g., $LiOH.H_2O$ is added at an appropriate room temperature, (about 15-30° C.). The mixture is stirred for an suitable amount of time, e.g., about 10 minutes, to allow for completion reaction to occur. The reaction is diluted with water and the product, 3.3, extracted with an appropriate solvent, e.g., ethyl acetate. The product, a compound of type 3.3, is isolated by methods known to one skilled in the art e.g., extraction with a solvent (e.g., ethyl acetate), washing (aqueous $NaHCO_3$, water, brine), drying, filtering and concentration under vacuum; followed by purification if necessary.

In one aspect compounds of type 3.2 can be prepared by the deprotection of compounds of type 3.1 using hydrogenolysis conditions. For example, the benzyl protected compounds of type 3.1 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 3.2, upon purification if necessary.

In one aspect compounds of type 3.4 can be prepared by the deprotection of compounds of type 3.3 using hydrogenolysis conditions. For example, the benzyl protected compounds of type 3.3 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 3.4, upon purification if necessary.

In one aspect, a suitable substituted 2-hydroxy-4-(2-(phenylsulfonamido)acetamido)benzoic acid analogs (3.3) to afford N-Boc derivatives 3.5. Amines of type 3.3 are mixed with a base, e.g., DIPEA in a suitable solvent, e.g., chloroform (about 0.1 M concentration). To this mixture is added $Boc_2O$, and mixture is allowed to stir overnight (8-18 hours) at room temperature (15-30° C.) until the reaction is completed. The product, a the Boc protected compound of type 3.5, is isolated by methods known to one skilled in the art e.g., extraction with a solvent (e.g., dichloromethane), washing (e.g., water and brine), drying, filtering and concentration under vacuum; followed by purification if necessary.

In one aspect, a suitable substituted 2-hydroxy-4-(2-(phenylsulfonamido)-acetamido)benzoic acid analogs (3.3) to afford amine derivatives 3.5. The desired secondary amine of the type 3.3 and the appropriate aryl halide, e.g., an aryl fluoride (R'F) or aryl chloride ($R^1Cl$), are dissolved in a appropriate, anhydrous solvent such as DMSO. An appropriate base, e.g., DIPEA, is added and then the reaction is heated a suitable temperature (about 120° C.) and sufficient time (overnight, about 8-18 hours) to allow for reaction to occur. The reaction is quenched with water. The product, compounds of type 3.5, is isolated by methods known to one skilled in the art e.g., extraction with a solvent (e.g., ethyl acetate), washing (e.g., brine), drying, filtering and concentration under vacuum; followed by purification if necessary.

In one aspect, a suitable substituted 2-hydroxy-4-(2-(phenylsulfonamido)acetamido)benzoic acid analogs (3.3) and the appropriate sulfonyl chloride, $R^3SO_2Cl$ are reacted to form compounds of type 3.5. To the amine, e.g., 3.3, dissolved in an appropriate solvent, e.g., dichloromethane, is added a suitable base, e.g., DIPEA. Then, the appropriate sulfonyl chloride, e.g., $R^3SO_2Cl$, is added and the reaction is stirred at room temperature (about 15-30° C.) until the reaction is complete (about 1 hour). The product, a compound of type 1.5, is isolated by methods known to one skilled in the art e.g., extraction with a solvent (e.g., dichloromethane), washing (e.g., water, brine), drying, filtering and concentration under vacuum; followed by purification if necessary.

In one aspect, a suitable substituted 2-hydroxy-4-(2-(phenylsulfonamido)acetamido)benzoic acid analogs (3.3) and the appropriate carboxylic acid, $R^3CO_2H$ are coupled to form compounds of type 3.5. The required carboxylic acid of type $R^3CO_2H$ is added to a solution of the coupling agent, e.g., HBTU and a suitable base, e.g., DIPEA in a suitable solvent, e.g., DMF at about a 0.1 M concentration. The resulting mixture is allowed to stir for about 10 minutes at room temperature (about 15-30° C.). The appropriate amine of type 3.3 is dissolved in a solution of a suitable base, e.g., DIPEA, and solvent, e.g., DMF at about a 0.1 M concentration, and then this mixture is added to the carboxylic acid/coupling agent solution. The reaction is stirred for a sufficient amount of time until completed (about 4 hours). The product, compounds of type 3.5, is isolated by methods known to one skilled in the art e.g., dissolved/extraction with a solvent (e.g., ethyl acetate), washings (e.g., about 2M HCl, saturated $NaHCO_3$, brine), drying, filtering and concentration under vacuum; followed by purification if necessary.

In one aspect compounds of type 3.6 can be prepared by the deprotection of compounds of type 3.5 using hydrogenolysis conditions. For example, the benzyl protected compounds of type 3.5 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 3.6, upon purification if necessary.

4. Route IV

In one aspect, substituted 2-hydroxy-4-(2-(phenylsulfonamido)acetamido)benzoic acid analogs of the present invention can be prepared generically by the synthetic scheme as shown below.

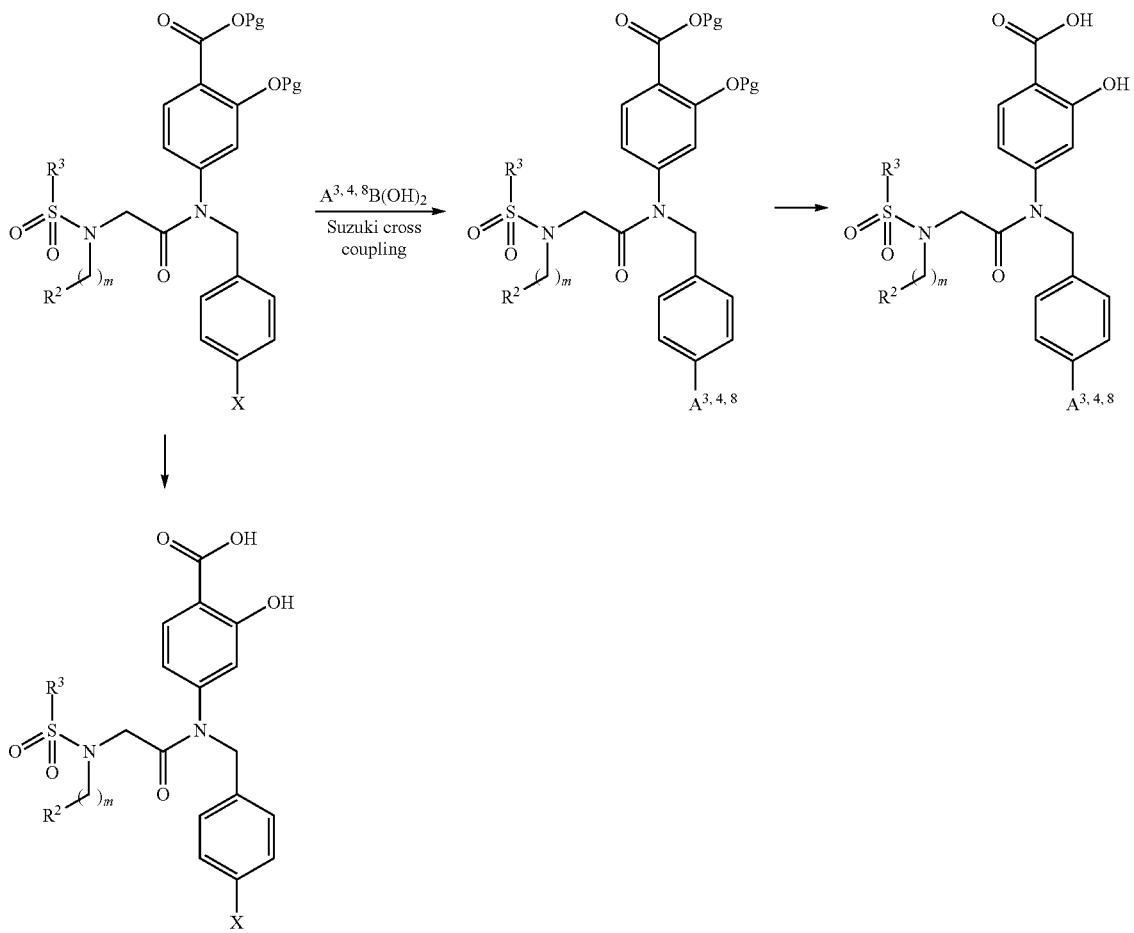

Pg = protecting group
X = halogen or appropriate leaving group

Compounds are represented in generic form, with substituents as noted in compound descriptions elsewhere herein. A more specific example is set forth below.

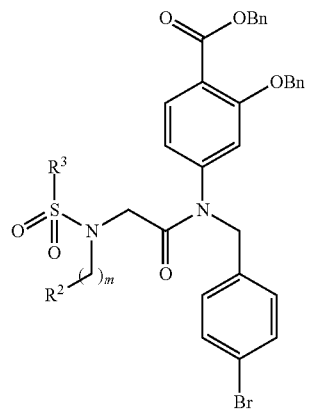

4.1

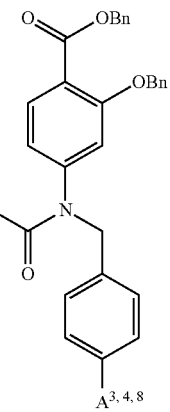

4.2

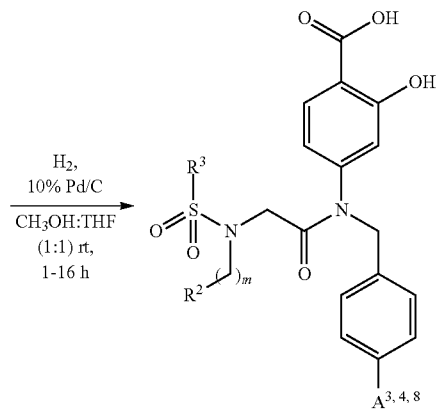

4.3

1. LiOH, THF:H₂O (3:1), rt, 24 h
2. TFA, toluene (1:1), rt, 10 min

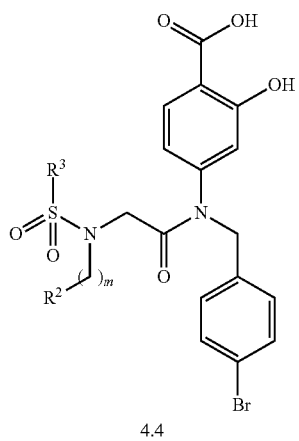

4.4

In one aspect, Route IV begins with a suitable substituted 2-hydroxy-4-(2-(phenylsulfonamido)acetamido)benzoic acid analogs (4.1) to afford biaryl derivatives 4.2. In one aspect compounds of type 4.2 can be prepared by the Pd mediated coupling of compounds of type 4.1 with aryl boronic acid derivatives of type $A^{3,4,8}B(OH)_2$ using Suzuki cross-coupling reaction conditions. A mixture of the appropriate aryl bromide of type 4.1, boronic acid of type $A^{3,4,8}B(OH)_2$, a suitable base, e.g., $K_2CO_3$, and an appropriate catalyst, e.g., $Pd(PPh_3)_4$ is suspended in a suitable solvent, e.g., DMF, in a sealed tube reaction vessel. The reaction mixture is irradiated using a microwave reactor at appropriate temperature of about 170° C. and for an appropriate amount of time for the coupling reaction to go to completion, e.g., about 17 minutes, After cooling to about room temperature (about 15-30° C.), the reaction is diluted with an appropriate solvent such as dichloromethane. The product, compounds of type 4.2, is isolated by methods known to one skilled in the art e.g., extraction with a solvent (e.g., dichloromethane), washing (e.g., brine), drying, filtering and concentration under vacuum; followed by purification if necessary.

In one aspect compounds of type 4.3 can be prepared by the deprotection of compounds of type 4.2 using hydrogenolysis conditions. For example, the benzyl protected compounds of type 4.2 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 4.3, upon purification if necessary.

For example, compounds of type 4.1 can be converted to compounds of type 4.4 under the appropriate two step hydrolysis procedure. Step 1: Compound 4.1 is dissolved in an appropriate solvent combination in the appropriate ratio, e.g., $CH_3OH$:THF:$H_2O$ (3:1:1) and then a base, e.g., $LiOH.H_2O$ is added at an appropriate room temperature, (about 15-30° C.). The mixture is stirred for an suitable amount of time, e.g., about 10 minutes, to allow for completion reaction to occur. The reaction is diluted with water and the mono-benzyl intermediate product of 4.4, extracted with an appropriate solvent, e.g., ethyl acetate. The product, a intermediate benzyl ether of type 4.4, is isolated by methods known to one skilled in the art e.g., extraction with a solvent (e.g., ethyl acetate), washing (aqueous NaHCO₃, water, brine), drying, filtering and concentration under vacuum, followed by purification if necessary. Step 2: The benzyl ether intermediate of type 4.4 is dissolved in a suitable solvent with trifluoroacetic acid, e.g., toluene:TFA (1:1, about 0.1 M). The mixture is stirred for a suitable amount of time to for completion of the reaction, e.g., 5 minutes, at the appropriate temperature, e.g., room temperature (about 15-30° C.). Upon completion of the reaction, the solvents are removed under reduced pressure to afford the product of type 4.4 upon purification if necessary.

5. Route V

In one aspect, substituted 2-hydroxy-4-(2-(phenylsulfonamido)acetamido)benzoic acid analogs of the present invention can be prepared generically by the synthetic scheme as shown below.

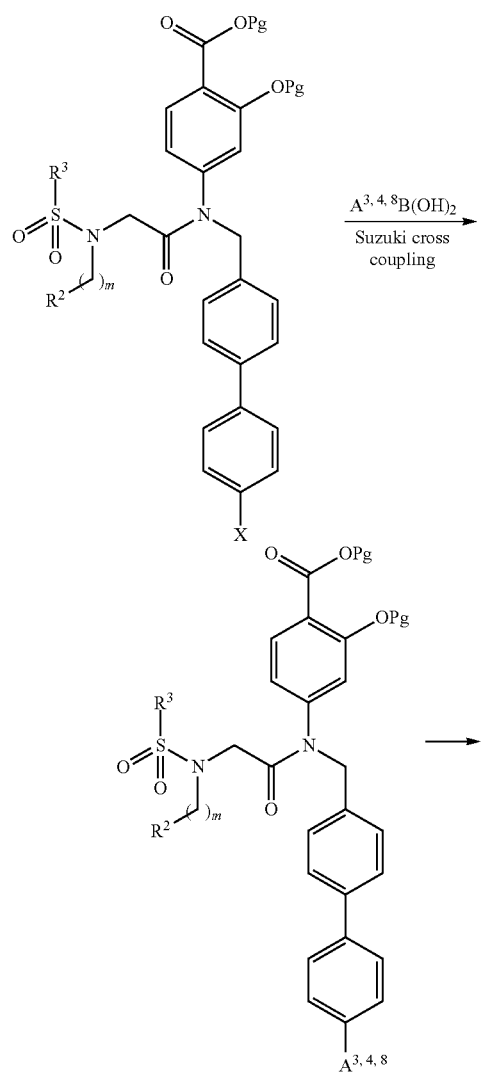

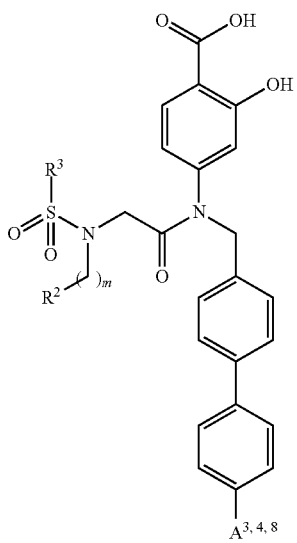

Pg = protecting group
X = halogen or appropriate leaving group

Compounds are represented in generic form, with substituents as noted in compound descriptions elsewhere herein. A more specific example is set forth below.

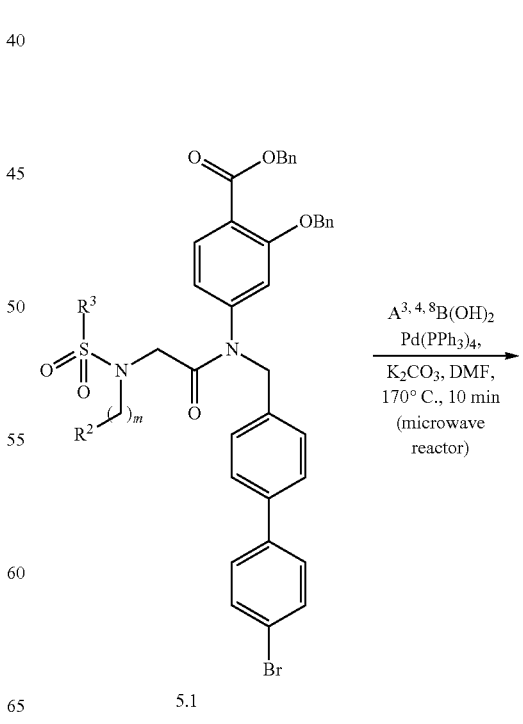

5.1

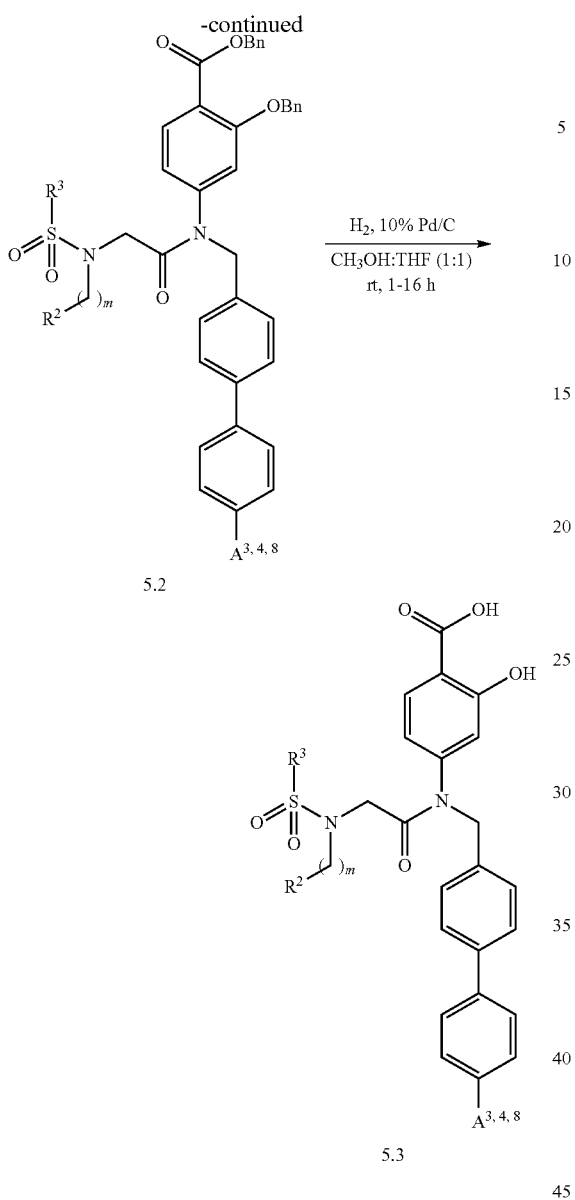

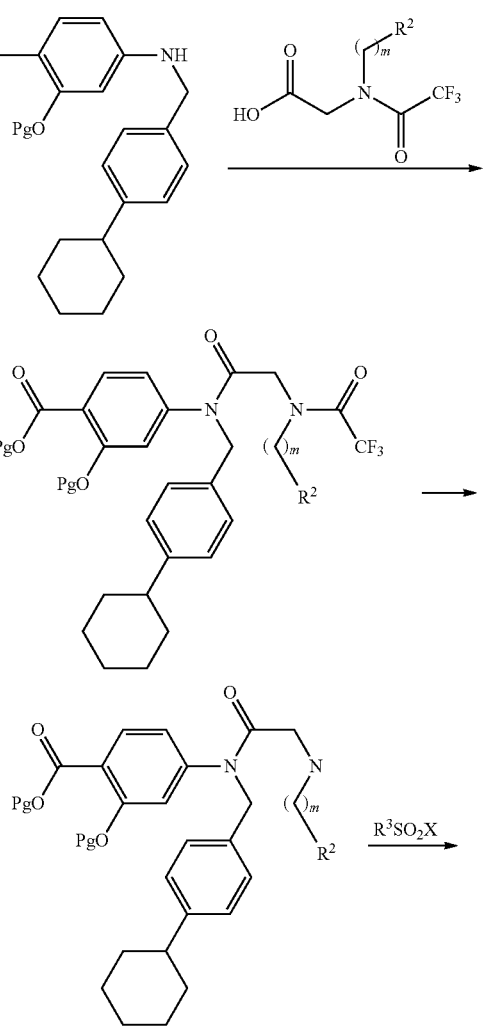

(e.g., dichloromethane), washing (e.g., brine), drying, filtering and concentration under vacuum; followed by purification if necessary.

In one aspect compounds of type 5.3 can be prepared by the deprotection of compounds of type 5.2 using hydrogenolysis conditions. For example, the benzyl protected compounds of type 5.2 are dissolved in a suitable solvent such as $CH_3OH:THF$ (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 5.3, upon purification if necessary.

6. Route VI

In one aspect, substituted 2-hydroxy-4-(2-(phenylsulfonamido)acetamido)benzoic acid analogs of the present invention can be prepared generically by the synthetic scheme as shown below.

In one aspect, Route V begins with a suitable substituted 2-hydroxy-4-(2-(phenylsulfonamido)acetamido)benzoic acid analogs (5.1) to afford terphenyl derivatives 5.2. In one aspect, compounds of type 5.2 can be prepared by the Pd mediated coupling of compounds of type 5.1 with aryl boronic acid derivatives of type $A^{3,4,8}B(OH)_2$ using Suzuki cross-coupling reaction conditions. A mixture of the appropriate aryl bromide of type 5.1, boronic acid of type $A^{3,4,8}B(OH)_2$, a suitable base, e.g., $K_2CO_3$, and an appropriate catalyst, e.g., $Pd(PPh_3)_4$ is suspended in a suitable solvent, e.g., DMF, in a sealed tube reaction vessel. The reaction mixture is irradiated using a microwave reactor at an appropriate temperature of about 170° C. and for an appropriate amount of time for the coupling reaction to go to completion, e.g., about 17 minutes, After cooling to about room temperature (about 15-30° C.), the reaction is diluted with an appropriate solvent such as dichloromethane. The product, compounds of type 5.2, is isolated by methods known to one skilled in the art e.g., extraction with a solvent 185
-continued
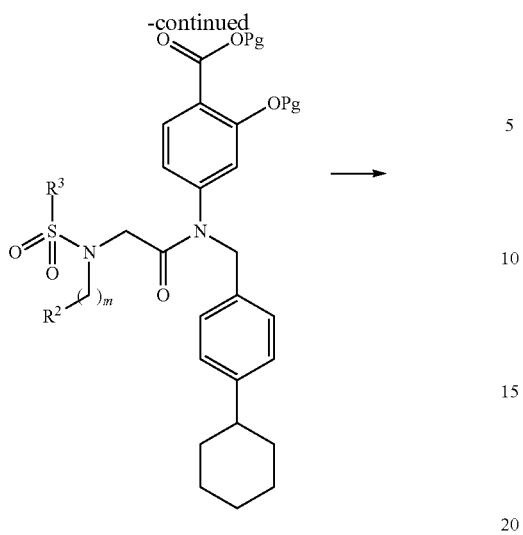
Pg = protecting group
X = halogen or leaving group
Compounds are represented in generic form, with substituents as noted in compound descriptions elsewhere herein. A more specific example is set forth below.
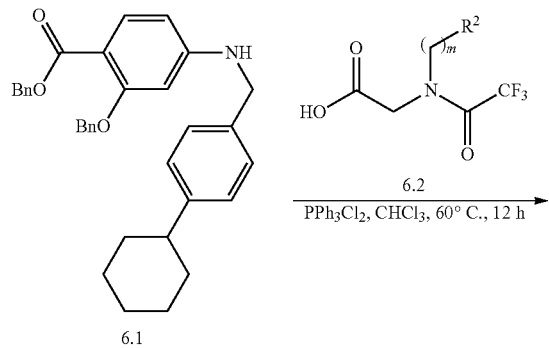
186
-continued
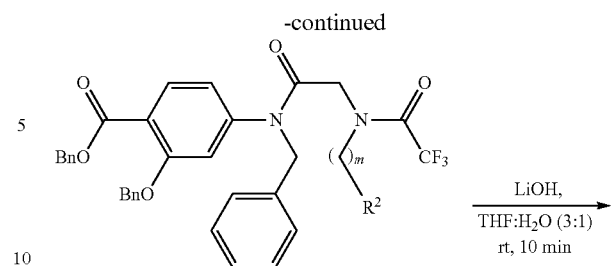
6.3
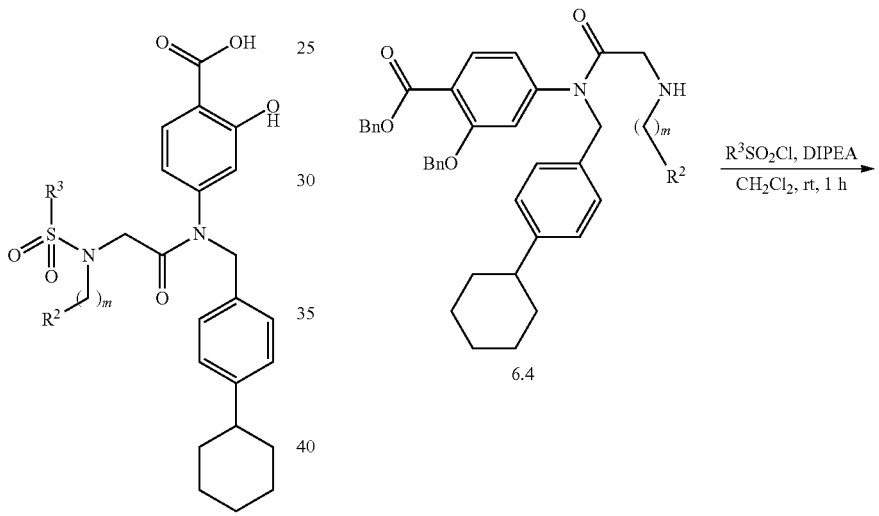
6.4
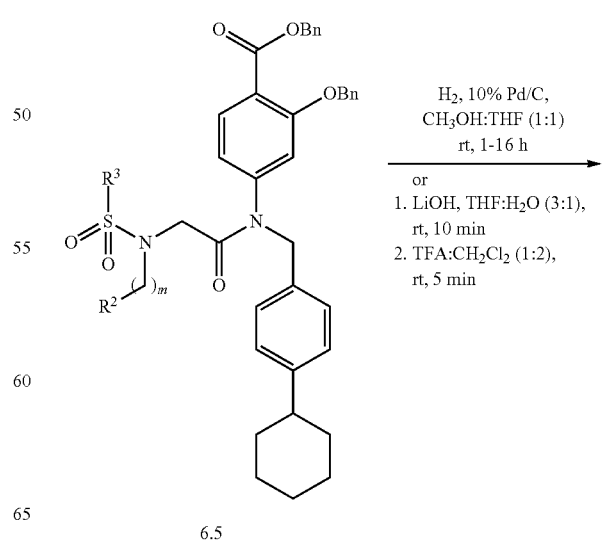
6.5

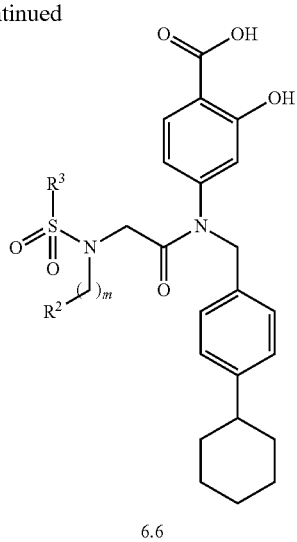

6.6

In one aspect, Route V begins with a suitable substituted 2-hydroxy-4-(2-(phenylsulfonamido)acetamido)benzoic acid analogs (6.1) to afford derivatives 6.3. To a stirred solution of the secondary aniline of type 6.1 and the carboxylic acid of type 6.2 in a suitable solvent, e.g., chloroform, is added $PPh_3Cl_2$. The reaction is heated overnight (about 8-18 hours) at an appropriate temperature, e.g., about 60° C. Upon cooling, the solvent(s) are removed under reduced pressure. The concentrated residue is absorbed directly onto a suitable stationary phase, e.g., silica gel, and subjected to chromatography to give the product 6.3.

In one aspect, compounds of type 6.3 can be converted to compounds of type 6.4 under the appropriate hydrolysis conditions. Compound 6.3 is dissolved in an appropriate solvent combination in the appropriate ratio, e.g., $CH_3OH$:THF:$H_2O$ (3:1:1) and then a base, e.g., $LiOH.H_2O$ is added at an appropriate room temperature, (about 15-30° C.). The mixture is stirred for an suitable amount of time, e.g., about 10 minutes, to allow for completion reaction to occur. The solvents are evaporated, except for water. The remaining aqueous mixture is washed with an appropriate solvent, e.g., ethyl acetate. The alkaline, aqueous solution is treated with an aqueous acid, e.g., HCl (aq) to acidify (about pH 2). The product, a compound of type 6.4, is isolated by methods known to one skilled in the art e.g., extraction with a solvent (e.g., ethyl acetate), drying, filtering and concentration under vacuum; followed by purification if necessary.

In one aspect, a suitable substituted 2-hydroxy-4-(2-(phenylsulfonamido)acetamido)benzoic acid analogs (6.4) and the appropriate sulfonyl chloride, $R^3SO_2Cl$ are reacted to form compounds of type 6.5. To the amine, e.g., 6.4, dissolved in an appropriate solvent, e.g., dichloromethane, is added a suitable base, e.g., DIPEA. Then, the appropriate sulfonyl chloride, e.g., $R^3SO_2Cl$, is added and the reaction is stirred at room temperature (about 15-30° C.) and for a time until the reaction is complete (about 1 hour). The product, a compound of type 6.5, is isolated by methods known to one skilled in the art e.g., extraction with a solvent (e.g., dichloromethane), washing (e.g., water, brine), drying, filtering and concentration under vacuum; followed by purification if necessary.

In one aspect compounds of type 6.5 can be prepared by the deprotection of compounds of type 6.6 using hydrogenolysis conditions. For example, the benzyl protected compounds of type 6.5 are dissolved in a suitable solvent such as $CH_3OH$:THF (1:1, about 0.1 M). The mixture is degassed before adding the hydrogenation catalyst, e.g., 10% Pd/C, Hydrogen gas is then bubbled through the reaction mixture for about 5 minutes and then the reaction mixture is put under an atmosphere of hydrogen gas and is allowed to stir for about 3 hours or a suitable amount of time to allow for complete reaction. Then, the mixture is filtered and concentrated under reduced pressure to afford the product 6.6, upon purification if necessary.

For example, compounds of type 6.5 can be converted to compounds of type 6.6 under the appropriate two step hydrolysis procedure. Step 1: Compound 6.5 is dissolved in an appropriate solvent combination in the appropriate ratio, e.g., $CH_3OH$:THF:$H_2O$ (3:1:1) and then a base, e.g., $LiOH.H_2O$ is added at an appropriate room temperature, (about 15-30° C.). The mixture is stirred for an suitable amount of time, e.g., about 10 minutes, to allow for completion reaction to occur. The reaction is diluted with water and the mono-benzyl intermediate product of 6.6, extracted with an appropriate solvent, e.g., ethyl acetate. The product, a intermediate benzyl ether of type 6.6, is isolated by methods known to one skilled in the art e.g., extraction with a solvent (e.g., ethyl acetate), washing (aqueous $NaHCO_3$, water, brine), drying, filtering and concentration under vacuum, followed by purification if necessary. Step 2: The benzyl ether intermediate of type 6.6 is dissolved in a suitable solvent with trifluoroacetic acid, e.g., toluene:TFA (1:1, about 0.1 M). The mixture is stirred for a suitable amount of time to for completion of the reaction, e.g., 5 minutes, at the appropriate temperature, e.g., room temperature (about 15-30° C.). Upon completion of the reaction, the solvents are removed under reduced pressure to afford the product of type 6.6 upon purification if necessary.

D. STAT Proteins

The STAT family of proteins mediate responses to cytokines and growth factors (Bromberg J (2000) *Breast Cancer Res.* 2(2):86-90; Darnell J E, Jr. (2002) *Nat. Rev. Cancer* 2:740-749). The recruitment via the SH2 domain to the receptor phosphotyrosine (pTyr) peptide motifs facilitates STATs phosphorylation on a key tyrosyl residue by tyrosine kinases of growth factor receptors and cytoplasmic tyrosine kinases, such as Janus kinases (Jaks) and the Src family. While preexisting dimers have been detected (Sehgal P B (2008) *Semin Cell Dev Biol.* 19:329-340), phosphorylation induces STAT:STAT dimerization through a reciprocal pTyr-SH2 domain interaction. The active dimers predominantly in the nucleus induce gene transcription by binding to specific DNA-response elements in the promoters of target genes. Recently, a transcriptional function has been also ascribed for unphosphorylated STAT monomers (Yang J, et al. (2005) *Cancer Res.* 65:939-947).

STATs have importance in carcinogenesis and tumorigenesis. The aberrant activation of the family member, Stat3, occurs in many human cancers (Yu H & Jove R (2004) *Nat. Rev. Cancer* 4:97-105; Yue P & Turkson J (2009) *Expert Opin Investig Drugs.* 18:45-56) and promotes tumor progression. The mechanisms of Stat3-mediated tumorigenesis include de-regulation of gene expression that lead to uncontrolled growth and survival of tumor cells, enhanced tumor angiogenesis, and metastasis (Yu H & Jove R (2004) *Nat. Rev. Cancer* 4:97-105, 7-10; Bromberg J & Darnell J E, Jr. (2000) *Oncogene* 19:2468-2473; Bowman T, Garcia R, Turkson J, & Jove R (2000) *Oncogene* 19:2474-2488; Turkson J & Jove R (2000) *Oncogene* 19:6613-6626; Turkson J (2004) *Expert Opin Ther Targets* 8(5):409-422). More recent data has also identify Stat3-dependent regulation of mitochondrial function that promotes malignant transformation (Gough D J, et al. (2009) *Science* 324:1713-1716). Also, tumor cell-associated constitutively-active Stat3 suppresses pro-inflammatory cytokine expression, including interleukin-6 (IL-6), RANTES, and IP-10, while promoting the induction of vascular endothelial growth factor (VEGF), interleukin-10 (IL-10) and other soluble factors that activate Stat3 and in dendritic cells and inhibit their maturation, thereby suppressing tumor-immune surveillance (Wang T, et al. (2004) *Nat Med* 10(1):48-54). Stat3 further engages in signaling cross-talk with NFἰB directing its functions in support of the malignant phenotype (Yu H, Pardoll D, & Jove R (2009) *Nat Rev Cancer* 9:798-809; Grivennikov S I & Karin M (2010) *Cytokine & Growth Factor Reviews* 21:11-19).

Without wishing to be bound by a particular theory, a model for activity of the disclosed compounds is shown in FIG. 1*a*, wherein the disclosed compounds mediate inhibition of Stat3 activation and transcriptional activity and the consequent effects on Stat3-dependent events, tumor processes, and tumor growth. In various aspects, in this model the disclosed compounds interact with the Stat3 SH2 domain, disrupt pre-existing Stat3: Stat3 dimers, prevent de novo Stat3 activation by blocking association with phospho (P)-Tyr peptide motifs of receptor (R), and block Stat3 nuclear translocation and transcriptional function. In various aspects, and without wishing to be bound by a particular theory, a further model for the action of the disclosed compounds is provided in FIG. 1*b*, wherein the disclosed compounds mediate inhibition of Stat3-dependent events, tumor processes and tumor growth. In various aspects, in this model, the disclosed compounds attenuate aberrant Stat3 signaling, and consequently suppressing nuclear Stat3-NFκB crosstalk and nuclear pNFκB levels, and the Stat3-mediated E-cadherin repression, paxillin, FAK, KLF8, and EPSTI1 induction, sICAM, G-CSF, MIF/GIF, Serpine1, and IL-1RA production, and c-Myc, Cyclin D1, Survivin, VEGF, Bcl-xL induction. Again, without wishing to be bound by a particular theory, the modulation of these events through inhibition of Stat3 activity leads to inhibition of tumor cell growth, survival, motility, migration, invasion, and tumor angiogenesis, growth and metastasis in vivo.

STAT5 protein is one of seven members belonging to the STAT family of cytosolic proteins. The STAT family of proteins play important and diverse cell signaling and transcriptional roles in cells. Stat5 signaling, like Stat3 signaling, is transiently activated in normal cells and is deactivated by a number of different cytosolic and nuclear regulators, including phosphatases, SOCS, PIAS, and proteasomal degradation (Lai, S. Y.; Johnson, F. M. Drug Resistance Updates 2010, 13, 67-78). Like STAT3, STAT5 has gained notoriety for its aberrant role in human cancers and tumorigenesis, having been found to be constitutively activated in many cancers including those of the breast, liver, prostate, blood, skin, head and neck (Müller, J., et al. ChemBioChem 2008, 9, 723-727). Despite significant evidence implicating STAT5's causal role in human malignancies, unlike STAT3, there has been very little progress in identifying small molecule inhibitors of STAT5 function. The majority of medicinal research on STAT function in transformed cells has been aimed at identifying an inhibitor of STAT3 protein. As a result, several direct inhibitors of STAT3 including peptidomimetics, small molecules and oligonucleotide-based inhibitors have entered preclinical trials as a STAT3-targeting therapeutic (Page, B. D., et al. Expert Opinion on Therapeutic Patents 2011, 21, 65-83; Fletcher, S., et al. Cell Biol. 2009, 87, 825-833; Haftchenary, S., et al. Anticancer Drugs 2011, 22, 115-127). Progress towards a potent and direct inhibitor of STAT5 function for the treatment of human malignancies has been disappointingly limited.

STAT5 activation involves a complex signaling cascade beginning at the cell surface. Stimulation by growth factors such as Kit ligand (SCF) erythropoietin or prolactin results in receptor dimerization and activation of Stat5 by intracellular kinases such as Janus Kinases (JAKs; Neculai, D., et al. J. Biol. Chem. 2005, 280, 40782-40787) In addition oncogenes such as BCR-ABL and FLT3-ITD induce activation of STAT5. Phosphorylation of the receptor's cytoplasmic tail provides docking sites for recruitment of monomeric, non-phosphorylated STAT5 proteins via their SH2 domain. Activated tyrosine kinases, such as JAK2 phosphorylate recruited STAT5 proteins at a specific tyrosine near the carboxy terminus (Tyr694 in Stat5A and Tyr699 in STAT5B). Phosphorylated STAT5 (pSTAT5) protein is released from the receptor, and dimerization occurs through reciprocal phosphotyrosine-SH2 domain interactions. Phosphorylation of a serine residue then allows the Stat5 dimers to translocate to the nucleus where Stat5 binds to a consensus DNA sequence and promotes gene expression (Müller, J., et al. ChemBioChem 2008, 9, 723-727, Tan, S. H.; Nevalainen, M. T. Endocr. Relat. Cancer 2008, 15, 367-390).

In cancer cells, STAT5 is routinely constitutively phosphorylated which leads to the aberrant expression of STAT5 target genes resulting in malignant transformation. Cancer cells harbouring persistently activated Stat5 over express anti-apoptotic proteins, such as Bcl-xL, Myc and MCL-1, conferring significant resistance to natural apoptotic cues and administered chemotherapeutic agents (Ferbeyre, G.; Moriggl, R. Biochimica et Biophysica Acta—Reviews on Cancer 2011, 1815, 104-114). Of particular interest, STAT5 has been identified as a key regulator in the development and progression of acute myelogenic (AML) and acute lymphoblastic leukemias (ALL; Gouilleux-Gruart, V., et al. Leukemia and Lymphoma 1997, 28, 83-88; Gouilleux-Gruart, V., et al. Blood 1996, 87, 1692-1697; Weber-Nordt, R. M., et al. Blood 1996, 88, 809-816). Moreover, inhibitors of upstream Stat5 activators (such as JAK and FLT3) have been shown to exhibit promising anti-cancer properties (Pardanani, A., et al. Leukemia 2011, 25, 218-225; Quintás-Cardama, A., et al. Nature Reviews Drug Discovery 2011, 10, 127-140). However, a shortcoming of tyrosine kinase inhibitors, and other upstream effectors of kinase activity, is the disruption of multiple downstream signaling pathways, increasing the likelihood of undesirable toxicity. In addition it is possible that other proteins in the malignant cell may also be activating STAT5; this signaling would not be affected by an upstream-targeted inhibitor. Therefore, silencing a downstream signaling target such as STAT5 would ultimately result in fewer side effects and would thus represent a more attractive candidate for a molecularly targeted drug for the treatment of human cancers harbouring aberrant STAT5 activity.

E. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In one aspect, the invention relates to a pharmaceutical composition comprising a pharmaceutically acceptable carrier and an effective amount of a compound of Formula I, II, III or IV, or a pharmaceutically acceptable salt, hydrate, solvate, or polymorph thereof. In a further aspect, the invention relates to a pharmaceutical composition comprising a pharmaceutically acceptable carrier and an effective amount of a compound of Formula V, or a pharmaceutically acceptable salt, hydrate, solvate, or polymorph thereof In a further aspect, the compound is any of the disclosed compounds or at least one product of the disclosed methods of making. In a yet further aspect, the pharmaceutical composition comprises one or more of any of the disclosed compounds or at least one product of the disclosed methods of making In a further aspect, the compound inhibits STAT protein activity with an $IC_{50}$ in an EMSA assay of less than about 100 µM, less than about 50 µM, less than about 10 µM, less than about 1 µM, less than about 500 nM, or of less than about 100 nM. In a further aspect, the $IC_{50}$ is inhibition of STAT3 protein activity. In a further aspect, the $IC_{50}$ is inhibition of STAT5 protein activity.

In a further aspect, the compound that inhibits cell growth. In a still further aspect, the compound inhibits cell growth with an $IC_{50}$ of less than about 500 µM. In a yet further aspect, the compound inhibits cell growth with an $IC_{50}$ of less than about 250 µM. In an even further aspect, the compound inhibits cell growth with an $IC_{50}$ of less than about 100 µM. In a still further aspect, the compound inhibits cell growth with an $IC_{50}$ of less than about 50 µM. In a yet further aspect, the compound inhibits cell growth with an $IC_{50}$ of less than about 10 µM. In an even further aspect, the compound inhibits cell growth with an $IC_{50}$ of less than about 1 µM. In a still further aspect, the $IC_{50}$ for inhibition of cell growth is determined in a cell line with a constitutively active STAT protein. In a yet further aspect, the $IC_{50}$ for inhibition of cell growth is determined in a cell line with a persistently active STAT protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT protein activity dysfunction. In a still further aspect, the $IC_{50}$ for inhibition of cell growth is determined in a cell line selected from MDA-MB-231, Panc-1, and DU 145. In a yet further aspect, the $IC_{50}$ for inhibition of cell growth is determined in a cell line transformed with v-Src. In an even further aspect, the $IC_{50}$ for inhibition of cell growth is determined in the NIH3T3 cell-line transformed with v-Src.

In a further aspect, the pharmaceutical composition treats a disorder of uncontrolled cellular proliferation. In a yet further aspect, the disorder of uncontrolled cellular proliferation is cancer. In a still further aspect, the cancer is selected from a cancer of the head, neck, pancreas, brain, ovary, kidney, prostate, breast, lung, colon, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further aspect, the cancer is pancreatic cancer.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, *acacia*, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of STAT protein activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating STAT protein activity activity (e.g., treatment of one or more disorders of uncontrolled cellular proliferation associated with a STAT3 protein activity dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. Methods of using the Compounds and Compositions

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetanldamycin®, Idarubicin, Ifex®, IFN-alphalfosfamide, IL-11IL-2Imatinib mesylate, Imidazole Carboxamidelnterferon alfa, Interferon Alfa-2b (PEG Conjugate), Interleukin-2, Interleukin-11, Intron A® (interferon alfa-2b)Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a)Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®.

In another aspect, the subject compounds can be administered in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetanldamycin®, Idarubicin, Ifex®, IFN-alphalfosfamide, IL-11IL-2Imatinib mesylate, Imidazole Carboxamidelnterferon alfa, Interferon Alfa-2b (PEG Conjugate), Interleukin-2, Interleukin-11, Intron A® (interferon alfa-2b)Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a)Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In another aspect, the subject compound can be used in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetanldamycin®, Idarubicin, Ifex®, IFN-alphalfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Oraped®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a)Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders of uncontrolled cellular proliferation associated with a STAT protein activity dysfunction. In a yet further aspect, the disorder of uncontrolled cellular proliferation is a cancer. In a still further aspect, the STAT protein activity dysfunction is that the STAT protein is persistently active. In a yet further aspect, the STAT protein is constitutively active. In an even further aspect, the STAT protein is overexpressed. In a still further aspect, the STAT protein is STAT3.

In one aspect, the invention relates to a method for the treatment of a disorder associated with a STAT protein activity dysfunction in a mammal comprising the step of administering to the mammal at least one disclosed compound or at least one disclosed product in a dosage and amount effective to treat the disorder in the mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas Examples of disorders such as a cancer associated with STAT protein activity dysfunction, e.g. a STAT3 activity dysfunction, include: Acute Lymphoblastic Leukemia, Adult Hairy Cell Leukemia, Acute Lymphoblastic Leukemia, Head and Neck Cancer, Childhood Hepatocellular (Liver) Cancer, Adult, Acute Myeloid Leukemia, Adult (Primary), Acute Myeloid Leukemia, Childhood Hepatocellular (Liver) Cancer, Childhood, Adrenocortical Carcinoma (Primary), Adrenocortical Carcinoma, Childhood Hodgkin's Lymphoma, AdultAIDS-Related Cancers Hodgkin's Lymphoma, ChildhoodAIDS-Related Lymphoma Hodgkin's Lymphoma During PregnancyAnal Cancer Hypopharyngeal CancerAstrocytoma, Childhood Cerebellar Hypothalamic and Visual Pathway Glioma, Astrocytoma, Childhood Cerebral ChildhoodBasal Cell Carcinoma Intraocular MelanomaBile Duct Cancer, Extrahepatic Islet Cell Carcinoma (Endocrine Pancreas) Bladder Cancer Kaposi's SarcomaBladder Cancer, Childhood Kidney (Renal Cell) CancerBone Cancer, Osteosarcoma/Malignant Fibrous Cancer, ChildhoodFibrous Histiocytoma Laryngeal CancerBrain Stem Glioma, Childhood Laryngeal Cancer, ChildhoodBrain Tumor, Adult Leukemia, Acute Lymphoblastic, AdultBrain Tumor, Brain Stem Glioma, Leukemia, Acute Lymphoblastic, ChildhoodChildhood Leukemia, Acute Myeloid, AdultBrain Tumor, Cerebellar Astrocytoma, Leukemia, Acute Myeloid, ChildhoodChildhood Leukemia, Chronic LymphocyticBrain Tumor, Cerebral Leukemia, Chronic MyelogenousAstrocytoma/Malignant Glioma, Leukemia, Hairy CellChildhood Lip and Oral Cavity CancerBrain Tumor, Ependymoma, Childhood Liver Cancer, Adult (Primary) Brain Tumor, Medulloblastoma, Liver Cancer, Childhood (Primary)Childhood Lung Cancer, Non-Small CellBrain Tumor, Supratentorial Primitive Lung Cancer, Small CellNeuroectodermal Tumors, Childhood Lymphoma, AIDS-RelatedBrain Tumor, Visual Pathway and Lymphoma, Burkitt'sHypothalamic Glioma, Childhood Lymphoma, Cutaneous T-Cell, see MycosisBrain Tumor, Childhood Fungoides and Sézary SyndromeBreast Cancer Lymphoma, Hodgkin's, AdultBreast Cancer, Childhood Lymphoma, Hodgkin's, ChildhoodBreast Cancer, Male Lymphoma, Hodgkin's During PregnancyBronchial Adenomas/Carcinoids, Lymphoma, Non-Hodgkin's, Adult-Childhood Lymphoma, Non-Hodgkin's, ChildhoodBurkitt's Lymphoma Lymphoma, Non-Hodgkin's DuringCarcinoid Tumor, Childhood PregnancyCarcinoid Tumor, Gastrointestinal Lymphoma, Primary Central Nervous SystemCarcinoma of Unknown Primary Macroglobulinemia, Waldenstrom'sCentral Nervous System Lymphoma, Malignant Fibrous Histiocytoma ofPrimary Bone/OsteosarcomaCerebellar Astrocytoma, Childhood Medulloblastoma, ChildhoodCerebral Astrocytoma/Malignant MelanomaGlio ma, Childhood Melanoma, Intraocular (Eye)Cervical Cancer Merkel Cell CarcinomaChildhood Cancers Mesothelioma, Adult MalignantChronic Lymphocytic Leukemia Mesothelioma, ChildhoodChronic Myelogenous Leukemia Metastatic Squamous Neck Cancer withChronic Myeloproliferative Disorders Occult PrimaryColon Cancer Multiple Endocrine Neoplasia Syndrome, Colorectal Cancer, Childhood ChildhoodCutaneous T-Cell Lymphoma, see Multiple Myeloma/Plasma Cell NeoplasmMycosis Fungoides and Sézary Mycosis FungoidesSyndrome Myelodysplastic SyndromesEndometrial Cancer Myelodysplastic/Myeloproliferative DiseasesEpendymoma, Childhood Myelogenous Leukemia, ChronicEsophageal Cancer Myeloid Leukemia, Adult AcuteEsophageal Cancer, Childhood Myeloid Leukemia, Childhood AcuteEwing's Family of Tumors Myeloma, MultipleExtracranial Germ Cell Tumor, Myeloproliferative Disorders, ChronicChildhood Nasal Cavity and Paranasal Sinus CancerExtragonadal Germ Cell Tumor Nasopharyngeal CancerExtrahepatic Bile Duct Cancer Nasopharyngeal Cancer, ChildhoodEye Cancer, Intraocular Melanoma NeuroblastomaEye Cancer, Retinoblastoma Non-Hodgkin's Lymphoma, AdultGallbladder Cancer Non-Hodgkin's Lymphoma, ChildhoodGastric (Stomach) Cancer Non-Hodgkin's Lymphoma During PregnancyGastric (Stomach) Cancer, Childhood Non-Small Cell Lung CancerGastrointestinal Carcinoid Tumor Oral Cancer, ChildhoodGerm Cell Tumor, Extracranial, Oral Cavity Cancer, Lip andChildhood Oropharyngeal CancerGerm Cell Tumor, Extragonadal Osteosarcoma/Malignant FibrousGerm Cell Tumor, Ovarian Histiocytoma of BoneGestational Trophoblastic Tumor Ovarian Cancer, ChildhoodGlioma, Adult Ovarian Epithelial CancerGlioma, Childhood Brain Stem Ovarian Germ Cell TumorGlioma, Childhood Cerebral Ovarian Low Malignant Potential TumorAstrocytoma Pancreatic CancerGlioma, Childhood Visual Pathway and Pancreatic Cancer, ChildhoodHypothalamic Pancreatic Cancer, Islet CellSkin Cancer (Melanoma) Paranasal Sinus and Nasal Cavity CancerSkin Carcinoma, Merkel Cell Parathyroid CancerSmall Cell Lung Cancer Penile CancerSmall Intestine Cancer PheochromocytomaSoft Tissue Sarcoma, Adult Pineoblastoma and Supratentorial PrimitiveSoft Tissue Sarcoma, Childhood Neuroectodermal Tumors, ChildhoodSquamous Cell Carcinoma, see Skin Pituitary TumorCancer (non-Melanoma) Plasma Cell Neoplasm/Multiple MyelomaSquamous Neck Cancer with Occult Pleuropulmonary BlastomaPrimary, Metastatic Pregnancy and Breast CancerStomach (Gastric) Cancer Pregnancy and Hodgkin's LymphomaStomach (Gastric) Cancer, Childhood Pregnancy and Non-Hodgkin's LymphomaSupratentorial Primitive Primary Central Nervous System LymphomaNeuroectodermal Tumors, Childhood Prostate CancerT-Cell Lymphoma, Cutaneous, see Rectal CancerMycosis Fungoides and Sézary Renal Cell (Kidney) CancerSyndrome Renal Cell (Kidney) Cancer, ChildhoodTesticular Cancer Renal Pelvis and Ureter, Transitional CellThymoma, Childhood CancerThymoma and Thymic Carcinoma RetinoblastomaThyroid Cancer Rhabdomyosarcoma, ChildhoodThyroid Cancer, Childhood Salivary Gland CancerTransitional Cell Cancer of the Renal Salivary Gland Cancer, ChildhoodPelvis and Ureter Sarcoma, Ewing's Family of TumorsTrophoblastic Tumor, Gestational Sarcoma, Kaposi'sUnknown Primary Site, Carcinoma of, Sarcoma, Soft Tissue, AdultAdult Sarcoma, Soft Tissue, ChildhoodUnknown Primary Site, Cancer of, Sarcoma, UterineChildhood Sezary SyndromeUnusual Cancers of Childhood Skin Cancer (non-Melanoma) Ureter and Renal Pelvis, Transitional Skin Cancer, ChildhoodCell CancerUrethral CancerUterine Cancer, EndometrialUterine SarcomaVaginal CancerVisual Pathway and Hypothalamic Glioma, ChildhoodVulvar CancerWaldenstrom's MacroglobulinemiaWilms' Tumor.

The disorders of uncontrolled cellular proliferation, e.g. a cancer, that can be treated or prevented by the compositions disclosed herein include.

Thus, provided is a method for treating or preventing a disorder of uncontrolled cellular proliferation, comprising: administering to a subject at least one disclosed compound; at least one disclosed pharmaceutical composition; and/or at least one disclosed product in a dosage and amount effective to treat the disorder in the subject.

a. Treatment of a Disorder Associated with Stat3 Activity Dysfunction

In various aspects, the invention relates to a method for the treatment of a disorder associated with STAT3 activity dysfunction in a mammal comprising the step of administering to the mammal a therapeutically effective amount of at least one compound having a structure represented by Formula I, II, III or IV, or a pharmaceutically acceptable salt, hydrate, solvate, or polymorph thereof.

In a further aspect, the compound administered is any of the disclosed compounds related to Formula I, II, III or IV, or at least one product of the disclosed methods of making a compound of Formula I, II, III or IV.

In a further aspect, the mammal is a human. In a yet further aspect, the mammal has been diagnosed with a need for treatment of the disorder prior to the administering step. In a still further aspect, the method further comprises the step of identifying a mammal in need of treatment of the disorder.

In a further aspect, the compound administered inhibits STAT3 protein activity. In a still further aspect, the compound administered prevents STAT3 protein dimerization. In a yet further aspect, the compound administered disrupts preformed or existing STAT3 dimers. In a still further aspect, the compound administered binds to the SH2 domain of STAT3.

In a further aspect, the compound administered inhibits STAT3 protein activity in an EMSA assay with an $IC_{50}$ of less than about 100 μM, less than about 50 μM, less than about 10 μM, less than about 1 μM, less than about 500 nM, or of less than about 100 nM.

In a further aspect, the compound administered inhibits cell growth. In a still further aspect, the compound inhibits cell growth with an $IC_{50}$ of less than about 500 μM. In a yet further aspect, the compound inhibits cell growth with an $IC_{50}$ of less than about 250 μM. In an even further aspect, the compound inhibits cell growth with an $IC_{50}$ of less than about 100 μM. In a still further aspect, the compound inhibits cell growth with an $IC_{50}$ of less than about 50 μM. In a yet further aspect, the compound inhibits cell growth with an $IC_{50}$ of less than about 10 μM. In an even further aspect, the compound inhibits cell growth with an $IC_{50}$ of less than about 1 μM. In a still further aspect, the $IC_{50}$ for inhibition of cell growth is determined in a cell line with a constitutively active STAT3 protein. In a yet further aspect, the $IC_{50}$ for inhibition of cell growth is determined in a cell line with a persistently active STAT3 protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT3 protein activity dysfunction. In a still further aspect, the $IC_{50}$ for inhibition of cell growth is determined in a cell line selected from MDA-MB-231, Panc-1, and DU 145. In a yet further aspect, the $IC_{50}$ for inhibition of cell growth is determined in a cell line transformed with v-Src. In an even further aspect, the $IC_{50}$ for inhibition of cell growth is determined in the NIH3T3 cell-line transformed with v-Src.

In a further aspect, the compound administered treats a disorder is associated with constitutively active STAT3.

In a further aspect, the compound administered treats a disorder selected from psoriasis and pulmonary arterial hypertension.

In a further aspect, the compound administered treats a disorder of uncontrolled cellular proliferation. In a yet further aspect, the disorder of uncontrolled cellular proliferation is cancer. In a still further aspect, the cancer is selected from a cancer of the head, neck, pancreas, brain, ovary, kidney, prostate, breast, lung, colon, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further aspect, the cancer is pancreatic cancer.

b. Inhibition of Stat3 Activity in a Mammal

In one aspect, the invention relates to a method for inhibition of STAT3 activity in a mammal comprising the step of administering to the mammal a therapeutically effective amount of least one compound having a structure represented by Formula I, II, III or IV, or a pharmaceutically acceptable salt, hydrate, solvate, or polymorph thereof In a further aspect, the compound administered is any of the disclosed compounds related to Formula I, II, III, or IV, or at least one product of the disclosed methods of making a compound of Formula I, II, III or IV.

In a further aspect, the mammal is a human. In a yet further aspect, the mammal has been diagnosed with a need for treatment of the disorder prior to the administering step. In a still further aspect, the method further comprises the step of identifying a mammal in need of treatment of the disorder.

In a further aspect, the compound administered inhibits STAT3 protein activity. In a still further aspect, the compound administered prevents STAT3 protein dimerization. In a yet further aspect, the compound administered disrupts preformed or existing STAT3 dimers. In a still further aspect, the compound administered binds to the SH2 domain of STAT3.

In a further aspect, the compound administered inhibits STAT3 protein activity with an $IC_{50}$ in an EMSA assay of less than about 100 µM, less than about 50 µM, less than about 10 µM, less than about 1 µM, less than about 500 nM, or of less than about 100 nM. In a further aspect, the $IC_{50}$ for inhibition of STAT3 activity.

In a further aspect, the compound administered inhibits cell growth. In a still further aspect, the compound inhibits cell growth with an $IC_{50}$ of less than about 500 µM. In a yet further aspect, the compound inhibits cell growth with an $IC_{50}$ of less than about 250 µM. In an even further aspect, the compound inhibits cell growth with an $IC_{50}$ of less than about 100 µM. In a still further aspect, the compound inhibits cell growth with an $IC_{50}$ of less than about 50 µM. In a yet further aspect, the compound inhibits cell growth with an $IC_{50}$ of less than about 10 µM. In an even further aspect, the compound inhibits cell growth with an $IC_{50}$ of less than about 1 µM. In a still further aspect, the $IC_{50}$ for inhibition of cell growth is determined in a cell line with a constitutively active STAT3 protein. In a yet further aspect, the $IC_{50}$ for inhibition of cell growth is determined in a cell line with a persistently active STAT3 protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT3 protein activity dysfunction. In a still further aspect, the $IC_{50}$ for inhibition of cell growth is determined in a cell line selected from MDA-MB-231, Panc-1, and DU 145. In a yet further aspect, the $IC_{50}$ for inhibition of cell growth is determined in a cell line transformed with v-Src. In an even further aspect, the $IC_{50}$ for inhibition of cell growth is determined in the NIH3T3 cell-line transformed with v-Src.

In a further aspect, the compound administered treats a disorder is associated with constitutively active STAT3.

In a further aspect, the compound administered treats a disorder selected from psoriasis and pulmonary arterial hypertension.

In a further aspect, the compound administered treats a disorder of uncontrolled cellular proliferation. In a yet further aspect, the disorder of uncontrolled cellular proliferation is cancer. In a still further aspect, the cancer is selected from a cancer of the head, neck, pancreas, brain, ovary, kidney, prostate, breast, lung, colon, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further.

c. Inhibiting Stat3 Activity in Cells

In one aspect, the invention relates to a method for inhibiting STAT3 activity in at least one cell, comprising the step of contacting the at least one cell with an effective amount of least one compound having a structure represented by Formula I, II, III or IV, or a pharmaceutically acceptable salt, hydrate, solvate, or polymorph thereof In a further aspect, the compound administered is any of the disclosed compounds represented by Formula I, II, III, or IV, or at least one product of the disclosed methods of making In a further aspect, the at least one cell is in a mammal. In a still further aspect, the method further comprises administering to the mammal the compound in an amount sufficient to contact at least one cell in the mammal. In yet further aspect, the cell is mammalian. In an even further aspect, the cell is human. In a further aspect, the cell has been isolated from a mammal prior to the contacting step.

In a further aspect, contacting is via administration to a mammal. In a further aspect, the mammal has been diagnosed with a need for modulating STAT3 protein activity prior to the administering step. In a further aspect, the mammal has been diagnosed with a need for treatment of a disorder related to a STAT3 protein activity dysfunction prior to the administering step.

In a further aspect, the at least one cell is in a human. In a yet further aspect, the mammal has been diagnosed with a need for treatment of the disorder prior to the contacting step. In a still further aspect, the method further comprises the step of identifying a mammal in need of treatment of the disorder.

In a further aspect, the compound contacting the cell inhibits STAT3 protein activity. In a still further aspect, the compound contacting the cell prevents STAT3 protein dimerization. In a yet further aspect the compound contacting the cell disrupts preformed or existing STAT3 dimers. In a still further aspect, the compound contacting the cell binds to the SH2 domain of STAT3.

In a further aspect, the compound contacting the cell inhibits STAT3 protein activity with an $IC_{50}$ in an EMSA assay of less than about 100 µM, less than about 50 µM, less than about 10 µM, less than about 1 µM, less than about 500 nM, or of less than about 100 nM. In a further aspect, the $IC_{50}$ for inhibition of STAT3 activity.

In a further aspect, the compound contacting the cell inhibits cell growth. In a still further aspect, the compound inhibits cell growth with an $IC_{50}$ of less than about 500 µM. In a yet further aspect, the compound inhibits cell growth with an $IC_{50}$ of less than about 250 µM. In an even further aspect, the compound inhibits cell growth with an $IC_{50}$ of less than about 100 µM. In a still further aspect, the compound inhibits cell growth with an $IC_{50}$ of less than about 50 µM. In a yet further aspect, the compound inhibits cell growth with an $IC_{50}$ of less than about 10 µM. In an even further aspect, the compound inhibits cell growth with an $IC_{50}$ of less than about 1 µM. In a still further aspect, the $IC_{50}$ for inhibition of cell growth is determined in a cell line with a constitutively active STAT3 protein. In a yet further aspect, the $IC_{50}$ for inhibition of cell growth is determined in a cell line with a persistently active STAT3 protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT3 protein activity dysfunction. In a still further aspect, the $IC_{50}$ for inhibition of cell growth is determined in a cell line selected from MDA-MB-231, Panc-1, and DU 145. In a yet further aspect, the $IC_{50}$ for inhibition of cell growth is determined in a cell line transformed with v-Src. In an even further aspect, the $IC_{50}$ for inhibition of cell growth is determined in the NIH3T3 cell-line transformed with v-Src.

In a further aspect, the compound contacting the cell treats a disorder is associated with constitutively active STAT3.

In a further aspect, the compound contacting the cell treats a disorder selected from psoriasis and pulmonary arterial hypertension.

In a further aspect, the compound contacting the cell treats a disorder of uncontrolled cellular proliferation. In a yet further aspect, the disorder of uncontrolled cellular proliferation is cancer. In a still further aspect, the cancer is selected from a cancer of the head, neck, pancreas, brain, ovary, kidney, prostate, breast, lung, colon, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further.

d. Treatment of a Disorder Associated with Stat5 Activity Dysfunction

In various aspects, the invention relates to a method for the treatment of a disorder associated with STAT5 activity dysfunction in a mammal comprising the step of administering to the mammal a therapeutically effective amount of at least one compound having a structure represented by Formula I, II, III or IV, or a pharmaceutically acceptable salt, hydrate, solvate, or polymorph thereof.

In various aspects, the invention relates to a method for the treatment of a disorder associated with STAT5 activity dysfunction in a mammal comprising the step of administering to the mammal a therapeutically effective amount of least one compound having a structure represented by a formula (V):

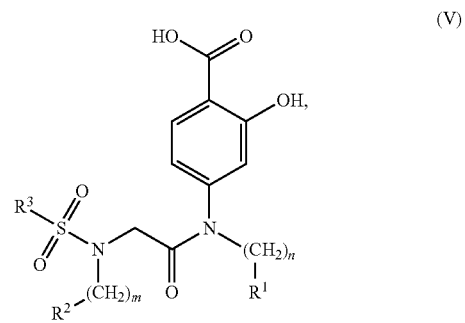

wherein each of m and n is independently an integer from 0-3; wherein $R^1$ is $-(A^5)-(A^6)-L-(A^7)$; wherein $A^5$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^8$, and $(C=O)NHR^8$; wherein $A^6$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^9$, and $(C=O)NHR^9$; wherein $A^7$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, $(C=O)OR^{10}$, and $(C=O)NHR^{10}$; wherein L is optionally present, and when present is selected from —(C=O)— and —SO$_2$—; wherein R$^2$ is selected from hydrogen, C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl, (C=O)OR$^{13}$, and (C=O)NR$^{13}$R$^{14}$; or wherein R$^2$ is aryl, and substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, CO$_2$H, (C=O)OR$^{13}$, and (C=O)NR$^{13}$R$^{14}$; wherein R$^3$ is aryl substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy; wherein each of R$^8$, R$^9$, R$^{10}$, R$^{13}$, and R$^{14}$ is independently selected from hydrogen, C1-C6 alkyl, C1-C6 haloalkyl, and C1-C6 polyhaloalkyl; or a pharmaceutically acceptable salt, hydrate, solvate, or polymorph thereof In a further aspect, the compound of Formula V is selected from:

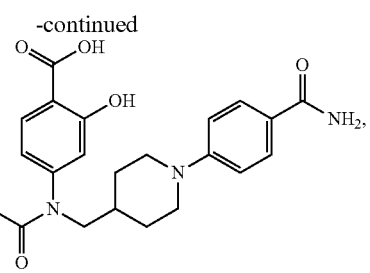

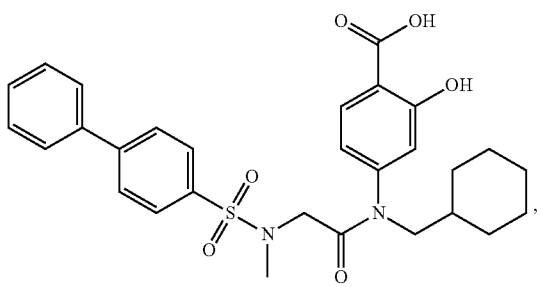

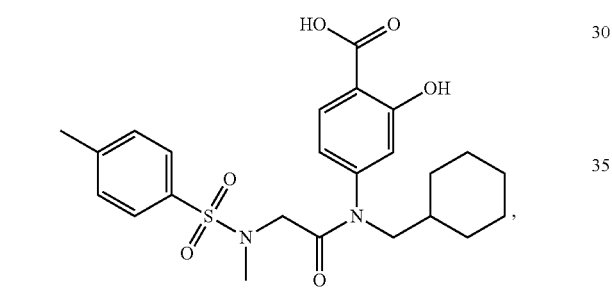

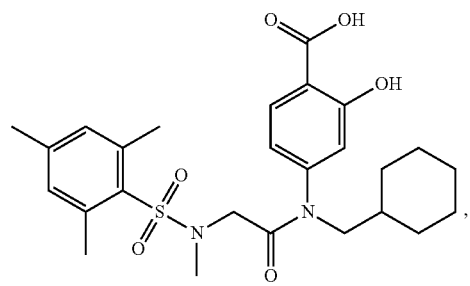

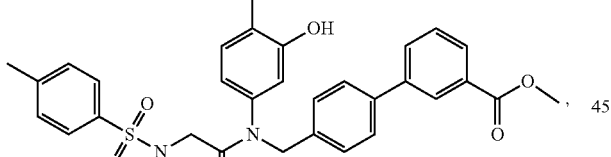

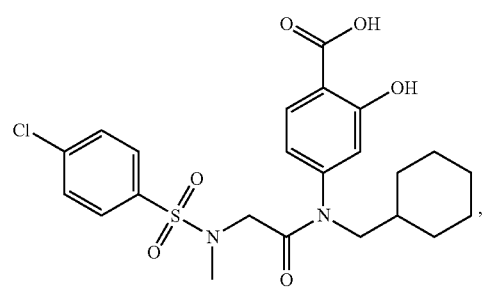

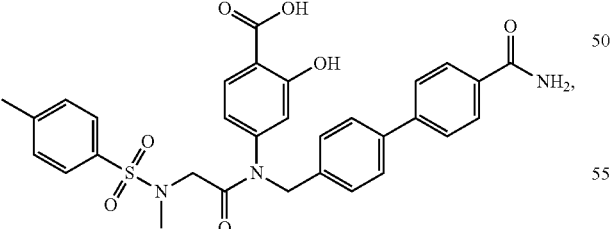

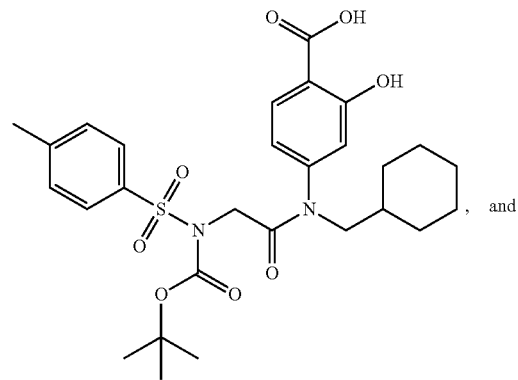

211
-continued
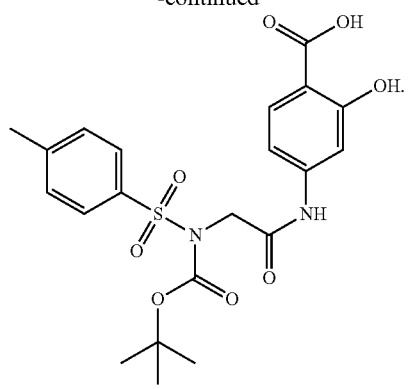
In a further aspect, the compound of Formula V is selected from:
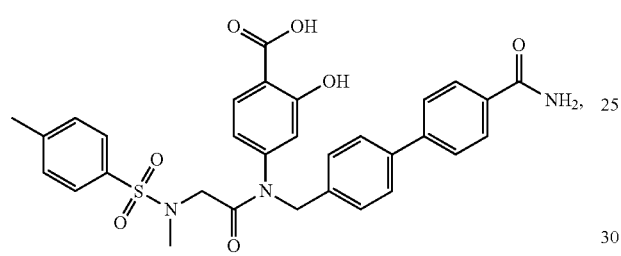
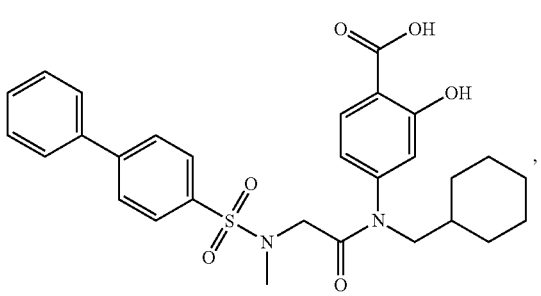
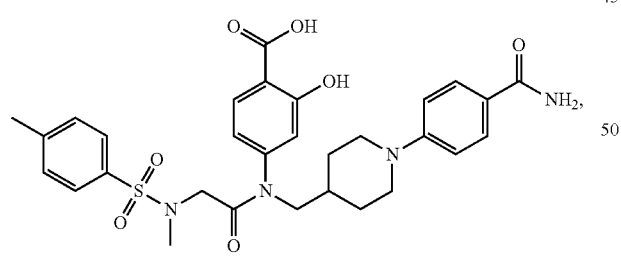
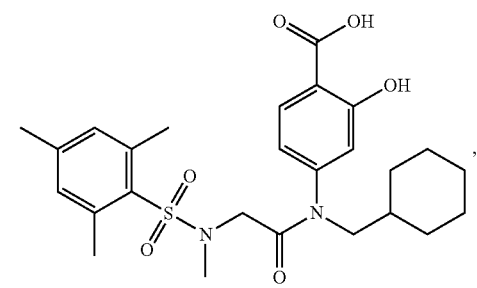
212
-continued
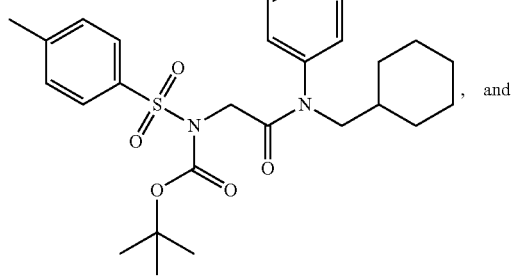, and
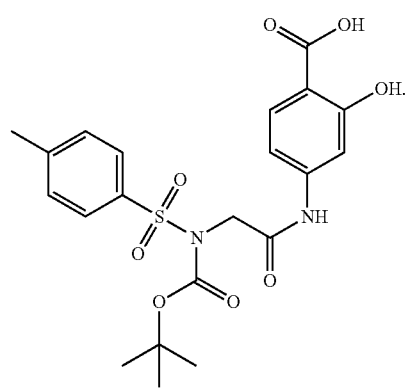 [SMILES: Cc1ccc(S(=O)(=O)N(CC(=O)Nc2ccc(C(=O)O)c(O)c2)C(=O)OC(C)(C)C)cc1]
In a further aspect, the compound of Formula V is selected from:
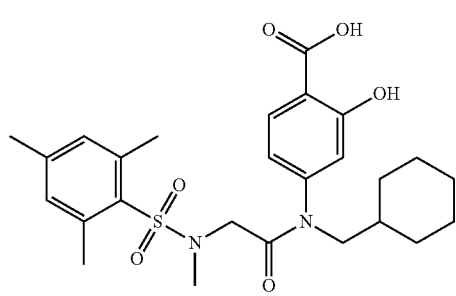,
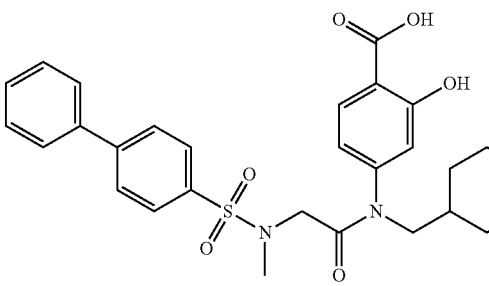,

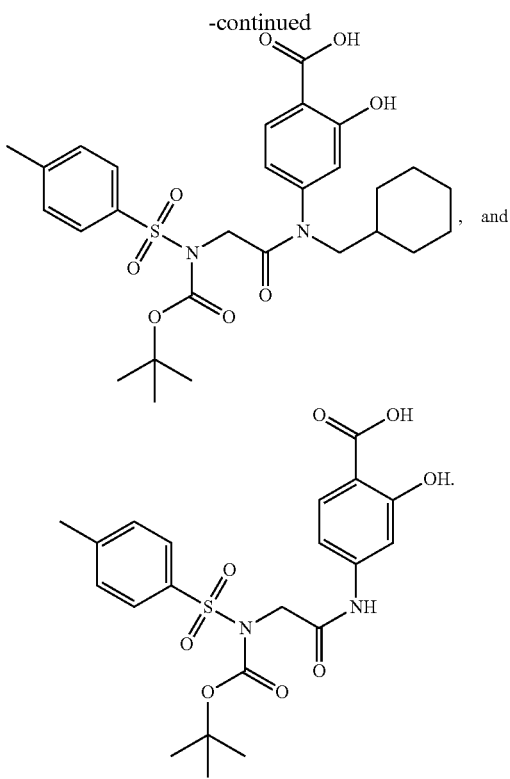

In various aspects, the invention relates to a method for the treatment of a disorder associated with STAT5 activity dysfunction in a mammal comprising the step of administering to the mammal a therapeutically effective amount of least one compound having a structure represented by a formula (VI):

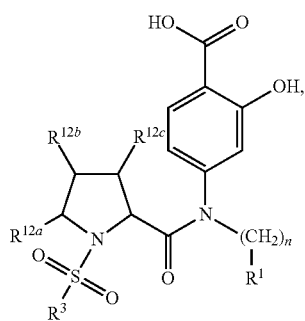

(VI)

wherein n is an integer from 0-3; wherein $R^1$ is -($A^5$)-($A^6$)-L-($A^7$); wherein $A^5$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, (C=O)$OR^8$, and (C=O)$NHR^8$; wherein $A^6$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, (C=O)$OR^9$, and (C=O)$NHR^9$; wherein $A^7$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, (C=O)$OR^{10}$, and (C=O)$NHR^{10}$; wherein L is optionally present, and when present is selected from —(C=O)— and —$SO_2$—; wherein $R^3$ is aryl substituted with 0-5 groups independently selected from halo, hydroxyl, amino, nitro, cyano, C1-C6 alkyl, C1-C6 haloalkyl, C1-C6 polyhaloalkyl, C1-C6 alkoxy, C1-C6 haloalkoxy, C1-C6 polyhaloalkoxy, C1-C6 alkylamino, C1-C6 dialkylamino, (C1-C6)-alk-(C1-C6)-alkoxy, (C1-C6)-alk-(C1-C6)-haloalkoxy, and (C1-C6)-alk-(C1-C6)-polyhaloalkoxy; wherein each of $R^8$, $R^9$, $R^{10}$, $R^{13}$, and $R^{14}$ is independently selected from hydrogen, C1-C6 alkyl, C1-C6 haloalkyl, and C1-C6 polyhaloalkyl;

wherein each of $R^{12a}$, $R^{12b}$, and $R^{12c}$ is independently selected from hydrogen, C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl, (C=O)$OR^{13}$, (C=O)$NR^{13}R^{14}$; and aryl, wherein aryl is substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alk-(C1-C6)-alkoxy, (C1-C6)-alk-(C1-C6)-haloalkoxy, (C1-C6)-alk-(C1-C6)-polyhaloalkoxy, (C1-C6)-alk-(C1-C6)-alkylthio, (C1-C6)-alk-(C1-C6)-haloalkythio, (C1-C6)-alk-(C1-C6)-polyhaloalkylthio, $CO_2H$, (C=O)$OR^{13}$, and (C=O)$NR^{13}R^{14}$; or a pharmaceutically acceptable salt, hydrate, solvate, or polymorph thereof In a further aspect, the mammal is a human. In a yet further aspect, the mammal has been diagnosed with a need for treatment of the disorder prior to the administering step. In a still further aspect, the method further comprises the step of identifying a mammal in need of treatment of the disorder.

In a further aspect, the compound administered prevents STAT5 protein dimerization. In a yet further aspect, the compound administered disrupts preformed or existing STAT5 dimers. In a still further aspect, the compound administered binds to the SH2 domain of STAT5.

In a further aspect, the compound administered inhibits STAT5 protein activity. In a still further aspect, inhibition of STAT5 protein activity is determined in an EMSA assay. In a yet further aspect, the compound inhibits STAT5 activity in an EMSA assay with an $IC_{50}$ of less than about 100 μM, less than about 50 μM, less than about 10 μM, less than about 1 μM, less than about 500 nM, or of less than about 100 nM.

In a further aspect, the compound administered inhibits phosphorylation of STAT5 with an $IC_{50}$ of less than about 100 µM, less than about 50 µM, less than about 10 µM, less than about 1 µM, less than about 500 nM, or of less than about 100 nM.

In a further aspect, the compound administered inhibits binding to the SH2 domain of STAT5. In a still further aspect, the inhibition of binding to the SH2 domain of STAT5 is determined in an in vitro fluorescence polarization assay using STAT5 protein and a reporter molecule. In a yet further aspect, the compound administered inhibits binding of a reporter molecule to STAT5 with a $K_i$ of less than about 100 µM, less than about 50 µM, less than about 10 µM, less than about 1 µM, less than about 500 nM, or of less than about 100 nM. In a still further aspect, the reporter molecule is 5-carboxyfluorescein-GpYLVLDKW.

In a further aspect, the compound administered inhibits cell growth. In a still further aspect, the compound inhibits cell growth with an $IC_{50}$ of less than about 500 µM. In a yet further aspect, the compound inhibits cell growth with an $IC_{50}$ of less than about 250 µM. In an even further aspect, the compound inhibits cell growth with an $IC_{50}$ of less than about 100 µM. In a still further aspect, the compound inhibits cell growth with an $IC_{50}$ of less than about 50 µM. In a yet further aspect, the compound inhibits cell growth with an $IC_{50}$ of less than about 10 µM. In an even further aspect, the compound inhibits cell growth with an $IC_{50}$ of less than about 1 µM. In a still further aspect, the $IC_{50}$ for inhibition of cell growth is determined in a cell line with a constitutively active STAT5 protein. In a still further aspect, the $IC_{50}$ for inhibition of cell growth is determined in a cell line with an activated STAT5 protein. In a yet further aspect, the $IC_{50}$ for inhibition of cell growth is determined in a cell line with a persistently active STAT5 protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT5 protein activity dysfunction. In a still further aspect, the $IC_{50}$ for inhibition of cell growth is determined in a cell line selected from MV-4-11 and K562. In a still further aspect, the $IC_{50}$ for inhibition of cell growth is determined in a cell line wherein STAT5 is activated due to the presence of constitutively active FLT-3. In a still further aspect, the $IC_{50}$ for inhibition of cell growth is determined in a cell line wherein STAT5 is activated due of BCR-Abl.

In a further aspect, the compound administered inhibits cell migration. In a still further aspect, the compound inhibits cell migration with an $IC_{50}$ of less than about 500 µM. In a yet further aspect, the compound inhibits cell migration with an $IC_{50}$ of less than about 250 µM. In an even further aspect, the compound inhibits cell migration with an $IC_{50}$ of less than about 100 µM. In a still further aspect, the compound inhibits cell migration with an $IC_{50}$ of less than about 50 µM. In a yet further aspect, the compound inhibits cell migration with an $IC_{50}$ of less than about 10 µM. In an even further aspect, the compound inhibits cell migration with an $IC_{50}$ of less than about 1 µM. In a still further aspect, the $IC_{50}$ for inhibition of cell migration is determined in a cell line with a constitutively active STAT5 protein. In a still further aspect, the $IC_{50}$ for inhibition of cell migration is determined in a cell line with an activated STAT5 protein. In a yet further aspect, the $IC_{50}$ for inhibition of cell migration is determined in a cell line with a persistently active STAT5 protein. In an even further aspect, the $IC_{50}$ for inhibition of cell migration is determined in a cell line derived from a cancer selected from breast cancer, pancreatic cancer, and prostate cancer. In a yet further aspect, the $IC_{50}$ for inhibition of cell migration is determined in a cell line derived from a cancer with a STAT5 protein activity dysfunction. In a still further aspect, the $IC_{50}$ for inhibition of cell migration is determined in a cell line selected from MV-4-11 and K562. In a still further aspect, the $IC_{50}$ for inhibition of cell migration is determined in a cell line wherein STAT5 is activated due to the presence of constitutively active FLT-3 in the cell. In a still further aspect, the $IC_{50}$ for inhibition of cell migration is determined in a cell line wherein STAT5 is activated due to the presence of BCR-Abl in the cell.

In a further aspect, the compound administered inhibits expression of STAT5-regulated genes. In a still further aspect, the STAT5-regulated gene is selected from Bcl-xL, cyclin D1, cyclin D2, c-myc, and MCL-1. In a still further aspect, the compound inhibits expression of a STAT5-regulated gene with an $IC_{50}$ of less than about 500 µM. In a yet further aspect, the compound inhibits cell migration with an $IC_{50}$ of less than about 250 µM. In an even further aspect, the compound inhibits expression of a STAT5-regulated gene with an $IC_{50}$ of less than about 100 µM. In a still further aspect, the compound inhibits expression of a STAT5-regulated gene with an $IC_{50}$ of less than about 50 µM. In a yet further aspect, the compound inhibits cell migration with an $IC_{50}$ of less than about 10 µM. In an even further aspect, the compound inhibits expression of a STAT5-regulated gene with an $IC_{50}$ of less than about 1 µM. In a still further aspect, the $IC_{50}$ for inhibition of expression of a STAT5-regulated gene is determined in a cell line with a constitutively active STAT5 protein. In a still further aspect, the $IC_{50}$ for inhibition of expression of a STAT5-regulated gene is determined in a cell line with an activated STAT5 protein. In a yet further aspect, the $IC_{50}$ for inhibition of expression of a STAT5-regulated gene is determined in a cell line with a persistently active STAT5 protein. In an even further aspect, the $IC_{50}$ for inhibition of inhibition of expression of a STAT5-regulated gene is determined in a cell line derived from a cancer selected from a leukemia, lymphoma, breast cancer, pancreatic cancer, and prostate cancer. In a yet further aspect, the $IC_{50}$ inhibition of expression of a STAT5-regulated gene is determined in a cell line derived from a cancer with a STAT5 protein activity dysfunction. In a still further aspect, the $IC_{50}$ for inhibition of expression of a STAT5-regulated gene is determined in a cell line selected from MV-4-11 and K562. In a still further aspect, the $IC_{50}$ for inhibition of expression of a STAT5-regulated gene is determined in a cell line wherein STAT5 is activated due to the presence of constitutively active FLT-3 in the cell. In a still further aspect, the $IC_{50}$ for inhibition of expression of a STAT5-regulated gene is determined in a cell line wherein STAT5 is activated due to the presence of BCR-Abl in the cell.

In a further aspect, the compound administered treats a disorder is associated with constitutively active STAT5. In a further aspect, the compound administered treats a disorder is associated with an activated STAT5.

In a further aspect, the compound administered treats a disorder of uncontrolled cellular proliferation. In a yet further aspect, the disorder of uncontrolled cellular proliferation is cancer.

In a still further aspect, the cancer is selected from a cancer of the head, neck, pancreas, brain, ovary, kidney, prostate, breast, lung, colon, rectum, uterine, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, cerebral menangioma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further aspect, the cancer is pancreatic cancer. In an even further aspect, the cancer is uterine cancer. In a yet further aspect, the cancer is colorectal cancer. In a still further aspect, the cancer is a melanoma. In an even further aspect, the cancer is non-small cell lung cancer. In a yet further aspect, the cancer is squamous cell carcinoma of the head and neck.

e. Inhibition of Stat5 Activity in a Mammal

In one aspect, the invention relates to a method for inhibition of STAT5 activity in a mammal comprising the step of administering to the mammal a therapeutically effective amount of least one compound having a structure represented by Formula I, II, III or IV, or a pharmaceutically acceptable salt, hydrate, solvate, or polymorph thereof In various aspects, the invention relates to a method for inhibition of STAT5 activity in a mammal comprising the step of administering to the mammal a therapeutically effective amount of least one compound having a structure represented by a Formula V or VI, or a pharmaceutically acceptable salt, hydrate, solvate, or polymorph thereof In a further aspect, the mammal is a human. In a yet further aspect, the mammal has been diagnosed with a need for inhibition of STAT5 activity prior to the administering step. In a still further aspect, the method further comprises the step of identifying a mammal in need of treatment of the disorder.

In a further aspect, inhibition of STAT5 activity treats a disorder of uncontrolled cellular proliferation. In a yet further aspect, the disorder of uncontrolled cellular proliferation is a cancer or tumor.

f. Inhibiting Stat5 Activity in Cells

In one aspect, the invention relates to a method for inhibiting STAT5 activity in at least one cell, comprising the step of contacting the at least one cell with an effective amount of least one compound having a structure represented by Formula I, II, III or IV, or a pharmaceutically acceptable salt, hydrate, solvate, or polymorph thereof In various aspects, the invention relates to a method for inhibiting STAT5 activity in at least one cell, comprising the step of contacting the at least one cell with an effective amount of least one compound having a structure represented by a Formula V or VI, or a pharmaceutically acceptable salt, hydrate, solvate, or polymorph thereof a further aspect, the at least one cell is in a mammal. In a still further aspect, the method further comprises administering to the mammal the compound in an amount sufficient to contact at least one cell in the mammal. In yet further aspect, the cell is mammalian. In an even further aspect, the cell is human. In a further aspect, the cell has been isolated from a mammal prior to the contacting step.

In a further aspect, contacting is via administration to a mammal. In a further aspect, the mammal has been diagnosed with a need for modulating STAT5 protein activity prior to the administering step. In a further aspect, the mammal has been diagnosed with a need for treatment of a disorder related to a STAT5 protein activity dysfunction prior to the administering step.

In a further aspect, the at least one cell is in a human. In a yet further aspect, the mammal has been diagnosed with a need for treatment of the disorder prior to the contacting step. In a still further aspect, the method further comprises the step of identifying a mammal in need of treatment of the disorder.

In a further aspect, the compound contacting the at least one cell prevents STAT5 protein dimerization. In a yet further aspect, the compound contacting the at least one cell disrupts preformed or existing STAT5 dimers. In a still further aspect, the compound contacting the at least one cell binds to the SH2 domain of STAT5.

In a further aspect, the compound contacting the at least one cell inhibits STAT5 protein activity. In a still further aspect, inhibition of STAT5 protein activity is determined in an EMSA assay. In a yet further aspect, the compound inhibits STAT5 activity in an EMSA assay with an $IC_{50}$ of less than about 100 µM, less than about 50 µM, less than about 10 µM, less than about 1 µM, less than about 500 nM, or of less than about 100 nM.

In a further aspect, the compound contacting the at least one cell inhibits phosphorylation of STAT5 with an $IC_{50}$ of less than about 100 µM, less than about 50 µM, less than about 10 µM, less than about 1 µM, less than about 500 nM, or of less than about 100 nM.

In a further aspect, the compound contacting the at least one cell inhibits binding to the SH2 domain of STAT5. In a still further aspect, the inhibition of binding to the SH2 domain of STAT5 is determined in an in vitro fluorescence polarization assay using STAT5 protein and a reporter molecule. In a yet further aspect, the compound contacting the at least one cell inhibits binding of a reporter molecule to STAT5 with a Ki of less than about 100 µM, less than about 50 µM, less than about 10 µM, less than about 1 µM, less than about 500 nM, or of less than about 100 nM. In a still further aspect, the compound contacting the at least one cell inhibits phosphorylation of STAT5 with an $IC_{50}$ for inhibition of phosphorylation of STAT5 of less than about 100 µM, In a still further aspect, the reporter molecule is 5-carboxyfluorescein-GpYLVLDKW.

In a further aspect, the compound contacting the at least one cell inhibits cell growth. In a still further aspect, the compound inhibits cell growth with an $IC_{50}$ of less than about 500 µM. In a yet further aspect, the compound inhibits cell growth with an $IC_{50}$ of less than about 250 µM. In an even further aspect, the compound inhibits cell growth with an $IC_{50}$ of less than about 100 μM. In a still further aspect, the compound inhibits cell growth with an $IC_{50}$ of less than about 50 μM. In a yet further aspect, the compound inhibits cell growth with an $IC_{50}$ of less than about 10 μM. In an even further aspect, the compound inhibits cell growth with an $IC_{50}$ of less than about 1 μM. In a still further aspect, the $IC_{50}$ for inhibition of cell growth is determined in a cell line with a constitutively active STAT5 protein. In a still further aspect, the $IC_{50}$ for inhibition of cell growth is determined in a cell line with an activated STAT5 protein. In a yet further aspect, the $IC_{50}$ for inhibition of cell growth is determined in a cell line with a persistently active STAT5 protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT5 protein activity dysfunction. In a still further aspect, the $IC_{50}$ for inhibition of cell growth is determined in a cell line selected from MV-4-11 and K562. In a still further aspect, the $IC_{50}$ for inhibition of cell growth is determined in a cell line wherein STAT5 is activated due to the presence of constitutively active FLT-3. In a still further aspect, the $IC_{50}$ for inhibition of cell growth is determined in a cell line wherein STAT5 is activated due of BCR-Abl.

In a further aspect, the compound contacting the at least one cell inhibits cell migration. In a still further aspect, the compound inhibits cell migration with an $IC_{50}$ of less than about 500 μM. In a yet further aspect, the compound inhibits cell migration with an $IC_{50}$ of less than about 250 μM. In an even further aspect, the compound inhibits cell migration with an $IC_{50}$ of less than about 100 μM. In a still further aspect, the compound inhibits cell migration with an $IC_{50}$ of less than about 50 μM. In a yet further aspect, the compound inhibits cell migration with an $IC_{50}$ of less than about 10 μM. In an even further aspect, the compound inhibits cell migration with an $IC_{50}$ of less than about 1 μM. In a still further aspect, the $IC_{50}$ for inhibition of cell migration is determined in a cell line with a constitutively active STAT5 protein. In a still further aspect, the $IC_{50}$ for inhibition of cell migration is determined in a cell line with an activated STAT5 protein. In a yet further aspect, the $IC_{50}$ for inhibition of cell migration is determined in a cell line with a persistently active STAT5 protein. In an even further aspect, the $IC_{50}$ for inhibition of cell migration is determined in a cell line derived from a cancer selected from breast cancer, pancreatic cancer, and prostate cancer. In a yet further aspect, the $IC_{50}$ for inhibition of cell migration is determined in a cell line derived from a cancer with a STAT5 protein activity dysfunction. In a still further aspect, the $IC_{50}$ for inhibition of cell migration is determined in a cell line selected from MV-4-11 and K562. In a still further aspect, the $IC_{50}$ for inhibition of cell migration is determined in a cell line wherein STAT5 is activated due to the presence of constitutively active FLT-3 in the cell. In a still further aspect, the $IC_{50}$ for inhibition of cell migration is determined in a cell line wherein STAT5 is activated due to the presence of BCR-Abl in the cell.

In a further aspect, the compound contacting the at least one cell inhibits expression of STAT5-regulated genes. In a still further aspect, the STAT5-regulated gene is selected from Bcl-xL, cyclin D1, cyclin D2, c-myc, and MCL-1. In a still further aspect, the compound inhibits expression of a STAT5-regulated gene with an $IC_{50}$ of less than about 500 μM. In a yet further aspect, the compound inhibits cell migration with an $IC_{50}$ of less than about 250 μM. In an even further aspect, the compound inhibits expression of a STAT5-regulated gene with an $IC_{50}$ of less than about 100 μM. In a still further aspect, the compound inhibits expression of a STAT5-regulated gene with an $IC_{50}$ of less than about 50 μM. In a yet further aspect, the compound inhibits cell migration with an $IC_{50}$ of less than about 10 μM. In an even further aspect, the compound inhibits expression of a STAT5-regulated gene with an $IC_{50}$ of less than about 1 μM. In a still further aspect, the $IC_{50}$ for inhibition of expression of a STAT5-regulated gene is determined in a cell line with a constitutively active STAT5 protein. In a still further aspect, the $IC_{50}$ for inhibition of expression of a STAT5-regulated gene is determined in a cell line with an activated STAT5 protein. In a yet further aspect, the $IC_{50}$ for inhibition of expression of a STAT5-regulated gene is determined in a cell line with a persistently active STAT5 protein. In an even further aspect, the $IC_{50}$ for inhibition of inhibition of expression of a STAT5-regulated gene is determined in a cell line derived from a cancer selected from a leukemia, lymphoma, breast cancer, pancreatic cancer, and prostate cancer. In a yet further aspect, the $IC_{50}$ inhibition of expression of a STAT5-regulated gene is determined in a cell line derived from a cancer with a STAT5 protein activity dysfunction. In a still further aspect, the $IC_{50}$ for inhibition of expression of a STAT5-regulated gene is determined in a cell line selected from MV-4-11 and K562. In a still further aspect, the $IC_{50}$ for inhibition of expression of a STAT5-regulated gene is determined in a cell line wherein STAT5 is activated due to the presence of constitutively active FLT-3 in the cell. In a still further aspect, the $IC_{50}$ for inhibition of expression of a STAT5-regulated gene is determined in a cell line wherein STAT5 is activated due to the presence of BCR-Abl in the cell.

In a further aspect, the compound contacting the at least one cell treats a disorder is associated with constitutively active STAT5. In a further aspect, the compound contacting the at least one cell treats a disorder is associated with an activated STAT5.

In a further aspect, the compound contacting the at least one cell treats a disorder of uncontrolled cellular proliferation. In a yet further aspect, the disorder of uncontrolled cellular proliferation is cancer.

In a still further aspect, the cancer is selected from a cancer of the head, neck, pancreas, brain, ovary, kidney, prostate, breast, lung, colon, rectum, uterine, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, cerebral menangioma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further aspect, the cancer is pancreatic cancer. In an even further aspect, the cancer is uterine cancer. In a yet further aspect, the cancer is colorectal cancer. In a still further aspect, the cancer is a melanoma. In an even further aspect, the cancer is non-small cell lung cancer. In a yet further aspect, the cancer is squamous cell carcinoma of the head and neck.

2. Manufacture of a Medicament

In one aspect, the invention relates to a method for the manufacture of a medicament for uncontrolled cellular proliferation activity in a mammal comprising combining a therapeutically effective amount of a disclosed compound or product of a disclosed method with a pharmaceutically acceptable carrier or diluent.

3. Use of Compounds

In one aspect, the invention relates to the use of a compound having a structure represented by Formula I, II, III, IV, V or VI, or a pharmaceutically acceptable salt, hydrate, solvate, or polymorph thereof.

In a further aspect, the compound is a disclosed compound described by Formula I, II, III, IV, V or VI or a product of a disclosed method.

In a further aspect, the use relates to inhibition of STAT protein activity. In a further aspect, the use relates to inhibition of STAT3 protein activity. In a still further aspect, the use relates to prevention of STAT3 protein dimerization. In a yet further aspect, the use relates to disruption of preformed or existing STAT3 dimers. In a still further aspect, the use relates to binding to the SH2 domain of STAT3.

In a further aspect, the use relates to inhibition of STAT5 protein activity. In a still further aspect, the use relates to prevention of STAT5 protein dimerization. In a yet further aspect, the use relates to disruption of preformed or existing STAT5 dimers. In a still further aspect, the use relates to binding to the SH2 domain of STAT5.

In a further aspect, the use relates to inhibition of STAT protein activity with an $IC_{50}$ in an EMSA assay of less than about 100 µM, less than about 50 µM, less than about 10 µM, less than about 1 µM, less than about 500 nM, or of less than about 100 nM. In a further aspect, the $IC_{50}$ is for inhibition of STAT3 activity. In a further aspect, the $IC_{50}$ is for inhibition of STAT5 activity.

In a further aspect, the use relates to inhibition of cell growth. In a still further aspect, the use relates to inhibition of cell growth with an $IC_{50}$ of less than about 500 µM. In a yet further aspect, the use relates to inhibition of cell growth with an $IC_{50}$ of less than about 250 µM. In an even further aspect, the use relates to inhibition of cell growth with an $IC_{50}$ of less than about 100 µM. In a still further aspect, the use relates to inhibition of cell growth with an $IC_{50}$ of less than about 50 µM. In a yet further aspect, the use relates to inhibition of inhibits cell growth with an $IC_{50}$ of less than about 10 µM. In an even further aspect, the use relates to inhibition of cell growth with an $IC_{50}$ of less than about 1 µM. In a still further aspect, the $IC_{50}$ for inhibition of cell growth is determined in a cell line with a constitutively active STAT protein. In a yet further aspect, the $IC_{50}$ for inhibition of cell growth is determined in a cell line with a persistently active STAT protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT protein activity dysfunction. In a still further aspect, the $IC_{50}$ for inhibition of cell growth is determined in a cell line selected from MDA-MB-231, Panc-1, and DU 145. In a yet further aspect, the $IC_{50}$ for inhibition of cell growth is determined in a cell line transformed with v-Src. In an even further aspect, the $IC_{50}$ for inhibition of cell growth is determined in the NIH3T3 cell-line transformed with v-Src. In a yet further aspect, the $IC_{50}$ for inhibition of cell growth is determined in a cell line selected from K562 and MV-4-11.

In a further aspect, the use treats a disorder is associated with constitutively active STAT3. In a still further aspect, the use treats a disorder is associated with constitutively active STAT5.

In a further aspect, the use treats a disorder selected from psoriasis and pulmonary arterial hypertension.

In a further aspect, the use treats a disorder of uncontrolled cellular proliferation. In a yet further aspect, the disorder of uncontrolled cellular proliferation is cancer. In a still further aspect, the cancer is selected from a cancer of the head, neck, pancreas, brain, ovary, kidney, prostate, breast, lung, colon, and liver.

In a further aspect, the use relates to the manufacture of a medicament for the treatment of a disorder associated with STAT protein activity dysfunction in a mammal. In a further aspect, the disorder is a disorder uncontrolled cellular proliferation. In a further aspect, the disorder is a disease of uncontrolled cellular proliferation. In a further aspect, a use relates to treatment of a disorder of controlled cellular proliferation associated with a STAT protein activity dysfunction in a mammal.

In a further aspect, the use relates to the manufacture of a medicament for the treatment of a disorder associated with STAT3 protein activity dysfunction in a mammal. In a further aspect, the disorder associated with a STAT3 dysfunction is a disorder uncontrolled cellular proliferation. In a further aspect, the disorder is a disease of uncontrolled cellular proliferation. In a further aspect, a use relates to treatment of a disorder of controlled cellular proliferation associated with a STAT3 protein activity dysfunction in a mammal.

In a further aspect, the use relates to the manufacture of a medicament for the treatment of a disorder associated with STAT5 protein activity dysfunction in a mammal. In a further aspect, the disorder associated with a STAT5 dysfunction is a disorder uncontrolled cellular proliferation. In a further aspect, the disorder is a disease of uncontrolled cellular proliferation. In a further aspect, a use relates to treatment of a disorder of controlled cellular proliferation associated with a STAT5 protein activity dysfunction in a mammal.

In one aspect, a use is associated with the treatment of a disorder associated with uncontrolled cellular proliferation. In a further aspect, the disorder is cancer. In a still further aspect, the cancer is selected from a cancer of the head, neck, pancreas, brain, ovary, kidney, prostate, breast, lung, colon, and liver.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In a further aspect, the cancer is selected from a cancer of the breast, ovary, prostate, head, neck, and kidney. In a still further aspect, the cancer is breast cancer. In a yet further In a further aspect, the disorder is selected from psoriasis and pulmonary arterial hypertension.

4. Kits

In one aspect, the invention relates to a kit comprising at least one compound having a structure represented by Formula I, II, III or IV, or a pharmaceutically acceptable salt, hydrate, solvate, or polymorph thereof, and one or more of: (a) at least one agent known to decrease STAT3 activity; (b) at least one agent known to increase STAT3 activity; (c) at least one agent know to treat a disease of uncontrolled cellular proliferation; (d) at least one agent known to treat psoriasis; (e) at least one agent known to treat pulmonary arterial hypertension; or (f) instructions for treating a disorder associated with STAT dysfunction.

In one aspect, the invention relates to a kit comprising at least one compound having a structure represented by Formula V or VI, or a pharmaceutically acceptable salt, hydrate, solvate, or polymorph thereof, and one or more of: (a) at least one agent known to decrease STAT5 activity; (b) at least one agent known to increase STAT5 activity; (c) at least one agent know to treat a disease of uncontrolled cellular proliferation; or (d) instructions for treating a disorder associated with STAT5 dysfunction.

In a further aspect, the kit comprises a disclosed compound described by Formula I, II, III, or IV, or a product of a disclosed method. In a still further aspect, the kit comprises a disclosed compound described by Formula IV or V, or a product of a disclosed method.

In a further aspect, the at least one compound and the at least one agent are co-formulated. In a still further aspect, the at least one compound and the at least one agent are co-packaged.

In a further aspect, the at least one compound in the kit exhibits inhibition of a STAT protein. In a yet further aspect, the compound in the kit inhibits the STAT protein is STAT3. In a still further aspect, the compound in the kit inhibits the STAT protein is STAT5.

In a further aspect, the at least one compound in the kit inhibits STAT protein activity with an $IC_{50}$ in an EMSA assay of less than about 100 µM, less than about 50 µM, less than about 10 µM, less than about 1 µM, less than about 500 nM, or of less than about 100 nM. In a further aspect, the $IC_{50}$ is for inhibition of STAT3 activity. In a further aspect, the $IC_{50}$ is for inhibition of STAT5 activity.

In a further aspect, the at least one compound in the kit inhibits cell growth. In a still further aspect, the compound inhibits cell growth with an $IC_{50}$ of less than about 500 µM. In a yet further aspect, the compound inhibits cell growth with an $IC_{50}$ of less than about 250 µM. In an even further aspect, the compound inhibits cell growth with an $IC_{50}$ of less than about 100 µM. In a still further aspect, the compound inhibits cell growth with an $IC_{50}$ of less than about 50 µM. In a yet further aspect, the compound inhibits cell growth with an $IC_{50}$ of less than about 10 µM. In an even further aspect, the compound inhibits cell growth with an $IC_{50}$ of less than about 1 µM. In a still further aspect, the $IC_{50}$ for inhibition of cell growth is determined in a cell line with a constitutively active STAT protein. In a yet further aspect, the $IC_{50}$ for inhibition of cell growth is determined in a cell line with a persistently active STAT protein. In an even further aspect, the $IC_{50}$ for inhibition of cell growth is determined in a cell line derived from a cancer selected from breast cancer, pancreatic cancer, and prostate cancer. In a yet further aspect, the $IC_{50}$ for inhibition of cell growth is determined in a cell line derived from a cancer with a STAT protein activity dysfunction. In a still further aspect, the $IC_{50}$ for inhibition of cell growth is determined in a cell line selected from MDA-MB-231, Panc-1, and DU 145. In a yet further aspect, the $IC_{50}$ for inhibition of cell growth is determined in a cell line transformed with v-Src. In an even further aspect, the $IC_{50}$ for inhibition of cell growth is determined in the NIH3T3 cell-line transformed with v-Src. In a yet further aspect, the $IC_{50}$ for inhibition of cell growth is determined in a cell line selected from K562 and MV-4-11.

In a further aspect, the at least one compound in the kit treats a disorder is associated with constitutively active STAT3. In a still further aspect, the at least one compound in the kit treats a disorder is associated with constitutively active STAT5.

In a further aspect, the at least one agent is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof In a further aspect, the at least one agent is a chemotherapeutic agent. In a yet further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent. In a still further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In a yet further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof. In an even further aspect, the mTor inhibitor agent is selected from one or more of the group consisting of everolimus, siroliumus, and temsirolimus, or a pharmaceutically acceptable salt, hydrate, solvate, or polymorph thereof In a further aspect, the at least one compound and the at least one agent are co-packaged. In a still further aspect, the at least one agent that is co-packaged with the at least one compound is one of the agents described herein.

In a further aspect, the at least one compound and the at least one agent are co-formulated. In a still further aspect, the at least one agent that is co-formulated with the at least one compound is one of the agents described herein.

In a further aspect, the instructions further comprise providing the compound in connection surgery. In a still further aspect, the instructions provide that surgery is performed prior to the administering of at least one compound. In a yet further aspect, the instructions provide that surgery is performed after the administering of at least one compound. In an even further aspect, the instructions provide that the administering of at least one compound is to effect presurgical debulking of a tumor. In a yet further aspect, the instructions provide that surgery is performed at about the same time as the administering of at least one compound.

In a further aspect, the instructions further comprise providing the compound in connection with radiotherapy. In a yet further aspect, the instructions provide that radiotherapy is performed prior to the administering of at least one compound. In a still further aspect, the instructions provide that radiotherapy is performed after the step of the administering of at least one compound. In an even further aspect, the instructions provide that radiotherapy is performed at about the same time as the step of the administering of at least one compound. In a still further aspect, the instructions further comprise providing the compound in connection with at least one agent that is a chemotherapeutic agent.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of inhibitors of STAT protein related activity in laboratory animals such as cats, dogs, rabbits, monkeys, rats and mice, as part of the search for new therapeutic agents targeting STAT protein. Also provided are the uses of the disclosed compounds and products as pharmacological tools in the development and standardization of in vitro and in vivo test systems for the evaluation of the effects of inhibitors of STAT protein related activity in laboratory animals such as cats, dogs, rabbits, monkeys, rats and mice, as part of the search for new therapeutic agents targeting STAT3 protein. In various further aspects, also provided are the uses of the disclosed compounds and products as pharmacological tools in the development and standardization of in vitro and in vivo test systems for the evaluation of the effects of inhibitors of STAT protein related activity in laboratory animals such as cats, dogs, rabbits, monkeys, rats and mice, as part of the search for new therapeutic agents targeting STAT5 protein.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods

Anhydrous solvents methanol, DMSO, $CH_2Cl_2$, THF and DMF were purchased from Sigma Aldrich and used directly from Sure-Seal bottles. Molecular sieves were activated by heating to 300° C. under vacuum overnight. All reactions were performed under an atmosphere of dry nitrogen in oven-dried glassware and were monitored for completeness by thin-layer chromatography (TLC) using silica gel (visualized by UV light, or developed by treatment with KMnO$_4$ stain or phosphomolybdic acid stain). $^1$H and $^{13}$C NMR spectra were recorded on Bruker 400 MHz and a Varian 500 MHz spectrometers in either CDCl$_3$, CD$_3$OD or d$_6$-DMSO. Chemical shifts (δ) are reported in parts per million after calibration to residual isotopic solvent. Coupling constants (J) are reported in Hz. Before biological testing, inhibitor purity was evaluated by reversed-phase HPLC (rpHPLC). Analysis by rpHPLC was performed using a Microsorb-MV 300 A C18 250 mm×4.6 mm column run at 1 mL/min, and using gradient mixtures of (A) water with 0.1M CH$_3$COONH$_4$ and (B) methanol. Ligand purity was confirmed using linear gradients from 75% A and 25% B to 100% B after an initial 2 minute period of 100% A. The linear gradient consisted of a changing solvent composition of either (I) 4.7% per minute and UV detection at 254 nm or (II) 1.4% per minute and detection at 214 nm, each ending with 5 minutes of 100% B. For reporting HPLC data, percentage purity is given in parentheses after the retention time for each condition. All biologically evaluated compounds are >95% chemical purity as measured by HPLC.

2. General Procedure A (Reductive Amination of Amino Salicyclic Acid)—Reaction of R$^1$ Aldehydes with Benzyl Protected 4-Aminosalicyclic Acid.

To a solution of amine (1.0 equiv) and acetic acid (1.5 equiv) stirred in anhydrous MeOH (0.1 M) with 4 Å molecular sieves was added 1.0 equiv of aldehyde. The solution was then heated to 45° C. for 3 h and then allowed to cool to rt. Next, NaCNBH$_3$ (1.3 equiv) was added portionwise and the reaction allowed to stir at rt overnight. When TLC indicated the reaction was complete, the reaction was diluted with CH$_2$Cl$_2$, filtered and concentrated in vacuo.

3. General Procedure B (PPh$_3$Cl$_2$ Mediated Amide Coupling)—Reaction of Secondary Anilines with Carboxylic Acids.

To a stirred solution of the secondary aniline (1.0 equiv) and carboxylic acid (1.0 equiv) in CHCl$_3$ (0.1 M) was added PPh$_3$Cl$_2$ (2.5 equiv). The reaction was then heated to 60° C. and stirred overnight. The reaction was allowed to cool and the solvents removed under reduced pressure. The concentrate was absorbed directly onto silica for column chromatography purification.

4. General Procedure C (Boc Protection).

To a stirred solution of the appropriate secondary amine (1.0 equiv) and DIPEA (2.0 equiv) in CHCl$_3$ (0.1 M), was added Boc$_2$O (1.1 equiv) and left to stir overnight at rt. The reaction was then diluted with CH$_2$Cl$_2$, washed with H$_2$O, brine and dried over Na$_2$SO$_4$, filtered and concentrated under reduced pressure.

5. General Procedure D (Nucleophilic Aromatic Substitution).

The desired secondary amine (1.0 equiv) and arylfluoride substrate (1.5 equiv) were dissolved in anhydrous DMSO (0.1 M) followed by the addition of DIPEA (3.0 equiv). The reaction was heated to 120° C. and allowed to stir overnight. The reaction was quenched with H$_2$O and the aqueous layer extracted repeatedly into EtOAc. The combined organic layers were then washed with brine, dried over anhydrous Na$_2$SO$_4$ and the solvent removed under reduced pressure.

6. General Procedure E (TFA Deprotection with K$_2$Co$_3$ and MeOH).

LiOH.H$_2$O (3.0 equiv) was added to a stirred solution of the TFA (trifluoroacetyl)-protected compound (1 equiv.) in THF and water (3:1, 0.1 M). The reaction was allowed to stir at room temperature for 10 min and then was then diluted with H$_2$O and the product was extracted into EtOAc. The organic layers were then combined, washed with saturated NaHCO$_3$, water, brine and dried over anhydrous Na$_2$SO$_4$, filtered and the solvent removed under reduced.

7. General Procedure F (HBTU Mediated Condensation Reactions).

The required carboxylic acid (1 equiv) was added in one portion to a solution of HBTU (1.1 equiv) and DIPEA (3.0 equiv) in DMF (0.1 M), and the resulting solution stirred at room temperature for 10 minutes. The required amine was then dissolved in a solution of DIPEA (2.0 equiv) in DMF (0.1 M) and added to the activated acid in one portion. The resulting solution was stirred for 4 h, then diluted with EtOAc (0.1 M) and washed successively with equal volumes of: 2M HCl, saturated bicarbonate and brine. The organic layer was dried over anhydrous Na$_2$SO$_4$, filtered and concentrated.

8. General Procedure G (Sulfonylation of Secondary Amines).

To a stirred solution of amine (1.0 equiv) dissolved in CH$_2$Cl$_2$ (0.1 M) was added DIPEA (1.1 equiv) and the appropriate sulfonyl chloride (1.1 equiv). After 1 h, the reaction was diluted with CH$_2$Cl$_2$, washed with water, followed by a brine wash and dried over Na$_2$SO$_4$. The organic layer was then concentrated under reduced pressure and purified by silica gel column chromatography to yield product.

9. General Procedure H (Suzuki Cross Coupling).

A mixture of arylbromide (1.0 equiv), boronic acid (1.1 equiv), K$_2$CO$_3$ (2.5 equiv) and Pd(PPh$_3$)$_4$ (0.03 equiv) was suspended in DMF (0.1 M) in a sealed tube vessel and irradiated in a Biotage Initiator microwave reactor (17 min, 170° C.). After cooling to rt, the reaction was diluted with water and repeatedly extracted with CH$_2$Cl$_2$. The combined organic extracts were washed with brine, dried over anhydrous Na$_2$SO$_4$, filtered and concentrated under reduced pressure.

10. General Procedure I (Hydrogenolysis of Benzyl Ether and Benzyl Ester)—Global Deprotection of Benzylated Salicyclic Acid.

The benzyl protected salicyclic acid (1 equiv) was dissolved in a stirred solution of MeOH/THF (1:1) (0.1 M). The solution was degassed thoroughly before careful addition of 10% Pd/C (10 mg/mmol). H$_2$ gas was bubbled through the solvent for 5 min before the solution was put under an atmosphere of H$_2$ gas and stirred continuously for 3 h. The H$_2$ gas was evacuated and the reaction filtered (to remove the Pd catalyst) and concentrated under reduced pressure.

11. General Procedure J (TFA Deprotection of Benzyl Ether).

The benzyl protected compound (1 equiv) was dissolved in a 1:1 mixture of TFA:toluene (0.1 M) at rt for 5 min, then all solvents were evaporated under reduced pressure.

12. Preparation of Benzyl 4-Amino-2-(Benzyloxy)Benzoate (1).

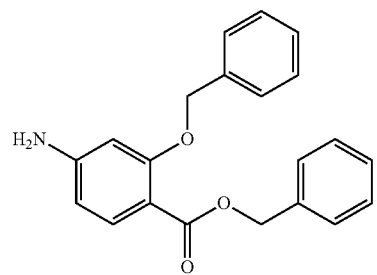 [SMILES: Nc1ccc(C(=O)OCc2ccccc2)c(OCc2ccccc2)c1]

To a stirred solution of 4-aminosalicyclic acid (3.00 g, 19.6 mmol) in DMF (0.1 M) at 0° C., was added KOtBu (2.42 g, 21.6 mmol). After 15 min, benzyl bromide (2.57 mL, 21.6 mmol) was added drop-wise. The suspension was allowed to stir at rt for a further 4 h before the reaction vessel was again cooled to 0° C. A further 1.1 equiv of KtOBu (2.42 g, 21.6 mmol) were added prior to the drop-wise addition of benzyl bromide (2.57 mL, 21.6 mmol). The reaction was then stirred overnight before quenching with $H_2O$. The solution was then repeatedly extracted with ethyl acetate and the organics combined. The organics were then washed with $H_2O$ and brine then concentrated, dried over $Na_2SO_4$ and concentrated in vacuo to afford the title compound (3.40 g, 74%): $\delta_H$ (400 MHz, $d_6$-DMSO) 5.07 (s, 2H, $CH_2Ph$), 5.21 (s, 2H, $CH_2Ph$), 5.99 (br s, 2H, $NH_2$), 6.18 (dd, J=8.6 and 1.8 Hz, 1H, CH (Ph)), 6.32 (d, J=1.7 Hz, 1H, CH (Ph)), 7.28-7.38 (8H, m, CH (Ph)), 7.47 (d, J=7.2 Hz, 2H, CH (Ph)), 7.60 (d, J=8.6 Hz, 1H, CH (Ph)); $\delta_C$ (100 MHz, $CDCl_3$) 65.8, 70.2, 99.1, 106.7, 109.0, 126.3, 126.8, 127.5, 127.7, 127.9, 128.1, 128.3, 128.4, 134.3, 136.6, 136.7, 152.2, 160.7, 165.7; LRMS (ES+) calcd for $[C_{21}H_{19}NO_3+H]$ 334.14 found 334.17.

13. Benzyl 2-(benzyloxy)-4-(4-bromobenzylamino)benzoate (2).

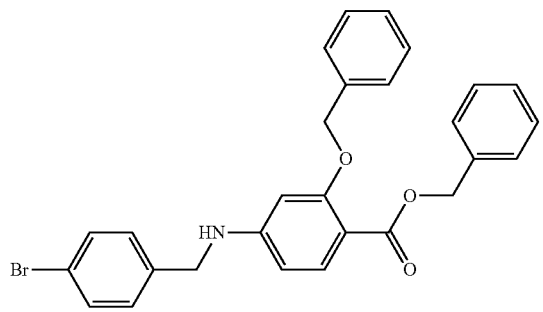 [SMILES: O=C(OCc1ccccc1)c1ccc(NCc2ccc(Br)cc2)cc1OCc1ccccc1]

Primary aniline 1 was coupled to 4-bromobenzaldehyde on a 0.7 mmol scale via General Procedure A to furnish 2 (274 mg, 78%): $\delta_H$ (400 MHz, $CDCl_3$) 4.12 (s, 2H, $CH_2$, $NHCH_2Ph$), 4.50 (br s, 1H, NH), 4.92 (s, 2H, $CH_2$, $CH_2Ph$), 5.18 (s, 2H, $CH_2$, $CH_2Ph$), 5.98 (d, J=1.8 Hz, 1H, CH (Ph)), 6.04 (dd, J=8.6 and 1.8 Hz, 1H, CH (Ph)), 7.02 (d, J=8.2 Hz, 2H, 2 CH (Ph)), 7.11-7.34 (m, 12H, 12 CH (Ph)), 7.70 (d, J=8.6 Hz, 1H, CH (Ph)); $\delta_C$ (100 MHz, $CDCl_3$) 46.5, 65.4, 69.9, 97.0, 104.5, 108.2, 120.7, 126.4, 127.2, 127.4, 127.6, 128.0, 128.1, 128.4, 131.4, 133.9, 136.3, 137.0, 152.3, 160.4, 165.3; LRMS (ES+) calcd for $[C_{28}H_{24}BrNO_3+H]$ 502.10, found 502.06.

14. Preparation of benzyl 2-(benzyloxy)-4-((cyclohexylmethyl)amino)benzoate (19e).

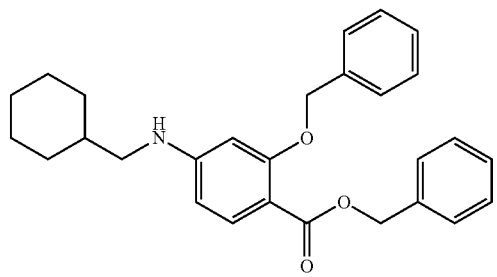 [SMILES: O=C(OCc1ccccc1)c1ccc(NCC2CCCCC2)cc1OCc1ccccc1]

Primary aniline 1 was coupled to cyclohexanecarboxaldehyde on a 0.6 mmol scale via General Procedure A to furnish 3 (184 mg, 72%): $\delta_H$ (400 MHz, $CDCl_3$) 1.15-1.30 (m, 5H, $CH_2$), 1.45-1.55 (m, 1H, CH), 1.65-1.81 (m, 5H, $CH_2$), 2.94 (d, J=6.4 Hz, 2H, $CH_2$), 5.14 (s, 2H, $CH_2$), 5.32 (s, 2H, $CH_2$), 6.11 (d, J=2.0 Hz, 1H, CH), 6.16 (d of d, J=8.8 and 2.0 Hz, 1H, CH), 7.29-7.36 (m, 10H, CH), 7.41 (d, J=8.0 Hz, 2H, CH), 7.48 (d, J=8.0 Hz, 2H, CH), 7.85 (d, J=8.8 Hz, 1H, CH); $\delta_C$ (100 MHz, $CDCl_3$) 25.7, 26.3, 31.0, 37.5, 49.8, 65.6, 70.3, 96.8, 104.6, 107.5, 126.8, 127.5, 127.6, 127.9, 128.3, 128.4, 134.2, 136.8, 136.9, 153.4, 161.0, 165.7, 171.0; LRMS (ES+) calcd for $[C_{28}H_{31}NO_3+H]$ 430.24 found 430.20.

15. Preparation of Benzyl 2-(benzyloxy)-4-(4-cyclohexylbenzylamino)benzoate (4).

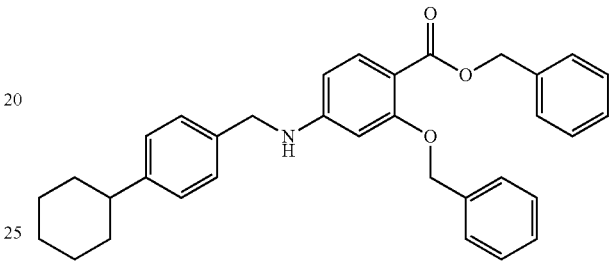

Primary aniline 17 was coupled to 4-cyclohexylbenzaldehyde on a 0.6 mmol scale via General Procedure A to furnish 4 (250 mg, 83%): $\delta_H$ (400 MHz, $CDCl_3$) 1.25-1.48 (m, 6H, $CH_2CH_2$), 1.74-1.95 (m, 4H, $CH_2CH_2$), 2.48-2.52 (m, 1H, CH), 4.28 (s, 2H, $NH_2CH_2$), 4.49 (br s, 1H, NH), 5.08 (s, 2H, $CH_2Ph$), 5.32 (s, 2H, $CH_2Ph$), 6.17 (d, J=2.0 Hz, 1H, CH (Ph)), 6.21 (dd, J=8.6 and 2.0 Hz, 1H, CH (Ph)), 7.19-7.27 (m, 4H, 4 CH (Ph)), 7.28-7.37 (m, 6H, 6 CH (Ph)), 7.40-7.49 (m, 4H, 4 CH (Ph)), 7.85 (d, J=8.6 Hz, 1H, 1 CH (Ar)); $\delta_C$ (100 MHz, $CDCl_3$) 26.0, 26.7, 34.3, 44.1, 47.3, 65.7, 70.3, 97.1, 104.8, 108.2, 126.8, 127.0, 127.4, 127.5, 127.6, 127.9, 128.2, 128.3, 134.2, 135.4, 136.7, 136.8, 147.4, 152.9, 160.8, 165.8; LRMS (ES+) calcd for $[C_{34}H_{35}NO_3+H]$ 506.27 found 506.22.

16. Preparation of benzyl 2-(benzyloxyl)-4-11(4'-bromo-[1,1'-biphenyl]-4-yl)methyl)amino)benzoate (5).

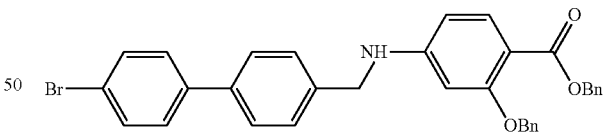

Primary aniline 1 was coupled to 4'-bromo-[1,1'-biphenyl]-4-carbaldehyde on a 3.7 mmol scale via General Procedure A to furnish 5 (1.52 g, 70%): $\delta_H$ (400 MHz, $CDCl_3$) 4.39 (s, 2H, $CH_2$), 4.59 (br s, 1H, NH), 5.10 (s, 2H, $CH_2$), 5.31 (s, 2H, $CH_2$), 6.20 (d, J=2.0 Hz, 1H, CH), 6.24 (d of d, J=8.6 and 2.0 Hz, 1H, CH), 7.25-7.36 (m, 6H, CH), 7.37-7.49 (m, 8H, CH), 7.53 (d, J=8.4 Hz, 2H, CH), 7.57 (d, J=8.4 Hz, 2H, CH) 7.85 (d, J=8.6 Hz, 1H, CH); $\delta_C$ (100 MHz, $CDCl_3$) 47.3, 65.7, 70.3, 97.4, 104.9, 108.7, 121.5, 126.8, 127.1, 127.5, 127.6, 127.8, 127.9, 128.3, 128.3, 128.5, 131.8, 134.3, 136.6, 136.7, 137.6, 139.1, 139.4, 152.6, 160.8, 165.6.

17. Preparation of methyl 2-(N,4-dimethylphenylsulfonamido)acetate (6).

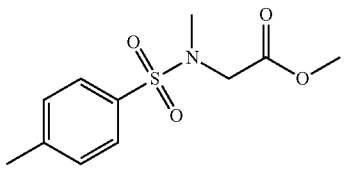

To a stirred solution of methyl 2-(4-methylphenylsulfonamido)acetate (3.10 g, 12.8 mmol) and Cs$_2$CO$_3$ (8.31 g, 25.5 mmol) in DMF (0.1 M) was added MeI (877 μL, 14.1 mmol). The reaction was allowed to stir overnight at rt. The reaction was then diluted with water and repeatedly extracted with CH$_2$Cl$_2$. The combined organic extracts were washed with brine, dried over anhydrous Na$_2$SO$_4$, filtered and concentrated under reduced pressure to furnish 6 (2.80 g, 85%): δ$_H$ (400 MHz, CDCl$_3$) 2.42 (s, 3H, CH$_3$), 2.87 (s, 3H, CH$_3$), 3.66 (s, 3H, CH$_3$), 3.97 (s, 2H, CH$_2$), 7.31 (d, J=8.4 Hz, 2H, CH), 7.69 (d, J=8.4 Hz, 2H, CH); LRMS (ES+) calcd for [C$_{11}$H$_{15}$NO$_4$S+H] 258.08, found 258.06 [M+H].

18. Preparation of 2-(N,4-dimethylphenylsulfonamido)acetic acid (7).

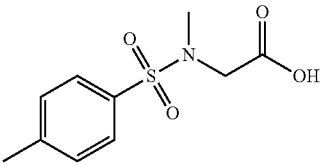 [SMILES: Cc1ccc(S(=O)(=O)N(C)CC(=O)O)cc1]

Methyl ester 6 (2.60 g, 10.1 mmol) was dissolved in a 3:1:1 mixture of MeOH-THF—H$_2$O. LiOH—H$_2$O (0.53 g, 12.6 mmol) was added at room temperature and the reaction allowed to stir for 3 h. All solvents were evaporated, apart from water. The remaining aqueous solvent was diluted further and thoroughly washed with ethyl acetate. The aqueous basic aqueous layer was then acidified to pH 2 with 1 M HCl and the product extracted with ethyl acetate. The organic layers were then combined and dried over Na$_2$SO$_4$, filtered and concentrated to afford the title compound. (2.33 g, 95%): δ$_H$ (400 MHz, CDCl$_3$) 2.43 (s, 3H, CH$_3$), 2.87 (s, 3H, CH$_3$), 3.99 (s, 2H, CH$_2$), 7.32 (d, J=8.0 Hz, 2H, CH), 7.69 (d, J=8.0 Hz, 2H, CH); δ$_C$ (100 MHz, CDCl$_3$) 21.4, 35.7, 50.6, 127.3, 129.6, 134.8, 143.7, 173.5; LRMS (ES+) calcd for [C$_{10}$H$_{13}$NO$_4$S+H] 244.06, found 244.07 [M+H].

19. Preparation of benzyl 2-(benzyloxy)-4-(2-(N,4-dimethylphenylsulfonamido)-acetamido)benzoate (8).

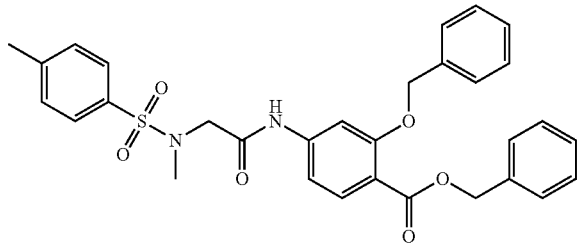 [SMILES: Cc1ccc(S(=O)(=O)N(C)CC(=O)Nc2ccc(C(=O)OCc3ccccc3)c(OCc3ccccc3)c2)cc1]

Primary aniline 17 was coupled to 7 on a 1.3 mmol scale via General Procedure B to furnish 8 (650 mg, 92%): δ$_H$ (400 MHz, CDCl$_3$) 2.38 (s, 3H, CH$_3$), 2.83 (s, 3H, CH$_3$), 3.75 (s, 2H, CH$_2$), 5.08 (s, 2H, CH$_2$), 5.33 (s, 2H, CH$_2$), 7.10 (d, J=8.4 Hz, 1H, CH), 7.25-7.34 (m, 8H, CH), 7.36-7.40 (m, 2H, CH), 7.43 (d, J=7.2 Hz, 2H, CH), 7.64 (s, 1H, CH), 7.67 (d, J=8.0 Hz, 2H, CH), 7.89 (d, J=8.0 Hz, 1H, CH); δ$_C$ (100 MHz, CDCl$_3$) 21.4, 37.1, 54.7, 66.4, 70.4, 104.6, 111.2, 115.6, 127.1, 127.5, 127.7, 127.9, 128.0, 128.3, 128.4, 130.0, 132.6, 133.0, 136.1, 136.2, 142.3, 144.5, 159.4, 165.5, 166.4; LRMS (ES+) calcd for [C$_{31}$H$_{30}$N$_2$O$_6$S+H] 559.19, found 559.19.

Benzyl 2-(benzyloxy)-4-(N-(4-bromobenzyl)-2-(N,4-dimethylphenylsulfonamido)acetamido)benzoate (9).

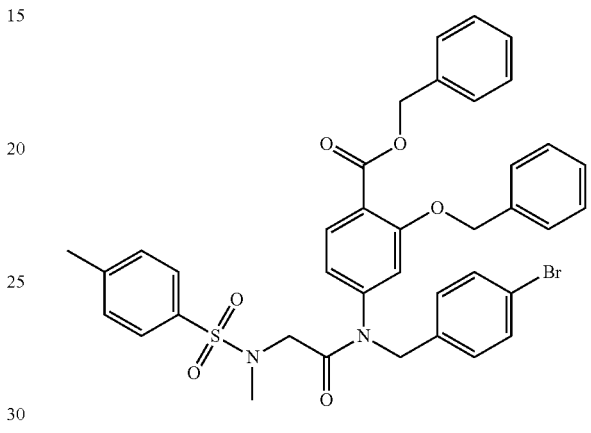

Secondary aniline 2 was coupled to carboxylic acid 6 on a 0.2 mmol scale via General Procedure B to furnish 9 (167 mg, 90%): δ$_H$ (400 MHz, CDCl$_3$) 2.33 (s, 3H, CH$_3$Ar), 2.73 (s, 3H, CH$_3$Ar), 3.54 (s, 2H, CH$_2$CO), 4.64 (s, 2H, CH$_2$Ar), 4.99 (s, 2H, CH$_2$Ar), 5.28 (s, 2H, CH$_2$Ar), 6.50 (br s, 1H, CH (Ar)), 6.55 (dd, J=8.3 and 1.8 Hz, 1H, CH (Ar)), 6.88 (d, J=8.3 Hz, 2H, 2 CH (Ar)), 7.16-7.34 (m, 14H, 14 CH (Ar)), 7.51 (d, J=8.3 Hz, 2H, 2 CH (Ar)), 7.75 (d, J=8.3 Hz, 1H, CH (Ar)); δ$_C$ (100 MHz, CDCl$_3$) 21.4, 29.6, 36.0, 51.2, 52.4, 53.3, 66.9, 70.7, 113.9, 119.8, 120.9, 121.7, 126.9, 127.3, 127.9, 128.2, 128.5, 129.4, 130.5, 131.6, 133.1, 135.2, 135.5, 135.6, 135.7, 143.3, 144.7, 158.7, 165.2, 167.0; LRMS (ES+) Calcd for [C$_{38}$H$_{35}$BrN$_2$O$_6$S+H] 727.15 found 726.83.

20. Preparation of benzyl 2-(benzyloxy)-4-(N-((4'-bromo-[1,1'-biphenyl]-4-yl)methyl)-2-(N,4-dimethylphenylsulfonamido)acetamido)benzoate (5).

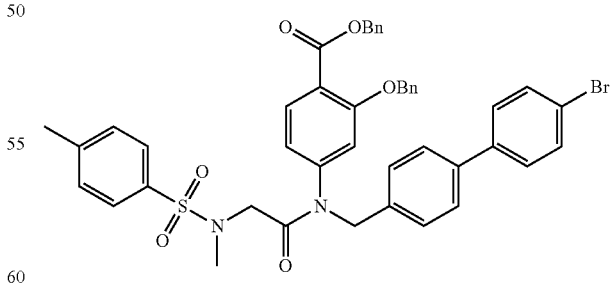

Secondary aniline 26ja was coupled to 7 on a 1.7 mmol scale via General Procedure B to furnish 5 (1.15 g, 84%) δ$_H$ (400 MHz, CDCl$_3$) 2.39 (s, 3H, CH$_3$), 2.82 (s, 3H, CH$_3$), 3.67 (s, 2H, CH$_2$), 4.82 (s, 2H, CH$_2$), 5.02 (s, 2H, CH$_2$), 5.34 (s, 2H, CH$_2$), 6.61 (s, 1H, CH), 6.68 (d, J=8.0 Hz, 1H, CH), 7.17 (d, J=8.0 Hz, 2H, CH), 7.22-7.46 (m, 16H, CH), 7.54

(d, J=8.4 Hz, 2H, CH), 7.60 (d, J=8.4 Hz, 2H, CH), 7.83 (d, J=8.0 Hz, 1H, CH); δ$_C$ (100 MHz, CDCl$_3$) 21.4, 35.9, 51.3, 52.7, 66.9, 70.7, 114.0, 119.9, 120.8, 121.6, 126.9, 127.4, 127.9, 128.1, 128.2, 128.4, 128.5, 129.3, 129.4, 131.8, 133.1, 135.2, 135.6, 135.6, 135.9, 139.3, 144.9, 158.7, 165.2, 166.9; LRMS (ES+) calcd for [C$_{44}$H$_{39}$BrN$_2$O$_6$S+H] 803.18 found 803.69.

21. Preparation of benzyl 2-(benzyloxy)-4-(N-(cyclohexylmethyl)-2-(N,4-dimethylphenyl-sulfonamido)acetamido)benzoate (11).

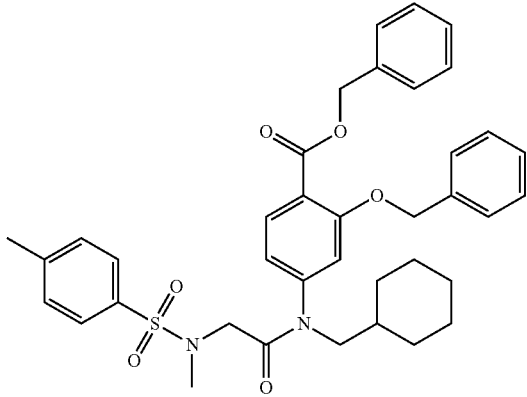 [SMILES: Cc1ccc(S(=O)(=O)N(C)CC(=O)N(CC2CCCCC2)c2ccc(C(=O)OCc3ccccc3)c(OCc3ccccc3)c2)cc1]

Secondary aniline 3 was coupled to carboxylic acid 7 on a 0.2 mmol scale via General Procedure B to furnish 11 (92 mg, 68%): δ$_H$ (400 MHz, CDCl$_3$) 1.04-1.17 (m, 3H, CH$_2$), 1.25-1.41 (m, 3H, CH$_2$ and CH), 1.50-1.71 (m, 5H, CH$_2$), 2.39 (s, 3H, CH$_3$), 2.86 (s, 3H, CH$_3$), 3.47 (d, J=8.4 Hz, 2H, CH$_2$), 3.67 (s, 2H, CH$_2$), 5.22 (s, 2H, CH$_2$), 5.38 (s, 2H, CH$_2$), 6.79-6.84 (m, 2H, CH), 7.25 (d, J=8.4 Hz, 2H, CH), 7.28-7.39 (m, 6H, CH), 7.40-7.47 (m, 4H, CH), 7.61 (d, J=8.4 Hz, 2H, CH), 7.91 (d, J=8.4 Hz, 1H, CH); δ$_C$ (100 MHz, CDCl$_3$) 21.5, 25.6, 26.2, 30.6, 35.9, 51.3, 55.4, 67.0, 70.8, 113.8, 119.8, 120.6, 127.0, 127.4, 128.0, 128.1, 128.2, 128.5, 128.6, 129.4, 133.1, 135.7, 135.9, 143.2, 145.9, 158.9, 165.4, 167.0; LRMS (ES+) calcd for [C$_{38}$H$_{42}$N$_2$O$_6$S+Na] 677.27 found 677.36.

22. Preparation of benzyl 2-(benzyloxy)-4-(N-(4-cyclohexylbenzyl)-2-(N,4-dimethylphenyl-sulfonamido)acetamido)benzoate (12).

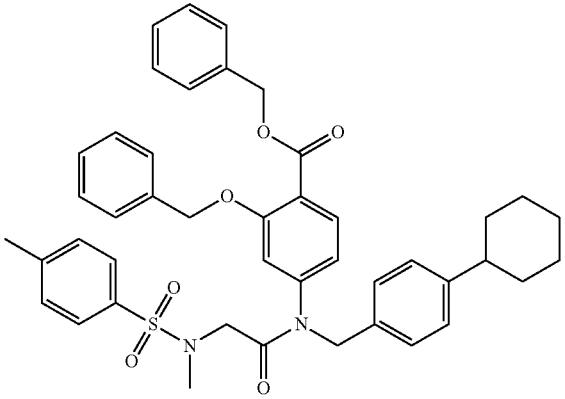 [SMILES: Cc1ccc(S(=O)(=O)N(C)CC(=O)N(Cc2ccc(C3CCCCC3)cc2)c2ccc(C(=O)OCc3ccccc3)c(OCc3ccccc3)c2)cc1]

Secondary aniline 4 was coupled to carboxylic acid 7 on a 0.2 mmol scale via General Procedure B to furnish 12 (145 mg, 86%): δ$_H$ (400 MHz, CDCl$_3$) 1.15-1.35 (m, 6H, CH$_2$), 1.61-1.80 (m, 4H, CH$_2$), 2.31 (s, 3H, CH$_3$Ar), 2.37-2.38 (m, 1H, CH), 2.73 (s, 3H, CH$_3$N), 3.57 (s, 2H, CH$_2$CO), 4.67 (s, 2H, CH$_2$Ar), 4.86 (s, 2H, CH$_2$Ar), 5.26 (s, 2H, CH$_2$Ar), 6.43 (s, 1H, CH (Ar)), 6.59 (dd, J=8.2 and 1.5 Hz, 1H, CH (Ar)), 6.93 (d, J=8.0 Hz, 2H, 2 CH (Ar)), 7.02 (d, J=8.0 Hz, 2H, 2 CH (Ar)), 7.14-7.35 (m, 12H, 12 CH (Ar)), 7.52 (d, J=8.2 Hz, 2H, 2 CH (Ar)), 7.75 (d, J=8.2 Hz, 2H, 2 CH (Ar)); δ$_C$ (400 MHz, CDCl$_3$) 21.4, 25.9, 26.6, 34.3, 35.8, 44.0, 51.2, 52.7, 66.8, 70.5, 114.1, 119.9, 120.5, 126.8, 126.9, 127.3, 127.8, 128.0, 128.1, 128.4, 128.5, 128.7, 129.3, 133.0, 133.8, 135.2, 135.6, 135.7, 143.1, 144.9, 147.6, 158.6, 165.2, 166.6; LRMS (ES+) calcd for [C$_{44}$H$_{46}$N$_2$O$_6$S+H] 731.32 found 731.28.

23. Preparation of Benzyl 2-(benzyloxy)-4-(2-(N,4-dimethylphenylsulfonamido)-N-(piperidin-4-ylmethyl)acetamido)benzoate (13).

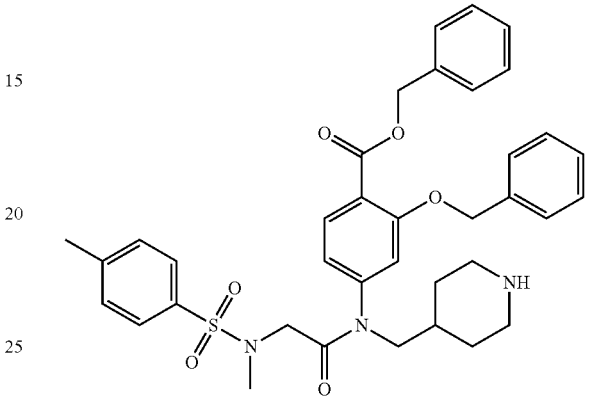

Secondary aniline tert-butyl 4-(((3-(benzyloxy)-4-((benzyloxy)carbonyl)phenyl)amino)methyl)piperidine-1-carboxylate was coupled to carboxylic acid 7 on a 2.8 mmol scale via General Procedure B to furnish 13 (1.50 g, 67%): δ$_H$ (400 MHz, CDCl$_3$) 1.40-1.86 (m, 4H, CH$_2$), 2.38 (s, 3H, CH$_3$Ar), 2.64-2.93 (m, 5H, CH and CH$_2$), 2.72 (s, 3H, NCH$_3$), 3.28-3.70 (m, 4H, CH$_2$), 5.24 (s, 2H, CH$_2$Bn), 5.38 (s, 2H, CH$_2$Bn), 6.85 (dd, J=8.2 and 1.7 Hz, 1H, CH (Ar)), 6.89 (d, J=1.7 Hz, 1H, CH (Ar)), 7.20-7.43 (m, 11H, 13 CH (Ar)), 7.58 (d, J=8.2 Hz, 1H, 1 CH (Ar)), 7.90 (d, J=8.2 Hz, 1H, CH (Ar)); δ$_C$ (100 MHz, CDCl$_3$) 21.4, 27.4, 29.7, 33.2, 36.1, 44.1, 51.5, 54.3, 67.0, 70.7, 113.7, 115.5, 120.9, 127.0, 127.3, 127.4, 128.0, 128.2, 128.5, 128.6, 129.4, 129.5, 133.3, 135.0, 135.7, 135.9, 143.5, 145.5, 158.9, 165.3, 167.1, 167.6; LRMS (ES+) calcd for [C$_{37}$H$_{41}$N$_3$O$_6$S+H] 656.28 found 656.44.

24. Preparation of tert-butyl 4-((N-(3-(benzyloxy)-4-(benzyloxycarbonyl)phenyl)-2-(N,4-dimethylphenyl-sulfonamido)acetamido)methyl)piperidine-1-carboxylate (14).

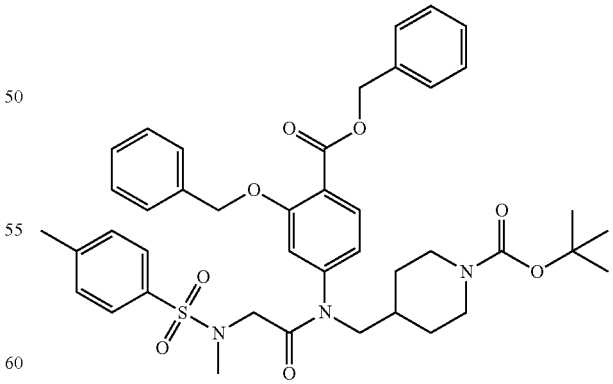

Compound 13 was Boc protected with (Boc)$_2$ via General Procedure C on a 0.15 mmol scale to furnish 14 (99 mg, 86%): δ$_H$ (400 MHz, CDCl$_3$) 0.80-1.02 (m, 3H, CH$_2$), 1.10-1.25 (m, 2H, CH$_2$), 1.36 (s, 9H, 3 CH$_3$), 2.31 (s, 3H, CH$_3$Ar), 2.45-2.55 (m, 2H, CH$_2$), 2.72 (s, 3H, NCH$_3$), 3.42 (s (br), 2H, CH$_2$), 3.58 (s, 2H, CH$_2$), 3.93 (br s, 2H, CH$_2$), 5.16 (s, 2H, CH$_2$Bn), 5.30 (s, 2H, CH$_2$Bn), 6.71-6.75 (m, 2H, 2 CH (Ar)), 7.15-7.38 (m, 12H, 12 CH (Ar)), 7.52 (d, J=8.2 Hz, 2H, 2 CH (Ar)), 7.83 (d, J=8.2 Hz, 1H, CH (Ar)); δ$_C$ (100 MHz, CDCl$_3$) 21.4, 28.3, 29.6, 34.5, 36.0, 36.5, 51.3, 54.7, 66.9, 70.7, 79.3, 113.7, 119.5, 120.7, 126.9, 127.3, 128.0, 128.1, 128.5, 128.6, 129.4, 133.2, 135.6, 135.8, 143.3, 145.6, 154.5, 158.9, 165.2, 167.2.

25. Preparation of benzyl 2-(benzyloxy)-4-(N-((1-(4-cyanophenyl)piperidin-4-yl)methyl)-2-(N,4-dimethylphenylsulfon amido)acetamido)benzoate (15).

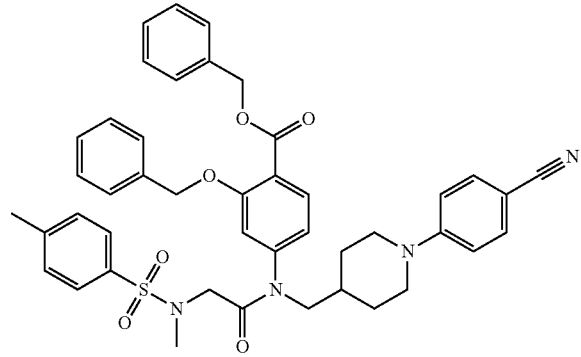 [SMILES: Cc1ccc(S(=O)(=O)N(C)CC(=O)N(CC2CCN(c3ccc(C#N)cc3)CC2)c2ccc(C(=O)OCc3ccccc3)c(OCc3ccccc3)c2)cc1]

Nucleophilic aromatic substitution of 13 with 4-fluorobenzonitrile on a 0.2 mmol scale via General Procedure D furnished 15 (87 mg, 76%): δ$_H$ (400 MHz, CDCl$_3$) 1.20-1.31 (m, 3H, CH$_2$), 1.60-1.68 (m, 2H, CH$_2$), 2.38 (s, 3H, CH$_3$Ar), 2.72 (t, J=12.0 Hz, 2H, CH$_2$), 2.78 (s, 3H, NCH$_3$), 3.55 (d, J=6.8 Hz, 2H, CH$_2$CH), 3.66 (s, 2H, CH$_2$), 3.74 (d, J=13.0 Hz, 2H, CH$_2$), 5.24 (s, 2H, CH$_2$Bn), 5.38 (s, 2H, CH$_2$Bn), 6.77-6.84 (m, 4H, 4 CH (Ar)), 7.21-7.47 (m, 14H, 14 CH (Ar)), 7.59 (d, J=8.2 Hz, 2H, 2 CH (Ar)), 7.91 (d, J=8.2 Hz, 1H, CH (Ar)); δ$_C$ (100 MHz, CDCl$_3$) 21.4, 28.9, 34.3, 36.1, 47.1, 51.3, 54.5, 67.0, 70.7, 99.2, 113.7, 114.1, 119.5, 120.1, 120.8, 126.9, 127.3, 128.0, 128.2, 128.5, 128.6, 129.4, 133.2, 133.4, 135.6, 135.8, 143.3, 145.6, 152.9, 158.8, 165.2, 167.3.

26. Preparation of benzyl 2-(benzyloxy)-4-(2-(N,4-dimethylphenylsulfonamido)-N-((1-(pyrimidin-2-yl)piperidin-4-yl)methyl)acetamido)benzoate (16).

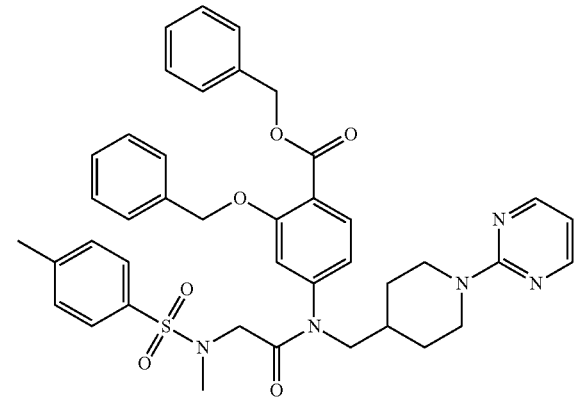 [SMILES: Cc1ccc(S(=O)(=O)N(C)CC(=O)N(CC2CCN(c3ncccn3)CC2)c2ccc(C(=O)OCc3ccccc3)c(OCc3ccccc3)c2)cc1]

Nucleophilic aromatic substitution of 13 with 2-chloropyrimidine on a 0.2 mmol scale via General Procedure D furnished 16 (108 mg, 96%): δ$_H$ (400 MHz, CDCl$_3$) 1.15-1.40 (m, 2H, CH$_2$), 1.54-1.75 (m, 3H, CH$_2$ and CH), 2.38 (s, 3H, CH$_3$), 2.74 (t, J=10.4 Hz, 2H, CH$_2$), 2.80 (s, 3H, CH$_3$), 3.52 (d, J=7.2 Hz, 2H, CH$_2$), 3.68 (s, 2H, CH$_2$), 4.64 (d, J=13.2 Hz, 2H, CH$_2$), 5.23 (s, 2H, CH$_2$), 5.37 (s, 2H, CH$_2$), 6.42 (t, J=4.8 Hz, 1H, CH), 6.80-6.85 (m, 2H, CH), 7.23-7.37 (m, 8H, CH), 7.38-7.45 (m, 4H, CH), 7.60 (d, J=8.0 Hz, 2H, CH), 7.91 (d, J=8.8 Hz, 1H, CH), 8.27 (d, J=4.8 Hz, 2H, CH); δ$_C$ (100 MHz, CDCl$_3$) 21.4, 29.4, 34.8, 35.9, 36.5, 43.4, 51.3, 54.8, 66.9, 70.7, 109.3, 113.7, 119.5, 120.7, 126.9, 127.3, 128.0, 128.1, 128.4, 128.6, 129.4, 133.2, 135.2, 135.6, 135.8, 143.3, 145.7, 157.5, 158.9, 161.2, 165.2, 167.1.

27. Preparation of 4-(1-(2,2,2-trifluoroacetyl)piperidin-4-yl)benzaldehyde (2 Step Procedure) (19).

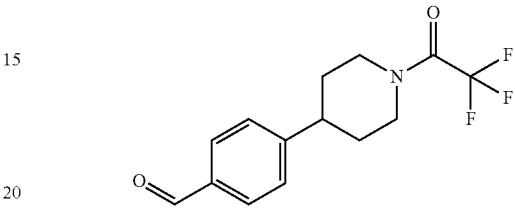

To a flask containing AlCl$_3$ (534 mg, 4.0 mmol) under an N$_2$ atmosphere was added anhydrous CH$_2$Cl$_2$ (0.1 M), and the drop wise addition of oxalyl chloride (523 μL, 6.0 mmol) over a 20 min period at 15° C. Next, a solution of 2,2,2-trifluoro-1-(4-phenylpiperidin-1-yl)ethanone (17) (2.0 mmol) in anhydrous CH$_2$Cl$_2$ (0.1 M) was added drop-wise to the initial solution over a 45 min period at 15° C. When the reaction was complete as judged by TLC, ice was added to the solution in addition to CaCl$_2$ (1.70 g). The product was extract into CH$_2$Cl$_2$, washed with brine and dried over anhydrous Na$_2$SO$_4$ before concentrating under reduced pressure to yield crude 4-(1-(2,2,2-trifluoroacetyl)piperidin-4-yl)benzoyl chloride (18). (b) To a stirred solution of 18 (2.0 mmol) and DIPEA (697 μL, 4.0 mmol) in EtOAc (0.1 M) was added 10% Pd/C. The flask was then evacuated and filled with H$_2$ gas and allowed to stir for 30 min. After which time the reaction contents were filtered and concentrated under reduced pressure to give crude product which was purified by silica gel column chromatography (hexanes:EtOAc, 2:1) to furnish 19 (320 mg, 59% (yield over 2 steps)) δ$_H$ (400 MHz, CDCl$_3$) 1.69-1.81 (m, 2H, CH$_2$), 1.98-2.06 (m, 2H, CH$_2$), 2.83-2.97 (m, 2H, CH$_2$), 3.27 (td, J=12.8 and 2.4 Hz, 1H, CH), 4.13-4.21 (m, 1H, CH), 4.70-4.76 (m, 1H, CH$_2$), 7.37 (d, J=8.4 Hz, 2H, CH), 7.85 (d, J=8.4 Hz, 2H, CH), 9.99 (s, 1H, CHO); LRMS (ES+) calcd for [C$_{14}$H$_{14}$F$_3$NO$_2$+Na] 308.09 found 308.19 [M+Na].

28. Preparation of benzyl 2-(benzyloxy)-4-(2-(N,4-dimethylphenylsulfonamido)-N-(4-(piperidin-4-yl)benzyl)acetamido)benzoate (21).

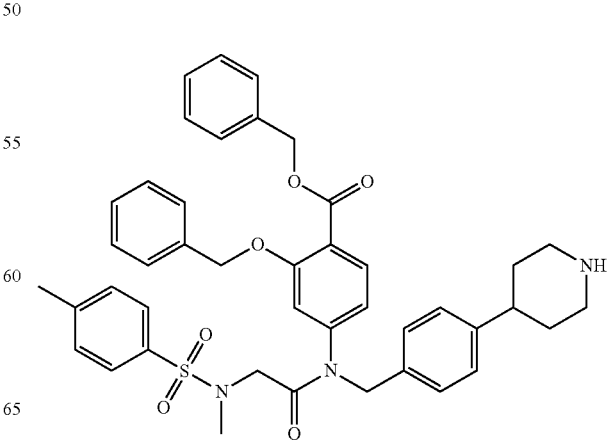

Benzyl 2-(benzyloxy)-4-(2-(N,4-dimethylphenylsulfonamido)-N-(4-(1-(2,2,2-trifluoroacetyl)piperidin-4-yl)benzyl)acetamido)benzoate (20) was TFA-deprotected on a 0.04 mmol scale via General Procedure E to furnish 21 (0.89 g, 81%): $\delta_H$ (400 MHz, CDCl$_3$) 1.68-1.82 (m, 2H, CH$_2$), 1.95-2.05 (m, 2H, CH$_2$) 2.41 (s, 3H, CH$_3$), 2.55-2.64 (m, 1H, CH), 2.69-2.78 (m, 2H, CH$_2$), 2.80 (s, 3H, CH$_3$), 3.17-3.21 (m, 2H, CH$_2$), 4.70 (s, 2H, CH$_2$), 4.75 (s, 2H, CH$_2$), 4.99 (s, 2H, CH$_2$), 5.30 (s, 2H, CH$_2$), 6.53 (s, 1H, CH), 6.66 (d, J=8.4 Hz, 1H, CH), 7.03 (d, J=8.0 Hz, 2H, CH), 7.11 (d, J=8.0 Hz, 2H, CH), 7.22-7.40 (m, 12H, CH), 7.60 (d, J=8.4 Hz, 2H, CH), 7.80 (d, J=8.4 Hz, 1H, CH); LRMS (ES+) calcd for [C$_{43}$H$_{45}$N$_3$O$_6$S+H] 732.31 found 732.40.

29. Preparation of tert-butyl 4-(4-((N-(3-(benzyloxy)-4-((benzyloxy)carbonyl)phenyl)-2-(N,4-dimethyl-phenylsulfonamido)acetamido)methyl)phenyl)piperidine-1-carboxylate (22).

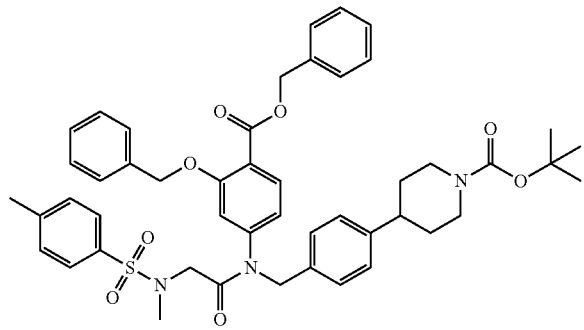 [SMILES: Cc1ccc(S(=O)(=O)N(C)CC(=O)N(Cc2ccc(C3CCN(C(=O)OC(C)(C)C)CC3)cc2)c2ccc(C(=O)OCc3ccccc3)c(OCc3ccccc3)c2)cc1]

Compound 21 was Boc protected with (Boc)$_2$ via General Procedure C on a 0.10 mmol scale to furnish 22 (83 mg, 99%): $\delta_H$ (400 MHz, CDCl$_3$) 1.47 (s, 9H, CH$_3$), 1.53-1.64 (m, 2H, CH$_2$), 1.72-1.80 (m, 2H, CH$_2$), 2.39 (s, 3H, CH$_3$), 2.54-2.64 (m, 2H, CH$_2$), 2.70-2.82 (m, 4H, CH$_3$ and CH), 3.64 (s, 2H, CH$_2$), 4.75 (s, 2H, CH$_2$), 4.97 (s, 2H, CH$_2$), 5.34 (s, 2H, CH$_2$), 6.56 (s, 1H, CH), 6.65 (dd, J=8.0 and 1.6 Hz, 1H, CH), 7.03 (d, J=8.0 Hz, 2H, CH), 7.09 (d, J=8.0 Hz, 2H, CH), 7.24 (d, J=8.0 Hz, 2H, CH), 7.28-7.40 (m, 10H, CH), 7.59 (d, J=8.0 Hz, 2H, CH), 7.81 (d, J=8.4 Hz, 1H, CH); $\delta_C$ (100 MHz, CDCl$_3$) 21.4, 28.3, 33.0, 35.9, 40.8, 42.2, 51.3, 52.7, 66.9, 70.6, 79.3, 114.0, 119.9, 120.6, 126.8, 127.0, 127.3, 127.9, 128.1, 128.2, 128.4, 128.5, 128.9, 129.4, 133.0, 134.5, 135.2, 135.6, 135.7, 143.2, 144.9, 145.3, 154.7, 158.6, 165.2, 166.7; LRMS (ES+) calcd for [C$_{48}$H$_{53}$N$_3$O$_8$S+Na] 854.35 found 854.62 [M+Na].

30. Preparation of benzyl 2-(benzyloxy)-4-(2-(N,4-dimethylphenylsulfonamido)-N-(4-(1-(pyrimidin-2-yl)piperidin-4-yl)benzyl)acetamido)benzoate (23).

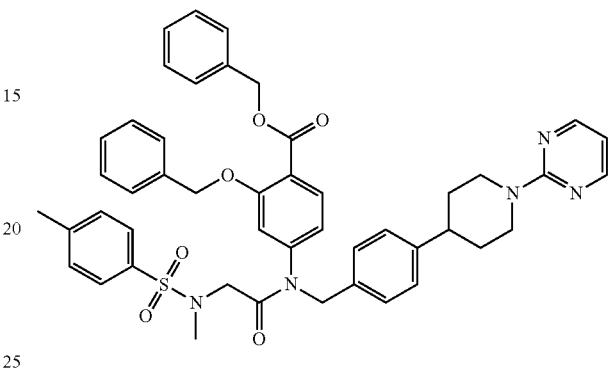

Nucleophilic aromatic substitution of 21 with 2-chloropyrimidine on a 0.1 mmol scale via General Procedure D furnished 23 (70 mg, 80%): $\delta_H$ (400 MHz, CDCl$_3$) 1.59-1.72 (m, 2H, CH$_2$), 1.83-1.94 (m, 2H, CH$_2$), 2.39 (s, 3H, CH$_3$), 2.71-2.83 (m, 4H, CH$_3$ and CH), 2.88-2.99 (m, 2H, CH$_2$), 3.65 (s, 2H, CH$_2$), 4.75 (s, 2H, CH$_2$), 4.86-4.94 (m, 2H, CH$_2$), 4.97 (s, 2H, CH$_2$), 5.34 (s, 2H, CH$_2$), 6.46 (t, J=8.4 Hz, 1H, CH), 6.56 (s, 1H, CH), 6.65 (dd, J=8.0 and 2.0 Hz, 1H, CH), 7.03 (d, J=8.0 Hz, 2H, CH), 7.11 (d, J=8.0 Hz, 2H, CH), 7.24 (d, J=8.4 Hz, 2H, CH), 7.27-7.41 (m, 10H, CH), 7.59 (d, J=8.4 Hz, 2H, CH), 7.82 (d, J=8.4 Hz, 1H, CH), 8.30 (d, J=8.8 Hz, 2H, CH); $\delta_C$ (100 MHz, CDCl$_3$) 21.4, 32.9, 35.8, 41.9, 48.1, 51.3, 52.7, 66.9, 70.6, 109.4, 113.9, 119.9, 120.6, 126.9, 127.0, 127.4, 127.9, 128.1, 128.2, 128.4, 128.5, 128.9, 129.4, 133.0, 134.4, 135.2, 135.6, 135.7, 143.2, 144.9, 145.5, 157.6, 158.6, 161.4, 165.2, 166.7; LRMS (ES+) calcd for [C$_{47}$H$_{47}$N$_5$O$_6$S+H] 810.33 found 810.44.

31. Preparation of benzyl 2-(benzyloxy)-4-(N-(4-(1-(4-cyanobenzoyl)piperidin-4-yl)benzyl)-2-(N,4-dimethylphenylsulfonamido)acetamido)benzoate (24).

Condensation of 21 with 4-cyanobenzoic acid on a 0.10 mmol scale via General Procedure F furnished 24 (63 mg, 89%): $\delta_H$ (400 MHz, CDCl$_3$) 1.59-1.72 (m, 4H, CH$_2$), 1.83-1.94 (m, 2H, CH$_2$), 2.39 (s, 3H, CH$_3$), 2.79-3.21 (m, 8H, CH$_3$, CH and CH$_2$), 3.65 (s, 2H, CH$_2$), 4.77 (s, 2H, CH$_2$), 4.95 (s, 2H, CH$_2$), 4.97 (s, 2H, CH$_2$), 5.34 (s, 2H, CH$_2$), 6.60 (t, J=8.4 Hz, 1H, CH), 6.69 (dd, J=8.0 and 1.6 Hz, 1H, CH), 7.03-7.12 (m, 4H, 4 CH (Ar)), 7.21-7.82 (m, 12H, 12 CH (Ar)); $\delta_C$ (100 MHz, CDCl$_3$) 21.4, 29.5, 35.9, 42.0, 48.1, 51.3, 52.7, 66.9, 70.6, 113.3, 113.9, 119.9, 120.7, 126.7, 126.9, 127.3, 127.4, 127.9, 128.1 (2), 128.4, 128.5, 129.0, 129.4, 132.3, 132.9, 134.8, 135.0, 135.5, 135.6, 140.0, 143.3, 144.0, 144.8, 158.6, 165.2, 167.0, 168.3; LRMS (ES+) calcd for [C$_{51}$H$_{48}$N$_4$O$_7$S+H] 861.33 found 861.38.

32. Preparation of benzyl 2-(benzyloxy)-4-(N-(4-(1-((4-cyanophenyl)sulfonyl)piperidin-4-yl)benzyl)-2-(N,4-dimethylphenylsulfonamido)acetamido)benzoate (25).

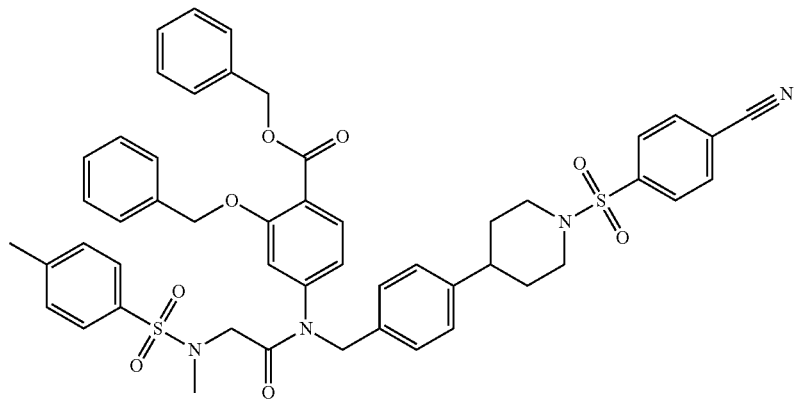 [SMILES: Cc1ccc(S(=O)(=O)N(C)CC(=O)N(Cc2ccc(C3CCN(S(=O)(=O)c4ccc(C#N)cc4)CC3)cc2)c2ccc(C(=O)OCc3ccccc3)c(OCc3ccccc3)c2)cc1]

Sulfonylation of secondary amine 21 with 4-cyano-benzene-1-sulfonyl chloride on a 0.08 mmol scale via General Procedure F furnished 25 (77 mgs, 99%): $\delta_H$ (400 MHz, CDCl$_3$) 1.72-1.91 (m, 4H, CH$_2$), 2.31-2.45 (m, 7H, CH$_3$ and 2CH$_2$), 2.80 (s, 3H, CH$_3$), 3.62 (s, 2H, CH$_2$), 3.89-3.99 (m, 2H, CH$_2$), 4.74 (s, 2H, CH$_2$), 5.01 (s, 2H, CH$_2$), 5.34 (s, 2H, CH$_2$), 6.60 (t, J=8.4 Hz, 1H, CH), 6.69 (dd, J=8.0 and 1.6 Hz, 1H, CH), 6.99-7.09 (m, 4H, 4 CH (Ar)), 7.21-7.91 (m, 12H, 12 CH (Ar)); $\delta_C$ (100 MHz, CDCl$_3$) 21.3, 29.5, 32.3, 35.9, 40.8, 41.1, 46.5, 51.3, 52.6, 66.9, 70.6, 113.9, 116.3, 117.1 119.9, 120.6, 126.6, 126.9, 127.3, 127.9, 128.0, 128.1 (2), 128.4, 128.5, 129.0, 129.3, 132.7, 132.9, 134.9, 135.1, 135.5, 135.6, 140.7, 143.2, 143.8, 144.9, 158.6, 165.2, 166.8; LRMS (ES+) calcd for [C$_{50}$H$_{48}$N$_4$O$_8$S$_2$+Na] 919.28 found 919.40.

33. Preparation of benzyl 2-(benzyloxy)-4-(N-(4-(1-(4-(tert-butoxycarbonyl)phenyl)piperidin-4-yl)benzyl)-2-(N,4-dimethylphenylsulfonamido)acetamido)benzoate (26).

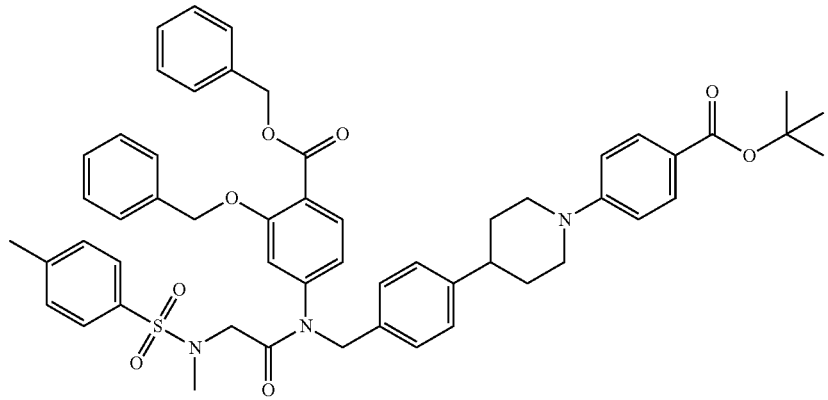 [SMILES: Cc1ccc(S(=O)(=O)N(C)CC(=O)N(Cc2ccc(C3CCN(c4ccc(C(=O)OC(C)(C)C)cc4)CC3)cc2)c2ccc(C(=O)OCc3ccccc3)c(OCc3ccccc3)c2)cc1]

Nucleophilic aromatic substitution of 21 with tert-butyl 4-fluorobenzoate on a 0.11 mmol scale via General Procedure D furnished 26 (113 mg, 98%): $\delta_H$ (400 MHz, CDCl$_3$) 1.57 (s, 9H, 3CH$_3$), 1.72-1.84 (m, 2H, CH$_2$), 1.86-1.96 (m, 2H, CH$_2$), 2.39 (s, 3H, CH$_3$), 2.64-2.75 (m, 1H, CH), 2.81 (s, 3H, CH$_3$), 2.91 (t, J=10.4 Hz, 2H, CH$_2$), 3.66 (s, 2H, CH$_2$), 3.93 (d, J=12.8 Hz, 2H, CH$_2$), 4.77 (s, 2H, CH$_2$), 4.98 (s, 2H, CH$_2$), 5.35 (s, 2H, CH$_2$), 6.57 (s, 1H, CH), 6.67 (d, J=8.0 Hz, 1H, CH), 6.88 (d, J=8.8 Hz, 2H, CH), 7.06 (d, J=8.0 Hz, 2H, CH), 7.12 (d, J=8.0 Hz, 2H, CH), 7.24 (d, J=7.6 Hz, 2H, CH), 7.29-7.39 (m, 10H, CH), 7.60 (d, J=8.0 Hz, 2H, CH), 7.83 (d, J=8.4 Hz, 1H, CH), 7.88 (d, J=8.8 Hz, 2H, CH); $\delta_C$ (100 MHz, CDCl$_3$) 21.4, 28.2, 32.6, 35.9, 42.1, 48.7, 51.3, 52.7, 66.9, 70.6, 79.9, 113.8, 114.0, 119.8, 120.3, 121.2, 126.8, 127.0, 127.4, 128.0, 128.1, 128.2, 128.4, 128.5, 129.0, 129.4, 130.9, 133.0, 134.5, 135.3, 135.6, 135.7, 143.2, 144.8, 145.2, 153.8, 158.6, 165.3, 165.9, 166.8.

34. Preparation of 4-(4-(4-((N-(4-((benzyloxy)carbonyl)-3-hydroxyphenyl)-2-(N,4-dimethylphenylsulfon-amido)acetamido)methyl)phenyl)piperidin-1-yl)benzoic acid (27).

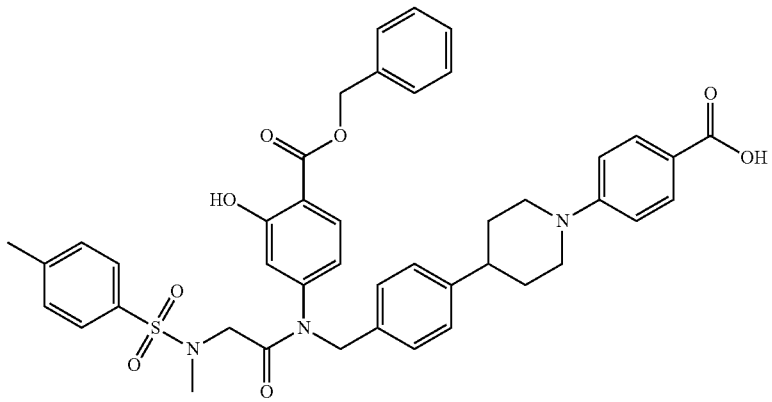 [SMILES: Cc1ccc(S(=O)(=O)N(C)CC(=O)N(Cc2ccc(C3CCN(c4ccc(C(=O)O)cc4)CC3)cc2)c2ccc(C(=O)OCc3ccccc3)c(O)c2)cc1]

t-Butyl ester 26 (0.14 mmol) was dissolved in a 1:1 mixture of TFA:toluene (2.8 ml) and stirred at rt for 4 h. All solvents were subsequently evaporated, and the crude product passed through a short pad of silica gel (CH$_2$Cl$_2$) to furnish 27 (130 mg, 95%): $\delta_H$ (400 MHz, CDCl$_3$) 1.73-1.85 (m, 2H, CH$_2$), 1.90-1.98 (m, 2H, CH$_2$), 2.40 (s, 3H, CH$_3$), 2.68-2.78 (m, 1H, CH), 2.86 (s, 3H, CH$_3$), 2.98 (t, J=12.0 Hz, 2H, CH$_2$), 3.82 (s, 2H, CH$_2$), 4.02 (d, J=12.8 Hz, 2H, CH$_2$), 4.80 (s, 2H, CH$_2$), 5.28 (s, 2H, CH$_2$), 5.39 (s, 2H, CH$_2$), 6.56 (dd, J=8.4 and 1.6 Hz, 1H, CH), 6.67 (d, J=1.6 Hz, 1H, CH), 6.91 (d, J=8.8 Hz, 2H, CH), 7.08 (d, J=8.0 Hz, 2H, CH), 7.12 (d, J=8.0 Hz, 2H, CH), 7.26 (d, J=7.6 Hz, 2H, CH), 7.34-7.48 (m, 5H, CH), 7.64 (d, J=8.0 Hz, 2H, CH), 7.87 (d, J=8.4 Hz, 1H, CH), 7.98 (d, J=8.8 Hz, 2H, CH); $\delta_C$ (100 MHz, CDCl$_3$) 21.4, 32.5, 35.7, 42.0, 48.3, 51.4, 52.7, 53.3, 67.3, 112.2, 113.5, 116.8, 117.9, 119.0, 126.8, 127.4, 128.3, 128.6 (br), 129.4, 131.4, 131.9, 134.4, 134.8, 135.2, 143.3, 144.9, 147.2, 154.4, 162.4, 166.7, 169.1, 171.9.

35. Preparation of 4-(N-(4-(1-(4-carbamoylphenyl)piperidin-4-yl)benzyl)-2-(N,4-dimethylphenyl-sulfonamido)acetamido)-2-hydroxybenzoate (61).

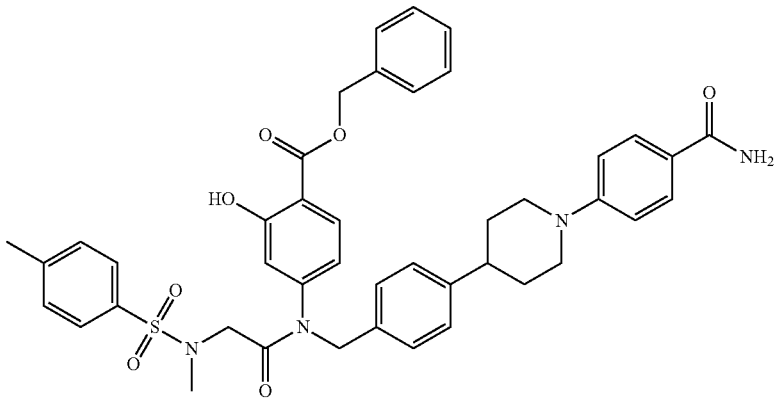 [SMILES: Cc1ccc(S(=O)(=O)N(C)CC(=O)N(Cc2ccc(C3CCN(c4ccc(C(N)=O)cc4)CC3)cc2)c2ccc(C(=O)OCc3ccccc3)c(O)c2)cc1]

Condensation of 26 with NH$_4$Cl on a 0.10 mmol scale via General Procedure F furnished 61 (58 mg, 98%): δ$_H$ (400 MHz, d-CDCl$_3$) 1.70-1.96 (m, 4H, CH$_2$), 2.39 (s, 3H, CH$_3$), 2.63-2.73 (m, 1H, CH), 2.85 (s, 3H, CH$_3$), 2.86-2.9 (m, 2H, CH$_2$), 3.80 (s, 2H, CH$_2$), 3.92-3.97 (m, 2H, CH$_2$), 4.79 (s, 2H, CH$_2$), 5.38 (s, 2H, CH$_2$), 6.56 (dd, J=8.4 and 2.0 Hz, 1H, CH), 6.67 (d, J=2.0 Hz, 1H, CH), 6.91 (d, J=8.4 Hz, 2H, CH), 7.03-7.14 (m, 4H, CH), 7.35-7.43 (m, 5H, CH), 7.63 (d, J=8.4 Hz, 2H, CH), 7.73 (d, J=7.6 Hz, 2H, CH), 7.86 (d, J=8.4 Hz, 1H, CH); δ$_C$ (100 MHz, d-CDCl$_3$) 21.4, 32.6, 35.7, 41.9, 48.7, 51.4, 52.7, 67.3, 112.2, 114.2, 116.8, 117.9, 118.9, 122.2, 126.8, 127.4, 128.3, 128.5, 128.6, 128.9, 129.4, 131.4, 134.4, 134.8, 135.2, 143.2, 145.0, 147.2, 153.6, 162.4, 166.6, 169.0; LRMS (ES+) Calcd for [C$_{43}$H$_{44}$N$_4$O$_7$S+Na] 783.28 found 783.34.

36. Preparation of Methyl 4'-((N-(3-(benzyloxy)-4-(benzyloxycarbonyl)phenyl)-2-(N,4-dimethylphenyl-sulfonamido)acetamido)methyl)biphenyl-3-carboxylate (28).

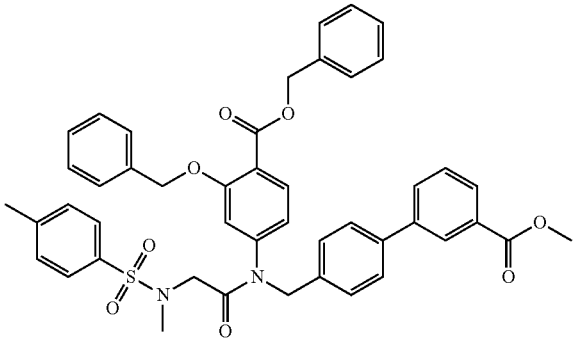

Aryl halide 9 was coupled to 3-(methoxycarbonyl)phenylboronic acid to give 28 on a 0.1 mmol scale via General Procedure H (65 mg, 62%): δ$_H$(400 MHz, CDCl$_3$) 2.40 (s, 3H, CH$_3$), 2.83 (s, 3H, CH$_3$), 3.68 (s, 2H, CH$_2$), 3.94 (s, 3H, CH$_3$), 4.84 (s, 2H, CH$_2$), 5.03 (s, 2H, CH$_2$), 5.35 (s, 2H, CH$_2$), 6.62 (s, 1H, CH), 6.68 (dd, J=8.0 and 1.6 Hz, 1H, CH), 7.19 (d, J=8.0 Hz, 2H, CH), 7.30-7.42 (m, 10H, CH), 7.52 (d, J=8.4 Hz, 2H, CH), 7.60-7.64 (m, 4H, CH), 7.78 (d, J=7.6 Hz, 2H, CH), 7.84 (d, 1H, J=8.0 Hz, CH), 8.02 (dt, J=8.0 and 1.2 Hz, 1H, CH), 8.25 (t, J=2.0 Hz, 1H, CH); δ$_C$ (100 MHz, CDCl$_3$) 21.5, 36.0, 52.2, 52.8, 56.0, 67.5, 70.7, 117.2, 117.5, 120.1, 125.2, 127.0, 127.2, 127.4, 127.5, 128.0, 128.1, 128.1, 128.2, 128.2, 128.5, 128.6, 128.9, 129.5, 130.7, 131.3, 133.2, 135.7, 135.7, 136.1, 139.5, 141.2, 142.4, 158.8, 161.7, 166.9, 167.0, 168.4; LRMS (ES+) calcd for [C$_{46}$H$_{42}$N$_2$O$_8$S+H] 783.27 found 783.26.

37. Preparation of benzyl 2-(benzyloxy)-4-(N-((3'-cyanobiphenyl-4-yl)methyl)-2-(N,4-dimethylphenyl-sulfonamido)acetamido)benzoate (29).

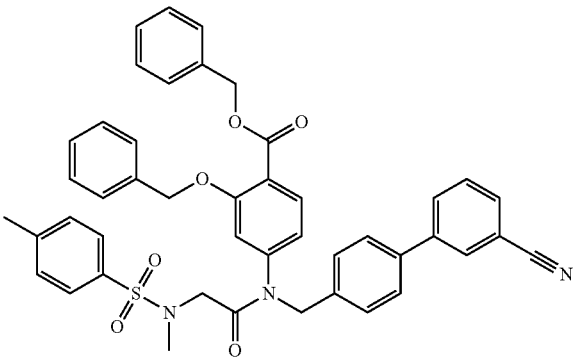 [SMILES: Cc1ccc(S(=O)(=O)N(C)CC(=O)N(Cc2ccc(-c3cccc(C#N)c3)cc2)c2ccc(C(=O)OCc3ccccc3)c(OCc3ccccc3)c2)cc1]

Aryl halide 9 was coupled to 3-cyanophenylboronic acid to give 29 on a 0.1 mmol scale via General Procedure H (58 mg, 60%): δ$_H$ (400 MHz, CDCl$_3$) 2.33 (s, 3H, CH$_3$), 2.76 (s, 3H, CH$_3$), 3.62 (s, 2H, CH$_2$), 4.78 (s, 2H, CH$_2$), 4.97 (s, 2H, CH$_2$), 5.28 (s, 2H, CH$_2$), 6.60-6.62 (m, 2H, CH), 7.14-7.28 (m, 12H, CH), 7.25-7.28 (m, 2H, CH), 7.38 (d, J=8.0 Hz, 2H, CH), 7.44-7.49 (m, 1H, CH), 7.54-7.57 (m, 3H, CH), 7.71 (dt, J=7.6 and 1.2 Hz, 1H, CH), 7.76 (s, 1H, CH), 7.78 (s, 1H, CH); δ$_C$ (100 MHz, CDCl$_3$) 21.4, 36.0, 51.4, 52.7, 67.0, 70.7, 112.9, 114.0, 118.6, 120.0, 120.9, 127.0, 127.1, 127.4, 128.0, 128.2, 128.2, 128.5, 128.6, 128.7, 129.5, 129.5, 129.6, 130.5, 130.8, 131.2, 133.1, 135.6, 135.7, 136.8, 138.2, 141.7, 143.3, 158.8, 165.2, 167.1, 167.7; LRMS (ES+) calcd for [C$_{45}$H$_{39}$N$_3$O$_6$S+H] 750.26 found 750.26.

38. Preparation of benzyl 2-(benzyloxy)-4-(N-((3'-carbamoylbiphenyl-4-yl)methyl)-2-(N,4-dimethyl phenylsulfonamido)acetamido)benzoate (30).

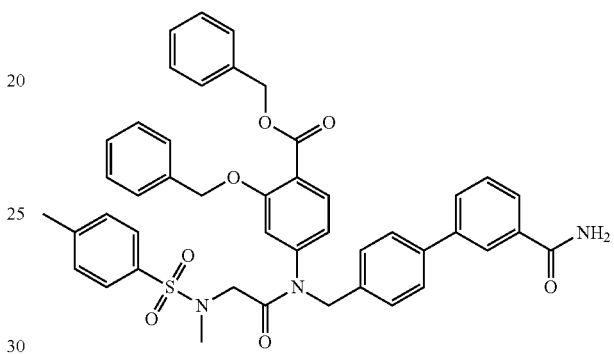

Aryl halide 9 was coupled to 3-carbamoylphenylboronic acid to give 30 on a 0.1 mmol scale via General Procedure H (57 mg, 52%): δ$_H$ (400 MHz, CDCl$_3$) 2.38 (s, 3H, CH$_3$), 2.81 (s, 3H, CH$_3$), 3.68 (s, 2H, CH$_2$), 4.83 (s, 2H, CH$_2$), 5.02 (s, 2H, CH$_2$), 5.34 (s, 2H, CH$_2$), 5.93 (s, 1H, NH$_2$), 6.33 (s, 2H, NH$_2$), 6.64 (s, 1H, CH), 6.67 (dd, J=6.0 and 1.2 Hz, 1H, CH), 7.18 (d, J=6.0 Hz, 2H, CH), 7.31-7.39 (m, 13H, CH), 7.50 (d, J=6.0 Hz, 2H, CH), 7.60 (d, J=6.3 Hz, 2H, CH), 7.70 (d, J=5.7 Hz, 1H, CH), 7.77 (d, J=5.7 Hz, 1H, CH), 7.83 (d, J=6.0 Hz, 1H, CH), 8.03 (s, 1H, CH); δ$_C$ (100 MHz, CDCl$_3$) 21.3, 35.9, 51.3, 52.7, 66.9, 70.6, 113.9, 119.2, 119.9, 126.0, 126.9, 127.0, 127.2, 127.3, 127.9, 128.1, 128.1, 128.4, 128.4, 128.7, 128.9, 129.2, 129.4, 130.3, 132.3, 133.0, 133.8, 135.1, 135.5, 135.6, 136.0, 139.4, 140.8, 143.3, 144.8, 158.7, 165.2, 167.0, 169.1; LRMS (ES+) calcd for [C$_{45}$H$_{41}$N$_3$O$_7$S+H] 768.27 found 768.27.

39. Preparation of methyl 4'-((N-(3-(benzyloxy)-4-(benzyloxycarbonyl)phenyl)-2-(N,4-dimethylphenyl-sulfonamido)acetamido)methyl)biphenyl-4-carboxylate (31).

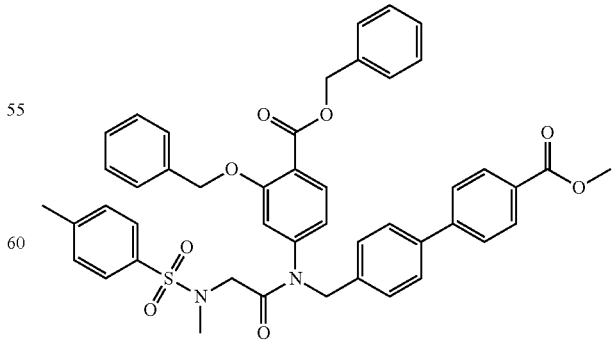

Aryl halide 9 was coupled to 4-(methoxycarbonyl)phenylboronic acid to give 31 on a 0.1 mmol scale via General Procedure H (53 mg, 52%): δ$_H$ (400 MHz, CDCl$_3$) 2.39 (s, 3H, CH$_3$), 2.82 (s, 3H, CH$_3$), 3.68 (s, 2H, CH$_2$), 3.93 (s, 3H, CH$_3$), 4.84 (s, 2H, CH$_2$), 5.03 (s, 2H, CH$_2$), 5.34 (s, 2H, CH$_2$), 6.64 (s, 1H, CH), 6.68 (dd, J=8.4 and 1.2 Hz, 1H, CH), 7.19 (d, J=8.0 Hz, 2H, CH), 7.23-7.34 (m, 8H, CH), 7.37-7.40 (m, 2H, CH), 7.50-7.54 (m, 3H, CH), 7.60 (d, J=8.0 Hz, 2H, CH), 7.22 (d, J=8.4 Hz, 2H, CH), 7.70 (dd, J=5.6 and 3.2 Hz, 1H, CH), 7.83 (d, J=8.0 Hz, 1H, CH) 8.09 (d, 2H, J=8.4 Hz, CH); δ$_C$ (100 MHz, CDCl$_3$) 21.4, 36.0, 51.4, 52.1, 52.8, 67.0, 70.7, 114.1, 120.0, 120.9, 126.8, 126.9, 127.3, 127.4, 128.0, 128.2, 128.2, 128.5, 128.6, 128.7, 129.0, 129.4, 129.5, 130.1, 132.4, 133.1, 135.3, 135.7, 135.7, 136.5, 139.3, 143.3, 144.8, 144.9, 158.8, 166.8, 167.0, 167.7; LRMS (ES+) calcd for [C$_{46}$H$_{42}$N$_2$O$_8$S+H] 783.27 found 783.26.

40. Preparation of 4'-((N-(3-(benzyloxy)-4-((benzyloxy) carbonyl)phenyl)-2-(N,4-dimethylphenylsulfonamido)acetamidomethyl)-[1,1'-biphenyl]-4-carboxylic acid (32).

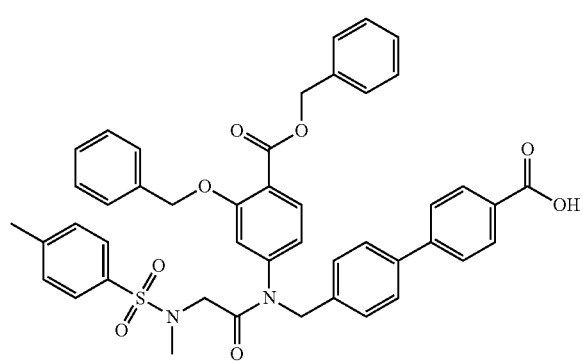 [SMILES: Cc1ccc(S(=O)(=O)N(C)CC(=O)N(Cc2ccc(-c3ccc(C(=O)O)cc3)cc2)c2ccc(C(=O)OCc3ccccc3)c(OCc3ccccc3)c2)cc1]

Aryl halide 9 was coupled to 4-carboxyphenylboronic acid to give 32 on a 0.1 mmol scale via General Procedure H. 32 was not purified at this stage and was deprotected without purification.

41. Preparation of benzyl 2-(benzyloxy)-4-(N-((4'-cyanobiphenyl-4-yl)methyl)-2-(N,4-dimethylphenyl-sulfonamido)acetamido)benzoate (33).

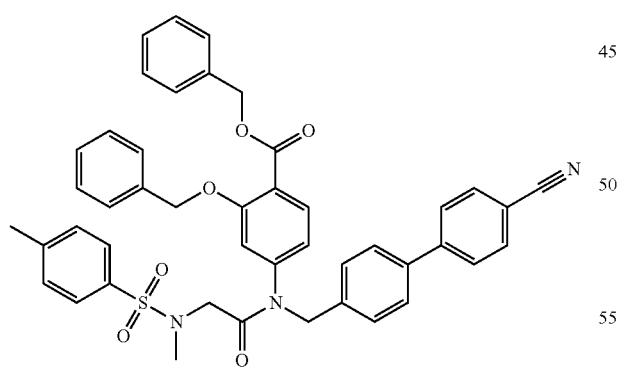

Aryl halide 9 was coupled to 4-cyanophenylboronic acid to give 33 on a 0.1 mmol scale via General Procedure H (73 mg, 71%): δ$_H$ (400 MHz, CDCl$_3$) 2.39 (s, 3H, CH$_3$), 2.82 (s, 3H, CH$_3$), 3.68 (s, 2H, CH$_2$), 4.85 (s, 2H, CH$_2$), 5.05 (s, 2H, CH$_2$), 5.35 (s, 2H, CH$_2$), 6.67 (s, 1H, CH), 6.69 (d, J=1.2 Hz, 1H, CH), 7.22-7.34 (m, 13H, CH), 7.38-7.40 (m, 2H, CH), 7.61 (d, J=8.0 Hz, 2H, CH), 7.64 (d, J=8.4 Hz, 2H, CH), 7.70-7.72 (m, 3H, CH), 7.84 (d, J=8.4 Hz, 1H, CH); δ$_C$ (100 MHz, CDCl$_3$) 21.4, 36.0, 51.4, 52.7, 67.0, 70.7, 111.0, 114.0, 118.7, 119.9, 120.8, 126.9, 127.3, 127.4, 127.5, 128.0, 128.2, 128.2, 128.5, 128.5, 128.7, 129.5, 130.8, 132.4, 132.5, 133.1, 135.6, 135.7, 137.1, 138.4, 143.3, 144.8, 158.8, 165.2, 167.1, 167.6; LRMS (ES+) calcd for [C$_{45}$H$_{39}$N$_3$O$_6$S+H] 750.26 found 750.26.

42. Preparation of benzyl 2-(benzyloxy)-4-(N-((4'-carbamoylbiphenyl-4-yl)methyl)-2-(N,4-dimethyl phenylsulfonamido)acetamido)benzoate (34).

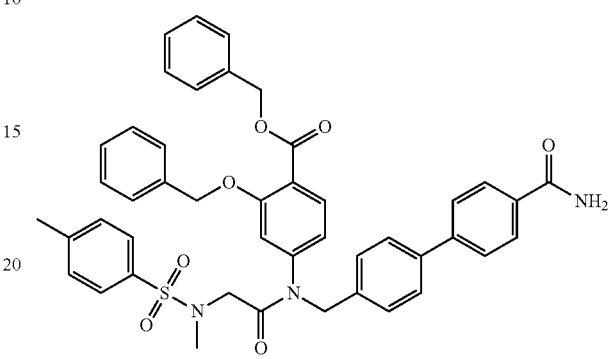

Aryl halide 9 was coupled to 4-carbamoylphenylboronic acid to give 34 on a 0.1 mmol scale via General Procedure H (62 mg, 49%): δ$_H$(400 MHz, CDCl$_3$) 2.38 (s, 3H, CH$_3$), 2.82 (s, 3H, CH$_3$), 3.68 (s, 2H, CH$_2$), 4.39 (s, 2H, CH$_2$), 5.03 (s, 2H, CH$_2$), 5.34 (s, 2H, CH$_2$), 5.91 (s, 1H, NH$_2$), 6.44 (s, 1H, NH), 6.65 (s, 1H, CH$_2$), 6.68 (d, 1H, CH), 7.19 (d, J=6.0 Hz, 2H, CH), 7.24-7.35 (m, 4H, CH), 7.38-7.41 (m, 2H, CH), 7.44-7.50 (m, 6H, CH), 7.53 (d, J=4.8 Hz, 1H, CH), 7.59 (s, 2H, CH), 7.61 (s, 2H, CH), 7.64 (d, J=5.4 Hz, 2H, CH), 7.68 (d, J=5.4 Hz, 2H, CH), 7.83 (d, J=6.3 Hz, 1H, CH), 7.89 (d, J=6.0 Hz, 2H, CH); δ$_C$ (100 MHz, CDCl$_3$) 21.3, 35.9, 51.3, 52.7, 66.9, 70.6, 113.9, 119.9, 120.8, 126.8, 126.9, 127.1, 127.3, 127.9, 128.1, 128.1, 128.3, 128.4, 128.4, 129.4, 131.8, 131.8, 131.8, 131.9, 132.0, 132.8, 133.0, 135.1, 135.5, 135.6, 136.3, 139.1, 143.2, 143.8, 144.8, 158.7, 165.2, 167.0, 168.8; LRMS (ES+) calcd for [C$_{45}$H$_{41}$N$_3$O$_7$S+H] 768.27 found 768.27.

43. Preparation of methyl 4'-((N-(3-(benzyloxy)-4-(benzyloxycarbonyl)phenyl)-2-(N,4-dimethylphenylsulfonamido)acetamido)methyl)terphenyl-3-carboxylate (35).

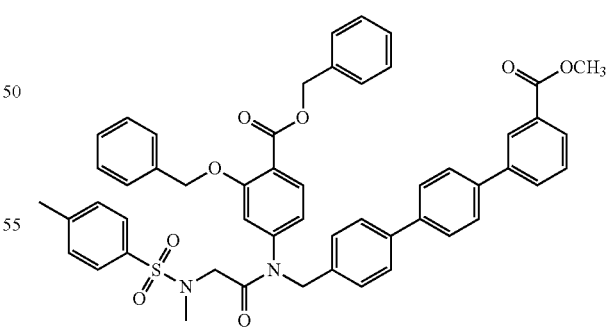

Aryl halide 5 was coupled to 3-(methoxycarbonyl)phenylboronic acid on a 0.1 mmol scale via General Procedure H to yield 35 (39 mg, 38%): δ$_H$ (400 MHz, CDCl$_3$) 2.40 (s, 3H, CH$_3$), 2.83 (s, 3H, CH$_3$), 3.68 (s, 2H, CH$_2$), 3.96 (s, 3H, CH$_3$), 4.84 (s, 2H, CH$_2$), 5.02 (s, 2H, CH$_2$), 5.35 (s, 2H, CH$_2$), 6.62 (s, 1H, CH), 6.70 (d, J=8.0 Hz, 1H, CH) 7.19 (d, J=8.0 Hz, 2H, CH), 7.26-7.34 (m, 10H, CH), 7.38-7.41 (m, 3H, CH), 7.54 (d, J=8.0 Hz, 2H, CH), 7.62 (d, J=8.4 Hz, 2H, CH), 7.68 (q, J=8.0 Hz, 4H, CH), 7.84 (t, J=8.0 Hz, 2H, CH), 8.03 (d, J=8.0 Hz, 1H, CH), 8.32 (s, 1H, CH); LRMS (ES+) Calcd for [C$_{52}$H$_{46}$N$_2$O$_8$S+H] 859.31 found 859.25.

44. Preparation of 4'-((N-(3-(benzyloxy)-4-(benzyloxycarbonyl)phenyl)-2-(N,4-dimethylphenylsulfon-amido)acetamido)methyl)terphenyl-3-carboxylic acid (36).

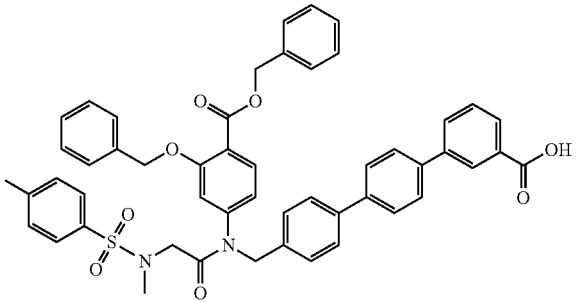 [SMILES: Cc1ccc(S(=O)(=O)N(C)CC(=O)N(Cc2ccc(-c3ccc(-c4cccc(C(=O)O)c4)cc3)cc2)c2ccc(C(=O)OCc3ccccc3)c(OCc3ccccc3)c2)cc1]

Aryl halide 5 was coupled to 3-carboxyphenylboronic acid on a 0.1 mmol scale via General Procedure H to yield 36 (76 mg, 64%): δ$_H$ (400 MHz, CDCl$_3$) 2.33 (s, 3H, CH$_3$), 2.78 (s, 3H, CH$_3$), 3.65 (s, 2H, CH$_2$), 4.80 (s, 2H, CH$_2$), 4.80 (s, 2H, CH$_2$), 5.30 (s, 2H, CH$_2$), 6.60 (s, 1H, CH), 6.66 (d, J=8.4 Hz, 2H, CH), 7.15 (d, J=8.0 Hz, 2H, CH), 7.13-7.28 (m, 12H, CH), 7.30-7.38 (m, 3H, CH), 7.50 (d, J=7.2 Hz, 2H, CH), 7.47-7.63 (m, 6H, CH), 7.90 (d, J=8.0 Hz, 2H, CH); LRMS (ES+) calcd for [C$_{51}$H$_{44}$N$_2$O$_8$S+H] 845.29 found 845.15.

45. Preparation of benzyl 2-(benzyloxy)-4-(N-((3'-cyanoterphenyl-4-yl)methyl)-2-(N,4-dimethylphenylsulfonamido)acetamido)benzoate (37).

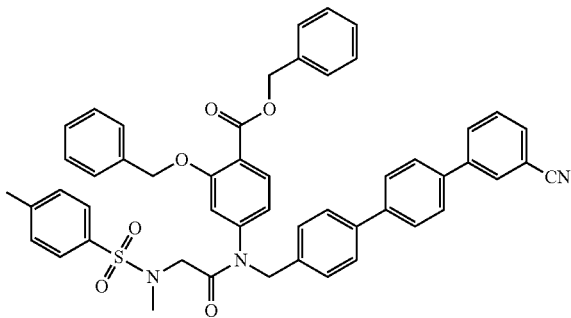 [SMILES: Cc1ccc(S(=O)(=O)N(C)CC(=O)N(Cc2ccc(-c3ccc(-c4cccc(C#N)c4)cc3)cc2)c2ccc(C(=O)OCc3ccccc3)c(OCc3ccccc3)c2)cc1]

Aryl halide 5 was coupled to 3-cyanophenylboronic acid on a 0.1 mmol scale via General Procedure H to yield 37 (59 mg, 56%): δ$_H$ (400 MHz, CDCl$_3$) 2.38 (s, 3H, CH$_3$), 2.83 (s, 3H, CH$_3$), 3.69 (s, 2H, CH$_2$), 4.85 (s, 2H, CH$_2$), 5.03 (s, 2H, CH$_2$), 5.34 (s, 2H, CH$_2$), 6.65 (s, 1H, CH), 6.70 (d, J=8.0 Hz, 1H, CH), 7.20 (d, J=8.0 Hz, 2H, CH), 7.23 (t, J=8.4 Hz, 4H, CH), 7.30-7.34 (m, 6H, CH), 7.38-7.40 (m, 3H, CH), 7.50 (d, J=8.4 Hz, 2H, CH), 7.60-7.63 (m, 5H, CH), 7.67 (d, J=8.4 Hz, 2H, CH), 7.81 (d, J=8.0 Hz, 2H, CH), 7.86 (s, 1H, CH). LRMS (ES+) calcd for [C$_{51}$H$_{43}$N$_3$O$_6$S+H] 848.28 found 848.45.

Preparation of benzyl 2-(benzyloxy)-4-(N-((3''-carbamoyl-[1,1':4',1''-terphenyl]-4-yl)methyl)-2-(N,4-dimethylphenylsulfonamido)acetamido)benzoate (38).

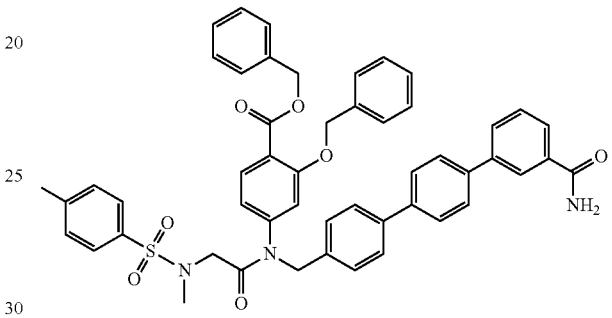

Aryl halide 5 was coupled to 3-carbamoylphenylboronic acid on a 0.1 mmol scale via General Procedure H to give 38 (38 mg, 32%): δ$_H$ (400 MHz, CDCl$_3$) 2.39 (s, 3H, CH$_3$), 2.83 (s, 3H, CH$_3$), 3.69 (s, 2H, CH$_2$), 4.84 (s, 2H, CH$_2$), 5.03 (s, 2H, CH$_2$), 5.35 (s, 2H, CH$_2$), 6.63 (s, 1H, CH), 6.70 (d, J=8.8 Hz, 1H, CH), 7.19 (d, J=8.0 Hz, 2H, CH), 7.30-7.36 (m, 10H, CH), 7.38-7.41 (m, 3H, CH), 7.54 (d, J=8.0 Hz, 2H, CH), 7.62 (d, J=8.0 Hz, 2H, CH), 7.67 (q, J=7.2 Hz, 4H, CH), 7.79 (t, 2H, J=7.6 Hz, CH), 7.85 (d, J=8.0 Hz, 1H, CH), 8.12 (s, 1H, CH). LRMS (ES+) Calcd for [C$_{51}$H$_{45}$N$_3$O$_7$S+Na] 866.29 found 866.51.

46. Preparation of methyl 4'-((N-(3-(benzyloxy)-4-(benzyloxycarbonyl)phenyl)-2-(N,4-dimethylphenylsulfonamido)acetamido)methyl)terphenyl-4-carboxylate (39).

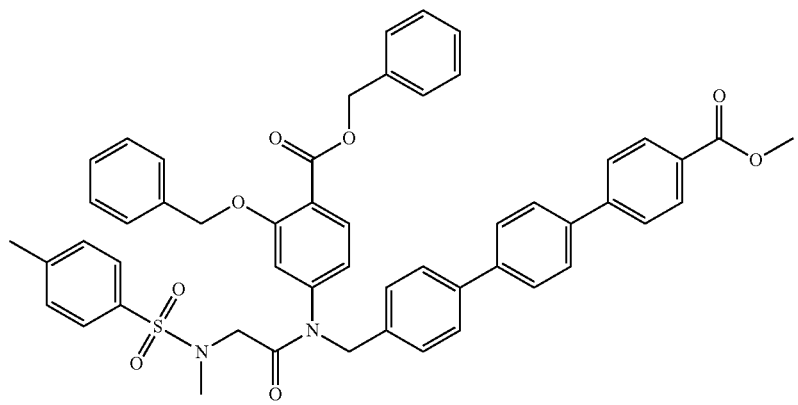

Aryl halide 5 was coupled to 4-(methoxycarbonyl)phenylboronic acid to give 39 on a 0.1 mmol scale via General Procedure H (59 mg, 47%): δ$_H$ (400 MHz, CDCl$_3$) 2.38 (s, 3H, CH$_3$), 2.83 (s, 3H, CH$_3$), 3.69 (s, 2H, CH$_2$), 3.93 (s, 3H, CH$_3$), 4.84 (s, 2H, CH$_2$), 5.02 (s, 2H, CH$_2$), 5.35 (s, 2H, CH$_2$), 6.64 (s, 1H, CH), 6.70 (dd, J=8.4 and 1.6 Hz, 1H, CH), 7.20 (d, J=8.0 Hz, 2H, CH), 7.24-7.28 (m, 6H, CH), 7.30-7.33 (m, 5H, CH), 7.36-7.41 (m, 3H, CH), 7.54 (d, J=8.4 Hz, 2H, CH), 7.61 (d, J=8.4 Hz, 2H, CH), 7.64-7.73 (m, 6H, CH), 7.85 (d, J=8.4 Hz, 1H, CH). LRMS (ES+) calcd for [C$_{52}$H$_{46}$N$_2$O$_8$S+H] 881.29, found 881.39.

47. Preparation of 4'-((N-(3-(benzyloxy)-4-(benzyloxycarbonyl)phenyl)-2-(N,4-dimethylphenyl-sulfonamido)acetamido)methyl)terphenyl-4-carboxylic acid (40).

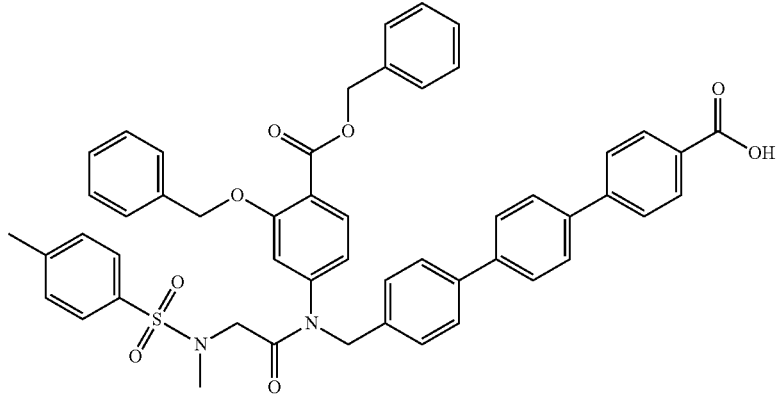 [SMILES: Cc1ccc(S(=O)(=O)N(C)CC(=O)N(Cc2ccc(-c3ccc(-c4ccc(C(=O)O)cc4)cc3)cc2)c2ccc(C(=O)OCc3ccccc3)c(OCc3ccccc3)c2)cc1]

Aryl halide 5 was coupled to 4-carboxyphenylboronic acid to give 40 on a 0.1 mmol scale via General Procedure H (47 mg, 47%): δ$_H$ (400 MHz, CDCl$_3$) 2.40 (s, 3H, CH$_3$), 2.84 (s, 2H, CH$_2$), 3.70 (s, 2H, CH$_2$), 4.86 (s, 2H, CH$_2$), 5.04 (s, 2H, CH$_2$), 5.36 (s, 2H, CH$_2$), 6.65 (s, 1H, CH), 6.71 (d, J=8.4 Hz, 1H, CH), 7.21 (d, J=8.0 Hz, 2H, CH), 7.27-7.43 (m, 12H, CH), 7.39-7.41 (m, 3H, CH), 7.55 (d, J=8.4 Hz, 2H, CH), 7.63 (d, J=8.0 Hz, 2H, CH), 7.67-7.75 (m, 4H, CH), 7.86 (d, J=8.0 Hz, 1H, CH), 8.20 (d, J=7.6 Hz, 1H, CH); LRMS (ES+) calcd for [C$_{51}$H$_{44}$N$_2$O$_8$S+H] 845.29 found 845.35.

48. Preparation of benzyl 2-(benzyloxy)-4-(N-((4'-cyanoterphenyl-4-yl)methyl)-2-(N,4-dimethylphenylsulfonamido)acetamido)benzoate (41).

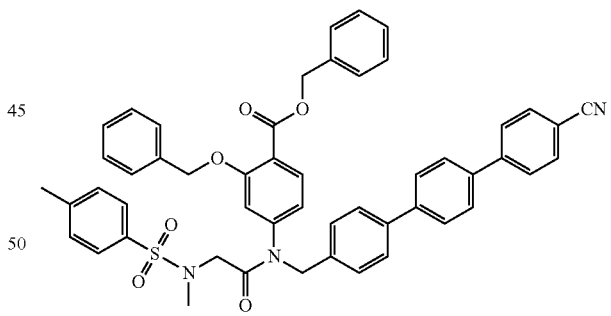

Aryl halide 5 was coupled to 4-cyanophenylboronic acid to give 41 on a 0.1 mmol scale via General Procedure H (32 mg, 30%): δ$_H$ (400 MHz, CDCl$_3$) 2.36 (s, 3H, CH$_3$), 2.79 (s, 3H, CH$_3$), 3.65 (s, 2H, CH$_2$), 4.81 (s, 2H, CH$_2$), 6.00 (s, 2H, CH$_2$), 5.31 (s, 2H, CH$_2$), 6.61 (s, 1H, CH), 6.66 (d, J=8.4 Hz, 1H, CH), 7.17 (d, J=8.4 Hz, 2H, CH), 7.23 (t, J=8.0 Hz, 4H, CH), 7.30-7.33 (m, 5H, CH), 7.36-7.40 (m, 3H, CH), 7.70 (d, J=8.0 Hz, 2H, CH), 7.58 (d, J=8.0 Hz, 2H, CH), 7.66-7.73 (m, 8H, CH), 7.81 (d, J=8.4 Hz, 1H, CH). LRMS (ES+) calcd for [C$_{51}$H$_{44}$N$_3$O$_6$S+H] 848.28 found 848.35.

49. Preparation of benzyl 2-(benzyloxy)-4-(N-((4'-carbamoylterphenyl-4-yl)methyl)-2-(N,4-dimethylphenylsulfonamido)acetamido)benzoate (42).

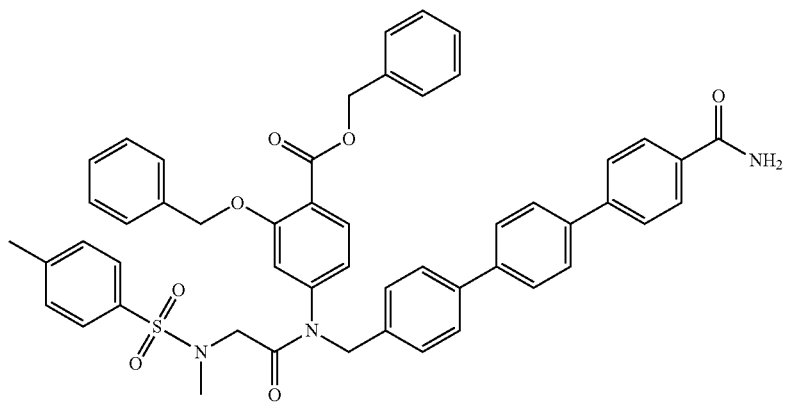 [SMILES: Cc1ccc(S(=O)(=O)N(C)CC(=O)N(Cc2ccc(-c3ccc(-c4ccc(C(N)=O)cc4)cc3)cc2)c2ccc(C(=O)OCc3ccccc3)c(OCc3ccccc3)c2)cc1]

Aryl halide 5 was coupled to 4-carbamoylphenylboronic acid to give 42 on a 0.1 mmol scale via General Procedure H (31 mg, 28%): $\delta_H$ (400 MHz, CDCl$_3$) 2.40 (s, 3H, CH$_3$), 2.83 (s, 3H, CH$_3$), 3.69 (s, 2H, CH$_2$), 4.58 (s, 2H, CH$_2$), 5.04 (s, 2H, CH$_2$), 5.36 (s, 2H, CH$_2$), 6.64 (s, 1H, CH), 6.70 (d, J=7.6 Hz, 1H, CH), 7.21 (d, J=8.0 Hz, CH), 7.24-7.29 (m, 5H, CH), 7.31-7.36 (m, 5H, CH), 7.38-7.42 (m, 2H, CH), 7.54 (d, J=8.4 Hz, 2H, CH), 7.62 (d, J=8.4 Hz, 2H, CH), 7.65-7.76 (m, 8H, CH), 7.85 (d, J=8.0 Hz, 1H, CH). LRMS (ES+) calcd for [C$_{51}$H$_{45}$N$_3$O$_7$S+Na] 866.29 found 866.32.

50. Preparation of tert-butyl 2-(2,2,2-trifluoro-N-methyl-acetamido)acetate (43).

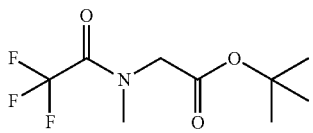 [SMILES: CN(CC(=O)OC(C)(C)C)C(=O)C(F)(F)F]

To a stirred solution of tert-butyl 2-(methylamino)acetate (2.00 g, 11 mmol) and DIPEA (3.65 g (4.80 ml), 27.5 mmol) in CHCl$_3$ (0.1 M) was added triflic anhydride (2.54 g, 12.1 mmol). The solution was allowed to stir at rt for 3 hr before quenching with water and extraction into CH$_2$Cl$_2$. The combined organic layers were washed with water and brine, dried over Na$_2$SO$_4$ and the solution concentrated under reduced pressure to give 43 (1.44 g, 88%): $\delta_H$ (400 MHz, d-CDCl$_3$) 1.46 (s, 9H, 3 CH$_3$), 3.08 (s, 1H, CH$_3$), 3.18 (s, 2H, CH$_3$), 4.04 (s, 2H, CH$_2$).

51. Preparation of 2-(2,2,2-trifluoro-N-methylacetamido) acetic acid (44).

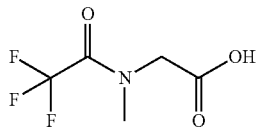

tert-Butyl ester 46 (2.00 g, 11.0 mmol) was dissolved in a TFA:CH$_2$Cl$_2$ (1:1) solution (0.1 M) and allowed to stir for 5 hrs at rt. The product was then concentrated under reduced pressure to yield pure compound 44 (2.50 g, 95%): $\delta_H$(400 MHz, CDCl$_3$) 3.22 (s, 3H, CH$_3$), 4.19 (s, 2H, CH$_2$).

52. Preparation of benzyl 2-(benzyloxy)-4-(N-(4-cyclo-hexylbenzyl)-2-(2,2,2-trifluoro-N-methylacetamido)acet-amido)benzoate (45).

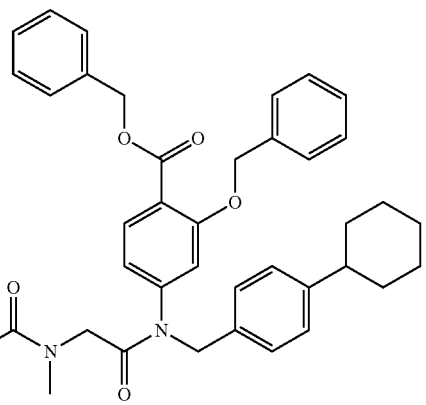

Secondary aniline 4 was coupled to carboxylic acid 44 on a 3.17 mmol scale via General Procedure B to furnish 45 (2.07 g, 97%): $\delta_H$ (400 MHz, CDCl$_3$) 1.35-1.44 (m, 5H, [Cy] CH$_2$), 1.71-1.90 (m, 6H, [Cy] CH$_2$), 3.17 (s, 3H, CH$_3$), 3.79 (s, 2H, CH$_2$), 4.84 (s, 2H, CH$_2$), 4.97 (s, 2H, CH$_2$), 5.35 (s, 2H, CH$_2$), 6.65 (s, 1H, CH), 6.78 (dd, J=8.4 and 1.6 Hz, 1H, CH), 7.10-7.19 (m, 4H, CH), 7.29-7.43 (m, 10H, CH), 7.86 (d, J=8.4 Hz, 1H, CH); $\delta_C$ (100 MHz, CDCl$_3$) 25.8, 26.6, 34.2, 44.0, 51.2, 52.6, 66.7, 70.4, 77.2, 113.9, 115.0, 117.6, 119.8, 126.8, 126.9, 127.7, 128.0, 128.3, 128.3, 128.4, 128.6, 132.9, 133.6, 135.5, 135.6, 144.6, 147.5, 157.0, 158.4, 165.1, 165.4; LRMS (ES+) calcd for [C$_{39}$H$_{39}$F$_3$N$_2$O$_5$+Na] 695.27 found 695.36.

53. Preparation of benzyl 2-(benzyloxy)-4-(N-(4-cyclo-hexylbenzyl)-2-(methylamino)-acetamido)benzoate (46).

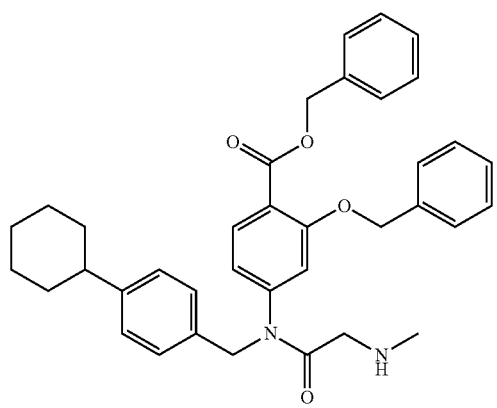 [SMILES: CNCC(=O)N(Cc1ccc(C2CCCCC2)cc1)c1ccc(C(=O)OCc2ccccc2)c(OCc2ccccc2)c1]

Compound 45 (2.68 mmol) was dissolved in a THF:H$_2$O (3:1) solution and treated with LiOH.H$_2$O (337 mg, 8.04 mmol). After 10 min the reaction was completed and diluted with H$_2$O. The product was extracted into EtOAc and the combined extracts washed with 50% sat. NaHCO$_3$, water, brine and dried over Na$_2$SO$_4$ and concentrated under reduced pressure to yield 46 (1.57 g, 99%): δ$_H$ (400 MHz, CDCl$_3$) 1.35 (m, 5H, [Cy] CH$_2$), 1.66-1.84 (m, 5H, [Cy] CH$_2$), 2.28 (s, 2H, CH$_3$), 2.44 (m, 1H, [Cy] CH), 3.02 (s, 2H, CH$_2$), 4.81 (s, 2H, CH$_2$), 4.89 (s, 2H, CH$_2$), 5.30 (s, 2H, CH$_2$), 6.52 (s, 1H, CH), 6.54 (d, 1H, J=8.0 Hz, CH), 7.05-7.13 (m, 4H, CH), 7.24-7.37 (m, 12H, CH), 7.80 (d, J=8.0 Hz, 1H, CH); δ$_C$ (100 MHz, CDCl$_3$) 25.6, 26.3, 34.0, 35.4, 43.7, 52.0, 52.2, 66.4, 70.0, 77.2, 113.6, 119.6, 119.9, 126.4, 126.6, 127.5, 127.6, 127.7, 128.0, 128.1, 128.3, 132.5, 133.9, 135.3, 135.43, 145.0, 147.0, 158.1, 164.8, 169.6; LRMS (ES+) calcd for [C$_{37}$H$_{40}$N$_2$O$_4$+H] 577.31 found 577.45.

54. Preparation of benzyl 2-(benzyloxy)-4-(N-(4-cyclohexylbenzyl)-2-(N,3-dimethylphenylsulfonamido)acetamido)benzoate (47).

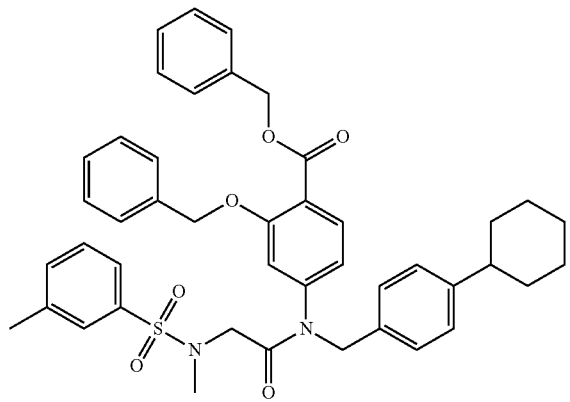 [SMILES: Cc1cccc(S(=O)(=O)N(C)CC(=O)N(Cc2ccc(C3CCCCC3)cc2)c2ccc(C(=O)OCc3ccccc3)c(OCc3ccccc3)c2)c1]

Secondary amine 46 was coupled to 3-methylbenzene-1-sulfonyl chloride on a 0.2 mmol scale via General Procedure G to furnish 47 (116 mg, 94%): δ$_H$ (400 MHz, CDCl$_3$) 1.31-1.44 (m, 5H, CH), 1.70-1.89 (m, 5H, CH), 2.36 (s, 3H, CH$_3$), 2.42-2.52 (m, 1H, CH), 2.83 (s, 3H, CH$_3$), 3.65 (s, 2H, CH$_2$), 4.77 (s, 2H, CH$_2$), 4.96 (s, 2H, CH$_2$), 5.35 (s, 2H, CH$_2$), 6.52 (s, 1H, CH), 6.69 (dd, J=8.0 and 1.2 Hz, 1H, CH), 7.03 (d, J=8.0 Hz, 2H, CH), 7.11 (d, J=8.0 Hz, 2H, CH), 7.27-7.42 (m, 12H, CH), 7.50-7.55 (m, 2H, CH), 7.84 (d, J=8.0 Hz, 1H, CH); δ$_C$ (100 MHz, CDCl$_3$) 21.2, 25.9, 26.7, 29.6, 34.2, 34.3, 35.9, 44.1, 51.3, 52.7, 66.9, 70.6, 114.2, 120.0, 120.6, 124.4, 126.9, 127.0, 127.6, 127.9, 128.1, 128.2, 128.4, 128.5, 128.8, 128.9, 133.0, 133.3, 133.8, 135.6, 135.7, 138.0, 138.9, 145.0, 147.6, 158.6, 165.3, 166.6; LRMS (ES+) calcd for [C$_{44}$H$_{46}$N$_2$O$_6$S+Na] 753.30 found 753.18.

55. Preparation of benzyl 2-(benzyloxy)-4-(N-(4-cyclohexylbenzyl)-2-(N,2,4,6-tetramethylphenylsulfonamido)acetamido)benzoate (48).

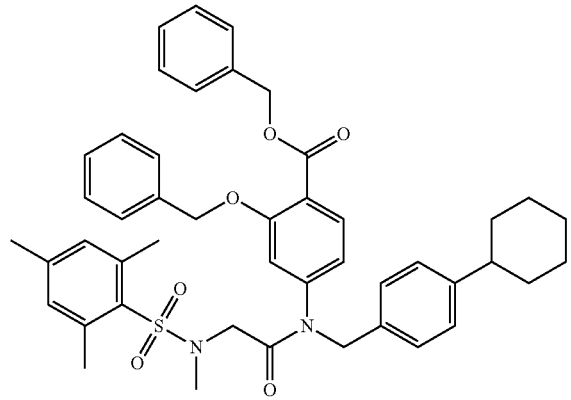 [SMILES: Cc1cc(C)c(S(=O)(=O)N(C)CC(=O)N(Cc2ccc(C3CCCCC3)cc2)c2ccc(C(=O)OCc3ccccc3)c(OCc3ccccc3)c2)c(C)c1]

Secondary amine 46 was coupled with 2,4,6-trimethylbenzenesulfonyl chloride on a 0.1 mmol scale via General Procedure G to furnish 48 (48 mg, 74%): δ$_H$ (400 MHz, CDCl$_3$) 1.34-1.43 (m, 5H, CH), 1.70-1.87 (m, 5H, CH), 2.29 (s, 3H, CH$_3$), 2.42-2.52 (m, 1H, CH), 2.56 (s, 6H, CH$_3$), 2.79 (s, 3H, CH$_3$), 3.67 (s, 2H, CH$_2$), 4.75 (s, 2H, CH$_2$), 4.90 (s, 2H, CH$_2$), 5.35 (s, 2H, CH$_2$), 6.43 (s, 1H, CH), 6.55 (dd, J=8.0 and 1.6 Hz, 1H, CH), 6.93 (s, 2H, CH), 7.00 (d, J=8.0 Hz, 2H, CH), 7.10 (d, J=8.0 Hz, 2H, CH), 7.29-7.42 (m, 10H, CH), 7.81 (d, J=8.0 Hz, 1H, CH); δ$_C$ (100 MHz, CDCl$_3$) 20.9, 22.7, 26.0, 26.7, 34.4, 34.7, 44.1, 49.6, 52.6, 69.9, 70.6, 113.9, 120.0, 120.8, 126.9, 127.0, 128.0, 128.1, 128.2, 128.5, 128.5, 128.8, 131.8, 133.1, 134.0, 135.6, 135.7, 140.5, 142.4, 147.6, 158.7, 165.3, 166.7; LRMS (ES+) calcd for [C$_{46}$H$_{50}$N$_2$O$_6$S+Na] 781.33 found 781.39.

56. Preparation of benzyl 2-(benzyloxy)-4-(N-(4-cyclohexylbenzyl)-2-(N-methylbiphenyl-4-ylsulfonamido)acetamido)benzoate (49).

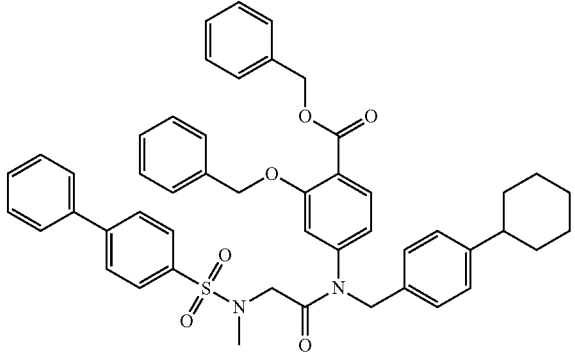 [SMILES: CN(CC(=O)N(Cc1ccc(C2CCCCC2)cc1)c1ccc(C(=O)OCc2ccccc2)c(OCc2ccccc2)c1)S(=O)(=O)c1ccc(-c2ccccc2)cc1]

Secondary amine 46 was combined with biphenyl-4-sulfonyl chloride on a 0.1 mmol scale via General Procedure G to furnish 49 (50 mg, 70%): δ$_H$ (400 MHz, CDCl$_3$) 1.32-1.41 (m, 5H, CH$_2$), 1.70-1.86 (m, 5H, CH$_2$), 2.38-2.52 (m, 1H, CH), 2.90 (s, 3H, CH$_3$), 3.72 (s, 2H, CH$_2$), 4.77 (s, 2H, CH$_2$), 4.97 (s, 2H, CH$_2$), 4.36 (s, 2H, CH$_2$), 6.53 (s, 1H, CH), 6.70 (dd, J=8.0 and 1.6 Hz, 1H, CH), 7.02 (d, J=8.0 Hz, 2H, CH), 7.09 (d, J=8.0 Hz, 2H, CH), 7.30-7.36 (m, 8H, CH), 7.38-7.42 (m, 2H, CH), 7.43-7.50 (m, 3H, CH), 7.60 (dt, J=7.2 and 1.6 Hz, 2H, CH), 7.68 (d, J=8.8 Hz, 2H, CH), 7.81 (d, J=8.4 Hz, 2H, CH), 7.86 (d, J=8.0 Hz, 1H, CH); δ$_C$ (100 MHz, CDCl$_3$) 26.0, 26.7, 34.3, 36.0, 44.1, 51.3, 52.8, 66.9, 70.6, 114.1, 120.0, 120.6, 126.9, 127.0, 127.2, 127.4, 127.9, 128.1, 128.2, 128.3, 128.5, 128.5, 128.8, 128.9, 132.0, 133.1, 138.8, 135.7, 135.7, 137.0, 139.3, 145.0, 145.3, 147.6, 158.7, 165.3, 166.7; LRMS (ES+) calcd for [C$_{49}$H$_{48}$N$_2$O$_6$S+Na] 815.31 found 815.44.

57. Preparation of benzyl 2-(benzyloxy)-4-(2-(4-chloro-N-methylphenylsulfonamido)-N-(4-cyclohexylbenzyl)acetamido)benzoate (50).

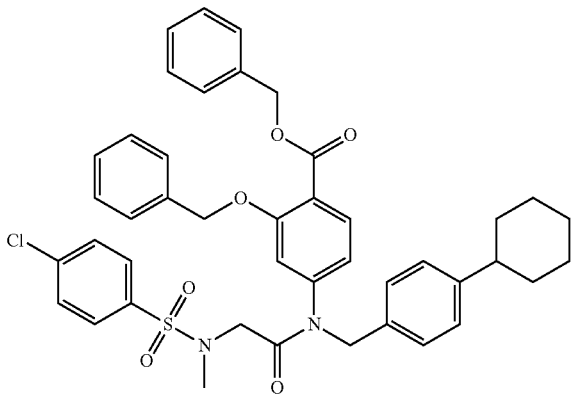 [SMILES: CN(CC(=O)N(Cc1ccc(C2CCCCC2)cc1)c1ccc(C(=O)OCc2ccccc2)c(OCc2ccccc2)c1)S(=O)(=O)c1ccc(Cl)cc1]

Secondary amine 46 was combined with 2-naphthylsulfonyl chloride on a 0.1 mmol scale via General Procedure G to furnish 50 (53 mg, 79%): $\delta_H$ (400 MHz, CDCl$_3$) 1.35-1.42 (m, 5H, CH$_2$), 1.71-1.89 (m, 5H, CH$_2$), 2.42-2.52 (m, 1H, CH), 2.85 (s, 3H, CH$_3$), 3.70 (s, 2H, CH$_2$), 4.74 (s, 2H, CH$_2$), 4.96 (s, 2H, CH$_2$), 5.36 (s, 2H, CH$_2$), 6.50 (s, 1H, CH), 6.68 (dd, J=8.4 and 1.6 Hz, 1H, CH), 7.01 (d, J=8.4 Hz, 2H, CH), 7.13 (d, J=8.0 Hz, 2H, CH), 7.29-7.36 (m, 8H, CH), 7.39-7.45 (m, 4H, CH), 7.70 (d, J=8.4 Hz, 2H, CH), 7.84 (d, J=8.4 Hz, 1H, CH); $\delta_C$ (100 MHz, CDCl$_3$) 25.9, 26.7, 34.3, 35.8, 44.1, 51.2, 52.7, 66.9, 70.6, 114.0, 119.9, 120.7, 126.8, 126.9, 127.9, 128.1, 128.2, 128.4, 128.5, 128.7, 128.8, 129.0, 133.1, 133.7, 135.6, 135.6, 137.1, 138.9, 144.8, 147.7, 158.6, 165.2, 166.4; LRMS (ES+) calcd for [C$_{47}$H$_{46}$N$_2$O$_6$S+Na] 789.30 found 789.32.

58. Preparation of benzyl 2-(benzyloxy)-4-(N-(4-cyclohexylbenzyl)-2-(N-methylnaphthalene-1-sulfonamido)acetamido)benzoate (62).

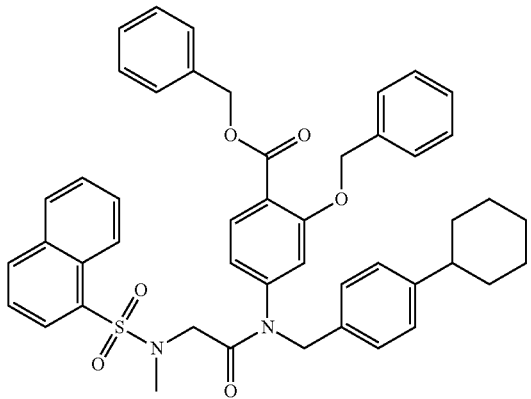 [SMILES: CN(CC(=O)N(Cc1ccc(C2CCCCC2)cc1)c1ccc(C(=O)OCc2ccccc2)c(OCc2ccccc2)c1)S(=O)(=O)c1cccc2ccccc12]

Secondary amine 46 was combined with 1-naphthylsulfonyl chloride on a 0.2 mmol scale via General Procedure G to furnish 62 (127 mg, 98%): $\delta_H$ (400 MHz, CDCl$_3$) 1.33-1.42 (m, 5H, CH$_2$), 1.71-1.89 (m, 5H, CH$_2$), 2.42-2.52 (m, 1H, CH), 2.96 (s, 3H, CH$_3$), 3.75 (s, 2H, CH$_2$), 4.76 (s, 2H, CH$_2$), 4.92 (s, 2H, CH$_2$), 5.37 (s, 2H, CH$_2$), 6.49 (s, 1H, CH), 6.67 (d, J=8.4 Hz, 1H, CH), 7.01 (d, J=8.0 Hz, 2H, CH), 7.11 (d, J=8.0 Hz, 2H, CH), 7.29-7.36 (m, 13H, CH), 7.83 (d, J=8.4 Hz, 1H, CH), 7.89 (d, J=8.4 Hz, 1H, CH), 8.01 (d, J=8.4 Hz, 1H, CH), 8.19 (d, J=8.0 Hz, 1H, CH), 8.57 (d, J=8.4 Hz, 1H, CH); $\delta_C$ (100 MHz, CDCl$_3$) 25.9, 26.7, 34.4, 36.6, 44.1, 52.7, 53.4, 66.9, 70.6, 114.2, 120.0, 120.7, 123.9, 124.9, 126.7, 127.0, 127.9, 128.1, 128.2, 128.5 (2), 128.6, 128.7, 128.8, 129.3, 133.0, 133.9, 134.0, 134.2, 134.3, 135.6, 135.7, 144.9, 147.6, 158.6, 165.3, 166.7; LRMS (ES+) calcd for [C$_{47}$H$_{46}$N$_2$O$_6$S+Na] 789.30 found 789.36.

59. Preparation of benzyl 2-(benzyloxy)-4-(N-(4-cyclohexylbenzyl)-2-(N-methylquinoline-8-sulfonamido)acetamido)benzoate (51).

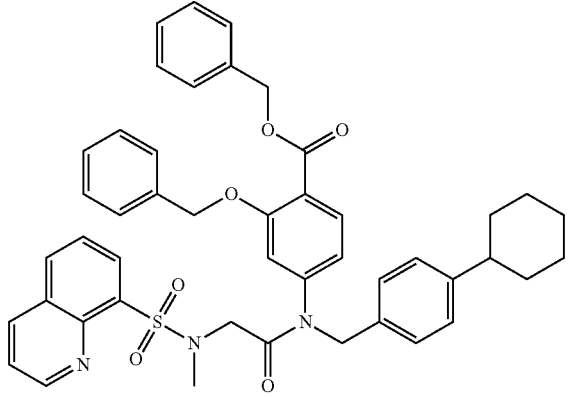 [SMILES: CN(CC(=O)N(Cc1ccc(C2CCCCC2)cc1)c1ccc(C(=O)OCc2ccccc2)c(OCc2ccccc2)c1)S(=O)(=O)c1cccc2cccnc12]

Secondary amine 46 was combined with quinoline-8-sulfonyl chloride on a 0.2 mmol scale via General Procedure G to furnish 51 (128 mg, 98%): $\delta_H$ (400 MHz, CDCl$_3$) 1.33-1.45 (m, 5H, CH$_2$), 1.70-1.88 (m, 5H, CH$_2$), 2.42-2.52 (m, 1H, CH), 2.95 (s, 3H, CH$_3$), 4.22 (s, 2H, CH$_2$), 4.81 (s, 2H, CH$_2$), 4.96 (s, 2H, CH$_2$), 5.37 (s, 2H, CH$_2$), 6.72 (s, 1H, CH), 6.81 (d, J=8.4 Hz, 1H, CH), 7.06 (d, J=8.0 Hz, 2H, CH), 7.11 (d, J=8.0 Hz, 2H, CH), 7.20-7.30 (m, 6H, CH), 7.32-7.36 (m, 3H, CH), 7.39-7.44 (m, 2H, CH), 7.55 (t, J=8.0 Hz, 1H, CH), 7.87 (d, J=8.0 Hz, 1H, CH), 7.96 (d, J=8.0 Hz, 1H, CH), 8.14 (d, J=8.0 Hz, 1H, CH), 8.45 (d, J=7.6 Hz, 1H, CH), 8.49 (s (br), 1H, CH); $\delta_C$(100 MHz, CDCl$_3$) 26.0, 26.7, 34.3, 36.2, 44.1, 52.6, 52.7, 66.9, 70.6, 114.4, 120.1, 120.3, 121.7, 125.2, 126.8, 127.0, 127.8, 128.1, 128.2, 128.4, 128.5, 128.8, 128.9, 132.6, 132.7, 133.2, 134.1, 135.7, 135.8, 136.3, 137.0, 143.7, 145.5, 147.4, 150.5, 158.5, 165.5, 168.0; LRMS (ES+) calcd for [C$_{46}$H$_{45}$N$_3$O$_6$S+Na] 790.29 found 790.36.

60. Preparation of benzyl 2-(benzyloxy)-4-(N-(4-cyclohexylbenzyl)-2-(5-(dimethylamino)-N-methylnaphthalene-1-sulfonamido)acetamido)benzoate (52).

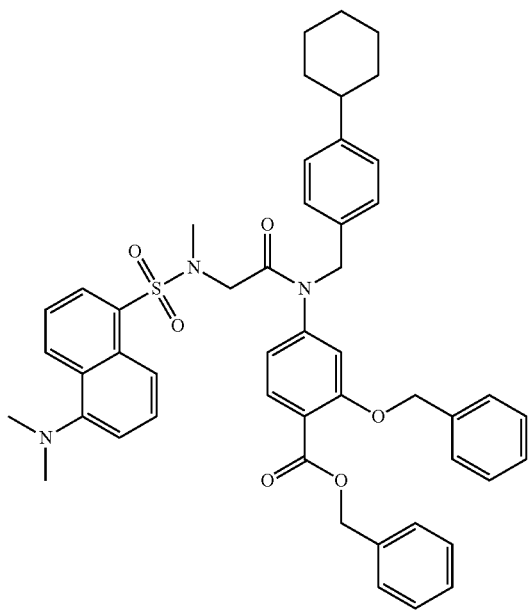 [SMILES: CN(C)c1cccc2c(S(=O)(=O)N(C)CC(=O)N(Cc3ccc(C4CCCCC4)cc3)c3ccc(C(=O)OCc4ccccc4)c(OCc4ccccc4)c3)cccc12]

Secondary amine 46 was combined with 5-(dimethylamino)naphthalene-1-sulfonyl chloride on a 0.2 mmol scale via General Procedure G to furnish 52 (132 mg, 96%): δ$_H$ (400 MHz, CDCl$_3$) 1.33-1.44 (m, 5H, CH$_2$), 1.69-1.88 (m, 5H, CH$_2$), 2.42-2.52 (m, 1H, CH), 2.86 (s, 6H, CH$_3$), 2.95 (s, 3H, CH$_3$), 3.76 (s, 2H, CH$_2$), 4.77 (s, 2H, CH$_2$), 4.92 (s, 2H, CH$_2$), 5.37 (s, 2H, CH$_2$), 6.50 (s, 1H, CH), 6.67 (d, J=8.4 Hz, 1H, CH), 7.03 (d, J=8.0 Hz, 2H, CH), 7.12 (d, J=8.0 Hz, 2H, CH), 7.23-7.38 (m, 9H, CH), 7.39-7.50 (m, 4H, CH), 7.83 (d, J=8.0 Hz, 1H, CH), 8.18 (d, J=7.2 Hz, 1H, CH), 8.23 (d, J=8.4 Hz, 1H, CH), 8.52 (d, J=8.0 Hz, 1H, CH); δ$_C$ (100 MHz, CDCl$_3$) 26.0, 26.7, 34.3, 36.1, 44.1, 45.3, 50.7, 52.6, 66.9, 70.6, 114.2, 115.1, 119.6, 119.9, 120.3, 123.0, 126.9, 127.0, 127.9, 128.1, 128.2, 128.4 (br), 128.8, 129.2, 129.8, 130.0, 130.1, 133.0, 133.9, 134.4, 135.6, 144.9, 147.6, 158.6, 165.3, 166.8.

61. Preparation of benzyl 2-(benzyloxy)-4-(N-(4-cyclohexylbenzyl)-2-(N,1-dimethyl-1H-imidazole-4-sulfonamido)acetamido)benzoate (53).

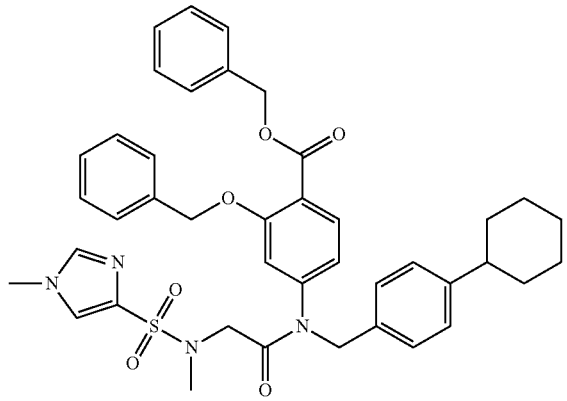 [SMILES: CN(CC(=O)N(Cc1ccc(C2CCCCC2)cc1)c1ccc(C(=O)OCc2ccccc2)c(OCc2ccccc2)c1)S(=O)(=O)c1cn(C)cn1]

Secondary amine 46 was combined with 1-methyl-1H-imidazole-4-sulfonyl chloride on a 0.2 mmol scale via General Procedure G to furnish 53 (116 mg, 95%): δ$_H$ (400 MHz, CDCl$_3$) 1.32-1.44 (m, 5H, CH$_2$), 1.68-1.86 (m, 5H, CH$_2$), 2.41-2.51 (m, 1H, CH), 2.92 (s, 3H, CH$_3$), 3.63 (s, 3H, CH$_2$), 3.80 (s, 2H, CH$_2$), 4.77 (s, 2H, CH$_2$), 4.96 (s, 2H, CH$_2$), 5.32 (s, 2H, CH$_2$), 6.69 (d, J=8.4 Hz, 1H, CH), 6.72 (s, 1H, CH), 7.05 (d, J=8.0 Hz, 2H, CH), 7.09 (d, J=8.0 Hz, 2H, CH), 7.27-7.40 (m, 12H, CH), 7.81 (d, J=8.0 Hz, 1H, CH); δ$_C$ (100 MHz, CDCl$_3$) 25.9, 26.7, 33.7, 34.3, 36.2, 44.1, 51.6, 53.3, 66.8, 70.6, 114.3, 119.9, 120.2, 123.8, 126.8, 127.1, 127.8, 128.0, 128.1, 128.4, 128.5, 128.7, 132.9, 133.9, 135.7, 135.9, 138.7, 138.8, 145.3, 147.4, 158.7, 165.4, 167.1; LRMS (ES+) calcd for [C$_{41}$H$_{44}$N$_4$O$_6$S+Na] 743.29 found 743.25.

62. Preparation of benzyl 2-(benzyloxy)-4-(2-(4-cyano-N-methylphenylsulfonamido)-N-(4-cyclohexylbenzyl)acetamido)benzoate (54).

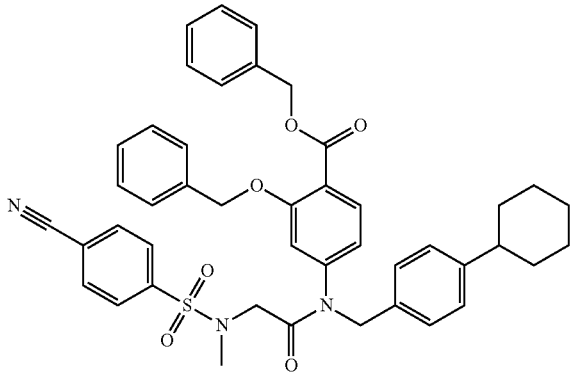 [SMILES: CN(CC(=O)N(Cc1ccc(C2CCCCC2)cc1)c1ccc(C(=O)OCc2ccccc2)c(OCc2ccccc2)c1)S(=O)(=O)c1ccc(C#N)cc1]

Secondary amine 46 was combined with 4-cyanobenzene-1-sulfonyl chloride on a 0.2 mmol scale via General Procedure G to furnish 54 (122 mg, 97%): δ$_H$ (400 MHz, CDCl$_3$) 1.21-1.39 (m, 5H, CH$_2$), 1.60-1.80 (m, 5H, CH$_2$), 2.38-2.58 (m, 1H, CH), 2.78 (s, 3H, CH$_3$), 3.65 (s, 2H, CH$_2$), 4.61 (s, 2H, CH$_2$), 4.87 (s, 2H, CH$_2$), 5.26 (s, 2H, CH$_2$), 6.39 (s, 1H, CH), 6.58 (d, J=8.0 Hz, 1H, CH), 6.89 (d, J=8.0 Hz, 2H, CH), 7.03 (d, J=8.0 Hz, 2H, CH), 7.18-7.35 (m, 10H, CH), 7.65 (d, J=8.4 Hz, 2H, CH) 7.75 (d, J=8.0 Hz, 1H, CH), 7.79 (d, J=8.4 Hz, 2H, CH); δ$_C$ (100 MHz, CDCl$_3$) 26.1, 26.8, 34.5, 35.9, 44.2, 52.9, 53.5, 67.1, 70.7, 114.1, 116.2, 117.5, 120.0, 121.1, 127.1, 128.2 (br), 128.3, 128.4, 128.6, 128.7, 128.9, 132.6, 133.3, 133.8, 135.7, 135.8, 143.2, 144.7, 147.9, 158.8, 165.3, 166.3; LRMS (ES+) calcd for [C$_{44}$H$_{43}$N$_3$O$_6$S+Na] 764.28 found 764.30.

63. Preparation of benzyl 2-(benzyloxy)-4-(2-(4-bromo-N-methylphenylsulfonamido)-N-(4-cyclohexylbenzyl)acetamido)benzoate (55).

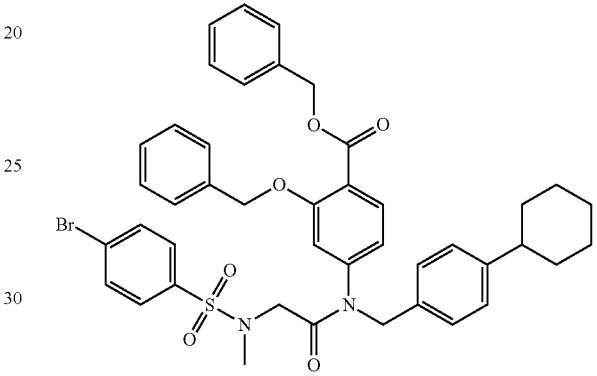

Secondary amine 46 was combined with 4-bromobenzene-1-sulfonyl chloride on a 0.2 mmol scale via General Procedure G to furnish 55 (123 mg, 95%): δ$_H$ (400 MHz, CDCl$_3$) 1.24-1.38 (m, 5H, CH$_2$), 1.61-1.80 (m, 5H, CH$_2$), 2.34-2.46 (m, 1H, CH), 2.75 (s, 3H, CH$_3$), 3.60 (s, 2H, CH$_2$), 4.64 (s, 2H, CH$_2$), 4.86 (s, 2H, CH$_2$), 5.27 (s, 2H, CH$_2$), 6.40 (s, 1H, CH), 6.58 (d, J=8.0 Hz, 1H, CH), 6.91 (d, J=8.0 Hz, 2H, CH), 7.03 (d, J=8.0 Hz, 2H, CH), 7.18-7.38 (m, 10H, CH), 7.49-7.54 (m, 4H, CH) 7.75 (d, J=8.0 Hz, 1H, CH); δ$_C$ (100 MHz, CDCl$_3$) 25.9, 26.7, 34.3, 35.8, 44.1, 51.2, 52.8, 66.9, 70.6, 114.1, 119.9, 120.8, 126.9, 130.0, 127.4, 127.9, 128.1, 128.2, 128.4, 128.5, 128.8, 128.9, 132.0, 133.1, 133.7, 135.6, 135.7, 137.7, 144.8, 147.7, 158.6, 165.2, 166.4; LRMS (ES+) calcd for [C$_{43}$H$_{43}$BrN$_2$O$_6$S+Na] 817.19 found 817.25.

64. Preparation of benzyl 2-(benzyloxy)-4-(2-(4-chloro-N-methylphenylsulfonamido)-N-(4-cyclohexylbenzyl)acetamido)benzoate (56).

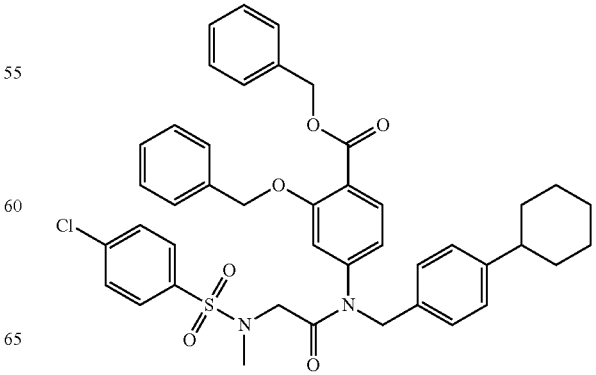

Secondary amine 46 was combined with 4-chlorobenzenesulfonyl chloride and on a 0.2 mmol scale via General Procedure G to furnish 56 (95 mg, 72%): $\delta_H$ (400 MHz, CDCl$_3$) 1.35-1.42 (m, 5H, CH$_2$), 1.71-1.89 (m, 5H, CH$_2$), 2.42-2.52 (m, 1H, CH), 2.85 (s, 3H, CH$_3$), 3.70 (s, 2H, CH$_2$), 4.74 (s, 2H, CH$_2$), 4.96 (s, 2H, CH$_2$), 5.36 (s, 2H, CH$_2$), 6.50 (s, 1H, CH), 6.68 (dd, J=8.4 and 1.6 Hz, 1H, CH), 7.01 (d, J=8.4 Hz, 2H, CH), 7.13 (d, J=8.0 Hz, 2H, CH), 7.29-7.36 (m, 8H, CH), 7.39-7.45 (m, 4H, CH), 7.70 (d, J=8.4 Hz, 2H, CH), 7.84 (d, J=8.4 Hz, 1H, CH); $\delta_C$ (100 MHz, CDCl$_3$) 25.9, 26.7, 34.3, 35.8, 44.1, 51.2, 52.7, 66.9, 70.6, 114.0, 119.9, 120.7, 126.8, 126.9, 127.8, 128.1, 128.2, 128.4, 128.5, 128.7, 128.8, 129.0, 133.1, 133.7, 135.6, 135.6, 137.1, 138.9, 144.8, 147.7, 158.6, 165.2, 166.4; LRMS (ES+) calcd for [C$_{43}$H$_{43}$ClN$_2$O$_6$S+Na] 773.24 found 773.14.

65. Preparation of benzyl 2-(benzyloxy)-4-(N-(4-cyclohexylbenzyl)-2-(4-fluoro-N-methylphenylsulfon-amido)acetamido)benzoate (57).

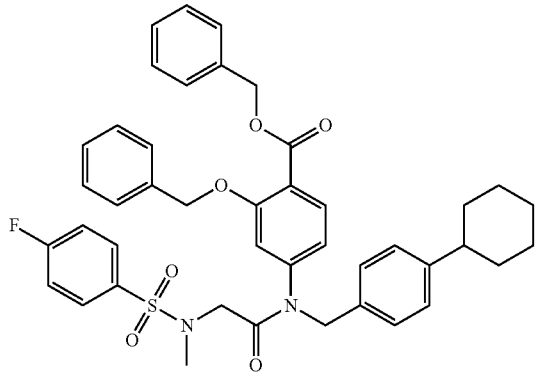 [SMILES: CN(CC(=O)N(Cc1ccc(C2CCCCC2)cc1)c1ccc(C(=O)OCc2ccccc2)c(OCc2ccccc2)c1)S(=O)(=O)c1ccc(F)cc1]

Secondary amine 46 was combined with 4-fluorobenzene-1-sulfonyl chloride on a 0.1 mmol scale via General Procedure G to furnish 57 (45 mg, 71%): $\delta_H$ (400 MHz, CDCl$_3$) 1.33-1.42 (m, 5H, CH$_2$), 1.70-1.86 (m, 5H, CH$_2$), 2.42-2.52 (m, 1H, CH), 2.84 (s, 3H, CH$_3$), 3.70 (s, 2H, CH$_2$), 4.74 (s, 2H, CH$_2$), 4.95 (s, 2H, CH$_2$), 5.35 (s, 2H, CH$_2$), 6.49 (s, 1H, CH), 6.67 (dd, J=8.4 and 1.6 Hz, 1H, CH), 7.00 (d, J=8.0 Hz, 2H, CH), 7.10-7.15 (m, 4H, CH), 7.29-7.38 (m, 8H, CH), 7.39-7.41 (m, 2H, CH), 7.75-7.79 (m, 2H, CH), 7.84 (d, J=8.0 Hz, 1H, CH); $\delta_C$ (100 MHz, CDCl$_3$) 26.0, 26.7, 34.4, 35.8, 44.1, 51.3, 52.8, 67.0, 70.6, 114.1, 115.5, 116.1, 120.0, 120.8, 126.9, 127.0, 128.0, 128.2, 128.2, 128.5, 128.5, 128.8, 130.1, 130.2, 133.1, 133.8, 134.7, 135.7, 135.7, 144.9, 147.7, 158.7, 163.7, 165.3, 166.6; LRMS (ES+) calcd for [C$_{43}$H$_{43}$FN$_2$O$_6$S+Na] 757.27 found 757.35.

66. Preparation of benzyl 2-(benzyloxy)-4-(N-(4-cyclohexylbenzyl)-2-(4-methoxy-N-methylphenylsulfonamido)acetamido)benzoate (58).

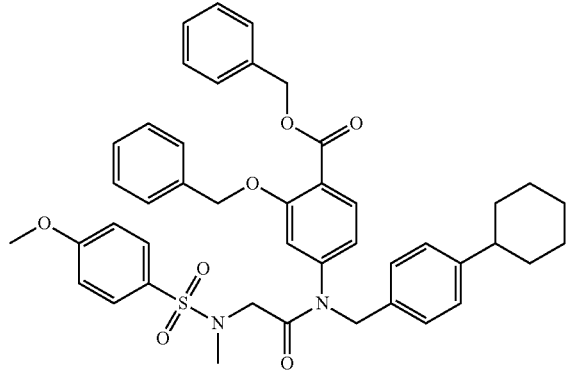 [SMILES: COc1ccc(S(=O)(=O)N(C)CC(=O)N(Cc2ccc(C3CCCCC3)cc2)c2ccc(C(=O)OCc3ccccc3)c(OCc3ccccc3)c2)cc1]

Secondary amine 46 was combined with 4-methoxybenzenesulfonyl chloride on a 0.1 mmol scale via General Procedure G to furnish 58 (56 mg, 79%): $\delta_H$ (400 MHz, CDCl$_3$) 1.33-1.42 (m, 5H, CH$_2$), 1.80-1.86 (m, 5H, CH$_2$), 2.42-2.51 (m, 1H, CH$_2$), 2.81 (s, 3H, CH$_3$), 3.66 (s, 2H, CH$_2$), 3.84 (s, 3H, CH$_3$), 4.76 (s, 2H, CH$_2$), 4.95 (s, 2H, CH$_2$), 5.35 (s, 2H, CH$_2$), 6.52 (s, 1H, CH), 6.68 (dd, J=8.0 and 1.6 Hz, 1H, CH), 6.92 (d, J=8.8 Hz, 2H, CH), 7.02 (d, J=8.0 Hz, 2H, CH), 7.11 (d, J=8.0 Hz, 2H, CH), 7.29-7.36 (m, 8H, CH), 7.37-741 (m, 2H, CH), 7.68 (d, J=8.8 Hz, 2H, CH), 7.84 (d, J=8.4 Hz, 1H, CH); $\delta_C$ (100 MHz, CDCl$_3$) 26.0, 26.7, 34.4, 35.4, 44.1, 51.3, 52.7, 55.4, 66.9, 70.6, 113.9, 114.1, 120.0, 120.6, 126.9, 127.0, 127.9, 128.1, 128.2, 128.5, 128.5, 128.8, 129.6, 129.9, 133.0, 133.9, 135.7, 135.7, 145.0, 147.6, 158.6, 162.7, 165.3, 166.8; LRMS (ES+) calcd for [C$_{43}$H$_{40}$F$_5$N$_2$O$_6$S+H] 807.25 found 807.20.

67. Preparation of benzyl 2-(benzyloxy)-4-(N-(4-cyclohexylbenzyl)-2-(N-methyl-4-nitrophenylsulfon-amido)acetamido)benzoate (59).

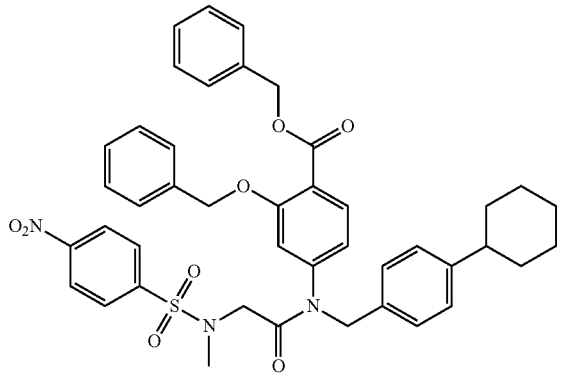 [SMILES: CN(CC(=O)N(Cc1ccc(C2CCCCC2)cc1)c1ccc(C(=O)OCc2ccccc2)c(OCc2ccccc2)c1)S(=O)(=O)c1ccc([N+](=O)[O-])cc1]

Secondary amine 46 was combined with 4-nitrobenzenesulfonyl chloride on a 0.2 mmol scale via General Procedure G to furnish 59 (88 mg, 69%): $\delta_H$ (400 MHz, CDCl$_3$) 1.33-1.42 (m, 5H, CH$_2$), 1.70-1.89 (m, 5H, CH$_2$), 2.43-2.51 (m, 1H, CH), 2.90 (s, 3H, CH$_3$), 3.78 (s, 2H, CH$_2$), 4.70 (s, 2H, CH$_2$), 4.70 (s, 2H, CH$_2$), 5.36 (s, 2H, CH$_2$), 6.49 (s, 1H, CH), 6.68 (dd, J=8.0 and 1.6 Hz, 1H, CH), 6.97 (d, J=8.4 Hz, 2H, CH), 7.13 (d, J=8.0 Hz, 2H, CH), 7.28-7.37 (m, 8H, CH), 7.39-7.42 (m, 2H, CH), 7.85 (d, J=8.0 Hz, 1H, CH), 7.95 (d, J=8.8 Hz, 2H, CH), 8.30 (d, J=8.8 Hz, 2H, CH); $\delta_C$ (100 MHz, CDCl$_3$) 25.9, 26.7, 34.3, 35.8, 44.1, 51.4, 52.8, 67.0, 70.6, 114.0, 119.9, 121.0, 123.9, 128.0, 128.2, 128.2, 128.5, 128.5, 128.6, 128.8, 133.2, 133.6, 135.6, 135.6, 144.5, 144.7, 147.9, 149.8, 158.6, 165.2, 166.1; LRMS (ES+) calcd for [C$_{43}$H$_{43}$N$_3$O$_8$S+Na] 784.27 found 784.25.

68. Preparation of benzyl 2-(benzyloxy)-4-(N-(4-cyclohexylbenzyl)-2-(2,3,4,5,6-pentafluoro-N-methylphenylsulfonamido)acetamido)benzoate (60).

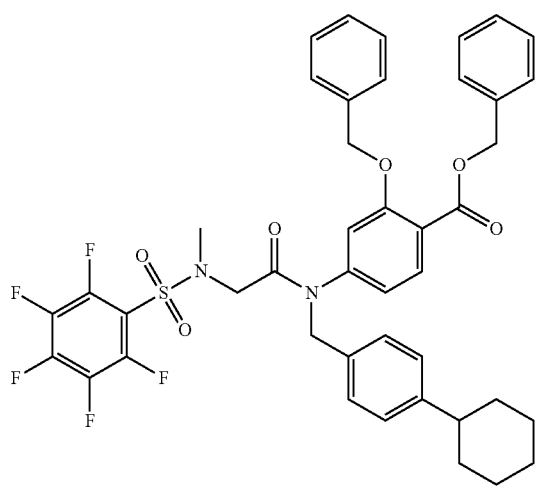 [SMILES: CN(CC(=O)N(Cc1ccc(C2CCCCC2)cc1)c1ccc(C(=O)OCc2ccccc2)c(OCc2ccccc2)c1)S(=O)(=O)c1c(F)c(F)c(F)c(F)c1F]

Secondary amine 46 was combined with pentafluorobenzenesulfonyl chloride on a 0.1 mmol scale via General Procedure G to furnish 60 (49 mg, 63%): $\delta_H$ (400 MHz, CDCl$_3$) 1.34-1.42 (m, 5H, CH$_2$), 1.70-1.86 (m, 5H, CH$_2$), 2.43-2.52 (m, 1H, CH), 3.05 (s, 3H, CH$_3$), 3.86 (s, 2H, CH$_2$), 4.67 (s, 2H, CH$_2$), 4.94 (s, 2H, CH$_2$), 5.35 (s, 2H, CH$_2$), 6.44 (s, 1H, CH), 6.66 (d, J=8.0 Hz, 1H, CH), 6.96 (d, J=7.2 Hz, 2H, CH), 7.12 (d, J=7.2 Hz, 2H, CH), 7.30-7.41 (m, 10H, CH), 7.84 (dd, J=8.0 and 1.2 Hz, 1H, CH); $\delta_C$ (100 MHz, CDCl$_3$) 26.0, 26.7, 34.4, 35.4, 44.1, 51.9, 52.7, 67.0, 70.70, 111.8, 114.0, 115.8, 119.9, 127.0, 127.1, 128.1, 128.2, 128.5, 128.6, 128.7, 133.3, 133.4, 135.6, 135.6, 137.8, 141.6, 142.9, 144.2, 147.9, 158.7, 165.2, 165.8; LRMS (ES+) calcd for [C$_{44}$H$_{46}$N$_2$O$_7$S+Na] 747.31 found 747.39.

69. Preparation of 4-(N-(cyclohexylmethyl)-2-(N,4-dimethylphenylsulfonamido)acetamido)-2-hydroxybenzoic acid (27E).

Benzyl protected 11 was globally deprotected on a 0.08 mmol scale via General Procedure I to furnish 27e (34 mg, 85%): $\delta_H$ (400 MHz, d$_6$-DMSO) 1.02-1.11 (m, 3H, CH$_2$), 1.19-2.26 (m, 2H, CH$_2$), 1.53-1.64 (m, 6H, CH$_2$ and CH), 2.35 (s, 3H, CH$_3$), 2.71 (s, 3H, CH$_3$), 2.45 (d, J=7.2 Hz, 2H, CH$_2$), 3.74 (s, 2H, CH$_2$), 5.73 (s, 2H, CH$_2$O, 6.83 (d, J=8.4 Hz, 1H, CH), 6.91 (s, 1H, CH), 7.33 (d, J=8.0 Hz, 2H, CH), 7.52 (d, J=8.4 Hz, 2H, CH), 7.82 (d, J=8.4 Hz, 1H, CH); $\delta_C$ (100 MHz, d$_6$-DMSO) 20.9, 25.2, 25.9, 30.0, 35.6, 35.8, 50.9, 54.1, 112.6, 116.2, 118.7, 126.9, 129.6, 131.5, 135.1, 143.0, 147.4, 161.8, 166.3, 171.2; HRMS (ES+) calcd for [C$_{24}$H$_{30}$N$_2$O$_6$S+H] 475.1897, found 475.1905; HPLC (III) t$_R$=18.62 min (90.58%), (IV) t$_R$=40.70 min (90.17%).

70. Preparation of 4-(2-(N,4-dimethylphenylsulfonamido)-N-(piperidin-4-ylmethyl)acetamido)-2-hydroxybenzoic acid (27JA).

Benzyl protected 13 was globally deprotected on a 0.10 mmol scale via General Procedure I to furnish 27ja (55 mg, 98%): $\delta_H$ (400 MHz, d$_6$-DMSO) 1.20-1.37 (m, 2H, CH$_2$), 1.61-1.80 (m, 2H, CH$_2$), 2.32 (s, 3H, CH$_3$), 2.71-2.73 (m, 4H, CH$_3$ and CH), 2.77 (t, J=12.0 Hz, 2H, CH$_2$), 3.24 (d, J=10.4 Hz, 2H, CH$_2$), 3.48 (d, J=6.8 Hz, 2H, CH$_2$), 3.71 (s, 2H, CH$_2$), 6.55 (dd, J=8.4 and 2.0 Hz, 1H, CH), 6.63 (d, J=2.0 Hz, 1H, CH), 7.32 (d, J=8.0 Hz, 2H, CH), 7.51 (d, J=8.0 Hz, 2H, CH), 7.73 (d, J=8.0 Hz, 1H, CH); $\delta_C$ (100 MHz, CDCl$_3$) 21.3, 26.4, 32.2, 39.2, 43.0, 48.9, 51.0, 53.1, 115.6, 115.8, 120.2, 127.2, 129.9, 131.4, 131.4, 135.6, 143.4, 143.9, 164.3, 167.0, 171.3; HRMS (ES+) calcd for [C$_{23}$H$_{29}$N$_3$O$_6$S+H] 476.1849, found 476.1850; HPLC (I) t$_R$=14.74 min (98.61%), (II) t$_R$=26.80 min (100%).

71. Preparation of 4-(N-((1-(tert-butoxycarbonyl)piperidin-4-yl)methyl)-2-(N,4-dimethylphenylsulfonamido)acetamido)-2-hydroxybenzoic acid (27JB).

Benzyl protected 14 was globally deprotected on a 0.10 mmol scale via General Procedure I to furnish 27jb (52 mg, 93%): $\delta_H$ (400 MHz, CDCl$_3$) 1.44 (s, 9H, 3 CH$_3$), 1.58-1.78 (m, 2H, CH$_2$), 2.39 (s, 3H, CH$_3$Ar), 2.63-2.70 (m, 2H, CH$_2$), 2.82 (s, 4H, CH$_3$ and CH), 3.59 (s (br), 2H, CH$_2$), 3.81 (s, 2H, CH$_2$), 4.06 (s br, 2H, CH$_2$), 6.75 (d, J=8.2 Hz, 1H, CH (Ar)), 6.81 (br s, 1H, CH (Ar)), 7.26 (d, J=8.2 Hz, 2H, 2 CH (Ar)), 7.63 (d, J=8.2 Hz, 2H, 2 CH (Ar)), 7.98 (d, J=8.3 Hz, 1H, CH (Ar)); $\delta_C$ (100 MHz, CDCl$_3$) 21.4, 28.4, 29.6, 34.6, 35.9, 51.5, 54.8, 80.0, 112.2, 116.5, 118.5, 127.4, 129.5, 132.5, 135.1, 143.4, 147.8, 155.0, 163.0, 167.4, 171.9; HRMS (ES+) calcd for [C$_{28}$H$_{37}$N$_3$O$_8$S+Na] 598.2193, found 598.2177; HPLC (I) t$_R$=19.33 min (98.24%), (II) t$_R$=39.65 min (97.61%).

72. Preparation of 4-(N-((1-(4-cyanophenyl)piperidin-4-yl)methyl)-2-(N,4-dimethylphenylsulfonamido)acetamido)-2-hydroxybenzoic acid (27JC).

Benzyl protected 15 was globally deprotected on a 0.09 mmol scale via General Procedure I to furnish 27jc (50 mg, 95%): $\delta_H$ (400 MHz, CDCl$_3$) 1.25-1.41 (m, 2H, CH$_2$), 1.70-1.89 (m, 2H, CH$_2$), 2.39 (s, 3H, CH$_3$Ar), 2.80-2.90 (m, 6H, CH, CH$_2$ and CH$_3$), 3.65 (d, J=6.7 Hz, 2H, CH$_2$CH), 3.59-3.91 (m, 4H, CH$_2$), 6.77-6.90 (m, 4H, 4 CH (Ar)), 7.27 (d, J=8.6 Hz, 2H, 2 CH (Ar)), 7.45 (d, J=8.6 Hz, 2H, 2 CH (Ar)), 7.63 (d, J=8.6 Hz, 2H, 2 CH (Ar)), 8.00 (d, J=8.2 Hz, 1H, CH (Ar)); $\delta_C$ (100 MHz, CDCl$_3$) 21.5, 28.9, 34.5, 36.0, 47.3, 51.7, 54.7, 99.3, 111.9, 114.3, 116.7, 118.7, 120.0, 127.4, 129.5, 132.6, 133.5, 134.9, 143.5, 148.0, 153.0, 163.1, 167.6, 172.2; HRMS (ES+) calcd for [C$_{30}$H$_{32}$N$_4$O$_6$S+H] 577.2115, found 477.2093; HPLC (I) t$_R$=20.91 min (98.25%), (II) t$_R$=43.52 min (98.91%).

73. Preparation of 4-(2-(N,4-dimethylphenylsulfonamido)-N-((1-(pyrimidin-2-yl)piperidin-4-yl)methyl)acetamido)-2-hydroxybenzoic acid (27JD).

Benzyl protected 16 was globally deprotected on a 0.08 mmol scale via General Procedure I to furnish 27jd (41 mg, 92%): $\delta_H$ (400 MHz, d$_6$-DMSO) 1.60-1.73 (m, 3H, CH$_2$), 2.34 (s, 3H, CH$_3$Ar), 2.46-2.48 (m, 2H, CH$_2$), 2.74 (s, 3H, CH$_3$N), 2.80 (t, J=12.0 Hz, 1H, CH$_2$), 3.52 (d, J=7.0 Hz, 2H, CH$_2$CH), 3.79 (s, 2H, CH$_2$), 4.57 (d, J=13.0 Hz, 2H, CH$_2$), 6.57 (t, J=4.7 Hz, 1H, CH (Ar)), 6.93 (dd, J=8.4 and 2.0 Hz, 1H, CH (Ar)), 7.02 (d, J=2.0 Hz, 1H, CH (Ar)), 7.35 (d, J=8.4 Hz, 2H, 2 CH (Ar)), 7.55 (d, J=8.2 Hz, 2H, 2 CH (Ar)), 7.86 (d, J=8.4 Hz, 1H, CH (Ar)), 8.32 (d, J=4.7 Hz, 2H, 2 CH (Ar)); $\delta_C$ (100 MHz, d$_6$-DMSO) 21.4, 29.9, 35.9, 44.1, 51.5, 53.3, 54.9, 109.3, 113.4, 116.3, 118.4, 127.4, 129.5, 132.5, 135.2, 143.4, 147.4, 157.6, 159.9, 163.0, 167.4, 172.3; HRMS (ES+) calcd for [C$_{27}$H$_{31}$N$_5$O$_6$S+H] 554.2067, found 554.2058; HPLC (I) t$_R$=23.04 min (100.00%), (II) t$_R$=31.37 min (98.54%).

74. Preparation of 4-(2-(N,4-dimethylphenylsulfonamido)-N-(4-(1-(2,2,2-trifluoroacetyl)piperidin-4-yl)benzyl)acetamido)-2-hydroxybenzoic acid (27KA).

Benzyl protected 20 was globally deprotected on a 0.08 mmol scale via General Procedure I to furnish 27ka (50 mg, 93%): $\delta_H$ (400 MHz, d$_6$-DMSO) 1.61-1.75 (m, 2H, CH$_2$), 1.96-2.00 (m, 2H, CH$_2$) 2.40 (s, 3H, CH$_3$), 2.82-2.87 (m, 5H, CH$_3$ and CH$_2$), 3.25 (t, J=12.4 Hz, 1H, CH$_2$), 3.84 (s, 2H, CH$_2$), 4.13 (d, J=12.4 Hz, 1H, CH$_2$), 4.69 (d, J=13.2 Hz, 1H, CH$_2$), 4.84 (s, 2H, CH$_2$), 6.61 (d, J=8.4 Hz, 1H, CH), 6.69 (s, 1H, CH), 7.09-7.15 (m, 4H, CH), 7.27 (d, J=7.2 Hz, 2H, CH), 7.64 (d, J=8.4 Hz, 2H, CH), 7.89 (d, J=8.4 Hz, 1H, CH); δ$_C$ (100 MHz, CDCl$_3$) 21.4, 32.4, 33.4, 35.8, 41.8, 44.1, 46.2, 51.5, 52.8, 53.3, 115.0, 116.8, 118.9, 126.8, 127.4, 128.8, 129.4, 132.2, 134.6, 134.8, 143.4, 143.7, 147.3, 155.2, 155.6, 162.8, 167.1, 172.0; HRMS (ES+) calcd for [C$_{31}$H$_{32}$N$_3$O$_7$S+H] 648.1985, found 648.1974; HPLC (I) t$_R$=21.52 min (95.85%), (II) t$_R$=45.49 min (97.12%).

75. Preparation of 4-(2-(N,4-dimethylphenylsulfonamido)-N-(4-(piperidin-4-yl)benzyl)acetamido)-2-hydroxybenzoic acid (27 KB).

Benzyl protected 21 was globally deprotected on a 0.07 mmol scale via General Procedure I to furnish 27kb (43 mg, 86%): δ$_H$ (400 MHz, d$_6$-DMSO) 1.63-1.78 (m, 2H, CH$_2$), 1.86-2.40 (m, 2H, CH$_2$), 2.29-2.33 (m, 1H, CH), 2.34 (s, 3H, CH$_3$), 2.73-2.80 (m, 5H, CH$_3$ and CH$_2$), 2.90-3.02 (m, 2H, CH$_2$), 3.81 (s, 2H, CH$_2$), 4.77 (s, 2H, CH$_2$), 6.63 (d, J=7.2 Hz, 1H, CH), 6.69 (s, 1H, CH), 7.12 (s (br), 4H, CH), 7.33 (d, J=8.0 Hz, 2H, CH), 7.51 (d, J=8.0 Hz, 2H, CH), 7.70 (d, J=8.0 Hz, 1H, CH); HRMS (ES+) calcd for [C$_{29}$H$_{33}$N$_3$O$_6$S+H] 552.2162, found 552.2149; HPLC (III) t$_R$=17.99 min (71.92%), (IV) t$_R$=35.58 min (71.04%).

76. Preparation of 4-(N-(4-(1-(tert-butoxycarbonyl)piperidin-4-yl)benzyl)-2-(N,4-dimethylphenylsulfon-amido)acetamido)-2-hydroxybenzoic acid (27KC).

Benzyl protected 22 was globally deprotected on a 0.08 mmol scale via General Procedure I to furnish 27kc (58 mg, 89%): δ$_H$ (400 MHz, d$_6$-DMSO) 1.38-1.39 (m, 2H, CH$_2$), 1.39 (s, 9H, CH$_3$), 1.69 (s, 2H, CH$_2$), 1.72 (s, 1H, CH$_2$), 2.36 (s (br), 2H, CH$_2$), 2.75-2.79 (m, 5H, CH$_3$ and CH$_2$), 4.05 (s, 2H, CH$_2$), 4.80 (s, 2H, CH$_2$), 6.79 (dd, J=8.4 and 2.0 Hz, 1H, CH), 6.87 (d, J=2.0 Hz, 1H, CH), 7.08 (d, J=8.0 Hz, 2H, CH), 7.15 (d, J=8.4 Hz, 2H, CH), 7.35 (d, J=8.0 Hz, 2H, CH), 7.54 (d, J=8.4 Hz, 2H, CH), 7.77 (d, J=8.4 Hz, 1H, CH); δ$_C$ (100 MHz, CDCl$_3$) 21.4, 28.3, 29.5, 29.8, 30.2, 32.9, 35.8, 42.1, 44.3, 51.4, 52.8, 79.9, 114.2, 116.6, 118.7, 126.8, 127.4, 128.6, 129.4, 132.1, 134.2, 135.1, 143.3, 145.0, 146.8, 155.0, 162.7, 166.9, 171.9; HRMS (ES+) calcd for [C$_{34}$H$_{41}$N$_3$O$_8$S+H] 652.2687, found 652.2658; HPLC (I) t$_R$=23.65 min (66.51%), (II) t$_R$=50.00 min (74.40%).

77. Preparation of 4-(2-(N,4-dimethylphenylsulfonamido)-N-(4-(1-(pyrimidin-2-yl)piperidin-4-yl)benzyl)-acetamido)-2-hydroxybenzoic acid (27KE).

Benzyl protected 23 was globally deprotected on a 0.07 mmol scale via General Procedure I to furnish 27ke (51 mg, 90%): δ$_H$ (400 MHz, CDCl$_3$) 1.65-1.67 (m, 2H, CH$_2$), 1.91-2.03 (m, 2H, CH$_2$), 2.30-2.32 (m, 1H, CH), 2.39 (s, 3H, CH$_3$), 2.76-2.79 (m, 2H, CH$_2$), 2.85 (s, 3H, CH$_3$), 2.97-3.05 (m, 2H, CH$_2$), 3.83 (s, 2H, CH$_2$), 4.80 (s, 2H, CH$_2$), 6.48-6.59 (m, 2H, CH), 6.68 (s, 1H, CH), 7.04-7.14 (m, 4H, CH), 7.28 (d, J=7.2 Hz, 2H, CH), 7.65 (d, J=7.2 Hz, 2H, CH), 7.85 (s, 1H, CH), 8.39-8.50 (m, 3H, CH); δ$_C$ (100 MHz, CDCl$_3$) 21.5, 32.7, 35.9, 41.9, 45.8, 51.8, 53.1, 109.0, 112.4, 116.8, 119.0, 122.8, 126.9, 127.6, 129.0, 129.5, 132.1, 134.8, 135.3, 137.6, 143.5, 144.0, 152.2, 157.0, 159.2, 161.5, 167.0, 171.5; HRMS (ES+) calcd for [C$_{33}$H$_{35}$N$_5$O$_6$S+H] 630.2380, found 630.2379; HPLC (I) t$_R$=18.68 min (100%), (II) t$_R$=37.21 min (95.91%).

78. Preparation of 4-(N-(4-(1-(4-cyanobenzoylpiperidin-4-yl)benzyl)-2-(N,4-dimethylphenylsulfon-amido)acetamido)-2-hydroxybenzoic acid (27KF).

Benzyl protected 24 was globally deprotected on a 0.07 mmol scale via General Procedure I to furnish 27kf (41 mg, 87%): δ$_H$ (400 MHz, CDCl$_3$) 1.60-2.03 (m, 4H, CH$_2$), 2.39 (s, 3H, CH$_3$), 2.73-2.96 (m, 5H, CH$_2$ and CH$_3$), 3.11-3.25 (m, 1H, CH), 3.72 (d, J=8.0 Hz, 2H, CH$_2$), 3.82 (s, 2H, CH$_2$), 4.82 (s, 2H, CH$_2$), 6.58 (d, J=8.0 Hz, 1H, CH), 7.11 (s br, 4H, CH), 7.26 (d, J=8.0 Hz, 2H, CH), 7.55 (d, J=7.6 Hz, 2H, CH), 7.64 (d, J=8.0 Hz, 2H, CH), 7.73 (d, J=8.4 Hz, 2H, CH), 7.85 (d, J=7.6 Hz, 1H, CH); δ$_C$ (100 MHz, CDCl$_3$) 21.4, 29.5, 32.5, 33.7, 35.8, 42.0, 43.0, 48.3, 51.5, 52.8, 113.5, 116.8, 117.9, 118.8, 126.7, 127.4, 127.5, 128.7, 129.4, 132.1, 132.4, 134.7, 135.0, 139.9, 143.4, 147.2, 162.7, 167.0, 168.6, 170.2; HRMS (ES+) calcd for [C$_{37}$H$_{36}$N$_4$O$_7$S+H] 681.2377, found 681.2365; HPLC (I) t$_R$=20.49 min (99.75%), (II) t$_R$=42.05 min (100%).

79. Preparation of 4-(N-(4-(1-((4-cyanophenyl)sulfonyl)piperidin-4-yl)benzyl)-2-(N,4-dimethylphenyl-sulfonamido)acetamido)-2-hydroxybenzoic acid (27KG).

Benzyl protected 25 was globally deprotected on a 0.08 mmol scale via General Procedure I to furnish 27kg (52 mg, 93%): δ$_H$ (400 MHz, d$_6$-DMSO) 2.00-2.24 (m, 4H, CH$_2$), 2.66-2.78 (m, 6H, CH$_3$, CH and CH$_2$), 3.15 (s, 3H, CH$_3$), 4.13 (s, 2H, CH$_2$), 4.24-4.27 (m, 2H, CH$_2$), 5.12 (s, 2H, CH$_2$), 6.88 (d, J=8.0 Hz, 1H, CH), 6.97 (s, 1H, CH), 7.44 (d, J=8.0 Hz, 2H, CH), 7.40 (d, J=8.0 Hz, 2H, CH), 7.57 (d, J=8.0 Hz, 2H, CH), 7.94 (d, J=8.0 Hz, 2H, CH), 8.15-8.24 (m, 5H, CH); δ$_C$ (100 MHz, d$_6$-DMSO) 21.4, 32.3, 35.8, 37.0, 41.2, 46.6, 51.5, 52.8, 116.3, 116.7, 116.8, 117.1, 118.7, 126.7, 127.4, 128.1, 128.7, 129.4, 132.2, 132.8, 134.7, 135.0, 140.7, 143.4, 143.8, 147.0, 162.7, 167.0, 170.6; HRMS (ES+) calcd for [C$_{36}$H$_{36}$N$_4$O$_8$S+H] 717.2047, found 717.2036; HPLC (I) t$_R$=22.01 min (94.07%), (II) t$_R$=46.38 min (100%).

80. Preparation of 4-(N-(4-(1-(4-carboxyphenyl)piperidin-4-yl)benzyl)-2-(N,4-dimethylphenylsulfonamido)acetamido)-2-hydroxybenzoic acid (27KH).

Benzyl protected 26 was globally deprotected on a 0.05 mmol scale via General Procedure I to furnish 27kh (25 mg, 81%): δ$_H$ (400 MHz, d$_6$-DMSO) 1.58-1.73 (m, 2H, CH$_2$), 1.82 (d, J=12.8 Hz, 2H, CH$_2$), 2.35 (s, 3H, CH$_3$), 2.69-2.79 (m, 4H, CH$_3$ and CH), 2.90 (t, J=11.2 Hz, 2H, CH$_2$), 3.84 (s, 2H, CH$_2$), 4.80 (s, 2H, CH$_2$), 6.79 (d, J=8.4 Hz, 1H, CH), 6.87 (s, 1H, CH), 6.99 (d, J=8.8 Hz, 2H, CH), 7.09 (d, J=8.0 Hz, 2H, CH), 7.18 (d, J=8.0 Hz, 2H, CH), 7.35 (d, J=8.0 Hz, 2H, CH), 7.54 (d, J=8.0 Hz, 2H, CH), 7.76 (d, J=8.8 Hz, 2H, CH), 7.78 (d, J=8.4 Hz, 1H, CH); δ$_C$ (100 MHz, CDCl$_3$) 21.3, 32.5, 36.2, 41.4, 48.1, 48.9, 51.3, 52.0, 113.9, 116.5, 119.0, 119.3, 121.8, 127.0, 127.3, 128.0, 129.9, 131.3, 131.7, 135.0, 135.4, 143.5, 145.1, 147.5, 153.9, 161.9, 167.0, 167.6, 171.5; HRMS (ES+) calcd for [C$_{36}$H$_{37}$N$_3$O$_8$S+H] 672.2374, found 672.2372; HPLC (III) t$_R$=19.17 min (82.84%), (IV) t$_R$=39.60 min (90.47%).

81. Preparation of 4-(N-(4-(1-(4-carbamoylphenyl)piperidin-4-yl)benzyl)-2-(N,4-dimethylphenylsulfonamido)acetamido)-2-hydroxybenzoic acid (27KI).

Benzyl protected 61 was globally deprotected on a 0.07 mmol scale via General Procedure I to furnish 27ki (22 mg, 90%): δ$_H$ (400 MHz, d$_6$-DMSO) 1.66-1.80 (m, 2H, CH$_2$), 1.82-1.91 (m, 2H, CH$_2$), 2.33 (s, 3H, CH$_3$), 2.58-2.68 (m, 1H, CH), 2.77 (s, 3H, CH$_3$), 2.86 (t, J=12.0 Hz, 2H, CH$_2$), 3.72 (s, 2H, CH$_2$), 3.89 (d, J=12.0 Hz, 2H, CH$_2$), 4.75 (s, 2H, CH$_2$), 6.49 (d, J=7.2 Hz, 1H, CH), 6.58 (s, 1H, CH), 6.87 (d, J=8.8 Hz, 2H, CH), 7.00-7.09 (m, 4H, CH), 7.20 (d, J=8.0 Hz, 1H, CH), 7.54 (d, J=8.0 Hz, 1H, CH), 7.67 (d, J=8.4 Hz, 2H, CH), 7.80 (d, J=8.0 Hz, 1H, CH); δ$_C$ (100 MHz, d$_6$-DMSO) 21.2, 29.4, 32.5, 35.7, 41.9, 51.3, 52.7, 114.1, 116.4, 118.6, 121.6, 126.7, 127.2, 128.5, 128.9, 129.4, 132.0, 134.2, 134.9, 143.4, 144.9, 146.5, 150.2, 153.6, 162.4, 166.8, 169.2, 171.3; HRMS (ES+) calcd for [C$_{36}$H$_{38}$N$_4$O$_7$S+H] 671.2533, found 671.2545; HPLC (III) t$_R$=17.72 min (84.23%), (IV) t$_R$=24.81 min (74.07%).

82. Preparation of 4-(2-(N,4-dimethylphenylsulfonamido)-N-((3'-(methoxycarbonyl)biphenyl-4-yl)methyl)acetamido)-2-hydroxybenzoic acid (27LA).

Benzyl protected 28 was globally deprotected on a 0.08 mmol scale via General Procedure I to furnish 271a (39 mg, 81%): $\delta_H$ (400 MHz, CDCl$_3$) 2.36 (s, 3H, CH$_3$), 2.78 (s, 3H, CH$_3$), 3.87 (s, 3H, CH$_3$), 3.88 (s, 2H, CH$_2$), 4.90 (s, 2H, CH$_2$), 6.82 (dd, J=8.4 and 2.0 Hz, 1H, CH), 6.92 (d, J=2.0 Hz, 1H, CH), 7.29 (d, J=8.0 Hz, 2H, CH), 7.36 (d, J=8.0 Hz, 2H, CH), 7.56 (d, J=8.0 Hz, 2H, CH), 7.69 (t, J=8.0 Hz, 1H, CH), 7.64 (d, J=8.0 Hz, 2H, CH), 7.78 (d, J=8.4 Hz, 1H, CH), 7.93 (dd, J=7.6 and 1.6 Hz, 2H, CH), 8.16 (t, J=1.6 Hz, 1H, CH); $\delta_C$ (100 MHz, CDCl$_3$) 21.4, 35.9, 51.5, 52.1, 52.8, 116.6, 117.8, 118.7, 127.2, 127.5, 128.1, 128.3, 128.8, 129.1, 129.4, 130.5, 131.4, 132.2, 135.4, 136.0, 139.4, 140.8, 143.3, 146.7, 162.9, 163.0, 167.0, 171.8; HRMS (ES+) calcd for [C$_{32}$H$_{31}$N$_2$O$_8$S+H] 603.1800, found 603.1795; HPLC (I) $t_R$=23.65 min (100.0%), (II) $t_R$=48.73 min (100.0%).

83. Preparation of 4-(N-((3'-cyanobiphenyl-4-yl)methyl)-2-(N,4-dimethylphenylsulfonamido)acetamido)-2-hydroxybenzoic acid (27LB).

Benzyl protected 29 was globally deprotected on a 0.08 mmol scale via General Procedure I to furnish 271b (40 mg, 90%): $\delta_H$ (400 MHz, CDCl$_3$) 2.37 (s, 3H, CH$_3$), 2.80 (s, 3H, CH$_3$), 3.90 (s, 2H, CH$_2$), 4.91 (s, 2H, CH$_2$), 6.84 (dd, J=8.4 and 1.6 Hz, 1H, CH), 6.93 (s, 1H, CH), 7.30 (d, J=8.0 Hz, 2H, CH), 7.37 (d, J=8.0 Hz, 2H, CH), 7.57 (d, J=8.0 Hz, 2H, CH), 7.65 (t, J=8.0 Hz, 1H, CH), 7.70 (d, J=8.0 Hz, 2H, CH), 7.80 (t, J=8.0 Hz, 2H, CH), 8.02 (d, J=8.0 Hz, 1H, CH), 8.15 (s, 1H, CH); $\delta_C$ (100 MHz, CDCl$_3$) 20.8, 35.8, 50.8, 51.4, 112.0, 116.0, 118.4, 118.7, 120.0, 126.8, 126.9, 128.3, 128.5, 129.5, 130.0, 130.9, 131.2, 131.3, 135.0, 136.7, 137.1, 140.6, 143.0, 146.6, 161.6, 166.7, 171.0; HRMS (ES+) calcd for [C$_{31}$H$_{28}$N$_3$O$_6$S+H] 570.1696, found 570.1693; HPLC (I) $t_R$=22.84 min (98.3%), (II) $t_R$=47.61 min (98.43%).

84. Preparation of 4-(N-((3'-carbamoylbiphenyl-4-yl)methyl)-2-(N,4-dimethylphenylsulfonamido)acetamido)-2-hydroxybenzoic acid (27LC).

Benzyl protected 30 was globally deprotected on a 0.07 mmol scale via General Procedure I to furnish 271c (40 mg, 92%): $\delta_H$ (400 MHz, d$_6$-DMSO) 2.37 (s, 3H, CH$_3$), 2.80 (s, 3H, CH$_3$), 3.90 (s, 2H, CH$_2$), 4.91 (s, 2H, CH$_2$), 6.84 (dd, J=8.4 Hz, J=2.0 Hz, 1H, CH), 6.93 (d, J=2 Hz, 1H, CH), 7.29 (d, J=8.0 Hz, 2H, CH), 7.37 (d, J=8.4 Hz, 2H, CH), 7.42 (s, 1H, CH), 7.51-7.58 (m, 3H, CH), 7.77 (d, J=8.0 Hz, 2H, CH), 7.78-7.85 (m, 3H, CH), 8.09 (s, 1H, CH), 8.14 (s, 1H, CH); $\delta_C$ (100 MHz, CDCl$_3$) 20.6, 35.6, 50.55, 51.3, 114.1, 115.5, 117.1, 125.2, 126.3, 126.32, 126.6, 128.1, 128.8, 128.9, 129.3, 130.9, 134.6, 134.8, 136.3, 138.1, 139.3, 142.8, 156.9, 162.1, 166.5, 167.4, 170.7; HRMS (ES+) calcd for [C$_{31}$H$_{30}$N$_3$O$_7$S+H] 588.1794, found 588.1794; HPLC (I) $t_R$=17.05 min (100%), (II) $t_R$=39.80 min (98.94%).

85. Preparation of 4-(2-(N,4-dimethylphenylsulfonamido)-N-((4'-(methoxycarbonyl)biphenyl-4-yl)methyl)acetamido)-2-hydroxybenzoic acid (27LD).

Benzyl protected 31 was globally deprotected on a 0.06 mmol scale via General Procedure I to furnish 271d (34 mg, 93%): $\delta_H$ (400 MHz, CDCl$_3$) 2.40 (s, 3H, CH$_3$), 2.87 (s, 3H, CH$_3$), 3.87 (s, 2H, CH$_2$), 3.94 (s, 3H, CH$_3$), 4.91 (s, 2H, CH$_2$), 6.64 (d, J=7.6, 1H, CH), 6.74 (d, J=1.2 Hz, 1H, CH), 7.25-7.28 (m, 3H, CH), 7.53 (d, J=8.4 Hz, 2H, CH), 7.63 (d, J=8.4 Hz, 2H, CH), 7.66 (d, J=8.4 Hz, 2H, CH), 7.90 (d, J=8.4 Hz, 1H, CH), 8.09 (d, J=8.4 Hz, 2H, CH); $\delta_C$ (100 MHz, CDCl$_3$) 21.5, 35.9, 51.6, 52.1, 52.9, 116.9, 117.0, 119.0 126.9, 127.4, 127.5, 128.9, 129.1, 129.5, 130.1, 132.4, 135.1, 136.3, 139.4, 143.5, 144.9, 147.5, 162.9, 167.0, 167.2, 171.2; HRMS (ES+) calcd for [C$_{32}$H$_{31}$N$_2$O$_8$S+H] 603.1816, found 603.1795; HPLC (I) $t_R$=23.76 min (99.37%), (II) $t_R$=48.78 min (100.0%).

86. Preparation of 4'-((N-(4-carboxy-3-hydroxyphenyl)-2-(N,4-dimethylphenylsulfonamido)acetamido)methyl)-[1,1'-biphenyl]-4-carboxylic acid (27LE).

Benzyl protected 32 was globally deprotected on a 0.1 mmol scale via General Procedure I to furnish 271e (51 mg, 87%): $\delta_H$ (400 MHz, d$_6$-DMSO) 2.37 (s, 3H, CH$_3$), 2.80 (s, 3H, CH$_3$), 3.88 (s, 2H, CH$_2$), 4.89 (s, 2H, CH$_2$), 6.72 (dd, J=8.4 Hz and 1.6 Hz, 1H, CH), 6.81 (d, J=1.6 Hz, 1H, CH), 7.30 (d, J=8.4 Hz, 2H, CH), 7.37 (d, J=8.0 Hz, 2H, CH), 7.56 (d, J=8.4 Hz, 2H, CH), 7.68 (d, J=8.4 Hz, 2H, CH), 7.75 (d, J=8.4 Hz, 1H, CH), 7.79 (d, J=8.4 Hz, 2H, CH), 8.00 (d, J=8.4 Hz, 2H, CH); $\delta_C$ (100 MHz, d$_6$-DMSO) 20.8, 35.8, 50.8, 51.5, 115.8, 117.6, 118.1, 126.5, 126.8, 126.8, 128.3, 129.4, 129.5, 129.8, 131.1, 135.0, 137.1, 137.7, 143.0, 143.7, 145.8, 162.2, 166.6, 167.0; HRMS (ES+) calcd for [C$_{31}$H$_{29}$N$_2$O$_8$S+H] 589.1628, found 589.1639; HPLC (I) $t_R$=20.29 min (98.59%), (II) $t_R$=41.50 min (98.69%).

87. Preparation of 4-(N-((4'-cyanobiphenyl-4-yl)methyl)-2-(N,4-dimethylphenylsulfonamido)acetamido)-2-hydroxybenzoic acid (27LF).

Benzyl protected 33 was globally deprotected on a 0.09 mmol scale via General Procedure I to furnish 271f (42 mg, 82%): $\delta_H$ (400 MHz, CDCl$_3$) 2.36 (s, 3H, CH$_3$), 2.80 (s, 3H, CH$_3$), 3.69 (s, 2H, CH$_2$), 4.91 (s, 2H, CH$_2$), 6.78 (dd, J=8.4 and 1.6 Hz, 1H, CH), 6.89 (d, J=2.0 Hz, 1H, CH), 7.30 (d, J=8.0 Hz, 2H, CH), 7.37 (d, J=8.0 Hz, 2H, CH), 7.57 (d, J=8.0 Hz, 2H, CH), 7.70 (d, J=8.0 Hz, 2H, CH), 7.78 (d, J=8.0 Hz, 1H, CH), 7.86-7.92 (m, 4H, CH); $\delta_C$ (100 MHz, CDCl$_3$) 21.2, 36.2, 51.2, 51.8, 110.2, 118.6, 118.7, 119.1, 127.2, 127.3, 127.7, 128.8, 129.9, 131.6, 131.8, 132.0, 133.1, 135.4, 137.3, 138.0, 143.4, 144.4, 146.8, 162.1, 167.1, 167.2, 171.4; HRMS (ES+) calcd for [C$_{31}$H$_{28}$N$_3$O$_6$S+H] 570.1696, found 570.1693; HPLC (I) $t_R$=23.18 min (100.0%), (II) $t_R$=47.81 min (98.78%).

88. Preparation of 4-(N-((4'-carbamoylbiphenyl-4-yl)methyl)-2-(N,4-dimethylphenylsulfonamido)acetamido)-2-hydroxybenzoic acid (27LG).

Benzyl protected 34 was globally deprotected on a 0.08 mmol scale via General Procedure I to furnish 271g (39 mg, 83%): $\delta_H$ (400 MHz, d$_6$-DMSO) 2.37 (s, 3H, CH$_3$), 2.79 (s, 3H, CH$_3$), 3.89 (s, 2H, CH$_2$), 4.90 (s, 2H, CH$_2$), 6.83 (dd, J=8.4 Hz and 2.0 Hz, 1H, CH), 6.92 (d, J=2 Hz, 1H, CH), 7.28 (d, J=7.6 Hz, 2H, CH), 7.37, d, J=8.0 Hz, CH), 7.56 (d, J=8.0 Hz, 2H, CH), 7.67 (d, J=8.0 Hz, 2H, CH), 7.74 (d, J=8.4 Hz, 2H, CH), 7.79 (d, J=8.4 Hz, 1H, CH), 7.94 (d, J=8.4 Hz, 2H, CH), 8.01 (s, 1H, OH); $\delta_C$(100 MHz, d$_6$-DMSO) 21.2, 36.2, 51.1, 52.0, 116.0, 117.2, 120.4, 126.6, 127.1, 127.2, 128.4, 128.7, 129.9, 131.4, 133.3, 135.5, 137.3, 138.3, 142.5, 143.4, 163.0, 167.1, 167.8, 171.2, 172.3; HRMS (ES+) calcd for [C$_{31}$H$_{30}$N$_3$O$_7$S+H] 588.1789, found 588.1798; HPLC (I) $t_R$=19.49 min (91.83%), (II) $t_R$=40.09 min (98.42%).

89. Preparation of 4-(2-(N,4-dimethylphenylsulfonamido)-N-((3'-(methoxycarbonyl)terphenyl-4-yl)methyl)-acetamido)-2-hydroxybenzoic acid (27NA).

Benzyl protected 35 was globally deprotected on a 0.06 mmol scale via General Procedure I to furnish 27na (42 mg, 100%): $\delta_H$ (400 MHz, d$_6$-DMSO) 2.36 (s, 3H, CH$_3$), 2.81 (s, 3H, CH$_3$), 4.90 (s, 2H, CH$_2$), 6.80 (d, 1H, J=8.4 Hz, CH), 6.89 (s, 1H, CH), 7.29 (d, J=8.4 Hz, 2H, CH), 7.36 (d, J=8.0 Hz, 2H, CH), 7.61-7.67 (m, 5H, CH), 7.76-7.79 (m, 4H, CH), 7.96 (d, J=7.6 Hz, 1H, CH), 8.00 (d, J=8.0 Hz, 1H, CH), 8.24 (s, 1H, CH), 8.32 (s, 1H, CH); $\delta_C$ (100 MHz, d$_6$-DMSO) 20.8, 35.8, 50.8, 51.5, 52.1, 115.9, 117.4, 118.1, 126.4, 126.8, 127.1, 127.2, 127.3, 127.8, 128.0, 128.3, 129.4, 129.5, 130.3, 131.2, 135.0, 136.3, 137.8, 138.1, 139.1, 139.9, 143.0, 146.3, 161.8, 166.0, 166.7, 171.0;

90. Preparation of 4'-((N-(4-carboxy-3-hydroxyphenyl)-2-(N,4-dimethylphenylsulfonamido)acetamido)methyl)terphenyl-3-carboxylic acid (27NB).

Benzyl protected 36 was globally deprotected on a 0.08 mmol scale via General Procedure I to furnish 27nb (46 mg, 87%): $\delta_H$ (400 MHz, $d_6$-DMSO) 2.37 (s, 3H, $CH_3$), 2.80 (s, 3H, $CH_3$), 3.87 (s, 2H, $CH_2$), 4.87 (s, 2H, $CH_2$), 6.68 (dd, J=8.4 and 1.2 Hz, 1H, CH), 6.76 (d, J=1.2 Hz, 1H, CH), 7.29 (d, J=8.0 Hz, 2H, CH), 7.37 (d, J=8.0 Hz, 2H, CH), 7.56 (d, J=8.0 Hz, 2H, CH), 7.62 (t, J=8.0 Hz, 2H, CH), 7.68 (d, J=8.0 Hz, 1H, CH), 7.73 (d, J=8.0 Hz, 1H, CH), 7.79 (s, 4H, CH), 7.94 (d, J=8.0 Hz, 1H, CH) 7.98 (d, J=8.0 Hz, 1H, CH), 8.23 (s, 1H, CH); $\delta_C$ (100 MHz, $d_6$-DMSO) 20.6, 35.8, 50.8, 51.5, 113.0, 116.0, 118.3, 126.4, 126.9, 127.0, 127.1, 127.2, 128.2, 128.3, 129.2, 129.5, 130.8, 131.3, 131.4, 135.0, 136.3, 138.0, 138.2, 138.9, 139.8, 143.0, 146.6, 161.7, 166.7, 167.1, 171.0; HRMS (ES+) calcd for $[C_{37}H_{32}N_2O_8S+H]$ 665.1952, found 665.1957; HPLC (I) $t_R$=21.07 min (96.72%), (II) $t_R$=44.44 min (97.21%).

91. Preparation of 4-(N-((3'-cyanoterphenyl-4-yl)methyl)-2-(N,4-dimethylphenylsulfonamido)acetamido)-2-hydroxybenzoic acid (27NC).

Benzyl protected 37 was globally deprotected on a 0.12 mmol scale via General Procedure I to furnish 27nc (64 mg, 83%): $\delta_H$ (400 MHz, $d_6$-DMSO) 2.36 (s, 3H, $CH_3$), 2.82 (s, 3H, $CH_3$), 3.92 (s, 2H, $CH_2$), 4.92 (s, 2H, $CH_2$), 6.85 (dd, J=8.4 and 1.6 Hz, 1H, CH), 6.95 (d, J=1.6 Hz, 1H, CH), 7.30 (d, J=8.0 Hz, 2H, CH), 7.36 (d, J=8.4 Hz, 2H, CH), 7.58 (d, J=8.4 Hz, 2H, CH), 7.66-7.71 (m, 3H, CH), 7.78-7.86 (m, 6H, CH), 8.05 (d, J=8.0 Hz, 1H, CH), 8.20 (s, 1H, CH); $\delta_C$ (100 MHz, $d_6$-DMSO) 20.8, 35.8, 50.9, 51.5, 112.0, 112.5, 116.0, 118.5, 118.7, 126.5, 126.9, 127.0, 127.3, 128.3, 129.5, 129.9, 130.0, 130.9, 131.2, 131.3, 135.0, 136.4, 136.8, 138.0, 139.4, 140.5, 143.0, 146.8, 161.6, 166.8, 171.1; HRMS (ES+) calcd for $[C_{37}H_{32}N_3O_6S+H]$ 646.2006, found 646.1986; HPLC (I) $t_R$=22.62 min (88.65%), (II) $t_R$=48.72 min (90.98%).

92. Preparation of 4-(N-((3'-carbamoylterphenyl-4-yl)methyl)-2-(N,4-dimethylphenylsulfonamido)acetamido)-2-hydroxybenzoic acid (27ND).

Benzyl protected 38 was globally deprotected on a 0.05 mmol scale via General Procedure I to furnish 27nd (31 mg, 97%): $\delta_H$ (400 MHz, $d_6$-DMSO) 2.36 (s, 3H, $CH_3$), 2.81 (s, 3H, $CH_3$), 3.91 (s, 2H, $CH_2$), 4.91 (s, 2H, $CH_2$), 6.91 (dd, J=7.6 and 1.2 Hz, 1H, CH), 6.90 (s, 1H, CH), 7.30 (d, J=8.0 Hz, 2H, CH), 7.37 (d, J=8.0 Hz, 2H, CH), 7.53-7.57 (m, 3H, CH), 7.68 (d, J=8.4 Hz, 2H, CH), 7.73 (d, J=7.6 Hz, 1H, CH), 7.75-7.88 (m, 6H, CH), 8.23 (s, 1H, CH); $\delta_C$ (100 MHz, $d_6$-DMSO) 20.8, 35.8, 50.8, 51.5, 113.3, 115.9, 118.2, 125.4, 126.4, 126.7, 126.9, 127.0, 127.2, 128.3, 128.8, 129.1, 129.3, 129.5, 131.2, 134.9, 135.0, 136.3, 138.2, 138.4, 139.4, 143.0, 146.4, 161.8, 166.7, 167.7, 171.0; HRMS (ES+) calcd for $[C_{37}H_{33}N_3O_7S+H]$ 663.2111, found 665.2109; HPLC (I) $t_R$=19.89 min (100%), (II) $t_R$=41.08 min (100%).

93. Preparation of 4-(2-(N,4-dimethylphenylsulfonamido)-N-((4'-(methoxycarbonyl)terphenyl-4-yl)methyl)-acetamido)-2-hydroxybenzoic acid (27NE).

Benzyl protected 39 was globally deprotected on a 0.07 mmol scale via General Procedure I to furnish 27ne (46 mg, 97%): $\delta_H$ (400 MHz, $d_6$-DMSO) 2.38 (s, 3H, $CH_3$), 2.81 (s, 3H, $CH_3$), 3.88 (s, 5H, $CH_2$ and $CH_3$), 4.91 (s, 2H, $CH_2$), 6.80 (d, J=8.4 Hz, 1H, CH), 6.89 (s, 1H, CH), 7.30 (d, J=8.4 Hz, 2H, CH), 7.38 (d, J=8.0 Hz, 2H, CH), 7.57 (d, J=8.4 Hz, 2H, CH), 7.69 (d, J=8.0 Hz, 2H, CH), 7.75-7.84 (m, 5H, CH), 7.90 (d, J=8.8 Hz, 2H, CH), 8.03 (d, J=8.8 Hz, 2H, CH) $\delta_C$ (100 MHz, $d_6$-DMSO) 20.8, 35.8, 50.8, 51.5, 52.0, 113.5, 115.9, 118.0, 126.4, 126.6, 126.8, 127.0, 127.2, 127.3, 128.3, 129.5, 129.7, 131.2, 135.0, 136.4, 137.5, 138.0, 139.4, 143.0, 143.9, 146.3, 161.8, 165.9, 166.7, 171.0; HRMS (ES+) calcd for $[C_{37}H_{32}N_2O_8S+H]$ 679.2108, found 679.2081; HPLC (I) $t_R$=23.54 min (100%), (II) $t_R$=51.01 min (100%).

94. Preparation of 4'-((N-(4-carboxy-3-hydroxyphenyl)-2-(N,4-dimethylphenylsulfonamido)acetamido)methyl)terphenyl-4-carboxylic acid (27NF).

Benzyl protected 46 was globally deprotected on a 0.05 mmol scale via General Procedure I to furnish 27nf (28 mg, 89%): $\delta_H$(400 MHz, $d_6$-DMSO) 2.37 (s, 2H, $CH_3$), 2.80 (s, 3H, $CH_3$), 3.88 (s, 2H, $CH_2$), 4.88 (s, 2H, $CH_2$), 6.72 (d, J=6.8 Hz, 1H, CH), 6.81 (s, 1H, CH), 7.29 (d, J=6.8 Hz, 2H, CH), 7.37 (d, J=7.6 Hz, 2H, CH), 7.56 (d, J=6.8 Hz, 2H, CH), 7.68 (d, J=7.2 Hz, 2H, CH), 7.78-7.85 (m, 7H, CH), 8.03 (d, J=7.2 Hz, 2H, CH); $\delta_C$ (100 MHz, $d_6$-DMSO) 20.8, 35.7, 51.5, 55.7, 107.4, 107.7, 117.4, 126.4, 126.5, 126.8, 127.1, 127.0, 127.3, 128.3, 129.5, 129.8, 131.1, 136.4, 137.0, 137.7, 138.0, 139.3, 143.0, 143.5, 158.0, 162.3, 166.7, 166.9, 171.4; HRMS (ES+) calcd for $[C_{37}H_{32}N_2O_8S+H]$ 665.1952, found 665.1962; HPLC (I) $t_R$=17.25 min (92.99%), (II) $t_R$=37.13 min (91.78%).

95. Preparation of 4-(N-((4'-cyanoterphenyl-4-yl)methyl)-2-(N,4-dimethylphenylsulfonamido)acetamido)-2-hydroxybenzoic acid (27NG).

Benzyl protected 44 was globally deprotected on a 0.1 mmol scale via General Procedure I to furnish 27ng (53 mg, 82%): $\delta_H$ (400 MHz, $d_6$-DMSO) 2.36 (s, 3H, $CH_3$), 2.81 (s, 3H, $CH_3$), 3.91 (s, 2H, $CH_2$), 4.92 (s, 2H, $CH_2$), 6.85 (d, J=8.4 Hz, 1H, CH), 6.95 (s, 1H, CH), 7.30 (d, J=8.0 Hz, 2H, CH), 7.36 (d, J=8.0 Hz, 2H, CH), 7.58 (d, J=8.0 Hz, 2H, CH), 7.68 (d, J=8.0 Hz, 2H, CH), 7.78-7.82 (m, 5H, CH), 7.93-7.95 (m, 4H, CH); $\delta_C$ (100 MHz, $d_6$-DMSO) 20.8, 35.8, 50.9, 51.5, 109.9, 112.5, 116.0, 118.5, 118.7, 126.5, 126.9, 127.1, 127.2, 127.5, 128.3, 129.5, 131.3, 132.7, 135.0, 136.5, 137.0, 138.0, 139.8, 143.0, 146.8, 161.5, 166.7, 171.1. HRMS (ES+) calcd for $[C_{37}H_{32}N_3O_6S+H]$ 646.2006, found 646.1987; HPLC (I) $t_R$=22.71 min (94.15%), (II) $t_R$=49.13 min (96.29%).

96. Preparation of 4-(N-((4''-carbamoyl-[1,1':4',1''-terphenyl]-4-yl)methyl)-2-(N,4-dimethylphenylsulfonamido)acetamido)-2-hydroxybenzoic acid (27NH).

Benzyl protected 45 was globally deprotected on a 0.05 mmol scale via General Procedure I to furnish 27nh (26 mg, 87%): $\delta_H$(400 MHz, $d_6$-DMSO) 2.35 (s, 3H, $CH_3$), 2.79 (s, 3H, $CH_3$), 3.87 (s, 2H, $CH_2$), 4.88 (s, 2H, $CH_2$), 6.78 (d, J=6.4 Hz, 1H, CH), 6.86 (s, 1H, CH), 7.29 (d, J=8.4 Hz, 2H, CH), 7.37 (d, J=8.0 Hz, 2H, CH), 7.55-7.69 (m, 6H, CH), 7.76-7.84 (m, 4H, CH), 7.95-8.04 (m, 3H, CH); $\delta_C$ (100 MHz, $d_6$-DMSO) 21.3, 30.7, 51.3, 52.0, 103.0, 116.2, 118.4, 126.2, 126.5, 127.0, 127.1, 127.3, 128.2, 128.4, 128.7, 128.8, 129.6, 131.4, 131.5, 132.0, 132.1, 132.2, 133.1, 133.2, 135.1, 136.4, 138.1, 138.3, 139.1, 142.1, 143.1, 146.8, 161.7, 166.8, 167.5, 171.1, 172.0; HRMS (ES+) calcd for $[C_{37}H_{33}N_3O_7S+H]$ 664.2111, found 664.2141; HPLC (III) $t_R$=19.22 min (76.63%), (IV) $t_R$=43.81 min (79.95%).

97. Preparation of 4-(N-(4-cyclohexylbenzyl)-2-(N,3-dimethylphenylsulfonamido)acetamido)-2-hydroxy-benzoic acid (45A).

Benzyl protected 47 was globally deprotected on a 0.13 mmol scale via General Procedure I to furnish 45a (68 mg, 91%): $\delta_H$ (400 MHz, $CDCl_3$) 1.31-1.41 (m, 5H, $CH_2$), 1.73-1.87 (m, 5H, $CH_2$), 2.40 (s, 3H, $CH_3$), 2.43-2.48 (m, 1H, CH), 2.89 (s, 3H, CH$_3$), 3.86 (s, 2H, CH$_2$), 4.84 (s, 2H, CH$_2$), 6.63 (dd, J=8.4 and 1.6 Hz, 1H, CH), 6.73 (d, J=2.0 Hz, 1H, CH), 7.08 (d, J=8.0 Hz, 2H, CH), 7.12 (d, J=8.0 Hz, 2H, CH), 7.35-7.40 (m, 2H, CH), 7.57 (s, 2H, CH), 7.89 (d, J=8.8 Hz, 1H, CH); δ$_C$ (100 MHz, CDCl$_3$) 21.4, 26.1, 26.9, 34.4, 36.0, 44.2, 51.7, 53.1, 111.2, 111.7, 119.2, 124.7, 127.1, 127.9, 128.4, 128.8, 132.2, 133.5, 133.6, 137.8, 139.1, 147.8, 148.1, 163.0, 167.0, 171.9; HRMS (ES+) calcd for [C$_{30}$H$_{34}$N$_2$O$_6$S+H] 551.2210, found 551.2199; HPLC (III) t$_R$=22.33 min (76.40%), (IV) t$_R$=50.92 min (100.00%).

98. Preparation of 4-(N-(4-cyclohexylbenzyl)-2-(N,2,4,6-tetramethylphenylsulfonamido)acetamido)-2-hydroxy-benzoic acid (45B).

Benzyl protected 48 was globally deprotected on a 0.06 mmol scale via General Procedure I to furnish 45b (31 mg, 89%): δ$_H$ (400 MHz, d$_6$-DMSO) 1.26-1.40 (m, 5H, CH$_2$), 1.64-1.81 (m, 5H, CH$_2$), 2.26 (s, 3H, CH$_3$), 2.44 (s, 7H, CH$_3$ and CH), 2.84 (s, 3H, CH$_3$), 3.84 (s, 2H, CH$_2$), 4.75 (s, 2H, CH$_2$), 6.62 (dd, J=8.4 and 2.0 Hz, 1H, CH), 6.70 (d, J=2.0 Hz, 1H, CH), 6.99 (d, J=8.0 Hz, 2H, CH), 7.03 (s, 2H, CH), 7.11 (d, J=8.0 Hz, 2H, CH), 7.75 (d, J=8.4 Hz, 1H, CH); δ$_C$ (100 MHz, d$_6$-DMSO) 20.3, 22.1, 25.4, 26.2, 33.8, 34.4, 43.2, 49.1, 51.5, 116.0, 118.4, 120.2, 126.5, 127.4, 131.2, 131.7, 132.1, 134.1, 139.4, 142.1, 146.7, 146.7, 161.5, 166.6, 171.0; HRMS (ES+) calcd for [C$_{32}$H$_{38}$N$_2$O$_6$S+H] 613.2366, found 613.2356; HPLC (V) t$_R$=21.29 min (96.82%), (VI) t$_R$=37.54 min (95.30%).

99. Preparation of 4-(N-(4-cyclohexylbenzyl)-2-(N-methylbiphenyl-4-ylsulfonamido)acetamido)-2-hydroxy-benzoic acid (45C).

Benzyl protected 49 was globally deprotected on a 0.06 mmol scale via General Procedure I to furnish 45c (34 mg, 97%): δ$_H$ (400 MHz, d$_6$-DMSO) 1.23-1.38 (m, 5H, CH$_2$), 1.62-1.78 (m, 5H, CH$_2$), 2.35-2.44 (m, 1H, CH), 2.08 (s, 3H, CH$_3$), 3.96 (s, 2H, CH$_2$), 4.78 (s, 2H, CH$_2$), 6.80 (dd, J=8.4 and 2.0 Hz, 1H, CH), 6.89 (d, J=2.0 Hz, 1H, CH), 7.04 (d, J=8.0 Hz, 2H, CH), 7.09 (d, J=8.4 Hz, 2H, CH), 7.44 (d, J=8.0 Hz, 1H, CH), 7.51 (t, J=7.6 Hz, 2H, CH), 7.68-7.81 (m, 5H, CH), 7.86 (d, J=8.4 Hz, 2H, CH); δ$_C$ (100 MHz, d$_6$-DMSO) 25.4, 26.2, 33.7, 35.8, 43.2, 50.7, 51.6, 115.9, 118.4, 120.3, 126.5, 126.9, 127.2, 127.4, 127.5, 128.4, 129.0, 131.3, 134.1, 136.9, 138.3, 144.1, 146.3, 146.8, 161.6, 166.5, 171.1; HRMS (ES+) calcd for [C$_{35}$H$_{36}$N$_2$O$_6$S+H] 613.2366, found 613.2356; HPLC (V) t$_R$=22.09 min (96.50%), (VI) t$_R$=38.47 min (89.47%).

100. Preparation of 4-(N-(4-cyclohexylbenzyl)-2-(N-methylnaphthalene-2-sulfonamido)acetamido)-2-hydroxy-benzoic acid (45D).

Benzyl protected 50 was globally deprotected on a 0.07 mmol scale via General Procedure I to furnish 45d (35 mg, 87%): δ$_H$ (400 MHz, d$_6$-DMSO) 1.28-1.39 (m, 5H, CH$_2$), 1.62-1.79 (m, 5H, CH$_2$), 2.37-2.46 (m, 1H, CH), 2.88 (s, 3H, CH$_3$), 3.95 (s, 2H, CH$_2$), 4.76 (s, 2H, CH$_2$), 6.80 (dd, J=8.4 and 2.4 Hz, 1H, CH), 6.88 (d, J=2.0 Hz, 1H, CH), 7.02 (d, J=8.0 Hz, 2H, CH), 7.08 (d, J=8.0 Hz, 2H, CH), 7.62-7.73 (m, 3H, CH), 7.79 (d, J=8.4 Hz, 1H, CH), 8.04 (d, J=8.4 Hz, 1H, CH), 8.09 (d, J=8.8 Hz, 1H, CH), 8.12 (d, J=8.0 Hz, 1H, CH), 8.35 (d, J=1.6 Hz, 1H, CH); δ$_C$(100 MHz, d$_6$-DMSO) 25.4, 26.2, 33.8, 35.9, 43.2, 50.8, 51.5, 112.5, 116.0, 118.5, 119.9, 122.5, 126.5, 127.4, 127.7, 127.8, 128.7, 129.1, 131.3, 131.6, 134.1, 134.2, 135.1, 146.3 146.8, 161.5, 166.5, 171.1; HRMS (ES+) calcd for [C$_{33}$H$_{34}$N$_2$O$_6$S+H] 587.2210, found 587.2196; HPLC (V) t$_R$=20.69 min (98.96%), (VI) t$_R$=35.01 min (95.03%).

101. Preparation of 4-(N-(4-cyclohexylbenzyl)-2-(N-methylnaphthalene-1-sulfonamido)acetamido)-2-hydroxy-benzoic acid (45E).

Benzyl protected 62 was globally deprotected on a 0.12 mmol scale via General Procedure I to furnish 45e (72 mg, 94%): δ$_H$ (400 MHz, CDCl$_3$) 1.30-1.45 (m, 5H, CH$_2$), 1.70-1.92 (m, 5H, CH$_2$), 2.42-2.52 (m, 1H, CH), 2.99 (s, 3H, CH$_3$), 3.98 (s, 2H, CH$_2$), 4.80 (s, 2H, CH$_2$), 6.58 (dd, J=8.0 and 2.0 Hz, 1H, CH), 6.70 (d, J=2.0 Hz, 1H, CH), 7.04 (d, J=8.0 Hz, 2H, CH), 7.11 (d, J=8.0 Hz, 2H, CH), 7.51 (t, J=8.0 Hz, 1H, CH), 7.56-7.61 (m, 2H, CH), 7.87 (d, J=8.4 Hz, 1H, CH), 7.89-7.92 (m, 1H, CH), 8.04 (d, J=8.0 Hz, 1H, CH), 8.25 (d, J=7.2 Hz, 1H, CH), 8.61 (d, J=8.0 Hz, 1H, CH); δ$_C$ (100 MHz, CDCl$_3$) 25.9, 26.7, 34.2, 35.9, 44.1, 50.9, 53.0, 112.8, 117.2, 119.1, 123.9, 124.9, 126.7, 126.9, 128.0, 128.3, 128.6, 128.7, 129.6, 132.2, 133.2, 133.7, 134.2, 147.6, 162.8, 167.0, 172.1; HRMS (ES+) calcd for [C$_{33}$H$_{34}$N$_2$O$_6$S+H] 587.2210. Found 587.2196; HPLC (III) t$_R$=19.22 min (76.63%), (IV) t$_R$=43.81 min (79.95%).

102. Preparation of 4-(N-(4-cyclohexylbenzyl)-2-(N-methylquinoline-8-sulfonamido)acetamido)-2-hydroxy-benzoic acid (45F).

Benzyl protected 51 was globally deprotected on a 0.29 mmol scale via General Procedure I to furnish 45f (123 mg, 84%): δ$_H$ (400 MHz, CDCl$_3$) 1.29-1.41 (m, 5H, CH$_2$), 1.69-1.86 (m, 5H, CH$_2$), 2.40-2.52 (m, 1H, CH), 2.77 (s, 3H, CH$_3$), 3.86 (s, 2H, CH$_2$), 4.85 (s, 2H, CH$_2$), 6.55 (t, J=8.0 Hz, 1H, CH), 6.61 (d, J=8.0 Hz, 1H, CH), 6.70 (s, 1H, CH), 7.04-7.14 (m, 8H, CH), 7.47 (d, J=8.0 Hz, 1H, CH), 7.86 (d, J=8.4 Hz, 1H, CH); δ$_C$ (100 MHz, CDCl$_3$) 26.7, 34.2, 36.1, 41.5, 44.1, 50.6, 53.1, 114.9, 116.9, 119.1, 123.8, 124.8, 126.9, 128.3, 128.9 (br), 132.2, 133.1, 134.4, 147.7, 162.8, 167.8, 171.9; HRMS (ES+) calcd for [C$_{32}$H$_{33}$N$_3$O$_6$S+H] 592.2475. Found 592.2467; HPLC (III) t$_R$=23.95 min (100.00%), (IV) t$_R$=53.41 min (100.00%).

103. Preparation of 4-(N-(4-cyclohexylbenzyl)-2-(5-(dimethylamino)-N-methylnaphthalene-1-sulfonamido)acetamido)-2-hydroxybenzoic acid (45G).

Benzyl protected 52 was globally deprotected on a 0.11 mmol scale via General Procedure I to furnish 45g (71 mg, 92%): δ$_H$ (400 MHz, CDCl$_3$) 1.23-1.40 (m, 5H, CH$_2$), 1.72-1.83 (m, 5H, CH$_2$), 2.42-2.46 (m, 1H, CH), 3.02 (s, 3H, CH$_3$), 3.33 (s, 6H, CH$_3$), 3.92 (s, 2H, CH$_2$), 4.78 (s, 2H, CH$_2$), 6.43 (d, J=8.0 Hz, 1H, CH), 6.56 (s, 1H, CH), 7.04 (d, J=8.0 Hz, 2H, CH), 7.10 (d, J=8.0 Hz, 2H, CH), 7.58-7.65 (m, 3H, CH), 7.70 (t, J=8.0 Hz, 1H, CH), 8.31 (d, J=7.2 Hz, 1H, CH), 8.59 (d, J=8.4 Hz, 1H, CH), 8.62-8.66 (m, 1H, CH); δ$_C$(100 MHz, CDCl$_3$) 26.2, 27.0, 34.5, 36.0, 44.3, 46.8, 51.3, 53.2, 112.4, 117.7, 118.9, 126.2, 126.3, 127.2, 127.3, 127.5, 128.6, 130.2, 130.6, 132.2, 133.5, 135.7, 140.0, 142.1, 147.2, 147.9, 158.2, 162.7, 166.9, 171.8; HRMS (ES+) calcd for [C$_{35}$H$_{39}$N$_3$O$_6$S+H] 630.2632, found 630.2622; HPLC (III) t$_R$=21.26 min (90.39%), (IV) t$_R$=46.32 min (93.61%).

104. Preparation of 4-(N-(4-cyclohexylbenzyl)-2-(N,1-dimethyl-1H-imidazole-4-sulfonamido)acetamido)-2-hydroxybenzoic acid (45H).

Benzyl protected 53 was globally deprotected on a 0.07 mmol scale via General Procedure I to furnish 45h (38 mg, 98%): δ$_H$(400 MHz, CDCl$_3$) 1.20-1.38 (m, 5H, CH$_2$), 1.70-1.83 (m, 5H, CH$_2$), 2.39-2.49 (m, 1H, CH), 2.91 (s, 3H, CH$_3$), 3.74 (s, 3H, CH$_3$), 3.96 (s, 2H, CH$_2$), 4.79 (s, 2H, CH$_2$), 6.55-6.64 (m, 1H, CH), 6.67 (s, 1H, CH), 7.03-7.10 (m, 4H, CH), 7.45 (s, 1H, CH), 7.74 (d, J=7.6 Hz, 1H, CH); δ$_C$ (100 MHz, CDCl$_3$) 26.2, 27.0, 34.5, 44.3, 52.1, 53.2, 113.1, 116.7, 119.0, 127.1, 127.2, 128.6, 132.2, 133.9, 139.2, 139.3, 146.9, 147.6, 163.0, 167.0, 172.2; HRMS (ES+) calcd for [C$_{27}$H$_{33}$N$_4$O$_6$S+H] 541.2115, found 541.2104; HPLC (III) t$_R$=19.10 min (100.00%), (IV) t$_R$=42.32 min (100.00%).

105. Preparation of 4-(2-(4-cyano-N-methylphenylsulfonamido)-N-(4-cyclohexylbenzyl)acetamido)-2-hydroxybenzoic acid (45I).

Benzyl protected 54 was globally deprotected on a 0.13 mmol scale via General Procedure I to furnish 45i (65 mg, 87%): $\delta_H$ (400 MHz, CDCl$_3$) 1.25-1.41 (m, 5H, CH$_2$), 1.71-1.85 (m, 5H, CH$_2$), 2.43-2.53 (m, 1H, CH), 2.93 (s, 3H, CH$_3$), 3.96 (s, 2H, CH$_2$), 4.78 (s, 2H, CH$_2$), 6.61 (dd, J=8.4 and 1.6 Hz, 1H, CH), 6.72 (d, J=1.6 Hz, 1H, CH), 7.03 (d, J=8.0 Hz, 2H, CH), 7.13 (d, J=8.0 Hz, 2H, CH), 7.77 (d, J=8.4 Hz, 2H, CH), 7.89-7.94 (m, 3H, CH); $\delta_C$ (100 MHz, CDCl$_3$) 26.2, 27.0, 34.5, 36.1, 44.4, 51.9, 53.4, 111.7, 116.4, 117.3, 117.6, 119.3, 127.3, 128.3, 128.6, 132.7, 132.8, 133.3, 143.2, 147.9, 148.2, 163.2, 166.8, 172.7; HRMS (ES+) calcd for [C$_{30}$H$_{31}$N$_3$O$_6$S+H] 562.2006, found 562.1997; HPLC (III) $t_R$=8.69 min (92.00%), (IV) $t_R$=45.44 min (91.69%).

106. Preparation of 4-(2-O-bromo-N-methylphenylsulfonamido)-(4-cyclohexylbenzyl)acetamido)-2-hydroxy-benzoic acid (45J).

Benzyl protected 55 was globally deprotected on a 0.12 mmol scale via General Procedure I to furnish 45j (68 mg, 87%): $\delta_H$ (400 MHz, CDCl$_3$) 1.24-1.40 (m, 5H, CH$_2$), 1.68-1.84 (m, 5H, CH$_2$), 2.42-2.51 (m, 1H, CH), 2.90 (s, 3H, CH$_3$), 3.85 (s, 2H, CH$_2$), 4.74 (s, 2H, CH$_2$), 6.50 (dd, J=8.4 and 1.6 Hz, 1H, CH), 6.63 (d, J=1.6 Hz, 1H, CH), 7.01 (d, J=8.0 Hz, 2H, CH), 7.08 (d, J=8.0 Hz, 2H, CH), 7.59 (d, J=8.8 Hz, 2H, CH), 7.64 (d, J=8.8 Hz, 2H, CH), 7.85 (d, J=8.4 Hz, 1H, CH); $\delta_C$ (100 MHz, CDCl$_3$) 26.2, 27.0, 34.5, 36.0, 39.5, 44.3, 51.5, 53.1, 113.2, 116.8, 118.8, 126.1, 127.1, 127.6, 129.2, 132.2, 132.3, 133.8, 138.0, 146.9, 147.7, 163.0, 166.6, 172.0; HRMS (ES+) calcd for [C$_{29}$H$_{31}$BrN$_2$O$_6$S+H] 615.1158, found 615.1132; HPLC (III) $t_R$=23.36 min (86.52%), (IV) $t_R$=53.43 min (100.00%).

107. Preparation of 4-(2-(4-chloro-N-methylphenylsulfonamido)-(4-cyclohexylbenzyl)acetamido)-2-hydroxy-benzoic acid (45K).

Benzyl protected 56 was globally deprotected on a 0.12 mmol scale via General Procedure I to furnish 45k (49 mg, 72%): $\delta_H$ (400 MHz, CDCl$_3$) 1.34 (m, 5H, CH$_2$), 1.75 (m, 5H, CH$_2$), 2.44 (m, 1H, CH), 2.84 (s, 3H, CH$_3$), 3.96 (s, 2H, CH$_2$), 4.77 (s, 2H, CH$_2$), 6.80 (dd, J=8.4 and 2.0 Hz, 1H, CH), 6.89 (d, J=2.0 Hz, 1H, CH), 7.04 (d, J=8.0 Hz, 2H, CH), 7.13 (d, J=8.0 Hz, 2H, CH), 7.64 (d, J=8.8 Hz, 2H, CH), 7.72 (d, J=8.8 Hz, 2H, CH), 7.78 (d, J=8.4 Hz, 1H, CH); $\delta_C$ (100 MHz, CDCl$_3$) 25.4, 26.2, 33.8, 35.8, 43.2, 50.8, 51.6, 112.4, 115.9, 118.4, 126.5, 127.4, 128.8, 129.1, 131.2, 134.1, 137.1, 137.5, 146.4, 146.8, 161.5, 166.4, 171.0; HRMS (ES+) calcd for [C$_{29}$H$_{31}$ClN$_2$O$_6$S+H] 571.1664, found 571.1682; HPLC (V) $t_R$=20.92 min (96.73%), (VI) $t_R$=35.97 min (97.88%).

108. Preparation of 4-(N-(4-cyclohexylbenzyl)-2-(4-fluoro-N-methylphenylsulfonamido)acetamido)-2-hydroxy benzoic acid (45L).

Benzyl protected 57 was globally deprotected on a 0.06 mmol scale via General Procedure I to furnish 45l (30 mg, 85%): $\delta_H$ (400 MHz, d$_6$-DMSO) 1.28-1.39 (m, 5H, CH$_2$), 1.62-1.79 (m, 5H, CH$_2$), 2.37-2.46 (m, 1H, CH), 2.88 (s, 3H, CH$_3$), 3.95 (s, 2H, CH$_2$), 4.76 (s, 2H, CH$_2$), 6.80 (dd, J=8.4 and 2.4 Hz, 1H, CH), 6.88 (d, J=2.0 Hz, 1H, CH), 7.02 (d, J=8.0 Hz, 2H, CH), 7.08 (d, J=8.0 Hz, 2H, CH), 7.62-7.73 (m, 3H, CH), 7.79 (d, J=8.4 Hz, 1H, CH), 8.04 (d, J=8.4 Hz, 1H, CH), 8.09 (d, J=8.8 Hz, 1H, CH), 8.12 (d, J=8.0 Hz, 1H, CH), 8.35 (d, J=1.6 Hz, 1H, CH); $\delta_C$(100 MHz, d$_6$-DMSO) 25.4, 26.2, 33.8, 35.9, 43.2, 50.8, 51.5, 112.5, 116.0, 118.5, 119.9, 122.5, 126.5, 127.4, 127.7, 127.8, 128.7, 129.1, 131.3, 131.6, 134.1, 134.2, 135.1, 146.3, 146.8, 161.5, 166.5, 171.1; HRMS (ES+) calcd for [C$_{33}$H$_{34}$N$_2$O$_6$S+H] 587.2210, found 587.2196; HPLC (V) $t_R$=19.62 min (95.61%), (VI) $t_R$=33.96 min (95.10%).

109. Preparation of 4-(N-(4-cyclohexylbenzyl)-2-(4-methoxy-N-methylphenylsulfonamido)acetamido)-2-hydroxybenzoic acid (45M).

Benzyl protected 58 was globally deprotected on a 0.08 mmol scale via General Procedure I to furnish 45m (40 mg, 94%): $\delta_H$ (400 MHz, d$_6$-DMSO) 1.32-1.38 (m, 5H, CH$_2$), 1.63-1.78 (m, 5H, CH$_2$), 2.39-2.49 (m, 1H, CH), 2.77 (s, 3H, CH$_3$), 3.82 (s, 3H, CH$_3$), 3.86 (s, 2H, CH$_2$), 4.80 (s, 2H, CH$_2$), 6.79 (dd, J=8.4 and 2.0 Hz, 1H, CH), 6.87 (d, J=2.0 Hz, 1H, CH), 7.07 (d, J=8.8 Hz, 4H, CH), 7.13 (d, J=8.0 Hz, 2H, CH), 7.61 (d, J=8.8 Hz, 2H, CH), 7.78 (d, J=8.4 Hz, 1H, CH); $\delta_C$ (100 MHz, d$_6$-DMSO) 25.4, 26.2, 33.8, 35.7, 43.2, 50.8, 51.6, 55.5, 114.2, 115.9, 118.4, 121.3, 126.5, 127.4, 129.0, 131.2, 131.4, 134.2, 146.3, 146.9, 161.5, 162.3, 166.6, 177.1; HRMS (ES+) calcd for [C$_{30}$H$_{34}$N$_2$O$_7$S+H] 567.2159, found 567.2170; HPLC (V) $t_R$=19.67 min (100%), (VI) $t_R$=33.74 min (95.49%).

110. Preparation of 4-(N-(4-cyclohexylbenzyl)-2-(N-methyl-4-nitrophenylsulfonamido)acetamido)-2-hydroxy benzoic acid (45N).

Benzyl protected 59 was globally deprotected on a 0.12 mmol scale via General Procedure I to furnish 45n (52 mg, 75%): $\delta_H$ (400 MHz, d$_6$-DMSO) 1.25-1.42 (m, 5H, CH$_2$), 1.63-1.80 (m, 5H, CH$_2$), 2.38-2.47 (m, 1H, CH), 2.90 (s, 3H, CH$_3$), 4.03 (s, 2H, CH$_2$), 4.74 (s, 2H, CH$_2$), 6.79 (dd, 1H, CH), 6.87 (d, J=2.0 Hz, 1H, CH), 7.02 (d, J=8.0 Hz, 2H, CH), 7.13 (d, J=8.0 Hz, 2H, CH), 7.78 (d, J=8.4 Hz, 1H, CH), 7.99 (d, J=8.8 Hz, 2H, CH), 8.38 (d, J=8.8 Hz, 2H, CH); $\delta_C$ (100 MHz, d$_6$-DMSO) 25.4, 26.2, 33.8, 35.7, 43.2, 50.8, 51.7, 115.6, 115.9, 118.2, 124.2, 126.5, 127.4, 128.5, 128.5, 134.0, 144.0, 146.4, 146.5, 149.5, 161.6, 166.2, 171.0; HRMS (ES+) calcd for [C$^{29}$H$^{31}$N$^3$O$_8$S+H] 582.1904, found 598.1878; HPLC (V) $t_R$=20.51 min (97.58%), (VI) $t_R$=35.00 min (95.66%).

111. Preparation of 4-(N-(4-cyclohexylbenzyl)-2-(2,3,4,5,6-pentafluoro-N-methylphenylsulfonamido)acetamido)-2-hydroxybenzoic acid (45O).

Benzyl protected 60 was globally deprotected on a 0.06 mmol scale via General Procedure I to furnish 45o (37 mg, 99%): $\delta_H$ (400 MHz, d$_6$-DMSO) 1.27-7.41 (m, 5H, CH$_2$), 1.64-1.79 (m, 5H, CH$_2$), 2.40-2.49 (m, 1H, CH), 3.00 (s, 3H, CH$_3$), 4.13 (s, 2H, CH$_2$), 4.77 (s, 2H, CH$_2$), 6.74 (dd, J=8.4 and 2.0 Hz, 1H, CH), 6.83 (d, J=2.0 Hz, 1H, CH), 7.04 (d, J=8.0 Hz, 2H, CH), 7.12 (d, J=8.0 Hz, 2H, CH), 7.80 (d, J=8.4 Hz, 1H, CH); $\delta_C$ (100 MHz, d$_6$-DMSO) 25.4, 26.2, 33.8, 35.5, 43.2, 51.2, 51.7, 116.1, 118.4, 118.8, 126.5, 127.5, 131.4, 133.9, 146.3, 146.5, 161.5, 165.9, 171.0; HRMS (ES+) calcd for [C$_{29}$H$_{27}$F$_5$N$_2$O$_6$S+H] 627.1582, found 627.1551; HPLC (V) $t_R$=22.71 min (97.47%), (VI) $t_R$=39.92 min (95.22%).

112. Molecule Characterization: 4-(N-(4-cyclohexylbenzyl)-2-(N,4-dimethylphenylsulfonamido)acetamido)-2-hydroxybenzoic acid (SF1-066).

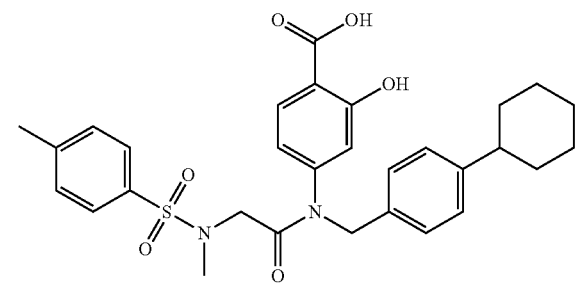 [SMILES: Cc1ccc(S(=O)(=O)N(C)CC(=O)N(Cc2ccc(C3CCCCC3)cc2)c2ccc(C(=O)O)c(O)c2)cc1]

$\delta_H$ (400 MHz, $d_6$-DMSO) 1.14-1.40 (m, 5H, $CH_2$), 1.64-1.81 (m, 5H, $CH_2$), 2.36 (s, 3H, $CH_3Ar$), 2.44 (s (br), 1H, CH), 2.77 (s, 3H, $NCH_3$), 3.86 (s, 2H, $COCH_2$), 4.79 (s, 2H, $CH_2Ar$), 6.79 (d, J=8.6 Hz, 1H, CH (Ar)), 6.86 (s (br), 1H, CH (Ar)), 7.06 (d, J=7.8 Hz, 2H, 2 CH (Ar)), 7.13 (d, J=7.8 Hz, 2H, 2 CH (Ar)), 7.35 (d, J=8.0 Hz, 2H, 2 CH (Ar)), 7.54 (d, J=8.0 Hz, 2H, 2 CH (Ar)), 7.77 (d, J=8.3 Hz, 1H, CH (Ar)), 11.30 (s (br), 1H, OH); $\delta_C$(400 MHz, $d_6$-DMSO) 21.2, 25.1 (2), 26.6, 34.2, 36.1, 42.3, 43.6, 51.2, 51.9, 112.7, 116.3, 118.9, 126.9, 127.2, 127.8, 129.9, 131.6, 134.5, 135.3, 143.4, 146.8, 147.3, 161.8, 167.0, 171.5; HRMS (ES+) calcd for $[C_{30}H_{35}N_2O_6S+H]$ 551.2223, found 551.2210; HPLC (I) $t_R$=24.35 min (98.11%), (II) $t_R$=52.80 min (98.16%).

HPLC was carried as follows: Analysis by rpHPLC was performed using a Microsorb-MV 300 A C18 250 mm×4.6 mm column run at 1 mL/min, and using gradient mixtures. The linear gradient consisted of a changing solvent composition of either (I) 100% $H_2O$ with 0.1% TFA for two minutes to 100% MeCN with 10% $H_2O$ and 0.1% TFA (v/v) at 22 minutes and UV detection at 254 nm or (II) 100% $H_2O$ with 0.1% TFA for two minutes to 100% MeCN with 10% $H_2O$ and 0.1% TFA (v/v) at 62 mins and UV detection at 214 nm or (III) 100% $H_2O$ (0.01 M $NH_4OAc$) for 2 mins to 100% MeOH at 22 minutes and UV detection at 254 nm or (IV) 100% $H_2O$ (0.01 M $NH_4OAc$) for 2 mins to 100% MeOH at 62 minutes and UV detection at 254 nm or (V) 100% $H_2O$ (0.01 M $NH_4OAc$) for 2 mins to 100% MeOH at 25 minutes and UV detection at 254 nm or (VI) 100% $H_2O$ (0.01 M $NH_4OAc$) for 2 mins to 100% MeOH at 62 mins and UV detection at 254 nm, each ending with 5 mins of 100% B. Percentage purity is given in parentheses after the retention time.

113. Molecule Characterization: 4-(2-(N-(tert-butoxycarbonyl)-4-methylphenylsulfonamido)-N-(4-cyclohexylbenzyl)acetamido)-2-hydroxybenzoic acid (SF1-087).

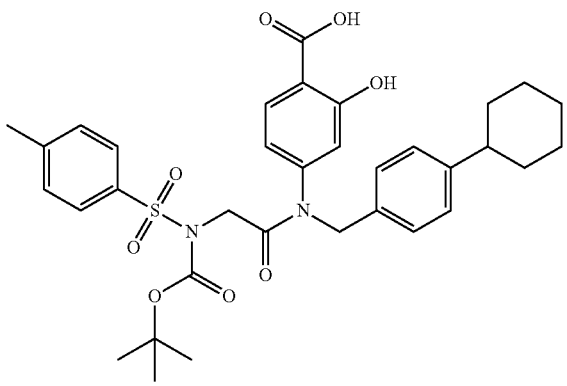 [SMILES: Cc1ccc(S(=O)(=O)N(CC(=O)N(Cc2ccc(C3CCCCC3)cc2)c2ccc(C(=O)O)c(O)c2)C(=O)OC(C)(C)C)cc1]

$\delta_H$ (400 MHz, CDCl3) 1.22-1.45 (m, 14H), 1.70-1.85 (m, 5H, $CH_2$), 2.42 (s, 3H, $CH_3$), 2.46 (s (br), 1H, CH), 4.46 (s, 2H, $COCH_2$), 4.91 (s, 2H, $CH_2Ar$), 6.70 (d, J=8.0 Hz, 1H, CH (Ar)), 6.82 (s (br), 1H, CH (Ar)), 7.10-7.15 (m, 4H, 4 CH (Ar)), 7.30 (d, J=8.0 Hz, 2H, 2 CH (Ar)), 7.88 (d, J=8.4 Hz, 1H, 1 CH (Ar)), 8.02 (d, J=8.2 Hz, 2H, 2 CH (Ar)), 10.66 (s (br), 1H, OH); !C (100 MHz, CDCl3) 21.6, 26.0, 26.8, 27.7, 34.3, 44.2, 47.5, 53.1, 84.7, 111.6, 117.2, 119.3, 126.9, 128.3, 128.8, 129.0, 132.3, 133.5, 136.6, 144.2, 147.5, 147.9, 50.5, 162.9, 166.7, 172.6; HRMS (ES+) calcd for $[C_{34}H_{41}N_2O_8S+H]$ 637.2547, found 637.2578; HPLC (I) $t_R$=26.55 min (97.80%), (II) $t_R$=59.27 min (100%). HPLC was carried as desribed above for compound SF1-066.

114. Molecule Characterization: 4-(N-benzyl-2-(N-(tert-butoxycarbonyl)-4-methylphenylsulfonamido)acetamido)-2-hydroxybenzoic acid (SF1-088).

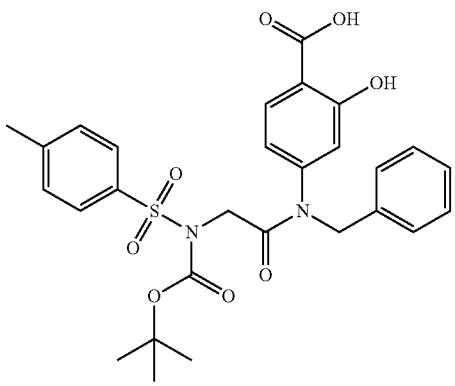 [SMILES: Cc1ccc(S(=O)(=O)N(CC(=O)N(Cc2ccccc2)c2ccc(C(=O)O)c(O)c2)C(=O)OC(C)(C)C)cc1]

$\delta_H$ (400 MHz, CDCl3) 1.31 (s, 9H, 3($CH_3$)), 2.41 (s, 3H, $CH_3Ar$), 4.47 (s, 2H, $COCH_2$), 4.95 (s, 2H, $CH_2Ar$), 6.69 (d, J=8.4 Hz, 1H, CH (Ar)), 6.81 (s, 1H, CH (Ar)), 7.20-7.32 (m, 7H, CH (Ar)), 7.87 (d, J=8.4 Hz, 1H, CH (Ar)), 8.00 (d, J=8.2 Hz, 2H, 2 CH (Ar)), 10.68 (s (br), 1H, OH); $\delta_C$ (400 MHz, CDCl3) 21.6, 27.7, 47.4, 53.3, 84.8, 111.6, 117.2, 119.2, 127.7, 128.4, 128.5, 128.7, 129.0, 132.3, 136.2, 136.6, 144.2, 147.7, 150.6, 162.9, 166.8, 172.6; HRMS (ES+) calcd for $[C_{28}H_{31}N_2O_8S+H]$ 557.1615, found 577.1615; HPLC (I) $t_R$=21.67 min (99.02%), (II) $t_R$=46.05 min (98.14%). HPLC was described above for compound SF1-066.

115. Cells and Reagents

Normal mouse fibroblasts (NIH3T3) and counterparts transformed by v-Src (NIH3T3/v-Src), human epidermal growth factor (EGF) receptor (NIH3T3/hEGFR), or v-Ras (NIH3T3/v-Ras), the human breast cancer line (MDA-MB-231) and counterpart expressing inducible KLF8 shRNA (231-K8ikd), the murine *thymus* epithelial stromal cells, the human prostate (DU145), non-small cell lung (A549), and pancreatic (Panc-1) cancer cells have all been previously reported (Turkson J, et al. (2001) J. Biol. Chem. 276:45443-45455, Turkson J, et al. (1998) Mol. Cell. Biol. 18:2545-2552, Wang X, et al. (2011) Oncogene 30:1901-1911, Zhao W, Jaganathan S, & Turkson J (2010) J Biol Chem. 285: 35855-35865, Zhang, X.; et al. Biochem. Pharmacol. 2010, 79, 1398-1409). The Stat3-dependent (pLucTKS3) and Stat3-independent (pLucSRE), and the pLucKLF8 luciferase reporters, and the vectors expressing v-Src (pMv-Src) and (3-galactosidase ((3-gal) have been previously reported (27, 28, 49). The Human Cytokine Array Kit, ARY005 was purchased from R&D Systems (Minneapolis, Minn.). G-CSF was purchased from Sigma Aldrich (St. Louis, Mo.) and was used at 100 ng/ml. Cells were grown in Dulbecco's modified Eagle's medium (DMEM) containing 10% heat-inactivated fetal bovine serum. Antibodies against STAT3, pY705STAT3, Erk1/2, and pErk1/2 are from Cell Signaling Technology (Danvers, Mass.). Recombinant human epidermal growth factor (rhEGF) was obtained from Invitrogen (Carlsbad, Calif.).

116. Cloning and Protein Expression

Coding regions for the murine STAT3 protein and STAT3 SH2 domain were amplified by PCR and cloned into vectors pET-44 Ek/LIC (Novagen) and pET SUMO (Invitrogen), respectively. The primers used for amplification were:

```
STAT3 Forward:
GACGACGACAAGATGGCTCAGTGGAACCAGCTGC;

STAT3 Reverse:
GAGGAGAAGCCCGGTTATCACATGGGGAGGTAGCACACT;

STAT3-SH2 Forward:
ATGGGTTTCATCAGCAAGGA;

STAT3-SH2 Reverse:
TCACCTACAGTACTTTCCAAATGC.
```

Clones were sequenced to verify the correct sequences and orientation. His-tagged recombinant proteins were expressed in BL21(DE3) cells, and purified on Ni-ion sepharose column. The molecular cloning, expression, and the purification of His-tagged STAT3 is described further in Razgulin AV & Mecozzi S (2006) *J. Med. Chem.* 49:7902-7906 and Zhao W., et al. (2010) *J Biol Chem.* 285:35855-35865.

117. Extract Preparation, Gel Shift Assays, and Densitometric Analysis

Nuclear extract preparations and electrophoretic mobility shift assay (EMSA) were carried out as previously described (Yang J, et al. (2005) *Cancer Res.* 65:939-947). The $^{32}$P-labeled oligonucleotide probe used was hSIE (high affinity sis-inducible element from the c-fos gene, m67 variant, 5'-AGCTTCATTTCCCGTAAATCCCTA) that binds Stat3 (Yu H & Jove R (2004) *Nat. Rev. Cancer* 4:97-105). For direct effect of a test compound on Stat3 DNA-binding activity, nuclear extracts were pre-incubated with the agent for 30 min at room temperature prior to incubation with the radiolabeled probe for 30 min at 30° C. before subjecting to EMSA analysis. Bands corresponding to DNA-binding activities were scanned, quantified for each concentration of test compound using ImageQuant and plotted as percent of control (vehicle) against concentration of compound, from which the $IC_{50}$ values were derived, as previously reported (Yue P & Turkson J (2009) Targeting STAT3 in cancer: how successful are we? *Expert Opin Investig Drugs.* 18:45-56). Cytosolic extract preparation from mammalian cells and luciferase assay previously described (Zhang X, et al. (2010) *Biochem Pharmacol* 79:1398-1409; Turkson J, et al. (1999) *Mol. Cell. Biol.* 19:7519-7528; Turkson J, et al. (1998) *Mol. Cell. Biol.* 18:2545-2552).)

118. Transient Transfection of Cells

Transient transfection of cells was carried as previously reported (Bromberg J & Darnell J E, Jr. (2000) *Oncogene* 19:2468-2473; Bowman T, et al. *Oncogene* 19:2474-24881; Yang J, et al. (2005) *Cancer Res.* 65:939-947). Eighteen hours following seeding, cells in 12-well plates were transiently co-transfected with 100 ng β-galactosidase (for normalizing), and 900 ng of pLucTKS3, pLucSRE, or pLucKLF8, and with or without 500 ng pMv-Src, where appropriate, for 3 h using Lipofectamine plus (Invitrogen) and following the manufacturer's protocol. Twelve hours after transfection, cells were treated or untreated with a test compound (0-60 µM) for 16-24 h, after which they were harvested and cytosolic extracts prepared for luciferase assay, as previously reported (Bowman T, et al. *Oncogene* 19:2474-24881; Yang J, et al. (2005) *Cancer Res.* 65:939-947).

119. Immunoprecipitation and Immunoblotting Assay

Immunoprecipitation, and SDS/PAGE and Western blotting analysis were performed as previously described (6, 16). Primary antibodies used were anti-STAT3, pY705STAT3, pY416Src, Src, pErk1/2, Erk1/2, pSTAT1, STAT1, (Cell Signaling), and antiphosphotyrosine, clone 4G10 (Upstate Biotechnology, Lake Placid, N.Y.). Where appropriate, cells were stimulated for 12 min by 9 ng/µrhEGF (12 µl into 3 ml culture) prior to preparation of whole-cell lysates for immunoprecipitation and/or immunoblotting analysis.

Immunoblotting analysis of whole-cell lysates were performed as previously described (Zhang X, et al. (2010) *Biochem Pharmacol* 79:1398-1409, Zhao W, et al. (2010) *J Biol Chem.* 285:35855-35865). Primary antibodies used were anti-Stat3, pY705Stat3, pY416Src, Src, pErk1/2, Erk1/2, pJak1, Jak1, pShc, Shc, Cyclin D1, c-Myc, Bcl-xL, Survivin, FAK, paxillin, E-cadherin, HDAC1, and β-Actin (Cell Signaling Technology, Danvers, Mass.), KLF8 (36), and VEGF (Santa Cruz Biotechnolgy, Santa Cruz, Calif.), and EPSTI1 (Sigma Aldrich, St. Louis, Mo.).

These studies were performed as previously reported (Siddiquee K A Z, et al. (2007) *ACS Chem. Biol.* 2:787-798) using whole-cell lysates or nuclear extracts (250 µg total protein) and 2 µg of anti-Stat3, anti-NF|B/p65RelA, or anti-IkappaB polyclonal antibody (Santa Cruz) or 5 µl of the monoclonal anti-Stat3 antibody (Cell Signaling Technology).

Cells were lysed in lysis buffer (50 mM Tris-HCL, 1 mM EDTA, 1% NP-40, 150 mM NaCl) for 30 minutes on ice, then freeze/thaw once at −80° C. and clarified by centrifugation at 12000 g for 15 minutes. Proteins were separated by 6.5% to 15% sodium dodecyl-polyacrylamide gel electrophoresis (SDS-PAGE) and immunoblotted with the specified antibody. Protein bands were visualized using secondary antibodies coupled to horseradish peroxidase and the Chemiluminescence Reagent Plus (from Perkin Elmer Life Sciences) according to the manufacturer's instructions. Anti cMyc was from Santa Cruz, anti surviving is from NOVUS Biologicals, Anti-Mcl-1, and anti-Bcl-x from BD Biosciences, (Mississauga, ON), anti-phospho STAT3 and STAT3, anti PARP are from Cell Signaling Technology, (Pickering, ON).

120. Cell Viability and Proliferation Assay

Cells in culture in 6-well or 96-well plates were treated with or without agents for 24-144 h and subjected to CyQuant cell proliferation assay (Invitrogen Corp/Life Technologies Corp, Carlsbad, Calif.). $IC_{50}$ values shown below were derived from the plot of viability versus drug concentration. Further details of cell viability assay methods are as described previously (Zhang X, et al. (2010) *Biochem Pharmacol* 79:1398-1409).

To determine whether STAT5 inhbitors could be cytotoxic in cell lines that have constitutive activation of STAT5, the cell lines K562 and MV-4-11 were cultured at concentration $1\times10^5$, to insure that the cells are at the exponential stage of growth, and treated with the different synthesized molecules at concentrations of 10, 20 and 40 µM. Viability were determined using Almar Blue (Invitrogen) in 96-well plate over 3 consecutive days. Fluorescence was quantified using Spectra Max M5 (Molecular Devices).

To further test activity of these molecules, a whole-cell study involving cancer lines with known abherrant STAT3 expression was conducted. These human cell lines, including prostate cancer (DU145), breast cancer (MDA468), and promyelocytic leukemia (HL-60) were treated with the peptidomimetics and incubated for 72 hours. Disruption of cell viability was measured by MTS assay and $IC_{50}$ values for the potential inhibitors was determined. OriginPro 8 (Northampton, Mass.) was used to evaluate $EC_{50}$ using the dose response curve defined as follows:

$$y = A1 + \frac{(A2 - A1)}{(1 + 10^{((\log x_e - x)\log p)})}$$

where y is the fraction of death, x is the log of drug concentration. A2 is the top asymptote, A1 is the bottom asymptote, $\log x_0$ is the center of the curve, and p is the hill slope. $IEC_{50}$ is determined by using this relationship: $IC50=10^{\log x_0}$.

121. Apoptosis/Immunoblotting Analysis

Figure 26:
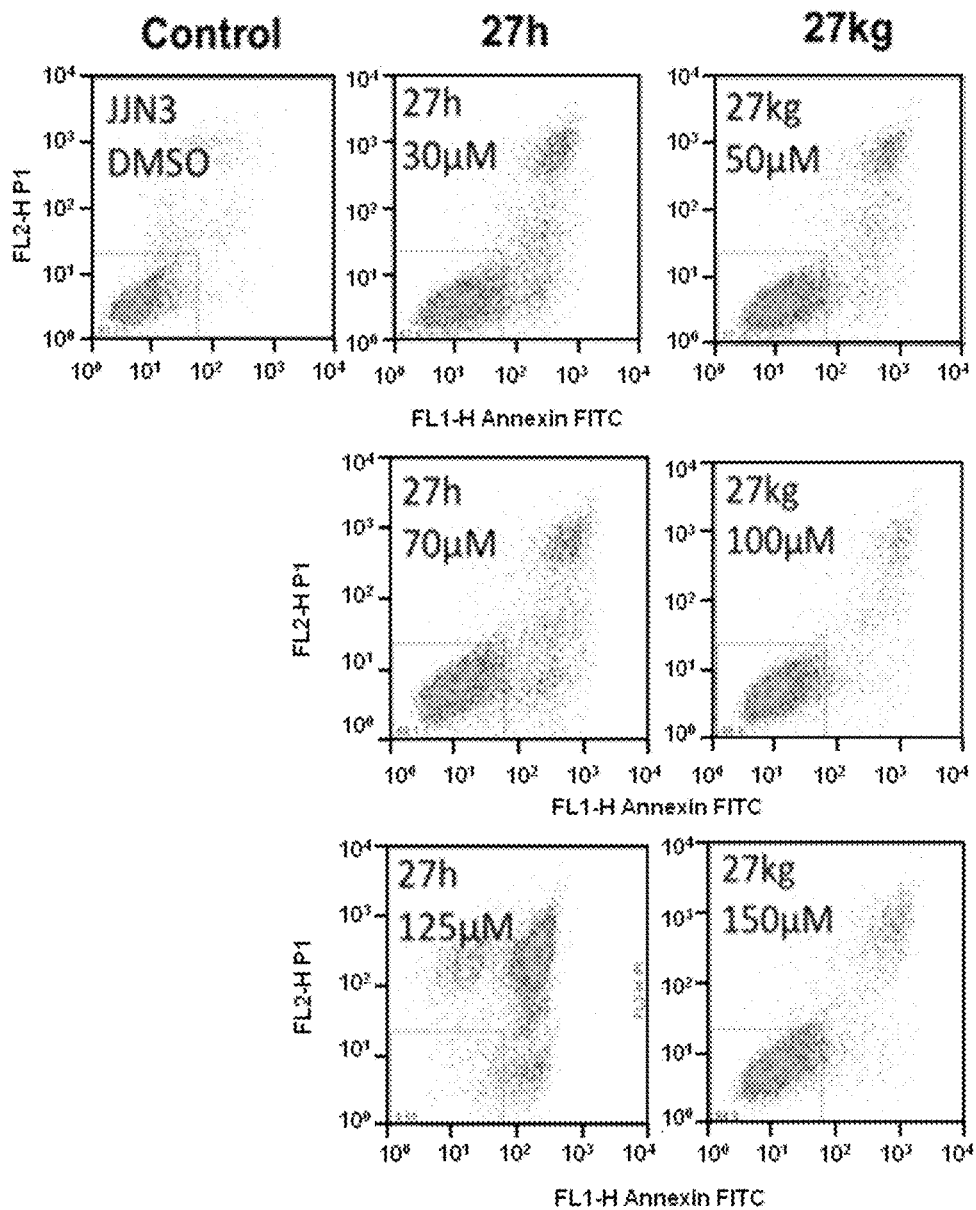
FIG. 26 shows representative data for the effect representative compounds on apoptosis in JJN3 cells.
Figure 26:
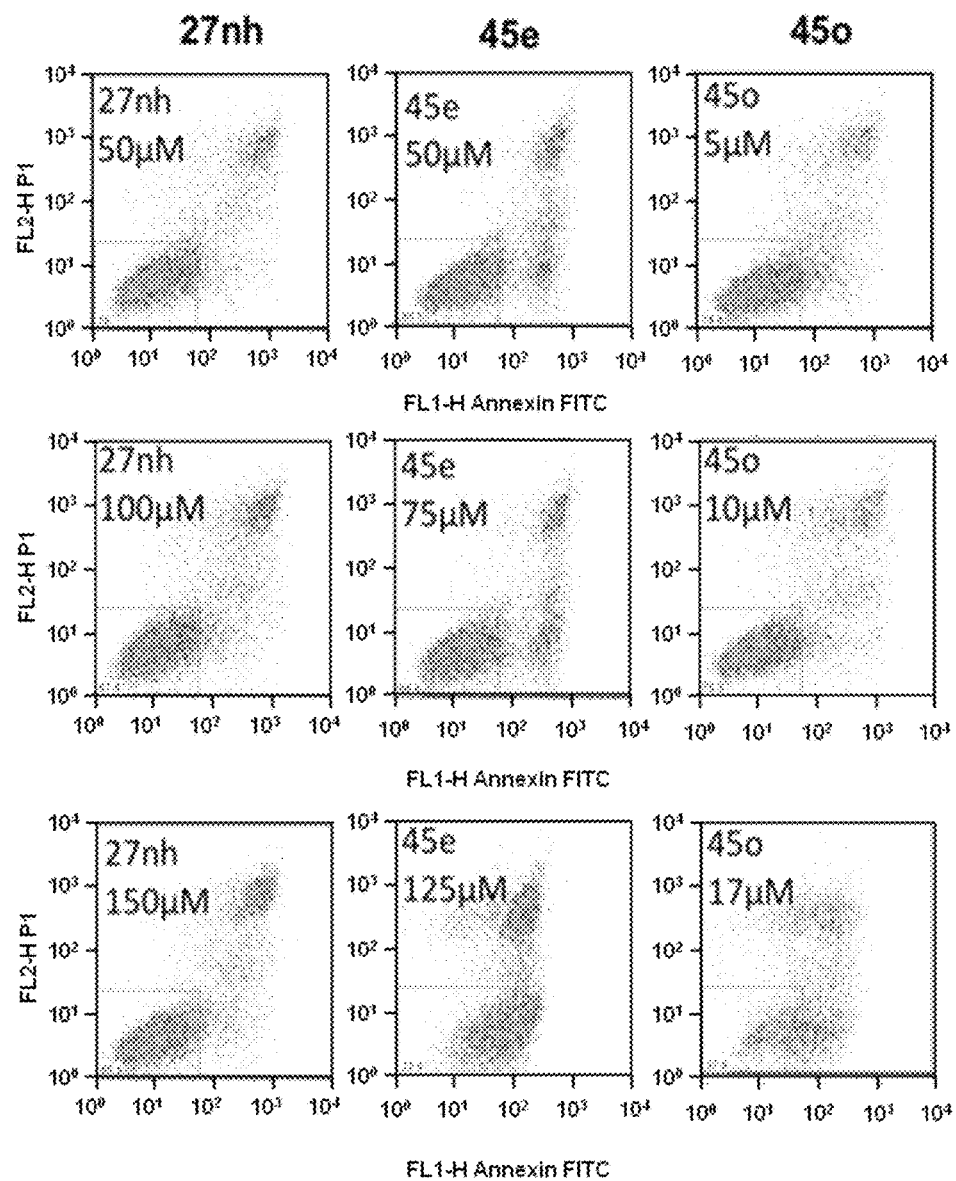
Figure 27:
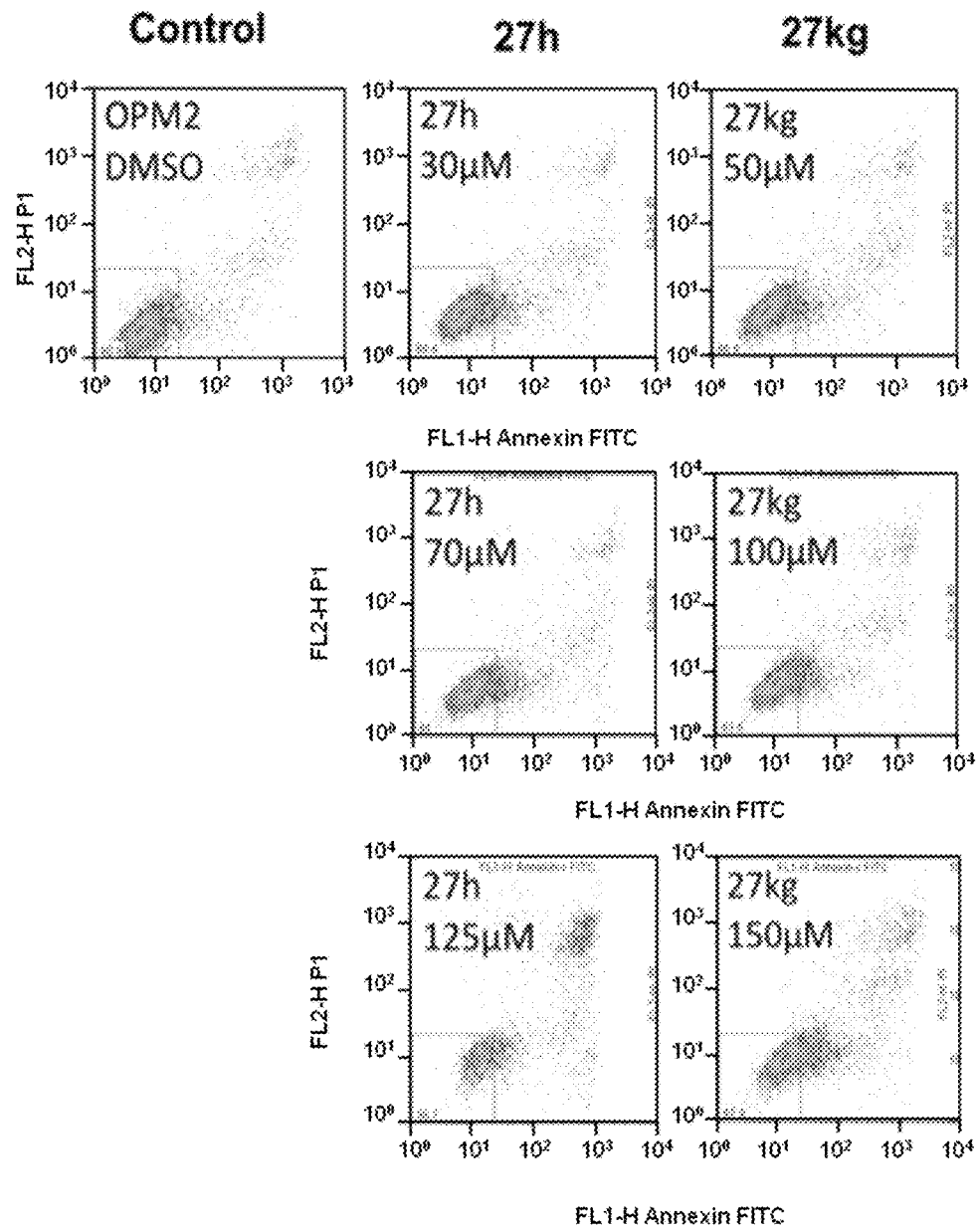
FIG. 27 shows representative data for the effect representative compounds on apoptosis in OPM2 cells.
Figure 27:
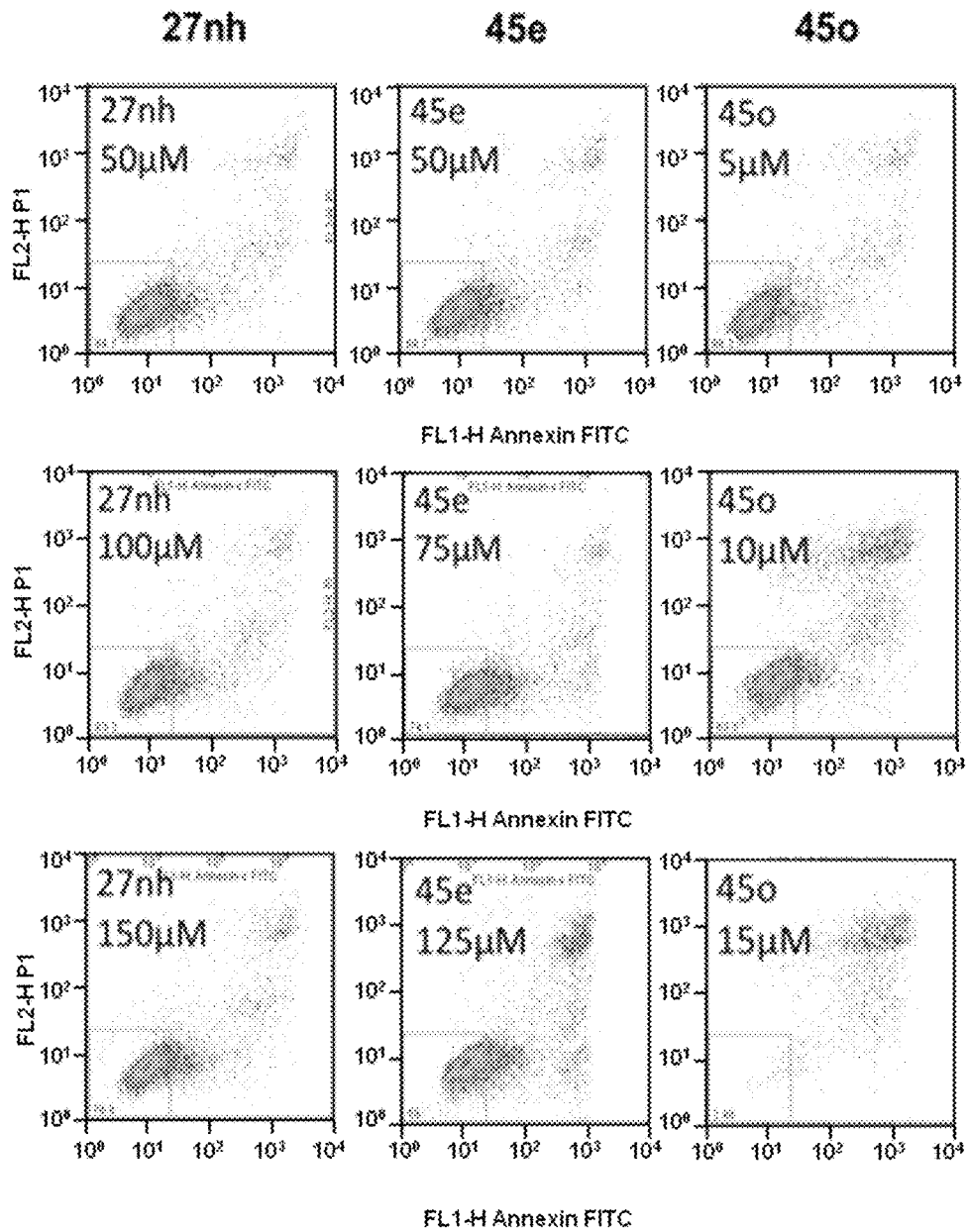

Apoptosis of compound-treated cells was measured using the Annexin V-Flus Staining Kit (Boehringer Mannheim, Indianapolis, Ind.). Cell lines were plated at a cell density of 5×10⁵ cells/mL in IMDM with 5% FCS in the presence of inhibitors/DMSO control at the indicated concentrations. Cells were harvested after 24 h, washed once in PBS and double stained with PI and FITC-conjugated Annexin V as per manufacturers instructions. Samples were analzed on a FACSCalibur flow cytometer (BD Biosciences, San Jose, Calif.) using Flowjo software (Tree Star. Ashland, Oreg.). Human MM cell lines JJN3 and OPM2 were maintained in Iscoves modified Dulbecco medium (IMDM) supplemented with 5% fetal calf serum (FCS), JJN3 were treated overnight with 5 agents. OPM2 were starved overnight and treated with 5 compounds for 2 hours before stimulated with 100 ng/ml rhIL-6 (R & D Systems) for 10 mins. Representative data obtained with representative compounds is shown in FIGS. 26 and 27.

In other assays, K562 cells were treated and used in an annexin V/PI assay. Briefly, K562 cells treated with 40 μM of BP1-108 for 24h or untreated were washed twice with PBS and then stained consequently with FITC-coupled Annexin V (Becton Dicknson) antibody for 15° and PI (Becton Dicknson) for 10°. Then, data were acquired using FacsCaliber® and analyzed using FlowJo® software.

122. Surface Plasmon Resonance Analysis

Surface Plasmon resonance analysis was performed to characterize the binding of compounds to STAT3, as previously reported (Zhang X, et al. (2010) *Biochem Pharmacol* 79:1398-1409; Zhao W, et al. (2010) *J Biol Chem.* 285: 35855-35865). SensiQ and its analysis software Qdat (ICX Technologies, Oklahoma City, Okla.) were used to analyze the interaction between agents and the STAT3 protein and to determine the binding affinity. Purified STAT3 was immobilized on a HisCap Sensor Chip by injecting 50 μg/ml of STAT3 onto the chip. Various concentrations of compounds in running buffer (1×PBS, 0.5% DMSO) were passed over the sensor chip to produce response signals. The association and dissociation rate constants were calculated using the Qdat software. The ratio of the association and dissociation rate constants was determined as the affinity ($K_D$).

123. Fluorescent Polarization Assay

The fluorescent polarization experiments were performed on an Infinite M1000 (Tecan, Crailsheim, Germany). All assays were performed in the same buffer conditions of 50 mM NaCl, 10 mM Hepes, pH 7.5, 1 mM EDTA, and 2 mM dithiothreitol. Fluorescent-labelled peptides were kept at a final concentration of 10nM in buffered solution. 7.5 mL of labelled peptides were added to 15 mL of a 300 nM STAT3 protein solution (provided by SignalChem in 50 mM Tris-HCl, pH 7.5, 150 mM NaCl, 0.25 mM DTT, 0.1 mM PMSF, 25% glycerol and stored at −80° C.). Inhibitory molecules were dissolved in pure DMSO and diluted using buffer solution to produce four final concentrations (250 μL, 31.25 μL, 3.90 μL, 0.49 μL). 7.5 μL of the inhibitory molecule solution was mixed with the STAT3 protein and labelled peptide solution in black 384-flat well microplates (Corning), and incubated for 15-30 minutes. The M1000 performed a shaking cycle and then read the plates. $IC_{50}$'s were derived from the output using the curve-fitting software OriginPro 8 (Northampton, MA). The FP data was modelled by the following equation:

$$\rho(X) = \frac{\rho_1 \times IC_{50} + \rho_2 \times X}{IC_{50} + X}$$

where X was the concentration of inhibitor and ρ was the corresponding fluorescence at that concentration. The free parameter was half the maximal inhibitory concentration ($IC_{50}$) and the limiting values was the maximal measured fluorescence polarization ($\rho_1$) and the minimal fluorescence polarization ($\rho_2$). Origin curve fitting software utilizes the Levenberg-Marquardt algorithm and reduced chi-square criterion for convergence. The inhibitor dissociation constant, $K_i$, was calculated from the derived $IC_{50}$ values, as per the following formula:

$$K_i = \frac{IC_{50}}{1 + [STAT3]/K_d}$$

where [STAT3] =150 nM and $K_d$=100 nM. Further details of the fluorescence polarization assay are as described previously (Zhang X, et al. (2010) A novel small-molecule disrupts Stat3 SH2domainphosphotyrosine interactions and Stat3-dependent tumor processes. *Biochem Pharmacol* 79: 1398-1409).

In other experiments, fluorescence polarization analysis of other STAT proteins used the following concentrations of protein: 120 nM, 150 nM and 105 nM for Stat1, Stat3 and Stat5, respectively. Concentrations of inhibitor compounds were varied between 200 to 0.2 μM final concentrations. In some experiments, the fluorescent probe was added at a final concentration of 10 nM. Protein, inhibitor and probe were combined and incubated for 15 minutes prior to analysis. Polarized fluorescence was plotted against concentration and fitted using a standard dose response curve, 124. Immunostaining with Laser-Scanning Confocal Imaging Studies are described in details in Supplemental Materials, Methods. Cells were grown on glass cover slips in multi-well plates, fixed with ice-cold methanol for 15 min, washed 3 times with 1X phosphate buffered saline (PBS), permeabilized with 0.2% Triton X-100 for 10 min, and further washed 3-4 times with PBS. Specimens were then blocked in 1% bovine serum albumin (BSA) for 30 min and incubated with anti-pY705Stat3 (Cell Signaling) or anti-pS536NFκB (Cell Signaling) antibody at 1:50 dilution (in 0.1% BSA) at 4° C. overnight. Subsequently, cells were rinsed 3 times with PBS and incubated with two AlexFluor secondary antibodies, ALexaFLuor546 (goat anti-mouse) and AlexaFluor488 (donkey anti-rabbit) (Molecular Probes, Invitrogen) for pY705Stat3 and pS536NFκB/p65 detection, respectively, for 1 h at room temperature in the dark. Specimens were then washed 3 times with PBS, mounted on slides with VECTASHIELD mounting medium containing DAPI (Vector Lab, Inc., Burlingame, Calif.), and examined immediately under a Leica TCS SP5 confocal microscope (Germany). Images were captured and processed using the Leica TCS SP 5 software.

125. Small-Interfering RNA (siRNA) Transfection

The Stat3 siRNA smart pool Stat3 (cat # M-003544) and the control, SiGENOME non-targeting siRNA pool were purchased from Dharmacon RNAi Technologies, Thermo Scientific (Lafayette, Colo.). Transfection into cells was performed following manufacturer's protocol and using 200 pmol siRNA with 10 µL of Lipofectamine RNAiMAX (Invitrogen Corporation, Carlsbad, Calif.) in serum-free OPTI-MEM culture medium (5 ml) (Invitrogen).

126. Cell Migration Assay: Wound-Healing Assay

Wounds were made using pipette tips in monolayer cultures of cells in six-well plates. Cells were treated with or without increasing concentrations of test compound and allowed to migrate into the denuded area for 16 h. Cells was visualized at a 10× magnification using an Axiovert 200 Inverted Fluorescence Microscope (Zeiss, Gottingen, Germany) and pictures of cells were taken using a mounted Canon Powershot A640 digital camera (Canon USA, Lake Success, N.Y.). Cells that migrated into the denuded area were quantified.

127. Additional Cell Migration/Invasion Assays

Cell migration/invasion experiments were carried out and quantified as previously reported (Turkson J & Jove R (2000) *Oncogene* 19:6613-6626; Turkson J (2004) *Expert Opin Ther Targets* 8(5):409-422; Gough D J, et al. (2009) *Science* 324:1713-1716) using Bio-Coat migration/invasion chambers (BD Biosciences, Bedford, Mass.) of 24-well companion plates with cell culture inserts containing 8 µm pore size filters and following the manufacturer's protocol, with some modifications. Briefly, for doxycycline (Dox) induction, cells were maintained un-induced, U (in the absence of Dox) or induced, I (in the presence of Dox) for three days. Cells were then resuspended in serum-free medium minus or plus Dox, transferred to the top chambers of the 24-well trans-well plates, and incubated for 16 h to allow the migration or invasion towards the serum-containing medium in the bottom chamber, and cells on the lower side were then counted. For treatment with test compound (15 µM), the drug was added to both the top and bottom chambers during the 16-h incubation. Where appropriate, the migration or invasion rates were normalized to the control, U cells in the absence of serum and in the bottom chambers.

128. Cytokine Assays

Cytokine analysis was performed using the human cytokine array kit and following the manufacturer's (R&D Systems, Minneapolis, Minn.) instructions. Briefly, following treatment of cells with 10 µM BP-1-102 for 48 h, 1 ml samples of conditioned culture medium or in the case of tumors, 500 ug of tumor tissues lysates in RIPA buffer (50 mM Tris-HCl, pH7.4, 1% NP-40, 150 mM NaCL, 2 mM EDTA, 0.1% SDS) were mixed with a cocktail of biotinylated detection antibodies. The mixture was incubated with the array membrane for antibody binding on the membrane. Membrane was processed for signal development using Streptavidin-HRP and chemilunimescent detection reagents, exposed to X-ray films, and then processed. The relative changes in cytokine levels between samples were analyzed by quantitation of pixel density in each spot of the array with ImageJ (National Institute of Health, Bethesda, Md.).

129. In Vivo Tumor Studies

Six-week-old female athymic nude mice were purchased from Harlan (Indianapolis, Ind.) and maintained in the institutional animal facilities approved by the American Association for Accreditation of Laboratory Animal Care. All mice studies were performed under an Institutional Animal Care and Use Committee (IACUC)-approved protocol. Athymic nude mice were injected subcutaneously in the left flank area with $1 \times 10^6$ human breast cancer MDA-MB-231 or non-small cell lung cancer A549 cells in 100 µl of PBS. After 5 to 10 days, tumors of a 30-100 mm$^3$ volume were established. Animals with established tumors were grouped so that the mean tumor sizes in all groups were nearly identical and then given test compound (in 0.05% DMSO in water) at 1 or 3 mg/kg (i.v.) every 2 or every 3 days or 3 mg/kg (oral gavage, 100 µl) every day for 15 or 20 days. Animals were monitored every day, and tumor sizes were measured with calipers and body weights taken every 2 or 3 days. Tumor volumes were calculated according to the formula $V=0.52 \times a^2 \times b$, where a, smallest superficial diameter, b, largest superficial diameter. For each treatment group, the tumor volumes for each set of measurements were statistically analyzed in comparison to the control (non-treated) group using paired t-test.

130. Plasma and Tumor Tissue Analysis

Test compound concentrations in mouse plasma and tumor tissue lysates were assayed using validated analytical procedure via high-performance liquid chromatography (Shimadzu Prominence UHPLC, Shimadzu Scientific Instruments, Columbia, Md.) and LC/MS/MS (API4000 Liner Ion Trap Mass Spectrometer, MDS Sciex, Ontario, Canada). The mass spectrometer was operated in a product ion scanning mode. BP-1-102 solution diluted in methanol was infused directly into the MS source at a flow of 10 µl/min. Tuning was evaluated in both positive and negative MS modes using both turbo ion spray and atmospheric pressure chemical ionization sources. The chromatography used a Phenomenx Kinetex C18 2.1×50 mm, 1.7µ UHPLC column (Phenomenex, Torrance, Calif.) with a flow rate of 0.300 ml/min using a 5 mM ammonium acetate (in water) and 5 mM ammonium acetate (in acetonitrile) as mobile phase A and B, respectively.

131. Statistical Analysis

Statistical analysis was performed on mean values using Prism GraphPad Software, Inc. (La Jolla, Calif.). The significance of differences between groups was determined by the paired t-test at $p<0.05^*$, $<0.01^{}$, and $<0.005^{*}$.

132. Assay of Inhibition of Intracellular STAT5, STAT3 and STAT1 Phosphorylation Cells were treated with the potential Stat5 inhibitors for 6 hr, then $1 \times 10^7$ were lysed using RIPA buffer. Lysates were loaded on SDS-PAGE in order to size-fractionate the proteins. Thereafter, proteins were blotted onto PVDF membrane (PALL Life Sciences). The membrane was blocked using 5% BSA in PBS containing 0.1% Tween 20 (Sigma) and then probed with antibodies against pSTAT5, STAT5, pSTAT3, STAT3 (Cell Signaling) and GAPDH. Secondary staining was performed with anti-rabbit IgG coupled with HRP (Amersham Bioecinces) and chemiluminescence reaction was carried out using ECL Plus (Amersham Biosciences). Proteins were quantified using Typhoon 9410 (Amersham Biosciences).

133. Real-Time RT-PCR

Total RNA was isolated using RNeasy kit (Qiagen, Mississagua, ON, Canada). All RNA samples were treated with Dnase during extraction according to the manufacturer's protocol (Qiagen, Mississagua, ON, Canada). An amount of 2 µg of RNA was reversed transcribed using TaqMan Kit (Applied Biosystems, Branchburg, N.J., USA); and 1 µl of cDNA was used for amplification. Real-time RT-PCR was performed SYBR® Green PCR Master Mix (Applied Biosystems, Warrington, UK) and amplification was performed using 96-well plate and 7700 Sequence Detection System (Applied Biosystems, Foster City, Calif., USA) according to manufacturer's instructions. All amplifications were done in duplicate on one plate. A standard curve was established using NB-4 cell line in order to calculate the PCR efficiency. DLK1 levels were normalized using GAPDH as an internal standard control and then calculated according to A A Ct formula.

134. Chromatin Immunoprecipitation (CHIP)

ChIP assay was performed using EZ ChIP Kit® (Millipore, Billerica, Mass., USA) as per manufacturer's instruction. Briefly, after crosslinking with formaldehyde (1%), cell were lysed using SDS Lysis Buffer containing Protease Inhibitor Cocktail and nuclear extract were obtained. Then, crosslinked DNA was sheared using sonication; sheared DNA size was checked on agarose gel and ranged, in all cases, between 300-500 bp. An amount of 1/20 of the shared chromatin was kept as an input. Sheared chromatin was incubated with rabbit polyclonal Phospho-Stat5 (Tyr694) Antibody (Cell Signaling, Danvers, Mass., USA) at dilution 1:50 or rabbit polyclonal IgG at appropriate concentration. Incubation was performed at 4° C. overnight. The antibody/chromatin complex was precipitated using Protein G Agarose beads. After elution, the crosslink of protein/DNA was reversed, and DNA was purified using Spin Columns. PCR was performed using platinum Taq™ (Invitrogen Canada, Burlington, ON, Canada). Two sets of primers were designed to amplify two DNA segments that contain STAT5-binding sites located 1672 bp and 428 bp upstream the start sites of C-Myc and Cyclin-D1, respectively. The STAT5-binding site in the C-MYC promoter is characterized by a 4N spacer and has the sequence (ttccccgaa), whereas the one in the Cyclin D1 promoter is characterized by a 3N spacer and has the sequence (ttcttggaa).

135. Activity of Substituted 2-hydroxy-4-(2-(phenylsulfonamido)acetamido)benzoic acid Analogs Compounds Substituted 2-hydroxy-4-(2-(phenylsulfonamido)acetamido)benzoic acid analogs were synthesized as described above. Specific examples of preparation and characterization data is provided above for compounds 27E, 27JA-27NH, and 45A-45O. The other compounds in Table 1 were prepared by similar methods to those described above. Activity ($K_i$ for inhibition of binding to STAT3 in a fluorescence polarization assay and $IC_{50}$ for inhibition of STAT3 activity in an EMSA) was determined as described above, and the data are shown below in Table 1. The compound identifier ("ID") corresponds to the number given parenthetically for the preparation of compounds described above.

TABLE 1

| Compound ID | Structure | $IC_{50}$ (EMSA) | $K_i$ (FP) |
|---|---|---|---|
| 27E | 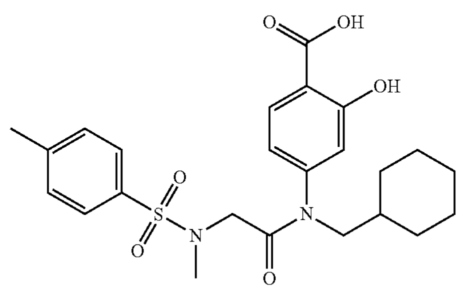 [SMILES: Cc1ccc(S(=O)(=O)N(C)CC(=O)N(CC2CCCCC2)c2ccc(C(=O)O)c(O)c2)cc1] | >300 | n.d. |
| 27JA | 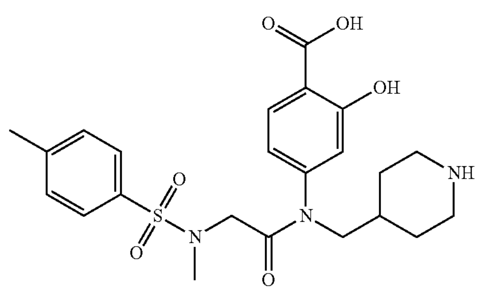 [SMILES: Cc1ccc(S(=O)(=O)N(C)CC(=O)N(CC2CCNCC2)c2ccc(C(=O)O)c(O)c2)cc1] | >300 | n.d. |
| 27JB | 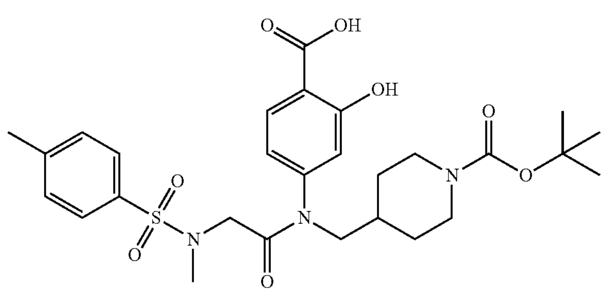 [SMILES: Cc1ccc(S(=O)(=O)N(C)CC(=O)N(CC2CCN(C(=O)OC(C)(C)C)CC2)c2ccc(C(=O)O)c(O)c2)cc1] | >300 | n.d. |

TABLE 1-continued

| Compound ID | Structure | IC$_{50}$ (EMSA) | K$_i$ (FP) |
|---|---|---|---|
| 27JC | 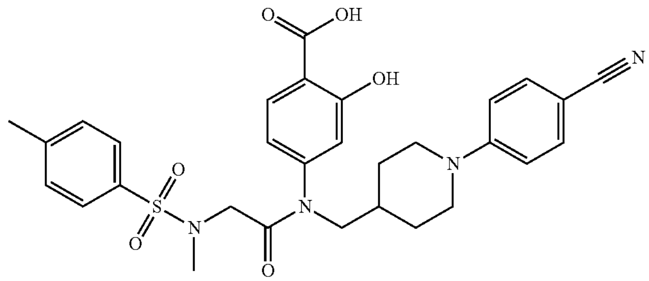 [SMILES: Cc1ccc(S(=O)(=O)N(C)CC(=O)N(CC2CCN(c3ccc(C#N)cc3)CC2)c2ccc(C(=O)O)c(O)c2)cc1] | >300 | n.d. |
| 27JD | 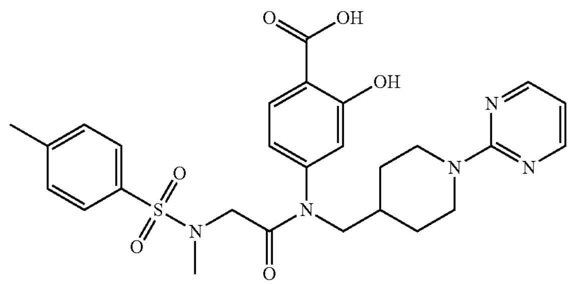 [SMILES: Cc1ccc(S(=O)(=O)N(C)CC(=O)N(CC2CCN(c3ncccn3)CC2)c2ccc(C(=O)O)c(O)c2)cc1] | >300 | n.d. |
| 27KA | 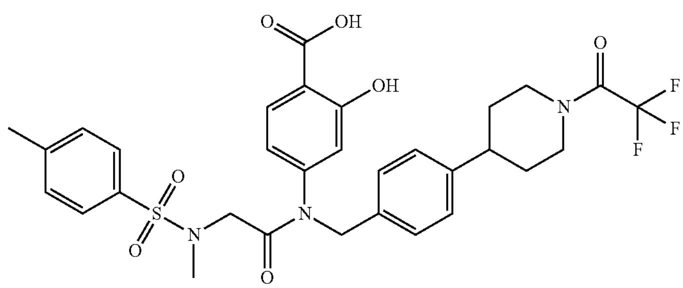 [SMILES: Cc1ccc(S(=O)(=O)N(C)CC(=O)N(Cc2ccc(C3CCN(C(=O)C(F)(F)F)CC3)cc2)c2ccc(C(=O)O)c(O)c2)cc1] | >300 | n.d. |
| 27KB | 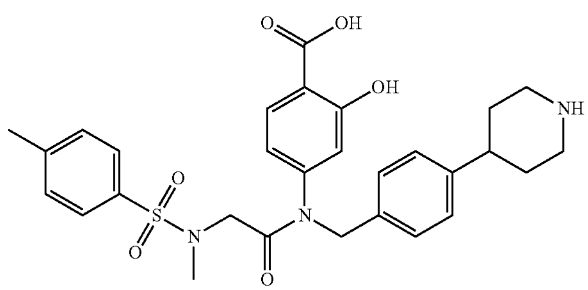 [SMILES: Cc1ccc(S(=O)(=O)N(C)CC(=O)N(Cc2ccc(C3CCNCC3)cc2)c2ccc(C(=O)O)c(O)c2)cc1] | >300 | n.d. |
| 27KC | 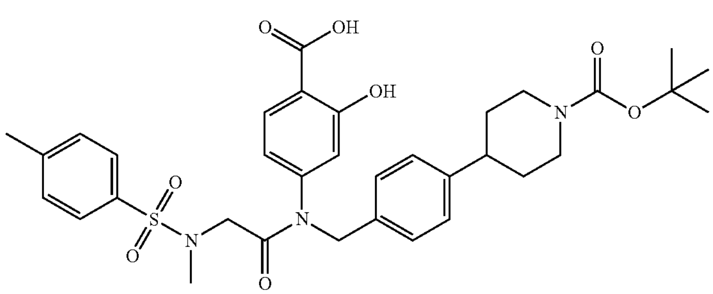 [SMILES: Cc1ccc(S(=O)(=O)N(C)CC(=O)N(Cc2ccc(C3CCN(C(=O)OC(C)(C)C)CC3)cc2)c2ccc(C(=O)O)c(O)c2)cc1] | >300 | 18.7 ± 1.4 |

TABLE 1-continued
| Compound ID | Structure | IC$_{50}$ (EMSA) | K$_i$ (FP) |
|---|---|---|---|
| 27KE | 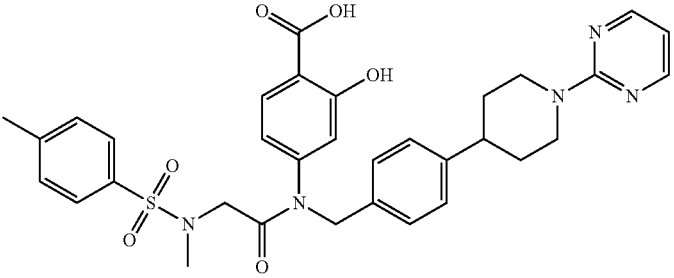 [SMILES: Cc1ccc(S(=O)(=O)N(C)CC(=O)N(Cc2ccc(C3CCN(c4ncccn4)CC3)cc2)c2ccc(C(=O)O)c(O)c2)cc1] | >300 | n.d. |
| 27KF | 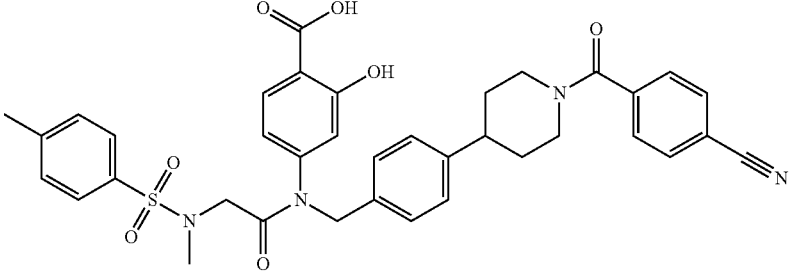 [SMILES: Cc1ccc(S(=O)(=O)N(C)CC(=O)N(Cc2ccc(C3CCN(C(=O)c4ccc(C#N)cc4)CC3)cc2)c2ccc(C(=O)O)c(O)c2)cc1] | >300 | n.d. |
| 27KG | 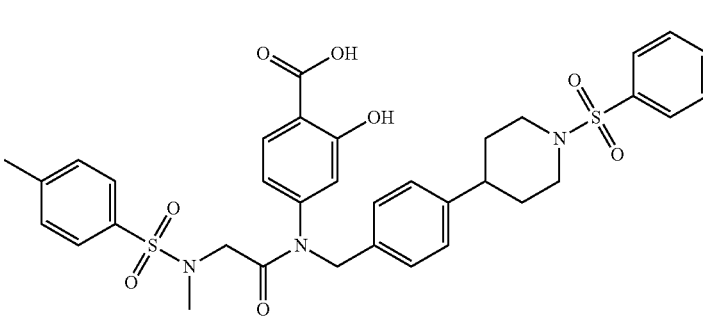 | 50 ± 15 | 21.5 ± 2.2 |
| 27KH | 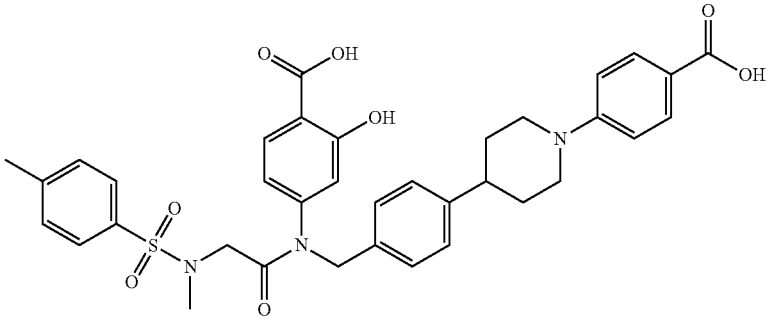 [SMILES: Cc1ccc(S(=O)(=O)N(C)CC(=O)N(Cc2ccc(C3CCN(c4ccc(C(=O)O)cc4)CC3)cc2)c2ccc(C(=O)O)c(O)c2)cc1] | >300 | n.d. |
| 27KI | 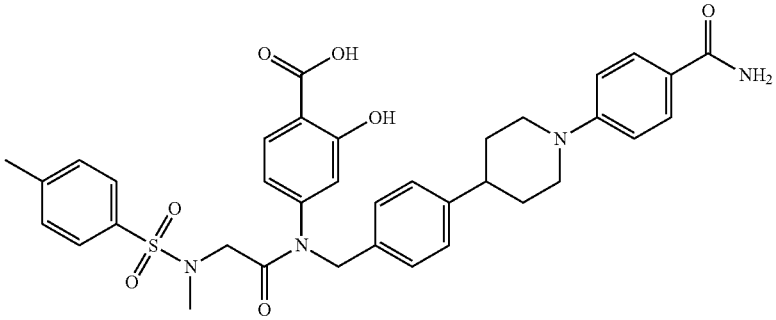 [SMILES: Cc1ccc(S(=O)(=O)N(C)CC(=O)N(Cc2ccc(C3CCN(c4ccc(C(N)=O)cc4)CC3)cc2)c2ccc(C(=O)O)c(O)c2)cc1] | >300 | n.d. |

TABLE 1-continued

| Compound ID | Structure | IC$_{50}$ (EMSA) | K$_i$ (FP) |
|---|---|---|---|
| 27LA | 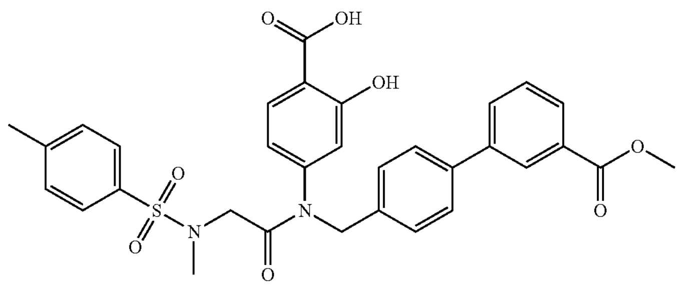 | 191 ± 8 | n.d. |
| 27LB | 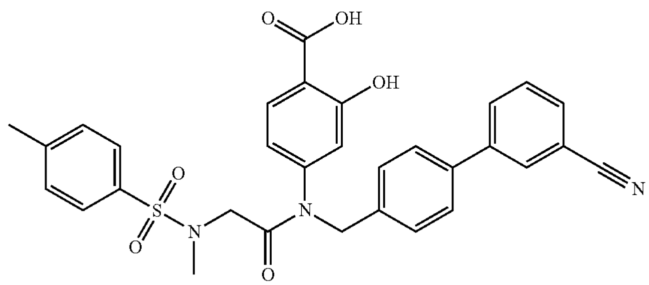 [SMILES: Cc1ccc(S(=O)(=O)N(C)CC(=O)N(Cc2ccc(-c3cccc(C#N)c3)cc2)c2ccc(C(=O)O)c(O)c2)cc1] | 250 ± 23 | n.d. |
| 27LC | 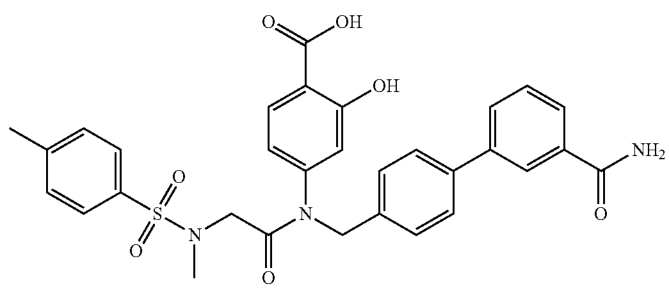 [SMILES: Cc1ccc(S(=O)(=O)N(C)CC(=O)N(Cc2ccc(-c3cccc(C(N)=O)c3)cc2)c2ccc(C(=O)O)c(O)c2)cc1] | >300 | n.d. |
| 27LD | 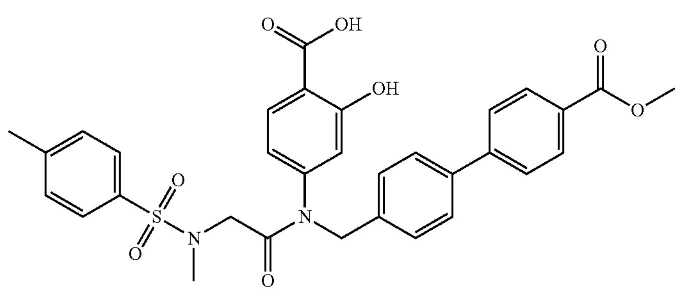 | 141 ± 10 | n.d. |
| 27LE | 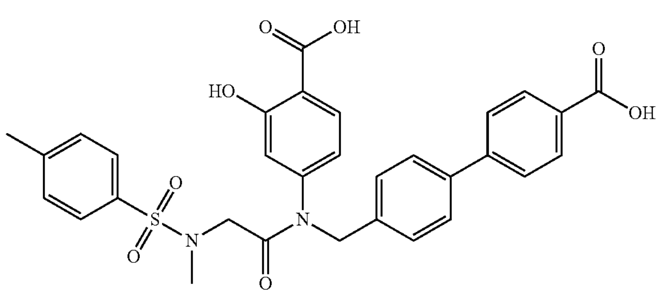 [SMILES: Cc1ccc(S(=O)(=O)N(C)CC(=O)N(Cc2ccc(-c3ccc(C(=O)O)cc3)cc2)c2ccc(C(=O)O)c(O)c2)cc1] | >300 | n.d. |

TABLE 1-continued

| Compound ID | Structure | IC$_{50}$ (EMSA) | K$_i$ (FP) |
|---|---|---|---|
| 27LF | 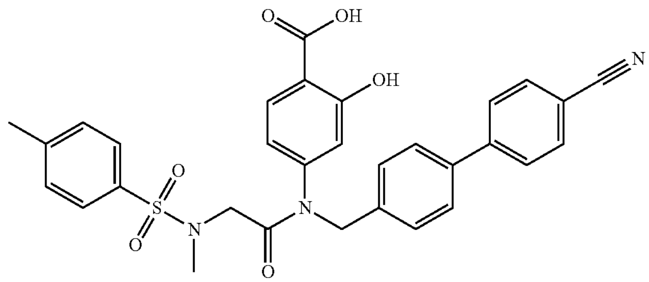 [SMILES: Cc1ccc(S(=O)(=O)N(C)CC(=O)N(Cc2ccc(-c3ccc(C#N)cc3)cc2)c2ccc(C(=O)O)c(O)c2)cc1] | 274 ± 10 | n.d. |
| 27LG | 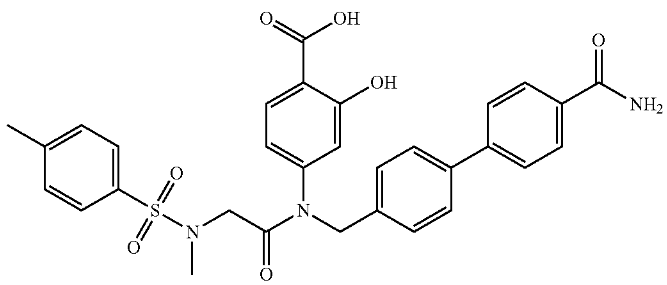 [SMILES: Cc1ccc(S(=O)(=O)N(C)CC(=O)N(Cc2ccc(-c3ccc(C(N)=O)cc3)cc2)c2ccc(C(=O)O)c(O)c2)cc1] | >300 | n.d. |
| 27NA | 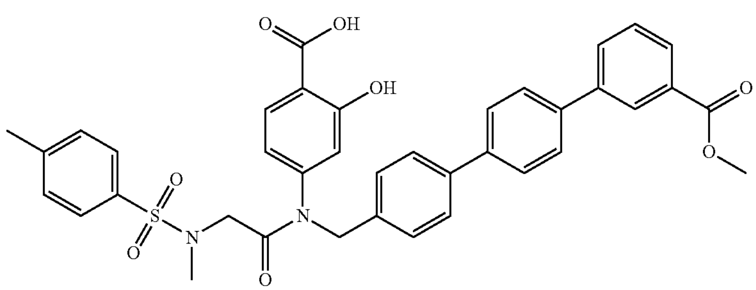 | 63 ± 2 | n.d. |
| 27NB | 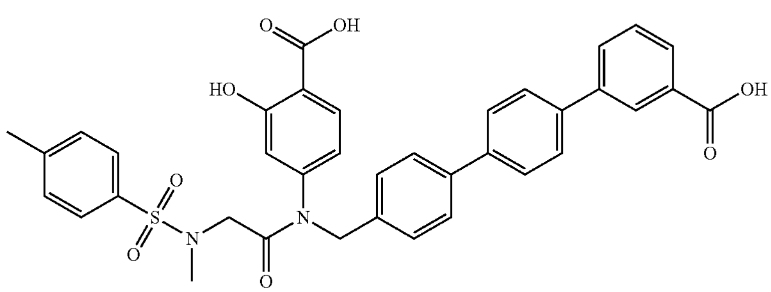 [SMILES: Cc1ccc(S(=O)(=O)N(C)CC(=O)N(Cc2ccc(-c3ccc(-c4cccc(C(=O)O)c4)cc3)cc2)c2ccc(C(=O)O)c(O)c2)cc1] | >300 | n.d. |
| 27NC | 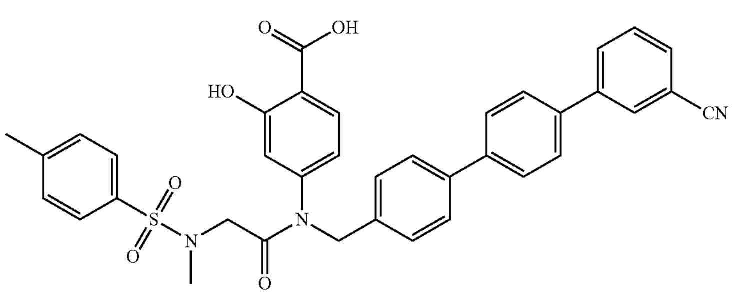 [SMILES: Cc1ccc(S(=O)(=O)N(C)CC(=O)N(Cc2ccc(-c3ccc(-c4cccc(C#N)c4)cc3)cc2)c2ccc(C(=O)O)c(O)c2)cc1] | 82 ± 1 | n.d. |

TABLE 1-continued

| Compound ID | Structure | IC$_{50}$ (EMSA) | K$_i$ (FP) |
| --- | --- | --- | --- |
| 27ND | 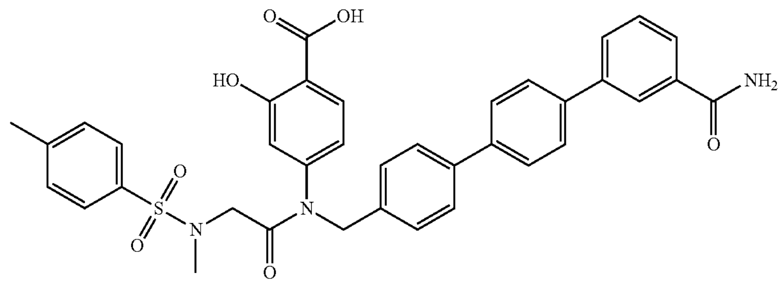 [SMILES: Cc1ccc(S(=O)(=O)N(C)CC(=O)N(Cc2ccc(-c3ccc(-c4cccc(C(N)=O)c4)cc3)cc2)c2ccc(C(=O)O)c(O)c2)cc1] | 90 | n.d. |
| 27NE | 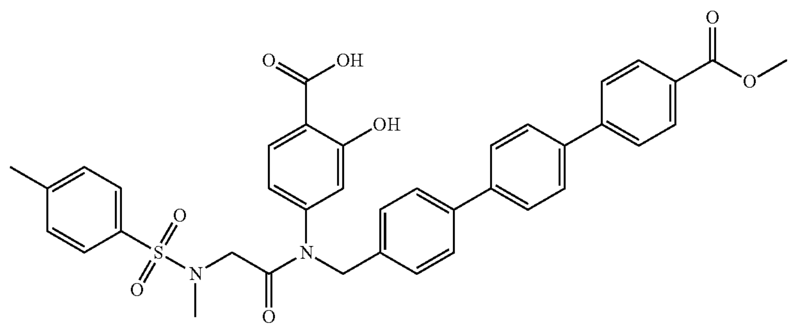 | 91 ± 17 | n.d. |
| 27NF | 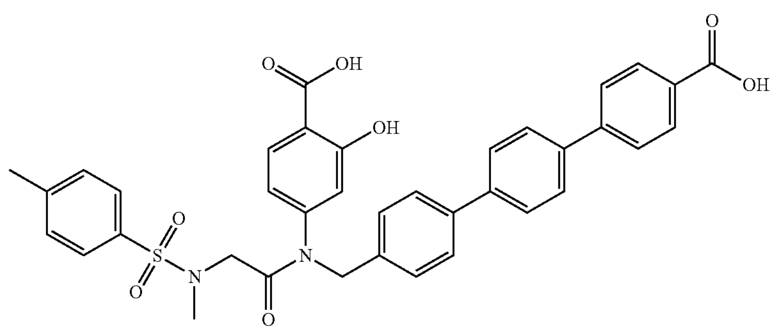 [SMILES: Cc1ccc(S(=O)(=O)N(C)CC(=O)N(Cc2ccc(-c3ccc(-c4ccc(C(=O)O)cc4)cc3)cc2)c2ccc(C(=O)O)c(O)c2)cc1] | >300 | n.d. |
| 27NG | 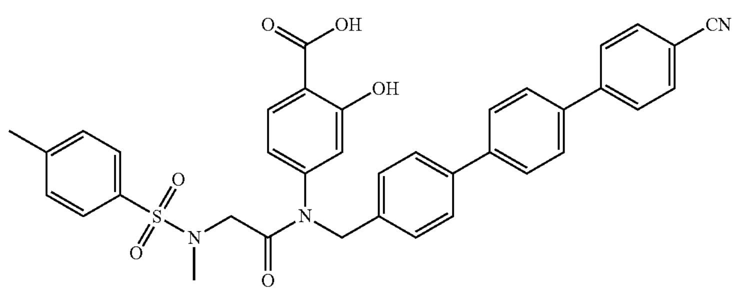 [SMILES: Cc1ccc(S(=O)(=O)N(C)CC(=O)N(Cc2ccc(-c3ccc(-c4ccc(C#N)cc4)cc3)cc2)c2ccc(C(=O)O)c(O)c2)cc1] | 74.3 ± 9.3 | 21.6 ± 0.9 |
| 27NH | 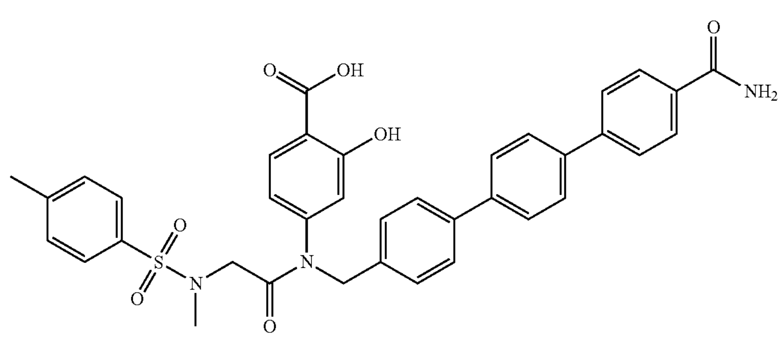 [SMILES: Cc1ccc(S(=O)(=O)N(C)CC(=O)N(Cc2ccc(-c3ccc(-c4ccc(C(N)=O)cc4)cc3)cc2)c2ccc(C(=O)O)c(O)c2)cc1] | 43 ± 1.3 | 16.7 ± 1.7 |

TABLE 1-continued
| Compound ID | Structure | IC$_{50}$ (EMSA) | K$_i$ (FP) |
|---|---|---|---|
| 45A | 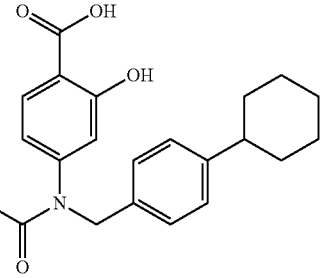 | 119 ± 1.9 | n.d. |
| 45B | 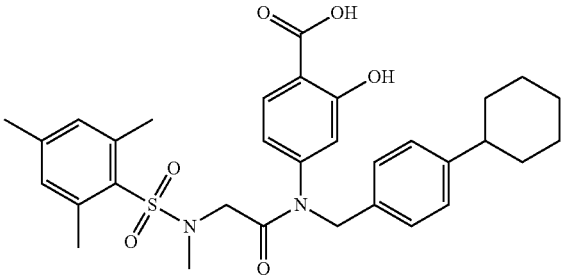 [SMILES: Cc1cc(C)c(S(=O)(=O)N(C)CC(=O)N(Cc2ccc(C3CCCCC3)cc2)c2ccc(C(=O)O)c(O)c2)c(C)c1] | 51.9 ± 2.4 | n.d. |
| 45C | 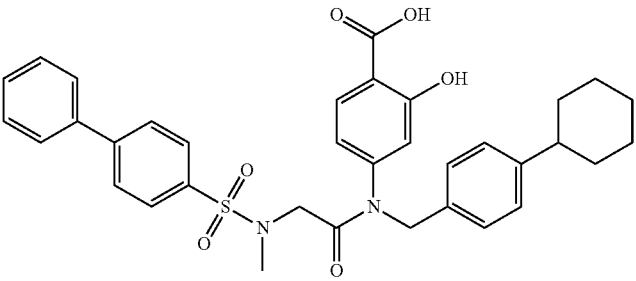 [SMILES: CN(CC(=O)N(Cc1ccc(C2CCCCC2)cc1)c1ccc(C(=O)O)c(O)c1)S(=O)(=O)c1ccc(-c2ccccc2)cc1] | 100 | n.d. |
| 45D | 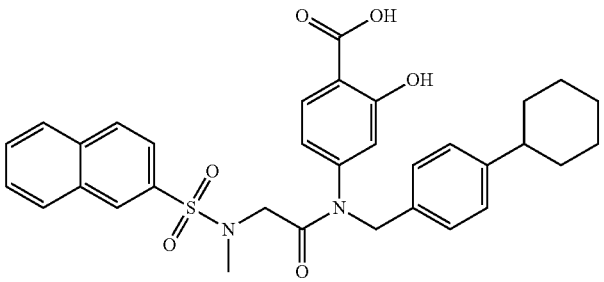 [SMILES: CN(CC(=O)N(Cc1ccc(C2CCCCC2)cc1)c1ccc(C(=O)O)c(O)c1)S(=O)(=O)c1ccc2ccccc2c1] | 79.2 ± 11.2 | n.d. |
| 45E | 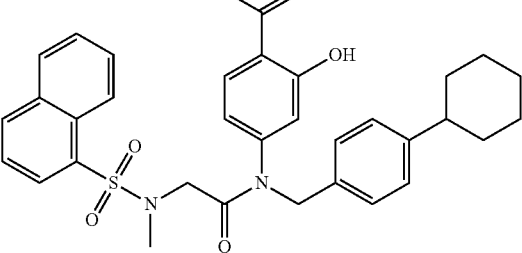 | 28.8 ± 2.0 | 26.5 ± 0.4 |

TABLE 1-continued

| Compound ID | Structure | IC$_{50}$ (EMSA) | K$_i$ (FP) |
|---|---|---|---|
| 45F | 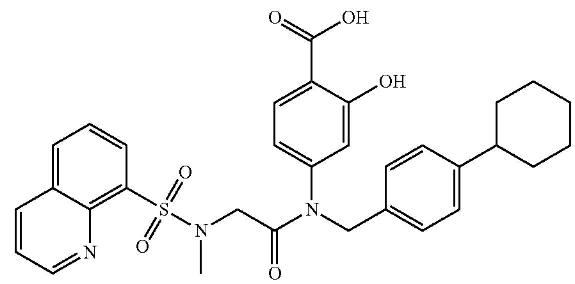 [SMILES: CN(CC(=O)N(Cc1ccc(C2CCCCC2)cc1)c1ccc(C(=O)O)c(O)c1)S(=O)(=O)c1cccc2cccnc12] | 24.6 ± 3.4 | 41.0 ± 0.4 |
| 45G | 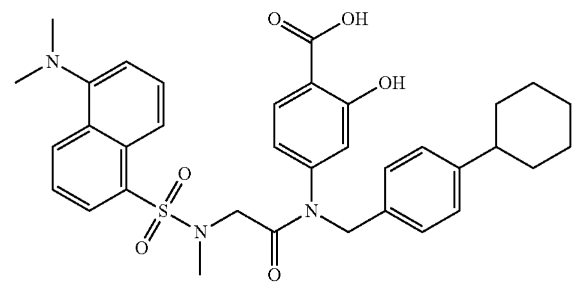 [SMILES: CN(C)c1cccc2c(S(=O)(=O)N(C)CC(=O)N(Cc3ccc(C4CCCCC4)cc3)c3ccc(C(=O)O)c(O)c3)cccc12] | 28.8 ± 1.9 | n.d. |
| 45H | 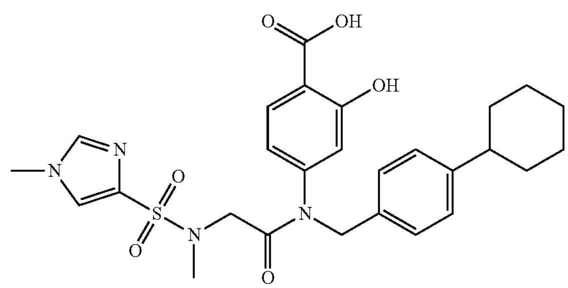 [SMILES: CN(CC(=O)N(Cc1ccc(C2CCCCC2)cc1)c1ccc(C(=O)O)c(O)c1)S(=O)(=O)c1cn(C)cn1] | >300 | n.d. |
| 45I | 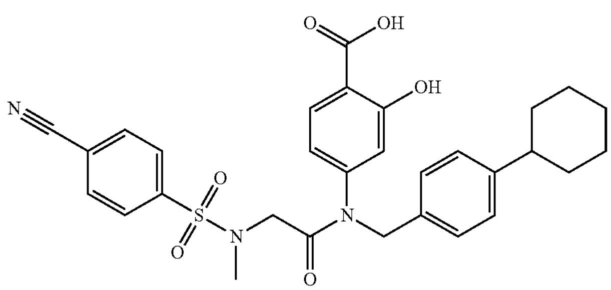 [SMILES: CN(CC(=O)N(Cc1ccc(C2CCCCC2)cc1)c1ccc(C(=O)O)c(O)c1)S(=O)(=O)c1ccc(C#N)cc1] | 126.2 ± 5.3 | n.d. |
| 45J | 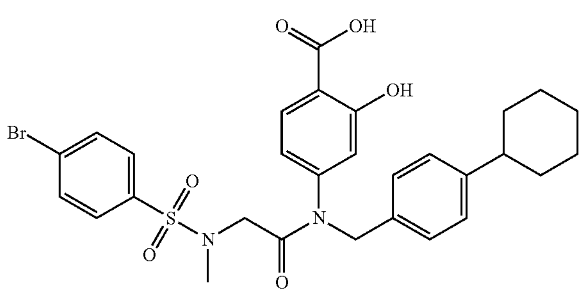 [SMILES: CN(CC(=O)N(Cc1ccc(C2CCCCC2)cc1)c1ccc(C(=O)O)c(O)c1)S(=O)(=O)c1ccc(Br)cc1] | 90.3 ± 4.5 | n.d. |

TABLE 1-continued

| Compound ID | Structure | IC$_{50}$ (EMSA) | K$_i$ (FP) |
|---|---|---|---|
| 45K | 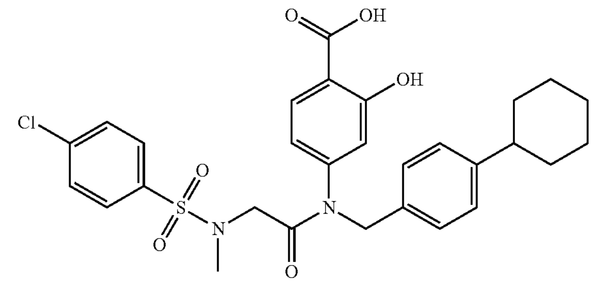 [SMILES: CN(CC(=O)N(Cc1ccc(C2CCCCC2)cc1)c1ccc(C(=O)O)c(O)c1)S(=O)(=O)c1ccc(Cl)cc1] | 100 | n.d. |
| 45L | 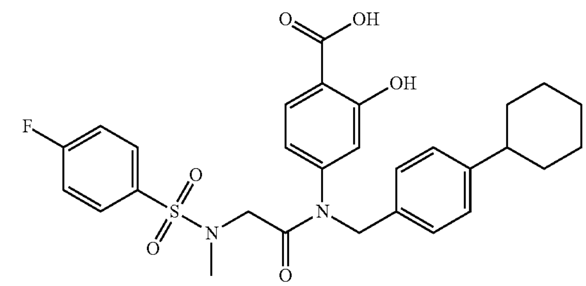 [SMILES: CN(CC(=O)N(Cc1ccc(C2CCCCC2)cc1)c1ccc(C(=O)O)c(O)c1)S(=O)(=O)c1ccc(F)cc1] | >300 | n.d. |
| 45M | 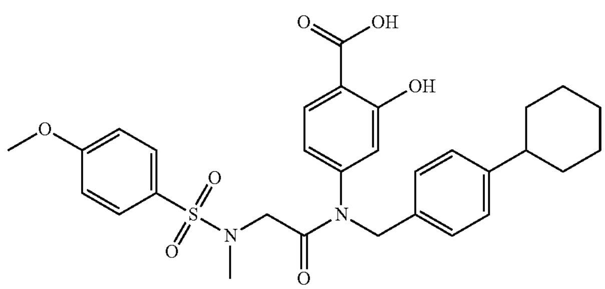 [SMILES: COc1ccc(S(=O)(=O)N(C)CC(=O)N(Cc2ccc(C3CCCCC3)cc2)c2ccc(C(=O)O)c(O)c2)cc1] | 100 | n.d. |
| 45N | 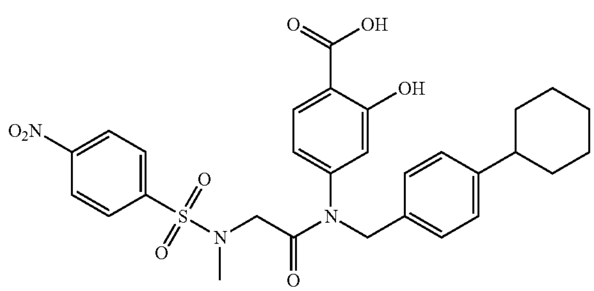 [SMILES: CN(CC(=O)N(Cc1ccc(C2CCCCC2)cc1)c1ccc(C(=O)O)c(O)c1)S(=O)(=O)c1ccc([N+](=O)[O-])cc1] | 62.2 ± 3.2 | n.d. |
| 45O | 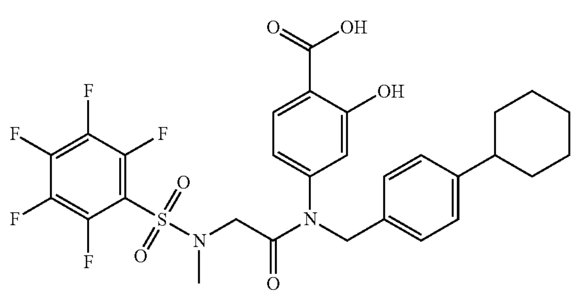 [SMILES: CN(CC(=O)N(Cc1ccc(C2CCCCC2)cc1)c1ccc(C(=O)O)c(O)c1)S(=O)(=O)c1c(F)c(F)c(F)c(F)c1F] | 6.8 ± 0.8 | 13 ± 0.3 |

TABLE 1-continued

| Compound ID | Structure | IC$_{50}$ (EMSA) | K$_i$ (FP) |
|---|---|---|---|
| BP2-027 | 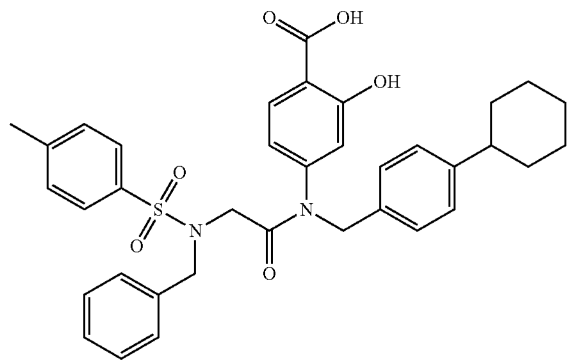 [SMILES: Cc1ccc(S(=O)(=O)N(CC(=O)N(Cc2ccc(C3CCCCC3)cc2)c2ccc(C(=O)O)c(O)c2)Cc2ccccc2)cc1] | n.d. | 7.2 ± 2.2 |
| BP2-028 | 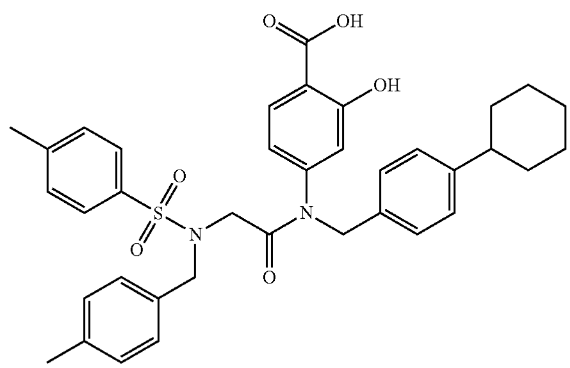 [SMILES: Cc1ccc(CN(CC(=O)N(Cc2ccc(C3CCCCC3)cc2)c2ccc(C(=O)O)c(O)c2)S(=O)(=O)c2ccc(C)cc2)cc1] | n.d. | >50 |
| BP2-029 | 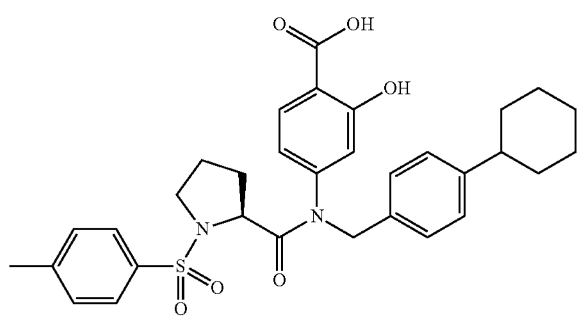 [SMILES: Cc1ccc(S(=O)(=O)N2CCC[C@H]2C(=O)N(Cc2ccc(C3CCCCC3)cc2)c2ccc(C(=O)O)c(O)c2)cc1] | n.d. | 33 ± 22 |
| BP2-032 | 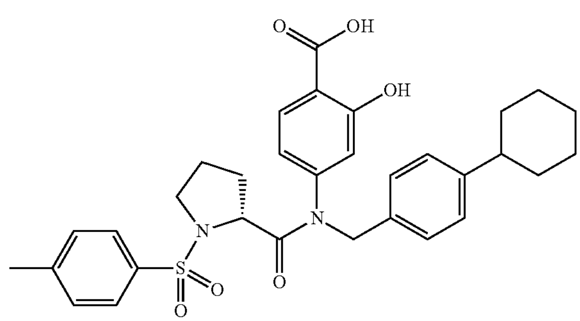 [SMILES: Cc1ccc(S(=O)(=O)N2CCC[C@@H]2C(=O)N(Cc2ccc(C3CCCCC3)cc2)c2ccc(C(=O)O)c(O)c2)cc1] | n.d. | >50 |

TABLE 1-continued
| Compound ID | Structure | IC$_{50}$ (EMSA) | K$_i$ (FP) |
|---|---|---|---|
| BP2-033 | 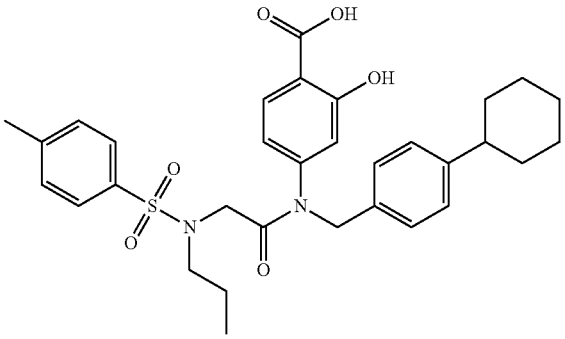 | n.d. | 8.9 ± 1.4 |
| BP2-046 | 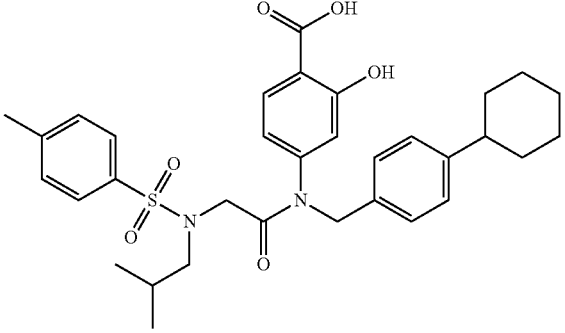 [SMILES: Cc1ccc(S(=O)(=O)N(CC(=O)N(Cc2ccc(C3CCCCC3)cc2)c2ccc(C(=O)O)c(O)c2)CC(C)C)cc1] | n.d. | 8.3 ± 0.3 |
| BP2-047 | 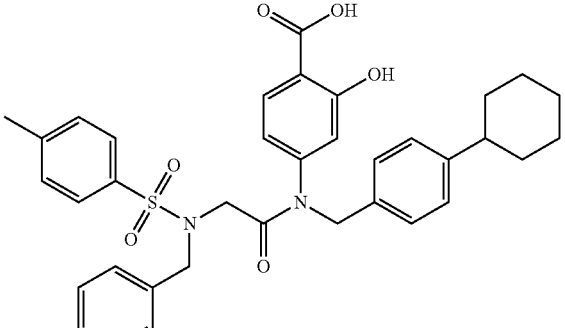 | n.d. | 2.6 ± 0.2 |
| BP2-056 | 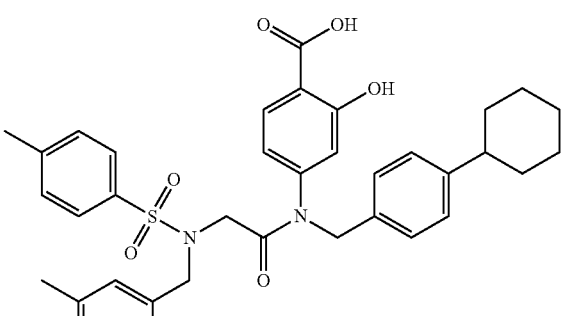 | n.d. | 2.6 ± 0.2 |

TABLE 1-continued
| Compound ID | Structure | IC$_{50}$ (EMSA) | K$_i$ (FP) |
|---|---|---|---|
| BP2-057 | 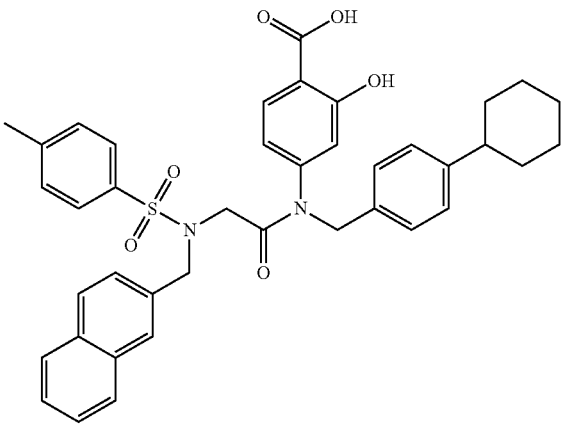 [SMILES: Cc1ccc(S(=O)(=O)N(CC(=O)N(Cc2ccc(C3CCCCC3)cc2)c2ccc(C(=O)O)c(O)c2)Cc2ccc3ccccc3c2)cc1] | n.d. | 2.5 ± 1.0 |
| BP2-061 | 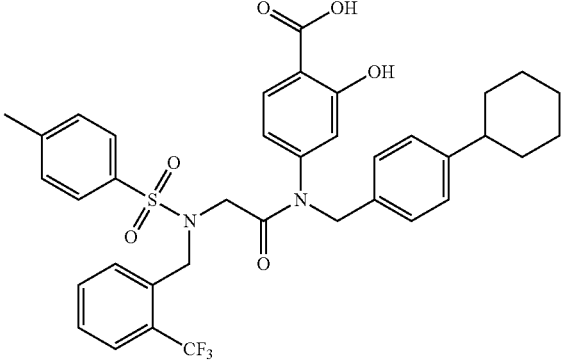 [SMILES: Cc1ccc(S(=O)(=O)N(CC(=O)N(Cc2ccc(C3CCCCC3)cc2)c2ccc(C(=O)O)c(O)c2)Cc2ccccc2C(F)(F)F)cc1] | n.d. | 1.8 ± 2.3 |
| BP2-065 | 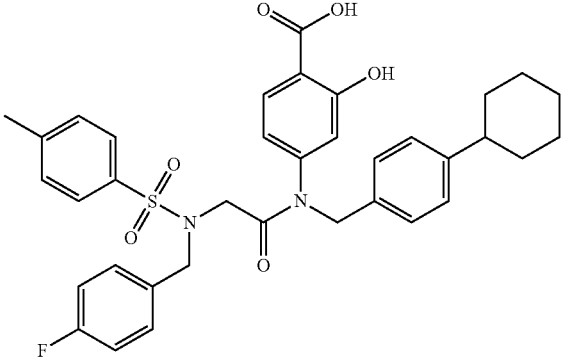 [SMILES: Cc1ccc(S(=O)(=O)N(CC(=O)N(Cc2ccc(C3CCCCC3)cc2)c2ccc(C(=O)O)c(O)c2)Cc2ccc(F)cc2)cc1] | n.d. | 3.8 ± 1.6 |
| BP2-066 | 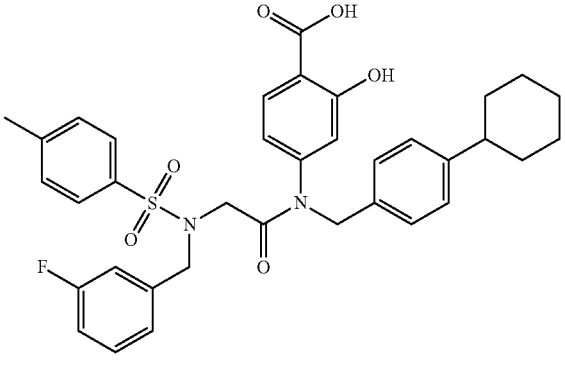 | n.d. | 4.4 ± 0.3 |

TABLE 1-continued

| Compound ID | Structure | IC$_{50}$ (EMSA) | K$_i$ (FP) |
|---|---|---|---|
| BP2-067 | 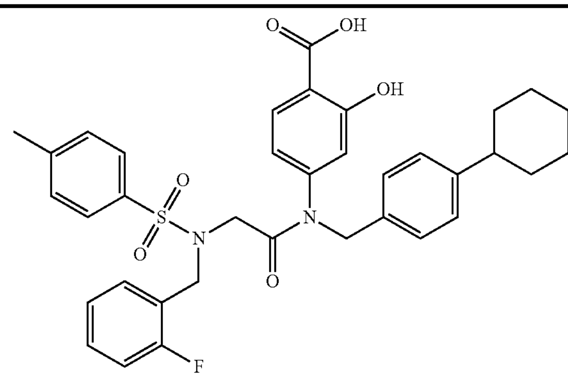 | n.d. | 5.3 ± 0.3 |
| BP2-068 | 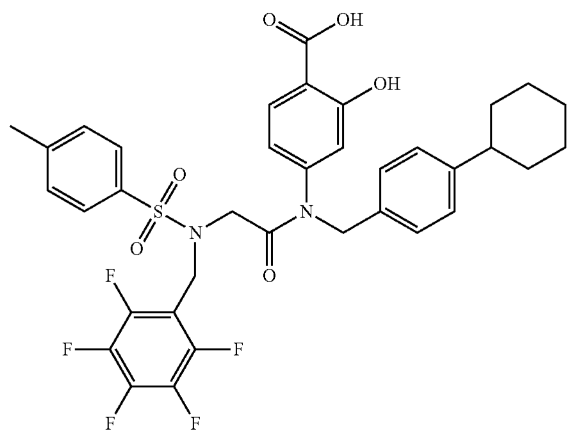 | n.d. | 4.5 ± 1.9 |
| BP2-086 | 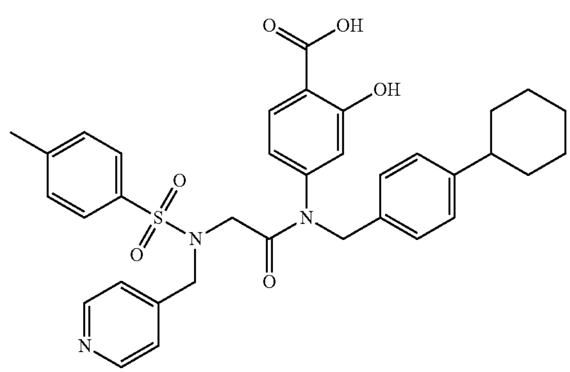 [SMILES: Cc1ccc(S(=O)(=O)N(CC(=O)N(Cc2ccc(C3CCCCC3)cc2)c2ccc(C(=O)O)c(O)c2)Cc2ccncc2)cc1] | n.d. | 23.3 ± 0.7 |
| BP2-119 | | n.d. | 7.7 ± 1.0 | ns

TABLE 1-continued

| Compound ID | Structure | IC$_{50}$ (EMSA) | K$_i$ (FP) |
|---|---|---|---|
| BP2-120 | 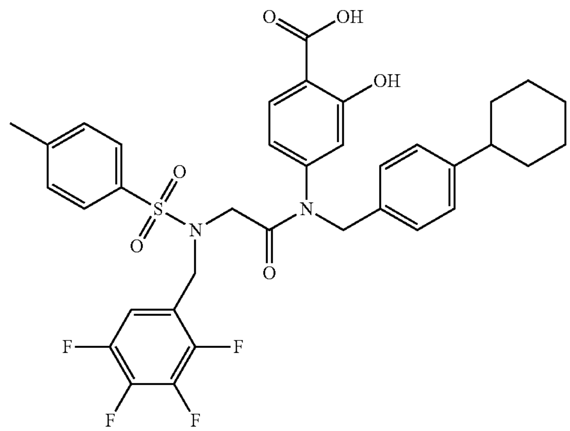 [SMILES: Cc1ccc(S(=O)(=O)N(CC(=O)N(Cc2ccc(C3CCCCC3)cc2)c2ccc(C(=O)O)c(O)c2)Cc2cc(F)c(F)c(F)c2F)cc1] | n.d. | 11.1 ± 0.6 |
| BP2-121 | 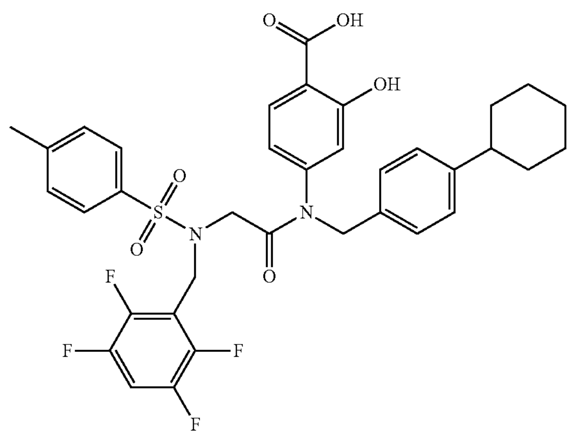 [SMILES: Cc1ccc(S(=O)(=O)N(CC(=O)N(Cc2ccc(C3CCCCC3)cc2)c2ccc(C(=O)O)c(O)c2)Cc2c(F)c(F)cc(F)c2F)cc1] | n.d. | 11.4 ± 0.4 |
| BP2-124 | 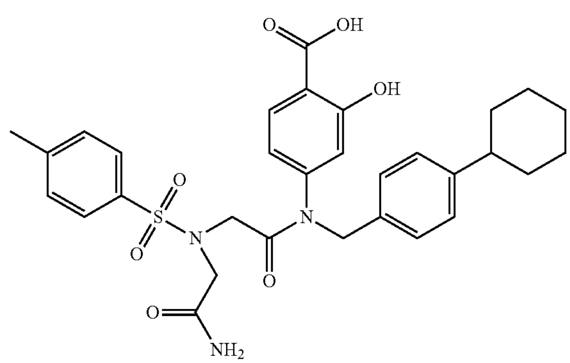 [SMILES: Cc1ccc(S(=O)(=O)N(CC(N)=O)CC(=O)N(Cc2ccc(C3CCCCC3)cc2)c2ccc(C(=O)O)c(O)c2)cc1] | n.d. | 48.7 ± 14.2 |
| BP2-125 | 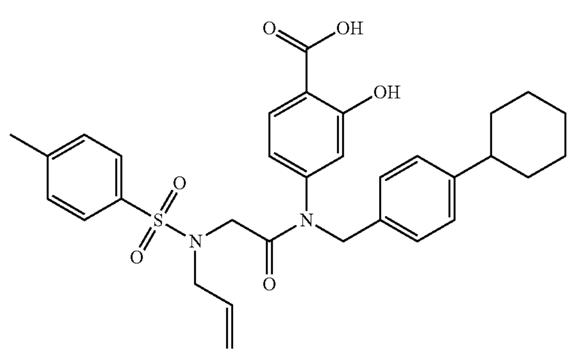 [SMILES: C=CCN(CC(=O)N(Cc1ccc(C2CCCCC2)cc1)c1ccc(C(=O)O)c(O)c1)S(=O)(=O)c1ccc(C)cc1] | n.d. | 27.9 ± 5.0 |

TABLE 1-continued

| Compound ID | Structure | IC$_{50}$ (EMSA) | K$_i$ (FP) |
|---|---|---|---|
| BP2-130 | 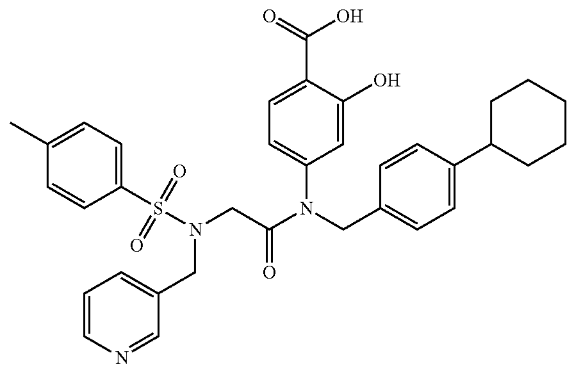 [SMILES: Cc1ccc(S(=O)(=O)N(CC(=O)N(Cc2ccc(C3CCCCC3)cc2)c2ccc(C(=O)O)c(O)c2)Cc2cccnc2)cc1] | n.d. | 25.4 ± 0.8 |
| BP2-131 | 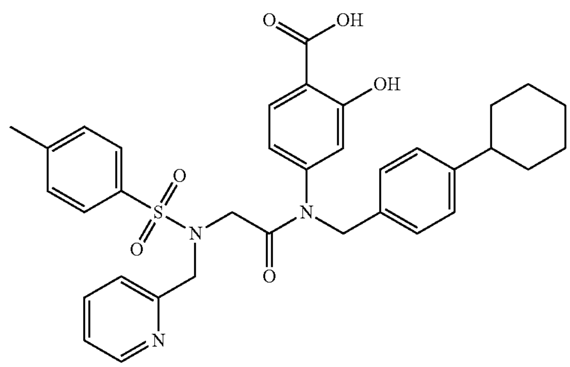 [SMILES: Cc1ccc(S(=O)(=O)N(CC(=O)N(Cc2ccc(C3CCCCC3)cc2)c2ccc(C(=O)O)c(O)c2)Cc2ccccn2)cc1] | n.d. | 22.6 ± 3.0 |
| BP3-014 | 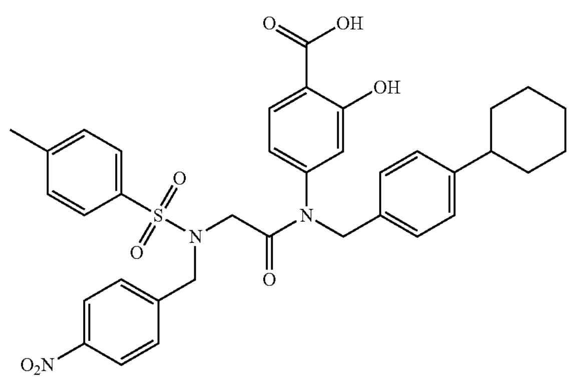 | n.d. | 5.5 ± 3.7 |
| BP3-016 | 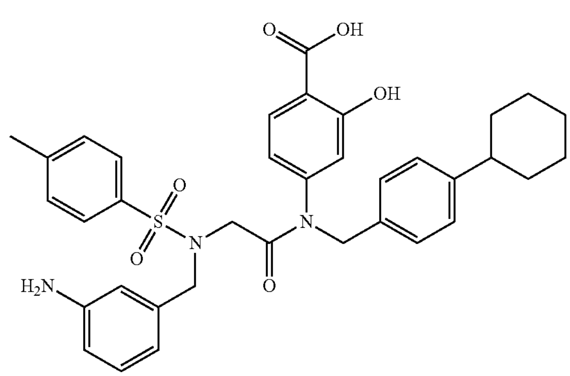 [SMILES: Cc1ccc(S(=O)(=O)N(CC(=O)N(Cc2ccc(C3CCCCC3)cc2)c2ccc(C(=O)O)c(O)c2)Cc2cccc(N)c2)cc1] | n.d. | 6.2 ± 1.6 |

TABLE 1-continued
| Compound ID | Structure | IC$_{50}$ (EMSA) | K$_i$ (FP) |
|---|---|---|---|
| BP3-018 | 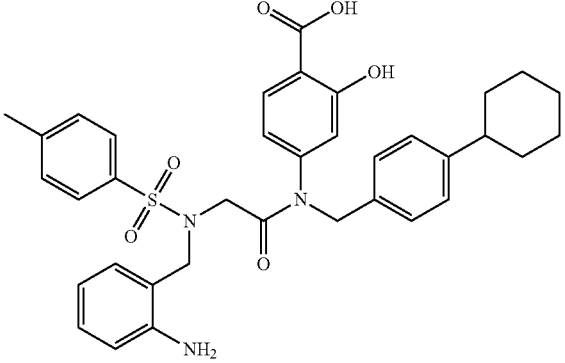 | n.d. | 12.0 ± 0.5 |
| BP3-019 | 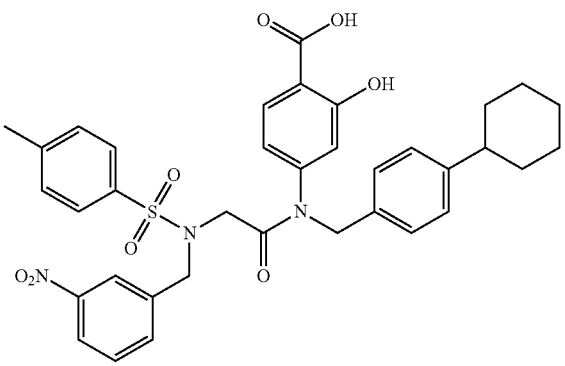 | n.d. | 2.5 ± 2.2 |
| BP3-020 | 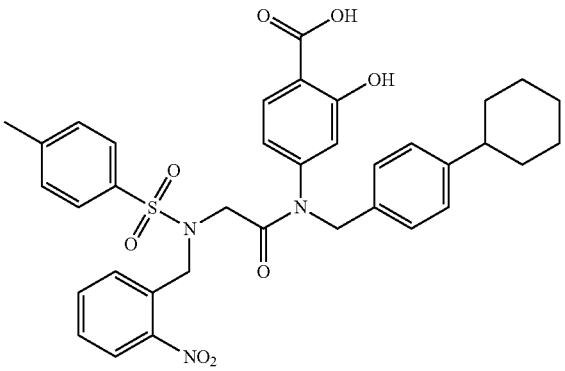 | n.d. | 5.0 ± 6.5 |
| BP3-021 | 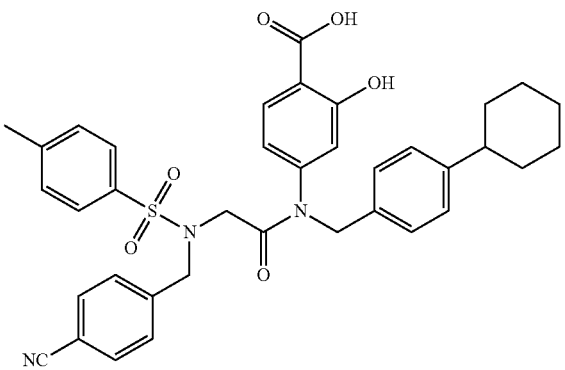 [SMILES: Cc1ccc(S(=O)(=O)N(CC(=O)N(Cc2ccc(C3CCCCC3)cc2)c2ccc(C(=O)O)c(O)c2)Cc2ccc(C#N)cc2)cc1] | n.d. | 4.3 ± 0.7 |

TABLE 1-continued

| Compound ID | Structure | IC$_{50}$ (EMSA) | K$_i$ (FP) |
|---|---|---|---|
| BP3-023 | 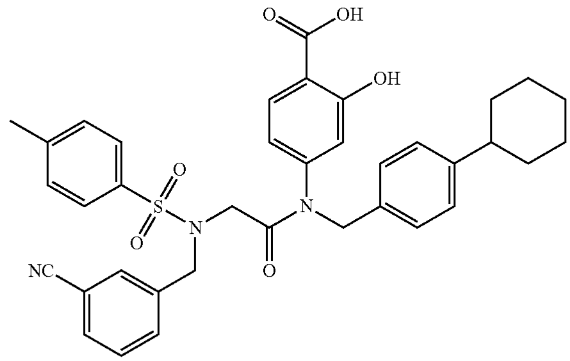 [SMILES: Cc1ccc(S(=O)(=O)N(CC(=O)N(Cc2ccc(C3CCCCC3)cc2)c2ccc(C(=O)O)c(O)c2)Cc2cccc(C#N)c2)cc1] | n.d. | 6.2 ± 0.8 |
| BP3-024 | 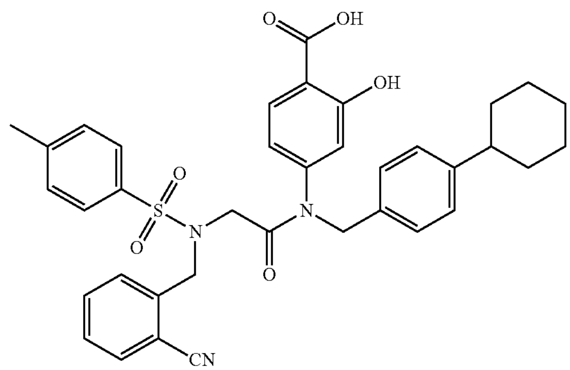 [SMILES: Cc1ccc(S(=O)(=O)N(CC(=O)N(Cc2ccc(C3CCCCC3)cc2)c2ccc(C(=O)O)c(O)c2)Cc2ccccc2C#N)cc1] | n.d. | 11.3 ± 0.8 |
| SH3-076 | 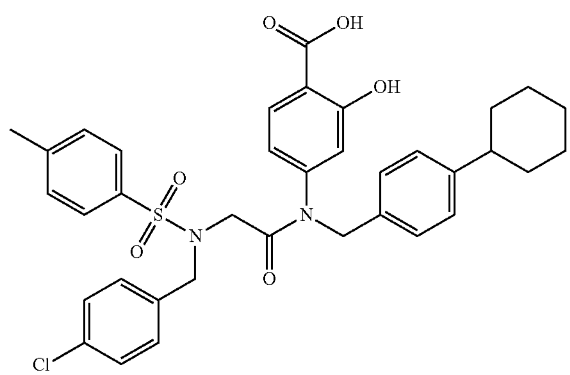 [SMILES: Cc1ccc(S(=O)(=O)N(CC(=O)N(Cc2ccc(C3CCCCC3)cc2)c2ccc(C(=O)O)c(O)c2)Cc2ccc(Cl)cc2)cc1] | n.d. | 3.1 ± 0.1 |
| SH3-077 | 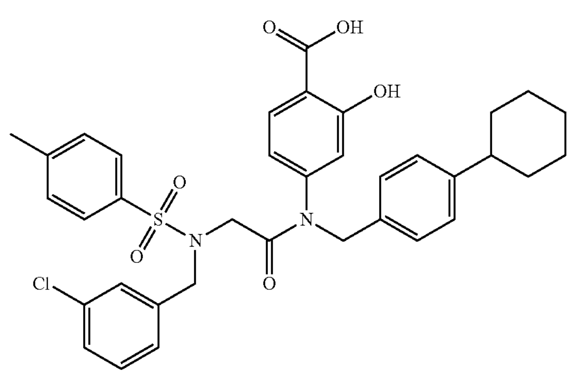 | n.d. | 3.0 ± 4.1 |

TABLE 1-continued
| Compound ID | Structure | IC$_{50}$ (EMSA) | K$_i$ (FP) |
|---|---|---|---|
| SH3-079 | 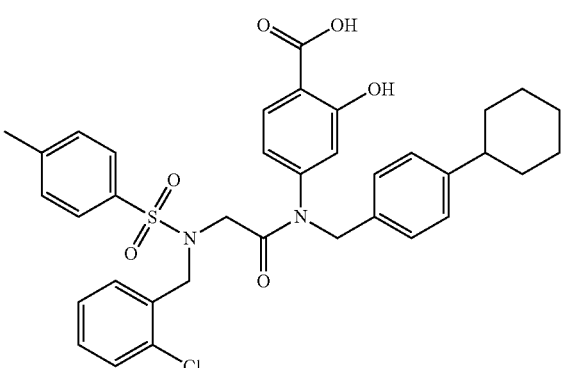 | n.d. | 7.9 ± 0.3 |
| XW1-053 | 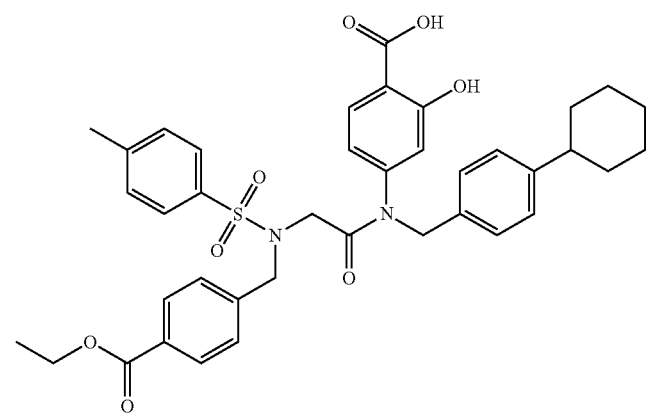 [SMILES: CCOC(=O)c1ccc(CN(CC(=O)N(Cc2ccc(C3CCCCC3)cc2)c2ccc(C(=O)O)c(O)c2)S(=O)(=O)c2ccc(C)cc2)cc1] | n.d. | 3.8 ± 1.5 |
| XW1-055 | 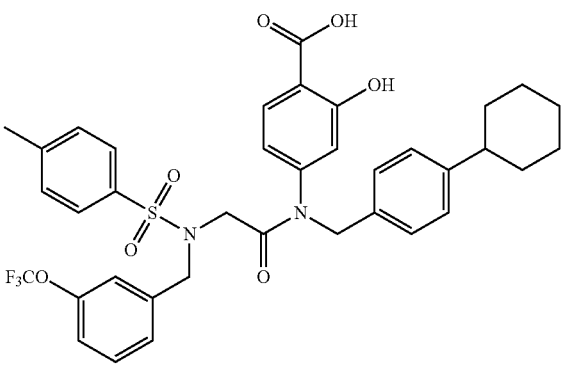 | n.d. | 4.0 ± 1.1 |
| XW1-057 | 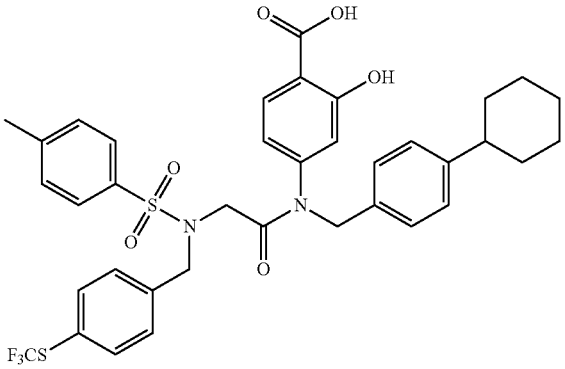 | n.d. | 4.8 ± 0.6 |

TABLE 1-continued

| Compound ID | Structure | IC$_{50}$ (EMSA) | K$_i$ (FP) |
|---|---|---|---|
| XW1-059 | 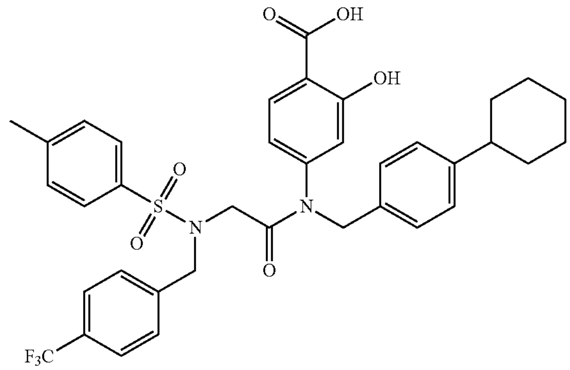 | n.d. | 4.6 ± 1.6 |
| XW1-061 | 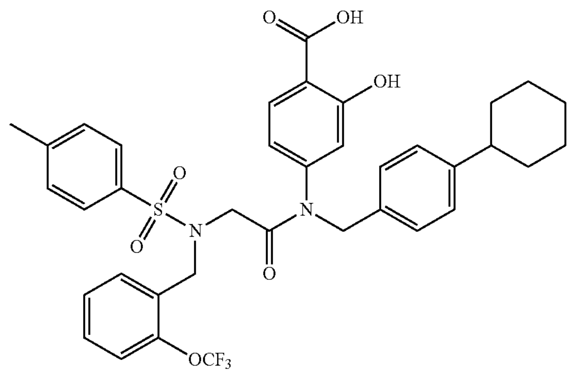 | n.d. | 3.6 ± 0.5 |
| XW1-075 | 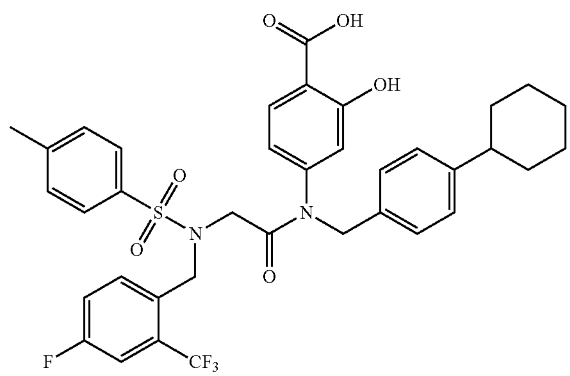 [SMILES: Cc1ccc(S(=O)(=O)N(CC(=O)N(Cc2ccc(C3CCCCC3)cc2)c2ccc(C(=O)O)c(O)c2)Cc2ccc(F)cc2C(F)(F)F)cc1] | n.d. | 5.5 ± 0.4 |
| XW1-077 | 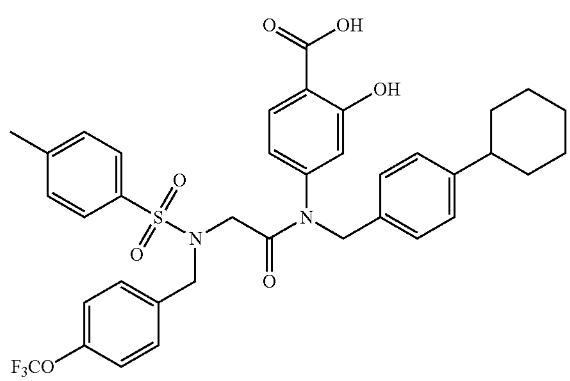 | n.d. | 5.9 ± 0.6 |

TABLE 1-continued

| Compound ID | Structure | IC$_{50}$ (EMSA) | K$_i$ (FP) |
|---|---|---|---|
| XW1-079 | 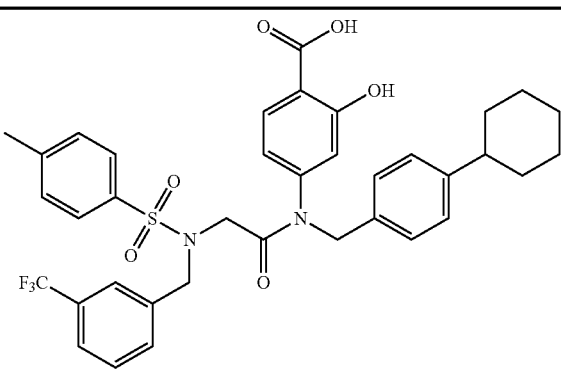 | n.d. | 5.1 ± 0.4 |
| XW1-081 | 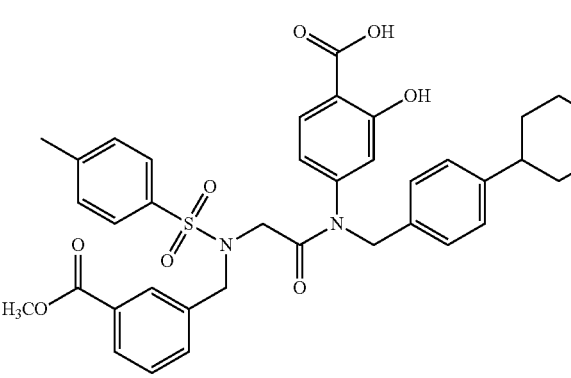 | n.d. | 9.2 ± 0.8 |
| XW1-083 | 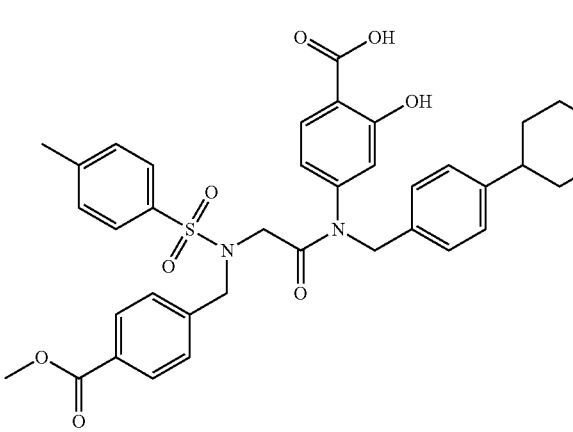 | n.d. | 5.8 ± 0.6 |

136. Effect of Substituted 2-hydroxy-4-(2-(phenylsulfonamido)acetamido)benzoic acid analogs on Cell Viability Using the assay methods described herein, the effect of representative compounds on cell viability was determined, and the data are shown in Tables 2 and 3 below. The compound identifier ("ID") corresponds to the number given parenthetically for the preparation of compounds described above.

TABLE 2

| ID code* | Structure | IC$_{50}$ (μM) | | | |
| --- | --- | --- | --- | --- | --- |
| | | MDA-468 | DU-145 | OCI-AML2 | HL60 |
| 27KG | 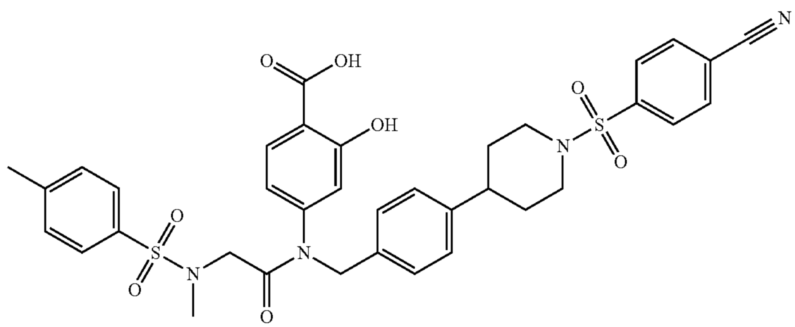 [SMILES: Cc1ccc(S(=O)(=O)N(C)CC(=O)N(Cc2ccc(C3CCN(S(=O)(=O)c4ccc(C#N)cc4)CC3)cc2)c2ccc(C(=O)O)c(O)c2)cc1] | 94.9 ± 8.8 | >100 | >100 | 83.1 ± 13.5 |
| 27LE | 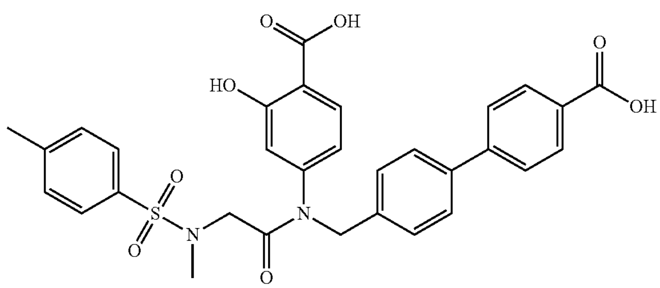 [SMILES: Cc1ccc(S(=O)(=O)N(C)CC(=O)N(Cc2ccc(-c3ccc(C(=O)O)cc3)cc2)c2ccc(C(=O)O)c(O)c2)cc1] | 52.9 ± 22.5 | >100 | 76.7 ± 27.1 | 68.0 ± 32.8 |
| 27NA | 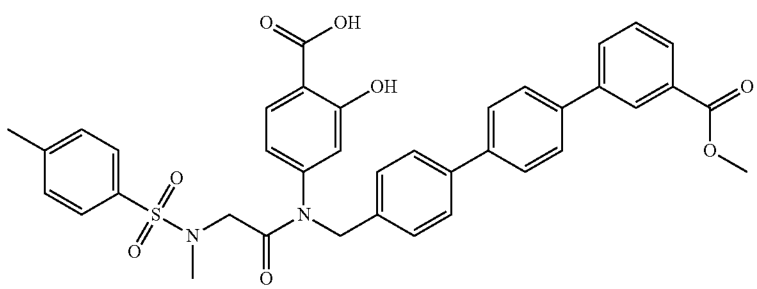 | 29.0 ± 2.3 | 81.5 ± 8.0 | 35.1 ± 19.4 | 33.2 ± 9.2 |
| 27NC | 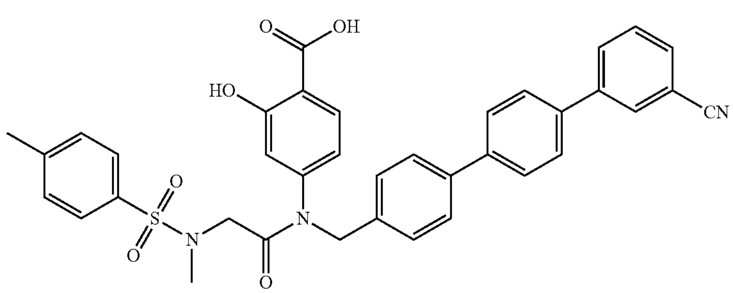 [SMILES: Cc1ccc(S(=O)(=O)N(C)CC(=O)N(Cc2ccc(-c3ccc(-c4cccc(C#N)c4)cc3)cc2)c2ccc(C(=O)O)c(O)c2)cc1] | 90.5 ± 63.2 | >100 | >100 | 82.8 ± 19.0 |
| 27NE | 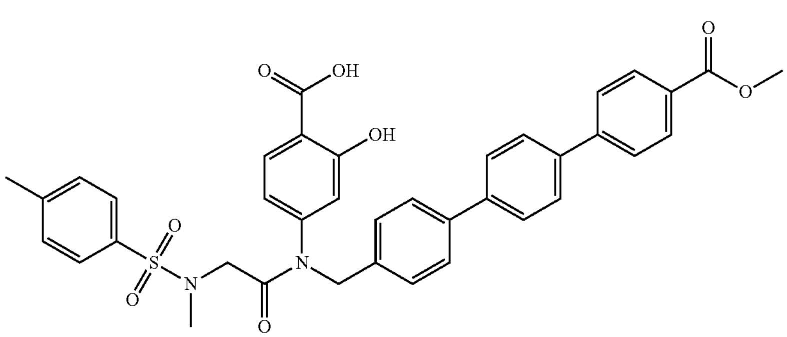 | 96.3 ± 31.7 | >100 | >100 | >100 |

TABLE 2-continued

| ID code* | Structure | IC$_{50}$ (μM) | | | |
|---|---|---|---|---|---|
| | | MDA-468 | DU-145 | OCI-AML2 | HL60 |
| 27NG | 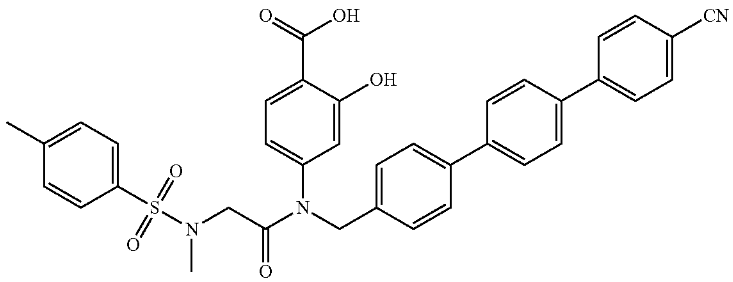 [SMILES: Cc1ccc(S(=O)(=O)N(C)CC(=O)N(Cc2ccc(-c3ccc(-c4ccc(C#N)cc4)cc3)cc2)c2ccc(C(=O)O)c(O)c2)cc1] | 32.5 ± 15.5 | 94.4 ± 6.8 | 58.4 ± 13.8 | 37.4 ± 14.0 |
| 45A | 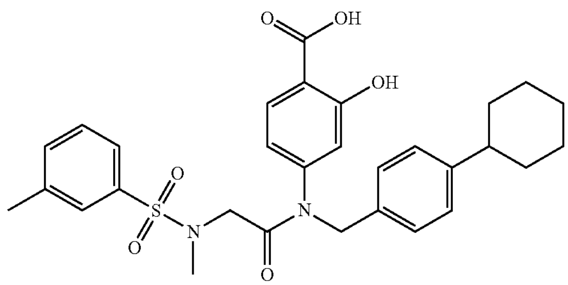 [SMILES: Cc1cccc(S(=O)(=O)N(C)CC(=O)N(Cc2ccc(C3CCCCC3)cc2)c2ccc(C(=O)O)c(O)c2)c1] | 59.6 ± 4.0 | 90.4 ± 3.1 | 85.9 ± 0.4 | 78.5 ± 1.8 |
| 45B | 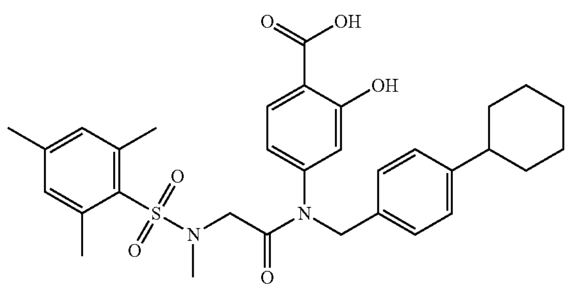 [SMILES: Cc1cc(C)c(S(=O)(=O)N(C)CC(=O)N(Cc2ccc(C3CCCCC3)cc2)c2ccc(C(=O)O)c(O)c2)c(C)c1] | 22.6 ± 8.3 | 44.5 ± 16.0 | 65.4 ± 13.0 | 40.4 ± 20.2 |
| 45C | 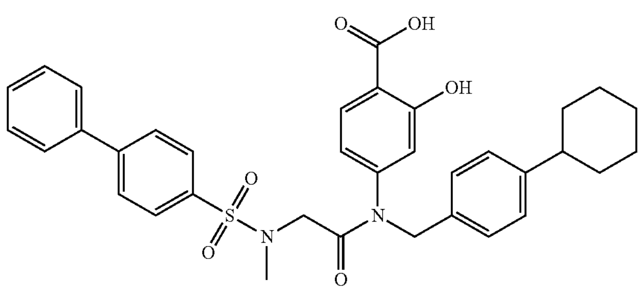 [SMILES: CN(CC(=O)N(Cc1ccc(C2CCCCC2)cc1)c1ccc(C(=O)O)c(O)c1)S(=O)(=O)c1ccc(-c2ccccc2)cc1] | 47.4 ± 6.2 | 80.0 ± 31.6 | 95.4 ± 33.7 | 74.8 ± 28.2 |
| 45D | 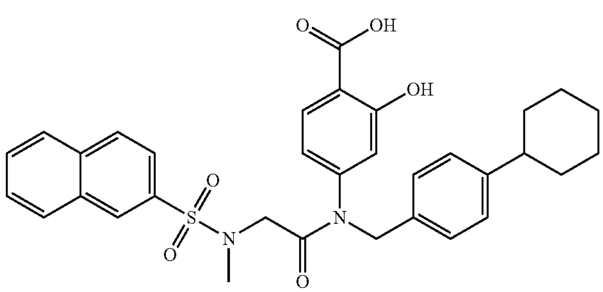 [SMILES: CN(CC(=O)N(Cc1ccc(C2CCCCC2)cc1)c1ccc(C(=O)O)c(O)c1)S(=O)(=O)c1ccc2ccccc2c1] | 45.4 ± 23.2 | 81.0 ± 39.3 | 93.5 ± 32.2 | 99.8 ± 15.6 |

TABLE 2-continued

| ID code* | Structure | IC$_{50}$ (μM) | | | |
|---|---|---|---|---|---|
| | | MDA-468 | DU-145 | OCI-AML2 | HL60 |
| 45E | 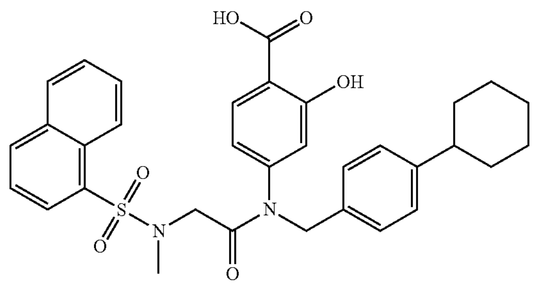 [SMILES: CN(CC(=O)N(Cc1ccc(C2CCCCC2)cc1)c1ccc(C(=O)O)c(O)c1)S(=O)(=O)c1cccc2ccccc12] | 46.5 ± 12.4 | 74.5 ± 30.2 | 33.3 ± 19.8 | 76.9 ± 50.5 |
| 45F | 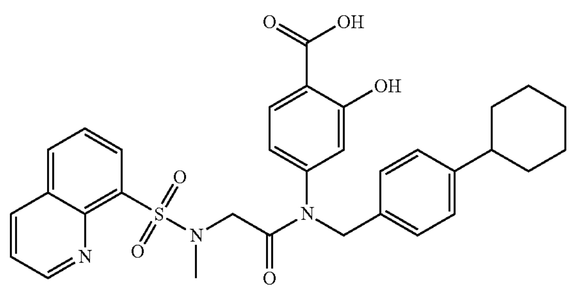 [SMILES: CN(CC(=O)N(Cc1ccc(C2CCCCC2)cc1)c1ccc(C(=O)O)c(O)c1)S(=O)(=O)c1cccc2cccnc12] | >100 | >100 | >100 | >100 |
| 45G | 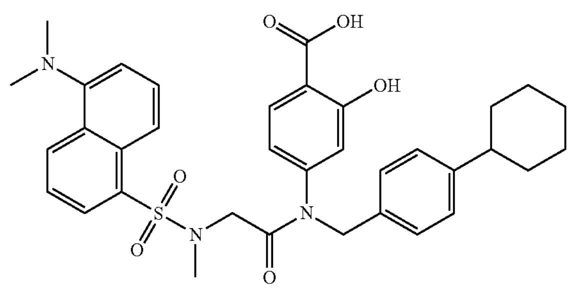 [SMILES: CN(C)c1cccc2c(S(=O)(=O)N(C)CC(=O)N(Cc3ccc(C4CCCCC4)cc3)c3ccc(C(=O)O)c(O)c3)cccc12] | 45.5 ± 7.9 | >100 | >100 | 74.9 ± 20.2 |
| 45H | 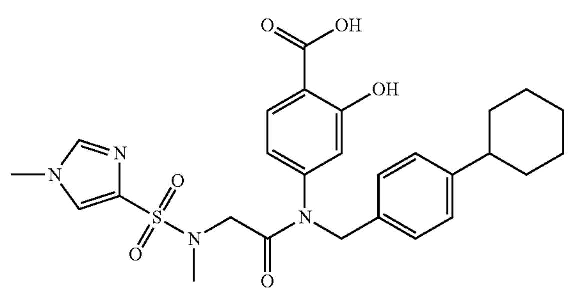 [SMILES: CN(CC(=O)N(Cc1ccc(C2CCCCC2)cc1)c1ccc(C(=O)O)c(O)c1)S(=O)(=O)c1cn(C)cn1] | >100 | >100 | >100 | >100 |
| 45I | 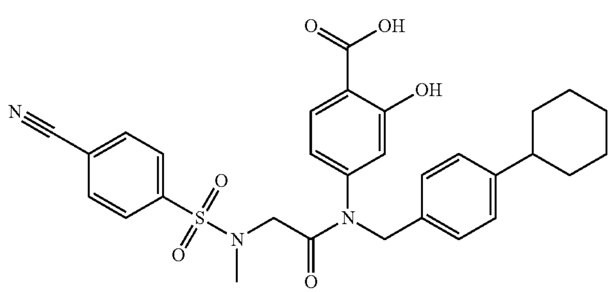 [SMILES: CN(CC(=O)N(Cc1ccc(C2CCCCC2)cc1)c1ccc(C(=O)O)c(O)c1)S(=O)(=O)c1ccc(C#N)cc1] | 27.0 ± 2.7 | 69.6 ± 3.4 | 53.5 ± 22.8 | 59.1 ± 11.5 |

TABLE 2-continued

| ID code* | Structure | IC$_{50}$ (μM) | | | |
|---|---|---|---|---|---|
| | | MDA-468 | DU-145 | OCI-AML2 | HL60 |
| 45J | 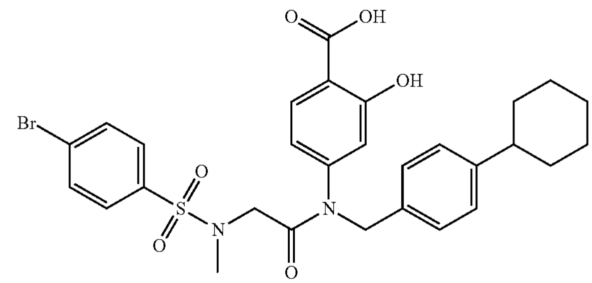 [SMILES: CN(CC(=O)N(Cc1ccc(C2CCCCC2)cc1)c1ccc(C(=O)O)c(O)c1)S(=O)(=O)c1ccc(Cl)cc1] | 19.5 ± 2.0 | 45.9 ± 8.6 | 44.9 ± 7.1 | 47.4 ± 8.2 |
| 45K | 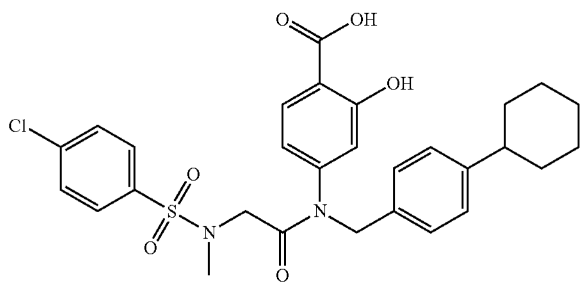 | 29.7 ± 16.7 | 67.5 ± 24.2 | 76.4 ± 10.8 | 56.3 ± 9.3 |
| 45L | 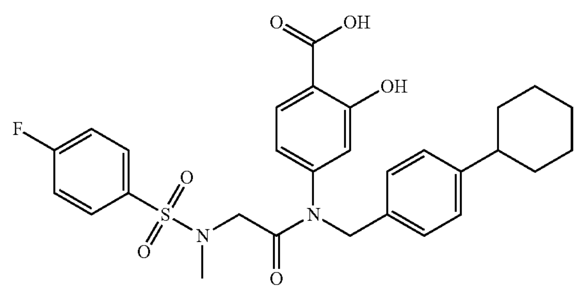 [SMILES: CN(CC(=O)N(Cc1ccc(C2CCCCC2)cc1)c1ccc(C(=O)O)c(O)c1)S(=O)(=O)c1ccc(F)cc1] | 41.3 ± 5.7 | 72.7 ± 18.4 | 84.4 ± 22.1 | 75.1 ± 25.1 |
| 45M | 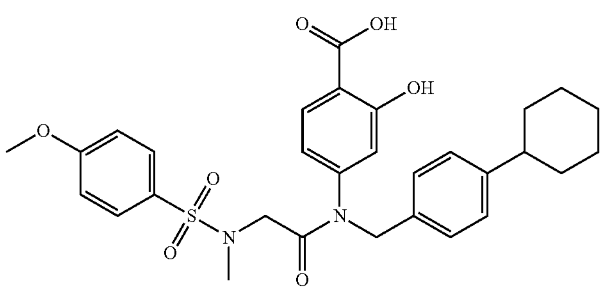 [SMILES: COc1ccc(S(=O)(=O)N(C)CC(=O)N(Cc2ccc(C3CCCCC3)cc2)c2ccc(C(=O)O)c(O)c2)cc1] | 71.4 ± 13.6 | 92.7 ± 27.9 | >100 | >100 |
| 45N | 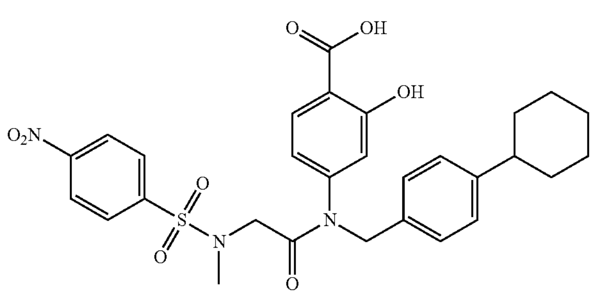 [SMILES: CN(CC(=O)N(Cc1ccc(C2CCCCC2)cc1)c1ccc(C(=O)O)c(O)c1)S(=O)(=O)c1ccc([N+](=O)[O-])cc1] | 51.7 ± 14.2 | >100 | 96.3 ± 18.5 | 99.3 ± 62.1 |

TABLE 2-continued

| ID code* | Structure | IC$_{50}$ (μM) MDA-468 | DU-145 | OCI-AML2 | HL60 |
|---|---|---|---|---|---|
| 45O | (structure shown) | 10.9 ± 3.0 | 22.7 ± 8.5 | 10.5 ± 6.2 | 10.4 ± 1.6 |

TABLE 3

| | IC$_{50}$ values (μM) | |
|---|---|---|
| Compound | MV-4-11 | K562 |
| SF-1-088 | >80 | 77 ± 5 |
| SF-1-087 | 51 ± 7 | >80 |
| 45b | >80 | 80 ± 18 |
| 45c | 17 ± 1 | 42 ± 16 |
| 27na | 24 ± 2 | 24 ± 3 |

137. STAT5 Activity of Substituted 2-hydroxy-4-(2-(phenylsulfonamido)acetamido)benzoic acid analogs The fluorescence polarization assay was as described herein was used to assess the STAT isoform selectivity of representative compounds. Data are given below in Table 4. The inhibitor codes given in Table 4 correspond as follows to the compound IDs used in Table 1: BP1-075=27na; BP2-122=27nh; SF2-096=27kg; SF3-005=27ki; BP1-107=45b; BP1-108=45c; BP1-111=45k. SF1-066, SF1-087 and SF-088 correspond to the same named compounds shown above with the corresponding compound characterization.

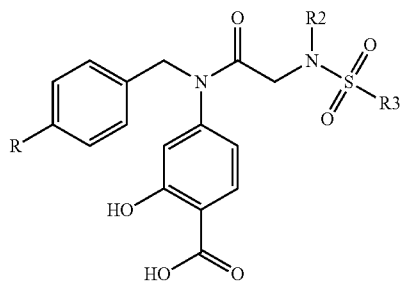

| Inhibitor | R | R3 | R2 | Stat5 | Stat3 | Stat1 |
|---|---|---|---|---|---|---|
| SF1-066 | cyclohexyl | p-tolyl | —CH$_3$ | >25 | 15.5 ± 4.7 | >25 |
| BP1-075 | 3'-CO$_2$Me-biphenyl | p-tolyl | —CH$_3$ | 3.8 ± 1.6 | 2.8 ± 1.1 | 3.2 ± 1.3 |
| BP2-122 | 4'-C(O)NH$_2$-biphenyl | p-tolyl | —CH$_3$ | 4.8 ± 1.6 | 8.4 ± 2.4 | 9.5 ± 2.4 |
| SF2-096 | 4-(4-cyanophenylsulfonyl)piperidinyl | p-tolyl | —CH$_3$ | 7.3 ± 0.9 | 8.4 ± 0.9 | >25 |

-continued

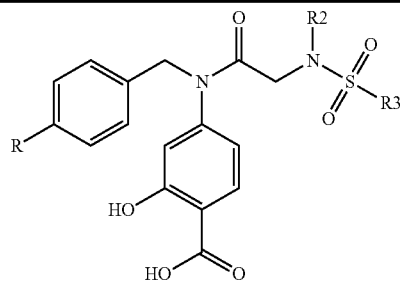

| Inhibitor | R | R3 | R2 | Stat5 | Stat3 | Stat1 |
|---|---|---|---|---|---|---|
| SF3-006 | piperidinyl-phenyl-C(O)NH$_2$ | 4-tolyl | —CH$_3$ | 10.1 ± 1.5 | 17.6 ± 0.8 | 27.8 ± 2.2 |
| BP1-107 | cyclohexyl | biphenyl | —CH$_3$ | 4.1 ± 0.5 | 6.2 ± 2.0 | 8.8 ± 1.6 |
| BP1-108 | cyclohexyl | 2,4,6-trimethylphenyl | —CH$_3$ | 2.8 ± 3.2 | 8.0 ± 2.4 | 9.7 ± 8.2 |
| BP1-111 | cyclohexyl | 4-chlorophenyl | —CH$_3$ | 7.9 ± 2.1 | 11.0 ± 0.2 | 20.4 ± 2.9 |
| SF1-087 | cyclohexyl | 4-tolyl | —Boc | 3.4 ± 0.9 | 7.9 ± 0.1 | >25 |
| SF1-088 | H | 4-tolyl | —Boc | 8.3 ± 6.1 | >25 | >25 |

138. Prospective In Vivo Activity

Generally compounds that inhibit STAT protein activity in preclinical animal models of tumor growth and pathology. In vivo effects of the compounds described in the preceding examples are expected to be show activity in various models cancer biology known to the skilled person, such as a mouse subcutaneous xenograft model or, alternatively, the mouse orthotopic xenograft model.

These models are typically conducted in an immunocompromised mouse, e.g. athymic nude mice, severely compromised immunodeficient (SCID) mice, or other immunocompromised mice (see reference (40) above), but may be conducted in other animal species as is convenient to the study goals. Alternatively, a genetically engineered mouse (GEM) model can be used to assess the efficacy of the disclosed compounds on inhibiting tumor growth. The genetic profile of GEM mice is altered such that one or several genes thought to be involved in transformation or malignancy are mutated, deleted or overexpressed; subsequently, the effect of altering these genes is studied over time and therapeutic responses to these tumors may be followed in vivo.

The subcutaneous xenograft model is frequently used by one skilled in the art to assess anti-cancer activity. Briefly, the cell-line of choice, e.g. MDA-MB-231, Panc-1, DU 145, or NIT3T3/v-Src cells, are grown in vitro in culture flasks, and then collected with using trypsin (if adherent) or by simple centrifugation (if suspension cultures), and then suspended in PBS at about 6×10 7 cells/mL. In one experimental approach, about $10^5$ cells are injected in mice subcutaneously on Day 0, and the tumors allowed to develop to about $10^6$ cells (about 7-10 days). Suitable mice strains to use in this include nu/nu nude mice or CAnN.Cg-Foxn1nu/CrlCrlj(nu/nu), and are readily available from suitable commercial sources (e.g. Harlan or Charles River). Drug is administered by a suitable route of administration, e.g. intravenous or intraperitoneally, on a dosing schedule suitable for the compound, e.g. daily for a period of five days or every third day for a period of two weeks or other schedule as determined from in vitro and in vivo data on potency, pharmacokinetics, and metabolism. The vehicle choice is determined based on the physical-chemical properties of the test compound. Exemplary vehicles include mixtures comprising DMSO, Cremaphor, and vegetable oils, e.g. 12.5% DMSO, 5% Cremaphor and 82.5% peanut oil; polysorbate:ethanol, e.g. 80:13; cremaphor:ethanol; and normal saline, e.g. phosphate-buffered saline. Body weight and tumor diameter are measured on a suitable schedule, e.g. every 3-4 days using calipers, and tumor volume determined by calculating the volume of an ellipsoid using the formula: length×width$^2$×0.5. Antitumor activities can be expressed as percent inhibition of tumor growth and percent regression of the tumor.

For example, compounds having a structure represented by a Formula I, II, III, or IV, or a pharmaceutically acceptable salt, hydrate, solvate, or polymorph thereof, are expected to show such in vivo effects.

For example, compounds having a structure represented by a Formula V or VI, or a pharmaceutically acceptable salt, hydrate, solvate, or polymorph thereof, are expected to show such in vivo effects.

Moreover, compounds prepared using the disclosed synthetic methods are also expected to show such in vivo effects.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

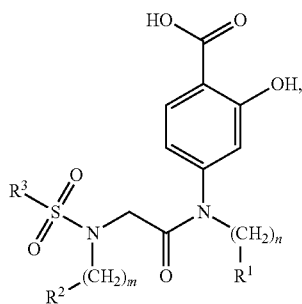

wherein each of m and n is independently an integer from 0-3;

wherein $R^1$ is selected from $A^1$, $A^2$, -($A^1$)-($A^2$), -($A^2$)-($A^3$), -($A^3$)-($A^2$), -($A^3$)-($A^4$), -($A^5$)-($A^1$)-($A^7$), -($A^5$)-($A^2$)-($A^8$), -($A^5$)-($A^3$)-($A^7$), and -($A^5$)-($A^6$)-L-($A^7$);

wherein $A^1$ is C3-C6 cycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)R4, (C=O)$OR^4$, and (C=O)$NHR^4$;

wherein $A^2$ is C3-C6 heterocycloalkyl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)$R^5$, (C=O)$OR^5$, and (C=O)$NHR^5$;

wherein $A^3$ is aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)$R^6$, (C=O)$OR^6$, and (C=O)$NHR^6$;

wherein $A^4$ is aryl, and substituted with 1-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)$R^7$, (C=O)$OR^7$, and (C=O)$NHR^7$;

wherein $A^5$ is selected from C3-C6 cycloalkyl, C3-C6 heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)$R^8$, (C=O)$OR^8$, and (C=O)$NHR^8$;

wherein $A^6$ is selected from C3-C6cycloalkyl, C3-C6heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)$R^9$, (C=O)$OR^9$, and (C=O)$NHR^9$;

wherein $A^7$ is selected from C3-C6cycloalkyl, C3-C6heterocycloalkyl, and aryl, and substituted with 0-3 groups selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C 6 alkylthio, C1-C6 haloalkythio, C1-C6 polyhaloalkylthio, C1-C6 alkylamino, C1-C 6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, $CO_2H$, (C=O)$R^{10}$, (C=O)$OR^{10}$, and (C=O)$NHR^{10}$;

wherein $A^8$ is selected from C3-C6cycloalkyl, C3-C6heterocycloalkyl, and aryl, and substituted with 0-3 groups selected from halo, hydroxyl, amino, nitro, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-

C6)-alkyl-(C1-C6)-alkylthio, (C1-C6)-alkyl-(C1-C6)-haloalkythio, (C1-C6)-alkyl-(C1-C6)-polyhaloalkylthio, CO$_2$H, (C=O)R$^{11}$, (C=O)OR$^{11}$, and (C=O)NHR$^{11}$;

wherein L is selected from —(C=O)— and SO$_2$—;

wherein R$^2$ is selected from C1-C6 alkyl, C2-C6 alkenyl, C2-C6 alkynyl, C1-C6 haloalkyl, C2-C6 haloalkenyl, C2-C6 haloalkynyl, C1-C6 polyhaloalkyl, C2-C6 polyhaloalkenyl, C2-C6 polyhaloalkynyl; or wherein R$^2$ is aryl substituted with 0-5 groups independently selected from halo, hydroxyl, amino, nitro, cyano, C1-C6 haloalkyl, C1-C6 polyhaloalkyl, C1-C6 alkoxy, C1-C6 haloalkoxy, C1-C6 polyhaloalkoxy, C1-C6 alkylthio, C1-C6 haloalkythio, C1-C6 polyhaloalkylthio, C1-C6 alkylamino, C1-C6 dialkylamino, (C1-C6)-alkyl-(C1-C6)-alkoxy, (C1-C6)-alkyl-(C1-C6)-haloalkoxy, (C1-C6)-alkyl-(C1-C6)-polyhaloalkoxy, (C1-C6)-alkyl-(C1-C6)-alkylthio, (C1-C6)-alkyl-(C1-C6)-haloalkythio, (C1-C6)-alkyl-(C1-C6)-polyhaloalkylthio, CO$_2$H, (C=O)OR$^{11}$, and (C=O)NHR$^{11}$;

wherein R$^3$ is a pentafluorophenyl; and wherein each of R$^4$, R$^5$, R$^6$, R$^7$, R$^8$, R$^9$, R$^{10}$, and R$^{11}$ is independently selected from hydrogen, C1-C6 alkyl, C1-C6 haloalkyl, and C1-C6 polyhaloalkyl;

or a pharmaceutically acceptable salt thereof.

2. The compound of claim 1, wherein the compound exhibits inhibition of STAT with an IC$_{50}$ of less than about 300 µM.

3. The compound of claim 1, wherein the compound exhibits inhibition of STAT with an K$_i$ of less than about 300 µM.

4. A pharmaceutical composition comprising a therapeutically effective amount of a compound of claim 1 and a pharmaceutically acceptable carrier.

5. The compound of claim 1, wherein the compound has a structure represented by a formula:

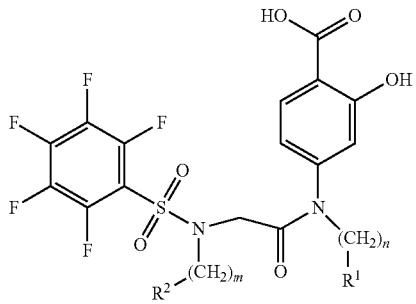

wherein R$^2$ is selected from a structure represented by a formula:

—(CH$_2$)$_2$CH$_3$, —CH$_2$CH(CH$_3$)2, —CH$_2$CH=CH$_2$,

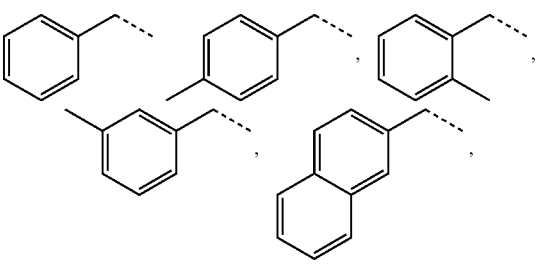

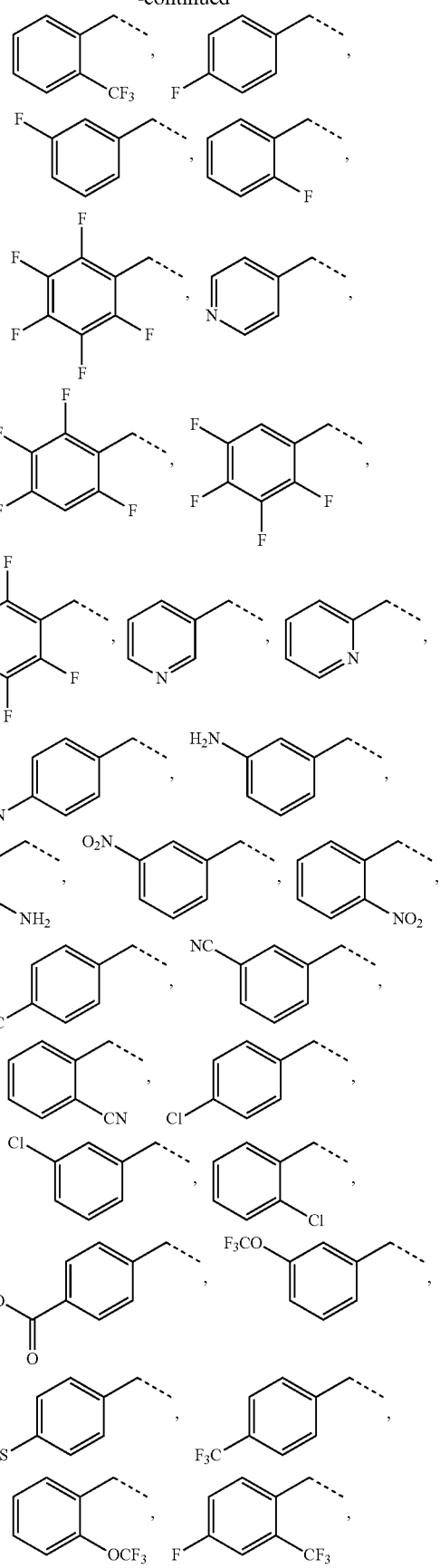

6. A compound having a structure represented by a formula:

wherein each of m is 0 and n is 0;

wherein R¹ is selected from a structure represented by a formula:

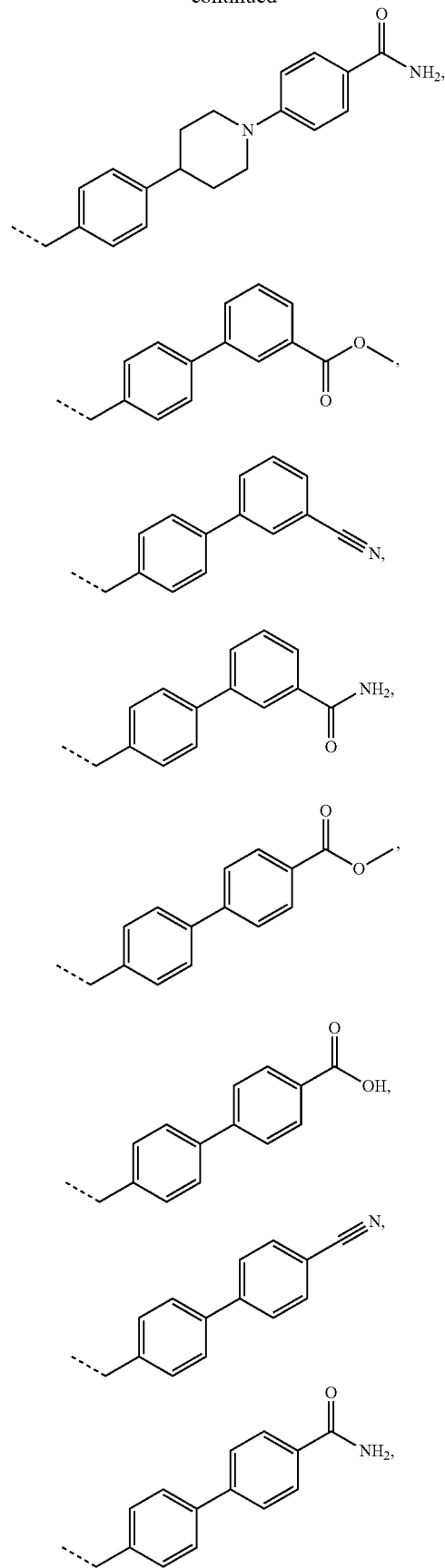
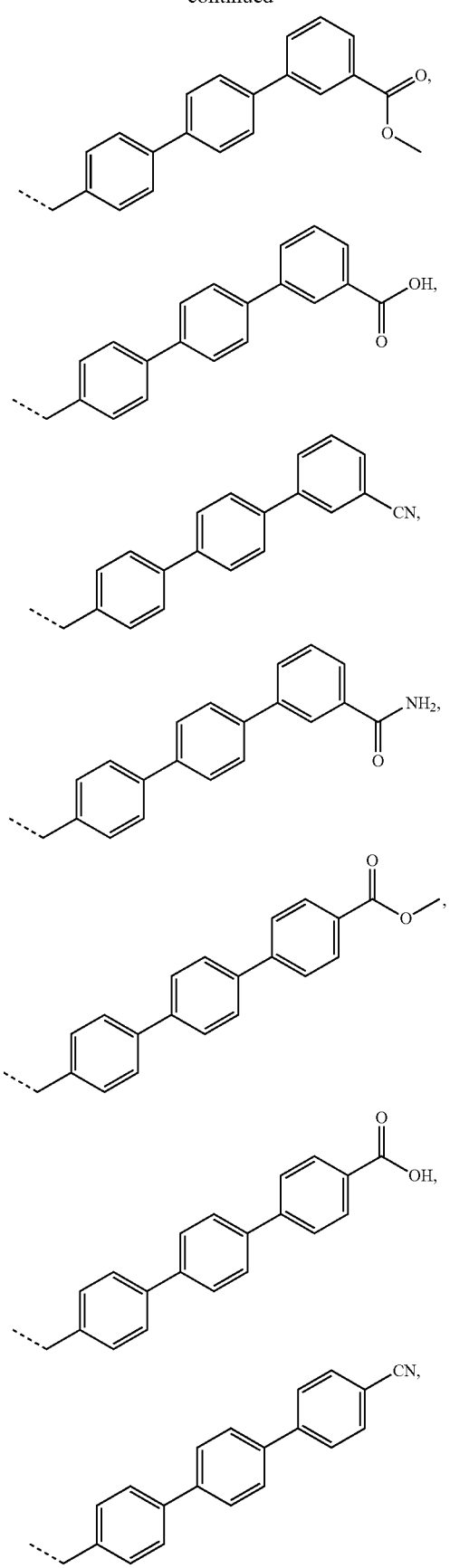

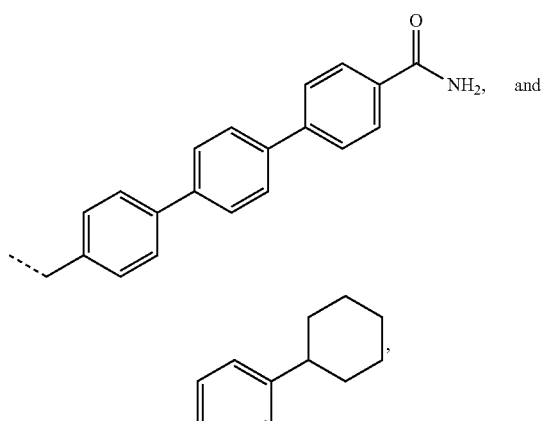
wherein R² is selected from a structure represented by a formula:
—CH₃, —CH₂(C=O)NH₂, —CH₂CH=CH₂, —(CH₂)₂CH₃, —CH₂CH(CH₃)₂,
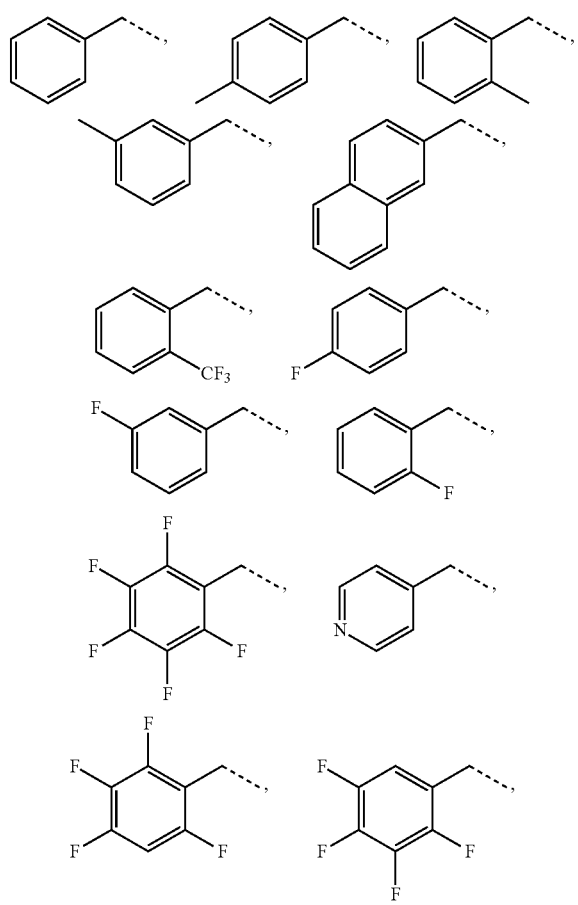
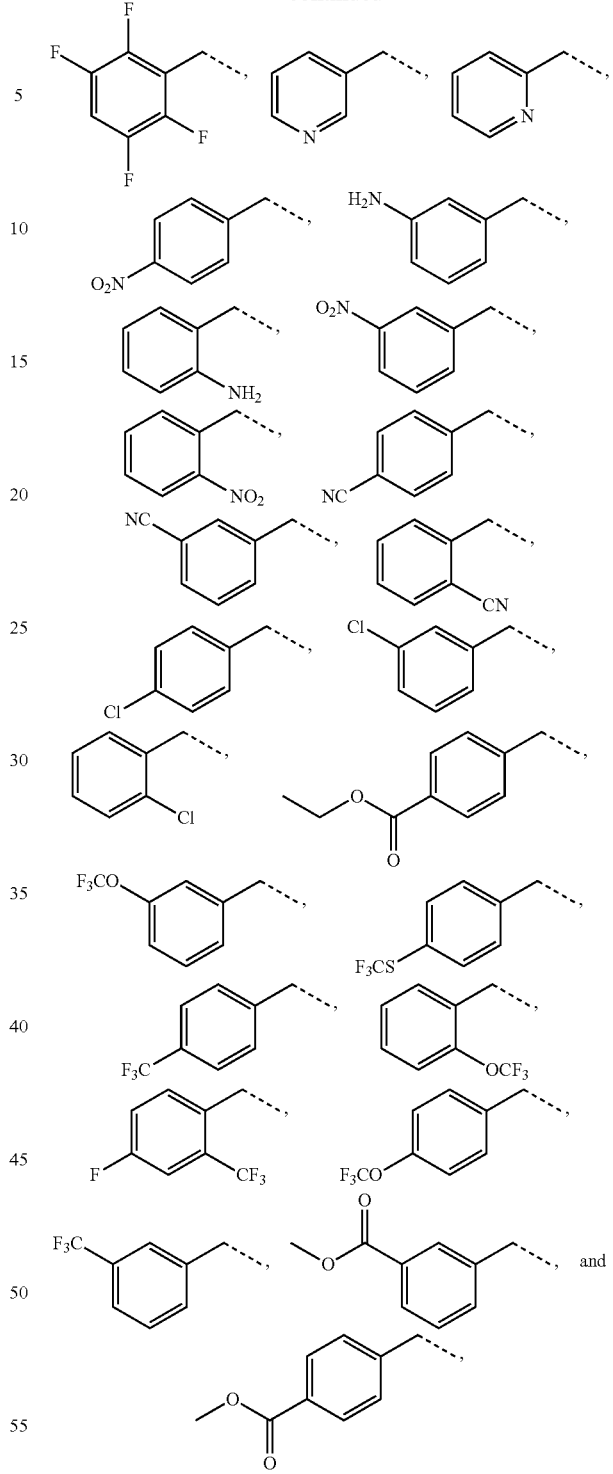
or a pharmaceutically acceptable salt, hydrate, solvate, or polymorph thereof.
* * * * *

SEQUENCE LISTING

```
<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 1
gacgacgaca agatggctca gtggaaccag ctgc                              34

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
gaggagaagc ccggttatca catgggggag gtagcacact                        40

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
atgggtttca tcagcaagga                                              20

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 4
tcacctacag tactttccaa atgc                                         24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct
```

```
<400> SEQUENCE: 5
agcttcattt cccgtaaatc ccta                                              24
```